(12) United States Patent
Pojer et al.

(10) Patent No.: US 8,252,973 B2
(45) Date of Patent: Aug. 28, 2012

(54) METABOLIC ENGINEERING OF LIPID METABOLISM BY IMPROVING FATTY ACID BINDING AND TRANSPORT

(75) Inventors: Florence Pojer, Del Mar, CA (US);
Joseph P. Noel, San Diego, CA (US);
Elise Larsen, Alpine, CA (US);
Marianne Bowman, San Diego, CA (US); Stephane Richard, Del Mar, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 13/107,558

(22) Filed: May 13, 2011
(Under 37 CFR 1.47)

(65) Prior Publication Data
US 2011/0223667 A1 Sep. 15, 2011

Related U.S. Application Data

(62) Division of application No. 11/879,026, filed on Jul. 13, 2007, now abandoned.

(60) Provisional application No. 60/831,046, filed on Jul. 13, 2006.

(51) Int. Cl.
*C12N 15/82* (2006.01)

(52) U.S. Cl. ............................ 800/281; 435/468

(58) Field of Classification Search ........................ None
See application file for complete search history.

(56) References Cited

U.S. PATENT DOCUMENTS

| 7,034,203 B1 | 4/2006 | Bovy et al. |
| 7,202,398 B2 | 4/2007 | McGonigle |

FOREIGN PATENT DOCUMENTS

WO  WO 02/10210 A2 *  2/2002

OTHER PUBLICATIONS

International Search Report from PCT/US2007/015943, dated Oct. 1, 2008.
GenBank Accession No. gi20148595 (At3g63170) Apr. 14, 2002.
Broun et al. (1999) "Genetic engineering of plant lipids." *Annual Review of Nutrition*, 19: 197-216.
Brunger et al. (1998) "Crystallography & NMR System: A New Software Suite for Macromolecular Structure Determination." *Acta Crystalfographica Section D: Biological Crystallography*, 54(Pt. 5): 905-921.
Gensheimer et al. (2004) "Chalcone isomerase family and fold: No longer unique to plants " *Protein Science*, 13: 540-544.
Jez and Noel (2000) "Mechanism of Chalcone Synthesis." *Journal of Biological Chemistry*, 275(50): 39640-39646.
Jez and Noel (2001) "Rection mechanism of Chalcone Isomerase" *Journal of Biological Chemistry*, 277(2): 1361-1369.
Jez et al. (2000) "Structural mechanism of the evolutionarily unique plant enzyme chalcone isomerase," *Nature Structural Biology*, 7(9): 786-791.
Jez et al. (2001) "Structure and mechanism of chalcone synthase-like polyketide synthases." *Journal of Industrial Microbiology & Biotechnology*, 27: 393-398.
Kabsch (2001) "Functional specification." Chapter 25.2.9.1 *XDS* in *International Tables for Crystallography*, vol. F. *Crystallography of Biological Macromolecules*, Rossmann, M.G. and Arnold, E.. Editors. Dordrecht: Kluwer Academic Publishers.
Koo et al. (2004) "On the Export of Fatty Acids from the Chloroplast" *Journal of Biological Chemistry*, 279(16): 16101-16110.
Lorenc-Kukula et al. (2005) "Pleiotropic Effect of Phenolic Compounds Content Increases in Transgenit Flax Plant." *Journal of Agricultural and Food Chemistry*, 53: 3685-3692.
Terwilliger (2004) "Solve and Resolve: automated structure solution, density modification and model building." *Journal of Synchrotron Radiation*, 11: 49-52.
Thelen and Ohlrogge (2002) "Metabolic engineering of fatty acid biosynthesis in Plants." *Metabolic Engineering*, 4(1): 12-21.
Vagin and Isupov (2001) "Spherically averaged phased translation function and its application to the search for molecules and fragments in electron-density maps." *Acta Crystallographica Section D: Biological Crystallography*, 57: 1451-1456.

* cited by examiner

*Primary Examiner* — David H Kruse
(74) *Attorney, Agent, or Firm* — Kilpatrick Townsend & Stockton LLP

(57) ABSTRACT

CHI like fatty acid binding proteins and genes, recombinant cells and organisms, methods of metabolic pathway engineering to improve lipid production in cells, Crystal structures of CHI like fatty acid binding proteins, methods of engineering CHI like fatty acid binding proteins and systems thereof are provided.

18 Claims, 57 Drawing Sheets

Fig. 1

| | At287 | At396 | At279 | At205 | At223 | AtCHI |
|---|---|---|---|---|---|---|
| *Fatty acid binding protein* | yes | nd | yes | no | nd | no |
| *Chalcone isomerase activity* | no | nd | no | yes | nd | yes |

| *3D structure* | At279 | AtCHI |
|---|---|---|
| - CHI fold is conserved among the family.<br>- Catalytic active site residues are not conserved among the CHI family. | | |
| *Function* | Transporter of fatty acids<br>Lauric acid (C12:0) | chalcone isomerase<br>chalcone → (2S)-naringenin | nd: no data

PDB AT246
REMARK coordinates from restrained individual B-factor refinement
REMARK refinement resolution: 99 - 1.55 A
REMARK starting r= 0.1828 free_r= 0.2100
REMARK final   r= 0.1772 free_r= 0.2067
REMARK B rmsd for bonded mainchain atoms= 2.343 target= 1.5
REMARK B rmsd for bonded sidechain atoms= 4.411 target= 2.0
REMARK B rmsd for angle mainchain atoms= 3.164 target= 2.0
REMARK B rmsd for angle sidechain atoms= 6.287 target= 2.5
REMARK rweight= 0.0100 (with wa= 1.10429)
REMARK target= mlf  steps= 50
REMARK sg= P2(1) a= 47.245 b= 63.781 c= 80.106 alpha= 90 beta= 96.702 gamma= 90
REMARK parameter file 1 : CNS_TOPPAR:protein_rep.param
REMARK parameter file 2 : CNS_TOPPAR:water_rep.param
REMARK parameter file 3 : no3.param
REMARK molecular structure file: generate.mtf
REMARK input coordinates: minimize_325.pdb
REMARK reflection file= AtCHI_native_fip_04_25_02.cv
REMARK ncs= none
REMARK B-correction resolution: 6.0 - 1.55
REMARK initial B-factor correction applied to fobs :
REMARK  B11= -3.376 B22=  2.252 B33=  1.123
REMARK  B12=  0.000 B13= -0.187 B23=  0.000
REMARK B-factor correction applied to coordinate array B:  0.015
REMARK bulk solvent: density level= 0.363303 e/A^3, B-factor= 49.9929 A^2
REMARK reflections with |Fobs|/sigma_F < 0.0 rejected
REMARK reflections with |Fobs| > 10000 * rms(Fobs) rejected
REMARK theoretical total number of refl. in resol. range:68656 ( 100.0 % )
REMARK number of unobserved reflections (no entry or |F|=0):5987 (8.7% )
REMARK number of reflections rejected:         0 ( 0.0 % )
REMARK total number of reflections used:       62669 ( 91.3 % )
REMARK number of reflections in working set:   59480 ( 86.6 % )
REMARK number of reflections in test set:       3189 ( 4.6 % )
CRYST1  47.245  63.781  80.106  90.00  96.70  90.00 P 21
REMARK FILENAME="bindividual_01.pdb"
REMARK DATE:03-Jun-2002 16:08:41   created by user: noel
REMARK VERSION:1.1

```
ATOM      1  CB  ALA A  15      24.590 31.512 44.915 1.00 38.38      A
ATOM      2  C   ALA A  15      25.974 30.662 42.970 1.00 38.12      A
ATOM      3  O   ALA A  15      27.188 30.934 43.202 1.00 34.52      A
ATOM      4  N   ALA A  15      23.608 31.447 42.586 1.00 42.46      A
ATOM      5  CA  ALA A  15      24.868 31.648 43.386 1.00 41.56      A
ATOM      6  N   VAL A  16      25.580 29.526 42.379 1.00 33.92      A
ATOM      7  CA  VAL A  16      26.584 28.554 41.948 1.00 24.05      A
ATOM      8  CB  VAL A  16      26.135 27.089 42.116 1.00 31.08      A
ATOM      9  CG1 VAL A  16      27.341 26.161 41.795 1.00 30.92      A
ATOM     10  CG2 VAL A  16      25.700 26.848 43.567 1.00 25.25      A
ATOM     11  C   VAL A  16      26.991 28.827 40.508 1.00 17.83      A
ATOM     12  O   VAL A  16      26.593 28.167 39.552 1.00 21.68      A
ATOM     13  N   THR A  17      27.821 29.845 40.405 1.00 21.14      A
ATOM     14  CA  THR A  17      28.349 30.311 39.134 1.00 21.10      A
ATOM     15  CB  THR A  17      28.625 31.829 39.216 1.00 26.31      A
ATOM     16  OG1 THR A  17      29.516 32.085 40.320 1.00 32.12      A
ATOM     17  CG2 THR A  17      27.351 32.590 39.462 1.00 30.38      A
ATOM     18  C   THR A  17      29.684 29.639 38.881 1.00 19.24      A
ATOM     19  O   THR A  17      30.286 29.063 39.787 1.00 16.47      A
ATOM     20  N   LYS A  18      30.169 29.738 37.649 1.00 16.94      A
ATOM     21  CA  LYS A  18      31.469 29.223 37.318 1.00 13.42      A
ATOM     22  CB  LYS A  18      31.648 29.209 35.791 1.00 15.93      A
ATOM     23  CG  LYS A  18      31.784 30.632 35.177 1.00 15.92      A
ATOM     24  CD  LYS A  18      31.795 30.558 33.623 1.00 17.65      A
ATOM     25  CE  LYS A  18      30.409 30.204 33.109 1.00 24.98      A
ATOM     26  NZ  LYS A  18      30.405 30.370 31.633 1.00 33.93      A
ATOM     27  C   LYS A  18      32.420 30.273 37.952 1.00 13.31      A
ATOM     28  O   LYS A  18      31.994 31.395 38.316 1.00 14.58      A
ATOM     29  N   LEU A  19      33.699 29.923 38.116 1.00 14.62      A
ATOM     30  CA  LEU A  19      34.683 30.869 38.655 1.00 13.20      A
ATOM     31  CB  LEU A  19      35.103 30.478 40.086 1.00 13.96      A
ATOM     32  CG  LEU A  19      34.058 30.671 41.164 1.00 15.50      A
ATOM     33  CD1 LEU A  19      34.601 30.054 42.457 1.00 14.28      A
ATOM     34  CD2 LEU A  19      33.730 32.164 41.343 1.00 17.00      A
ATOM     35  C   LEU A  19      35.927 30.913 37.795 1.00 12.54      A
ATOM     36  O   LEU A  19      36.472 29.874 37.409 1.00 12.80      A
ATOM     37  N   HIS A  20      36.361 32.123 37.471 1.00 13.02      A
ATOM     38  CA  HIS A  20      37.570 32.319 36.668 1.00 13.53      A
ATOM     39  CB  HIS A  20      37.339 33.475 35.640 1.00 14.57      A
ATOM     40  CG  HIS A  20      36.180 33.255 34.708 1.00 12.37      A
ATOM     41  CD2 HIS A  20      35.007 33.940 34.565 1.00 18.10      A
ATOM     42  ND1 HIS A  20      36.147 32.251 33.776 1.00 16.13      A
ATOM     43  CE1 HIS A  20      35.010 32.310 33.089 1.00 16.07      A
ATOM     44  NE2 HIS A  20      34.306 33.334 33.556 1.00 15.28      A
ATOM     45  C   HIS A  20      38.690 32.681 37.651 1.00 12.96      A
ATOM     46  O   HIS A  20      38.601 33.679 38.380 1.00 17.06      A
ATOM     47  N   VAL A  21      39.707 31.824 37.716 1.00 11.52      A
ATOM     48  CA  VAL A  21      40.849 31.981 38.630 1.00 10.40      A
ATOM     49  CB  VAL A  21      40.789 30.889 39.745 1.00 15.00      A
ATOM     50  CG1 VAL A  21      41.990 31.005 40.644 1.00 18.82      A
ATOM     51  CG2 VAL A  21      39.520 31.058 40.523 1.00 20.84      A
ATOM     52  C   VAL A  21      42.105 31.843 37.818 1.00 15.55      A
ATOM     53  O   VAL A  21      42.338 30.843 37.160 1.00 15.40      A
ATOM     54  N   ASP A  22      42.913 32.906 37.830 1.00 15.80      A
ATOM     55  CA  ASP A  22      44.117 32.942 37.032 1.00 13.98      A
ATOM     56  CB  ASP A  22      45.126 31.887 37.497 1.00 18.73      A
ATOM     57  CG  ASP A  22      46.477 32.081 36.861 1.00 21.67      A
ATOM     58  OD1 ASP A  22      46.767 31.403 35.865 1.00 23.65      A
ATOM     59  OD2 ASP A  22      47.240 32.941 37.324 1.00 23.94      A
ATOM     60  C   ASP A  22      43.599 32.709 35.613 1.00 16.16      A
ATOM     61  O   ASP A  22      42.605 33.310 35.248 1.00 17.21      A
ATOM     62  N   SER A  23      44.201 31.821 34.841 1.00 18.35      A
ATOM     63  CA  SER A  23      43.700 31.632 33.477 1.00 20.57      A
ATOM     64  CB  SER A  23      44.873 31.400 32.547 1.00 20.68      A
ATOM     65  OG  SER A  23      45.515 30.179 32.873 1.00 20.63      A
ATOM     66  C   SER A  23      42.721 30.456 33.353 1.00 24.16      A
ATOM     67  O   SER A  23      42.202 30.157 32.244 1.00 21.63      A
ATOM     68  N   VAL A  24      42.435 29.819 34.488 1.00 16.41      A
ATOM     69  CA  VAL A  24      41.546 28.658 34.516 1.00 13.97      A
ATOM     70  CB  VAL A  24      42.025 27.661 35.610 1.00 14.01      A
ATOM     71  CG1 VAL A  24      41.044 26.469 35.746 1.00 18.05      A
ATOM     72  CG2 VAL A  24      43.439 27.166 35.278 1.00 18.67      A
ATOM     73  C   VAL A  24      40.087 29.003 34.772 1.00 12.64      A
ATOM     74  O   VAL A  24      39.760 29.977 35.460 1.00 16.73      A
ATOM     75  N   THR A  25      39.191 28.233 34.192 1.00 12.99      A
ATOM     76  CA  THR A  25      37.785 28.438 34.466 1.00 13.65      A
ATOM     77  CB  THR A  25      36.995 28.746 33.175 1.00 20.75      A
ATOM     78  OG1 THR A  25      37.379 30.060 32.716 1.00 18.45      A
ATOM     79  CG2 THR A  25      35.528 28.767 33.454 1.00 14.86      A
ATOM     80  C   THR A  25      37.249 27.154 35.088 1.00 14.78      A
ATOM     81  O   THR A  25      37.368 26.086 34.484 1.00 16.78      A
ATOM     82  N   PHE A  26      36.711 27.264 36.309 1.00 13.85      A
ATOM     83  CA  PHE A  26      36.103 26.119 36.991 1.00 11.93      A
ATOM     84  CB  PHE A  26      36.378 26.180 38.515 1.00  9.56      A
ATOM     85  CG  PHE A  26      37.838 25.937 38.877 1.00 10.41      A
ATOM     86  CD1 PHE A  26      38.709 27.010 39.059 1.00 13.94      A
ATOM     87  CD2 PHE A  26      38.344 24.633 38.968 1.00 10.57      A
ATOM     88  CE1 PHE A  26      40.067 26.791 39.325 1.00 14.23      A
ATOM     89  CE2 PHE A  26      39.729 24.419 39.237 1.00 12.53      A
ATOM     90  CZ  PHE A  26      40.570 25.481 39.410 1.00 12.77      A
ATOM     91  C   PHE A  26      34.600 26.166 36.717 1.00 10.43      A
ATOM     92  O   PHE A  26      33.939 27.152 37.010 1.00 13.25      A
ATOM     93  N   VAL A  27      34.061 25.061 36.208 1.00 11.79      A
ATOM     94  CA  VAL A  27      32.629 25.020 35.881 1.00 12.84      A
ATOM     95  CB  VAL A  27      32.355 23.989 34.794 1.00 17.84      A
ATOM     96  CG1 VAL A  27      33.243 24.333 33.597 1.00 20.92      A
ATOM     97  CG2 VAL A  27      32.615 22.551 35.294 1.00 15.71      A
ATOM     98  C   VAL A  27      31.823 24.792 37.139 1.00 11.84      A
ATOM     99  O   VAL A  27      32.339 24.281 38.145 1.00 13.31      A
ATOM    100  N   PRO A  28      30.559 25.183 37.129 1.00 14.89      A
ATOM    101  CD  PRO A  28      29.839 25.820 36.008 1.00 16.16      A
ATOM    102  CA  PRO A  28      29.720 25.041 38.312 1.00 12.68      A
ATOM    103  CB  PRO A  28      28.428 25.810 37.965 1.00 17.11      A
ATOM    104  CG  PRO A  28      28.415 25.883 36.510 1.00 22.16      A
ATOM    105  C   PRO A  28      29.470 23.676 38.892 1.00 13.74      A
ATOM    106  O   PRO A  28      29.228 23.574 40.092 1.00 13.29      A
ATOM    107  N   SER A  29      29.520 22.639 38.075 1.00 14.46      A
ATOM    108  CA  SER A  29      29.310 21.285 38.578 1.00 17.60      A
ATOM    109  CB  SER A  29      27.825 20.885 38.411 1.00 21.98      A
ATOM    110  OG  SER A  29      27.614 19.547 38.848 1.00 27.99      A
ATOM    111  C   SER A  29      30.178 20.283 37.838 1.00 19.12      A
ATOM    112  O   SER A  29      30.451 20.456 36.640 1.00 18.49      A
ATOM    113  N   VAL A  30      30.634 19.245 38.547 1.00 14.95      A
ATOM    114  CA  VAL A  30      31.413 18.181 37.942 1.00 16.42      A
ATOM    115  CB  VAL A  30      32.921 18.230 38.261 1.00 15.89      A
ATOM    116  CG1 VAL A  30      33.515 19.509 37.755 1.00 17.81      A
ATOM    117  CG2 VAL A  30      33.150 18.112 39.771 1.00 17.91      A
ATOM    118  C   VAL A  30      30.867 16.876 38.460 1.00 16.51      A
ATOM    119  O   VAL A  30      30.225 16.834 39.496 1.00 15.83      A
ATOM    120  N   LYS A  31      31.106 15.826 37.695 1.00 14.85      A
```

Fig. 4

| | | | | | | | | | | |
|---|---|---|---|---|---|---|---|---|---|---|
| ATOM | 121 | CA  | LYS A 31 | 30.668 14.491 38.054 1.00 15.65 | A | ATOM | 201 | N   | GLY A 42 | 32.295 24.799 45.222 1.00 10.54 | A |
| ATOM | 122 | CB  | LYS A 31 | 30.251 13.735 36.763 1.00 18.65 | A | ATOM | 202 | CA  | GLY A 42 | 32.274 25.544 46.484 1.00 9.62  | A |
| ATOM | 123 | CG  | LYS A 31 | 29.644 12.377 36.959 1.00 24.58 | A | ATOM | 203 | C   | GLY A 42 | 33.155 26.785 46.456 1.00 10.00 | A |
| ATOM | 124 | CD  | LYS A 31 | 29.040 11.986 35.586 1.00 27.57 | A | ATOM | 204 | O   | GLY A 42 | 32.793 27.801 47.007 1.00 11.93 | A |
| ATOM | 125 | CE  | LYS A 31 | 28.385 10.623 35.537 1.00 37.31 | A | ATOM | 205 | N   | GLY A 43 | 34.328 26.696 45.842 1.00 10.81 | A |
| ATOM | 126 | NZ  | LYS A 31 | 29.292  9.526 35.010 1.00 51.90 | A | ATOM | 206 | CA  | GLY A 43 | 35.174 27.898 45.768 1.00 11.39 | A |
| ATOM | 127 | C   | LYS A 31 | 31.857 13.817 38.744 1.00 17.56 | A | ATOM | 207 | C   | GLY A 43 | 36.426 27.528 45.005 1.00 8.68  | A |
| ATOM | 128 | O   | LYS A 31 | 32.957 13.733 38.176 1.00 16.65 | A | ATOM | 208 | O   | GLY A 43 | 36.696 26.339 44.737 1.00 10.63 | A |
| ATOM | 129 | N   | SER A 32 | 31.644 13.378 39.989 1.00 15.07 | A | ATOM | 209 | N   | ALA A 44 | 37.231 28.543 44.693 1.00 9.70  | A |
| ATOM | 130 | CA  | SER A 32 | 32.718 12.721 40.719 1.00 14.59 | A | ATOM | 210 | CA  | ALA A 44 | 38.460 28.292 43.946 1.00 10.06 | A |
| ATOM | 131 | CB  | SER A 32 | 32.210 12.294 42.099 1.00 13.97 | A | ATOM | 211 | CB  | ALA A 44 | 38.162 28.220 42.428 1.00 11.20 | A |
| ATOM | 132 | OG  | SER A 32 | 33.184 11.459 42.689 1.00 17.12 | A | ATOM | 212 | C   | ALA A 44 | 39.452 29.390 44.217 1.00 9.50  | A |
| ATOM | 133 | C   | SER A 32 | 33.258 11.475 40.019 1.00 15.81 | A | ATOM | 213 | O   | ALA A 44 | 39.073 30.509 44.548 1.00 12.26 | A |
| ATOM | 134 | O   | SER A 32 | 32.476 10.613 39.634 1.00 15.26 | A | ATOM | 214 | N   | GLY A 45 | 40.737 29.073 44.049 1.00 10.16 | A |
| ATOM | 135 | N   | PRO A 33 | 34.596 11.350 39.858 1.00 14.58 | A | ATOM | 215 | CA  | GLY A 45 | 41.753 30.085 44.306 1.00 11.70 | A |
| ATOM | 136 | CD  | PRO A 33 | 35.631 12.344 40.188 1.00 19.09 | A | ATOM | 216 | C   | GLY A 45 | 43.111 29.579 43.864 1.00 11.30 | A |
| ATOM | 137 | CA  | PRO A 33 | 35.170 10.150 39.200 1.00 17.98 | A | ATOM | 217 | O   | GLY A 45 | 43.188 28.568 43.172 1.00 17.35 | A |
| ATOM | 138 | CB  | PRO A 33 | 36.661 10.477 39.023 1.00 19.71 | A | ATOM | 218 | N   | VAL A 46 | 44.186 30.283 44.202 1.00 13.13 | A |
| ATOM | 139 | CG  | PRO A 33 | 36.768 11.976 39.262 1.00 22.45 | A | ATOM | 219 | CA  | VAL A 46 | 45.509 29.831 43.786 1.00 15.19 | A |
| ATOM | 140 | C   | PRO A 33 | 34.997  8.929 40.105 1.00 17.75 | A | ATOM | 220 | CB  | VAL A 46 | 46.256 30.921 42.952 1.00 17.94 | A |
| ATOM | 141 | O   | PRO A 33 | 35.109  7.800 39.657 1.00 18.68 | A | ATOM | 221 | CG1 | VAL A 46 | 45.392 31.365 41.787 1.00 23.69 | A |
| ATOM | 142 | N   | ALA A 34 | 34.738  9.170 41.392 1.00 16.39 | A | ATOM | 222 | CG2 | VAL A 46 | 46.610 32.117 43.815 1.00 17.89 | A |
| ATOM | 143 | CA  | ALA A 34 | 34.564  8.077 42.346 1.00 17.03 | A | ATOM | 223 | C   | VAL A 46 | 46.416 29.479 44.947 1.00 14.53 | A |
| ATOM | 144 | CB  | ALA A 34 | 35.070  8.537 43.741 1.00 14.97 | A | ATOM | 224 | O   | VAL A 46 | 46.154 29.844 46.096 1.00 14.44 | A |
| ATOM | 145 | C   | ALA A 34 | 33.123  7.582 42.464 1.00 19.05 | A | ATOM | 225 | N   | ARG A 47 | 47.472 28.735 44.628 1.00 12.92 | A |
| ATOM | 146 | O   | ALA A 34 | 32.841  6.358 42.424 1.00 21.15 | A | ATOM | 226 | CA  | ARG A 47 | 48.493 28.392 45.604 1.00 16.80 | A |
| ATOM | 147 | N   | SER A 35 | 32.202  8.516 42.609 1.00 16.85 | A | ATOM | 227 | CB  | ARG A 47 | 48.712 26.877 45.676 1.00 21.02 | A |
| ATOM | 148 | CA  | SER A 35 | 30.811  8.164 42.834 1.00 16.57 | A | ATOM | 228 | CG  | ARG A 47 | 49.428 26.469 46.934 1.00 26.54 | A |
| ATOM | 149 | CB  | SER A 35 | 30.240  8.994 43.974 1.00 15.14 | A | ATOM | 229 | CD  | ARG A 47 | 50.810 25.914 46.727 1.00 26.16 | A |
| ATOM | 150 | OG  | SER A 35 | 30.137 10.352 43.567 1.00 16.28 | A | ATOM | 230 | NE  | ARG A 47 | 50.795 24.692 45.944 1.00 29.22 | A |
| ATOM | 151 | C   | SER A 35 | 29.915  8.416 41.658 1.00 17.10 | A | ATOM | 231 | CZ  | ARG A 47 | 51.879 23.961 45.676 1.00 32.64 | A |
| ATOM | 152 | O   | SER A 35 | 28.751  7.942 41.662 1.00 18.28 | A | ATOM | 232 | NH1 | ARG A 47 | 53.065 24.330 46.148 1.00 29.16 | A |
| ATOM | 153 | N   | SER A 36 | 30.437  9.173 40.694 1.00 15.52 | A | ATOM | 233 | NH2 | ARG A 47 | 51.776 22.872 44.914 1.00 26.46 | A |
| ATOM | 154 | CA  | SER A 36 | 29.691  9.613 39.511 1.00 13.83 | A | ATOM | 234 | C   | ARG A 47 | 49.741 29.067 45.045 1.00 16.74 | A |
| ATOM | 155 | CB  | SER A 36 | 29.160  8.417 38.674 1.00 18.35 | A | ATOM | 235 | O   | ARG A 47 | 50.200 28.738 43.933 1.00 17.49 | A |
| ATOM | 156 | OG  | SER A 36 | 30.228  7.622 38.182 1.00 21.67 | A | ATOM | 236 | N   | GLY A 48 | 50.268 30.031 45.787 1.00 19.01 | A |
| ATOM | 157 | C   | SER A 36 | 28.528 10.534 39.926 1.00 16.42 | A | ATOM | 237 | CA  | GLY A 48 | 51.436 30.731 45.300 1.00 23.71 | A |
| ATOM | 158 | O   | SER A 36 | 27.651 10.842 39.115 1.00 20.97 | A | ATOM | 238 | C   | GLY A 48 | 52.323 31.129 46.455 1.00 24.29 | A |
| ATOM | 159 | N   | ASN A 37 | 28.508 10.995 41.175 1.00 16.91 | A | ATOM | 239 | O   | GLY A 48 | 51.908 31.058 47.620 1.00 23.37 | A |
| ATOM | 160 | CA  | ASN A 37 | 27.446 11.933 41.591 1.00 14.62 | A | ATOM | 240 | N   | LEU A 49 | 53.541 31.545 46.129 1.00 29.47 | A |
| ATOM | 161 | CB  | ASN A 37 | 27.213 11.868 43.099 1.00 17.08 | A | ATOM | 241 | CA  | LEU A 49 | 54.471 31.961 47.168 1.00 30.97 | A |
| ATOM | 162 | CG  | ASN A 37 | 26.615 10.548 43.546 1.00 28.82 | A | ATOM | 242 | CB  | LEU A 49 | 55.293 30.763 47.641 1.00 37.49 | A |
| ATOM | 163 | OD1 | ASN A 37 | 26.839 10.088 44.667 1.00 27.08 | A | ATOM | 243 | CG  | LEU A 49 | 55.923 30.858 49.043 1.00 49.04 | A |
| ATOM | 164 | ND2 | ASN A 37 | 25.840  9.935 42.665 1.00 25.59 | A | ATOM | 244 | CD1 | LEU A 49 | 54.842 31.165 50.110 1.00 48.26 | A |
| ATOM | 165 | C   | ASN A 37 | 27.864 13.385 41.260 1.00 16.64 | A | ATOM | 245 | CD2 | LEU A 49 | 56.633 29.534 49.359 1.00 45.45 | A |
| ATOM | 166 | O   | ASN A 37 | 29.046 13.695 41.160 1.00 16.03 | A | ATOM | 246 | C   | LEU A 49 | 55.399 33.052 46.649 1.00 32.26 | A |
| ATOM | 167 | N   | PRO A 38 | 26.887 14.289 41.049 1.00 18.85 | A | ATOM | 247 | O   | LEU A 49 | 55.702 33.102 45.451 1.00 24.54 | A |
| ATOM | 168 | CD  | PRO A 38 | 25.426 14.667 41.004 1.00 19.93 | A | ATOM | 248 | N   | ASP A 50 | 55.830 33.930 47.556 1.00 34.71 | A |
| ATOM | 169 | CA  | PRO A 38 | 27.205 15.687 40.750 1.00 19.24 | A | ATOM | 249 | CA  | ASP A 50 | 56.749 35.005 47.205 1.00 35.53 | A |
| ATOM | 170 | CB  | PRO A 38 | 25.876 16.247 40.240 1.00 18.43 | A | ATOM | 250 | CB  | ASP A 50 | 56.809 36.072 48.321 1.00 43.74 | A |
| ATOM | 171 | CG  | PRO A 38 | 24.882 15.476 41.071 1.00 21.13 | A | ATOM | 251 | CG  | ASP A 50 | 57.452 37.403 47.857 1.00 49.11 | A |
| ATOM | 172 | C   | PRO A 38 | 27.655 16.416 42.019 1.00 21.11 | A | ATOM | 252 | OD1 | ASP A 50 | 58.585 37.393 47.332 1.00 56.28 | A |
| ATOM | 173 | O   | PRO A 38 | 27.153 16.186 43.097 1.00 17.94 | A | ATOM | 253 | OD2 | ASP A 50 | 56.824 38.475 48.030 1.00 54.09 | A |
| ATOM | 174 | N   | LEU A 39 | 28.646 17.278 41.870 1.00 16.76 | A | ATOM | 254 | C   | ASP A 50 | 58.106 34.334 47.076 1.00 36.87 | A |
| ATOM | 175 | CA  | LEU A 39 | 29.160 18.068 42.990 1.00 11.72 | A | ATOM | 255 | O   | ASP A 50 | 58.622 33.745 48.032 1.00 38.78 | A |
| ATOM | 176 | CB  | LEU A 39 | 30.553 17.594 43.372 1.00 14.08 | A | ATOM | 256 | N   | ILE A 51 | 58.659 34.488 45.878 1.00 30.48 | A |
| ATOM | 177 | CG  | LEU A 39 | 30.652 16.078 43.684 1.00 18.82 | A | ATOM | 257 | CA  | ILE A 51 | 59.968 33.848 45.609 1.00 33.42 | A |
| ATOM | 178 | CD1 | LEU A 39 | 32.129 15.697 43.884 1.00 18.22 | A | ATOM | 258 | CB  | ILE A 51 | 59.926 32.798 44.509 1.00 30.69 | A |
| ATOM | 179 | CD2 | LEU A 39 | 29.881 15.764 44.921 1.00 17.03 | A | ATOM | 259 | CG2 | ILE A 51 | 61.331 32.470 44.049 1.00 33.05 | A |
| ATOM | 180 | C   | LEU A 39 | 29.232 19.505 42.511 1.00 12.60 | A | ATOM | 260 | CG1 | ILE A 51 | 59.207 31.552 45.014 1.00 34.00 | A |
| ATOM | 181 | O   | LEU A 39 | 29.618 19.764 41.360 1.00 15.21 | A | ATOM | 261 | CD1 | ILE A 51 | 59.118 30.471 43.988 1.00 40.54 | A |
| ATOM | 182 | N   | PHE A 40 | 28.890 20.431 43.393 1.00 10.43 | A | ATOM | 262 | C   | ILE A 51 | 60.797 35.043 45.132 1.00 37.74 | A |
| ATOM | 183 | CA  | PHE A 40 | 28.874 21.850 43.032 1.00 11.64 | A | ATOM | 263 | O   | ILE A 51 | 60.551 35.600 44.051 1.00 32.67 | A |
| ATOM | 184 | CB  | PHE A 40 | 27.666 22.587 43.667 1.00 11.93 | A | ATOM | 264 | N   | GLN A 52 | 61.760 35.439 45.956 1.00 40.17 | A |
| ATOM | 185 | CG  | PHE A 40 | 27.806 22.893 45.159 1.00 10.89 | A | ATOM | 265 | CA  | GLN A 52 | 62.633 36.571 45.653 1.00 43.16 | A |
| ATOM | 186 | CD1 | PHE A 40 | 27.355 21.986 46.127 1.00 13.61 | A | ATOM | 266 | CB  | GLN A 52 | 63.707 36.168 44.630 1.00 45.76 | A |
| ATOM | 187 | CD2 | PHE A 40 | 28.360 24.104 45.572 1.00 15.54 | A | ATOM | 267 | CG  | GLN A 52 | 63.188 35.589 43.330 1.00 50.75 | A |
| ATOM | 188 | CE1 | PHE A 40 | 27.448 22.293 47.504 1.00 11.99 | A | ATOM | 268 | CD  | GLN A 52 | 64.308 35.221 42.376 1.00 57.48 | A |
| ATOM | 189 | CE2 | PHE A 40 | 28.461 24.427 46.956 1.00 15.80 | A | ATOM | 269 | OE1 | GLN A 52 | 65.323 34.641 42.784 1.00 61.37 | A |
| ATOM | 190 | CZ  | PHE A 40 | 28.000 23.525 47.910 1.00 12.68 | A | ATOM | 270 | NE2 | GLN A 52 | 64.130 35.546 41.092 1.00 60.83 | A |
| ATOM | 191 | C   | PHE A 40 | 30.164 22.574 43.409 1.00 11.64 | A | ATOM | 271 | C   | GLN A 52 | 61.897 37.821 45.167 1.00 39.53 | A |
| ATOM | 192 | O   | PHE A 40 | 30.867 22.182 44.344 1.00 12.88 | A | ATOM | 272 | O   | GLN A 52 | 62.224 38.385 44.118 1.00 36.46 | A |
| ATOM | 193 | N   | LEU A 41 | 30.467 23.617 42.646 1.00 11.62 | A | ATOM | 273 | N   | GLY A 53 | 60.911 38.239 45.952 1.00 34.09 | A |
| ATOM | 194 | CA  | LEU A 41 | 31.669 24.412 42.896 1.00 12.02 | A | ATOM | 274 | CA  | GLY A 53 | 60.152 39.434 45.640 1.00 33.56 | A |
| ATOM | 195 | CB  | LEU A 41 | 31.943 25.342 41.675 1.00 8.86  | A | ATOM | 275 | C   | GLY A 53 | 59.029 39.270 44.640 1.00 29.90 | A |
| ATOM | 196 | CG  | LEU A 41 | 33.181 26.248 41.806 1.00 9.59  | A | ATOM | 276 | O   | GLY A 53 | 58.239 40.198 44.458 1.00 34.71 | A |
| ATOM | 197 | CD1 | LEU A 41 | 34.472 25.418 41.963 1.00 13.26 | A | ATOM | 277 | N   | LYS A 54 | 58.941 38.112 43.995 1.00 24.93 | A |
| ATOM | 198 | CD2 | LEU A 41 | 33.288 27.076 40.500 1.00 12.61 | A | ATOM | 278 | CA  | LYS A 54 | 57.896 37.894 42.998 1.00 26.29 | A |
| ATOM | 199 | C   | LEU A 41 | 31.583 25.240 44.179 1.00 10.86 | A | ATOM | 279 | CB  | LYS A 54 | 58.538 37.473 41.686 1.00 31.58 | A |
| ATOM | 200 | O   | LEU A 41 | 30.891 26.254 44.226 1.00 11.07 | A | ATOM | 280 | CG  | LYS A 54 | 57.546 37.204 40.566 1.00 48.92 | A |

Fig. 4 cont.

| | | | | | | | | | | | |
|---|---|---|---|---|---|---|---|---|---|---|---|
| ATOM | 281 | CD LYS A 54 | 58.266 36.793 39.270 1.00 49.86 | A | | ATOM | 361 | CE1 TYR A 64 | 35.429 21.920 40.808 1.00 13.35 | A |
| ATOM | 282 | CE LYS A 54 | 57.270 36.194 38.272 1.00 42.62 | A | | ATOM | 362 | CD2 TYR A 64 | 32.779 21.351 41.492 1.00 10.90 | A |
| ATOM | 283 | NZ LYS A 54 | 57.947 35.349 37.236 1.00 57.53 | A | | ATOM | 363 | CE2 TYR A 64 | 33.065 22.083 40.342 1.00 9.68 | A |
| ATOM | 284 | C LYS A 54 | 56.892 36.839 43.466 1.00 27.34 | A | | ATOM | 364 | CZ TYR A 64 | 34.374 22.356 40.017 1.00 12.80 | A |
| ATOM | 285 | O LYS A 54 | 57.284 35.806 44.011 1.00 23.68 | A | | ATOM | 365 | OH TYR A 64 | 34.619 23.109 38.889 1.00 12.12 | A |
| ATOM | 286 | N PHE A 55 | 55.597 37.108 43.271 1.00 21.08 | A | | ATOM | 366 | C TYR A 64 | 33.031 20.187 46.076 1.00 12.94 | A |
| ATOM | 287 | CA PHE A 55 | 54.592 36.153 43.716 1.00 22.12 | A | | ATOM | 367 | O TYR A 64 | 33.753 19.409 46.708 1.00 11.91 | A |
| ATOM | 288 | CB PHE A 55 | 53.262 36.832 44.040 1.00 24.44 | A | | ATOM | 368 | N LEU A 65 | 31.737 20.385 46.337 1.00 11.76 | A |
| ATOM | 289 | CG PHE A 55 | 52.267 35.910 44.666 1.00 26.18 | A | | ATOM | 369 | CA LEU A 65 | 31.067 19.750 47.463 1.00 10.03 | A |
| ATOM | 290 | CD1 PHE A 55 | 52.381 35.543 46.006 1.00 30.15 | A | | ATOM | 370 | CB LEU A 65 | 30.778 20.803 48.531 1.00 10.44 | A |
| ATOM | 291 | CD2 PHE A 55 | 51.221 35.379 43.902 1.00 30.72 | A | | ATOM | 371 | CG LEU A 65 | 32.039 21.484 49.060 1.00 13.50 | A |
| ATOM | 292 | CE1 PHE A 55 | 51.466 34.667 46.588 1.00 29.98 | A | | ATOM | 372 | CD1 LEU A 65 | 31.593 22.613 49.993 1.00 19.38 | A |
| ATOM | 293 | CE2 PHE A 55 | 50.301 34.504 44.467 1.00 30.67 | A | | ATOM | 373 | CD2 LEU A 65 | 32.925 20.475 49.856 1.00 16.16 | A |
| ATOM | 294 | CZ PHE A 55 | 50.423 34.144 45.814 1.00 29.32 | A | | ATOM | 374 | C LEU A 65 | 29.754 19.093 47.049 1.00 15.11 | A |
| ATOM | 295 | C PHE A 55 | 54.417 35.171 42.599 1.00 21.77 | A | | ATOM | 375 | O LEU A 65 | 29.169 19.419 46.032 1.00 13.09 | A |
| ATOM | 296 | O PHE A 55 | 53.899 35.502 41.543 1.00 22.85 | A | | ATOM | 376 | N GLU A 66 | 29.289 18.171 47.889 1.00 18.64 | A |
| ATOM | 297 | N VAL A 56 | 54.858 33.948 42.848 1.00 20.59 | A | | ATOM | 377 | CA GLU A 66 | 28.014 17.485 47.642 1.00 18.97 | A |
| ATOM | 298 | CA VAL A 56 | 54.823 32.892 41.851 1.00 22.71 | A | | ATOM | 378 | CB GLU A 66 | 27.925 16.199 48.505 1.00 20.10 | A |
| ATOM | 299 | CB VAL A 56 | 56.128 32.121 41.886 1.00 28.95 | A | | ATOM | 379 | CG GLU A 66 | 27.137 15.109 47.802 1.00 27.79 | A |
| ATOM | 300 | CG1 VAL A 56 | 56.118 31.007 40.836 1.00 26.93 | A | | ATOM | 380 | CD GLU A 66 | 27.011 13.816 48.603 1.00 34.99 | A |
| ATOM | 301 | CG2 VAL A 56 | 57.282 33.089 41.676 1.00 25.19 | A | | ATOM | 381 | OE1 GLU A 66 | 26.083 13.022 48.278 1.00 43.92 | A |
| ATOM | 302 | C VAL A 56 | 53.677 31.920 42.095 1.00 18.68 | A | | ATOM | 382 | OE2 GLU A 66 | 27.819 13.573 49.521 1.00 25.83 | A |
| ATOM | 303 | O VAL A 56 | 53.591 31.325 43.164 1.00 19.05 | A | | ATOM | 383 | C GLU A 66 | 26.903 18.470 48.006 1.00 17.22 | A |
| ATOM | 304 | N ILE A 57 | 52.795 31.792 41.110 1.00 18.55 | A | | ATOM | 384 | O GLU A 66 | 27.002 19.265 48.946 1.00 17.04 | A |
| ATOM | 305 | CA ILE A 57 | 51.657 30.876 41.238 1.00 19.19 | A | | ATOM | 385 | N GLY A 67 | 25.801 18.420 47.257 1.00 18.16 | A |
| ATOM | 306 | CB ILE A 57 | 50.473 31.328 40.349 1.00 19.49 | A | | ATOM | 386 | CA GLY A 67 | 24.747 19.369 47.550 1.00 16.78 | A |
| ATOM | 307 | CG2 ILE A 57 | 49.386 30.223 40.346 1.00 16.40 | A | | ATOM | 387 | C GLY A 67 | 24.184 19.250 48.960 1.00 16.09 | A |
| ATOM | 308 | CG1 ILE A 57 | 49.929 32.682 40.842 1.00 23.66 | A | | ATOM | 388 | O GLY A 67 | 23.784 20.249 49.552 1.00 18.66 | A |
| ATOM | 309 | CD1 ILE A 57 | 48.785 33.211 40.052 1.00 26.98 | A | | ATOM | 389 | N ASN A 68 | 24.150 18.035 49.490 1.00 19.60 | A |
| ATOM | 310 | C ILE A 57 | 52.068 29.473 40.829 1.00 15.59 | A | | ATOM | 390 | CA ASN A 68 | 23.586 17.820 50.828 1.00 20.37 | A |
| ATOM | 311 | O ILE A 57 | 52.532 29.292 39.712 1.00 19.13 | A | | ATOM | 391 | CB ASN A 68 | 23.381 16.308 51.099 1.00 25.24 | A |
| ATOM | 312 | N PHE A 58 | 51.894 28.500 41.727 1.00 18.70 | A | | ATOM | 392 | CG ASN A 68 | 24.678 15.541 51.207 1.00 35.50 | A |
| ATOM | 313 | CA PHE A 58 | 52.239 27.121 41.416 1.00 17.49 | A | | ATOM | 393 | OD1 ASN A 68 | 24.954 14.886 52.232 1.00 47.31 | A |
| ATOM | 314 | CB PHE A 58 | 52.754 26.392 42.668 1.00 19.03 | A | | ATOM | 394 | ND2 ASN A 68 | 25.493 15.601 50.156 1.00 38.04 | A |
| ATOM | 315 | CG PHE A 58 | 54.161 26.758 43.070 1.00 25.00 | A | | ATOM | 395 | C ASN A 68 | 24.422 18.466 51.919 1.00 19.07 | A |
| ATOM | 316 | CD1 PHE A 58 | 54.455 28.010 43.597 1.00 31.01 | A | | ATOM | 396 | O ASN A 68 | 23.978 18.574 53.082 1.00 22.31 | A |
| ATOM | 317 | CD2 PHE A 58 | 55.181 25.824 42.975 1.00 37.45 | A | | ATOM | 397 | N ALA A 69 | 25.619 18.909 51.554 1.00 17.24 | A |
| ATOM | 318 | CE1 PHE A 58 | 55.754 28.325 44.030 1.00 33.14 | A | | ATOM | 398 | CA ALA A 69 | 26.489 19.578 52.517 1.00 15.89 | A |
| ATOM | 319 | CE2 PHE A 58 | 56.485 26.140 43.408 1.00 35.01 | A | | ATOM | 399 | CB ALA A 69 | 27.868 19.858 51.898 1.00 18.70 | A |
| ATOM | 320 | CZ PHE A 58 | 56.759 27.392 43.932 1.00 34.76 | A | | ATOM | 400 | C ALA A 69 | 25.864 20.900 52.934 1.00 16.31 | A |
| ATOM | 321 | C PHE A 58 | 51.046 26.331 40.865 1.00 16.94 | A | | ATOM | 401 | O ALA A 69 | 26.068 21.351 54.071 1.00 18.37 | A |
| ATOM | 322 | O PHE A 58 | 51.185 25.617 39.860 1.00 17.58 | A | | ATOM | 402 | N VAL A 70 | 25.127 21.555 52.022 1.00 16.07 | A |
| ATOM | 323 | N THR A 59 | 49.890 26.439 41.539 1.00 15.85 | A | | ATOM | 403 | CA VAL A 70 | 24.556 22.863 52.338 1.00 15.33 | A |
| ATOM | 324 | CA THR A 59 | 48.697 25.715 41.104 1.00 12.36 | A | | ATOM | 404 | CB VAL A 70 | 23.992 23.564 51.071 1.00 16.96 | A |
| ATOM | 325 | CB THR A 59 | 48.481 24.397 41.932 1.00 14.35 | A | | ATOM | 405 | CG1 VAL A 70 | 23.316 24.894 51.460 1.00 16.88 | A |
| ATOM | 326 | OG1 THR A 59 | 48.293 24.723 43.309 1.00 17.44 | A | | ATOM | 406 | CG2 VAL A 70 | 25.146 23.830 50.118 1.00 17.44 | A |
| ATOM | 327 | CG2 THR A 59 | 49.681 23.488 41.804 1.00 16.58 | A | | ATOM | 407 | C VAL A 70 | 23.526 22.801 53.469 1.00 13.17 | A |
| ATOM | 328 | C THR A 59 | 47.466 26.569 41.281 1.00 15.78 | A | | ATOM | 408 | O VAL A 70 | 23.657 23.542 54.455 1.00 14.55 | A |
| ATOM | 329 | O THR A 59 | 47.497 27.565 42.010 1.00 14.28 | A | | ATOM | 409 | N PRO A 71 | 22.501 21.938 53.352 1.00 14.55 | A |
| ATOM | 330 | N VAL A 60 | 46.397 26.142 40.589 1.00 11.08 | A | | ATOM | 410 | CD PRO A 71 | 21.917 21.297 52.150 1.00 14.73 | A |
| ATOM | 331 | CA VAL A 60 | 45.085 26.796 40.584 1.00 12.97 | A | | ATOM | 411 | CA PRO A 71 | 21.551 21.895 54.467 1.00 19.41 | A |
| ATOM | 332 | CB VAL A 60 | 44.790 27.334 39.185 1.00 17.15 | A | | ATOM | 412 | CB PRO A 71 | 20.431 20.959 53.966 1.00 21.46 | A |
| ATOM | 333 | CG1 VAL A 60 | 43.496 28.088 39.203 1.00 20.11 | A | | ATOM | 413 | CG PRO A 71 | 20.965 20.300 52.753 1.00 20.41 | A |
| ATOM | 334 | CG2 VAL A 60 | 45.964 28.308 38.759 1.00 18.79 | A | | ATOM | 414 | C PRO A 71 | 22.216 21.366 55.734 1.00 18.13 | A |
| ATOM | 335 | C VAL A 60 | 44.122 25.690 41.045 1.00 14.85 | A | | ATOM | 415 | O PRO A 71 | 21.844 21.738 56.827 1.00 18.26 | A |
| ATOM | 336 | O VAL A 60 | 44.048 24.607 40.438 1.00 15.39 | A | | ATOM | 416 | N SER A 72 | 23.221 20.519 55.584 1.00 19.01 | A |
| ATOM | 337 | N ILE A 61 | 43.391 25.971 42.114 1.00 11.64 | A | | ATOM | 417 | CA SER A 72 | 23.911 19.994 56.758 1.00 17.45 | A |
| ATOM | 338 | CA ILE A 61 | 42.608 24.942 42.780 1.00 11.37 | A | | ATOM | 418 | CB SER A 72 | 24.924 18.904 56.351 1.00 19.50 | A |
| ATOM | 339 | CB ILE A 61 | 43.142 24.813 44.247 1.00 12.76 | A | | ATOM | 419 | OG SER A 72 | 25.662 18.469 57.491 1.00 19.88 | A |
| ATOM | 340 | CG2 ILE A 61 | 42.404 23.691 45.007 1.00 13.79 | A | | ATOM | 420 | C SER A 72 | 24.641 21.112 57.500 1.00 16.73 | A |
| ATOM | 341 | CG1 ILE A 61 | 44.631 24.487 44.232 1.00 13.25 | A | | ATOM | 421 | O SER A 72 | 24.514 21.267 58.727 1.00 17.54 | A |
| ATOM | 342 | CD1 ILE A 61 | 45.360 24.708 45.606 1.00 17.27 | A | | ATOM | 422 | N LEU A 73 | 25.419 21.906 56.764 1.00 14.70 | A |
| ATOM | 343 | C ILE A 61 | 41.128 25.198 42.880 1.00 12.35 | A | | ATOM | 423 | CA LEU A 73 | 26.141 22.994 57.405 1.00 12.94 | A |
| ATOM | 344 | O ILE A 61 | 40.720 26.321 43.196 1.00 12.69 | A | | ATOM | 424 | CB LEU A 73 | 27.156 23.634 56.417 1.00 14.24 | A |
| ATOM | 345 | N GLY A 62 | 40.337 24.155 42.614 1.00 12.20 | A | | ATOM | 425 | CG LEU A 73 | 28.321 22.701 56.025 1.00 13.87 | A |
| ATOM | 346 | CA GLY A 62 | 38.902 24.285 42.754 1.00 9.55 | A | | ATOM | 426 | CD1 LEU A 73 | 28.978 23.179 54.724 1.00 15.38 | A |
| ATOM | 347 | C GLY A 62 | 38.397 23.218 43.725 1.00 10.46 | A | | ATOM | 427 | CD2 LEU A 73 | 29.377 22.662 57.109 1.00 14.93 | A |
| ATOM | 348 | O GLY A 62 | 38.847 22.075 43.677 1.00 12.62 | A | | ATOM | 428 | C LEU A 73 | 25.202 24.081 57.907 1.00 15.69 | A |
| ATOM | 349 | N VAL A 63 | 37.503 23.605 44.620 1.00 9.11 | A | | ATOM | 429 | O LEU A 73 | 25.513 24.770 58.862 1.00 14.48 | A |
| ATOM | 350 | CA VAL A 63 | 36.935 22.670 45.603 1.00 10.55 | A | | ATOM | 430 | N SER A 74 | 24.053 24.241 57.262 1.00 15.73 | A |
| ATOM | 351 | CB VAL A 63 | 37.193 23.214 47.043 1.00 11.15 | A | | ATOM | 431 | CA SER A 74 | 23.127 25.303 57.640 1.00 15.84 | A |
| ATOM | 352 | CG1 VAL A 63 | 36.493 22.304 48.066 1.00 11.35 | A | | ATOM | 432 | CB SER A 74 | 21.951 25.368 56.657 1.00 22.66 | A |
| ATOM | 353 | CG2 VAL A 63 | 38.657 23.168 47.337 1.00 11.77 | A | | ATOM | 433 | OG SER A 74 | 22.418 25.815 55.385 1.00 22.70 | A |
| ATOM | 354 | C VAL A 63 | 35.426 22.534 45.357 1.00 11.25 | A | | ATOM | 434 | C SER A 74 | 22.604 25.168 59.069 1.00 17.44 | A |
| ATOM | 355 | O VAL A 63 | 34.693 23.540 45.314 1.00 10.33 | A | | ATOM | 435 | O SER A 74 | 22.322 26.186 59.714 1.00 19.13 | A |
| ATOM | 356 | N TYR A 64 | 34.990 21.284 45.161 1.00 12.24 | A | | ATOM | 436 | N VAL A 75 | 22.515 23.935 59.549 1.00 17.72 | A |
| ATOM | 357 | CA TYR A 64 | 33.591 20.956 44.912 1.00 9.01 | A | | ATOM | 437 | CA VAL A 75 | 21.991 23.703 60.893 1.00 21.66 | A |
| ATOM | 358 | CB TYR A 64 | 33.472 20.113 43.616 1.00 11.11 | A | | ATOM | 438 | CB VAL A 75 | 22.097 22.178 61.293 1.00 20.43 | A |
| ATOM | 359 | CG TYR A 64 | 33.804 20.897 42.331 1.00 10.40 | A | | ATOM | 439 | CG1 VAL A 75 | 21.545 21.962 62.706 1.00 22.18 | A |
| ATOM | 360 | CD1 TYR A 64 | 35.131 21.187 41.996 1.00 12.65 | A | | ATOM | 440 | CG2 VAL A 75 | 21.297 21.323 60.321 1.00 20.79 | A |

Fig. 4 cont.

| | | | | | | | | | | | | | |
|---|---|---|---|---|---|---|---|---|---|---|---|---|---|
| ATOM | 441 | C | VAL A 75 | 22.708 24.608 61.898 1.00 24.34 | A | ATOM | 521 | CA | LEU A 85 | 33.185 31.777 58.265 1.00 11.45 | A |
| ATOM | 442 | O | VAL A 75 | 22.060 25.366 62.664 1.00 23.37 | A | ATOM | 522 | CB | LEU A 85 | 32.305 31.367 57.055 1.00 10.46 | A |
| ATOM | 443 | N | LYS A 76 | 24.041 24.582 61.875 1.00 17.77 | A | ATOM | 523 | CG | LEU A 85 | 30.795 31.288 57.345 1.00 13.21 | A |
| ATOM | 444 | CA | LYS A 76 | 24.820 25.386 62.807 1.00 15.71 | A | ATOM | 524 | CD1 | LEU A 85 | 30.014 30.940 56.066 1.00 16.35 | A |
| ATOM | 445 | CB | LYS A 76 | 26.021 24.576 63.267 1.00 19.87 | A | ATOM | 525 | CD2 | LEU A 85 | 30.530 30.229 58.418 1.00 13.69 | A |
| ATOM | 446 | CG | LYS A 76 | 26.904 25.293 64.294 1.00 20.21 | A | ATOM | 526 | C | LEU A 85 | 34.677 31.631 57.893 1.00 12.57 | A |
| ATOM | 447 | CD | LYS A 76 | 28.013 24.357 64.784 1.00 24.87 | A | ATOM | 527 | O | LEU A 85 | 35.289 30.586 58.167 1.00 13.14 | A |
| ATOM | 448 | CE | LYS A 76 | 28.961 25.023 65.775 1.00 25.88 | A | ATOM | 528 | N | THR A 86 | 35.252 32.664 57.291 1.00 14.57 | A |
| ATOM | 449 | NZ | LYS A 76 | 29.857 23.961 66.312 1.00 23.84 | A | ATOM | 529 | CA | THR A 86 | 36.666 32.616 56.886 1.00 13.23 | A |
| ATOM | 450 | C | LYS A 76 | 25.317 26.730 62.291 1.00 16.12 | A | ATOM | 530 | CB | THR A 86 | 37.091 33.918 56.155 1.00 14.69 | A |
| ATOM | 451 | O | LYS A 76 | 25.451 27.690 63.054 1.00 17.31 | A | ATOM | 531 | OG1 | THR A 86 | 36.255 34.087 54.991 1.00 17.07 | A |
| ATOM | 452 | N | TRP A 77 | 25.498 26.816 60.966 1.00 15.08 | A | ATOM | 532 | CG2 | THR A 86 | 38.520 33.811 55.663 1.00 16.03 | A |
| ATOM | 453 | CA | TRP A 77 | 26.115 27.976 60.355 1.00 15.43 | A | ATOM | 533 | C | THR A 86 | 37.585 32.416 58.110 1.00 14.43 | A |
| ATOM | 454 | CB | TRP A 77 | 27.309 27.451 59.545 1.00 13.42 | A | ATOM | 534 | O | THR A 86 | 38.537 31.635 58.064 1.00 14.85 | A |
| ATOM | 455 | CG | TRP A 77 | 28.218 26.561 60.405 1.00 11.44 | A | ATOM | 535 | N | GLU A 87 | 37.244 33.098 59.204 1.00 15.50 | A |
| ATOM | 456 | CD2 | TRP A 77 | 29.205 27.008 61.329 1.00 12.53 | A | ATOM | 536 | CA | GLU A 87 | 38.010 33.040 60.448 1.00 14.68 | A |
| ATOM | 457 | CE2 | TRP A 77 | 29.822 25.858 61.867 1.00 14.14 | A | ATOM | 537 | CB | GLU A 87 | 37.662 34.296 61.301 1.00 17.95 | A |
| ATOM | 458 | CE3 | TRP A 77 | 29.629 28.264 61.741 1.00 16.46 | A | ATOM | 538 | CG | GLU A 87 | 38.083 35.573 60.589 1.00 26.01 | A |
| ATOM | 459 | CD1 | TRP A 77 | 28.259 25.199 60.420 1.00 13.07 | A | ATOM | 539 | CD | GLU A 87 | 37.526 36.861 61.198 1.00 34.19 | A |
| ATOM | 460 | NE1 | TRP A 77 | 29.227 24.759 61.301 1.00 16.98 | A | ATOM | 540 | OE1 | GLU A 87 | 37.170 36.870 62.415 1.00 30.30 | A |
| ATOM | 461 | CZ2 | TRP A 77 | 30.848 25.934 62.820 1.00 14.47 | A | ATOM | 541 | OE2 | GLU A 87 | 37.477 37.861 60.425 1.00 33.92 | A |
| ATOM | 462 | CZ3 | TRP A 77 | 30.645 28.360 62.688 1.00 17.35 | A | ATOM | 542 | C | GLU A 87 | 37.753 31.808 61.292 1.00 17.73 | A |
| ATOM | 463 | CH2 | TRP A 77 | 31.248 27.189 63.221 1.00 13.28 | A | ATOM | 543 | O | GLU A 87 | 38.532 31.500 62.195 1.00 19.77 | A |
| ATOM | 464 | C | TRP A 77 | 25.326 28.977 59.527 1.00 14.56 | A | ATOM | 544 | N | SER A 88 | 36.672 31.092 60.988 1.00 14.80 | A |
| ATOM | 465 | O | TRP A 77 | 25.873 30.009 59.138 1.00 15.47 | A | ATOM | 545 | CA | SER A 88 | 36.252 29.955 61.766 1.00 14.50 | A |
| ATOM | 466 | N | LYS A 78 | 24.064 28.674 59.266 1.00 17.42 | A | ATOM | 546 | CB | SER A 88 | 34.744 29.729 61.591 1.00 15.03 | A |
| ATOM | 467 | CA | LYS A 78 | 23.245 29.585 58.470 1.00 18.95 | A | ATOM | 547 | OG | SER A 88 | 34.302 28.622 62.343 1.00 13.66 | A |
| ATOM | 468 | CB | LYS A 78 | 21.820 29.033 58.319 1.00 18.46 | A | ATOM | 548 | C | SER A 88 | 36.955 28.634 61.536 1.00 17.65 | A |
| ATOM | 469 | CG | LYS A 78 | 20.892 30.005 57.585 1.00 25.92 | A | ATOM | 549 | O | SER A 88 | 36.777 27.966 60.486 1.00 15.38 | A |
| ATOM | 470 | CD | LYS A 78 | 19.515 29.380 57.372 1.00 24.94 | A | ATOM | 550 | N | ILE A 89 | 37.752 28.245 62.517 1.00 17.03 | A |
| ATOM | 471 | CE | LYS A 78 | 18.587 30.255 56.523 1.00 31.96 | A | ATOM | 551 | CA | ILE A 89 | 38.392 26.963 62.426 1.00 18.12 | A |
| ATOM | 472 | NZ | LYS A 78 | 17.253 29.563 56.401 1.00 37.72 | A | ATOM | 552 | CB | ILE A 89 | 39.453 26.777 63.553 1.00 22.11 | A |
| ATOM | 473 | C | LYS A 78 | 23.195 30.976 59.107 1.00 22.67 | A | ATOM | 553 | CG2 | ILE A 89 | 39.907 25.311 63.602 1.00 19.47 | A |
| ATOM | 474 | O | LYS A 78 | 22.964 31.101 60.316 1.00 20.87 | A | ATOM | 554 | CG1 | ILE A 89 | 40.638 27.698 63.260 1.00 22.02 | A |
| ATOM | 475 | N | GLY A 79 | 23.417 32.002 58.287 1.00 17.39 | A | ATOM | 555 | CD1 | ILE A 89 | 41.600 27.890 64.423 1.00 36.91 | A |
| ATOM | 476 | CA | GLY A 79 | 23.397 33.384 58.763 1.00 18.79 | A | ATOM | 556 | C | ILE A 89 | 37.323 25.849 62.460 1.00 16.96 | A |
| ATOM | 477 | C | GLY A 79 | 24.761 33.974 59.066 1.00 19.65 | A | ATOM | 557 | O | ILE A 89 | 37.359 24.946 61.642 1.00 16.20 | A |
| ATOM | 478 | O | GLY A 79 | 24.894 35.187 59.269 1.00 20.04 | A | ATOM | 558 | N | PRO A 90 | 36.335 25.907 63.373 1.00 13.76 | A |
| ATOM | 479 | N | LYS A 80 | 25.794 33.131 59.129 1.00 18.05 | A | ATOM | 559 | CD | PRO A 90 | 36.181 26.885 64.490 1.00 16.32 | A |
| ATOM | 480 | CA | LYS A 80 | 27.136 33.667 59.359 1.00 16.40 | A | ATOM | 560 | CA | PRO A 90 | 35.315 24.847 63.413 1.00 17.06 | A |
| ATOM | 481 | CB | LYS A 80 | 28.143 32.543 59.648 1.00 19.31 | A | ATOM | 561 | CB | PRO A 90 | 34.423 25.233 64.608 1.00 20.16 | A |
| ATOM | 482 | CG | LYS A 80 | 27.874 31.766 60.913 1.00 23.17 | A | ATOM | 562 | CG | PRO A 90 | 35.315 26.131 65.458 1.00 17.63 | A |
| ATOM | 483 | CD | LYS A 80 | 28.143 32.615 62.120 1.00 21.50 | A | ATOM | 563 | C | PRO A 90 | 34.483 24.688 62.127 1.00 15.25 | A |
| ATOM | 484 | CE | LYS A 80 | 28.087 31.736 63.361 1.00 21.06 | A | ATOM | 564 | O | PRO A 90 | 34.131 23.587 61.734 1.00 15.70 | A |
| ATOM | 485 | NZ | LYS A 80 | 28.215 32.560 64.589 1.00 27.57 | A | ATOM | 565 | N | PHE A 91 | 34.162 25.811 61.489 1.00 14.25 | A |
| ATOM | 486 | C | LYS A 80 | 27.602 34.392 58.115 1.00 14.77 | A | ATOM | 566 | CA | PHE A 91 | 33.351 25.700 60.265 1.00 9.78 | A |
| ATOM | 487 | O | LYS A 80 | 27.290 33.981 56.988 1.00 17.30 | A | ATOM | 567 | CB | PHE A 91 | 33.018 27.092 59.729 1.00 9.80 | A |
| ATOM | 488 | N | THR A 81 | 28.368 35.452 58.324 1.00 15.48 | A | ATOM | 568 | CG | PHE A 91 | 32.281 27.061 58.397 1.00 11.55 | A |
| ATOM | 489 | CA | THR A 81 | 28.895 36.227 57.214 1.00 16.76 | A | ATOM | 569 | CD1 | PHE A 91 | 30.995 26.545 58.323 1.00 12.81 | A |
| ATOM | 490 | CB | THR A 81 | 29.340 37.631 57.664 1.00 19.90 | A | ATOM | 570 | CD2 | PHE A 91 | 32.875 27.595 57.255 1.00 15.05 | A |
| ATOM | 491 | OG1 | THR A 81 | 30.469 37.522 58.542 1.00 18.99 | A | ATOM | 571 | CE1 | PHE A 91 | 30.276 26.562 57.128 1.00 14.30 | A |
| ATOM | 492 | CG2 | THR A 81 | 28.177 38.386 58.388 1.00 20.94 | A | ATOM | 572 | CE2 | PHE A 91 | 32.183 27.623 56.043 1.00 11.64 | A |
| ATOM | 493 | C | THR A 81 | 30.137 35.553 56.631 1.00 16.91 | A | ATOM | 573 | CZ | PHE A 91 | 30.872 27.108 55.968 1.00 12.18 | A |
| ATOM | 494 | O | THR A 81 | 30.693 34.624 57.203 1.00 18.41 | A | ATOM | 574 | C | PHE A 91 | 34.095 24.902 59.190 1.00 11.71 | A |
| ATOM | 495 | N | THR A 82 | 30.579 36.068 55.502 1.00 16.37 | A | ATOM | 575 | O | PHE A 91 | 33.553 23.982 58.584 1.00 11.23 | A |
| ATOM | 496 | CA | THR A 82 | 31.780 35.558 54.861 1.00 16.45 | A | ATOM | 576 | N | PHE A 92 | 35.344 25.268 58.962 1.00 13.22 | A |
| ATOM | 497 | CB | THR A 82 | 32.094 36.395 53.615 1.00 18.45 | A | ATOM | 577 | CA | PHE A 92 | 36.095 24.540 57.946 1.00 12.26 | A |
| ATOM | 498 | OG1 | THR A 82 | 31.025 36.225 52.675 1.00 17.98 | A | ATOM | 578 | CB | PHE A 92 | 37.308 25.352 57.536 1.00 11.86 | A |
| ATOM | 499 | CG2 | THR A 82 | 33.476 36.007 52.989 1.00 15.97 | A | ATOM | 579 | CG | PHE A 92 | 36.977 26.351 56.469 1.00 10.63 | A |
| ATOM | 500 | C | THR A 82 | 32.967 35.666 55.807 1.00 14.57 | A | ATOM | 580 | CD1 | PHE A 92 | 36.522 27.629 56.791 1.00 10.23 | A |
| ATOM | 501 | O | THR A 82 | 33.739 34.718 55.948 1.00 16.56 | A | ATOM | 581 | CD2 | PHE A 92 | 37.034 25.962 55.113 1.00 12.14 | A |
| ATOM | 502 | N | GLU A 83 | 33.119 36.822 56.453 1.00 17.03 | A | ATOM | 582 | CE1 | PHE A 92 | 36.113 28.533 55.781 1.00 14.19 | A |
| ATOM | 503 | CA | GLU A 83 | 34.245 37.034 57.356 1.00 18.00 | A | ATOM | 583 | CE2 | PHE A 92 | 36.633 26.857 54.093 1.00 10.58 | A |
| ATOM | 504 | CB | GLU A 83 | 34.240 38.499 57.823 1.00 21.86 | A | ATOM | 584 | CZ | PHE A 92 | 36.174 28.131 54.419 1.00 12.25 | A |
| ATOM | 505 | CG | GLU A 83 | 34.389 39.460 56.659 1.00 29.72 | A | ATOM | 585 | C | PHE A 92 | 36.441 23.117 58.365 1.00 14.89 | A |
| ATOM | 506 | CD | GLU A 83 | 33.049 40.053 56.162 1.00 37.44 | A | ATOM | 586 | O | PHE A 92 | 36.589 22.227 57.531 1.00 13.48 | A |
| ATOM | 507 | OE1 | GLU A 83 | 32.056 39.329 55.931 1.00 26.17 | A | ATOM | 587 | N | ARG A 93 | 36.537 22.883 59.662 1.00 13.97 | A |
| ATOM | 508 | OE2 | GLU A 83 | 32.996 41.298 56.003 1.00 58.51 | A | ATOM | 588 | CA | ARG A 93 | 36.799 21.533 60.105 1.00 16.82 | A |
| ATOM | 509 | C | GLU A 83 | 34.221 36.073 58.553 1.00 17.07 | A | ATOM | 589 | CB | ARG A 93 | 37.184 21.542 61.590 1.00 15.22 | A |
| ATOM | 510 | O | GLU A 83 | 35.267 35.513 58.941 1.00 16.46 | A | ATOM | 590 | CG | ARG A 93 | 38.660 21.924 61.806 1.00 18.56 | A |
| ATOM | 511 | N | GLU A 84 | 33.033 35.886 59.127 1.00 14.43 | A | ATOM | 591 | CD | ARG A 93 | 39.617 20.863 61.225 1.00 25.77 | A |
| ATOM | 512 | CA | GLU A 84 | 32.868 34.986 60.269 1.00 16.55 | A | ATOM | 592 | NE | ARG A 93 | 39.372 19.543 61.798 1.00 29.95 | A |
| ATOM | 513 | CB | GLU A 84 | 31.390 34.981 60.731 1.00 19.83 | A | ATOM | 593 | CZ | ARG A 93 | 39.863 18.398 61.317 1.00 31.98 | A |
| ATOM | 514 | CG | GLU A 84 | 30.955 36.266 61.464 1.00 28.01 | A | ATOM | 594 | NH1 | ARG A 93 | 40.637 18.381 60.233 1.00 30.33 | A |
| ATOM | 515 | CD | GLU A 84 | 29.488 36.214 61.907 1.00 28.06 | A | ATOM | 595 | NH2 | ARG A 93 | 39.572 17.270 61.935 1.00 32.81 | A |
| ATOM | 516 | OE1 | GLU A 84 | 28.613 35.995 61.052 1.00 22.25 | A | ATOM | 596 | C | ARG A 93 | 35.547 20.697 59.832 1.00 16.74 | A |
| ATOM | 517 | OE2 | GLU A 84 | 29.202 36.401 63.139 1.00 41.09 | A | ATOM | 597 | O | ARG A 93 | 35.646 19.519 59.464 1.00 16.96 | A |
| ATOM | 518 | C | GLU A 84 | 33.269 33.559 59.875 1.00 16.58 | A | ATOM | 598 | N | GLU A 94 | 34.364 21.312 59.958 1.00 13.06 | A |
| ATOM | 519 | O | GLU A 84 | 33.921 32.843 60.658 1.00 16.86 | A | ATOM | 599 | CA | GLU A 94 | 33.110 20.621 59.670 1.00 14.60 | A |
| ATOM | 520 | N | LEU A 85 | 32.860 33.137 58.680 1.00 14.31 | A | ATOM | 600 | CB | GLU A 94 | 31.872 21.437 60.147 1.00 11.75 | A |

Fig. 4 cont.

| | | | | | | | | | | | |
|---|---|---|---|---|---|---|---|---|---|---|---|
| ATOM | 601 | CG  | GLU A 94  | 30.593 20.640 60.129 1.00 17.01 | A | ATOM | 681 | CG2 | ILE A 104 | 41.503 19.994 45.499 1.00 13.02 | A |
| ATOM | 602 | CD  | GLU A 94  | 29.390 21.375 60.743 1.00 20.62 | A | ATOM | 682 | CG1 | ILE A 104 | 40.095 18.511 47.000 1.00 13.70 | A |
| ATOM | 603 | OE1 | GLU A 94  | 29.533 21.985 61.834 1.00 20.59 | A | ATOM | 683 | CD1 | ILE A 104 | 41.200 18.149 48.054 1.00 11.28 | A |
| ATOM | 604 | OE2 | GLU A 94  | 28.289 21.329 60.138 1.00 20.77 | A | ATOM | 684 | C   | ILE A 104 | 40.095 18.721 43.176 1.00 10.86 | A |
| ATOM | 605 | C   | GLU A 94  | 32.997 20.314 58.156 1.00 14.77 | A | ATOM | 685 | O   | ILE A 104 | 40.505 17.633 42.788 1.00 10.88 | A |
| ATOM | 606 | O   | GLU A 94  | 32.472 19.280 57.769 1.00 15.55 | A | ATOM | 686 | N   | LYS A 105 | 40.157 19.832 42.445 1.00 10.58 | A |
| ATOM | 607 | N   | ILE A 95  | 33.488 21.210 57.309 1.00 12.20 | A | ATOM | 687 | CA  | LYS A 105 | 40.814 19.844 41.139 1.00 9.54  | A |
| ATOM | 608 | CA  | ILE A 95  | 33.496 20.921 55.869 1.00 13.66 | A | ATOM | 688 | CB  | LYS A 105 | 39.872 20.378 40.050 1.00 12.87 | A |
| ATOM | 609 | CB  | ILE A 95  | 34.002 22.112 55.076 1.00 11.53 | A | ATOM | 689 | CG  | LYS A 105 | 40.561 20.571 38.657 1.00 11.61 | A |
| ATOM | 610 | CG2 | ILE A 95  | 34.202 21.662 53.568 1.00 14.05 | A | ATOM | 690 | CD  | LYS A 105 | 39.550 20.877 37.563 1.00 14.39 | A |
| ATOM | 611 | CG1 | ILE A 95  | 33.010 23.299 55.200 1.00 10.55 | A | ATOM | 691 | CE  | LYS A 105 | 40.248 21.104 36.205 1.00 12.29 | A |
| ATOM | 612 | CD1 | ILE A 95  | 33.462 24.537 54.464 1.00 13.37 | A | ATOM | 692 | NZ  | LYS A 105 | 40.835 22.501 36.101 1.00 15.53 | A |
| ATOM | 613 | C   | ILE A 95  | 34.434 19.724 55.577 1.00 16.34 | A | ATOM | 693 | C   | LYS A 105 | 42.015 20.773 41.308 1.00 10.95 | A |
| ATOM | 614 | O   | ILE A 95  | 34.048 18.761 54.938 1.00 15.04 | A | ATOM | 694 | O   | LYS A 105 | 41.818 21.966 41.599 1.00 11.73 | A |
| ATOM | 615 | N   | VAL A 96  | 35.659 19.803 56.084 1.00 14.38 | A | ATOM | 695 | N   | VAL A 106 | 43.231 20.244 41.131 1.00 11.22 | A |
| ATOM | 616 | CA  | VAL A 96  | 36.657 18.757 55.866 1.00 14.91 | A | ATOM | 696 | CA  | VAL A 106 | 44.459 21.016 41.274 1.00 11.98 | A |
| ATOM | 617 | CB  | VAL A 96  | 37.995 19.173 56.533 1.00 15.55 | A | ATOM | 697 | CB  | VAL A 106 | 45.445 20.322 42.227 1.00 12.27 | A |
| ATOM | 618 | CG1 | VAL A 96  | 38.980 17.965 56.565 1.00 14.63 | A | ATOM | 698 | CG1 | VAL A 106 | 46.756 21.142 42.299 1.00 11.43 | A |
| ATOM | 619 | CG2 | VAL A 96  | 38.629 20.336 55.762 1.00 16.62 | A | ATOM | 699 | CG2 | VAL A 106 | 44.832 20.228 43.614 1.00 14.89 | A |
| ATOM | 620 | C   | VAL A 96  | 36.248 17.362 56.369 1.00 13.45 | A | ATOM | 700 | C   | VAL A 106 | 45.070 21.095 39.873 1.00 13.34 | A |
| ATOM | 621 | O   | VAL A 96  | 36.439 16.365 55.654 1.00 16.38 | A | ATOM | 701 | O   | VAL A 106 | 45.489 20.092 39.313 1.00 13.86 | A |
| ATOM | 622 | N   | THR A 97  | 35.652 17.304 57.562 1.00 14.40 | A | ATOM | 702 | N   | THR A 107 | 45.131 22.290 39.315 1.00 14.36 | A |
| ATOM | 623 | CA  | THR A 97  | 35.257 16.025 58.166 1.00 16.73 | A | ATOM | 703 | CA  | THR A 107 | 45.645 22.433 37.956 1.00 13.32 | A |
| ATOM | 624 | CB  | THR A 97  | 35.492 16.060 59.683 1.00 15.47 | A | ATOM | 704 | CB  | THR A 107 | 44.610 23.197 37.114 1.00 13.57 | A |
| ATOM | 625 | OG1 | THR A 97  | 34.599 17.011 60.287 1.00 16.27 | A | ATOM | 705 | OG1 | THR A 107 | 43.411 22.389 37.027 1.00 16.35 | A |
| ATOM | 626 | CG2 | THR A 97  | 36.933 16.467 59.961 1.00 18.84 | A | ATOM | 706 | CG2 | THR A 107 | 45.165 23.486 35.679 1.00 15.66 | A |
| ATOM | 627 | C   | THR A 97  | 33.798 15.608 57.961 1.00 15.29 | A | ATOM | 707 | C   | THR A 107 | 46.988 23.143 38.003 1.00 13.22 | A |
| ATOM | 628 | O   | THR A 97  | 33.382 14.538 58.424 1.00 16.41 | A | ATOM | 708 | O   | THR A 107 | 47.134 24.227 38.618 1.00 13.33 | A |
| ATOM | 629 | N   | GLY A 98  | 33.025 16.425 57.256 1.00 15.71 | A | ATOM | 709 | N   | MET A 108 | 47.985 22.549 37.347 1.00 15.32 | A |
| ATOM | 630 | CA  | GLY A 98  | 31.614 16.175 57.083 1.00 19.31 | A | ATOM | 710 | CA  | MET A 108 | 49.328 23.138 37.389 1.00 19.42 | A |
| ATOM | 631 | C   | GLY A 98  | 31.340 14.822 56.336 1.00 19.51 | A | ATOM | 711 | CB  | MET A 108 | 50.384 22.085 36.990 1.00 17.71 | A |
| ATOM | 632 | O   | GLY A 98  | 32.150 14.384 55.521 1.00 17.35 | A | ATOM | 712 | CG  | MET A 108 | 51.039 21.296 38.144 1.00 17.55 | A |
| ATOM | 633 | N   | ALA A 99  | 30.191 14.194 56.606 1.00 20.23 | A | ATOM | 713 | SD  | MET A 108 | 49.863 20.627 39.330 1.00 17.73 | A |
| ATOM | 634 | CA  | ALA A 99  | 29.891 12.940 55.936 1.00 18.95 | A | ATOM | 714 | CE  | MET A 108 | 48.880 19.510 38.357 1.00 19.67 | A |
| ATOM | 635 | CB  | ALA A 99  | 29.029 12.015 56.820 1.00 23.77 | A | ATOM | 715 | C   | MET A 108 | 49.519 24.402 36.522 1.00 18.03 | A |
| ATOM | 636 | C   | ALA A 99  | 29.227 13.101 54.589 1.00 24.32 | A | ATOM | 716 | O   | MET A 108 | 49.025 24.496 35.386 1.00 17.79 | A |
| ATOM | 637 | O   | ALA A 99  | 28.090 12.791 54.355 1.00 25.97 | A | ATOM | 717 | N   | LYS A 109 | 50.185 25.389 37.108 1.00 18.40 | A |
| ATOM | 638 | N   | PHE A 100 | 29.989 13.778 53.702 1.00 16.85 | A | ATOM | 718 | CA  | LYS A 109 | 50.518 26.582 36.326 1.00 19.61 | A |
| ATOM | 639 | CA  | PHE A 100 | 29.544 14.059 52.363 1.00 16.31 | A | ATOM | 719 | CB  | LYS A 109 | 50.319 27.853 37.119 1.00 20.01 | A |
| ATOM | 640 | CB  | PHE A 100 | 28.797 15.404 52.252 1.00 18.78 | A | ATOM | 720 | CG  | LYS A 109 | 50.529 29.073 36.210 1.00 29.03 | A |
| ATOM | 641 | CG  | PHE A 100 | 29.355 16.529 53.091 1.00 26.18 | A | ATOM | 721 | CD  | LYS A 109 | 50.179 30.371 36.865 1.00 30.95 | A |
| ATOM | 642 | CD1 | PHE A 100 | 30.505 17.252 52.689 1.00 28.96 | A | ATOM | 722 | CE  | LYS A 109 | 50.263 31.517 35.859 1.00 32.08 | A |
| ATOM | 643 | CD2 | PHE A 100 | 28.688 16.925 54.261 1.00 23.41 | A | ATOM | 723 | NZ  | LYS A 109 | 50.081 32.829 36.562 1.00 36.71 | A |
| ATOM | 644 | CE1 | PHE A 100 | 31.007 18.377 53.467 1.00 18.99 | A | ATOM | 724 | C   | LYS A 109 | 52.002 26.371 35.973 1.00 25.95 | A |
| ATOM | 645 | CE2 | PHE A 100 | 29.163 18.025 55.025 1.00 30.15 | A | ATOM | 725 | O   | LYS A 109 | 52.432 26.672 34.849 1.00 28.09 | A |
| ATOM | 646 | CZ  | PHE A 100 | 30.333 18.751 54.619 1.00 26.58 | A | ATOM | 726 | N   | LEU A 110 | 52.775 25.875 36.936 1.00 22.55 | A |
| ATOM | 647 | C   | PHE A 100 | 30.765 14.044 51.517 1.00 17.05 | A | ATOM | 727 | CA  | LEU A 110 | 54.192 25.576 36.714 1.00 26.51 | A |
| ATOM | 648 | O   | PHE A 100 | 31.873 14.160 52.041 1.00 16.03 | A | ATOM | 728 | CB  | LEU A 110 | 55.047 25.984 37.902 1.00 28.35 | A |
| ATOM | 649 | N   | GLU A 101 | 30.578 13.848 50.213 1.00 15.17 | A | ATOM | 729 | CG  | LEU A 110 | 55.075 27.436 38.324 1.00 36.97 | A |
| ATOM | 650 | CA  | GLU A 101 | 31.739 13.810 49.333 1.00 10.62 | A | ATOM | 730 | CD1 | LEU A 110 | 56.131 27.627 39.394 1.00 41.45 | A |
| ATOM | 651 | CB  | GLU A 101 | 31.361 13.157 48.003 1.00 12.05 | A | ATOM | 731 | CD2 | LEU A 110 | 55.393 28.269 37.115 1.00 41.13 | A |
| ATOM | 652 | CG  | GLU A 101 | 32.538 12.975 47.071 1.00 14.22 | A | ATOM | 732 | C   | LEU A 110 | 54.341 24.062 36.581 1.00 27.89 | A |
| ATOM | 653 | CD  | GLU A 101 | 32.205 12.146 45.829 1.00 20.14 | A | ATOM | 733 | O   | LEU A 110 | 53.509 23.286 37.084 1.00 25.04 | A |
| ATOM | 654 | OE1 | GLU A 101 | 30.987 11.986 45.512 1.00 16.26 | A | ATOM | 734 | N   | PRO A 111 | 55.398 23.607 35.899 1.00 22.82 | A |
| ATOM | 655 | OE2 | GLU A 101 | 33.161 11.677 45.170 1.00 17.18 | A | ATOM | 735 | CD  | PRO A 111 | 56.423 24.311 35.094 1.00 23.43 | A |
| ATOM | 656 | C   | GLU A 101 | 32.290 15.229 49.071 1.00 11.80 | A | ATOM | 736 | CA  | PRO A 111 | 55.527 22.152 35.809 1.00 24.36 | A |
| ATOM | 657 | O   | GLU A 101 | 31.530 16.230 49.008 1.00 13.65 | A | ATOM | 737 | CB  | PRO A 111 | 56.599 21.961 34.738 1.00 26.84 | A |
| ATOM | 658 | N   | LYS A 102 | 33.607 15.289 48.883 1.00 10.63 | A | ATOM | 738 | CG  | PRO A 111 | 57.456 23.223 34.872 1.00 28.05 | A |
| ATOM | 659 | CA  | LYS A 102 | 34.279 16.535 48.504 1.00 9.42  | A | ATOM | 739 | C   | PRO A 111 | 55.959 21.618 37.181 1.00 21.71 | A |
| ATOM | 660 | CB  | LYS A 102 | 35.209 17.081 49.587 1.00 12.33 | A | ATOM | 740 | O   | PRO A 111 | 56.793 22.214 37.848 1.00 24.16 | A |
| ATOM | 661 | CG  | LYS A 102 | 34.527 17.263 50.935 1.00 13.87 | A | ATOM | 741 | N   | LEU A 112 | 55.376 20.503 37.610 1.00 22.58 | A |
| ATOM | 662 | CD  | LYS A 102 | 34.793 16.036 51.820 1.00 11.88 | A | ATOM | 742 | CA  | LEU A 112 | 55.741 19.905 38.890 1.00 20.71 | A |
| ATOM | 663 | CE  | LYS A 102 | 33.933 16.110 53.087 1.00 16.61 | A | ATOM | 743 | CB  | LEU A 112 | 54.686 20.172 39.966 1.00 19.20 | A |
| ATOM | 664 | NZ  | LYS A 102 | 34.363 15.123 54.119 1.00 17.69 | A | ATOM | 744 | CG  | LEU A 112 | 54.321 21.626 40.273 1.00 20.40 | A |
| ATOM | 665 | C   | LYS A 102 | 35.147 16.152 47.313 1.00 11.10 | A | ATOM | 745 | CD1 | LEU A 112 | 53.165 21.666 41.249 1.00 20.93 | A |
| ATOM | 666 | O   | LYS A 102 | 35.541 14.988 47.133 1.00 12.17 | A | ATOM | 746 | CD2 | LEU A 112 | 55.510 22.348 40.837 1.00 26.00 | A |
| ATOM | 667 | N   | PHE A 103 | 35.490 17.150 46.503 1.00 9.50  | A | ATOM | 747 | C   | LEU A 112 | 55.841 18.398 38.712 1.00 19.51 | A |
| ATOM | 668 | CA  | PHE A 103 | 36.317 16.865 45.323 1.00 8.99  | A | ATOM | 748 | O   | LEU A 112 | 55.057 17.799 37.992 1.00 21.25 | A |
| ATOM | 669 | CB  | PHE A 103 | 35.406 16.642 44.106 1.00 12.02 | A | ATOM | 749 | N   | THR A 113 | 56.801 17.775 39.368 1.00 22.95 | A |
| ATOM | 670 | CG  | PHE A 103 | 36.144 16.452 42.807 1.00 12.67 | A | ATOM | 750 | CA  | THR A 113 | 56.895 16.316 39.302 1.00 25.18 | A |
| ATOM | 671 | CD1 | PHE A 103 | 36.672 15.210 42.461 1.00 12.67 | A | ATOM | 751 | CB  | THR A 113 | 58.300 15.816 39.637 1.00 24.35 | A |
| ATOM | 672 | CD2 | PHE A 103 | 36.312 17.521 41.945 1.00 16.14 | A | ATOM | 752 | OG1 | THR A 113 | 58.584 16.118 41.009 1.00 23.16 | A |
| ATOM | 673 | CE1 | PHE A 103 | 37.371 15.019 41.253 1.00 14.43 | A | ATOM | 753 | CG2 | THR A 113 | 59.335 16.489 38.740 1.00 27.76 | A |
| ATOM | 674 | CE2 | PHE A 103 | 37.007 17.349 40.726 1.00 14.17 | A | ATOM | 754 | C   | THR A 113 | 55.944 15.752 40.377 1.00 22.46 | A |
| ATOM | 675 | CZ  | PHE A 103 | 37.530 16.101 40.390 1.00 15.11 | A | ATOM | 755 | O   | THR A 113 | 55.613 16.411 41.376 1.00 19.88 | A |
| ATOM | 676 | C   | PHE A 103 | 37.257 18.060 45.097 1.00 14.03 | A | ATOM | 756 | N   | GLY A 114 | 55.499 14.527 40.177 1.00 20.21 | A |
| ATOM | 677 | O   | PHE A 103 | 36.871 19.202 45.276 1.00 12.36 | A | ATOM | 757 | CA  | GLY A 114 | 54.605 13.927 41.143 1.00 19.15 | A |
| ATOM | 678 | N   | ILE A 104 | 38.494 17.773 44.752 1.00 10.09 | A | ATOM | 758 | C   | GLY A 114 | 55.233 13.791 42.514 1.00 21.69 | A |
| ATOM | 679 | CA  | ILE A 104 | 39.479 18.833 44.563 1.00 11.40 | A | ATOM | 759 | O   | GLY A 114 | 54.545 13.872 43.509 1.00 19.65 | A |
| ATOM | 680 | CB  | ILE A 104 | 40.636 18.715 45.563 1.00 11.37 | A | ATOM | 760 | N   | GLN A 115 | 56.548 13.573 42.558 1.00 19.18 | A |

Fig. 4 cont.

| | | | | | | | | | | | |
|---|---|---|---|---|---|---|---|---|---|---|---|
| ATOM | 761 | CA GLN A 115 | 57.261 13.440 43.817 1.00 23.39 | A | | ATOM | 841 | OD1 ASN A 124 | 54.189 21.005 57.751 1.00 27.52 | A |
| ATOM | 762 | CB GLN A 115 | 58.714 12.995 43.576 1.00 25.58 | A | | ATOM | 842 | ND2 ASN A 124 | 52.452 21.709 56.501 1.00 32.57 | A |
| ATOM | 763 | CG GLN A 115 | 59.476 12.820 44.867 1.00 34.72 | A | | ATOM | 843 | C ASN A 124 | 52.033 17.303 58.177 1.00 17.46 | A |
| ATOM | 764 | CD GLN A 115 | 60.856 12.236 44.655 1.00 46.23 | A | | ATOM | 844 | O ASN A 124 | 51.976 17.247 59.390 1.00 18.81 | A |
| ATOM | 765 | OE1 GLN A 115 | 60.996 11.065 44.300 1.00 47.59 | A | | ATOM | 845 | N CYS A 125 | 51.383 16.431 57.403 1.00 17.69 | A |
| ATOM | 766 | NE2 GLN A 115 | 61.886 13.059 44.853 1.00 50.24 | A | | ATOM | 846 | CA CYS A 125 | 50.445 15.565 58.091 1.00 16.09 | A |
| ATOM | 767 | C GLN A 115 | 57.237 14.792 44.543 1.00 23.83 | A | | ATOM | 847 | CB CYS A 125 | 49.479 14.887 57.107 1.00 25.33 | A |
| ATOM | 768 | O GLN A 115 | 56.931 14.841 45.733 1.00 23.51 | A | | ATOM | 848 | SG CYS A 125 | 50.258 13.970 55.821 1.00 28.16 | A |
| ATOM | 769 | N GLN A 116 | 57.548 15.868 43.813 1.00 22.91 | A | | ATOM | 849 | C CYS A 125 | 50.981 14.581 59.122 1.00 17.95 | A |
| ATOM | 770 | CA GLN A 116 | 57.529 17.233 44.370 1.00 21.13 | A | | ATOM | 850 | O CYS A 125 | 50.310 14.360 60.120 1.00 17.26 | A |
| ATOM | 771 | CB GLN A 116 | 57.774 18.274 43.262 1.00 31.17 | A | | ATOM | 851 | N VAL A 126 | 52.174 14.018 58.937 1.00 14.97 | A |
| ATOM | 772 | CG GLN A 116 | 59.239 18.395 42.857 1.00 36.70 | A | | ATOM | 852 | CA VAL A 126 | 52.680 13.095 59.953 1.00 18.94 | A |
| ATOM | 773 | CD GLN A 116 | 59.428 19.099 41.517 1.00 39.85 | A | | ATOM | 853 | CB VAL A 126 | 53.987 12.378 59.495 1.00 22.32 | A |
| ATOM | 774 | OE1 GLN A 116 | 58.475 19.570 40.886 1.00 28.63 | A | | ATOM | 854 | CG1 VAL A 126 | 54.750 11.788 60.703 1.00 26.84 | A |
| ATOM | 775 | NE2 GLN A 116 | 60.690 19.171 41.077 1.00 48.56 | A | | ATOM | 855 | CG2 VAL A 126 | 53.591 11.225 58.559 1.00 24.04 | A |
| ATOM | 776 | C GLN A 116 | 56.146 17.507 44.939 1.00 21.35 | A | | ATOM | 856 | C VAL A 126 | 52.907 13.825 61.290 1.00 19.16 | A |
| ATOM | 777 | O GLN A 116 | 55.986 17.826 46.133 1.00 22.56 | A | | ATOM | 857 | O VAL A 126 | 52.532 13.301 62.344 1.00 16.80 | A |
| ATOM | 778 | N TYR A 117 | 55.159 17.389 44.064 1.00 18.99 | A | | ATOM | 858 | N ALA A 127 | 53.509 15.015 61.238 1.00 18.74 | A |
| ATOM | 779 | CA TYR A 117 | 53.781 17.667 44.454 1.00 16.90 | A | | ATOM | 859 | CA ALA A 127 | 53.772 15.777 62.442 1.00 17.92 | A |
| ATOM | 780 | CB TYR A 117 | 52.826 17.478 43.269 1.00 21.47 | A | | ATOM | 860 | CB ALA A 127 | 54.565 17.044 62.115 1.00 18.92 | A |
| ATOM | 781 | CG TYR A 117 | 51.404 17.799 43.670 1.00 21.01 | A | | ATOM | 861 | C ALA A 127 | 52.458 16.132 63.101 1.00 15.20 | A |
| ATOM | 782 | CD1 TYR A 117 | 50.980 19.120 43.810 1.00 19.56 | A | | ATOM | 862 | O ALA A 127 | 52.367 16.095 64.328 1.00 17.29 | A |
| ATOM | 783 | CE1 TYR A 117 | 49.705 19.422 44.279 1.00 21.91 | A | | ATOM | 863 | N ILE A 128 | 51.450 16.494 62.309 1.00 13.37 | A |
| ATOM | 784 | CD2 TYR A 117 | 50.509 16.779 43.996 1.00 17.09 | A | | ATOM | 864 | CA ILE A 128 | 50.152 16.814 62.883 1.00 12.77 | A |
| ATOM | 785 | CE2 TYR A 117 | 49.241 17.058 44.443 1.00 21.17 | A | | ATOM | 865 | CB ILE A 128 | 49.207 17.356 61.784 1.00 14.17 | A |
| ATOM | 786 | CZ TYR A 117 | 48.835 18.374 44.592 1.00 21.74 | A | | ATOM | 866 | CG2 ILE A 128 | 47.776 17.331 62.277 1.00 17.59 | A |
| ATOM | 787 | OH TYR A 117 | 47.572 18.637 45.085 1.00 21.74 | A | | ATOM | 867 | CG1 ILE A 128 | 49.637 18.761 61.403 1.00 15.97 | A |
| ATOM | 788 | C TYR A 117 | 53.303 16.830 45.642 1.00 18.04 | A | | ATOM | 868 | CD1 ILE A 128 | 48.919 19.278 60.161 1.00 21.38 | A |
| ATOM | 789 | O TYR A 117 | 52.786 17.381 46.620 1.00 18.60 | A | | ATOM | 869 | C ILE A 128 | 49.516 15.583 63.544 1.00 13.92 | A |
| ATOM | 790 | N SER A 118 | 53.470 15.510 45.576 1.00 16.25 | A | | ATOM | 870 | O ILE A 128 | 48.987 15.676 64.666 1.00 12.53 | A |
| ATOM | 791 | CA SER A 118 | 53.017 14.645 46.660 1.00 12.04 | A | | ATOM | 871 | N TRP A 129 | 49.533 14.420 62.879 1.00 11.27 | A |
| ATOM | 792 | CB SER A 118 | 53.126 13.149 46.255 1.00 19.19 | A | | ATOM | 872 | CA TRP A 129 | 48.931 13.259 63.502 1.00 9.20 | A |
| ATOM | 793 | OG SER A 118 | 54.450 12.803 45.877 1.00 20.15 | A | | ATOM | 873 | CB TRP A 129 | 48.902 12.085 62.530 1.00 14.14 | A |
| ATOM | 794 | C SER A 118 | 53.728 14.904 47.975 1.00 22.58 | A | | ATOM | 874 | CG TRP A 129 | 48.059 12.404 61.309 1.00 12.07 | A |
| ATOM | 795 | O SER A 118 | 53.106 14.804 49.028 1.00 19.98 | A | | ATOM | 875 | CD2 TRP A 129 | 48.281 11.920 59.972 1.00 11.75 | A |
| ATOM | 796 | N GLU A 119 | 55.021 15.244 47.936 1.00 18.94 | A | | ATOM | 876 | CE2 TRP A 129 | 47.223 12.393 59.173 1.00 12.58 | A |
| ATOM | 797 | CA GLU A 119 | 55.734 15.535 49.188 1.00 20.55 | A | | ATOM | 877 | CE3 TRP A 129 | 49.283 11.126 59.386 1.00 16.72 | A |
| ATOM | 798 | CB GLU A 119 | 57.248 15.564 48.954 1.00 20.40 | A | | ATOM | 878 | CD1 TRP A 129 | 46.902 13.149 61.263 1.00 13.49 | A |
| ATOM | 799 | CG GLU A 119 | 57.820 14.178 48.668 1.00 25.51 | A | | ATOM | 879 | NE1 TRP A 129 | 46.392 13.142 59.969 1.00 13.75 | A |
| ATOM | 800 | CD GLU A 119 | 59.342 14.183 48.441 1.00 34.73 | A | | ATOM | 880 | CZ2 TRP A 129 | 47.132 12.095 57.783 1.00 12.36 | A |
| ATOM | 801 | OE1 GLU A 119 | 59.919 15.278 48.266 1.00 32.36 | A | | ATOM | 881 | CZ3 TRP A 129 | 49.193 10.835 58.009 1.00 14.99 | A |
| ATOM | 802 | OE2 GLU A 119 | 59.939 13.087 48.435 1.00 32.41 | A | | ATOM | 882 | CH2 TRP A 129 | 48.131 11.317 57.241 1.00 14.01 | A |
| ATOM | 803 | C GLU A 119 | 55.241 16.862 49.753 1.00 22.27 | A | | ATOM | 883 | C TRP A 129 | 49.683 12.871 64.782 1.00 11.99 | A |
| ATOM | 804 | O GLU A 119 | 55.172 17.044 50.970 1.00 21.31 | A | | ATOM | 884 | O TRP A 129 | 49.063 12.456 65.746 1.00 13.26 | A |
| ATOM | 805 | N LYS A 120 | 54.900 17.796 48.865 1.00 19.32 | A | | ATOM | 885 | N LYS A 130 | 51.013 12.977 64.773 1.00 15.19 | A |
| ATOM | 806 | CA LYS A 120 | 54.377 19.089 49.296 1.00 20.28 | A | | ATOM | 886 | CA LYS A 130 | 51.749 12.668 66.025 1.00 16.10 | A |
| ATOM | 807 | CB LYS A 120 | 54.253 20.042 48.092 1.00 18.79 | A | | ATOM | 887 | CB LYS A 130 | 53.271 12.708 65.794 1.00 15.19 | A |
| ATOM | 808 | CG LYS A 120 | 53.520 21.374 48.433 1.00 22.06 | A | | ATOM | 888 | CG LYS A 130 | 53.797 11.624 64.895 1.00 19.58 | A |
| ATOM | 809 | CD LYS A 120 | 54.246 22.139 49.562 1.00 27.81 | A | | ATOM | 889 | CD LYS A 130 | 55.310 11.807 64.681 1.00 26.37 | A |
| ATOM | 810 | CE LYS A 120 | 53.504 23.438 49.957 1.00 30.14 | A | | ATOM | 890 | CE LYS A 130 | 55.882 10.559 64.058 1.00 35.28 | A |
| ATOM | 811 | NZ LYS A 120 | 54.295 24.215 50.969 1.00 31.78 | A | | ATOM | 891 | NZ LYS A 130 | 57.302 10.787 63.657 1.00 39.07 | A |
| ATOM | 812 | C LYS A 120 | 53.009 18.930 49.985 1.00 18.27 | A | | ATOM | 892 | C LYS A 130 | 51.384 13.683 67.120 1.00 17.39 | A |
| ATOM | 813 | O LYS A 120 | 52.803 19.483 51.066 1.00 20.99 | A | | ATOM | 893 | O LYS A 130 | 51.257 13.325 68.312 1.00 17.81 | A |
| ATOM | 814 | N VAL A 121 | 52.083 18.169 49.399 1.00 16.70 | A | | ATOM | 894 | N GLN A 131 | 51.219 14.944 66.752 1.00 14.66 | A |
| ATOM | 815 | CA VAL A 121 | 50.752 17.979 49.987 1.00 18.72 | A | | ATOM | 895 | CA GLN A 131 | 50.854 15.963 67.725 1.00 16.42 | A |
| ATOM | 816 | CB VAL A 121 | 49.842 17.145 49.062 1.00 20.27 | A | | ATOM | 896 | CB GLN A 131 | 50.777 17.316 67.009 1.00 16.86 | A |
| ATOM | 817 | CG1 VAL A 121 | 48.522 16.809 49.774 1.00 23.32 | A | | ATOM | 897 | CG GLN A 131 | 50.580 18.515 67.902 1.00 15.51 | A |
| ATOM | 818 | CG2 VAL A 121 | 49.554 17.932 47.799 1.00 20.24 | A | | ATOM | 898 | CD GLN A 131 | 51.867 18.902 68.677 1.00 15.25 | A |
| ATOM | 819 | C VAL A 121 | 50.831 17.287 51.352 1.00 17.89 | A | | ATOM | 899 | OE1 GLN A 131 | 52.903 18.294 68.509 1.00 16.60 | A |
| ATOM | 820 | O VAL A 121 | 50.048 17.590 52.267 1.00 20.95 | A | | ATOM | 900 | NE2 GLN A 131 | 51.765 19.912 69.511 1.00 14.80 | A |
| ATOM | 821 | N THR A 122 | 51.789 16.392 51.510 1.00 17.24 | A | | ATOM | 901 | C GLN A 131 | 49.511 15.608 68.384 1.00 17.28 | A |
| ATOM | 822 | CA THR A 122 | 51.928 15.650 52.769 1.00 13.75 | A | | ATOM | 902 | O GLN A 131 | 49.321 15.790 69.609 1.00 14.90 | A |
| ATOM | 823 | CB THR A 122 | 52.195 14.140 52.520 1.00 17.09 | A | | ATOM | 903 | N LEU A 132 | 48.587 15.041 67.601 1.00 13.19 | A |
| ATOM | 824 | OG1 THR A 122 | 53.343 13.991 51.678 1.00 19.86 | A | | ATOM | 904 | CA LEU A 132 | 47.261 14.702 68.103 1.00 14.11 | A |
| ATOM | 825 | CG2 THR A 122 | 51.024 13.493 51.845 1.00 20.58 | A | | ATOM | 905 | CB LEU A 132 | 46.211 14.857 66.968 1.00 14.22 | A |
| ATOM | 826 | C THR A 122 | 53.024 16.105 53.698 1.00 16.74 | A | | ATOM | 906 | CG LEU A 132 | 46.089 16.276 66.383 1.00 13.26 | A |
| ATOM | 827 | O THR A 122 | 53.319 15.384 54.663 1.00 23.10 | A | | ATOM | 907 | CD1 LEU A 132 | 45.241 16.219 65.166 1.00 16.54 | A |
| ATOM | 828 | N GLU A 123 | 53.630 17.260 53.443 1.00 18.46 | A | | ATOM | 908 | CD2 LEU A 132 | 45.559 17.272 67.409 1.00 16.72 | A |
| ATOM | 829 | CA GLU A 123 | 54.737 17.685 54.293 1.00 23.68 | A | | ATOM | 909 | C LEU A 132 | 47.122 13.297 68.702 1.00 12.75 | A |
| ATOM | 830 | CB GLU A 123 | 55.411 18.953 53.753 1.00 27.02 | A | | ATOM | 910 | O LEU A 132 | 46.054 12.934 69.188 1.00 14.27 | A |
| ATOM | 831 | CG GLU A 123 | 54.541 20.199 53.721 1.00 29.27 | A | | ATOM | 911 | N GLY A 133 | 48.218 12.537 68.651 1.00 12.87 | A |
| ATOM | 832 | CD GLU A 123 | 55.298 21.421 53.174 1.00 40.14 | A | | ATOM | 912 | CA GLY A 133 | 48.262 11.172 69.164 1.00 16.62 | A |
| ATOM | 833 | OE1 GLU A 123 | 56.362 21.223 52.525 1.00 47.68 | A | | ATOM | 913 | C GLY A 133 | 47.469 10.213 68.286 1.00 18.63 | A |
| ATOM | 834 | OE2 GLU A 123 | 54.831 22.564 53.372 1.00 38.37 | A | | ATOM | 914 | O GLY A 133 | 46.985 9.167 68.755 1.00 18.98 | A |
| ATOM | 835 | C GLU A 123 | 54.432 17.881 55.766 1.00 21.54 | A | | ATOM | 915 | N LEU A 134 | 47.412 10.551 67.000 1.00 14.72 | A |
| ATOM | 836 | O GLU A 123 | 55.336 17.759 56.579 1.00 22.76 | A | | ATOM | 916 | CA LEU A 134 | 46.610 9.785 66.035 1.00 13.26 | A |
| ATOM | 837 | N ASN A 124 | 53.195 18.195 56.124 1.00 19.03 | A | | ATOM | 917 | CB LEU A 134 | 45.612 10.747 65.330 1.00 14.93 | A |
| ATOM | 838 | CA ASN A 124 | 52.914 18.360 57.548 1.00 21.23 | A | | ATOM | 918 | CG LEU A 134 | 44.517 11.451 66.173 1.00 15.19 | A |
| ATOM | 839 | CB ASN A 124 | 52.212 19.696 57.819 1.00 21.09 | A | | ATOM | 919 | CD1 LEU A 134 | 43.652 12.385 65.279 1.00 18.10 | A |
| ATOM | 840 | CG ASN A 124 | 53.031 20.872 57.361 1.00 24.83 | A | | ATOM | 920 | CD2 LEU A 134 | 43.637 10.367 66.866 1.00 17.35 | A |

Fig. 4 cont.

| | | | | | | | | | | | | | | |
|---|---|---|---|---|---|---|---|---|---|---|---|---|---|---|
| ATOM | 921 | C | LEU A 134 | 47.391 | 9.004 | 64.973 | 1.00 | 15.08 | A | ATOM | 1001 | CA LYS A 145 | 50.722 | 4.369 | 49.065 | 1.00 | 19.42 | A |
| ATOM | 922 | O | LEU A 134 | 46.795 | 8.340 | 64.110 | 1.00 | 15.55 | A | ATOM | 1002 | CB LYS A 145 | 49.382 | 3.772 | 49.481 | 1.00 | 12.89 | A |
| ATOM | 923 | N | TYR A 135 | 48.703 | 9.069 | 65.015 | 1.00 | 13.63 | A | ATOM | 1003 | CG LYS A 145 | 48.462 | 3.387 | 48.296 | 1.00 | 12.93 | A |
| ATOM | 924 | CA | TYR A 135 | 49.508 | 8.427 | 64.009 | 1.00 | 14.18 | A | ATOM | 1004 | CD LYS A 145 | 47.295 | 2.559 | 48.800 | 1.00 | 14.13 | A |
| ATOM | 925 | CB | TYR A 135 | 50.872 | 9.074 | 63.983 | 1.00 | 15.88 | A | ATOM | 1005 | CE LYS A 145 | 46.322 | 2.197 | 47.659 | 1.00 | 17.36 | A |
| ATOM | 926 | CG | TYR A 135 | 51.751 | 8.606 | 62.845 | 1.00 | 18.88 | A | ATOM | 1006 | NZ LYS A 145 | 45.251 | 1.257 | 48.130 | 1.00 | 15.65 | A |
| ATOM | 927 | CD1 | TYR A 135 | 51.313 | 8.675 | 61.513 | 1.00 | 17.43 | A | ATOM | 1007 | C  LYS A 145 | 50.513 | 5.640 | 48.241 | 1.00 | 18.90 | A |
| ATOM | 928 | CE1 | TYR A 135 | 52.146 | 8.294 | 60.453 | 1.00 | 20.40 | A | ATOM | 1008 | O  LYS A 145 | 50.618 | 5.633 | 46.992 | 1.00 | 13.89 | A |
| ATOM | 929 | CD2 | TYR A 135 | 53.038 | 8.149 | 63.083 | 1.00 | 24.89 | A | ATOM | 1009 | N  PHE A 146 | 50.194 | 6.740 | 48.924 | 1.00 | 12.42 | A |
| ATOM | 930 | CE2 | TYR A 135 | 53.884 | 7.780 | 62.029 | 1.00 | 30.23 | A | ATOM | 1010 | CA PHE A 146 | 49.995 | 8.026 | 48.262 | 1.00 | 12.01 | A |
| ATOM | 931 | CZ | TYR A 135 | 53.429 | 7.856 | 60.715 | 1.00 | 24.98 | A | ATOM | 1011 | CB PHE A 146 | 49.728 | 9.106 | 49.346 | 1.00 | 12.45 | A |
| ATOM | 932 | OH | TYR A 135 | 54.270 | 7.522 | 59.669 | 1.00 | 23.96 | A | ATOM | 1012 | CG PHE A 146 | 49.391 | 10.458 | 48.799 | 1.00 | 15.17 | A |
| ATOM | 933 | C | TYR A 135 | 49.651 | 6.939 | 64.264 | 1.00 | 16.89 | A | ATOM | 1013 | CD1 PHE A 146 | 48.085 | 10.741 | 48.391 | 1.00 | 14.90 | A |
| ATOM | 934 | O | TYR A 135 | 50.272 | 6.518 | 65.262 | 1.00 | 16.09 | A | ATOM | 1014 | CD2 PHE A 146 | 50.360 | 11.475 | 48.733 | 1.00 | 11.05 | A |
| ATOM | 935 | N | THR A 136 | 49.100 | 6.138 | 63.366 | 1.00 | 15.31 | A | ATOM | 1015 | CE1 PHE A 146 | 47.738 | 12.036 | 47.935 | 1.00 | 14.09 | A |
| ATOM | 936 | CA | THR A 136 | 49.205 | 4.679 | 63.522 | 1.00 | 17.84 | A | ATOM | 1016 | CE2 PHE A 146 | 50.020 | 12.759 | 48.279 | 1.00 | 14.12 | A |
| ATOM | 937 | CB | THR A 136 | 47.853 | 4.016 | 63.768 | 1.00 | 18.98 | A | ATOM | 1017 | CZ PHE A 146 | 48.701 | 13.035 | 47.880 | 1.00 | 14.02 | A |
| ATOM | 938 | OG1 | THR A 136 | 47.111 | 3.937 | 62.538 | 1.00 | 20.03 | A | ATOM | 1018 | C  PHE A 146 | 51.272 | 8.394 | 47.473 | 1.00 | 14.08 | A |
| ATOM | 939 | CG2 | THR A 136 | 47.053 | 4.820 | 64.806 | 1.00 | 18.26 | A | ATOM | 1019 | O  PHE A 146 | 51.230 | 8.744 | 46.282 | 1.00 | 14.21 | A |
| ATOM | 940 | C | THR A 136 | 49.780 | 4.097 | 62.237 | 1.00 | 16.00 | A | ATOM | 1020 | N  LEU A 147 | 52.414 | 8.308 | 48.148 | 1.00 | 16.78 | A |
| ATOM | 941 | O | THR A 136 | 50.043 | 4.825 | 61.277 | 1.00 | 16.21 | A | ATOM | 1021 | CA LEU A 147 | 53.656 | 8.684 | 47.492 | 1.00 | 16.95 | A |
| ATOM | 942 | N | ASP A 137 | 50.009 | 2.789 | 62.222 | 1.00 | 16.77 | A | ATOM | 1022 | CB LEU A 147 | 54.812 | 8.679 | 48.502 | 1.00 | 17.86 | A |
| ATOM | 943 | CA | ASP A 137 | 50.580 | 2.187 | 61.023 | 1.00 | 20.45 | A | ATOM | 1023 | CG LEU A 147 | 54.729 | 9.753 | 49.614 | 1.00 | 16.78 | A |
| ATOM | 944 | CB | ASP A 137 | 50.880 | 0.695 | 61.240 | 1.00 | 25.16 | A | ATOM | 1024 | CD1 LEU A 147 | 55.762 | 9.420 | 50.695 | 1.00 | 20.82 | A |
| ATOM | 945 | CG | ASP A 137 | 51.785 | 0.459 | 62.438 | 1.00 | 41.14 | A | ATOM | 1025 | CD2 LEU A 147 | 54.947 | 11.153 | 49.025 | 1.00 | 20.82 | A |
| ATOM | 946 | OD1 | ASP A 137 | 52.793 | 1.199 | 62.598 | 1.00 | 38.70 | A | ATOM | 1026 | C  LEU A 147 | 53.928 | 7.746 | 46.309 | 1.00 | 17.52 | A |
| ATOM | 947 | OD2 | ASP A 137 | 51.477 | -0.478 | 63.227 | 1.00 | 53.46 | A | ATOM | 1027 | O  LEU A 147 | 54.408 | 8.216 | 45.276 | 1.00 | 18.27 | A |
| ATOM | 948 | C | ASP A 137 | 49.692 | 2.341 | 59.817 | 1.00 | 17.79 | A | ATOM | 1028 | N  GLU A 148 | 53.600 | 6.463 | 46.443 | 1.00 | 17.17 | A |
| ATOM | 949 | O | ASP A 137 | 50.218 | 2.334 | 58.694 | 1.00 | 19.69 | A | ATOM | 1029 | CA GLU A 148 | 53.814 | 5.535 | 45.317 | 1.00 | 18.06 | A |
| ATOM | 950 | N | CYS A 138 | 48.379 | 2.435 | 60.032 | 1.00 | 17.02 | A | ATOM | 1030 | CB GLU A 148 | 53.522 | 4.109 | 45.762 | 1.00 | 16.45 | A |
| ATOM | 951 | CA | CYS A 138 | 47.444 | 2.620 | 58.923 | 1.00 | 17.44 | A | ATOM | 1031 | CG GLU A 148 | 54.620 | 3.553 | 46.615 | 1.00 | 21.06 | A |
| ATOM | 952 | CB | CYS A 138 | 45.995 | 2.697 | 59.381 | 1.00 | 17.93 | A | ATOM | 1032 | CD GLU A 148 | 54.262 | 2.262 | 47.326 | 1.00 | 20.88 | A |
| ATOM | 953 | SG | CYS A 138 | 45.413 | 1.149 | 60.065 | 1.00 | 27.52 | A | ATOM | 1033 | OE1 GLU A 148 | 53.069 | 1.928 | 47.463 | 1.00 | 20.35 | A |
| ATOM | 954 | C | CYS A 138 | 47.779 | 3.912 | 58.205 | 1.00 | 17.04 | A | ATOM | 1034 | OE2 GLU A 148 | 55.198 | 1.579 | 47.796 | 1.00 | 26.07 | A |
| ATOM | 955 | O | CYS A 138 | 47.767 | 3.945 | 56.976 | 1.00 | 15.66 | A | ATOM | 1035 | C  GLU A 148 | 52.952 | 5.876 | 44.106 | 1.00 | 18.16 | A |
| ATOM | 956 | N | GLU A 139 | 48.065 | 4.976 | 58.961 | 1.00 | 14.11 | A | ATOM | 1036 | O  GLU A 148 | 53.395 | 5.777 | 42.959 | 1.00 | 18.30 | A |
| ATOM | 957 | CA | GLU A 139 | 48.410 | 6.224 | 58.310 | 1.00 | 11.99 | A | ATOM | 1037 | N  ILE A 149 | 51.708 | 6.255 | 44.337 | 1.00 | 15.90 | A |
| ATOM | 958 | CB | GLU A 139 | 48.378 | 7.386 | 59.327 | 1.00 | 11.53 | A | ATOM | 1038 | CA ILE A 149 | 50.819 | 6.620 | 43.233 | 1.00 | 18.35 | A |
| ATOM | 959 | CG | GLU A 139 | 46.961 | 7.795 | 59.735 | 1.00 | 14.57 | A | ATOM | 1039 | CB ILE A 149 | 49.415 | 6.964 | 43.802 | 1.00 | 18.30 | A |
| ATOM | 960 | CD | GLU A 139 | 46.255 | 6.741 | 60.593 | 1.00 | 15.16 | A | ATOM | 1040 | CG2 ILE A 149 | 48.554 | 7.714 | 42.782 | 1.00 | 17.22 | A |
| ATOM | 961 | OE1 | GLU A 139 | 46.874 | 6.275 | 61.592 | 1.00 | 16.51 | A | ATOM | 1041 | CG1 ILE A 149 | 48.733 | 5.678 | 44.270 | 1.00 | 20.37 | A |
| ATOM | 962 | OE2 | GLU A 139 | 45.085 | 6.400 | 60.291 | 1.00 | 14.56 | A | ATOM | 1042 | CD1 ILE A 149 | 47.492 | 5.937 | 45.156 | 1.00 | 17.10 | A |
| ATOM | 963 | C | GLU A 139 | 49.774 | 6.146 | 57.623 | 1.00 | 13.77 | A | ATOM | 1043 | C  ILE A 149 | 51.393 | 7.790 | 42.423 | 1.00 | 20.39 | A |
| ATOM | 964 | O | GLU A 139 | 49.968 | 6.686 | 56.565 | 1.00 | 14.72 | A | ATOM | 1044 | O  ILE A 149 | 51.293 | 7.821 | 41.181 | 1.00 | 17.97 | A |
| ATOM | 965 | N | ALA A 140 | 50.730 | 5.463 | 58.239 | 1.00 | 15.94 | A | ATOM | 1045 | N  PHE A 150 | 52.043 | 8.730 | 43.113 | 1.00 | 15.71 | A |
| ATOM | 966 | CA | ALA A 140 | 52.056 | 5.366 | 57.620 | 1.00 | 16.55 | A | ATOM | 1046 | CA PHE A 150 | 52.583 | 9.909 | 42.443 | 1.00 | 15.95 | A |
| ATOM | 967 | CB | ALA A 140 | 52.998 | 4.596 | 58.530 | 1.00 | 17.18 | A | ATOM | 1047 | CB PHE A 150 | 52.456 | 11.150 | 43.377 | 1.00 | 17.59 | A |
| ATOM | 968 | C | ALA A 140 | 51.902 | 4.643 | 56.277 | 1.00 | 14.64 | A | ATOM | 1048 | CG PHE A 150 | 51.072 | 11.734 | 43.428 | 1.00 | 15.22 | A |
| ATOM | 969 | O | ALA A 140 | 52.493 | 5.069 | 55.273 | 1.00 | 18.59 | A | ATOM | 1049 | CD1 PHE A 150 | 50.146 | 11.300 | 44.389 | 1.00 | 14.28 | A |
| ATOM | 970 | N | LYS A 141 | 51.101 | 3.583 | 56.273 | 1.00 | 16.05 | A | ATOM | 1050 | CD2 PHE A 150 | 50.710 | 12.720 | 42.539 | 1.00 | 15.58 | A |
| ATOM | 971 | CA | LYS A 141 | 50.858 | 2.825 | 55.027 | 1.00 | 19.65 | A | ATOM | 1051 | CE1 PHE A 150 | 48.847 | 11.872 | 44.444 | 1.00 | 13.75 | A |
| ATOM | 972 | CB | LYS A 141 | 50.039 | 1.572 | 55.328 | 1.00 | 21.79 | A | ATOM | 1052 | CE2 PHE A 150 | 49.441 | 13.297 | 42.578 | 1.00 | 12.34 | A |
| ATOM | 973 | CG | LYS A 141 | 50.857 | 0.473 | 55.974 | 1.00 | 27.52 | A | ATOM | 1053 | CZ PHE A 150 | 48.506 | 12.884 | 43.524 | 1.00 | 12.75 | A |
| ATOM | 974 | CD | LYS A 141 | 49.980 | -0.733 | 56.303 | 1.00 | 39.39 | A | ATOM | 1054 | C  PHE A 150 | 54.041 | 9.827 | 42.014 | 1.00 | 18.97 | A |
| ATOM | 975 | CE | LYS A 141 | 50.624 | -1.632 | 57.369 | 1.00 | 46.46 | A | ATOM | 1055 | O  PHE A 150 | 54.521 | 10.656 | 41.234 | 1.00 | 20.02 | A |
| ATOM | 976 | NZ | LYS A 141 | 52.018 | -2.039 | 57.011 | 1.00 | 52.23 | A | ATOM | 1056 | N  LYS A 151 | 54.741 | 8.827 | 42.514 | 1.00 | 19.20 | A |
| ATOM | 977 | C | LYS A 141 | 50.130 | 3.677 | 53.996 | 1.00 | 17.71 | A | ATOM | 1057 | CA LYS A 151 | 56.175 | 8.735 | 42.319 | 1.00 | 22.09 | A |
| ATOM | 978 | O | LYS A 141 | 50.426 | 3.625 | 52.796 | 1.00 | 16.41 | A | ATOM | 1058 | CB LYS A 151 | 56.652 | 7.386 | 42.851 | 1.00 | 23.29 | A |
| ATOM | 979 | N | ALA A 142 | 49.178 | 4.486 | 54.460 | 1.00 | 16.06 | A | ATOM | 1059 | CG LYS A 151 | 58.151 | 7.257 | 42.927 | 1.00 | 30.86 | A |
| ATOM | 980 | CA | ALA A 142 | 48.437 | 5.360 | 53.549 | 1.00 | 16.77 | A | ATOM | 1060 | CD LYS A 151 | 58.719 | 8.009 | 44.124 | 1.00 | 42.33 | A |
| ATOM | 981 | CB | ALA A 142 | 47.306 | 6.064 | 54.309 | 1.00 | 12.74 | A | ATOM | 1061 | CE LYS A 151 | 60.115 | 7.464 | 44.478 | 1.00 | 51.09 | A |
| ATOM | 982 | C | ALA A 142 | 49.372 | 6.393 | 52.887 | 1.00 | 17.05 | A | ATOM | 1062 | NZ LYS A 151 | 61.083 | 7.646 | 43.338 | 1.00 | 57.05 | A |
| ATOM | 983 | O | ALA A 142 | 49.256 | 6.646 | 51.688 | 1.00 | 13.73 | A | ATOM | 1063 | C  LYS A 151 | 56.752 | 8.952 | 40.931 | 1.00 | 24.62 | A |
| ATOM | 984 | N | VAL A 143 | 50.289 | 6.995 | 53.653 | 1.00 | 13.79 | A | ATOM | 1064 | O  LYS A 151 | 57.726 | 9.687 | 40.761 | 1.00 | 23.66 | A |
| ATOM | 985 | CA | VAL A 143 | 51.202 | 7.982 | 53.067 | 1.00 | 12.79 | A | ATOM | 1065 | N  GLU A 152 | 56.154 | 8.317 | 39.937 | 1.00 | 22.06 | A |
| ATOM | 986 | CB | VAL A 143 | 52.028 | 8.676 | 54.200 | 1.00 | 14.21 | A | ATOM | 1066 | CA GLU A 152 | 56.691 | 8.428 | 38.587 | 1.00 | 29.94 | A |
| ATOM | 987 | CG1 | VAL A 143 | 53.165 | 9.500 | 53.618 | 1.00 | 18.43 | A | ATOM | 1067 | CB GLU A 152 | 56.739 | 7.038 | 37.946 | 1.00 | 30.02 | A |
| ATOM | 988 | CG2 | VAL A 143 | 51.096 | 9.583 | 55.003 | 1.00 | 15.90 | A | ATOM | 1068 | CG GLU A 152 | 57.517 | 6.013 | 38.755 | 1.00 | 36.91 | A |
| ATOM | 989 | C | VAL A 143 | 52.131 | 7.285 | 52.056 | 1.00 | 16.89 | A | ATOM | 1069 | CD GLU A 152 | 58.946 | 6.472 | 39.036 | 1.00 | 48.39 | A |
| ATOM | 990 | O | VAL A 143 | 52.413 | 7.809 | 50.978 | 1.00 | 15.09 | A | ATOM | 1070 | OE1 GLU A 152 | 59.565 | 7.058 | 38.119 | 1.00 | 55.97 | A |
| ATOM | 991 | N | GLU A 144 | 52.603 | 6.099 | 52.424 | 1.00 | 17.97 | A | ATOM | 1071 | OE2 GLU A 152 | 59.459 | 6.249 | 40.159 | 1.00 | 56.14 | A |
| ATOM | 992 | CA | GLU A 144 | 53.476 | 5.354 | 51.525 | 1.00 | 21.31 | A | ATOM | 1072 | C  GLU A 152 | 55.919 | 9.372 | 37.692 | 1.00 | 30.37 | A |
| ATOM | 993 | CB | GLU A 144 | 53.888 | 4.022 | 52.168 | 1.00 | 20.21 | A | ATOM | 1073 | O  GLU A 152 | 56.182 | 9.442 | 36.484 | 1.00 | 30.02 | A |
| ATOM | 994 | CG | GLU A 144 | 54.771 | 3.201 | 51.233 | 1.00 | 28.11 | A | ATOM | 1074 | N  GLU A 153 | 54.983 | 10.121 | 38.265 | 1.00 | 21.31 | A |
| ATOM | 995 | CD | GLU A 144 | 55.153 | 1.837 | 51.791 | 1.00 | 38.31 | A | ATOM | 1075 | CA GLU A 153 | 54.179 | 11.030 | 37.452 | 1.00 | 22.42 | A |
| ATOM | 996 | OE1 | GLU A 144 | 54.263 | 0.950 | 51.931 | 1.00 | 42.07 | A | ATOM | 1076 | CB GLU A 153 | 52.810 | 11.244 | 38.100 | 1.00 | 23.56 | A |
| ATOM | 997 | OE2 | GLU A 144 | 56.357 | 1.646 | 52.087 | 1.00 | 43.84 | A | ATOM | 1077 | CG GLU A 153 | 52.062 | 9.958 | 38.384 | 1.00 | 28.65 | A |
| ATOM | 998 | C | GLU A 144 | 52.770 | 5.097 | 50.186 | 1.00 | 18.42 | A | ATOM | 1078 | CD GLU A 153 | 51.560 | 9.250 | 37.129 | 1.00 | 35.31 | A |
| ATOM | 999 | O | GLU A 144 | 53.361 | 5.304 | 49.104 | 1.00 | 18.01 | A | ATOM | 1079 | OE1 GLU A 153 | 51.214 | 9.942 | 36.146 | 1.00 | 35.27 | A |
| ATOM | 1000 | N | LYS A 145 | 51.513 | 4.644 | 50.263 | 1.00 | 17.07 | A | ATOM | 1080 | OE2 GLU A 153 | 51.473 | 7.996 | 37.140 | 1.00 | 36.38 | A |

Fig. 4 cont.

| | | | |
|---|---|---|---|
| ATOM 1081 C GLU A 153 | 54.852 12.373 37.234 1.00 16.40 | A | |
| ATOM 1082 O GLU A 153 | 55.704 12.799 37.996 1.00 21.32 | A | |
| ATOM 1083 N THR A 154 | 54.476 13.021 36.151 1.00 20.37 | A | |
| ATOM 1084 CA THR A 154 | 54.997 14.334 35.828 1.00 23.27 | A | |
| ATOM 1085 CB THR A 154 | 56.043 14.256 34.677 1.00 31.60 | A | |
| ATOM 1086 OG1 THR A 154 | 56.539 15.569 34.417 1.00 44.25 | A | |
| ATOM 1087 CG2 THR A 154 | 55.431 13.696 33.412 1.00 32.94 | A | |
| ATOM 1088 C THR A 154 | 53.790 15.191 35.425 1.00 22.44 | A | |
| ATOM 1089 O THR A 154 | 52.879 14.724 34.737 1.00 21.43 | A | |
| ATOM 1090 N PHE A 155 | 53.772 16.450 35.854 1.00 21.40 | A | |
| ATOM 1091 CA PHE A 155 | 52.628 17.313 35.537 1.00 21.14 | A | |
| ATOM 1092 CB PHE A 155 | 51.843 17.609 36.815 1.00 19.94 | A | |
| ATOM 1093 CG PHE A 155 | 51.322 16.377 37.481 1.00 14.42 | A | |
| ATOM 1094 CD1 PHE A 155 | 50.136 15.803 37.064 1.00 18.18 | A | |
| ATOM 1095 CD2 PHE A 155 | 52.069 15.755 38.492 1.00 21.07 | A | |
| ATOM 1096 CE1 PHE A 155 | 49.677 14.592 37.655 1.00 17.07 | A | |
| ATOM 1097 CE2 PHE A 155 | 51.643 14.564 39.085 1.00 20.12 | A | |
| ATOM 1098 CZ PHE A 155 | 50.436 13.978 38.658 1.00 18.01 | A | |
| ATOM 1099 C PHE A 155 | 52.986 18.625 34.871 1.00 21.02 | A | |
| ATOM 1100 O PHE A 155 | 53.418 19.568 35.530 1.00 20.90 | A | |
| ATOM 1101 N PRO A 156 | 52.798 18.707 33.545 1.00 20.29 | A | |
| ATOM 1102 CD PRO A 156 | 52.347 17.642 32.637 1.00 18.46 | A | |
| ATOM 1103 CA PRO A 156 | 53.112 19.951 32.821 1.00 21.96 | A | |
| ATOM 1104 CB PRO A 156 | 53.160 19.494 31.361 1.00 21.93 | A | |
| ATOM 1105 CG PRO A 156 | 52.096 18.386 31.332 1.00 24.19 | A | |
| ATOM 1106 C PRO A 156 | 52.030 21.009 33.079 1.00 23.19 | A | |
| ATOM 1107 O PRO A 156 | 50.936 20.675 33.570 1.00 20.94 | A | |
| ATOM 1108 N PRO A 157 | 52.318 22.296 32.781 1.00 24.09 | A | |
| ATOM 1109 CD PRO A 157 | 53.500 22.908 32.139 1.00 23.80 | A | |
| ATOM 1110 CA PRO A 157 | 51.291 23.317 33.016 1.00 22.11 | A | |
| ATOM 1111 CB PRO A 157 | 51.900 24.577 32.402 1.00 18.54 | A | |
| ATOM 1112 CG PRO A 157 | 53.373 24.339 32.567 1.00 22.21 | A | |
| ATOM 1113 C PRO A 157 | 50.016 22.927 32.295 1.00 19.97 | A | |
| ATOM 1114 O PRO A 157 | 50.035 22.462 31.137 1.00 22.09 | A | |
| ATOM 1115 N GLY A 158 | 48.896 23.110 32.971 1.00 18.93 | A | |
| ATOM 1116 CA GLY A 158 | 47.630 22.785 32.378 1.00 16.56 | A | |
| ATOM 1117 C GLY A 158 | 47.085 21.414 32.750 1.00 17.44 | A | |
| ATOM 1118 O GLY A 158 | 45.862 21.211 32.616 1.00 17.03 | A | |
| ATOM 1119 N SER A 159 | 47.968 20.495 33.159 1.00 15.72 | A | |
| ATOM 1120 CA SER A 159 | 47.497 19.175 33.583 1.00 13.74 | A | |
| ATOM 1121 CB SER A 159 | 48.625 18.155 33.681 1.00 15.18 | A | |
| ATOM 1122 OG SER A 159 | 49.621 18.530 34.587 1.00 18.34 | A | |
| ATOM 1123 C SER A 159 | 46.852 19.345 34.958 1.00 19.38 | A | |
| ATOM 1124 O SER A 159 | 47.035 20.381 35.622 1.00 17.22 | A | |
| ATOM 1125 N SER A 160 | 46.083 18.337 35.363 1.00 15.18 | A | |
| ATOM 1126 CA SER A 160 | 45.398 18.428 36.661 1.00 15.99 | A | |
| ATOM 1127 CB SER A 160 | 43.912 18.730 36.453 1.00 14.10 | A | |
| ATOM 1128 OG SER A 160 | 43.719 19.939 35.714 1.00 16.46 | A | |
| ATOM 1129 C SER A 160 | 45.493 17.157 37.479 1.00 14.44 | A | |
| ATOM 1130 O SER A 160 | 45.594 16.056 36.946 1.00 15.87 | A | |
| ATOM 1131 N ILE A 161 | 45.438 17.345 38.803 1.00 11.90 | A | |
| ATOM 1132 CA ILE A 161 | 45.410 16.244 39.766 1.00 14.64 | A | |
| ATOM 1133 CB ILE A 161 | 46.518 16.435 40.771 1.00 14.46 | A | |
| ATOM 1134 CG2 ILE A 161 | 46.317 15.510 41.974 1.00 14.92 | A | |
| ATOM 1135 CG1 ILE A 161 | 47.861 16.286 40.030 1.00 16.02 | A | |
| ATOM 1136 CD1 ILE A 161 | 49.027 16.706 40.827 1.00 15.38 | A | |
| ATOM 1137 C ILE A 161 | 44.005 16.349 40.397 1.00 15.90 | A | |
| ATOM 1138 O ILE A 161 | 43.617 17.435 40.873 1.00 13.35 | A | |
| ATOM 1139 N LEU A 162 | 43.254 15.240 40.399 1.00 13.38 | A | |
| ATOM 1140 CA LEU A 162 | 41.886 15.223 40.936 1.00 15.08 | A | |
| ATOM 1141 CB LEU A 162 | 40.891 14.668 39.888 1.00 12.91 | A | |
| ATOM 1142 CG LEU A 162 | 40.744 15.369 38.522 1.00 20.50 | A | |
| ATOM 1143 CD1 LEU A 162 | 40.740 16.900 38.705 1.00 16.08 | A | |
| ATOM 1144 CD2 LEU A 162 | 41.835 14.948 37.610 1.00 26.11 | A | |
| ATOM 1145 C LEU A 162 | 41.803 14.339 42.156 1.00 13.21 | A | |
| ATOM 1146 O LEU A 162 | 42.296 13.203 42.122 1.00 14.55 | A | |
| ATOM 1147 N PHE A 163 | 41.188 14.831 43.227 1.00 9.55 | A | |
| ATOM 1148 CA PHE A 163 | 41.014 14.062 44.442 1.00 8.81 | A | |
| ATOM 1149 CB PHE A 163 | 41.738 14.738 45.620 1.00 11.44 | A | |
| ATOM 1150 CG PHE A 163 | 43.242 14.737 45.514 1.00 14.64 | A | |
| ATOM 1151 CD1 PHE A 163 | 43.963 13.543 45.532 1.00 13.87 | A | |
| ATOM 1152 CD2 PHE A 163 | 43.923 15.941 45.478 1.00 12.75 | A | |
| ATOM 1153 CE1 PHE A 163 | 45.371 13.553 45.529 1.00 13.64 | A | |
| ATOM 1154 CE2 PHE A 163 | 45.320 15.971 45.472 1.00 13.54 | A | |
| ATOM 1155 CZ PHE A 163 | 46.048 14.786 45.503 1.00 12.74 | A | |
| ATOM 1156 C PHE A 163 | 39.513 14.021 44.814 1.00 12.43 | A | |
| ATOM 1157 O PHE A 163 | 38.869 15.063 44.866 1.00 13.21 | A | |
| ATOM 1158 N ALA A 164 | 38.963 12.830 45.067 1.00 10.83 | A | |
| ATOM 1159 CA ALA A 164 | 37.583 12.722 45.541 1.00 10.31 | A | |
| ATOM 1160 CB ALA A 164 | 36.791 11.737 44.664 1.00 12.35 | A | |
| ATOM 1161 C ALA A 164 | 37.702 12.157 46.963 1.00 11.09 | A |
| ATOM 1162 O ALA A 164 | 38.451 11.198 47.191 1.00 13.69 | A |
| ATOM 1163 N LEU A 165 | 36.978 12.763 47.892 1.00 11.97 | A |
| ATOM 1164 CA LEU A 165 | 37.016 12.341 49.316 1.00 12.52 | A |
| ATOM 1165 CB LEU A 165 | 37.282 13.545 50.236 1.00 12.49 | A |
| ATOM 1166 CG LEU A 165 | 38.734 14.054 50.272 1.00 14.03 | A |
| ATOM 1167 CD1 LEU A 165 | 39.158 14.678 48.924 1.00 13.61 | A |
| ATOM 1168 CD2 LEU A 165 | 38.847 15.061 51.405 1.00 14.62 | A |
| ATOM 1169 C LEU A 165 | 35.626 11.787 49.575 1.00 14.54 | A |
| ATOM 1170 O LEU A 165 | 34.653 12.542 49.538 1.00 13.84 | A |
| ATOM 1171 N SER A 166 | 35.524 10.481 49.860 1.00 11.75 | A |
| ATOM 1172 CA SER A 166 | 34.188 9.928 50.065 1.00 14.00 | A |
| ATOM 1173 CB SER A 166 | 34.232 8.405 49.951 1.00 15.67 | A |
| ATOM 1174 OG SER A 166 | 34.648 7.837 51.195 1.00 14.68 | A |
| ATOM 1175 C SER A 166 | 33.623 10.331 51.428 1.00 18.49 | A |
| ATOM 1176 O SER A 166 | 34.351 10.764 52.341 1.00 15.54 | A |
| ATOM 1177 N PRO A 167 | 32.307 10.153 51.607 1.00 16.95 | A |
| ATOM 1178 CD PRO A 167 | 31.321 9.732 50.611 1.00 18.43 | A |
| ATOM 1179 CA PRO A 167 | 31.651 10.505 52.867 1.00 20.00 | A |
| ATOM 1180 CB PRO A 167 | 30.188 10.123 52.617 1.00 17.92 | A |
| ATOM 1181 CG PRO A 167 | 30.025 10.337 51.187 1.00 19.85 | A |
| ATOM 1182 C PRO A 167 | 32.245 9.782 54.078 1.00 20.36 | A |
| ATOM 1183 O PRO A 167 | 32.133 10.281 55.207 1.00 22.63 | A |
| ATOM 1184 N THR A 168 | 32.856 8.616 53.847 1.00 18.07 | A |
| ATOM 1185 CA THR A 168 | 33.482 7.855 54.932 1.00 19.74 | A |
| ATOM 1186 CB THR A 168 | 33.119 6.357 54.823 1.00 23.81 | A |
| ATOM 1187 OG1 THR A 168 | 33.396 5.870 53.505 1.00 22.70 | A |
| ATOM 1188 CG2 THR A 168 | 31.625 6.176 55.132 1.00 24.18 | A |
| ATOM 1189 C THR A 168 | 35.006 8.017 55.014 1.00 24.25 | A |
| ATOM 1190 O THR A 168 | 35.673 7.425 55.879 1.00 25.69 | A |
| ATOM 1191 N GLY A 169 | 35.582 8.813 54.124 1.00 21.55 | A |
| ATOM 1192 CA GLY A 169 | 37.012 9.017 54.202 1.00 19.02 | A |
| ATOM 1193 C GLY A 169 | 37.934 8.296 53.237 1.00 20.36 | A |
| ATOM 1194 O GLY A 169 | 39.122 8.224 53.503 1.00 22.54 | A |
| ATOM 1195 N SER A 170 | 37.426 7.753 52.126 1.00 18.17 | A |
| ATOM 1196 CA SER A 170 | 38.311 7.122 51.159 1.00 14.08 | A |
| ATOM 1197 CB SER A 170 | 37.604 5.992 50.401 1.00 17.58 | A |
| ATOM 1198 OG SER A 170 | 37.488 4.864 51.253 1.00 24.30 | A |
| ATOM 1199 C SER A 170 | 38.735 8.175 50.155 1.00 14.17 | A |
| ATOM 1200 O SER A 170 | 37.898 8.955 49.683 1.00 17.38 | A |
| ATOM 1201 N LEU A 171 | 40.026 8.181 49.834 1.00 12.24 | A |
| ATOM 1202 CA LEU A 171 | 40.560 9.156 48.895 1.00 12.04 | A |
| ATOM 1203 CB LEU A 171 | 41.905 9.711 49.438 1.00 12.07 | A |
| ATOM 1204 CG LEU A 171 | 42.612 10.706 48.512 1.00 16.63 | A |
| ATOM 1205 CD1 LEU A 171 | 41.872 12.050 48.473 1.00 12.33 | A |
| ATOM 1206 CD2 LEU A 171 | 44.073 10.899 49.017 1.00 18.96 | A |
| ATOM 1207 C LEU A 171 | 40.790 8.517 47.513 1.00 12.47 | A |
| ATOM 1208 O LEU A 171 | 41.604 7.593 47.389 1.00 14.55 | A |
| ATOM 1209 N THR A 172 | 40.092 9.008 46.488 1.00 12.42 | A |
| ATOM 1210 CA THR A 172 | 40.278 8.529 45.128 1.00 12.18 | A |
| ATOM 1211 CB THR A 172 | 38.927 8.426 44.391 1.00 11.47 | A |
| ATOM 1212 OG1 THR A 172 | 38.139 7.380 44.994 1.00 15.91 | A |
| ATOM 1213 CG2 THR A 172 | 39.152 8.084 42.885 1.00 14.76 | A |
| ATOM 1214 C THR A 172 | 41.190 9.542 44.414 1.00 11.38 | A |
| ATOM 1215 O THR A 172 | 40.982 10.780 44.488 1.00 14.03 | A |
| ATOM 1216 N VAL A 173 | 42.244 9.039 43.783 1.00 12.37 | A |
| ATOM 1217 CA VAL A 173 | 43.190 9.896 43.057 1.00 12.26 | A |
| ATOM 1218 CB VAL A 173 | 44.664 9.551 43.407 1.00 14.09 | A |
| ATOM 1219 CG1 VAL A 173 | 45.595 10.477 42.676 1.00 17.86 | A |
| ATOM 1220 CG2 VAL A 173 | 44.864 9.656 44.942 1.00 15.76 | A |
| ATOM 1221 C VAL A 173 | 43.018 9.663 41.567 1.00 15.49 | A |
| ATOM 1222 O VAL A 173 | 42.892 8.530 41.158 1.00 14.86 | A |
| ATOM 1223 N ALA A 174 | 43.035 10.731 40.780 1.00 15.51 | A |
| ATOM 1224 CA ALA A 174 | 42.921 10.627 39.306 1.00 13.76 | A |
| ATOM 1225 CB ALA A 174 | 41.459 10.725 38.854 1.00 13.78 | A |
| ATOM 1226 C ALA A 174 | 43.717 11.772 38.695 1.00 15.45 | A |
| ATOM 1227 O ALA A 174 | 44.011 12.766 39.367 1.00 16.11 | A |
| ATOM 1228 N PHE A 175 | 44.063 11.641 37.421 1.00 15.20 | A |
| ATOM 1229 CA PHE A 175 | 44.801 12.686 36.734 1.00 14.79 | A |
| ATOM 1230 CB PHE A 175 | 46.234 12.233 36.413 1.00 17.67 | A |
| ATOM 1231 CG PHE A 175 | 46.961 11.622 37.566 1.00 19.25 | A |
| ATOM 1232 CD1 PHE A 175 | 47.483 10.329 37.454 1.00 23.09 | A |
| ATOM 1233 CD2 PHE A 175 | 47.134 12.316 38.775 1.00 16.90 | A |
| ATOM 1234 CE1 PHE A 175 | 48.163 9.744 38.551 1.00 23.16 | A |
| ATOM 1235 CE2 PHE A 175 | 47.805 11.747 39.847 1.00 18.70 | A |
| ATOM 1236 CZ PHE A 175 | 48.320 10.464 39.742 1.00 21.99 | A |
| ATOM 1237 C PHE A 175 | 44.118 13.010 35.415 1.00 18.12 | A |
| ATOM 1238 O PHE A 175 | 43.328 12.220 34.871 1.00 18.96 | A |
| ATOM 1239 N SER A 176 | 44.434 14.185 34.899 1.00 16.56 | A |
| ATOM 1240 CA SER A 176 | 43.925 14.606 33.604 1.00 13.85 | A |

Fig. 4 cont.

```
ATOM 1241 CB  SER A 176    42.605 15.343 33.763 1.00 17.71  A    ATOM 1321 CB  ALA A 187    44.978  4.194 43.156 1.00 16.04  A
ATOM 1242 OG  SER A 176    42.169 15.898 32.531 1.00 17.55  A    ATOM 1322 C   ALA A 187    42.751  4.988 43.959 1.00 14.42  A
ATOM 1243 C   SER A 176    44.944 15.507 32.911 1.00 19.30  A    ATOM 1323 O   ALA A 187    42.478  6.197 43.950 1.00 14.29  A
ATOM 1244 O   SER A 176    45.677 16.257 33.544 1.00 17.56  A    ATOM 1324 N   VAL A 188    42.449  4.158 44.953 1.00 15.01  A
ATOM 1245 N   LYS A 177    44.987 15.417 31.581 1.00 19.83  A    ATOM 1325 CA  VAL A 188    41.750  4.583 46.163 1.00 14.98  A
ATOM 1246 CA  LYS A 177    45.908 16.228 30.808 1.00 19.46  A    ATOM 1326 CB  VAL A 188    40.397  3.835 46.315 1.00 16.73  A
ATOM 1247 CB  LYS A 177    46.047 15.615 29.399 1.00 20.76  A    ATOM 1327 CG1 VAL A 188    39.642  4.329 47.532 1.00 20.74  A
ATOM 1248 CG  LYS A 177    44.752 15.672 28.602 1.00 24.09  A    ATOM 1328 CG2 VAL A 188    39.565  4.020 45.049 1.00 16.39  A
ATOM 1249 CD  LYS A 177    44.949 15.148 27.167 1.00 35.32  A    ATOM 1329 C   VAL A 188    42.607  4.258 47.398 1.00 13.61  A
ATOM 1250 CE  LYS A 177    43.737 15.499 26.304 1.00 41.76  A    ATOM 1330 O   VAL A 188    43.156  3.152 47.532 1.00 14.00  A
ATOM 1251 NZ  LYS A 177    42.466 15.094 27.020 1.00 48.46  A    ATOM 1331 N   ILE A 189    42.751  5.237 48.292 1.00 13.36  A
ATOM 1252 C   LYS A 177    45.438 17.689 30.679 1.00 19.13  A    ATOM 1332 CA  ILE A 189    43.453  5.023 49.559 1.00 15.45  A
ATOM 1253 O   LYS A 177    46.205 18.549 30.276 1.00 20.48  A    ATOM 1333 CB  ILE A 189    44.497  6.122 49.812 1.00 12.92  A
ATOM 1254 N   ASP A 178    44.191 17.977 31.035 1.00 17.94  A    ATOM 1334 CG2 ILE A 189    45.268  5.870 51.140 1.00 11.96  A
ATOM 1255 CA  ASP A 178    43.650 19.339 30.915 1.00 20.30  A    ATOM 1335 CG1 ILE A 189    45.494  6.141 48.665 1.00 18.31  A
ATOM 1256 CB  ASP A 178    43.013 19.534 29.526 1.00 22.19  A    ATOM 1336 CD1 ILE A 189    46.593  7.202 48.793 1.00 20.99  A
ATOM 1257 CG  ASP A 178    42.118 18.377 29.133 1.00 28.46  A    ATOM 1337 C   ILE A 189    42.357  5.077 50.655 1.00 13.11  A
ATOM 1258 OD1 ASP A 178    41.482 17.727 30.012 1.00 21.10  A    ATOM 1338 O   ILE A 189    41.718  6.121 50.893 1.00 13.11  A
ATOM 1259 OD2 ASP A 178    42.035 18.110 27.907 1.00 27.72  A    ATOM 1339 N   GLU A 190    42.166  3.955 51.352 1.00 15.14  A
ATOM 1260 C   ASP A 178    42.603 19.569 32.000 1.00 21.15  A    ATOM 1340 CA  GLU A 190    41.130  3.859 52.364 1.00 11.82  A
ATOM 1261 O   ASP A 178    42.798 19.134 33.145 1.00 18.67  A    ATOM 1341 CB  GLU A 190    40.575  2.415 52.375 1.00 17.07  A
ATOM 1262 N   ASP A 179    41.496 20.217 31.653 1.00 17.87  A    ATOM 1342 CG  GLU A 190    40.047  2.049 50.999 1.00 24.08  A
ATOM 1263 CA  ASP A 179    40.474 20.485 32.654 1.00 15.44  A    ATOM 1343 CD  GLU A 190    39.490  0.633 50.902 1.00 42.05  A
ATOM 1264 CB  ASP A 179    39.830 21.853 32.443 1.00 18.29  A    ATOM 1344 OE1 GLU A 190    39.981 -0.295 51.587 1.00 41.02  A
ATOM 1265 CG  ASP A 179    40.818 22.976 32.532 1.00 20.88  A    ATOM 1345 OE2 GLU A 190    38.551  0.459 50.090 1.00 48.26  A
ATOM 1266 OD1 ASP A 179    41.664 22.976 33.455 1.00 17.67  A    ATOM 1346 C   GLU A 190    41.653  4.274 53.724 1.00 14.91  A
ATOM 1267 OD2 ASP A 179    40.760 23.852 31.641 1.00 21.21  A    ATOM 1347 O   GLU A 190    41.928  3.442 54.600 1.00 16.90  A
ATOM 1268 C   ASP A 179    39.371 19.444 32.696 1.00 18.24  A    ATOM 1348 N   ASN A 191    41.837  5.584 53.867 1.00 12.46  A
ATOM 1269 O   ASP A 179    38.477 19.545 33.543 1.00 19.09  A    ATOM 1349 CA  ASN A 191    42.329  6.178 55.117 1.00 10.16  A
ATOM 1270 N   SER A 180    39.399 18.454 31.794 1.00 19.00  A    ATOM 1350 CB  ASN A 191    43.849  6.224 55.134 1.00 11.90  A
ATOM 1271 CA  SER A 180    38.348 17.446 31.808 1.00 15.77  A    ATOM 1351 CG  ASN A 191    44.379  6.668 56.482 1.00 14.72  A
ATOM 1272 CB  SER A 180    38.389 16.592 30.531 1.00 18.23  A    ATOM 1352 OD1 ASN A 191    44.496  7.851 56.727 1.00 12.21  A
ATOM 1273 OG  SER A 180    39.556 15.798 30.491 1.00 23.84  A    ATOM 1353 ND2 ASN A 191    44.655  5.695 57.380 1.00 11.01  A
ATOM 1274 C   SER A 180    38.472 16.532 33.039 1.00 19.39  A    ATOM 1354 C   ASN A 191    41.751  7.574 55.297 1.00 10.61  A
ATOM 1275 O   SER A 180    39.584 16.321 33.578 1.00 19.79  A    ATOM 1355 O   ASN A 191    42.112  8.522 54.567 1.00 11.75  A
ATOM 1276 N   ILE A 181    37.330 16.004 33.471 1.00 17.45  A    ATOM 1356 N   LYS A 192    40.851  7.688 56.283 1.00 12.42  A
ATOM 1277 CA  ILE A 181    37.277 15.119 34.640 1.00 18.13  A    ATOM 1357 CA  LYS A 192    40.152  8.915 56.563 1.00 11.93  A
ATOM 1278 CB  ILE A 181    36.093 15.487 35.564 1.00 17.97  A    ATOM 1358 CB  LYS A 192    39.135  8.696 57.708 1.00 12.26  A
ATOM 1279 CG2 ILE A 181    36.144 14.636 36.824 1.00 19.01  A    ATOM 1359 CG  LYS A 192    38.305  9.920 58.023 1.00 15.48  A
ATOM 1280 CG1 ILE A 181    36.124 16.976 35.941 1.00 20.37  A    ATOM 1360 CD  LYS A 192    37.331  9.567 59.144 1.00 23.26  A
ATOM 1281 CD1 ILE A 181    37.399 17.426 36.551 1.00 20.83  A    ATOM 1361 CE  LYS A 192    36.238 10.638 59.315 1.00 31.26  A
ATOM 1282 C   ILE A 181    37.037 13.681 34.123 1.00 20.43  A    ATOM 1362 NZ  LYS A 192    36.661 11.729 60.223 1.00 27.74  A
ATOM 1283 O   ILE A 181    36.043 13.413 33.426 1.00 20.72  A    ATOM 1363 C   LYS A 192    41.085 10.062 56.903 1.00 10.77  A
ATOM 1284 N   PRO A 182    37.931 12.739 34.469 1.00 18.23  A    ATOM 1364 O   LYS A 192    40.898 11.169 56.423 1.00 11.17  A
ATOM 1285 CD  PRO A 182    39.075 12.851 35.390 1.00 21.13  A    ATOM 1365 N   LEU A 193    42.086  9.820 57.745 1.00 12.02  A
ATOM 1286 CA  PRO A 182    37.759 11.356 34.005 1.00 20.71  A    ATOM 1366 CA  LEU A 193    42.984 10.909 58.086 1.00 10.91  A
ATOM 1287 CB  PRO A 182    39.075 10.693 34.393 1.00 28.54  A    ATOM 1367 CB  LEU A 193    43.973 10.491 59.201 1.00 12.47  A
ATOM 1288 CG  PRO A 182    39.452 11.394 35.620 1.00 27.92  A    ATOM 1368 CG  LEU A 193    43.275 10.441 60.558 1.00 14.49  A
ATOM 1289 C   PRO A 182    36.529 10.692 34.644 1.00 23.15  A    ATOM 1369 CD1 LEU A 193    44.266  9.915 61.573 1.00 14.48  A
ATOM 1290 O   PRO A 182    36.083 11.112 35.709 1.00 18.83  A    ATOM 1370 CD2 LEU A 193    42.821 11.824 60.994 1.00 15.74  A
ATOM 1291 N   GLU A 183    35.974  9.671 33.981 1.00 20.63  A    ATOM 1371 C   LEU A 193    43.745 11.447 56.896 1.00 12.55  A
ATOM 1292 CA  GLU A 183    34.782  8.967 34.485 1.00 18.76  A    ATOM 1372 O   LEU A 193    43.864 12.680 56.754 1.00 11.39  A
ATOM 1293 CB  GLU A 183    34.112  8.149 33.350 1.00 25.39  A    ATOM 1373 N   LEU A 194    44.233 10.565 56.023 1.00 10.66  A
ATOM 1294 CG  GLU A 183    34.887  6.948 32.860 1.00 31.28  A    ATOM 1374 CA  LEU A 194    44.949 11.092 54.857 1.00 10.67  A
ATOM 1295 CD  GLU A 183    34.236  6.233 31.642 1.00 40.63  A    ATOM 1375 CB  LEU A 194    45.656  9.965 54.095 1.00 14.43  A
ATOM 1296 OE1 GLU A 183    32.991  6.329 31.456 1.00 36.11  A    ATOM 1376 CG  LEU A 194    46.448 10.407 52.862 1.00 16.43  A
ATOM 1297 OE2 GLU A 183    34.989  5.559 30.894 1.00 33.77  A    ATOM 1377 CD1 LEU A 194    47.632 11.326 53.220 1.00 16.90  A
ATOM 1298 C   GLU A 183    35.084  8.033 35.665 1.00 17.78  A    ATOM 1378 CD2 LEU A 194    46.946  9.184 52.157 1.00 23.32  A
ATOM 1299 O   GLU A 183    34.173  7.556 36.349 1.00 18.46  A    ATOM 1379 C   LEU A 194    43.994 11.837 53.914 1.00 13.62  A
ATOM 1300 N   THR A 184    36.364  7.768 35.902 1.00 15.98  A    ATOM 1380 O   LEU A 194    44.335 12.902 53.399 1.00 12.76  A
ATOM 1301 CA  THR A 184    36.764  6.863 36.977 1.00 13.57  A    ATOM 1381 N   ALA A 195    42.799 11.291 53.722 1.00 11.48  A
ATOM 1302 CB  THR A 184    36.778  5.387 36.457 1.00 19.26  A    ATOM 1382 CA  ALA A 195    41.817 11.944 52.838 1.00 14.06  A
ATOM 1303 OG1 THR A 184    36.888  4.494 37.570 1.00 19.70  A    ATOM 1383 CB  ALA A 195    40.500 11.117 52.815 1.00 14.43  A
ATOM 1304 CG2 THR A 184    37.964  5.146 35.503 1.00 21.78  A    ATOM 1384 C   ALA A 195    41.554 13.360 53.320 1.00 13.58  A
ATOM 1305 C   THR A 184    38.168  7.270 37.474 1.00 18.36  A    ATOM 1385 O   ALA A 195    41.652 14.340 52.550 1.00 12.95  A
ATOM 1306 O   THR A 184    38.925  7.934 36.745 1.00 20.95  A    ATOM 1386 N   GLU A 196    41.252 13.487 54.615 1.00 10.66  A
ATOM 1307 N   GLY A 185    38.519  6.892 38.691 1.00 17.37  A    ATOM 1387 CA  GLU A 196    40.980 14.796 55.170 1.00 12.15  A
ATOM 1308 CA  GLY A 185    39.838  7.281 39.171 1.00 17.14  A    ATOM 1388 CB  GLU A 196    40.519 14.632 56.608 1.00 13.35  A
ATOM 1309 C   GLY A 185    40.913  6.234 38.898 1.00 16.66  A    ATOM 1389 CG  GLU A 196    39.157 13.963 56.647 1.00 12.51  A
ATOM 1310 O   GLY A 185    40.654  5.204 38.234 1.00 21.05  A    ATOM 1390 CD  GLU A 196    38.634 13.648 58.033 1.00 15.72  A
ATOM 1311 N   ILE A 186    42.122  6.494 39.379 1.00 14.61  A    ATOM 1391 OE1 GLU A 196    37.463 13.197 58.123 1.00 17.34  A
ATOM 1312 CA  ILE A 186    43.230  5.567 39.218 1.00 14.57  A    ATOM 1392 OE2 GLU A 196    39.388 13.836 59.018 1.00 18.03  A
ATOM 1313 CB  ILE A 186    44.576  6.304 39.164 1.00 17.06  A    ATOM 1393 C   GLU A 196    42.187 15.725 55.095 1.00 11.68  A
ATOM 1314 CG2 ILE A 186    45.707  5.281 39.245 1.00 21.31  A    ATOM 1394 O   GLU A 196    42.036 16.926 54.848 1.00 13.07  A
ATOM 1315 CG1 ILE A 186    44.670  7.157 37.888 1.00 19.78  A    ATOM 1395 N   ALA A 197    43.385 15.167 55.281 1.00 10.63  A
ATOM 1316 CD1 ILE A 186    44.654  6.340 36.621 1.00 30.33  A    ATOM 1396 CA  ALA A 197    44.606 15.957 55.253 1.00 12.40  A
ATOM 1317 C   ILE A 186    43.276  4.591 40.386 1.00 14.82  A    ATOM 1397 CB  ALA A 197    45.817 15.062 55.596 1.00 12.61  A
ATOM 1318 O   ILE A 186    43.218  3.370 40.217 1.00 18.03  A    ATOM 1398 C   ALA A 197    44.820 16.618 53.899 1.00 11.67  A
ATOM 1319 N   ALA A 187    43.391  5.143 41.590 1.00 13.44  A    ATOM 1399 O   ALA A 197    45.304 17.744 53.814 1.00 12.68  A
ATOM 1320 CA  ALA A 187    43.493  4.352 42.790 1.00 15.24  A    ATOM 1400 N   VAL A 198    44.462 15.918 52.824 1.00 10.99  A
```

Fig. 4 cont.

| | | | |
|---|---|---|---|
| ATOM 1401 CA VAL A 198 | 44.643 16.513 51.513 1.00 11.43 | A |
| ATOM 1402 CB VAL A 198 | 44.306 15.458 50.416 1.00 13.83 | A |
| ATOM 1403 CG1 VAL A 198 | 44.358 16.113 49.043 1.00 15.82 | A |
| ATOM 1404 CG2 VAL A 198 | 45.337 14.309 50.469 1.00 13.36 | A |
| ATOM 1405 C VAL A 198 | 43.812 17.792 51.359 1.00 11.88 | A |
| ATOM 1406 O VAL A 198 | 44.330 18.817 50.908 1.00 13.15 | A |
| ATOM 1407 N LEU A 199 | 42.557 17.760 51.816 1.00 11.89 | A |
| ATOM 1408 CA LEU A 199 | 41.737 18.975 51.715 1.00 10.88 | A |
| ATOM 1409 CB LEU A 199 | 40.257 18.637 51.894 1.00 9.23 | A |
| ATOM 1410 CG LEU A 199 | 39.296 19.824 51.770 1.00 10.96 | A |
| ATOM 1411 CD1 LEU A 199 | 39.434 20.540 50.442 1.00 13.72 | A |
| ATOM 1412 CD2 LEU A 199 | 37.853 19.265 51.950 1.00 14.44 | A |
| ATOM 1413 C LEU A 199 | 42.160 20.032 52.740 1.00 10.88 | A |
| ATOM 1414 O LEU A 199 | 42.190 21.237 52.436 1.00 11.86 | A |
| ATOM 1415 N GLU A 200 | 42.488 19.572 53.945 1.00 9.51 | A |
| ATOM 1416 CA GLU A 200 | 42.920 20.518 55.000 1.00 10.25 | A |
| ATOM 1417 CB GLU A 200 | 43.250 19.702 56.261 1.00 12.95 | A |
| ATOM 1418 CG GLU A 200 | 43.793 20.486 57.418 1.00 26.15 | A |
| ATOM 1419 CD GLU A 200 | 42.713 21.157 58.239 1.00 29.90 | A |
| ATOM 1420 OE1 GLU A 200 | 41.530 20.746 58.139 1.00 28.74 | A |
| ATOM 1421 OE2 GLU A 200 | 43.073 22.085 59.013 1.00 35.18 | A |
| ATOM 1422 C GLU A 200 | 44.170 21.273 54.520 1.00 12.75 | A |
| ATOM 1423 O GLU A 200 | 44.365 22.450 54.884 1.00 12.26 | A |
| ATOM 1424 N SER A 201 | 45.046 20.592 53.758 1.00 11.40 | A |
| ATOM 1425 CA SER A 201 | 46.271 21.252 53.281 1.00 13.93 | A |
| ATOM 1426 CB SER A 201 | 47.196 20.257 52.556 1.00 18.60 | A |
| ATOM 1427 OG SER A 201 | 46.726 20.004 51.240 1.00 18.05 | A |
| ATOM 1428 C SER A 201 | 45.978 22.443 52.360 1.00 16.45 | A |
| ATOM 1429 O SER A 201 | 46.845 23.296 52.122 1.00 19.12 | A |
| ATOM 1430 N ILE A 202 | 44.767 22.513 51.838 1.00 12.99 | A |
| ATOM 1431 CA ILE A 202 | 44.409 23.624 50.973 1.00 12.93 | A |
| ATOM 1432 CB ILE A 202 | 43.628 23.113 49.749 1.00 15.55 | A |
| ATOM 1433 CG2 ILE A 202 | 43.126 24.289 48.890 1.00 16.62 | A |
| ATOM 1434 CG1 ILE A 202 | 44.587 22.266 48.891 1.00 18.51 | A |
| ATOM 1435 CD1 ILE A 202 | 43.892 21.307 48.045 1.00 21.62 | A |
| ATOM 1436 C ILE A 202 | 43.565 24.664 51.711 1.00 15.28 | A |
| ATOM 1437 O ILE A 202 | 43.916 25.879 51.698 1.00 14.05 | A |
| ATOM 1438 N ILE A 203 | 42.481 24.216 52.363 1.00 12.00 | A |
| ATOM 1439 CA ILE A 203 | 41.585 25.179 53.014 1.00 11.76 | A |
| ATOM 1440 CB ILE A 203 | 40.114 25.010 52.533 1.00 11.36 | A |
| ATOM 1441 CG2 ILE A 203 | 40.017 25.283 50.988 1.00 12.35 | A |
| ATOM 1442 CG1 ILE A 203 | 39.591 23.609 52.901 1.00 13.75 | A |
| ATOM 1443 CD1 ILE A 203 | 38.148 23.369 52.492 1.00 14.43 | A |
| ATOM 1444 C ILE A 203 | 41.561 25.242 54.521 1.00 13.15 | A |
| ATOM 1445 O ILE A 203 | 40.795 26.045 55.095 1.00 14.13 | A |
| ATOM 1446 N GLY A 204 | 42.367 24.414 55.163 1.00 13.63 | A |
| ATOM 1447 CA GLY A 204 | 42.431 24.420 56.624 1.00 12.44 | A |
| ATOM 1448 C GLY A 204 | 43.211 25.614 57.167 1.00 12.72 | A |
| ATOM 1449 O GLY A 204 | 43.754 26.414 56.397 1.00 13.79 | A |
| ATOM 1450 N LYS A 205 | 43.280 25.740 58.490 1.00 14.38 | A |
| ATOM 1451 CA LYS A 205 | 44.006 26.859 59.077 1.00 16.06 | A |
| ATOM 1452 CB LYS A 205 | 43.873 26.762 60.611 1.00 18.53 | A |
| ATOM 1453 CG LYS A 205 | 44.784 27.674 61.436 1.00 27.12 | A |
| ATOM 1454 CD LYS A 205 | 44.557 27.314 62.912 1.00 24.50 | A |
| ATOM 1455 CE LYS A 205 | 45.345 28.205 63.859 1.00 33.44 | A |
| ATOM 1456 NZ LYS A 205 | 44.819 28.089 65.271 1.00 31.26 | A |
| ATOM 1457 C LYS A 205 | 45.477 26.912 58.653 1.00 15.99 | A |
| ATOM 1458 O LYS A 205 | 46.050 28.000 58.481 1.00 16.50 | A |
| ATOM 1459 N ASN A 206 | 46.067 25.729 58.525 1.00 21.61 | A |
| ATOM 1460 CA ASN A 206 | 47.465 25.592 58.121 1.00 24.52 | A |
| ATOM 1461 CB ASN A 206 | 48.132 24.362 58.819 1.00 28.70 | A |
| ATOM 1462 CG ASN A 206 | 48.177 24.470 60.353 1.00 45.08 | A |
| ATOM 1463 OD1 ASN A 206 | 47.388 23.810 61.071 1.00 38.68 | A |
| ATOM 1464 ND2 ASN A 206 | 49.093 25.306 60.866 1.00 39.34 | A |
| ATOM 1465 C ASN A 206 | 47.537 25.381 56.604 1.00 23.54 | A |
| ATOM 1466 O ASN A 206 | 48.583 24.950 56.108 1.00 21.41 | A |
| ATOM 1467 N GLY A 207 | 46.450 25.696 55.881 1.00 17.36 | A |
| ATOM 1468 CA GLY A 207 | 46.388 25.498 54.431 1.00 17.25 | A |
| ATOM 1469 C GLY A 207 | 47.262 26.406 53.570 1.00 15.30 | A |
| ATOM 1470 O GLY A 207 | 47.766 27.428 54.047 1.00 18.66 | A |
| ATOM 1471 N VAL A 208 | 47.423 26.050 52.304 1.00 15.43 | A |
| ATOM 1472 CA VAL A 208 | 48.272 26.806 51.418 1.00 18.37 | A |
| ATOM 1473 CB VAL A 208 | 49.052 25.865 50.463 1.00 21.57 | A |
| ATOM 1474 CG1 VAL A 208 | 49.872 24.885 51.264 1.00 28.20 | A |
| ATOM 1475 CG2 VAL A 208 | 48.073 25.148 49.531 1.00 27.66 | A |
| ATOM 1476 C VAL A 208 | 47.578 27.817 50.531 1.00 16.34 | A |
| ATOM 1477 O VAL A 208 | 48.268 28.537 49.804 1.00 17.63 | A |
| ATOM 1478 N SER A 209 | 46.238 27.880 50.567 1.00 14.31 | A |
| ATOM 1479 CA SER A 209 | 45.538 28.812 49.671 1.00 13.80 | A |
| ATOM 1480 CB SER A 209 | 44.840 28.027 48.532 1.00 12.96 | A |
| ATOM 1481 OG SER A 209 | 44.193 28.930 47.631 1.00 13.15 | A |
| ATOM 1482 C SER A 209 | 44.490 29.679 50.381 1.00 13.20 | A |
| ATOM 1483 O SER A 209 | 43.329 29.274 50.510 1.00 12.50 | A |
| ATOM 1484 N PRO A 210 | 44.877 30.882 50.835 1.00 13.75 | A |
| ATOM 1485 CD PRO A 210 | 46.249 31.393 50.975 1.00 14.05 | A |
| ATOM 1486 CA PRO A 210 | 43.912 31.760 51.507 1.00 13.65 | A |
| ATOM 1487 CB PRO A 210 | 44.728 33.027 51.818 1.00 14.99 | A |
| ATOM 1488 CG PRO A 210 | 46.086 32.471 52.068 1.00 15.66 | A |
| ATOM 1489 C PRO A 210 | 42.762 32.082 50.583 1.00 15.56 | A |
| ATOM 1490 O PRO A 210 | 41.624 32.216 51.020 1.00 12.23 | A |
| ATOM 1491 N GLY A 211 | 43.083 32.225 49.300 1.00 12.92 | A |
| ATOM 1492 CA GLY A 211 | 42.062 32.554 48.310 1.00 15.01 | A |
| ATOM 1493 C GLY A 211 | 40.998 31.498 48.166 1.00 13.34 | A |
| ATOM 1494 O GLY A 211 | 39.832 31.815 48.046 1.00 12.22 | A |
| ATOM 1495 N THR A 212 | 41.395 30.225 48.165 1.00 11.91 | A |
| ATOM 1496 CA THR A 212 | 40.399 29.161 48.051 1.00 12.11 | A |
| ATOM 1497 CB THR A 212 | 41.071 27.830 47.824 1.00 13.54 | A |
| ATOM 1498 OG1 THR A 212 | 41.873 27.910 46.637 1.00 13.58 | A |
| ATOM 1499 CG2 THR A 212 | 40.022 26.720 47.622 1.00 11.35 | A |
| ATOM 1500 C THR A 212 | 39.520 29.111 49.309 1.00 12.81 | A |
| ATOM 1501 O THR A 212 | 38.315 28.969 49.211 1.00 12.08 | A |
| ATOM 1502 N ARG A 213 | 40.137 29.271 50.486 1.00 8.75 | A |
| ATOM 1503 CA ARG A 213 | 39.350 29.229 51.727 1.00 11.33 | A |
| ATOM 1504 CB ARG A 213 | 40.295 29.371 52.955 1.00 11.09 | A |
| ATOM 1505 CG ARG A 213 | 39.542 29.325 54.268 1.00 11.06 | A |
| ATOM 1506 CD ARG A 213 | 40.506 29.334 55.434 1.00 9.84 | A |
| ATOM 1507 NE ARG A 213 | 39.821 29.493 56.732 1.00 10.73 | A |
| ATOM 1508 CZ ARG A 213 | 39.663 28.552 57.659 1.00 12.06 | A |
| ATOM 1509 NH1 ARG A 213 | 40.131 27.316 57.487 1.00 11.55 | A |
| ATOM 1510 NH2 ARG A 213 | 39.036 28.900 58.802 1.00 12.59 | A |
| ATOM 1511 C ARG A 213 | 38.329 30.381 51.720 1.00 10.90 | A |
| ATOM 1512 O ARG A 213 | 37.157 30.189 52.052 1.00 11.94 | A |
| ATOM 1513 N LEU A 214 | 38.786 31.572 51.329 1.00 10.57 | A |
| ATOM 1514 CA LEU A 214 | 37.883 32.728 51.324 1.00 11.18 | A |
| ATOM 1515 CB LEU A 214 | 38.636 34.019 50.957 1.00 14.02 | A |
| ATOM 1516 CG LEU A 214 | 37.779 35.247 50.658 1.00 17.56 | A |
| ATOM 1517 CD1 LEU A 214 | 37.035 35.691 51.919 1.00 19.18 | A |
| ATOM 1518 CD2 LEU A 214 | 38.712 36.361 50.142 1.00 16.52 | A |
| ATOM 1519 C LEU A 214 | 36.740 32.534 50.342 1.00 12.81 | A |
| ATOM 1520 O LEU A 214 | 35.591 32.854 50.654 1.00 12.66 | A |
| ATOM 1521 N SER A 215 | 37.070 32.013 49.159 1.00 11.75 | A |
| ATOM 1522 CA SER A 215 | 36.047 31.778 48.134 1.00 12.09 | A |
| ATOM 1523 CB SER A 215 | 36.744 31.202 46.900 1.00 12.65 | A |
| ATOM 1524 OG SER A 215 | 35.804 30.930 45.860 1.00 12.41 | A |
| ATOM 1525 C SER A 215 | 34.965 30.828 48.626 1.00 11.92 | A |
| ATOM 1526 O SER A 215 | 33.749 31.054 48.407 1.00 12.01 | A |
| ATOM 1527 N VAL A 216 | 35.397 29.727 49.265 1.00 10.32 | A |
| ATOM 1528 CA VAL A 216 | 34.439 28.767 49.840 1.00 9.03 | A |
| ATOM 1529 CB VAL A 216 | 35.169 27.545 50.439 1.00 10.31 | A |
| ATOM 1530 CG1 VAL A 216 | 34.162 26.668 51.209 1.00 12.47 | A |
| ATOM 1531 CG2 VAL A 216 | 35.849 26.745 49.300 1.00 12.20 | A |
| ATOM 1532 C VAL A 216 | 33.584 29.439 50.905 1.00 12.50 | A |
| ATOM 1533 O VAL A 216 | 32.348 29.243 50.970 1.00 12.82 | A |
| ATOM 1534 N ALA A 217 | 34.221 30.233 51.767 1.00 13.74 | A |
| ATOM 1535 CA ALA A 217 | 33.450 30.944 52.799 1.00 14.97 | A |
| ATOM 1536 CB ALA A 217 | 34.382 31.740 53.678 1.00 13.54 | A |
| ATOM 1537 C ALA A 217 | 32.381 31.868 52.221 1.00 16.16 | A |
| ATOM 1538 O ALA A 217 | 31.222 31.869 52.673 1.00 16.57 | A |
| ATOM 1539 N GLU A 218 | 32.783 32.654 51.237 1.00 12.16 | A |
| ATOM 1540 CA GLU A 218 | 31.870 33.603 50.592 1.00 13.58 | A |
| ATOM 1541 CB GLU A 218 | 32.627 34.361 49.519 1.00 18.61 | A |
| ATOM 1542 CG GLU A 218 | 31.864 35.513 48.883 1.00 32.02 | A |
| ATOM 1543 CD GLU A 218 | 32.696 36.161 47.785 1.00 42.30 | A |
| ATOM 1544 OE1 GLU A 218 | 33.956 35.992 47.826 1.00 49.92 | A |
| ATOM 1545 OE2 GLU A 218 | 32.104 36.824 46.896 1.00 53.68 | A |
| ATOM 1546 C GLU A 218 | 30.690 32.899 49.958 1.00 13.93 | A |
| ATOM 1547 O GLU A 218 | 29.531 33.260 50.163 1.00 17.23 | A |
| ATOM 1548 N ARG A 219 | 30.964 31.875 49.169 1.00 14.97 | A |
| ATOM 1549 CA ARG A 219 | 29.881 31.181 48.505 1.00 15.49 | A |
| ATOM 1550 CB ARG A 219 | 30.460 30.318 47.381 1.00 14.63 | A |
| ATOM 1551 CG ARG A 219 | 31.050 31.209 46.277 1.00 17.62 | A |
| ATOM 1552 CD ARG A 219 | 32.066 30.447 45.386 1.00 17.33 | A |
| ATOM 1553 NE ARG A 219 | 31.430 29.400 44.584 1.00 17.85 | A |
| ATOM 1554 CZ ARG A 219 | 30.929 29.603 43.365 1.00 21.83 | A |
| ATOM 1555 NH1 ARG A 219 | 30.998 30.831 42.818 1.00 21.17 | A |
| ATOM 1556 NH2 ARG A 219 | 30.379 28.600 42.701 1.00 15.04 | A |
| ATOM 1557 C ARG A 219 | 28.980 30.401 49.433 1.00 14.16 | A |
| ATOM 1558 O ARG A 219 | 27.766 30.412 49.270 1.00 16.33 | A |
| ATOM 1559 N LEU A 220 | 29.548 29.727 50.435 1.00 14.96 | A |
| ATOM 1560 CA LEU A 220 | 28.685 28.977 51.345 1.00 13.11 | A |

Fig. 4 cont.

```
ATOM 1561 CB  LEU A 220    29.503 28.004 52.229 1.00 11.77  A
ATOM 1562 CG  LEU A 220    30.042 26.819 51.435 1.00 16.45  A
ATOM 1563 CD1 LEU A 220    30.958 25.958 52.330 1.00 15.52  A
ATOM 1564 CD2 LEU A 220    28.853 25.989 50.941 1.00 24.49  A
ATOM 1565 C   LEU A 220    27.875 29.927 52.230 1.00 13.07  A
ATOM 1566 O   LEU A 220    26.750 29.587 52.595 1.00 13.62  A
ATOM 1567 N   SER A 221    28.427 31.087 52.575 1.00 13.10  A
ATOM 1568 CA  SER A 221    27.661 32.034 53.396 1.00 16.19  A
ATOM 1569 CB  SER A 221    28.449 33.310 53.642 1.00 19.23  A
ATOM 1570 OG  SER A 221    27.689 34.253 54.371 1.00 19.91  A
ATOM 1571 C   SER A 221    26.375 32.381 52.629 1.00 16.18  A
ATOM 1572 O   SER A 221    25.302 32.409 53.205 1.00 17.98  A
ATOM 1573 N   GLN A 222    26.521 32.634 51.325 1.00 15.05  A
ATOM 1574 CA  GLN A 222    25.378 32.958 50.475 1.00 19.10  A
ATOM 1575 CB  GLN A 222    25.877 33.417 49.096 1.00 21.05  A
ATOM 1576 CG  GLN A 222    26.582 34.732 49.138 1.00 31.62  A
ATOM 1577 CD  GLN A 222    27.148 35.118 47.777 1.00 42.54  A
ATOM 1578 OE1 GLN A 222    26.995 34.371 46.791 1.00 49.79  A
ATOM 1579 NE2 GLN A 222    27.800 36.280 47.709 1.00 40.08  A
ATOM 1580 C   GLN A 222    24.424 31.780 50.305 1.00 20.67  A
ATOM 1581 O   GLN A 222    23.209 31.939 50.448 1.00 18.84  A
ATOM 1582 N   LEU A 223    24.952 30.593 50.026 1.00 14.64  A
ATOM 1583 CA  LEU A 223    24.080 29.447 49.816 1.00 15.74  A
ATOM 1584 CB  LEU A 223    24.869 28.246 49.299 1.00 17.55  A
ATOM 1585 CG  LEU A 223    25.333 28.222 47.836 1.00 24.49  A
ATOM 1586 CD1 LEU A 223    25.910 29.556 47.451 1.00 40.69  A
ATOM 1587 CD2 LEU A 223    26.358 27.102 47.608 1.00 23.78  A
ATOM 1588 C   LEU A 223    23.306 29.011 51.058 1.00 20.15  A
ATOM 1589 O   LEU A 223    22.172 28.559 50.953 1.00 20.44  A
ATOM 1590 N   MET A 224    23.905 29.117 52.239 1.00 19.18  A
ATOM 1591 CA  MET A 224    23.164 28.680 53.433 1.00 19.76  A
ATOM 1592 CB  MET A 224    24.079 28.585 54.657 1.00 15.80  A
ATOM 1593 CG  MET A 224    25.153 27.538 54.455 1.00 15.73  A
ATOM 1594 SD  MET A 224    26.057 27.291 55.997 1.00 16.26  A
ATOM 1595 CE  MET A 224    27.029 28.747 56.044 1.00 14.03  A
ATOM 1596 C   MET A 224    21.999 29.600 53.742 1.00 26.44  A
ATOM 1597 O   MET A 224    21.001 29.161 54.304 1.00 24.61  A
ATOM 1598 N   MET A 225    22.131 30.870 53.379 1.00 25.76  A
ATOM 1599 CA  MET A 225    21.044 31.800 53.615 1.00 35.64  A
ATOM 1600 CB  MET A 225    21.587 33.227 53.646 1.00 28.07  A
ATOM 1601 CG  MET A 225    22.473 33.438 54.868 1.00 39.84  A
ATOM 1602 SD  MET A 225    22.671 35.148 55.447 1.00 52.30  A
ATOM 1603 CE  MET A 225    24.414 35.486 55.096 1.00 51.18  A
ATOM 1604 C   MET A 225    19.986 31.592 52.529 1.00 37.44  A
ATOM 1605 O   MET A 225    18.795 31.852 52.733 1.00 40.06  A
ATOM 1606 N   LYS A 226    20.428 31.053 51.395 1.00 39.71  A
ATOM 1607 CA  LYS A 226    19.558 30.801 50.261 1.00 46.28  A
ATOM 1608 CB  LYS A 226    20.351 30.351 49.037 1.00 47.88  A
ATOM 1609 CG  LYS A 226    20.557 31.486 48.079 1.00 48.01  A
ATOM 1610 CD  LYS A 226    21.138 31.042 46.766 1.00 53.42  A
ATOM 1611 CE  LYS A 226    21.517 32.276 45.977 1.00 56.84  A
ATOM 1612 NZ  LYS A 226    21.839 31.938 44.563 1.00 68.09  A
ATOM 1613 C   LYS A 226    18.437 29.839 50.500 1.00 52.19  A
ATOM 1614 O   LYS A 226    18.580 28.606 50.485 1.00 56.16  A
ATOM 1615 N   ASN A 227    17.293 30.457 50.712 1.00 60.62  A
ATOM 1616 CA  ASN A 227    16.045 29.776 50.938 1.00 65.19  A
ATOM 1617 CB  ASN A 227    15.039 30.802 51.459 1.00 64.96  A
ATOM 1618 CG  ASN A 227    13.644 30.250 51.543 1.00 70.66  A
ATOM 1619 OD1 ASN A 227    12.762 30.613 50.749 1.00 63.60  A
ATOM 1620 ND2 ASN A 227    13.430 29.352 52.503 1.00 64.45  A
ATOM 1621 C   ASN A 227    15.571 29.138 49.612 1.00 69.69  A
ATOM 1622 O   ASN A 227    15.310 27.904 49.618 1.00 68.85  A
ATOM 1623 OXT ASN A 227    15.478 29.872 48.584 1.00 69.45  A
ATOM 1624 CB  ALA B 15     49.689 21.292 95.435 1.00 46.88  B
ATOM 1625 C   ALA B 15     49.237 20.046 93.332 1.00 45.13  B
ATOM 1626 O   ALA B 15     49.239 18.877 93.743 1.00 52.19  B
ATOM 1627 N   ALA B 15     47.368 20.859 94.668 1.00 51.09  B
ATOM 1628 CA  ALA B 15     48.767 21.179 94.234 1.00 47.63  B
ATOM 1629 N   VAL B 16     49.614 20.412 92.113 1.00 31.87  B
ATOM 1630 CA  VAL B 16     50.097 19.495 91.102 1.00 19.09  B
ATOM 1631 CB  VAL B 16     50.003 20.175 89.723 1.00 24.64  B
ATOM 1632 CG1 VAL B 16     48.560 20.644 89.487 1.00 29.31  B
ATOM 1633 CG2 VAL B 16     50.938 21.382 89.648 1.00 17.97  B
ATOM 1634 C   VAL B 16     51.545 19.147 91.414 1.00 15.69  B
ATOM 1635 O   VAL B 16     52.190 19.806 92.221 1.00 16.36  B
ATOM 1636 N   THR B 17     52.060 18.112 90.768 1.00 15.55  B
ATOM 1637 CA  THR B 17     53.439 17.687 90.984 1.00 15.73  B
ATOM 1638 CB  THR B 17     53.620 16.173 90.607 1.00 18.09  B
ATOM 1639 OG1 THR B 17     53.444 16.000 89.182 1.00 22.51  B
ATOM 1640 CG2 THR B 17     52.610 15.308 91.333 1.00 22.51  B
ATOM 1641 C   THR B 17     54.449 18.434 90.104 1.00 13.85  B
ATOM 1642 O   THR B 17     54.109 19.023 89.055 1.00 13.10  B
ATOM 1643 N   LYS B 18     55.705 18.382 90.514 1.00 13.27  B
ATOM 1644 CA  LYS B 18     56.761 18.905 89.673 1.00 10.94  B
ATOM 1645 CB  LYS B 18     58.083 18.967 90.485 1.00 13.52  B
ATOM 1646 CG  LYS B 18     58.658 17.582 90.805 1.00 16.24  B
ATOM 1647 CD  LYS B 18     59.868 17.689 91.734 1.00 14.66  B
ATOM 1648 CE  LYS B 18     59.470 18.166 93.128 1.00 18.53  B
ATOM 1649 NZ  LYS B 18     60.608 17.840 94.001 1.00 26.39  B
ATOM 1650 C   LYS B 18     56.896 17.884 88.509 1.00 10.86  B
ATOM 1651 O   LYS B 18     56.382 16.753 88.553 1.00 12.00  B
ATOM 1652 N   LEU B 19     57.606 18.282 87.464 1.00 9.75   B
ATOM 1653 CA  LEU B 19     57.862 17.337 86.356 1.00 8.64   B
ATOM 1654 CB  LEU B 19     57.071 17.705 85.107 1.00 10.05  B
ATOM 1655 CG  LEU B 19     55.563 17.471 85.188 1.00 9.84   B
ATOM 1656 CD1 LEU B 19     54.910 18.069 83.967 1.00 12.01  B
ATOM 1657 CD2 LEU B 19     55.269 15.972 85.245 1.00 12.70  B
ATOM 1658 C   LEU B 19     59.318 17.338 86.007 1.00 10.01  B
ATOM 1659 O   LEU B 19     59.923 18.397 85.853 1.00 10.28  B
ATOM 1660 N   HIS B 20     59.876 16.135 85.866 1.00 10.76  B
ATOM 1661 CA  HIS B 20     61.265 15.975 85.426 1.00 12.34  B
ATOM 1662 CB  HIS B 20     61.916 14.803 86.183 1.00 10.23  B
ATOM 1663 CG  HIS B 20     61.952 15.013 87.670 1.00 8.98   B
ATOM 1664 CD2 HIS B 20     61.353 14.326 88.678 1.00 10.91  B
ATOM 1665 ND1 HIS B 20     62.637 16.052 88.254 1.00 13.17  B
ATOM 1666 CE1 HIS B 20     62.450 16.004 89.569 1.00 12.73  B
ATOM 1667 NE2 HIS B 20     61.684 14.967 89.845 1.00 11.41  B
ATOM 1668 C   HIS B 20     61.159 15.623 83.947 1.00 9.63   B
ATOM 1669 O   HIS B 20     60.509 14.625 83.594 1.00 11.87  B
ATOM 1670 N   VAL B 21     61.746 16.453 83.092 1.00 9.70   B
ATOM 1671 CA  VAL B 21     61.731 16.287 81.624 1.00 9.92   B
ATOM 1672 CB  VAL B 21     60.776 17.344 80.966 1.00 12.13  B
ATOM 1673 CG1 VAL B 21     60.807 17.249 79.430 1.00 18.51  B
ATOM 1674 CG2 VAL B 21     59.330 17.117 81.499 1.00 15.28  B
ATOM 1675 C   VAL B 21     63.168 16.451 81.145 1.00 11.08  B
ATOM 1676 O   VAL B 21     63.818 17.486 81.357 1.00 11.35  B
ATOM 1677 N   ASP B 22     63.684 15.415 80.485 1.00 10.17  B
ATOM 1678 CA  ASP B 22     65.081 15.395 80.090 1.00 9.88   B
ATOM 1679 CB  ASP B 22     65.357 16.391 78.961 1.00 14.32  B
ATOM 1680 CG  ASP B 22     66.682 16.134 78.310 1.00 18.54  B
ATOM 1681 OD1 ASP B 22     67.590 16.979 78.448 1.00 20.39  B
ATOM 1682 OD2 ASP B 22     66.828 15.064 77.685 1.00 26.17  B
ATOM 1683 C   ASP B 22     65.900 15.695 81.368 1.00 10.85  B
ATOM 1684 O   ASP B 22     65.677 15.029 82.365 1.00 14.22  B
ATOM 1685 N   SER B 23     66.805 16.669 81.367 1.00 11.16  B
ATOM 1686 CA  SER B 23     67.603 16.924 82.576 1.00 13.25  B
ATOM 1687 CB  SER B 23     69.050 17.237 82.172 1.00 16.05  B
ATOM 1688 OG  SER B 23     69.098 18.462 81.462 1.00 24.70  B
ATOM 1689 C   SER B 23     67.066 18.090 83.392 1.00 17.26  B
ATOM 1690 O   SER B 23     67.675 18.484 84.392 1.00 20.37  B
ATOM 1691 N   VAL B 24     65.918 18.619 82.984 1.00 12.59  B
ATOM 1692 CA  VAL B 24     65.331 19.767 83.664 1.00 11.65  B
ATOM 1693 CB  VAL B 24     64.707 20.745 82.602 1.00 13.29  B
ATOM 1694 CG1 VAL B 24     63.985 21.975 83.326 1.00 14.75  B
ATOM 1695 CG2 VAL B 24     65.815 21.231 81.654 1.00 15.82  B
ATOM 1696 C   VAL B 24     64.244 19.371 84.643 1.00 11.63  B
ATOM 1697 O   VAL B 24     63.582 18.343 84.476 1.00 13.08  B
ATOM 1698 N   THR B 25     64.062 20.163 85.692 1.00 11.53  B
ATOM 1699 CA  THR B 25     62.967 19.900 86.591 1.00 10.07  B
ATOM 1700 CB  THR B 25     63.421 19.616 88.032 1.00 14.15  B
ATOM 1701 OG1 THR B 25     64.158 18.387 88.059 1.00 13.99  B
ATOM 1702 CG2 THR B 25     62.166 19.430 88.942 1.00 15.26  B
ATOM 1703 C   THR B 25     62.129 21.169 86.633 1.00 10.94  B
ATOM 1704 O   THR B 25     62.665 22.242 86.937 1.00 13.54  B
ATOM 1705 N   PHE B 26     60.841 21.039 86.331 1.00 9.91   B
ATOM 1706 CA  PHE B 26     59.904 22.142 86.384 1.00 9.14   B
ATOM 1707 CB  PHE B 26     58.893 22.051 85.216 1.00 9.22   B
ATOM 1708 CG  PHE B 26     59.507 22.276 83.868 1.00 9.76   B
ATOM 1709 CD1 PHE B 26     59.915 21.210 83.074 1.00 9.77   B
ATOM 1710 CD2 PHE B 26     59.728 23.566 83.403 1.00 9.27   B
ATOM 1711 CE1 PHE B 26     60.528 21.440 81.831 1.00 10.67  B
ATOM 1712 CE2 PHE B 26     60.340 23.787 82.167 1.00 9.87   B
ATOM 1713 CZ  PHE B 26     60.739 22.712 81.381 1.00 8.84   B
ATOM 1714 C   PHE B 26     59.168 22.094 87.687 1.00 10.43  B
ATOM 1715 O   PHE B 26     58.538 21.067 88.010 1.00 9.96   B
ATOM 1716 N   VAL B 27     59.221 23.192 88.451 1.00 9.53   B
ATOM 1717 CA  VAL B 27     58.536 23.220 89.766 1.00 9.72   B
ATOM 1718 CB  VAL B 27     59.096 24.304 90.680 1.00 11.56  B
ATOM 1719 CG1 VAL B 27     60.602 23.994 90.909 1.00 16.96  B
ATOM 1720 CG2 VAL B 27     58.852 25.689 90.092 1.00 12.09  B
```

Fig. 4 cont.

```
ATOM  1721  C   VAL B  27    57.027 23.377 89.563 1.00  9.84   B
ATOM  1722  O   VAL B  27    56.560 23.805 88.525 1.00 11.25   B
ATOM  1723  N   PRO B  28    56.243 22.988 90.549 1.00  9.45   B
ATOM  1724  CD  PRO B  28    56.687 22.405 91.837 1.00 11.53   B
ATOM  1725  CA  PRO B  28    54.776 23.043 90.459 1.00 10.58   B
ATOM  1726  CB  PRO B  28    54.316 22.404 91.773 1.00 14.39   B
ATOM  1727  CG  PRO B  28    55.472 21.706 92.289 1.00 16.29   B
ATOM  1728  C   PRO B  28    54.108 24.402 90.275 1.00 12.79   B
ATOM  1729  O   PRO B  28    52.980 24.471 89.741 1.00 10.62   B
ATOM  1730  N   SER B  29    54.754 25.462 90.750 1.00 10.62   B
ATOM  1731  CA  SER B  29    54.138 26.779 90.639 1.00 12.22   B
ATOM  1732  CB  SER B  29    53.387 27.111 91.951 1.00 18.51   B
ATOM  1733  OG  SER B  29    52.823 28.426 91.892 1.00 20.58   B
ATOM  1734  C   SER B  29    55.216 27.821 90.411 1.00 13.07   B
ATOM  1735  O   SER B  29    56.328 27.695 90.947 1.00 15.01   B
ATOM  1736  N   VAL B  30    54.921 28.810 89.574 1.00 12.27   B
ATOM  1737  CA  VAL B  30    55.848 29.923 89.373 1.00 13.28   B
ATOM  1738  CB  VAL B  30    56.545 29.881 88.033 1.00 15.11   B
ATOM  1739  CG1 VAL B  30    57.410 28.641 87.959 1.00 14.44   B
ATOM  1740  CG2 VAL B  30    55.532 29.934 86.909 1.00 14.38   B
ATOM  1741  C   VAL B  30    55.059 31.226 89.467 1.00 14.37   B
ATOM  1742  O   VAL B  30    53.843 31.229 89.372 1.00 13.90   B
ATOM  1743  N   LYS B  31    55.791 32.291 89.770 1.00 11.39   B
ATOM  1744  CA  LYS B  31    55.240 33.632 89.906 1.00 12.84   B
ATOM  1745  CB  LYS B  31    56.003 34.365 91.024 1.00 14.53   B
ATOM  1746  CG  LYS B  31    55.431 35.762 91.288 1.00 18.47   B
ATOM  1747  CD  LYS B  31    55.990 36.340 92.615 1.00 24.18   B
ATOM  1748  CE  LYS B  31    57.496 36.602 92.512 1.00 36.94   B
ATOM  1749  NZ  LYS B  31    57.897 37.555 91.390 1.00 40.86   B
ATOM  1750  C   LYS B  31    55.449 34.319 88.561 1.00 12.69   B
ATOM  1751  O   LYS B  31    56.586 34.470 88.117 1.00 12.74   B
ATOM  1752  N   SER B  32    54.357 34.713 87.910 1.00 10.29   B
ATOM  1753  CA  SER B  32    54.466 35.366 86.622 1.00 10.89   B
ATOM  1754  CB  SER B  32    53.079 35.697 86.097 1.00 13.31   B
ATOM  1755  OG  SER B  32    53.206 36.557 84.984 1.00 15.19   B
ATOM  1756  C   SER B  32    55.298 36.650 86.680 1.00 12.65   B
ATOM  1757  O   SER B  32    55.106 37.470 87.576 1.00 12.92   B
ATOM  1758  N   PRO B  33    56.258 36.828 85.750 1.00 10.47   B
ATOM  1759  CD  PRO B  33    56.742 35.881 84.741 1.00 12.44   B
ATOM  1760  CA  PRO B  33    57.060 38.062 85.762 1.00 12.66   B
ATOM  1761  CB  PRO B  33    58.155 37.828 84.730 1.00 15.06   B
ATOM  1762  CG  PRO B  33    58.125 36.393 84.458 1.00 20.45   B
ATOM  1763  C   PRO B  33    56.196 39.213 85.290 1.00 15.43   B
ATOM  1764  O   PRO B  33    56.578 40.373 85.460 1.00 17.83   B
ATOM  1765  N   ALA B  34    55.050 38.928 84.683 1.00 10.64   B
ATOM  1766  CA  ALA B  34    54.179 39.988 84.200 1.00 12.82   B
ATOM  1767  CB  ALA B  34    53.451 39.518 82.908 1.00 15.79   B
ATOM  1768  C   ALA B  34    53.161 40.450 85.241 1.00 17.41   B
ATOM  1769  O   ALA B  34    53.033 41.665 85.546 1.00 20.65   B
ATOM  1770  N   SER B  35    52.470 39.483 85.827 1.00 13.92   B
ATOM  1771  CA  SER B  35    51.413 39.792 86.776 1.00 13.94   B
ATOM  1772  CB  SER B  35    50.206 38.908 86.488 1.00 14.39   B
ATOM  1773  OG  SER B  35    50.551 37.570 86.814 1.00 14.59   B
ATOM  1774  C   SER B  35    51.775 39.575 88.213 1.00 13.26   B
ATOM  1775  O   SER B  35    51.055 40.034 89.089 1.00 14.33   B
ATOM  1776  N   SER B  36    52.878 38.877 88.465 1.00 13.97   B
ATOM  1777  CA  SER B  36    53.302 38.490 89.810 1.00 15.69   B
ATOM  1778  CB  SER B  36    53.545 39.714 90.749 1.00 15.54   B
ATOM  1779  OG  SER B  36    54.548 40.578 90.217 1.00 18.29   B
ATOM  1780  C   SER B  36    52.323 37.523 90.475 1.00 13.45   B
ATOM  1781  O   SER B  36    52.417 37.298 91.711 1.00 18.19   B
ATOM  1782  N   ASN B  37    51.391 36.961 89.712 1.00 12.83   B
ATOM  1783  CA  ASN B  37    50.439 35.986 90.255 1.00 14.09   B
ATOM  1784  CB  ASN B  37    49.117 36.041 89.500 1.00 16.11   B
ATOM  1785  CG  ASN B  37    48.360 37.363 89.691 1.00 17.59   B
ATOM  1786  OD1 ASN B  37    47.689 37.851 88.770 1.00 22.58   B
ATOM  1787  ND2 ASN B  37    48.445 37.919 90.877 1.00 18.80   B
ATOM  1788  C   ASN B  37    51.009 34.564 90.052 1.00 13.39   B
ATOM  1789  O   ASN B  37    51.781 34.322 89.149 1.00 14.30   B
ATOM  1790  N   PRO B  38    50.611 33.613 90.892 1.00 12.88   B
ATOM  1791  CD  PRO B  38    49.779 33.836 92.092 1.00 16.29   B
ATOM  1792  CA  PRO B  38    51.076 32.215 90.793 1.00 11.55   B
ATOM  1793  CB  PRO B  38    50.746 31.638 92.162 1.00 14.12   B
ATOM  1794  CG  PRO B  38    49.481 32.437 92.521 1.00 21.31   B
ATOM  1795  C   PRO B  38    50.320 31.479 89.673 1.00 13.49   B
ATOM  1796  O   PRO B  38    49.112 31.681 89.445 1.00 15.08   B
ATOM  1797  N   LEU B  39    51.074 30.654 88.949 1.00 11.03   B
ATOM  1798  CA  LEU B  39    50.531 29.842 87.874 1.00 10.02   B
ATOM  1799  CB  LEU B  39    51.060 30.325 86.531 1.00  8.76   B
ATOM  1800  CG  LEU B  39    50.709 31.800 86.254 1.00 10.55   B
ATOM  1801  CD1 LEU B  39    51.519 32.308 85.037 1.00 15.00   B
ATOM  1802  CD2 LEU B  39    49.215 31.932 86.037 1.00 15.88   B
ATOM  1803  C   LEU B  39    51.025 28.428 88.133 1.00 11.08   B
ATOM  1804  O   LEU B  39    52.142 28.238 88.594 1.00 11.03   B
ATOM  1805  N   PHE B  40    50.165 27.445 87.898 1.00 11.22   B
ATOM  1806  CA  PHE B  40    50.538 26.055 88.119 1.00  9.42   B
ATOM  1807  CB  PHE B  40    49.357 25.264 88.697 1.00 11.44   B
ATOM  1808  CG  PHE B  40    48.296 24.890 87.683 1.00 11.38   B
ATOM  1809  CD1 PHE B  40    47.218 25.751 87.406 1.00 11.14   B
ATOM  1810  CD2 PHE B  40    48.399 23.663 87.003 1.00 11.36   B
ATOM  1811  CE1 PHE B  40    46.242 25.401 86.451 1.00 10.27   B
ATOM  1812  CE2 PHE B  40    47.426 23.298 86.036 1.00 11.00   B
ATOM  1813  CZ  PHE B  40    46.348 24.162 85.760 1.00 10.98   B
ATOM  1814  C   PHE B  40    51.055 25.332 86.882 1.00  8.66   B
ATOM  1815  O   PHE B  40    50.749 25.697 85.739 1.00  9.68   B
ATOM  1816  N   LEU B  41    51.879 24.312 87.114 1.00  9.34   B
ATOM  1817  CA  LEU B  41    52.458 23.545 85.993 1.00  8.71   B
ATOM  1818  CB  LEU B  41    53.615 22.684 86.571 1.00  7.41   B
ATOM  1819  CG  LEU B  41    54.316 21.761 85.534 1.00  8.72   B
ATOM  1820  CD1 LEU B  41    54.877 22.595 84.334 1.00 11.20   B
ATOM  1821  CD2 LEU B  41    55.424 21.049 86.299 1.00 10.53   B
ATOM  1822  C   LEU B  41    51.409 22.692 85.265 1.00  8.68   B
ATOM  1823  O   LEU B  41    50.969 21.673 85.779 1.00 11.28   B
ATOM  1824  N   GLY B  42    51.014 23.129 84.070 1.00  7.52   B
ATOM  1825  CA  GLY B  42    50.038 22.382 83.265 1.00  9.12   B
ATOM  1826  C   GLY B  42    50.645 21.174 82.612 1.00  9.39   B
ATOM  1827  O   GLY B  42    50.000 20.136 82.550 1.00 10.08   B
ATOM  1828  N   GLY B  43    51.871 21.300 82.107 1.00  9.82   B
ATOM  1829  CA  GLY B  43    52.525 20.131 81.499 1.00 10.75   B
ATOM  1830  C   GLY B  43    53.902 20.516 80.973 1.00  8.33   B
ATOM  1831  O   GLY B  43    54.226 21.707 80.899 1.00  9.21   B
ATOM  1832  N   ALA B  44    54.705 19.531 80.561 1.00  7.58   B
ATOM  1833  CA  ALA B  44    56.058 19.821 80.103 1.00  8.41   B
ATOM  1834  CB  ALA B  44    57.029 19.927 81.312 1.00  9.25   B
ATOM  1835  C   ALA B  44    56.509 18.738 79.163 1.00  8.92   B
ATOM  1836  O   ALA B  44    56.039 17.586 79.236 1.00  9.92   B
ATOM  1837  N   GLY B  45    57.430 19.097 78.282 1.00  8.11   B
ATOM  1838  CA  GLY B  45    57.897 18.124 77.279 1.00  9.15   B
ATOM  1839  C   GLY B  45    59.093 18.679 76.560 1.00 12.79   B
ATOM  1840  O   GLY B  45    59.647 19.670 76.965 1.00 13.68   B
ATOM  1841  N   VAL B  46    59.514 18.030 75.490 1.00 11.51   B
ATOM  1842  CA  VAL B  46    60.679 18.526 74.718 1.00 12.61   B
ATOM  1843  CB  VAL B  46    61.823 17.444 74.620 1.00 15.46   B
ATOM  1844  CG1 VAL B  46    62.173 16.986 76.028 1.00 16.65   B
ATOM  1845  CG2 VAL B  46    61.414 16.236 73.711 1.00 13.91   B
ATOM  1846  C   VAL B  46    60.318 18.877 73.286 1.00 12.51   B
ATOM  1847  O   VAL B  46    59.271 18.489 72.781 1.00 13.04   B
ATOM  1848  N   ARG B  47    61.206 19.643 72.665 1.00 12.58   B
ATOM  1849  CA  ARG B  47    61.093 20.009 71.276 1.00 11.56   B
ATOM  1850  CB  ARG B  47    61.132 21.519 71.108 1.00 15.37   B
ATOM  1851  CG  ARG B  47    60.638 21.917 69.714 1.00 22.85   B
ATOM  1852  CD  ARG B  47    61.634 22.603 68.848 1.00 23.46   B
ATOM  1853  NE  ARG B  47    62.141 23.867 69.365 1.00 22.61   B
ATOM  1854  CZ  ARG B  47    63.126 24.550 68.756 1.00 23.63   B
ATOM  1855  NH1 ARG B  47    63.659 24.054 67.651 1.00 22.19   B
ATOM  1856  NH2 ARG B  47    63.576 25.702 69.242 1.00 19.49   B
ATOM  1857  C   ARG B  47    62.346 19.390 70.662 1.00 11.86   B
ATOM  1858  O   ARG B  47    63.469 19.766 71.001 1.00 13.24   B
ATOM  1859  N   GLY B  48    62.147 18.398 69.803 1.00 17.58   B
ATOM  1860  CA  GLY B  48    63.292 17.736 69.201 1.00 19.36   B
ATOM  1861  C   GLY B  48    62.939 17.272 67.808 1.00 23.91   B
ATOM  1862  O   GLY B  48    61.759 17.228 67.437 1.00 25.66   B
ATOM  1863  N   LEU B  49    63.959 16.907 67.051 1.00 21.97   B
ATOM  1864  CA  LEU B  49    63.753 16.493 65.673 1.00 24.01   B
ATOM  1865  CB  LEU B  49    64.002 17.704 64.787 1.00 26.35   B
ATOM  1866  CG  LEU B  49    63.736 17.792 63.293 1.00 42.47   B
ATOM  1867  CD1 LEU B  49    62.764 18.932 63.017 1.00 49.58   B
ATOM  1868  CD2 LEU B  49    65.045 18.098 62.598 1.00 41.80   B
ATOM  1869  C   LEU B  49    64.747 15.388 65.327 1.00 20.96   B
ATOM  1870  O   LEU B  49    65.857 15.340 65.872 1.00 19.44   B
ATOM  1871  N   ASP B  50    64.333 14.507 64.422 1.00 20.22   B
ATOM  1872  CA  ASP B  50    65.209 13.439 63.977 1.00 24.34   B
ATOM  1873  CB  ASP B  50    64.422 12.370 63.236 1.00 28.87   B
ATOM  1874  CG  ASP B  50    65.311 11.232 62.756 1.00 33.77   B
ATOM  1875  OD1 ASP B  50    65.442 10.215 63.470 1.00 36.28   B
ATOM  1876  OD2 ASP B  50    65.896 11.371 61.664 1.00 34.47   B
ATOM  1877  C   ASP B  50    66.207 14.074 63.021 1.00 23.64   B
ATOM  1878  O   ASP B  50    65.819 14.775 62.076 1.00 31.22   B
ATOM  1879  N   ILE B  51    67.480 13.852 63.277 1.00 22.60   B
ATOM  1880  CA  ILE B  51    68.551 14.373 62.444 1.00 23.05   B
```

Fig. 4 cont.

```
ATOM 1881 CB  ILE B 51    69.382 15.402 63.197 1.00 26.91   B
ATOM 1882 CG2 ILE B 51    70.594 15.787 62.379 1.00 28.66   B
ATOM 1883 CG1 ILE B 51    68.524 16.631 63.517 1.00 31.35   B
ATOM 1884 CD1 ILE B 51    69.303 17.752 64.163 1.00 40.74   B
ATOM 1885 C   ILE B 51    69.448 13.175 62.108 1.00 27.55   B
ATOM 1886 O   ILE B 51    70.151 12.663 62.972 1.00 25.15   B
ATOM 1887 N   GLN B 52    69.398 12.731 60.857 1.00 29.94   B
ATOM 1888 CA  GLN B 52    70.208 11.593 60.415 1.00 32.06   B
ATOM 1889 CB  GLN B 52    71.695 11.932 60.481 1.00 34.60   B
ATOM 1890 CG  GLN B 52    72.086 13.128 59.656 1.00 46.13   B
ATOM 1891 CD  GLN B 52    73.586 13.190 59.397 1.00 60.35   B
ATOM 1892 OE1 GLN B 52    74.410 13.232 60.339 1.00 65.41   B
ATOM 1893 NE2 GLN B 52    73.956 13.190 58.111 1.00 63.63   B
ATOM 1894 C   GLN B 52    69.958 10.354 61.265 1.00 31.46   B
ATOM 1895 O   GLN B 52    70.917  9.650 61.628 1.00 33.82   B
ATOM 1896 N   GLY B 53    68.685 10.087 61.574 1.00 22.50   B
ATOM 1897 CA  GLY B 53    68.357  8.915 62.373 1.00 25.98   B
ATOM 1898 C   GLY B 53    68.525  9.062 63.880 1.00 26.25   B
ATOM 1899 O   GLY B 53    68.244  8.117 64.634 1.00 27.88   B
ATOM 1900 N   LYS B 54    68.992 10.227 64.333 1.00 19.72   B
ATOM 1901 CA  LYS B 54    69.176 10.460 65.767 1.00 17.77   B
ATOM 1902 CB  LYS B 54    70.595 10.912 66.032 1.00 24.06   B
ATOM 1903 CG  LYS B 54    70.821 11.524 67.413 1.00 35.42   B
ATOM 1904 CD  LYS B 54    72.315 11.605 67.720 1.00 42.51   B
ATOM 1905 CE  LYS B 54    72.584 12.470 68.963 1.00 46.25   B
ATOM 1906 NZ  LYS B 54    71.404 12.518 69.892 1.00 53.23   B
ATOM 1907 C   LYS B 54    68.197 11.508 66.278 1.00 21.42   B
ATOM 1908 O   LYS B 54    68.052 12.560 65.669 1.00 18.91   B
ATOM 1909 N   PHE B 55    67.508 11.229 67.381 1.00 16.70   B
ATOM 1910 CA  PHE B 55    66.572 12.208 67.886 1.00 18.45   B
ATOM 1911 CB  PHE B 55    65.534 11.589 68.808 1.00 21.17   B
ATOM 1912 CG  PHE B 55    64.391 12.523 69.118 1.00 18.99   B
ATOM 1913 CD1 PHE B 55    63.430 12.806 68.161 1.00 20.88   B
ATOM 1914 CD2 PHE B 55    64.303 13.132 70.372 1.00 21.44   B
ATOM 1915 CE1 PHE B 55    62.389 13.678 68.426 1.00 25.09   B
ATOM 1916 CE2 PHE B 55    63.266 14.010 70.656 1.00 24.64   B
ATOM 1917 CZ  PHE B 55    62.311 14.289 69.698 1.00 30.21   B
ATOM 1918 C   PHE B 55    67.376 13.221 68.667 1.00 20.54   B
ATOM 1919 O   PHE B 55    68.066 12.880 69.631 1.00 23.21   B
ATOM 1920 N   VAL B 56    67.290 14.477 68.247 1.00 13.20   B
ATOM 1921 CA  VAL B 56    68.045 15.522 68.874 1.00 13.26   B
ATOM 1922 CB  VAL B 56    68.856 16.291 67.800 1.00 19.69   B
ATOM 1923 CG1 VAL B 56    69.612 17.452 68.454 1.00 19.17   B
ATOM 1924 CG2 VAL B 56    69.814 15.321 67.096 1.00 17.76   B
ATOM 1925 C   VAL B 56    67.102 16.521 69.573 1.00 10.62   B
ATOM 1926 O   VAL B 56    66.216 17.084 68.935 1.00 13.15   B
ATOM 1927 N   ILE B 57    67.296 16.669 70.890 1.00 12.15   B
ATOM 1928 CA  ILE B 57    66.480 17.605 71.676 1.00 11.32   B
ATOM 1929 CB  ILE B 57    66.412 17.115 73.138 1.00 13.27   B
ATOM 1930 CG2 ILE B 57    65.658 18.168 74.023 1.00 10.96   B
ATOM 1931 CG1 ILE B 57    65.672 15.767 73.168 1.00 12.41   B
ATOM 1932 CD1 ILE B 57    65.704 15.065 74.526 1.00 15.28   B
ATOM 1933 C   ILE B 57    67.101 19.001 71.597 1.00 11.70   B
ATOM 1934 O   ILE B 57    68.292 19.186 71.870 1.00 12.78   B
ATOM 1935 N   PHE B 58    66.285 19.970 71.188 1.00 12.03   B
ATOM 1936 CA  PHE B 58    66.699 21.361 71.093 1.00 11.35   B
ATOM 1937 CB  PHE B 58    66.003 22.056 69.915 1.00 10.71   B
ATOM 1938 CG  PHE B 58    66.571 21.700 68.583 1.00 16.85   B
ATOM 1939 CD1 PHE B 58    66.604 20.384 68.165 1.00 20.51   B
ATOM 1940 CD2 PHE B 58    67.050 22.709 67.724 1.00 18.47   B
ATOM 1941 CE1 PHE B 58    67.103 20.040 66.899 1.00 21.03   B
ATOM 1942 CE2 PHE B 58    67.553 22.370 66.451 1.00 20.42   B
ATOM 1943 CZ  PHE B 58    67.576 21.034 66.048 1.00 19.18   B
ATOM 1944 C   PHE B 58    66.340 22.124 72.363 1.00 11.81   B
ATOM 1945 O   PHE B 58    67.161 22.832 72.903 1.00 11.80   B
ATOM 1946 N   THR B 59    65.087 21.982 72.802 1.00 10.85   B
ATOM 1947 CA  THR B 59    64.640 22.688 74.004 1.00 10.92   B
ATOM 1948 CB  THR B 59    63.861 23.956 73.681 1.00 12.98   B
ATOM 1949 OG1 THR B 59    62.659 23.618 72.983 1.00 12.43   B
ATOM 1950 CG2 THR B 59    64.671 24.854 72.760 1.00 12.59   B
ATOM 1951 C   THR B 59    63.735 21.814 74.864 1.00  9.62   B
ATOM 1952 O   THR B 59    63.224 20.796 74.402 1.00 10.50   B
ATOM 1953 N   VAL B 60    63.554 22.241 76.111 1.00  9.01   B
ATOM 1954 CA  VAL B 60    62.733 21.536 77.068 1.00  9.82   B
ATOM 1955 CB  VAL B 60    63.604 20.994 78.218 1.00 14.19   B
ATOM 1956 CG1 VAL B 60    62.744 20.151 79.156 1.00 17.26   B
ATOM 1957 CG2 VAL B 60    64.749 20.155 77.624 1.00 15.64   B
ATOM 1958 C   VAL B 60    61.760 22.615 77.546 1.00 12.06   B
ATOM 1959 O   VAL B 60    62.183 23.686 78.004 1.00 13.14   B
ATOM 1960 N   ILE B 61    60.475 22.305 77.465 1.00  8.39   B
ATOM 1961 CA  ILE B 61    59.432 23.308 77.681 1.00  9.60   B
ATOM 1962 CB  ILE B 61    58.643 23.440 76.355 1.00 11.00   B
ATOM 1963 CG2 ILE B 61    57.498 24.522 76.497 1.00 10.56   B
ATOM 1964 CG1 ILE B 61    59.617 23.760 75.197 1.00 12.34   B
ATOM 1965 CD1 ILE B 61    58.943 23.642 73.766 1.00 17.38   B
ATOM 1966 C   ILE B 61    58.427 22.998 78.757 1.00  7.73   B
ATOM 1967 O   ILE B 61    57.972 21.847 78.846 1.00  9.98   B
ATOM 1968 N   GLY B 62    58.107 24.013 79.569 1.00  8.02   B
ATOM 1969 CA  GLY B 62    57.084 23.876 80.592 1.00  9.23   B
ATOM 1970 C   GLY B 62    55.960 24.883 80.345 1.00  9.22   B
ATOM 1971 O   GLY B 62    56.231 26.046 80.041 1.00 10.48   B
ATOM 1972 N   VAL B 63    54.703 24.447 80.432 1.00  7.89   B
ATOM 1973 CA  VAL B 63    53.572 25.344 80.227 1.00 10.56   B
ATOM 1974 CB  VAL B 63    52.650 24.776 79.145 1.00  8.12   B
ATOM 1975 CG1 VAL B 63    51.352 25.580 79.079 1.00 10.42   B
ATOM 1976 CG2 VAL B 63    53.345 24.865 77.773 1.00 12.23   B
ATOM 1977 C   VAL B 63    52.838 25.461 81.552 1.00  9.58   B
ATOM 1978 O   VAL B 63    52.454 24.452 82.141 1.00  9.58   B
ATOM 1979 N   TYR B 64    52.644 26.706 82.007 1.00  7.59   B
ATOM 1980 CA  TYR B 64    51.968 27.011 83.276 1.00  8.99   B
ATOM 1981 CB  TYR B 64    52.862 27.896 84.165 1.00  9.92   B
ATOM 1982 CG  TYR B 64    54.093 27.184 84.736 1.00  7.44   B
ATOM 1983 CD1 TYR B 64    55.228 26.946 83.950 1.00 10.50   B
ATOM 1984 CE1 TYR B 64    56.325 26.249 84.468 1.00  7.76   B
ATOM 1985 CD2 TYR B 64    54.078 26.708 86.056 1.00  6.64   B
ATOM 1986 CE2 TYR B 64    55.175 26.000 86.579 1.00  9.07   B
ATOM 1987 CZ  TYR B 64    56.288 25.784 85.764 1.00 10.19   B
ATOM 1988 OH  TYR B 64    57.376 25.066 86.263 1.00 10.00   B
ATOM 1989 C   TYR B 64    50.659 27.718 82.979 1.00 10.00   B
ATOM 1990 O   TYR B 64    50.571 28.508 82.043 1.00  9.16   B
ATOM 1991 N   LEU B 65    49.656 27.467 83.811 1.00  9.64   B
ATOM 1992 CA  LEU B 65    48.322 28.021 83.573 1.00 10.53   B
ATOM 1993 CB  LEU B 65    47.408 26.882 83.094 1.00 11.07   B
ATOM 1994 CG  LEU B 65    47.834 26.139 81.815 1.00  9.11   B
ATOM 1995 CD1 LEU B 65    46.928 24.909 81.625 1.00 16.09   B
ATOM 1996 CD2 LEU B 65    47.756 27.093 80.605 1.00 13.76   B
ATOM 1997 C   LEU B 65    48.594 28.594 84.861 1.00  9.63   B
ATOM 1998 O   LEU B 65    48.242 28.365 85.942 1.00 10.26   B
ATOM 1999 N   GLU B 66    46.640 29.332 84.730 1.00 13.89   B
ATOM 2000 CA  GLU B 66    45.980 29.899 85.908 1.00 14.42   B
ATOM 2001 CB  GLU B 66    45.059 31.043 85.502 1.00 17.76   B
ATOM 2002 CG  GLU B 66    45.614 32.362 85.661 1.00 22.46   B
ATOM 2003 CD  GLU B 66    44.524 33.435 85.622 1.00 24.59   B
ATOM 2004 OE1 GLU B 66    43.569 33.380 86.433 1.00 24.06   B
ATOM 2005 OE2 GLU B 66    44.626 34.331 84.795 1.00 21.45   B
ATOM 2006 C   GLU B 66    45.086 28.852 86.576 1.00 13.15   B
ATOM 2007 O   GLU B 66    44.347 28.147 85.919 1.00 15.69   B
ATOM 2008 N   GLY B 67    45.103 28.822 87.906 1.00 15.74   B
ATOM 2009 CA  GLY B 67    44.273 27.852 88.578 1.00 18.42   B
ATOM 2010 C   GLY B 67    42.817 28.080 88.178 1.00 14.80   B
ATOM 2011 O   GLY B 67    42.063 27.123 88.049 1.00 16.56   B
ATOM 2012 N   ASN B 68    42.442 29.337 87.972 1.00 16.65   B
ATOM 2013 CA  ASN B 68    41.050 29.635 87.625 1.00 17.89   B
ATOM 2014 CB  ASN B 68    40.778 31.147 87.611 1.00 21.56   B
ATOM 2015 CG  ASN B 68    40.895 31.787 88.998 1.00 30.83   B
ATOM 2016 OD1 ASN B 68    40.473 31.216 90.011 1.00 30.70   B
ATOM 2017 ND2 ASN B 68    41.480 32.987 89.045 1.00 32.59   B
ATOM 2018 C   ASN B 68    40.663 29.049 86.290 1.00 19.93   B
ATOM 2019 O   ASN B 68    39.476 28.918 85.966 1.00 19.80   B
ATOM 2020 N   ALA B 69    41.653 28.686 85.483 1.00 16.33   B
ATOM 2021 CA  ALA B 69    41.292 28.069 84.217 1.00 18.19   B
ATOM 2022 CB  ALA B 69    42.497 27.994 83.302 1.00 17.72   B
ATOM 2023 C   ALA B 69    40.714 26.668 84.372 1.00 15.04   B
ATOM 2024 O   ALA B 69    39.988 26.198 83.483 1.00 19.78   B
ATOM 2025 N   VAL B 70    41.049 25.979 85.459 1.00 15.09   B
ATOM 2026 CA  VAL B 70    40.581 24.608 85.613 1.00 14.94   B
ATOM 2027 CB  VAL B 70    41.333 23.897 86.763 1.00 16.79   B
ATOM 2028 CG1 VAL B 70    40.776 22.519 86.960 1.00 17.51   B
ATOM 2029 CG2 VAL B 70    42.807 23.769 86.374 1.00 17.44   B
ATOM 2030 C   VAL B 70    39.061 24.552 85.760 1.00 13.81   B
ATOM 2031 O   VAL B 70    38.405 23.786 85.049 1.00 14.78   B
ATOM 2032 N   PRO B 71    38.477 25.331 86.672 1.00 14.62   B
ATOM 2033 CD  PRO B 71    38.984 26.216 87.728 1.00 18.84   B
ATOM 2034 CA  PRO B 71    37.002 25.212 86.722 1.00 21.12   B
ATOM 2035 CB  PRO B 71    36.618 26.085 87.928 1.00 22.27   B
ATOM 2036 CG  PRO B 71    37.762 27.045 88.056 1.00 26.89   B
ATOM 2037 C   PRO B 71    36.342 25.693 85.424 1.00 19.65   B
ATOM 2038 O   PRO B 71    35.280 25.201 85.022 1.00 19.53   B
ATOM 2039 N   SER B 72    36.975 26.649 84.748 1.00 15.64   B
ATOM 2040 CA  SER B 72    36.441 27.143 83.489 1.00 17.16   B
```

Fig. 4 cont.

| ATOM | 2041 | CB  | SER B 72  | 37.265 28.334 83.003 1.00 18.57 | B |
|------|------|-----|-----------|---------------------------------|---|
| ATOM | 2042 | OG  | SER B 72  | 36.825 28.742 81.719 1.00 17.67 | B |
| ATOM | 2043 | C   | SER B 72  | 36.445 26.055 82.396 1.00 20.63 | B |
| ATOM | 2044 | O   | SER B 72  | 35.454 25.864 81.686 1.00 20.36 | B |
| ATOM | 2045 | N   | LEU B 73  | 37.560 25.344 82.246 1.00 14.84 | B |
| ATOM | 2046 | CA  | LEU B 73  | 37.639 24.268 81.251 1.00 17.44 | B |
| ATOM | 2047 | CB  | LEU B 73  | 39.108 23.768 81.149 1.00 17.03 | B |
| ATOM | 2048 | CG  | LEU B 73  | 40.107 24.750 80.497 1.00 15.90 | B |
| ATOM | 2049 | CD1 | LEU B 73  | 41.554 24.342 80.874 1.00 17.79 | B |
| ATOM | 2050 | CD2 | LEU B 73  | 39.920 24.761 78.995 1.00 15.63 | B |
| ATOM | 2051 | C   | LEU B 73  | 36.726 23.076 81.655 1.00 16.23 | B |
| ATOM | 2052 | O   | LEU B 73  | 36.221 22.342 80.799 1.00 16.28 | B |
| ATOM | 2053 | N   | SER B 74  | 36.554 22.868 82.959 1.00 14.67 | B |
| ATOM | 2054 | CA  | SER B 74  | 35.733 21.759 83.467 1.00 15.99 | B |
| ATOM | 2055 | CB  | SER B 74  | 35.713 21.755 84.987 1.00 18.87 | B |
| ATOM | 2056 | OG  | SER B 74  | 36.978 21.437 85.491 1.00 19.87 | B |
| ATOM | 2057 | C   | SER B 74  | 34.302 21.801 82.969 1.00 18.60 | B |
| ATOM | 2058 | O   | SER B 74  | 33.697 20.761 82.715 1.00 17.42 | B |
| ATOM | 2059 | N   | VAL B 75  | 33.798 23.014 82.789 1.00 19.72 | B |
| ATOM | 2060 | CA  | VAL B 75  | 32.420 23.227 82.338 1.00 21.63 | B |
| ATOM | 2061 | CB  | VAL B 75  | 32.170 24.734 82.066 1.00 24.32 | B |
| ATOM | 2062 | CG1 | VAL B 75  | 30.841 24.927 81.344 1.00 28.50 | B |
| ATOM | 2063 | CG2 | VAL B 75  | 32.159 25.520 83.402 1.00 21.07 | B |
| ATOM | 2064 | C   | VAL B 75  | 32.105 22.395 81.103 1.00 25.10 | B |
| ATOM | 2065 | O   | VAL B 75  | 31.084 21.680 81.058 1.00 22.58 | B |
| ATOM | 2066 | N   | LYS B 76  | 32.985 22.429 80.113 1.00 18.10 | B |
| ATOM | 2067 | CA  | LYS B 76  | 32.742 21.659 78.890 1.00 17.77 | B |
| ATOM | 2068 | CB  | LYS B 76  | 32.991 22.570 77.672 1.00 21.96 | B |
| ATOM | 2069 | CG  | LYS B 76  | 32.888 21.876 76.320 1.00 22.37 | B |
| ATOM | 2070 | CD  | LYS B 76  | 33.188 22.886 75.226 1.00 31.80 | B |
| ATOM | 2071 | CE  | LYS B 76  | 33.009 22.294 73.810 1.00 31.72 | B |
| ATOM | 2072 | NZ  | LYS B 76  | 33.386 23.334 72.760 1.00 27.51 | B |
| ATOM | 2073 | C   | LYS B 76  | 33.539 20.371 78.734 1.00 24.55 | B |
| ATOM | 2074 | O   | LYS B 76  | 33.106 19.433 78.022 1.00 24.54 | B |
| ATOM | 2075 | N   | TRP B 77  | 34.653 20.263 79.460 1.00 17.19 | B |
| ATOM | 2076 | CA  | TRP B 77  | 35.560 19.139 79.272 1.00 18.71 | B |
| ATOM | 2077 | CB  | TRP B 77  | 36.944 19.710 78.850 1.00 14.47 | B |
| ATOM | 2078 | CG  | TRP B 77  | 36.827 20.650 77.677 1.00 11.83 | B |
| ATOM | 2079 | CD2 | TRP B 77  | 36.709 20.270 76.300 1.00 13.96 | B |
| ATOM | 2080 | CE2 | TRP B 77  | 36.613 21.462 75.536 1.00 17.86 | B |
| ATOM | 2081 | CE3 | TRP B 77  | 36.663 19.030 75.638 1.00 15.32 | B |
| ATOM | 2082 | CD1 | TRP B 77  | 36.805 22.004 77.707 1.00 14.96 | B |
| ATOM | 2083 | NE1 | TRP B 77  | 36.678 22.513 76.423 1.00 15.73 | B |
| ATOM | 2084 | CZ2 | TRP B 77  | 36.484 21.458 74.130 1.00 16.83 | B |
| ATOM | 2085 | CZ3 | TRP B 77  | 36.532 19.015 74.211 1.00 14.26 | B |
| ATOM | 2086 | CH2 | TRP B 77  | 36.439 20.230 73.487 1.00 18.78 | B |
| ATOM | 2087 | C   | TRP B 77  | 35.763 18.122 80.381 1.00 16.51 | B |
| ATOM | 2088 | O   | TRP B 77  | 36.444 17.108 80.176 1.00 15.34 | B |
| ATOM | 2089 | N   | LYS B 78  | 35.174 18.358 81.537 1.00 16.57 | B |
| ATOM | 2090 | CA  | LYS B 78  | 35.354 17.413 82.648 1.00 18.04 | B |
| ATOM | 2091 | CB  | LYS B 78  | 34.573 17.877 83.876 1.00 19.84 | B |
| ATOM | 2092 | CG  | LYS B 78  | 34.623 16.870 85.027 1.00 23.34 | B |
| ATOM | 2093 | CD  | LYS B 78  | 33.875 17.433 86.246 1.00 21.71 | B |
| ATOM | 2094 | CE  | LYS B 78  | 33.952 16.457 87.407 1.00 33.79 | B |
| ATOM | 2095 | NZ  | LYS B 78  | 33.144 16.958 88.562 1.00 39.31 | B |
| ATOM | 2096 | C   | LYS B 78  | 34.879 16.036 82.237 1.00 17.81 | B |
| ATOM | 2097 | O   | LYS B 78  | 33.810 15.908 81.636 1.00 17.96 | B |
| ATOM | 2098 | N   | GLY B 79  | 35.694 15.016 82.525 1.00 14.12 | B |
| ATOM | 2099 | CA  | GLY B 79  | 35.364 13.641 82.169 1.00 16.83 | B |
| ATOM | 2100 | C   | GLY B 79  | 36.077 13.114 80.929 1.00 14.69 | B |
| ATOM | 2101 | O   | GLY B 79  | 36.127 11.921 80.694 1.00 17.46 | B |
| ATOM | 2102 | N   | LYS B 80  | 36.614 14.008 80.104 1.00 14.24 | B |
| ATOM | 2103 | CA  | LYS B 80  | 37.350 13.552 78.942 1.00 15.67 | B |
| ATOM | 2104 | CB  | LYS B 80  | 37.665 14.741 78.017 1.00 15.78 | B |
| ATOM | 2105 | CG  | LYS B 80  | 36.433 15.387 77.398 1.00 19.60 | B |
| ATOM | 2106 | CD  | LYS B 80  | 35.757 14.522 76.347 1.00 26.39 | B |
| ATOM | 2107 | CE  | LYS B 80  | 34.480 15.206 75.866 1.00 28.49 | B |
| ATOM | 2108 | NZ  | LYS B 80  | 33.774 14.363 74.879 1.00 35.60 | B |
| ATOM | 2109 | C   | LYS B 80  | 38.658 12.891 79.375 1.00 14.44 | B |
| ATOM | 2110 | O   | LYS B 80  | 39.327 13.338 80.317 1.00 17.95 | B |
| ATOM | 2111 | N   | THR B 81  | 39.055 11.869 78.645 1.00 13.02 | B |
| ATOM | 2112 | CA  | THR B 81  | 40.268 11.129 78.946 1.00 13.22 | B |
| ATOM | 2113 | CB  | THR B 81  | 40.216  9.719 78.305 1.00 16.79 | B |
| ATOM | 2114 | OG1 | THR B 81  | 40.225  9.854 76.882 1.00 16.99 | B |
| ATOM | 2115 | CG2 | THR B 81  | 38.890  9.023 78.731 1.00 22.12 | B |
| ATOM | 2116 | C   | THR B 81  | 41.463 11.870 78.344 1.00 10.85 | B |
| ATOM | 2117 | O   | THR B 81  | 41.295 12.814 77.539 1.00 13.50 | B |
| ATOM | 2118 | N   | THR B 82  | 42.648 11.408 78.721 1.00 13.00 | B |
| ATOM | 2119 | CA  | THR B 82  | 43.876 12.006 78.195 1.00 14.34 | B |
| ATOM | 2120 | CB  | THR B 82  | 45.106 11.227 78.686 1.00 15.65 | B |
| ATOM | 2121 | OG1 | THR B 82  | 45.205 11.352 80.107 1.00 15.44 | B |
| ATOM | 2122 | CG2 | THR B 82  | 46.365 11.781 78.087 1.00 15.35 | B |
| ATOM | 2123 | C   | THR B 82  | 43.857 11.931 76.661 1.00 12.32 | B |
| ATOM | 2124 | O   | THR B 82  | 44.169 12.921 75.974 1.00 11.39 | B |
| ATOM | 2125 | N   | GLU B 83  | 43.503 10.756 76.124 1.00 14.05 | B |
| ATOM | 2126 | CA  | GLU B 83  | 43.477 10.589 74.667 1.00 15.47 | B |
| ATOM | 2127 | CB  | GLU B 83  | 43.189  9.126 74.306 1.00 17.29 | B |
| ATOM | 2128 | CG  | GLU B 83  | 44.252  8.126 74.746 1.00 24.96 | B |
| ATOM | 2129 | CD  | GLU B 83  | 44.315  7.864 76.262 1.00 32.88 | B |
| ATOM | 2130 | OE1 | GLU B 83  | 43.305  8.079 77.006 1.00 26.90 | B |
| ATOM | 2131 | OE2 | GLU B 83  | 45.408  7.416 76.698 1.00 37.74 | B |
| ATOM | 2132 | C   | GLU B 83  | 42.479 11.497 73.981 1.00 13.58 | B |
| ATOM | 2133 | O   | GLU B 83  | 42.766 12.094 72.917 1.00 14.48 | B |
| ATOM | 2134 | N   | GLU B 84  | 41.298 11.633 74.564 1.00 11.69 | B |
| ATOM | 2135 | CA  | GLU B 84  | 40.292 12.503 74.012 1.00 14.16 | B |
| ATOM | 2136 | CB  | GLU B 84  | 38.969 12.366 74.776 1.00 14.23 | B |
| ATOM | 2137 | CG  | GLU B 84  | 38.306 11.006 74.494 1.00 18.41 | B |
| ATOM | 2138 | CD  | GLU B 84  | 37.162 10.673 75.472 1.00 28.40 | B |
| ATOM | 2139 | OE1 | GLU B 84  | 37.116 11.197 76.605 1.00 20.26 | B |
| ATOM | 2140 | OE2 | GLU B 84  | 36.298  9.836 75.107 1.00 34.38 | B |
| ATOM | 2141 | C   | GLU B 84  | 40.739 13.950 73.988 1.00 12.01 | B |
| ATOM | 2142 | O   | GLU B 84  | 40.515 14.650 73.007 1.00 14.99 | B |
| ATOM | 2143 | N   | LEU B 85  | 41.357 14.401 75.075 1.00 11.18 | B |
| ATOM | 2144 | CA  | LEU B 85  | 41.829 15.779 75.086 1.00 11.67 | B |
| ATOM | 2145 | CB  | LEU B 85  | 42.198 16.154 76.517 1.00 10.23 | B |
| ATOM | 2146 | CG  | LEU B 85  | 41.036 16.166 77.510 1.00 11.96 | B |
| ATOM | 2147 | CD1 | LEU B 85  | 41.578 16.575 78.889 1.00 13.06 | B |
| ATOM | 2148 | CD2 | LEU B 85  | 39.938 17.150 77.063 1.00 11.97 | B |
| ATOM | 2149 | C   | LEU B 85  | 43.021 15.998 74.161 1.00 10.96 | B |
| ATOM | 2150 | O   | LEU B 85  | 43.157 17.093 73.542 1.00 11.12 | B |
| ATOM | 2151 | N   | THR B 86  | 43.887 14.995 74.053 1.00 11.66 | B |
| ATOM | 2152 | CA  | THR B 86  | 45.074 15.159 73.207 1.00 12.18 | B |
| ATOM | 2153 | CB  | THR B 86  | 46.000 13.938 73.308 1.00 12.47 | B |
| ATOM | 2154 | OG1 | THR B 86  | 46.437 13.792 74.683 1.00 14.26 | B |
| ATOM | 2155 | CG2 | THR B 86  | 47.220 14.074 72.400 1.00 12.52 | B |
| ATOM | 2156 | C   | THR B 86  | 44.661 15.352 71.748 1.00 12.66 | B |
| ATOM | 2157 | O   | THR B 86  | 45.277 16.135 71.015 1.00 12.31 | B |
| ATOM | 2158 | N   | GLU B 87  | 43.623 14.621 71.326 1.00 12.91 | B |
| ATOM | 2159 | CA  | GLU B 87  | 43.154 14.715 69.928 1.00 14.08 | B |
| ATOM | 2160 | CB  | GLU B 87  | 42.351 13.457 69.544 1.00 17.70 | B |
| ATOM | 2161 | CG  | GLU B 87  | 43.138 12.154 69.493 1.00 35.27 | B |
| ATOM | 2162 | CD  | GLU B 87  | 42.225 10.919 69.603 1.00 40.34 | B |
| ATOM | 2163 | OE1 | GLU B 87  | 41.055 11.029 69.125 1.00 40.96 | B |
| ATOM | 2164 | OE2 | GLU B 87  | 42.679  9.868 70.145 1.00 40.11 | B |
| ATOM | 2165 | C   | GLU B 87  | 42.265 15.901 69.661 1.00 17.25 | B |
| ATOM | 2166 | O   | GLU B 87  | 41.995 16.225 68.506 1.00 16.79 | B |
| ATOM | 2167 | N   | SER B 88  | 41.812 16.581 70.705 1.00 12.35 | B |
| ATOM | 2168 | CA  | SER B 88  | 40.870 17.654 70.517 1.00 12.59 | B |
| ATOM | 2169 | CB  | SER B 88  | 40.000 17.788 71.774 1.00 15.01 | B |
| ATOM | 2170 | OG  | SER B 88  | 39.146 18.903 71.677 1.00 14.71 | B |
| ATOM | 2171 | C   | SER B 88  | 41.428 19.014 70.164 1.00 14.84 | B |
| ATOM | 2172 | O   | SER B 88  | 42.098 19.668 70.979 1.00 15.20 | B |
| ATOM | 2173 | N   | ILE B 89  | 41.152 19.451 68.947 1.00 16.59 | B |
| ATOM | 2174 | CA  | ILE B 89  | 41.568 20.790 68.539 1.00 16.41 | B |
| ATOM | 2175 | CB  | ILE B 89  | 41.256 21.040 67.025 1.00 18.45 | B |
| ATOM | 2176 | CG2 | ILE B 89  | 41.570 22.489 66.651 1.00 21.01 | B |
| ATOM | 2177 | CG1 | ILE B 89  | 41.994 20.019 66.166 1.00 28.08 | B |
| ATOM | 2178 | CD1 | ILE B 89  | 43.346 19.632 66.627 1.00 32.99 | B |
| ATOM | 2179 | C   | ILE B 89  | 40.845 21.847 69.382 1.00 13.84 | B |
| ATOM | 2180 | O   | ILE B 89  | 41.477 22.754 69.924 1.00 16.08 | B |
| ATOM | 2181 | N   | PRO B 90  | 39.512 21.740 69.557 1.00 15.29 | B |
| ATOM | 2182 | CD  | PRO B 90  | 38.558 20.813 68.908 1.00 15.72 | B |
| ATOM | 2183 | CA  | PRO B 90  | 38.807 22.754 70.350 1.00 15.34 | B |
| ATOM | 2184 | CB  | PRO B 90  | 37.317 22.302 70.289 1.00 17.85 | B |
| ATOM | 2185 | CG  | PRO B 90  | 37.254 21.564 69.040 1.00 15.59 | B |
| ATOM | 2186 | C   | PRO B 90  | 39.290 22.928 71.790 1.00 15.05 | B |
| ATOM | 2187 | O   | PRO B 90  | 39.318 24.065 72.298 1.00 16.25 | B |
| ATOM | 2188 | N   | PHE B 91  | 39.618 21.798 72.445 1.00 13.64 | B |
| ATOM | 2189 | CA  | PHE B 91  | 40.065 21.862 73.832 1.00 12.15 | B |
| ATOM | 2190 | CB  | PHE B 91  | 40.375 20.457 74.373 1.00 10.21 | B |
| ATOM | 2191 | CG  | PHE B 91  | 40.895 20.477 75.790 1.00 10.47 | B |
| ATOM | 2192 | CD1 | PHE B 91  | 40.112 20.962 76.855 1.00 12.05 | B |
| ATOM | 2193 | CD2 | PHE B 91  | 42.172 19.990 76.051 1.00 11.69 | B |
| ATOM | 2194 | CE1 | PHE B 91  | 40.596 20.954 78.182 1.00 14.41 | B |
| ATOM | 2195 | CE2 | PHE B 91  | 42.666 19.976 77.368 1.00 12.16 | B |
| ATOM | 2196 | CZ  | PHE B 91  | 41.881 20.456 78.436 1.00 12.44 | B |
| ATOM | 2197 | C   | PHE B 91  | 41.317 22.722 73.946 1.00 10.08 | B |
| ATOM | 2198 | O   | PHE B 91  | 41.413 23.610 74.798 1.00 11.28 | B |
| ATOM | 2199 | N   | PHE B 92  | 42.308 22.387 73.129 1.00 12.53 | B |
| ATOM | 2200 | CA  | PHE B 92  | 43.534 23.169 73.183 1.00 11.97 | B |

Fig. 4 cont.

| | | | | | |
|---|---|---|---|---|---|
| ATOM | 2201 CB PHE B 92 | 44.670 22.414 72.481 1.00 11.44 | B |
| ATOM | 2202 CG PHE B 92 | 45.333 21.421 73.385 1.00 11.81 | B |
| ATOM | 2203 CD1 PHE B 92 | 44.820 20.136 73.549 1.00 10.65 | B |
| ATOM | 2204 CD2 PHE B 92 | 46.414 21.827 74.164 1.00 10.76 | B |
| ATOM | 2205 CE1 PHE B 92 | 45.362 19.263 74.472 1.00 13.18 | B |
| ATOM | 2206 CE2 PHE B 92 | 46.977 20.967 75.107 1.00 9.20 | B |
| ATOM | 2207 CZ PHE B 92 | 46.451 19.677 75.269 1.00 10.97 | B |
| ATOM | 2208 C PHE B 92 | 43.365 24.576 72.680 1.00 11.53 | B |
| ATOM | 2209 O PHE B 92 | 44.048 25.489 73.153 1.00 14.59 | B |
| ATOM | 2210 N ARG B 93 | 42.454 24.792 71.729 1.00 14.08 | B |
| ATOM | 2211 CA ARG B 93 | 42.226 26.167 71.312 1.00 14.72 | B |
| ATOM | 2212 CB ARG B 93 | 41.317 26.227 70.059 1.00 16.76 | B |
| ATOM | 2213 CG ARG B 93 | 42.044 25.882 68.745 1.00 21.52 | B |
| ATOM | 2214 CD ARG B 93 | 43.022 27.000 68.336 1.00 27.68 | B |
| ATOM | 2215 NE ARG B 93 | 42.313 28.258 68.098 1.00 33.30 | B |
| ATOM | 2216 CZ ARG B 93 | 42.887 29.463 68.058 1.00 37.35 | B |
| ATOM | 2217 NH1 ARG B 93 | 44.190 29.585 68.243 1.00 35.55 | B |
| ATOM | 2218 NH2 ARG B 93 | 42.145 30.550 67.863 1.00 40.59 | B |
| ATOM | 2219 C ARG B 93 | 41.589 26.952 72.481 1.00 14.04 | B |
| ATOM | 2220 O ARG B 93 | 41.859 28.143 72.674 1.00 15.91 | B |
| ATOM | 2221 N GLU B 94 | 40.737 26.306 73.279 1.00 13.33 | B |
| ATOM | 2222 CA GLU B 94 | 40.130 27.002 74.422 1.00 16.95 | B |
| ATOM | 2223 CB GLU B 94 | 39.025 26.133 75.074 1.00 13.57 | B |
| ATOM | 2224 CG GLU B 94 | 38.302 26.807 76.239 1.00 16.39 | B |
| ATOM | 2225 CD GLU B 94 | 37.097 25.987 76.760 1.00 19.07 | B |
| ATOM | 2226 OE1 GLU B 94 | 36.436 25.321 75.948 1.00 19.51 | B |
| ATOM | 2227 OE2 GLU B 94 | 36.804 26.013 77.981 1.00 21.38 | B |
| ATOM | 2228 C GLU B 94 | 41.210 27.363 75.483 1.00 16.27 | B |
| ATOM | 2229 O GLU B 94 | 41.138 28.398 76.142 1.00 16.24 | B |
| ATOM | 2230 N ILE B 95 | 42.184 26.475 75.658 1.00 12.49 | B |
| ATOM | 2231 CA ILE B 95 | 43.288 26.760 76.584 1.00 11.44 | B |
| ATOM | 2232 CB ILE B 95 | 44.279 25.589 76.652 1.00 13.62 | B |
| ATOM | 2233 CG2 ILE B 95 | 45.546 26.036 77.409 1.00 13.23 | B |
| ATOM | 2234 CG1 ILE B 95 | 43.623 24.399 77.357 1.00 13.32 | B |
| ATOM | 2235 CD1 ILE B 95 | 44.427 23.073 77.249 1.00 13.86 | B |
| ATOM | 2236 C ILE B 95 | 44.064 27.996 76.077 1.00 14.62 | B |
| ATOM | 2237 O ILE B 95 | 44.309 28.943 76.826 1.00 16.70 | B |
| ATOM | 2238 N VAL B 96 | 44.447 27.960 74.804 1.00 12.23 | B |
| ATOM | 2239 CA VAL B 96 | 45.244 29.045 74.207 1.00 14.89 | B |
| ATOM | 2240 CB VAL B 96 | 45.644 28.658 72.789 1.00 14.01 | B |
| ATOM | 2241 CG1 VAL B 96 | 46.265 29.859 72.055 1.00 19.57 | B |
| ATOM | 2242 CG2 VAL B 96 | 46.625 27.478 72.814 1.00 14.85 | B |
| ATOM | 2243 C VAL B 96 | 44.557 30.408 74.163 1.00 14.42 | B |
| ATOM | 2244 O VAL B 96 | 45.202 31.435 74.406 1.00 15.23 | B |
| ATOM | 2245 N THR B 97 | 43.262 30.423 73.836 1.00 15.33 | B |
| ATOM | 2246 CA THR B 97 | 42.509 31.674 73.710 1.00 14.51 | B |
| ATOM | 2247 CB THR B 97 | 41.490 31.582 72.552 1.00 20.05 | B |
| ATOM | 2248 OG1 THR B 97 | 40.490 30.614 72.888 1.00 18.04 | B |
| ATOM | 2249 CG2 THR B 97 | 42.189 31.218 71.267 1.00 19.83 | B |
| ATOM | 2250 C THR B 97 | 41.742 32.143 74.938 1.00 14.64 | B |
| ATOM | 2251 O THR B 97 | 41.224 33.262 74.963 1.00 17.34 | B |
| ATOM | 2252 N GLY B 98 | 41.682 31.310 75.974 1.00 14.66 | B |
| ATOM | 2253 CA GLY B 98 | 40.956 31.677 77.171 1.00 15.79 | B |
| ATOM | 2254 C GLY B 98 | 41.433 32.957 77.851 1.00 15.81 | B |
| ATOM | 2255 O GLY B 98 | 42.616 33.348 77.754 1.00 15.37 | B |
| ATOM | 2256 N ALA B 99 | 40.512 33.634 78.534 1.00 16.10 | B |
| ATOM | 2257 CA ALA B 99 | 40.828 34.879 79.210 1.00 17.38 | B |
| ATOM | 2258 CB ALA B 99 | 39.561 35.768 79.313 1.00 19.85 | B |
| ATOM | 2259 C ALA B 99 | 41.446 34.633 80.577 1.00 20.32 | B |
| ATOM | 2260 O ALA B 99 | 40.893 34.973 81.649 1.00 17.46 | B |
| ATOM | 2261 N PHE B 100 | 42.618 34.009 80.515 1.00 12.94 | B |
| ATOM | 2262 CA PHE B 100 | 43.405 33.664 81.698 1.00 14.19 | B |
| ATOM | 2263 CB PHE B 100 | 43.168 32.224 82.085 1.00 15.06 | B |
| ATOM | 2264 CG PHE B 100 | 41.736 31.913 82.384 1.00 18.85 | B |
| ATOM | 2265 CD1 PHE B 100 | 40.911 31.343 81.403 1.00 19.84 | B |
| ATOM | 2266 CD2 PHE B 100 | 41.200 32.233 83.624 1.00 17.63 | B |
| ATOM | 2267 CE1 PHE B 100 | 39.544 31.097 81.680 1.00 22.14 | B |
| ATOM | 2268 CE2 PHE B 100 | 39.822 31.986 83.907 1.00 18.10 | B |
| ATOM | 2269 CZ PHE B 100 | 39.009 31.424 82.927 1.00 16.99 | B |
| ATOM | 2270 C PHE B 100 | 44.847 33.795 81.283 1.00 12.31 | B |
| ATOM | 2271 O PHE B 100 | 45.150 33.789 80.082 1.00 13.95 | B |
| ATOM | 2272 N GLU B 101 | 45.716 33.928 82.282 1.00 14.45 | B |
| ATOM | 2273 CA GLU B 101 | 47.126 34.070 81.987 1.00 12.73 | B |
| ATOM | 2274 CB GLU B 101 | 47.851 34.700 83.179 1.00 12.72 | B |
| ATOM | 2275 CG GLU B 101 | 49.354 34.902 82.888 1.00 15.64 | B |
| ATOM | 2276 CD GLU B 101 | 50.079 35.742 83.904 1.00 12.90 | B |
| ATOM | 2277 OE1 GLU B 101 | 49.631 35.801 85.074 1.00 14.58 | B |
| ATOM | 2278 OE2 GLU B 101 | 51.127 36.331 83.505 1.00 15.38 | B |
| ATOM | 2279 C GLU B 101 | 47.739 32.696 81.697 1.00 10.66 | B |
| ATOM | 2280 O GLU B 101 | 47.312 31.686 82.244 1.00 13.88 | B |
| ATOM | 2281 N LYS B 102 | 48.727 32.672 80.808 1.00 9.63 | B |
| ATOM | 2282 CA LYS B 102 | 49.482 31.437 80.572 1.00 7.08 | B |
| ATOM | 2283 CB LYS B 102 | 49.176 30.743 79.222 1.00 9.33 | B |
| ATOM | 2284 CG LYS B 102 | 47.683 30.586 78.876 1.00 10.33 | B |
| ATOM | 2285 CD LYS B 102 | 47.194 31.763 78.048 1.00 12.75 | B |
| ATOM | 2286 CE LYS B 102 | 45.688 31.642 77.857 1.00 14.32 | B |
| ATOM | 2287 NZ LYS B 102 | 45.155 32.708 76.987 1.00 16.05 | B |
| ATOM | 2288 C LYS B 102 | 50.955 31.856 80.613 1.00 9.89 | B |
| ATOM | 2289 O LYS B 102 | 51.295 33.036 80.493 1.00 9.83 | B |
| ATOM | 2290 N PHE B 103 | 51.827 30.899 80.904 1.00 7.70 | B |
| ATOM | 2291 CA PHE B 103 | 53.249 31.208 80.969 1.00 8.31 | B |
| ATOM | 2292 CB PHE B 103 | 53.644 31.448 82.426 1.00 9.37 | B |
| ATOM | 2293 CG PHE B 103 | 55.113 31.686 82.643 1.00 11.58 | B |
| ATOM | 2294 CD1 PHE B 103 | 55.694 32.931 82.385 1.00 11.44 | B |
| ATOM | 2295 CD2 PHE B 103 | 55.921 30.665 83.128 1.00 12.83 | B |
| ATOM | 2296 CE1 PHE B 103 | 57.080 33.147 82.620 1.00 13.47 | B |
| ATOM | 2297 CE2 PHE B 103 | 57.303 30.886 83.364 1.00 13.28 | B |
| ATOM | 2298 CZ PHE B 103 | 57.865 32.123 83.110 1.00 12.11 | B |
| ATOM | 2299 C PHE B 103 | 54.020 30.030 80.391 1.00 9.93 | B |
| ATOM | 2300 O PHE B 103 | 53.628 28.865 80.592 1.00 12.11 | B |
| ATOM | 2301 N ILE B 104 | 55.079 30.329 79.642 1.00 8.38 | B |
| ATOM | 2302 CA ILE B 104 | 55.881 29.269 79.009 1.00 8.17 | B |
| ATOM | 2303 CB ILE B 104 | 55.813 29.399 77.462 1.00 9.35 | B |
| ATOM | 2304 CG2 ILE B 104 | 56.407 28.105 76.809 1.00 10.72 | B |
| ATOM | 2305 CG1 ILE B 104 | 54.373 29.562 76.998 1.00 10.00 | B |
| ATOM | 2306 CD1 ILE B 104 | 54.260 29.891 75.470 1.00 10.43 | B |
| ATOM | 2307 C ILE B 104 | 57.331 29.441 79.394 1.00 10.45 | B |
| ATOM | 2308 O ILE B 104 | 57.848 30.555 79.308 1.00 8.16 | B |
| ATOM | 2309 N LYS B 105 | 57.971 28.354 79.801 1.00 8.83 | B |
| ATOM | 2310 CA LYS B 105 | 59.405 28.357 80.119 1.00 10.06 | B |
| ATOM | 2311 CB LYS B 105 | 59.689 27.838 81.550 1.00 9.96 | B |
| ATOM | 2312 CG LYS B 105 | 61.211 27.676 81.872 1.00 9.19 | B |
| ATOM | 2313 CD LYS B 105 | 61.403 27.411 83.358 1.00 10.53 | B |
| ATOM | 2314 CE LYS B 105 | 62.882 27.286 83.741 1.00 11.36 | B |
| ATOM | 2315 NZ LYS B 105 | 63.387 25.941 83.349 1.00 11.87 | B |
| ATOM | 2316 C LYS B 105 | 60.078 27.473 79.081 1.00 8.73 | B |
| ATOM | 2317 O LYS B 105 | 59.778 26.292 79.030 1.00 8.65 | B |
| ATOM | 2318 N VAL B 106 | 60.955 28.038 78.234 1.00 7.69 | B |
| ATOM | 2319 CA VAL B 106 | 61.639 27.281 77.195 1.00 6.92 | B |
| ATOM | 2320 CB VAL B 106 | 61.493 27.997 75.836 1.00 8.93 | B |
| ATOM | 2321 CG1 VAL B 106 | 62.276 27.217 74.751 1.00 8.50 | B |
| ATOM | 2322 CG2 VAL B 106 | 60.008 28.060 75.445 1.00 9.56 | B |
| ATOM | 2323 C VAL B 106 | 63.090 27.272 77.620 1.00 11.38 | B |
| ATOM | 2324 O VAL B 106 | 63.720 28.330 77.652 1.00 10.58 | B |
| ATOM | 2325 N THR B 107 | 63.620 26.084 77.949 1.00 9.70 | B |
| ATOM | 2326 CA THR B 107 | 64.998 25.978 78.446 1.00 9.25 | B |
| ATOM | 2327 CB THR B 107 | 65.024 25.217 79.769 1.00 13.45 | B |
| ATOM | 2328 OG1 THR B 107 | 64.279 25.974 80.755 1.00 14.21 | B |
| ATOM | 2329 CG2 THR B 107 | 66.473 25.046 80.249 1.00 10.18 | B |
| ATOM | 2330 C THR B 107 | 65.817 25.275 77.364 1.00 10.07 | B |
| ATOM | 2331 O THR B 107 | 65.425 24.213 76.847 1.00 10.82 | B |
| ATOM | 2332 N MET B 108 | 66.928 25.911 76.994 1.00 9.72 | B |
| ATOM | 2333 CA MET B 108 | 67.760 25.375 75.905 1.00 11.07 | B |
| ATOM | 2334 CB MET B 108 | 68.757 26.449 75.430 1.00 16.20 | B |
| ATOM | 2335 CG MET B 108 | 68.307 27.223 74.216 1.00 13.86 | B |
| ATOM | 2336 SD MET B 108 | 66.577 27.884 74.348 1.00 14.25 | B |
| ATOM | 2337 CE MET B 108 | 66.736 29.035 75.696 1.00 14.11 | B |
| ATOM | 2338 C MET B 108 | 68.560 24.142 76.297 1.00 12.95 | B |
| ATOM | 2339 O MET B 108 | 69.120 24.085 77.384 1.00 13.38 | B |
| ATOM | 2340 N LYS B 109 | 68.584 23.151 75.405 1.00 11.57 | B |
| ATOM | 2341 CA LYS B 109 | 69.424 21.971 75.649 1.00 13.98 | B |
| ATOM | 2342 CB LYS B 109 | 68.713 20.647 75.289 1.00 12.03 | B |
| ATOM | 2343 CG LYS B 109 | 69.589 19.432 75.741 1.00 17.56 | B |
| ATOM | 2344 CD LYS B 109 | 68.955 18.077 75.431 1.00 24.72 | B |
| ATOM | 2345 CE LYS B 109 | 69.876 16.890 75.837 1.00 25.95 | B |
| ATOM | 2346 NZ LYS B 109 | 70.123 16.764 77.322 1.00 28.64 | B |
| ATOM | 2347 C LYS B 109 | 70.617 22.224 74.706 1.00 15.53 | B |
| ATOM | 2348 O LYS B 109 | 71.780 22.055 75.106 1.00 18.62 | B |
| ATOM | 2349 N LEU B 110 | 70.323 22.595 73.462 1.00 15.13 | B |
| ATOM | 2350 CA LEU B 110 | 71.368 22.968 72.510 1.00 15.95 | B |
| ATOM | 2351 CB LEU B 110 | 70.947 22.673 71.075 1.00 19.75 | B |
| ATOM | 2352 CG LEU B 110 | 70.989 21.231 70.587 1.00 26.48 | B |
| ATOM | 2353 CD1 LEU B 110 | 70.453 21.184 69.177 1.00 24.61 | B |
| ATOM | 2354 CD2 LEU B 110 | 72.428 20.726 70.648 1.00 25.09 | B |
| ATOM | 2355 C LEU B 110 | 71.509 24.476 72.597 1.00 17.52 | B |
| ATOM | 2356 O LEU B 110 | 70.572 25.166 72.986 1.00 16.35 | B |
| ATOM | 2357 N PRO B 111 | 72.687 25.017 72.241 1.00 17.76 | B |
| ATOM | 2358 CD PRO B 111 | 73.975 24.371 71.903 1.00 21.51 | B |
| ATOM | 2359 CA PRO B 111 | 72.800 26.472 72.301 1.00 20.53 | B |
| ATOM | 2360 CB PRO B 111 | 74.311 26.741 72.119 1.00 21.07 | B |

Fig. 4 cont.

| | | | | | |
|---|---|---|---|---|---|
| ATOM | 2361 CG PRO B 111 | 74.793 25.542 71.344 1.00 20.78 | B |
| ATOM | 2362 C PRO B 111 | 72.006 26.988 71.112 1.00 13.61 | B |
| ATOM | 2363 O PRO B 111 | 71.984 26.367 70.056 1.00 17.26 | B |
| ATOM | 2364 N LEU B 112 | 71.304 28.107 71.298 1.00 14.97 | B |
| ATOM | 2365 CA LEU B 112 | 70.548 28.709 70.202 1.00 15.02 | B |
| ATOM | 2366 CB LEU B 112 | 69.048 28.400 70.327 1.00 13.45 | B |
| ATOM | 2367 CG LEU B 112 | 68.575 26.958 70.233 1.00 13.83 | B |
| ATOM | 2368 CD1 LEU B 112 | 67.051 26.921 70.468 1.00 18.82 | B |
| ATOM | 2369 CD2 LEU B 112 | 68.909 26.429 68.829 1.00 17.82 | B |
| ATOM | 2370 C LEU B 112 | 70.694 30.232 70.172 1.00 15.81 | B |
| ATOM | 2371 O LEU B 112 | 70.756 30.866 71.229 1.00 14.86 | B |
| ATOM | 2372 N THR B 113 | 70.761 30.817 68.984 1.00 15.93 | B |
| ATOM | 2373 CA THR B 113 | 70.812 32.263 68.931 1.00 13.69 | B |
| ATOM | 2374 CB THR B 113 | 71.445 32.776 67.634 1.00 14.43 | B |
| ATOM | 2375 OG1 THR B 113 | 70.630 32.419 66.512 1.00 15.10 | B |
| ATOM | 2376 CG2 THR B 113 | 72.839 32.162 67.467 1.00 17.83 | B |
| ATOM | 2377 C THR B 113 | 69.367 32.752 68.982 1.00 14.65 | B |
| ATOM | 2378 O THR B 113 | 68.450 32.045 68.572 1.00 15.21 | B |
| ATOM | 2379 N GLY B 114 | 69.168 33.956 69.508 1.00 14.54 | B |
| ATOM | 2380 CA GLY B 114 | 67.830 34.516 69.556 1.00 16.09 | B |
| ATOM | 2381 C GLY B 114 | 67.253 34.657 68.154 1.00 14.69 | B |
| ATOM | 2382 O GLY B 114 | 66.081 34.509 67.946 1.00 14.45 | B |
| ATOM | 2383 N GLN B 115 | 68.098 34.982 67.186 1.00 14.08 | B |
| ATOM | 2384 CA GLN B 115 | 67.641 35.141 65.822 1.00 13.77 | B |
| ATOM | 2385 CB GLN B 115 | 68.839 35.540 64.947 1.00 21.59 | B |
| ATOM | 2386 CG GLN B 115 | 68.530 35.487 63.489 1.00 25.38 | B |
| ATOM | 2387 CD GLN B 115 | 69.620 36.121 62.672 1.00 41.66 | B |
| ATOM | 2388 OE1 GLN B 115 | 69.848 37.328 62.753 1.00 42.18 | B |
| ATOM | 2389 NE2 GLN B 115 | 70.313 35.312 61.884 1.00 49.23 | B |
| ATOM | 2390 C GLN B 115 | 67.015 33.842 65.286 1.00 14.71 | B |
| ATOM | 2391 O GLN B 115 | 65.897 33.840 64.797 1.00 15.73 | B |
| ATOM | 2392 N GLN B 116 | 67.719 32.728 65.427 1.00 16.50 | B |
| ATOM | 2393 CA GLN B 116 | 67.160 31.499 64.895 1.00 14.98 | B |
| ATOM | 2394 CB GLN B 116 | 68.221 30.413 64.761 1.00 15.62 | B |
| ATOM | 2395 CG GLN B 116 | 68.768 29.855 66.049 1.00 19.22 | B |
| ATOM | 2396 CD GLN B 116 | 70.074 29.056 65.837 1.00 19.32 | B |
| ATOM | 2397 OE1 GLN B 116 | 70.313 28.490 64.748 1.00 27.87 | B |
| ATOM | 2398 NE2 GLN B 116 | 70.900 29.000 66.859 1.00 14.10 | B |
| ATOM | 2399 C GLN B 116 | 65.963 31.012 65.701 1.00 16.48 | B |
| ATOM | 2400 O GLN B 116 | 64.994 30.532 65.120 1.00 16.40 | B |
| ATOM | 2401 N TYR B 117 | 66.000 31.186 67.008 1.00 12.59 | B |
| ATOM | 2402 CA TYR B 117 | 64.891 30.736 67.842 1.00 12.61 | B |
| ATOM | 2403 CB TYR B 117 | 65.260 30.881 69.328 1.00 14.67 | B |
| ATOM | 2404 CG TYR B 117 | 64.103 30.555 70.254 1.00 13.51 | B |
| ATOM | 2405 CD1 TYR B 117 | 63.763 29.229 70.517 1.00 11.15 | B |
| ATOM | 2406 CE1 TYR B 117 | 62.616 28.907 71.215 1.00 16.56 | B |
| ATOM | 2407 CD2 TYR B 117 | 63.266 31.559 70.723 1.00 14.07 | B |
| ATOM | 2408 CE2 TYR B 117 | 62.093 31.249 71.415 1.00 13.61 | B |
| ATOM | 2409 CZ TYR B 117 | 61.781 29.915 71.654 1.00 13.91 | B |
| ATOM | 2410 OH TYR B 117 | 60.626 29.597 72.342 1.00 16.81 | B |
| ATOM | 2411 C TYR B 117 | 63.641 31.542 67.535 1.00 14.58 | B |
| ATOM | 2412 O TYR B 117 | 62.559 30.986 67.344 1.00 16.55 | B |
| ATOM | 2413 N SER B 118 | 63.785 32.866 67.471 1.00 12.17 | B |
| ATOM | 2414 CA SER B 118 | 62.618 33.689 67.211 1.00 10.30 | B |
| ATOM | 2415 CB SER B 118 | 62.963 35.171 67.418 1.00 12.47 | B |
| ATOM | 2416 OG SER B 118 | 63.982 35.592 66.537 1.00 13.98 | B |
| ATOM | 2417 C SER B 118 | 62.004 33.461 65.834 1.00 17.01 | B |
| ATOM | 2418 O SER B 118 | 60.775 33.493 65.810 1.00 14.25 | B |
| ATOM | 2419 N GLU B 119 | 62.862 33.210 64.840 1.00 16.13 | B |
| ATOM | 2420 CA GLU B 119 | 62.406 32.913 63.497 1.00 19.73 | B |
| ATOM | 2421 CB GLU B 119 | 63.591 32.941 62.526 1.00 15.85 | B |
| ATOM | 2422 CG GLU B 119 | 63.962 34.366 62.196 1.00 22.06 | B |
| ATOM | 2423 CD GLU B 119 | 65.224 34.504 61.359 1.00 37.25 | B |
| ATOM | 2424 OE1 GLU B 119 | 65.644 33.520 60.706 1.00 48.39 | B |
| ATOM | 2425 OE2 GLU B 119 | 65.787 35.624 61.342 1.00 40.33 | B |
| ATOM | 2426 C GLU B 119 | 61.688 31.544 63.472 1.00 17.25 | B |
| ATOM | 2427 O GLU B 119 | 60.716 31.371 62.730 1.00 19.29 | B |
| ATOM | 2428 N LYS B 120 | 62.147 30.602 64.295 1.00 14.72 | B |
| ATOM | 2429 CA LYS B 120 | 61.541 29.268 64.385 1.00 15.25 | B |
| ATOM | 2430 CB LYS B 120 | 62.436 28.352 65.256 1.00 17.54 | B |
| ATOM | 2431 CG LYS B 120 | 61.838 26.990 65.638 1.00 19.92 | B |
| ATOM | 2432 CD LYS B 120 | 61.593 26.135 64.398 1.00 28.27 | B |
| ATOM | 2433 CE LYS B 120 | 61.001 24.775 64.737 1.00 31.70 | B |
| ATOM | 2434 NZ LYS B 120 | 60.779 24.001 63.489 1.00 32.78 | B |
| ATOM | 2435 C LYS B 120 | 60.147 29.382 64.994 1.00 18.71 | B |
| ATOM | 2436 O LYS B 120 | 59.167 28.843 64.449 1.00 18.15 | B |
| ATOM | 2437 N VAL B 121 | 60.023 30.121 66.098 1.00 13.46 | B |
| ATOM | 2438 CA VAL B 121 | 58.734 30.274 66.772 1.00 14.14 | B |
| ATOM | 2439 CB VAL B 121 | 58.902 31.143 68.035 1.00 15.70 | B |
| ATOM | 2440 CG1 VAL B 121 | 57.541 31.529 68.643 1.00 17.23 | B |
| ATOM | 2441 CG2 VAL B 121 | 59.700 30.360 69.037 1.00 13.27 | B |
| ATOM | 2442 C VAL B 121 | 57.711 30.931 65.860 1.00 16.76 | B |
| ATOM | 2443 O VAL B 121 | 56.530 30.568 65.897 1.00 18.10 | B |
| ATOM | 2444 N THR B 122 | 58.159 31.855 65.022 1.00 13.57 | B |
| ATOM | 2445 CA THR B 122 | 57.214 32.590 64.146 1.00 13.13 | B |
| ATOM | 2446 CB THR B 122 | 57.512 34.106 64.134 1.00 16.04 | B |
| ATOM | 2447 OG1 THR B 122 | 58.882 34.328 63.769 1.00 17.40 | B |
| ATOM | 2448 CG2 THR B 122 | 57.279 34.710 65.519 1.00 16.97 | B |
| ATOM | 2449 C THR B 122 | 57.207 32.141 62.697 1.00 17.28 | B |
| ATOM | 2450 O THR B 122 | 56.691 32.853 61.843 1.00 19.82 | B |
| ATOM | 2451 N GLU B 123 | 57.761 30.965 62.443 1.00 19.57 | B |
| ATOM | 2452 CA GLU B 123 | 57.871 30.389 61.102 1.00 24.30 | B |
| ATOM | 2453 CB GLU B 123 | 58.368 28.971 61.269 1.00 30.56 | B |
| ATOM | 2454 CG GLU B 123 | 59.146 28.348 60.158 1.00 48.51 | B |
| ATOM | 2455 CD GLU B 123 | 59.939 27.184 60.739 1.00 46.09 | B |
| ATOM | 2456 OE1 GLU B 123 | 59.299 26.207 61.211 1.00 40.37 | B |
| ATOM | 2457 OE2 GLU B 123 | 61.192 27.273 60.773 1.00 48.57 | B |
| ATOM | 2458 C GLU B 123 | 56.539 30.338 60.354 1.00 23.17 | B |
| ATOM | 2459 O GLU B 123 | 56.479 30.622 59.161 1.00 25.17 | B |
| ATOM | 2460 N ASN B 124 | 55.479 29.954 61.059 1.00 19.85 | B |
| ATOM | 2461 CA ASN B 124 | 54.177 29.799 60.413 1.00 23.05 | B |
| ATOM | 2462 CB ASN B 124 | 53.624 28.424 60.734 1.00 23.47 | B |
| ATOM | 2463 CG ASN B 124 | 54.599 27.348 60.429 1.00 33.36 | B |
| ATOM | 2464 OD1 ASN B 124 | 55.081 26.651 61.332 1.00 33.19 | B |
| ATOM | 2465 ND2 ASN B 124 | 54.945 27.225 59.151 1.00 27.82 | B |
| ATOM | 2466 C ASN B 124 | 53.067 30.763 60.722 1.00 22.36 | B |
| ATOM | 2467 O ASN B 124 | 52.038 30.734 60.044 1.00 19.63 | B |
| ATOM | 2468 N CYS B 125 | 53.236 31.634 61.706 1.00 16.73 | B |
| ATOM | 2469 CA CYS B 125 | 52.096 32.444 62.039 1.00 19.11 | B |
| ATOM | 2470 CB CYS B 125 | 52.298 33.124 63.400 1.00 29.99 | B |
| ATOM | 2471 SG CYS B 125 | 53.619 34.266 63.462 1.00 26.83 | B |
| ATOM | 2472 C CYS B 125 | 51.564 33.407 60.962 1.00 18.39 | B |
| ATOM | 2473 O CYS B 125 | 50.357 33.538 60.865 1.00 18.15 | B |
| ATOM | 2474 N VAL B 126 | 52.410 34.021 60.135 1.00 16.50 | B |
| ATOM | 2475 CA VAL B 126 | 51.885 34.936 59.124 1.00 18.87 | B |
| ATOM | 2476 CB VAL B 126 | 52.995 35.708 58.414 1.00 22.60 | B |
| ATOM | 2477 CG1 VAL B 126 | 52.416 36.471 57.232 1.00 21.73 | B |
| ATOM | 2478 CG2 VAL B 126 | 53.632 36.683 59.404 1.00 21.45 | B |
| ATOM | 2479 C VAL B 126 | 51.024 34.191 58.092 1.00 17.97 | B |
| ATOM | 2480 O VAL B 126 | 49.934 34.659 57.740 1.00 16.47 | B |
| ATOM | 2481 N ALA B 127 | 51.493 33.028 57.635 1.00 16.81 | B |
| ATOM | 2482 CA ALA B 127 | 50.703 32.264 56.665 1.00 15.88 | B |
| ATOM | 2483 CB ALA B 127 | 51.471 31.031 56.200 1.00 17.76 | B |
| ATOM | 2484 C ALA B 127 | 49.359 31.869 57.276 1.00 16.02 | B |
| ATOM | 2485 O ALA B 127 | 48.349 31.872 56.585 1.00 16.99 | B |
| ATOM | 2486 N ILE B 128 | 49.336 31.521 58.562 1.00 14.17 | B |
| ATOM | 2487 CA ILE B 128 | 48.097 31.155 59.239 1.00 14.39 | B |
| ATOM | 2488 CB ILE B 128 | 48.399 30.628 60.667 1.00 16.07 | B |
| ATOM | 2489 CG2 ILE B 128 | 47.126 30.566 61.509 1.00 15.40 | B |
| ATOM | 2490 CG1 ILE B 128 | 49.047 29.251 60.581 1.00 20.91 | B |
| ATOM | 2491 CD1 ILE B 128 | 49.647 28.771 61.909 1.00 22.79 | B |
| ATOM | 2492 C ILE B 128 | 47.146 32.348 59.322 1.00 15.81 | B |
| ATOM | 2493 O ILE B 128 | 45.950 32.234 59.037 1.00 15.37 | B |
| ATOM | 2494 N TRP B 129 | 47.663 33.506 59.722 1.00 12.39 | B |
| ATOM | 2495 CA TRP B 129 | 46.782 34.668 59.823 1.00 11.92 | B |
| ATOM | 2496 CB TRP B 129 | 47.497 35.859 60.446 1.00 11.48 | B |
| ATOM | 2497 CG TRP B 129 | 47.981 35.525 61.858 1.00 11.24 | B |
| ATOM | 2498 CD2 TRP B 129 | 49.137 36.080 62.499 1.00 10.46 | B |
| ATOM | 2499 CE2 TRP B 129 | 49.182 35.547 63.816 1.00 11.36 | B |
| ATOM | 2500 CE3 TRP B 129 | 50.134 36.960 62.081 1.00 13.36 | B |
| ATOM | 2501 CD1 TRP B 129 | 47.381 34.709 62.787 1.00 10.55 | B |
| ATOM | 2502 NE1 TRP B 129 | 48.109 34.713 63.972 1.00 12.59 | B |
| ATOM | 2503 CZ2 TRP B 129 | 50.219 35.899 64.746 1.00 10.23 | B |
| ATOM | 2504 CZ3 TRP B 129 | 51.154 37.299 62.980 1.00 16.84 | B |
| ATOM | 2505 CH2 TRP B 129 | 51.189 36.759 64.307 1.00 12.60 | B |
| ATOM | 2506 C TRP B 129 | 46.225 35.042 58.441 1.00 14.89 | B |
| ATOM | 2507 O TRP B 129 | 45.063 35.437 58.342 1.00 14.30 | B |
| ATOM | 2508 N LYS B 130 | 47.061 34.924 57.402 1.00 13.96 | B |
| ATOM | 2509 CA LYS B 130 | 46.560 35.212 56.041 1.00 14.61 | B |
| ATOM | 2510 CB LYS B 130 | 47.702 35.140 55.021 1.00 16.71 | B |
| ATOM | 2511 CG LYS B 130 | 48.627 36.325 55.058 1.00 19.65 | B |
| ATOM | 2512 CD LYS B 130 | 49.734 36.197 54.030 1.00 22.99 | B |
| ATOM | 2513 CE LYS B 130 | 50.530 37.481 53.936 1.00 27.88 | B |
| ATOM | 2514 NZ LYS B 130 | 51.721 37.317 53.046 1.00 35.61 | B |
| ATOM | 2515 C LYS B 130 | 45.469 34.208 55.662 1.00 13.43 | B |
| ATOM | 2516 O LYS B 130 | 44.474 34.568 55.016 1.00 15.20 | B |
| ATOM | 2517 N GLN B 131 | 45.645 32.950 56.047 1.00 14.16 | B |
| ATOM | 2518 CA GLN B 131 | 44.661 31.910 55.743 1.00 12.42 | B |
| ATOM | 2519 CB GLN B 131 | 45.249 30.589 56.235 1.00 17.21 | B |
| ATOM | 2520 CG GLN B 131 | 44.588 29.371 55.801 1.00 16.95 | B |

Fig. 4 cont.

| | | | | | | | | | | |
|---|---|---|---|---|---|---|---|---|---|---|
| ATOM | 2521 | CD GLN B 131 | 44.688 29.077 54.304 1.00 17.54 | B | ATOM | 2601 | O LYS B 141 | 55.936 44.539 65.231 1.00 12.95 | B |
| ATOM | 2522 | OE1 GLN B 131 | 45.399 29.739 53.527 1.00 15.93 | B | ATOM | 2602 | N ALA B 142 | 53.829 43.671 65.252 1.00 12.22 | B |
| ATOM | 2523 | NE2 GLN B 131 | 43.968 28.041 53.907 1.00 16.56 | B | ATOM | 2603 | CA ALA B 142 | 54.117 42.787 66.396 1.00 13.54 | B |
| ATOM | 2524 | C GLN B 131 | 43.299 32.241 56.392 1.00 17.01 | B | ATOM | 2604 | CB ALA B 142 | 52.833 42.043 66.831 1.00 11.90 | B |
| ATOM | 2525 | O GLN B 131 | 42.234 32.076 55.786 1.00 15.83 | B | ATOM | 2605 | C ALA B 142 | 55.234 41.787 66.082 1.00 11.03 | B |
| ATOM | 2526 | N LEU B 132 | 43.317 32.757 57.623 1.00 13.56 | B | ATOM | 2606 | O ALA B 142 | 56.108 41.539 66.920 1.00 12.25 | B |
| ATOM | 2527 | CA LEU B 132 | 42.070 33.112 58.317 1.00 13.87 | B | ATOM | 2607 | N VAL B 143 | 55.194 41.164 64.895 1.00 10.00 | B |
| ATOM | 2528 | CB LEU B 132 | 42.260 32.993 59.844 1.00 12.94 | B | ATOM | 2608 | CA VAL B 143 | 56.235 40.228 64.547 1.00 10.98 | B |
| ATOM | 2529 | CG LEU B 132 | 42.778 31.649 60.321 1.00 15.79 | B | ATOM | 2609 | CB VAL B 143 | 55.873 39.477 63.214 1.00 12.31 | B |
| ATOM | 2530 | CD1 LEU B 132 | 43.078 31.698 61.831 1.00 17.75 | B | ATOM | 2610 | CG1 VAL B 143 | 57.088 38.697 62.677 1.00 13.36 | B |
| ATOM | 2531 | CD2 LEU B 132 | 41.743 30.591 59.980 1.00 19.39 | B | ATOM | 2611 | CG2 VAL B 143 | 54.724 38.521 63.508 1.00 13.20 | B |
| ATOM | 2532 | C LEU B 132 | 41.528 34.525 58.015 1.00 16.48 | B | ATOM | 2612 | C VAL B 143 | 57.592 40.918 64.449 1.00 12.25 | B |
| ATOM | 2533 | O LEU B 132 | 40.459 34.905 58.525 1.00 17.86 | B | ATOM | 2613 | O VAL B 143 | 58.600 40.373 64.916 1.00 12.75 | B |
| ATOM | 2534 | N GLY B 133 | 42.287 35.285 57.221 1.00 15.15 | B | ATOM | 2614 | N GLU B 144 | 57.610 42.119 63.870 1.00 14.39 | B |
| ATOM | 2535 | CA GLY B 133 | 41.925 36.652 56.835 1.00 17.28 | B | ATOM | 2615 | CA GLU B 144 | 58.839 42.882 63.744 1.00 16.22 | B |
| ATOM | 2536 | C GLY B 133 | 42.074 37.593 58.012 1.00 15.79 | B | ATOM | 2616 | CB GLU B 144 | 58.558 44.195 62.975 1.00 19.24 | B |
| ATOM | 2537 | O GLY B 133 | 41.348 38.583 58.120 1.00 18.73 | B | ATOM | 2617 | CG GLU B 144 | 59.770 45.123 62.890 1.00 31.16 | B |
| ATOM | 2538 | N LEU B 134 | 43.039 37.312 58.884 1.00 15.50 | B | ATOM | 2618 | CD GLU B 144 | 59.481 46.397 62.087 1.00 42.51 | B |
| ATOM | 2539 | CA LEU B 134 | 43.255 38.146 60.072 1.00 13.33 | B | ATOM | 2619 | OE1 GLU B 144 | 59.240 46.305 60.854 1.00 47.38 | B |
| ATOM | 2540 | CB LEU B 134 | 43.189 37.274 61.343 1.00 15.71 | B | ATOM | 2620 | OE2 GLU B 144 | 59.486 47.488 62.703 1.00 45.41 | B |
| ATOM | 2541 | CG LEU B 134 | 41.886 36.521 61.620 1.00 17.01 | B | ATOM | 2621 | C GLU B 144 | 59.444 43.157 65.130 1.00 13.53 | B |
| ATOM | 2542 | CD1 LEU B 134 | 42.055 35.567 62.807 1.00 18.82 | B | ATOM | 2622 | O GLU B 144 | 60.650 42.949 65.357 1.00 13.17 | B |
| ATOM | 2543 | CD2 LEU B 134 | 40.775 37.504 61.826 1.00 18.25 | B | ATOM | 2623 | N LYS B 145 | 58.585 43.560 66.065 1.00 10.77 | B |
| ATOM | 2544 | C LEU B 134 | 44.579 38.897 60.091 1.00 17.29 | B | ATOM | 2624 | CA LYS B 145 | 59.020 43.871 67.439 1.00 10.91 | B |
| ATOM | 2545 | O LEU B 134 | 44.892 39.558 61.091 1.00 16.17 | B | ATOM | 2625 | CB LYS B 145 | 57.837 44.439 68.220 1.00 12.05 | B |
| ATOM | 2546 | N TYR B 135 | 45.348 38.821 59.017 1.00 15.03 | B | ATOM | 2626 | CG LYS B 145 | 58.206 44.841 69.629 1.00 11.72 | B |
| ATOM | 2547 | CA TYR B 135 | 46.653 39.486 59.007 1.00 14.44 | B | ATOM | 2627 | CD LYS B 145 | 57.063 45.657 70.226 1.00 14.13 | B |
| ATOM | 2548 | CB TYR B 135 | 47.573 38.833 57.993 1.00 17.89 | B | ATOM | 2628 | CE LYS B 145 | 57.319 46.062 71.683 1.00 14.05 | B |
| ATOM | 2549 | CG TYR B 135 | 48.989 39.326 58.008 1.00 17.21 | B | ATOM | 2629 | NZ LYS B 145 | 56.245 46.986 72.302 1.00 14.64 | B |
| ATOM | 2550 | CD1 TYR B 135 | 49.729 39.347 59.204 1.00 17.66 | B | ATOM | 2630 | C LYS B 145 | 59.575 42.607 68.128 1.00 12.94 | B |
| ATOM | 2551 | CE1 TYR B 135 | 51.081 39.727 59.216 1.00 18.03 | B | ATOM | 2631 | O LYS B 145 | 60.600 42.627 68.810 1.00 10.47 | B |
| ATOM | 2552 | CD2 TYR B 135 | 49.633 39.689 56.832 1.00 23.35 | B | ATOM | 2632 | N PHE B 146 | 58.888 41.489 67.931 1.00 10.55 | B |
| ATOM | 2553 | CE2 TYR B 135 | 50.985 40.062 56.832 1.00 22.96 | B | ATOM | 2633 | CA PHE B 146 | 59.328 40.212 68.491 1.00 10.36 | B |
| ATOM | 2554 | CZ TYR B 135 | 51.697 40.078 58.025 1.00 21.26 | B | ATOM | 2634 | CB PHE B 146 | 58.291 39.132 68.059 1.00 13.24 | B |
| ATOM | 2555 | OH TYR B 135 | 53.024 40.457 58.006 1.00 26.49 | B | ATOM | 2635 | CG PHE B 146 | 58.520 37.775 68.638 1.00 11.28 | B |
| ATOM | 2556 | C TYR B 135 | 46.541 40.963 58.716 1.00 16.69 | B | ATOM | 2636 | CD1 PHE B 146 | 58.043 37.478 69.917 1.00 10.62 | B |
| ATOM | 2557 | O TYR B 135 | 46.122 41.354 57.618 1.00 19.80 | B | ATOM | 2637 | CD2 PHE B 146 | 59.168 36.775 67.892 1.00 11.56 | B |
| ATOM | 2558 | N THR B 136 | 46.875 41.788 59.704 1.00 16.11 | B | ATOM | 2638 | CE1 PHE B 146 | 58.207 36.171 70.443 1.00 11.57 | B |
| ATOM | 2559 | CA THR B 136 | 46.814 43.235 59.496 1.00 16.78 | B | ATOM | 2639 | CE2 PHE B 146 | 59.329 35.479 68.412 1.00 13.01 | B |
| ATOM | 2560 | CB THR B 136 | 45.755 43.884 60.391 1.00 15.03 | B | ATOM | 2640 | CZ PHE B 146 | 58.849 35.178 69.676 1.00 12.91 | B |
| ATOM | 2561 | OG1 THR B 136 | 46.227 43.950 61.753 1.00 16.97 | B | ATOM | 2641 | C PHE B 146 | 60.729 39.860 67.986 1.00 10.46 | B |
| ATOM | 2562 | CG2 THR B 136 | 44.468 43.075 60.338 1.00 18.16 | B | ATOM | 2642 | O PHE B 146 | 61.616 39.514 68.770 1.00 12.08 | B |
| ATOM | 2563 | C THR B 136 | 48.175 43.831 59.853 1.00 17.25 | B | ATOM | 2643 | N LEU B 147 | 60.930 39.967 66.662 1.00 11.98 | B |
| ATOM | 2564 | O THR B 136 | 49.073 43.124 60.307 1.00 15.13 | B | ATOM | 2644 | CA LEU B 147 | 62.244 39.640 66.095 1.00 12.36 | B |
| ATOM | 2565 | N ASP B 137 | 48.320 45.132 59.652 1.00 17.31 | B | ATOM | 2645 | CB LEU B 147 | 62.189 39.676 64.575 1.00 14.27 | B |
| ATOM | 2566 | CA ASP B 137 | 49.574 45.773 60.000 1.00 18.11 | B | ATOM | 2646 | CG LEU B 147 | 61.286 38.597 63.955 1.00 13.67 | B |
| ATOM | 2567 | CB ASP B 137 | 49.575 47.245 59.519 1.00 29.24 | B | ATOM | 2647 | CD1 LEU B 147 | 61.177 38.867 62.430 1.00 18.69 | B |
| ATOM | 2568 | CG ASP B 137 | 49.992 47.381 58.020 1.00 47.27 | B | ATOM | 2648 | CD2 LEU B 147 | 61.820 37.202 64.281 1.00 16.53 | B |
| ATOM | 2569 | OD1 ASP B 137 | 50.057 46.361 57.298 1.00 53.03 | B | ATOM | 2649 | C LEU B 147 | 63.315 40.619 66.620 1.00 13.58 | B |
| ATOM | 2570 | OD2 ASP B 137 | 50.268 48.509 57.548 1.00 57.74 | B | ATOM | 2650 | O LEU B 147 | 64.437 40.193 66.897 1.00 14.99 | B |
| ATOM | 2571 | C ASP B 137 | 49.874 45.663 61.511 1.00 16.19 | B | ATOM | 2651 | N GLU B 148 | 62.956 41.903 66.792 1.00 11.19 | B |
| ATOM | 2572 | O ASP B 137 | 51.037 45.710 61.896 1.00 19.04 | B | ATOM | 2652 | CA GLU B 148 | 63.942 42.846 67.344 1.00 13.04 | B |
| ATOM | 2573 | N CYS B 138 | 48.866 45.497 62.359 1.00 15.45 | B | ATOM | 2653 | CB GLU B 148 | 63.383 44.278 67.308 1.00 13.68 | B |
| ATOM | 2574 | CA CYS B 138 | 49.158 45.237 63.800 1.00 14.56 | B | ATOM | 2654 | CG GLU B 148 | 63.344 44.817 65.887 1.00 14.14 | B |
| ATOM | 2575 | CB CYS B 138 | 47.890 45.166 64.655 1.00 14.80 | B | ATOM | 2655 | CD GLU B 148 | 62.544 46.109 65.699 1.00 18.11 | B |
| ATOM | 2576 | SG CYS B 138 | 46.902 46.698 64.640 1.00 28.99 | B | ATOM | 2656 | OE1 GLU B 148 | 61.663 46.423 66.515 1.00 17.43 | B |
| ATOM | 2577 | C CYS B 138 | 49.989 44.073 63.999 1.00 15.53 | B | ATOM | 2657 | OE2 GLU B 148 | 62.762 46.827 64.686 1.00 20.19 | B |
| ATOM | 2578 | O CYS B 138 | 50.971 44.061 64.780 1.00 14.34 | B | ATOM | 2658 | C GLU B 148 | 64.365 42.505 68.780 1.00 12.71 | B |
| ATOM | 2579 | N GLU B 139 | 49.598 42.998 63.315 1.00 13.52 | B | ATOM | 2659 | O GLU B 148 | 65.538 42.618 69.131 1.00 14.52 | B |
| ATOM | 2580 | CA GLU B 139 | 50.361 41.755 63.448 1.00 13.20 | B | ATOM | 2660 | N ILE B 149 | 63.413 42.093 69.617 1.00 11.64 | B |
| ATOM | 2581 | CB GLU B 139 | 49.624 40.561 62.828 1.00 11.71 | B | ATOM | 2661 | CA ILE B 149 | 63.715 41.767 71.019 1.00 12.66 | B |
| ATOM | 2582 | CG GLU B 139 | 48.392 40.088 63.624 1.00 15.15 | B | ATOM | 2662 | CB ILE B 149 | 62.413 41.378 71.770 1.00 12.77 | B |
| ATOM | 2583 | CD GLU B 139 | 47.301 41.145 63.681 1.00 13.88 | B | ATOM | 2663 | CG2 ILE B 149 | 62.720 40.653 73.096 1.00 13.86 | B |
| ATOM | 2584 | OE1 GLU B 139 | 46.912 41.647 62.598 1.00 15.01 | B | ATOM | 2664 | CG1 ILE B 149 | 61.553 42.629 72.000 1.00 12.07 | B |
| ATOM | 2585 | OE2 GLU B 139 | 46.821 41.494 64.779 1.00 13.72 | B | ATOM | 2665 | CD1 ILE B 149 | 60.106 42.321 72.375 1.00 13.91 | B |
| ATOM | 2586 | C GLU B 139 | 51.744 41.885 62.806 1.00 13.86 | B | ATOM | 2666 | C ILE B 149 | 64.733 40.624 71.056 1.00 13.69 | B |
| ATOM | 2587 | O GLU B 139 | 52.710 41.352 63.302 1.00 13.62 | B | ATOM | 2667 | O ILE B 149 | 65.661 40.643 71.870 1.00 15.92 | B |
| ATOM | 2588 | N ALA B 140 | 51.859 42.582 61.685 1.00 14.52 | B | ATOM | 2668 | N PHE B 150 | 64.593 39.647 70.146 1.00 11.92 | B |
| ATOM | 2589 | CA ALA B 140 | 53.185 42.718 61.074 1.00 13.74 | B | ATOM | 2669 | CA PHE B 150 | 65.508 38.498 70.146 1.00 13.41 | B |
| ATOM | 2590 | CB ALA B 140 | 53.088 43.448 59.704 1.00 17.37 | B | ATOM | 2670 | CB PHE B 150 | 64.788 37.234 69.642 1.00 14.66 | B |
| ATOM | 2591 | C ALA B 140 | 54.086 43.499 62.018 1.00 14.16 | B | ATOM | 2671 | CG PHE B 150 | 63.863 36.614 70.656 1.00 10.70 | B |
| ATOM | 2592 | O ALA B 140 | 55.252 43.141 62.191 1.00 15.26 | B | ATOM | 2672 | CD1 PHE B 150 | 62.545 37.066 70.758 1.00 11.20 | B |
| ATOM | 2593 | N LYS B 141 | 53.547 44.547 62.627 1.00 13.69 | B | ATOM | 2673 | CD2 PHE B 150 | 64.325 35.635 71.511 1.00 13.19 | B |
| ATOM | 2594 | CA LYS B 141 | 54.342 45.327 63.567 1.00 16.71 | B | ATOM | 2674 | CE1 PHE B 150 | 61.686 36.509 71.761 1.00 11.98 | B |
| ATOM | 2595 | CB LYS B 141 | 53.548 46.534 64.060 1.00 19.71 | B | ATOM | 2675 | CE2 PHE B 150 | 63.498 35.081 72.487 1.00 13.66 | B |
| ATOM | 2596 | CG LYS B 141 | 53.449 47.636 62.995 1.00 29.33 | B | ATOM | 2676 | CZ PHE B 150 | 62.170 35.519 72.619 1.00 13.24 | B |
| ATOM | 2597 | CD LYS B 141 | 54.808 48.288 62.756 1.00 43.01 | B | ATOM | 2677 | C PHE B 150 | 66.752 38.606 69.264 1.00 14.66 | B |
| ATOM | 2598 | CE LYS B 141 | 55.430 48.701 64.098 1.00 50.76 | B | ATOM | 2678 | O PHE B 150 | 67.687 37.828 69.440 1.00 16.83 | B |
| ATOM | 2599 | NZ LYS B 141 | 56.539 49.692 64.021 1.00 48.62 | B | ATOM | 2679 | N LYS B 151 | 66.753 39.558 68.341 1.00 16.21 | B |
| ATOM | 2600 | C LYS B 141 | 54.771 44.463 64.763 1.00 14.56 | B | ATOM | 2680 | CA LYS B 151 | 67.805 39.643 67.312 1.00 18.31 | B |

Fig. 4 cont.

| | | | |
|---|---|---|---|
| ATOM 2681 CB LYS B 151 | 67.620 40.936 66.520 1.00 17.12 | B | |
| ATOM 2682 CG LYS B 151 | 68.170 40.880 65.107 1.00 28.63 | B | |
| ATOM 2683 CD LYS B 151 | 69.662 40.985 65.124 1.00 41.96 | B | |
| ATOM 2684 CE LYS B 151 | 70.239 40.871 63.679 1.00 49.25 | B | |
| ATOM 2685 NZ LYS B 151 | 69.482 41.779 62.761 1.00 51.91 | B | |
| ATOM 2686 C LYS B 151 | 69.252 39.501 67.710 1.00 16.89 | B | |
| ATOM 2687 O LYS B 151 | 70.017 38.771 67.043 1.00 19.85 | B | |
| ATOM 2688 N GLU B 152 | 69.626 40.159 68.800 1.00 14.93 | B | |
| ATOM 2689 CA GLU B 152 | 71.004 40.138 69.246 1.00 22.19 | B | |
| ATOM 2690 CB GLU B 152 | 71.459 41.578 69.540 1.00 24.26 | B | |
| ATOM 2691 CG GLU B 152 | 71.338 42.468 68.300 1.00 29.83 | B | |
| ATOM 2692 CD GLU B 152 | 72.196 41.955 67.136 1.00 42.18 | B | |
| ATOM 2693 OE1 GLU B 152 | 71.909 42.268 65.954 1.00 48.52 | B | |
| ATOM 2694 OE2 GLU B 152 | 73.175 41.229 67.408 1.00 52.34 | B | |
| ATOM 2695 C GLU B 152 | 71.259 39.245 70.462 1.00 24.91 | B | |
| ATOM 2696 O GLU B 152 | 72.335 39.288 71.037 1.00 22.49 | B | |
| ATOM 2697 N GLU B 153 | 70.274 38.440 70.852 1.00 15.76 | B | |
| ATOM 2698 CA GLU B 153 | 70.467 37.589 72.025 1.00 17.77 | B | |
| ATOM 2699 CB GLU B 153 | 69.135 37.379 72.744 1.00 21.24 | B | |
| ATOM 2700 CG GLU B 153 | 68.415 38.662 73.197 1.00 24.53 | B | |
| ATOM 2701 CD GLU B 153 | 69.030 39.299 74.439 1.00 40.31 | B | |
| ATOM 2702 OE1 GLU B 153 | 69.789 38.622 75.158 1.00 41.14 | B | |
| ATOM 2703 OE2 GLU B 153 | 68.742 40.482 74.723 1.00 44.94 | B | |
| ATOM 2704 C GLU B 153 | 71.040 36.227 71.659 1.00 16.33 | B | |
| ATOM 2705 O GLU B 153 | 70.893 35.766 70.529 1.00 18.97 | B | |
| ATOM 2706 N THR B 154 | 71.715 35.610 72.625 1.00 16.09 | B | |
| ATOM 2707 CA THR B 154 | 72.285 34.270 72.466 1.00 17.18 | B | |
| ATOM 2708 CB THR B 154 | 73.805 34.332 72.386 1.00 31.82 | B | |
| ATOM 2709 OG1 THR B 154 | 74.169 35.234 71.335 1.00 41.24 | B | |
| ATOM 2710 CG2 THR B 154 | 74.360 32.959 72.044 1.00 39.41 | B | |
| ATOM 2711 C THR B 154 | 71.911 33.442 73.692 1.00 15.32 | B | |
| ATOM 2712 O THR B 154 | 71.944 33.954 74.817 1.00 18.36 | B | |
| ATOM 2713 N PHE B 155 | 71.550 32.175 73.487 1.00 13.16 | B | |
| ATOM 2714 CA PHE B 155 | 71.114 31.351 74.606 1.00 14.60 | B | |
| ATOM 2715 CB PHE B 155 | 69.638 30.991 74.401 1.00 12.46 | B | |
| ATOM 2716 CG PHE B 155 | 68.741 32.189 74.376 1.00 14.08 | B | |
| ATOM 2717 CD1 PHE B 155 | 68.306 32.750 75.588 1.00 16.43 | B | |
| ATOM 2718 CD2 PHE B 155 | 68.402 32.803 73.182 1.00 14.68 | B | |
| ATOM 2719 CE1 PHE B 155 | 67.540 33.917 75.576 1.00 16.48 | B | |
| ATOM 2720 CE2 PHE B 155 | 67.617 33.998 73.184 1.00 14.90 | B | |
| ATOM 2721 CZ PHE B 155 | 67.200 34.536 74.395 1.00 16.20 | B | |
| ATOM 2722 C PHE B 155 | 71.924 30.075 74.758 1.00 13.95 | B | |
| ATOM 2723 O PHE B 155 | 71.757 29.126 73.998 1.00 15.99 | B | |
| ATOM 2724 N PRO B 156 | 72.811 30.031 75.761 1.00 14.48 | B | |
| ATOM 2725 CD PRO B 156 | 73.304 31.126 76.607 1.00 16.29 | B | |
| ATOM 2726 CA PRO B 156 | 73.610 28.817 75.959 1.00 18.54 | B | |
| ATOM 2727 CB PRO B 156 | 74.718 29.289 76.902 1.00 20.37 | B | |
| ATOM 2728 CG PRO B 156 | 74.064 30.384 77.677 1.00 20.37 | B | |
| ATOM 2729 C PRO B 156 | 72.754 27.737 76.613 1.00 16.75 | B | |
| ATOM 2730 O PRO B 156 | 71.688 28.033 77.144 1.00 14.44 | B | |
| ATOM 2731 N PRO B 157 | 73.205 26.465 76.583 1.00 16.62 | B | |
| ATOM 2732 CD PRO B 157 | 74.459 25.949 75.987 1.00 23.94 | B | |
| ATOM 2733 CA PRO B 157 | 72.421 25.387 77.205 1.00 13.95 | B | |
| ATOM 2734 CB PRO B 157 | 73.365 24.171 77.124 1.00 14.83 | B | |
| ATOM 2735 CG PRO B 157 | 74.175 24.461 75.860 1.00 14.99 | B | |
| ATOM 2736 C PRO B 157 | 72.128 25.763 78.647 1.00 16.08 | B | |
| ATOM 2737 O PRO B 157 | 73.007 26.301 79.340 1.00 17.03 | B | |
| ATOM 2738 N GLY B 158 | 70.909 25.481 79.104 1.00 12.84 | B | |
| ATOM 2739 CA GLY B 158 | 70.518 25.801 80.465 1.00 14.02 | B | |
| ATOM 2740 C GLY B 158 | 69.841 27.157 80.625 1.00 14.27 | B | |
| ATOM 2741 O GLY B 158 | 69.114 27.343 81.594 1.00 13.89 | B | |
| ATOM 2742 N SER B 159 | 70.101 28.104 79.718 1.00 12.16 | B | |
| ATOM 2743 CA SER B 159 | 69.427 29.408 79.803 1.00 11.03 | B | |
| ATOM 2744 CB SER B 159 | 70.106 30.449 78.895 1.00 11.93 | B | |
| ATOM 2745 OG SER B 159 | 69.909 30.157 77.534 1.00 13.45 | B | |
| ATOM 2746 C SER B 159 | 67.960 29.190 79.381 1.00 11.21 | B | |
| ATOM 2747 O SER B 159 | 67.617 28.133 78.806 1.00 11.67 | B | |
| ATOM 2748 N SER B 160 | 67.099 30.160 79.689 1.00 11.20 | B | |
| ATOM 2749 CA SER B 160 | 65.668 30.053 79.409 1.00 10.64 | B | |
| ATOM 2750 CB SER B 160 | 64.888 29.747 80.703 1.00 12.25 | B | |
| ATOM 2751 OG SER B 160 | 65.338 28.568 81.352 1.00 11.27 | B | |
| ATOM 2752 C SER B 160 | 65.062 31.299 78.829 1.00 10.77 | B | |
| ATOM 2753 O SER B 160 | 65.525 32.433 79.118 1.00 12.63 | B | |
| ATOM 2754 N ILE B 161 | 64.027 31.087 77.999 1.00 9.73 | B | |
| ATOM 2755 CA ILE B 161 | 63.234 32.160 77.391 1.00 10.34 | B | |
| ATOM 2756 CB ILE B 161 | 63.138 31.919 75.905 1.00 8.86 | B | |
| ATOM 2757 CG2 ILE B 161 | 62.078 32.844 75.276 1.00 12.04 | B | |
| ATOM 2758 CG1 ILE B 161 | 64.535 32.094 75.324 1.00 14.93 | B | |
| ATOM 2759 CD1 ILE B 161 | 64.626 31.744 73.880 1.00 14.27 | B | |
| ATOM 2760 C ILE B 161 | 61.882 31.986 78.075 1.00 10.40 | B | |
| ATOM 2761 O ILE B 161 | 61.352 30.863 78.118 1.00 9.66 | B | |
| ATOM 2762 N LEU B 162 | 61.337 33.092 78.595 1.00 8.88 | B | |
| ATOM 2763 CA LEU B 162 | 60.104 33.070 79.358 1.00 11.31 | B | |
| ATOM 2764 CB LEU B 162 | 60.393 33.606 80.764 1.00 12.99 | B | |
| ATOM 2765 CG LEU B 162 | 61.598 32.921 81.445 1.00 16.02 | B | |
| ATOM 2766 CD1 LEU B 162 | 61.919 33.595 82.729 1.00 20.10 | B | |
| ATOM 2767 CD2 LEU B 162 | 61.305 31.407 81.613 1.00 11.70 | B | |
| ATOM 2768 C LEU B 162 | 59.056 33.917 78.679 1.00 11.80 | B | |
| ATOM 2769 O LEU B 162 | 59.321 35.067 78.367 1.00 12.64 | B | |
| ATOM 2770 N PHE B 163 | 57.863 33.375 78.475 1.00 7.87 | B | |
| ATOM 2771 CA PHE B 163 | 56.782 34.117 77.839 1.00 8.35 | B | |
| ATOM 2772 CB PHE B 163 | 56.339 33.431 76.535 1.00 8.33 | B | |
| ATOM 2773 CG PHE B 163 | 57.372 33.442 75.444 1.00 10.18 | B | |
| ATOM 2774 CD1 PHE B 163 | 57.780 34.631 74.858 1.00 10.13 | B | |
| ATOM 2775 CD2 PHE B 163 | 57.881 32.228 74.960 1.00 10.16 | B | |
| ATOM 2776 CE1 PHE B 163 | 58.684 34.641 73.787 1.00 11.27 | B | |
| ATOM 2777 CE2 PHE B 163 | 58.787 32.211 73.882 1.00 13.50 | B | |
| ATOM 2778 CZ PHE B 163 | 59.189 33.425 73.292 1.00 10.97 | B | |
| ATOM 2779 C PHE B 163 | 55.571 34.135 78.761 1.00 10.30 | B | |
| ATOM 2780 O PHE B 163 | 55.176 33.094 79.243 1.00 10.69 | B | |
| ATOM 2781 N ALA B 164 | 55.015 35.322 79.037 1.00 9.96 | B | |
| ATOM 2782 CA ALA B 164 | 53.783 35.404 79.844 1.00 9.74 | B | |
| ATOM 2783 CB ALA B 164 | 53.971 36.390 81.015 1.00 12.38 | B | |
| ATOM 2784 C ALA B 164 | 52.731 35.939 78.864 1.00 9.85 | B | |
| ATOM 2785 O ALA B 164 | 52.989 36.946 78.150 1.00 12.65 | B | |
| ATOM 2786 N LEU B 165 | 51.572 35.278 78.783 1.00 9.34 | B | |
| ATOM 2787 CA LEU B 165 | 50.483 35.685 77.897 1.00 8.64 | B | |
| ATOM 2788 CB LEU B 165 | 49.955 34.496 77.105 1.00 11.96 | B | |
| ATOM 2789 CG LEU B 165 | 50.826 33.965 75.962 1.00 12.45 | B | |
| ATOM 2790 CD1 LEU B 165 | 52.099 33.341 76.502 1.00 15.12 | B | |
| ATOM 2791 CD2 LEU B 165 | 49.989 32.934 75.227 1.00 14.60 | B | |
| ATOM 2792 C LEU B 165 | 49.363 36.174 78.814 1.00 11.33 | B | |
| ATOM 2793 O LEU B 165 | 48.808 35.404 79.575 1.00 12.52 | B | |
| ATOM 2794 N SER B 166 | 49.026 37.447 78.726 1.00 11.88 | B | |
| ATOM 2795 CA SER B 166 | 47.982 37.974 79.617 1.00 13.04 | B | |
| ATOM 2796 CB SER B 166 | 48.069 39.515 79.675 1.00 10.46 | B | |
| ATOM 2797 OG SER B 166 | 47.346 40.069 78.572 1.00 11.88 | B | |
| ATOM 2798 C SER B 166 | 46.588 37.546 79.172 1.00 12.08 | B | |
| ATOM 2799 O SER B 166 | 46.387 37.105 78.044 1.00 11.92 | B | |
| ATOM 2800 N PRO B 167 | 45.579 37.694 80.058 1.00 10.96 | B | |
| ATOM 2801 CD PRO B 167 | 45.647 38.158 81.457 1.00 15.12 | B | |
| ATOM 2802 CA PRO B 167 | 44.227 37.288 79.687 1.00 14.77 | B | |
| ATOM 2803 CB PRO B 167 | 43.391 37.680 80.917 1.00 15.08 | B | |
| ATOM 2804 CG PRO B 167 | 44.367 37.590 82.063 1.00 19.66 | B | |
| ATOM 2805 C PRO B 167 | 43.710 37.980 78.419 1.00 14.05 | B | |
| ATOM 2806 O PRO B 167 | 42.852 37.437 77.721 1.00 17.34 | B | |
| ATOM 2807 N THR B 168 | 44.222 39.174 78.127 1.00 12.88 | B | |
| ATOM 2808 CA THR B 168 | 43.806 39.917 76.937 1.00 13.40 | B | |
| ATOM 2809 CB THR B 168 | 43.630 41.425 77.238 1.00 16.67 | B | |
| ATOM 2810 OG1 THR B 168 | 44.858 41.982 77.712 1.00 15.70 | B | |
| ATOM 2811 CG2 THR B 168 | 42.544 41.628 78.320 1.00 23.07 | B | |
| ATOM 2812 C THR B 168 | 44.765 39.777 75.767 1.00 14.89 | B | |
| ATOM 2813 O THR B 168 | 44.602 40.426 74.724 1.00 17.18 | B | |
| ATOM 2814 N GLY B 169 | 45.787 38.951 75.936 1.00 13.52 | B | |
| ATOM 2815 CA GLY B 169 | 46.667 38.731 74.817 1.00 16.63 | B | |
| ATOM 2816 C GLY B 169 | 47.928 39.561 74.705 1.00 15.75 | B | |
| ATOM 2817 O GLY B 169 | 48.456 39.693 73.584 1.00 16.77 | B | |
| ATOM 2818 N SER B 170 | 48.394 40.137 75.813 1.00 12.36 | B | |
| ATOM 2819 CA SER B 170 | 49.680 40.855 75.767 1.00 11.69 | B | |
| ATOM 2820 CB SER B 170 | 49.761 41.957 76.821 1.00 16.54 | B | |
| ATOM 2821 OG SER B 170 | 49.089 43.093 76.295 1.00 20.83 | B | |
| ATOM 2822 C SER B 170 | 50.772 39.827 76.052 1.00 11.73 | B | |
| ATOM 2823 O SER B 170 | 50.650 39.043 76.969 1.00 14.26 | B | |
| ATOM 2824 N LEU B 171 | 51.837 39.861 75.272 1.00 10.57 | B | |
| ATOM 2825 CA LEU B 171 | 52.955 38.930 75.429 1.00 9.62 | B | |
| ATOM 2826 CB LEU B 171 | 53.384 38.417 74.050 1.00 10.67 | B | |
| ATOM 2827 CG LEU B 171 | 54.538 37.409 74.041 1.00 11.32 | B | |
| ATOM 2828 CD1 LEU B 171 | 54.120 36.073 74.604 1.00 11.32 | B | |
| ATOM 2829 CD2 LEU B 171 | 54.963 37.209 72.582 1.00 12.83 | B | |
| ATOM 2830 C LEU B 171 | 54.152 39.579 76.100 1.00 11.48 | B | |
| ATOM 2831 O LEU B 171 | 54.752 40.485 75.541 1.00 12.63 | B | |
| ATOM 2832 N THR B 172 | 54.487 39.138 77.307 1.00 8.87 | B | |
| ATOM 2833 CA THR B 172 | 55.658 39.658 77.990 1.00 10.02 | B | |
| ATOM 2834 CB THR B 172 | 55.391 39.790 79.464 1.00 10.63 | B | |
| ATOM 2835 OG1 THR B 172 | 54.340 40.741 79.659 1.00 13.29 | B | |
| ATOM 2836 CG2 THR B 172 | 56.652 40.244 80.200 1.00 13.28 | B | |
| ATOM 2837 C THR B 172 | 56.783 38.669 77.778 1.00 10.94 | B | |
| ATOM 2838 O THR B 172 | 56.594 37.478 77.949 1.00 12.53 | B | |
| ATOM 2839 N VAL B 173 | 57.931 39.159 77.336 1.00 8.82 | B | |
| ATOM 2840 CA VAL B 173 | 59.116 38.325 77.095 1.00 10.64 | B | |

Fig. 4 cont.

```
ATOM 2841 CB  VAL B 173    59.780 38.724 75.742 1.00 10.94   B
ATOM 2842 CG1 VAL B 173    60.998 37.828 75.437 1.00 11.89   B
ATOM 2843 CG2 VAL B 173    58.759 38.629 74.615 1.00 10.31   B
ATOM 2844 C   VAL B 173    60.148 38.617 78.176 1.00 10.98   B
ATOM 2845 O   VAL B 173    60.372 39.789 78.520 1.00 11.90   B
ATOM 2846 N   ALA B 174    60.812 37.597 78.692 1.00 10.36   B
ATOM 2847 CA  ALA B 174    61.870 37.775 79.700 1.00 9.49    B
ATOM 2848 CB  ALA B 174    61.310 37.695 81.126 1.00 14.35   B
ATOM 2849 C   ALA B 174    62.858 36.632 79.467 1.00 13.30   B
ATOM 2850 O   ALA B 174    62.485 35.615 78.844 1.00 11.10   B
ATOM 2851 N   PHE B 175    64.078 36.792 79.977 1.00 12.60   B
ATOM 2852 CA  PHE B 175    65.130 35.782 79.840 1.00 13.10   B
ATOM 2853 CB  PHE B 175    66.284 36.293 78.935 1.00 11.62   B
ATOM 2854 CG  PHE B 175    65.828 36.824 77.612 1.00 11.54   B
ATOM 2855 CD1 PHE B 175    65.002 36.066 76.801 1.00 13.65   B
ATOM 2856 CD2 PHE B 175    66.222 38.086 77.174 1.00 18.88   B
ATOM 2857 CE1 PHE B 175    64.555 36.522 75.568 1.00 15.90   B
ATOM 2858 CE2 PHE B 175    65.779 38.577 75.920 1.00 19.93   B
ATOM 2859 CZ  PHE B 175    64.938 37.790 75.115 1.00 18.58   B
ATOM 2860 C   PHE B 175    65.732 35.449 81.190 1.00 16.74   B
ATOM 2861 O   PHE B 175    65.650 36.225 82.135 1.00 14.71   B
ATOM 2862 N   SER B 176    66.349 34.277 81.270 1.00 12.70   B
ATOM 2863 CA  SER B 176    67.020 33.892 82.496 1.00 10.46   B
ATOM 2864 CB  SER B 176    66.111 33.052 83.386 1.00 14.44   B
ATOM 2865 OG  SER B 176    66.813 32.569 84.537 1.00 14.26   B
ATOM 2866 C   SER B 176    68.257 33.068 82.117 1.00 15.77   B
ATOM 2867 O   SER B 176    68.257 32.391 81.077 1.00 14.83   B
ATOM 2868 N   LYS B 177    69.303 33.134 82.959 1.00 14.58   B
ATOM 2869 CA  LYS B 177    70.512 32.331 82.707 1.00 12.66   B
ATOM 2870 CB  LYS B 177    71.726 32.862 83.504 1.00 19.17   B
ATOM 2871 CG  LYS B 177    72.044 34.319 83.255 1.00 31.66   B
ATOM 2872 CD  LYS B 177    73.573 34.579 83.379 1.00 39.93   B
ATOM 2873 CE  LYS B 177    73.905 36.068 83.301 1.00 41.48   B
ATOM 2874 NZ  LYS B 177    73.412 36.787 84.524 1.00 43.07   B
ATOM 2875 C   LYS B 177    70.289 30.891 83.161 1.00 15.26   B
ATOM 2876 O   LYS B 177    71.085 30.017 82.836 1.00 16.69   B
ATOM 2877 N   ASP B 178    69.238 30.648 83.942 1.00 14.01   B
ATOM 2878 CA  ASP B 178    69.017 29.284 84.425 1.00 13.07   B
ATOM 2879 CB  ASP B 178    69.738 29.112 85.764 1.00 15.12   B
ATOM 2880 CG  ASP B 178    69.403 30.212 86.752 1.00 21.76   B
ATOM 2881 OD1 ASP B 178    68.319 30.830 86.645 1.00 17.13   B
ATOM 2882 OD2 ASP B 178    70.248 30.459 87.657 1.00 19.81   B
ATOM 2883 C   ASP B 178    67.522 28.981 84.550 1.00 15.55   B
ATOM 2884 O   ASP B 178    66.749 29.368 83.673 1.00 12.98   B
ATOM 2885 N   ASP B 179    67.114 28.320 85.624 1.00 14.98   B
ATOM 2886 CA  ASP B 179    65.699 27.998 85.818 1.00 12.38   B
ATOM 2887 CB  ASP B 179    65.535 26.630 86.484 1.00 15.42   B
ATOM 2888 CG  ASP B 179    66.097 25.491 85.631 1.00 16.88   B
ATOM 2889 OD1 ASP B 179    65.920 25.521 84.395 1.00 14.80   B
ATOM 2890 OD2 ASP B 179    66.715 24.556 86.210 1.00 17.36   B
ATOM 2891 C   ASP B 179    64.959 29.026 86.650 1.00 13.81   B
ATOM 2892 O   ASP B 179    63.735 28.902 86.837 1.00 13.64   B
ATOM 2893 N   SER B 180    65.668 30.054 87.129 1.00 12.85   B
ATOM 2894 CA  SER B 180    65.000 31.047 87.921 1.00 13.06   B
ATOM 2895 CB  SER B 180    66.005 31.886 88.699 1.00 14.82   B
ATOM 2896 OG  SER B 180    66.849 32.614 87.830 1.00 19.10   B
ATOM 2897 C   SER B 180    64.101 31.954 87.072 1.00 12.43   B
ATOM 2898 O   SER B 180    64.356 32.176 85.866 1.00 15.73   B
ATOM 2899 N   ILE B 181    63.036 32.456 87.704 1.00 16.96   B
ATOM 2900 CA  ILE B 181    62.069 33.287 87.000 1.00 15.58   B
ATOM 2901 CB  ILE B 181    60.610 32.864 87.349 1.00 19.32   B
ATOM 2902 CG2 ILE B 181    59.596 33.705 86.522 1.00 15.19   B
ATOM 2903 CG1 ILE B 181    60.403 31.355 87.118 1.00 18.05   B
ATOM 2904 CD1 ILE B 181    60.739 30.878 85.737 1.00 15.46   B
ATOM 2905 C   ILE B 181    62.295 34.716 87.503 1.00 13.96   B
ATOM 2906 O   ILE B 181    62.252 34.958 88.708 1.00 13.58   B
ATOM 2907 N   PRO B 182    62.518 35.687 86.596 1.00 14.99   B
ATOM 2908 CD  PRO B 182    62.765 35.630 85.148 1.00 16.67   B
ATOM 2909 CA  PRO B 182    62.735 37.040 87.118 1.00 17.28   B
ATOM 2910 CB  PRO B 182    63.349 37.792 85.923 1.00 19.22   B
ATOM 2911 CG  PRO B 182    62.754 37.122 84.768 1.00 14.87   B
ATOM 2912 C   PRO B 182    61.458 37.689 87.620 1.00 18.05   B
ATOM 2913 O   PRO B 182    60.356 37.259 87.304 1.00 16.27   B
ATOM 2914 N   GLU B 183    61.617 38.745 88.406 1.00 18.66   B
ATOM 2915 CA  GLU B 183    60.444 39.392 88.968 1.00 21.71   B
ATOM 2916 CB  GLU B 183    60.835 40.107 90.278 1.00 25.91   B
ATOM 2917 CG  GLU B 183    61.636 41.353 90.097 1.00 30.94   B
ATOM 2918 CD  GLU B 183    61.866 42.131 91.424 1.00 42.44   B
ATOM 2919 OE1 GLU B 183    61.207 41.853 92.461 1.00 46.05   B
ATOM 2920 OE2 GLU B 183    62.706 43.053 91.419 1.00 42.93   B
ATOM 2921 C   GLU B 183    59.733 40.345 88.007 1.00 16.00   B
ATOM 2922 O   GLU B 183    58.625 40.822 88.290 1.00 16.60   B
ATOM 2923 N   THR B 184    60.333 40.597 86.843 1.00 14.99   B
ATOM 2924 CA  THR B 184    59.708 41.489 85.888 1.00 13.68   B
ATOM 2925 CB  THR B 184    60.063 42.989 86.232 1.00 17.01   B
ATOM 2926 OG1 THR B 184    59.212 43.858 85.476 1.00 16.22   B
ATOM 2927 CG2 THR B 184    61.526 43.337 85.891 1.00 20.68   B
ATOM 2928 C   THR B 184    60.221 41.083 84.501 1.00 12.96   B
ATOM 2929 O   THR B 184    61.254 40.453 84.404 1.00 16.48   B
ATOM 2930 N   GLY B 185    59.495 41.431 83.451 1.00 16.12   B
ATOM 2931 CA  GLY B 185    59.946 41.092 82.113 1.00 16.69   B
ATOM 2932 C   GLY B 185    60.813 42.140 81.453 1.00 15.65   B
ATOM 2933 O   GLY B 185    61.181 43.161 82.082 1.00 16.37   B
ATOM 2934 N   ILE B 186    61.165 41.891 80.206 1.00 12.72   B
ATOM 2935 CA  ILE B 186    61.972 42.850 79.433 1.00 13.04   B
ATOM 2936 CB  ILE B 186    62.936 42.103 78.451 1.00 16.70   B
ATOM 2937 CG2 ILE B 186    63.586 43.076 77.446 1.00 20.87   B
ATOM 2938 CG1 ILE B 186    64.009 41.409 79.285 1.00 21.41   B
ATOM 2939 CD1 ILE B 186    64.778 40.366 78.543 1.00 34.99   B
ATOM 2940 C   ILE B 186    61.076 43.787 78.638 1.00 14.01   B
ATOM 2941 O   ILE B 186    61.184 45.008 78.753 1.00 13.18   B
ATOM 2942 N   ALA B 187    60.171 43.224 77.843 1.00 11.29   B
ATOM 2943 CA  ALA B 187    59.306 44.014 76.970 1.00 11.64   B
ATOM 2944 CB  ALA B 187    59.971 44.182 75.588 1.00 13.26   B
ATOM 2945 C   ALA B 187    57.987 43.321 76.789 1.00 11.72   B
ATOM 2946 O   ALA B 187    57.891 42.103 76.996 1.00 11.78   B
ATOM 2947 N   VAL B 188    56.981 44.097 76.423 1.00 10.71   B
ATOM 2948 CA  VAL B 188    55.637 43.591 76.228 1.00 11.30   B
ATOM 2949 CB  VAL B 188    54.687 44.318 77.201 1.00 16.74   B
ATOM 2950 CG1 VAL B 188    53.303 43.837 77.028 1.00 19.01   B
ATOM 2951 CG2 VAL B 188    55.168 44.102 78.638 1.00 16.89   B
ATOM 2952 C   VAL B 188    55.191 43.895 74.785 1.00 10.99   B
ATOM 2953 O   VAL B 188    55.431 44.999 74.284 1.00 11.63   B
ATOM 2954 N   ILE B 189    54.583 42.901 74.125 1.00 9.81    B
ATOM 2955 CA  ILE B 189    54.074 43.099 72.766 1.00 11.46   B
ATOM 2956 CB  ILE B 189    54.603 42.023 71.794 1.00 10.80   B
ATOM 2957 CG2 ILE B 189    54.082 42.260 70.408 1.00 11.63   B
ATOM 2958 CG1 ILE B 189    56.126 42.081 71.739 1.00 13.47   B
ATOM 2959 CD1 ILE B 189    56.721 41.071 70.771 1.00 13.40   B
ATOM 2960 C   ILE B 189    52.568 42.983 72.892 1.00 12.44   B
ATOM 2961 O   ILE B 189    52.047 41.921 73.234 1.00 13.25   B
ATOM 2962 N   GLU B 190    51.867 44.083 72.639 1.00 13.33   B
ATOM 2963 CA  GLU B 190    50.420 44.100 72.779 1.00 15.52   B
ATOM 2964 CB  GLU B 190    49.960 45.524 73.164 1.00 15.95   B
ATOM 2965 CG  GLU B 190    50.414 45.812 74.594 1.00 29.77   B
ATOM 2966 CD  GLU B 190    50.083 47.208 75.092 1.00 40.74   B
ATOM 2967 OE1 GLU B 190    49.407 47.973 74.363 1.00 49.78   B
ATOM 2968 OE2 GLU B 190    50.511 47.525 76.227 1.00 39.34   B
ATOM 2969 C   GLU B 190    49.697 43.635 71.540 1.00 15.58   B
ATOM 2970 O   GLU B 190    49.148 44.451 70.792 1.00 14.41   B
ATOM 2971 N   ASN B 191    49.756 42.323 71.298 1.00 10.52   B
ATOM 2972 CA  ASN B 191    49.101 41.725 70.140 1.00 10.33   B
ATOM 2973 CB  ASN B 191    50.050 41.697 68.952 1.00 10.47   B
ATOM 2974 CG  ASN B 191    49.352 41.264 67.680 1.00 11.00   B
ATOM 2975 OD1 ASN B 191    49.233 40.099 67.398 1.00 11.54   B
ATOM 2976 ND2 ASN B 191    48.857 42.242 66.923 1.00 12.21   B
ATOM 2977 C   ASN B 191    48.641 40.319 70.463 1.00 10.87   B
ATOM 2978 O   ASN B 191    49.466 39.403 70.646 1.00 11.60   B
ATOM 2979 N   LYS B 192    47.316 40.173 70.557 1.00 11.70   B
ATOM 2980 CA  LYS B 192    46.681 38.901 70.926 1.00 13.92   B
ATOM 2981 CB  LYS B 192    45.146 39.125 71.027 1.00 11.81   B
ATOM 2982 CG  LYS B 192    44.339 37.938 71.493 1.00 14.84   B
ATOM 2983 CD  LYS B 192    42.897 38.403 71.744 1.00 19.75   B
ATOM 2984 CE  LYS B 192    42.028 37.298 72.330 1.00 25.85   B
ATOM 2985 NZ  LYS B 192    41.818 36.173 71.354 1.00 20.37   B
ATOM 2986 C   LYS B 192    47.016 37.744 69.970 1.00 10.41   B
ATOM 2987 O   LYS B 192    47.303 36.621 70.440 1.00 10.52   B
ATOM 2988 N   LEU B 193    46.991 37.979 68.653 1.00 10.40   B
ATOM 2989 CA  LEU B 193    47.307 36.886 67.730 1.00 10.87   B
ATOM 2990 CB  LEU B 193    47.042 37.263 66.257 1.00 10.66   B
ATOM 2991 CG  LEU B 193    45.533 37.335 65.953 1.00 12.75   B
ATOM 2992 CD1 LEU B 193    45.350 37.948 64.545 1.00 11.95   B
ATOM 2993 CD2 LEU B 193    44.903 35.920 65.998 1.00 14.32   B
ATOM 2994 C   LEU B 193    48.764 36.413 67.901 1.00 13.02   B
ATOM 2995 O   LEU B 193    49.022 35.199 67.897 1.00 11.45   B
ATOM 2996 N   LEU B 194    49.704 37.341 68.073 1.00 9.74    B
ATOM 2997 CA  LEU B 194    51.075 36.880 68.264 1.00 9.69    B
ATOM 2998 CB  LEU B 194    52.048 38.064 68.249 1.00 11.10   B
ATOM 2999 CG  LEU B 194    53.497 37.629 68.441 1.00 13.11   B
ATOM 3000 CD1 LEU B 194    53.988 36.737 67.287 1.00 12.00   B
```

Fig. 4 cont.

| | | | | | | | | | | | | | |
|---|---|---|---|---|---|---|---|---|---|---|---|---|---|
| ATOM | 3001 | CD2 LEU B 194 | 54.333 38.910 68.550 1.00 18.19 | B | | ATOM | 3081 | O   LYS B 205 | 49.466 19.956 65.088 1.00 17.80 | B |
| ATOM | 3002 | C   LEU B 194 | 51.224 36.119 69.585 1.00 10.95 | B | | ATOM | 3082 | N   ASN B 206 | 49.441 22.184 64.953 1.00 21.33 | B |
| ATOM | 3003 | O   LEU B 194 | 51.879 35.063 69.638 1.00 10.69 | B | | ATOM | 3083 | CA  ASN B 206 | 50.667 22.107 64.160 1.00 26.26 | B |
| ATOM | 3004 | N   ALA B 195 | 50.627 36.649 70.648 1.00 10.72 | B | | ATOM | 3084 | CB  ASN B 206 | 50.610 22.905 62.839 1.00 33.38 | B |
| ATOM | 3005 | CA  ALA B 195 | 50.732 35.988 71.954 1.00 12.47 | B | | ATOM | 3085 | CG  ASN B 206 | 51.453 22.217 61.704 1.00 45.85 | B |
| ATOM | 3006 | CB  ALA B 195 | 49.908 36.756 72.988 1.00 13.01 | B | | ATOM | 3086 | OD1 ASN B 206 | 51.504 22.694 60.557 1.00 50.97 | B |
| ATOM | 3007 | C   ALA B 195 | 50.232 34.538 71.835 1.00 13.15 | B | | ATOM | 3087 | ND2 ASN B 206 | 52.112 21.095 62.039 1.00 42.06 | B |
| ATOM | 3008 | O   ALA B 195 | 50.924 33.606 72.201 1.00 12.73 | B | | ATOM | 3088 | C   ASN B 206 | 51.853 22.544 65.009 1.00 23.81 | B |
| ATOM | 3009 | N   GLU B 196 | 49.040 34.372 71.268 1.00  9.84 | B | | ATOM | 3089 | O   ASN B 206 | 52.834 23.088 64.501 1.00 22.85 | B |
| ATOM | 3010 | CA  GLU B 196 | 48.475 33.060 71.109 1.00 11.05 | B | | ATOM | 3090 | N   GLY B 207 | 51.760 22.250 66.301 1.00 17.19 | B |
| ATOM | 3011 | CB  GLU B 196 | 47.048 33.161 70.556 1.00 12.71 | B | | ATOM | 3091 | CA  GLY B 207 | 52.820 22.599 67.238 1.00 17.39 | B |
| ATOM | 3012 | CG  GLU B 196 | 46.159 33.836 71.607 1.00 12.80 | B | | ATOM | 3092 | C   GLY B 207 | 54.036 21.689 67.127 1.00 14.89 | B |
| ATOM | 3013 | CD  GLU B 196 | 44.722 34.095 71.148 1.00 14.85 | B | | ATOM | 3093 | O   GLY B 207 | 54.001 20.625 66.489 1.00 18.67 | B |
| ATOM | 3014 | OE1 GLU B 196 | 44.410 33.848 69.952 1.00 18.57 | B | | ATOM | 3094 | N   VAL B 208 | 55.108 22.092 67.778 1.00 12.86 | B |
| ATOM | 3015 | OE2 GLU B 196 | 43.918 34.529 72.009 1.00 15.99 | B | | ATOM | 3095 | CA  VAL B 208 | 56.365 21.373 67.724 1.00 14.89 | B |
| ATOM | 3016 | C   GLU B 196 | 49.344 32.191 70.226 1.00 11.58 | B | | ATOM | 3096 | CB  VAL B 208 | 57.563 22.390 67.714 1.00 18.78 | B |
| ATOM | 3017 | O   GLU B 196 | 49.520 31.003 70.491 1.00 12.47 | B | | ATOM | 3097 | CG1 VAL B 208 | 57.486 23.268 66.488 1.00 22.13 | B |
| ATOM | 3018 | N   ALA B 197 | 49.874 32.781 69.168 1.00 10.68 | B | | ATOM | 3098 | CG2 VAL B 208 | 57.570 23.237 68.995 1.00 18.98 | B |
| ATOM | 3019 | CA  ALA B 197 | 50.707 32.006 68.245 1.00 11.91 | B | | ATOM | 3099 | C   VAL B 208 | 56.649 20.367 68.823 1.00 17.33 | B |
| ATOM | 3020 | CB  ALA B 197 | 51.127 32.882 67.080 1.00 12.52 | B | | ATOM | 3100 | O   VAL B 208 | 57.660 19.669 68.759 1.00 13.92 | B |
| ATOM | 3021 | C   ALA B 197 | 51.938 31.372 68.886 1.00 10.96 | B | | ATOM | 3101 | N   SER B 209 | 55.795 20.299 69.849 1.00 12.41 | B |
| ATOM | 3022 | O   ALA B 197 | 52.350 30.258 68.504 1.00 10.29 | B | | ATOM | 3102 | CA  SER B 209 | 56.069 19.384 70.947 1.00 12.79 | B |
| ATOM | 3023 | N   VAL B 198 | 52.534 32.072 69.840 1.00 10.83 | B | | ATOM | 3103 | CB  SER B 209 | 56.443 20.155 72.229 1.00  9.84 | B |
| ATOM | 3024 | CA  VAL B 198 | 53.690 31.530 70.531 1.00 10.09 | B | | ATOM | 3104 | OG  SER B 209 | 56.761 19.263 73.286 1.00 12.58 | B |
| ATOM | 3025 | CB  VAL B 198 | 54.259 32.538 71.514 1.00 12.20 | B | | ATOM | 3105 | C   SER B 209 | 54.903 18.470 71.267 1.00 11.17 | B |
| ATOM | 3026 | CG1 VAL B 198 | 55.362 31.888 72.351 1.00 13.48 | B | | ATOM | 3106 | O   SER B 209 | 54.026 18.830 72.059 1.00 10.62 | B |
| ATOM | 3027 | CG2 VAL B 198 | 54.838 33.734 70.713 1.00 12.95 | B | | ATOM | 3107 | N   PRO B 210 | 54.873 17.280 70.666 1.00 10.74 | B |
| ATOM | 3028 | C   VAL B 198 | 53.294 30.252 71.273 1.00 11.73 | B | | ATOM | 3108 | CD  PRO B 210 | 55.649 16.827 69.489 1.00 11.94 | B |
| ATOM | 3029 | O   VAL B 198 | 53.990 29.225 71.176 1.00 13.01 | B | | ATOM | 3109 | CA  PRO B 210 | 53.769 16.366 70.973 1.00 11.06 | B |
| ATOM | 3030 | N   LEU B 199 | 52.174 30.274 71.988 1.00 10.55 | B | | ATOM | 3110 | CB  PRO B 210 | 54.046 15.138 70.087 1.00 14.21 | B |
| ATOM | 3031 | CA  LEU B 199 | 51.778 29.059 72.687 1.00 10.82 | B | | ATOM | 3111 | CG  PRO B 210 | 54.785 15.679 68.932 1.00 15.85 | B |
| ATOM | 3032 | CB  LEU B 199 | 50.688 29.366 73.731 1.00  9.80 | B | | ATOM | 3112 | C   PRO B 210 | 53.768 15.987 72.460 1.00 11.56 | B |
| ATOM | 3033 | CG  LEU B 199 | 50.227 28.178 74.588 1.00 10.38 | B | | ATOM | 3113 | O   PRO B 210 | 52.705 15.823 73.068 1.00 10.61 | B |
| ATOM | 3034 | CD1 LEU B 199 | 51.383 27.474 75.330 1.00 11.99 | B | | ATOM | 3114 | N   GLY B 211 | 54.960 15.863 73.057 1.00  8.87 | B |
| ATOM | 3035 | CD2 LEU B 199 | 49.202 28.760 75.589 1.00 11.17 | B | | ATOM | 3115 | CA  GLY B 211 | 55.054 15.481 74.464 1.00 10.67 | B |
| ATOM | 3036 | C   LEU B 199 | 51.280 27.985 71.697 1.00  8.89 | B | | ATOM | 3116 | C   GLY B 211 | 54.463 16.535 75.401 1.00  9.57 | B |
| ATOM | 3037 | O   LEU B 199 | 51.586 26.793 71.868 1.00 10.75 | B | | ATOM | 3117 | O   GLY B 211 | 53.826 16.191 76.397 1.00 10.58 | B |
| ATOM | 3038 | N   GLU B 200 | 50.552 28.402 70.642 1.00  9.76 | B | | ATOM | 3118 | N   THR B 212 | 54.689 17.816 75.075 1.00  9.02 | B |
| ATOM | 3039 | CA  GLU B 200 | 50.043 27.437 69.664 1.00 13.35 | B | | ATOM | 3119 | CA  THR B 212 | 54.120 18.864 75.951 1.00  8.80 | B |
| ATOM | 3040 | CB  GLU B 200 | 49.203 28.186 68.598 1.00 17.81 | B | | ATOM | 3120 | CB  THR B 212 | 54.680 20.238 75.592 1.00  9.71 | B |
| ATOM | 3041 | CG  GLU B 200 | 48.668 27.329 67.435 1.00 27.56 | B | | ATOM | 3121 | OG1 THR B 212 | 56.108 20.201 75.700 1.00 10.74 | B |
| ATOM | 3042 | CD  GLU B 200 | 47.345 26.655 67.767 1.00 30.48 | B | | ATOM | 3122 | CG2 THR B 212 | 54.156 21.304 76.590 1.00  9.68 | B |
| ATOM | 3043 | OE1 GLU B 200 | 46.727 27.019 68.800 1.00 32.93 | B | | ATOM | 3123 | C   THR B 212 | 52.598 18.865 75.831 1.00 10.82 | B |
| ATOM | 3044 | OE2 GLU B 200 | 46.916 25.791 66.969 1.00 34.73 | B | | ATOM | 3124 | O   THR B 212 | 51.887 19.019 76.842 1.00  9.59 | B |
| ATOM | 3045 | C   GLU B 200 | 51.232 26.723 68.986 1.00 12.75 | B | | ATOM | 3125 | N   ARG B 213 | 52.074 18.683 74.613 1.00  8.44 | B |
| ATOM | 3046 | O   GLU B 200 | 51.134 25.545 68.613 1.00 11.81 | B | | ATOM | 3126 | CA  ARG B 213 | 50.611 18.675 74.448 1.00  8.19 | B |
| ATOM | 3047 | N   SER B 201 | 52.359 27.437 68.801 1.00  9.77 | B | | ATOM | 3127 | CB  ARG B 213 | 50.233 18.576 72.952 1.00  9.49 | B |
| ATOM | 3048 | CA  SER B 201 | 53.508 26.823 68.142 1.00 12.26 | B | | ATOM | 3128 | CG  ARG B 213 | 48.740 18.637 72.683 1.00  8.49 | B |
| ATOM | 3049 | CB  SER B 201 | 54.645 27.870 67.883 1.00 12.68 | B | | ATOM | 3129 | CD  ARG B 213 | 48.428 17.785 71.185 1.00 10.85 | B |
| ATOM | 3050 | OG  SER B 201 | 55.354 28.149 69.065 1.00 16.32 | B | | ATOM | 3130 | NE  ARG B 213 | 46.990 18.336 70.947 1.00 10.18 | B |
| ATOM | 3051 | C   SER B 201 | 54.059 25.626 68.904 1.00 14.83 | B | | ATOM | 3131 | CZ  ARG B 213 | 46.149 19.265 70.517 1.00 11.67 | B |
| ATOM | 3052 | O   SER B 201 | 54.753 24.787 68.317 1.00 15.46 | B | | ATOM | 3132 | NH1 ARG B 213 | 46.553 20.519 70.265 1.00 12.07 | B |
| ATOM | 3053 | N   ILE B 202 | 53.752 25.529 70.184 1.00 11.85 | B | | ATOM | 3133 | NH2 ARG B 213 | 44.884 18.921 70.248 1.00 10.75 | B |
| ATOM | 3054 | CA  ILE B 202 | 54.210 24.435 70.985 1.00 10.28 | B | | ATOM | 3134 | C   ARG B 213 | 50.059 17.496 75.233 1.00  9.38 | B |
| ATOM | 3055 | CB  ILE B 202 | 54.669 24.970 72.371 1.00 12.29 | B | | ATOM | 3135 | O   ARG B 213 | 49.093 17.646 75.964 1.00 10.83 | B |
| ATOM | 3056 | CG2 ILE B 202 | 55.071 23.837 73.329 1.00 12.31 | B | | ATOM | 3136 | N   LEU B 214 | 50.689 16.327 75.095 1.00  8.31 | B |
| ATOM | 3057 | CG1 ILE B 202 | 55.848 25.938 72.133 1.00 14.43 | B | | ATOM | 3137 | CA  LEU B 214 | 50.221 15.131 75.820 1.00 11.10 | B |
| ATOM | 3058 | CD1 ILE B 202 | 56.088 26.830 73.301 1.00 18.16 | B | | ATOM | 3138 | CB  LEU B 214 | 51.093 13.929 75.464 1.00 12.28 | B |
| ATOM | 3059 | C   ILE B 202 | 53.136 23.341 71.182 1.00 10.03 | B | | ATOM | 3139 | CG  LEU B 214 | 50.782 12.639 76.245 1.00 14.07 | B |
| ATOM | 3060 | O   ILE B 202 | 53.384 22.166 70.879 1.00 11.70 | B | | ATOM | 3140 | CD1 LEU B 214 | 49.352 12.176 75.955 1.00 15.36 | B |
| ATOM | 3061 | N   ILE B 203 | 51.946 23.735 71.637 1.00 10.60 | B | | ATOM | 3141 | CD2 LEU B 214 | 51.788 11.580 75.779 1.00 16.05 | B |
| ATOM | 3062 | CA  ILE B 203 | 50.907 22.745 71.951 1.00  9.04 | B | | ATOM | 3142 | C   LEU B 214 | 50.219 15.339 77.353 1.00 11.90 | B |
| ATOM | 3063 | CB  ILE B 203 | 50.365 22.916 73.375 1.00 10.09 | B | | ATOM | 3143 | O   LEU B 214 | 49.283 14.948 78.054 1.00 10.57 | B |
| ATOM | 3064 | CG2 ILE B 203 | 51.493 22.741 74.389 1.00 12.96 | B | | ATOM | 3144 | N   SER B 215 | 51.282 15.956 77.852 1.00  9.66 | B |
| ATOM | 3065 | CG1 ILE B 203 | 49.654 24.284 73.504 1.00  8.55 | B | | ATOM | 3145 | CA  SER B 215 | 51.448 16.194 79.277 1.00  9.71 | B |
| ATOM | 3066 | CD1 ILE B 203 | 49.107 24.470 74.905 1.00 13.19 | B | | ATOM | 3146 | CB  SER B 215 | 52.828 16.831 79.503 1.00  9.94 | B |
| ATOM | 3067 | C   ILE B 203 | 49.711 22.687 71.020 1.00 12.43 | B | | ATOM | 3147 | OG  SER B 215 | 52.971 17.079 80.912 1.00  9.59 | B |
| ATOM | 3068 | O   ILE B 203 | 48.774 21.883 71.262 1.00 11.34 | B | | ATOM | 3148 | C   SER B 215 | 50.324 17.098 79.793 1.00  9.09 | B |
| ATOM | 3069 | N   GLY B 204 | 49.731 23.517 69.981 1.00 11.69 | B | | ATOM | 3149 | O   SER B 215 | 49.701 16.826 80.829 1.00  9.53 | B |
| ATOM | 3070 | CA  GLY B 204 | 48.643 23.521 69.005 1.00 11.30 | B | | ATOM | 3150 | N   VAL B 216 | 50.061 18.185 79.081 1.00  9.04 | B |
| ATOM | 3071 | C   GLY B 204 | 48.699 22.317 68.085 1.00 12.03 | B | | ATOM | 3151 | CA  VAL B 216 | 48.994 19.102 79.459 1.00  9.27 | B |
| ATOM | 3072 | O   GLY B 204 | 49.647 21.544 68.150 1.00 13.38 | B | | ATOM | 3152 | CB  VAL B 216 | 48.958 20.308 78.481 1.00 10.31 | B |
| ATOM | 3073 | N   LYS B 205 | 47.703 22.172 67.201 1.00 15.47 | B | | ATOM | 3153 | CG1 VAL B 216 | 47.686 21.165 78.743 1.00 11.07 | B |
| ATOM | 3074 | CA  LYS B 205 | 47.681 21.054 66.272 1.00 16.97 | B | | ATOM | 3154 | CG2 VAL B 216 | 50.228 21.178 78.682 1.00  7.86 | B |
| ATOM | 3075 | CB  LYS B 205 | 46.376 21.109 65.439 1.00 23.83 | B | | ATOM | 3155 | C   VAL B 216 | 47.659 18.353 79.427 1.00  9.96 | B |
| ATOM | 3076 | CG  LYS B 205 | 46.291 20.213 64.240 1.00 27.80 | B | | ATOM | 3156 | O   VAL B 216 | 46.870 18.488 80.378 1.00 10.13 | B |
| ATOM | 3077 | CD  LYS B 205 | 44.917 20.396 63.586 1.00 28.76 | B | | ATOM | 3157 | N   ALA B 217 | 47.417 17.562 78.364 1.00 11.55 | B |
| ATOM | 3078 | CE  LYS B 205 | 44.775 19.615 62.280 1.00 41.53 | B | | ATOM | 3158 | CA  ALA B 217 | 46.157 16.810 78.286 1.00 11.89 | B |
| ATOM | 3079 | NZ  LYS B 205 | 43.386 19.763 61.685 1.00 34.32 | B | | ATOM | 3159 | CB  ALA B 217 | 46.121 16.036 76.970 1.00 10.13 | B |
| ATOM | 3080 | C   LYS B 205 | 48.944 21.026 65.384 1.00 16.73 | B | | ATOM | 3160 | C   ALA B 217 | 45.995 15.841 79.463 1.00 10.83 | B |

Fig. 4 cont.

| | | | | | | | | | | | | |
|---|---|---|---|---|---|---|---|---|---|---|---|---|
| ATOM | 3161 | O | ALA B 217 | 44.942 | 15.776 | 80.078 | 1.00 | 14.01 | B | | | |
| ATOM | 3162 | N | GLU B 218 | 47.044 | 15.096 | 79.774 | 1.00 | 11.49 | B | | | |
| ATOM | 3163 | CA | GLU B 218 | 46.939 | 14.138 | 80.886 | 1.00 | 11.52 | B | | | |
| ATOM | 3164 | CB | GLU B 218 | 48.210 | 13.307 | 80.951 | 1.00 | 16.96 | B | | | |
| ATOM | 3165 | CG | GLU B 218 | 48.275 | 12.374 | 82.132 | 1.00 | 27.75 | B | | | |
| ATOM | 3166 | CD | GLU B 218 | 49.640 | 11.694 | 82.242 | 1.00 | 36.98 | B | | | |
| ATOM | 3167 | OE1 | GLU B 218 | 50.648 | 12.236 | 81.708 | 1.00 | 44.43 | B | | | |
| ATOM | 3168 | OE2 | GLU B 218 | 49.706 | 10.624 | 82.880 | 1.00 | 52.42 | B | | | |
| ATOM | 3169 | C | GLU B 218 | 46.691 | 14.824 | 82.216 | 1.00 | 12.37 | B | | | |
| ATOM | 3170 | O | GLU B 218 | 45.858 | 14.378 | 83.027 | 1.00 | 14.44 | B | | | |
| ATOM | 3171 | N | ARG B 219 | 47.407 | 15.918 | 82.464 | 1.00 | 10.15 | B | | | |
| ATOM | 3172 | CA | ARG B 219 | 47.274 | 16.557 | 83.767 | 1.00 | 12.24 | B | | | |
| ATOM | 3173 | CB | ARG B 219 | 48.447 | 17.498 | 84.003 | 1.00 | 12.05 | B | | | |
| ATOM | 3174 | CG | ARG B 219 | 49.741 | 16.693 | 84.153 | 1.00 | 14.98 | B | | | |
| ATOM | 3175 | CD | ARG B 219 | 51.013 | 17.523 | 83.941 | 1.00 | 15.88 | B | | | |
| ATOM | 3176 | NE | ARG B 219 | 51.247 | 18.508 | 85.002 | 1.00 | 13.05 | B | | | |
| ATOM | 3177 | CZ | ARG B 219 | 51.802 | 18.262 | 86.197 | 1.00 | 12.23 | B | | | |
| ATOM | 3178 | NH1 | ARG B 219 | 52.206 | 17.043 | 86.553 | 1.00 | 13.37 | B | | | |
| ATOM | 3179 | NH2 | ARG B 219 | 51.972 | 19.258 | 87.058 | 1.00 | 10.54 | B | | | |
| ATOM | 3180 | C | ARG B 219 | 45.959 | 17.272 | 83.914 | 1.00 | 10.94 | B | | | |
| ATOM | 3181 | O | ARG B 219 | 45.354 | 17.206 | 84.988 | 1.00 | 12.84 | B | | | |
| ATOM | 3182 | N | LEU B 220 | 45.488 | 17.938 | 82.854 | 1.00 | 12.74 | B | | | |
| ATOM | 3183 | CA | LEU B 220 | 44.208 | 18.630 | 82.948 | 1.00 | 13.57 | B | | | |
| ATOM | 3184 | CB | LEU B 220 | 43.983 | 19.595 | 81.774 | 1.00 | 11.25 | B | | | |
| ATOM | 3185 | CG | LEU B 220 | 44.829 | 20.888 | 81.865 | 1.00 | 15.06 | B | | | |
| ATOM | 3186 | CD1 | LEU B 220 | 44.629 | 21.678 | 80.593 | 1.00 | 14.54 | B | | | |
| ATOM | 3187 | CD2 | LEU B 220 | 44.443 | 21.748 | 83.082 | 1.00 | 15.41 | B | | | |
| ATOM | 3188 | C | LEU B 220 | 43.072 | 17.606 | 83.008 | 1.00 | 11.32 | B | | | |
| ATOM | 3189 | O | LEU B 220 | 42.101 | 17.864 | 83.655 | 1.00 | 14.24 | B | | | |
| ATOM | 3190 | N | SER B 221 | 43.208 | 16.466 | 82.346 | 1.00 | 10.57 | B | | | |
| ATOM | 3191 | CA | SER B 221 | 42.133 | 15.455 | 82.418 | 1.00 | 12.74 | B | | | |
| ATOM | 3192 | CB | SER B 221 | 42.474 | 14.213 | 81.585 | 1.00 | 14.98 | B | | | |
| ATOM | 3193 | OG | SER B 221 | 41.515 | 13.179 | 81.838 | 1.00 | 17.23 | B | | | |
| ATOM | 3194 | C | SER B 221 | 41.944 | 15.063 | 83.890 | 1.00 | 14.53 | B | | | |
| ATOM | 3195 | O | SER B 221 | 40.821 | 14.971 | 84.373 | 1.00 | 17.24 | B | | | |
| ATOM | 3196 | N | GLN B 222 | 43.048 | 14.893 | 84.605 | 1.00 | 14.54 | B | | | |
| ATOM | 3197 | CA | GLN B 222 | 42.966 | 14.531 | 86.024 | 1.00 | 15.44 | B | | | |
| ATOM | 3198 | CB | GLN B 222 | 44.337 | 14.034 | 86.516 | 1.00 | 17.33 | B | | | |
| ATOM | 3199 | CG | GLN B 222 | 44.908 | 12.877 | 85.712 | 1.00 | 26.02 | B | | | |
| ATOM | 3200 | CD | GLN B 222 | 46.393 | 12.614 | 86.010 | 1.00 | 37.56 | B | | | |
| ATOM | 3201 | OE1 | GLN B 222 | 47.122 | 13.499 | 86.510 | 1.00 | 42.49 | B | | | |
| ATOM | 3202 | NE2 | GLN B 222 | 46.848 | 11.410 | 85.690 | 1.00 | 42.42 | B | | | |
| ATOM | 3203 | C | GLN B 222 | 42.497 | 15.715 | 86.884 | 1.00 | 16.54 | B | | | |
| ATOM | 3204 | O | GLN B 222 | 41.678 | 15.554 | 87.796 | 1.00 | 16.48 | B | | | |
| ATOM | 3205 | N | LEU B 223 | 42.991 | 16.924 | 86.624 | 1.00 | 14.23 | B | | | |
| ATOM | 3206 | CA | LEU B 223 | 42.579 | 18.047 | 87.453 | 1.00 | 12.99 | B | | | |
| ATOM | 3207 | CB | LEU B 223 | 43.400 | 19.300 | 87.106 | 1.00 | 15.29 | B | | | |
| ATOM | 3208 | CG | LEU B 223 | 44.769 | 19.506 | 87.768 | 1.00 | 18.37 | B | | | |
| ATOM | 3209 | CD1 | LEU B 223 | 45.579 | 18.230 | 87.740 | 1.00 | 34.62 | B | | | |
| ATOM | 3210 | CD2 | LEU B 223 | 45.540 | 20.593 | 87.069 | 1.00 | 19.21 | B | | | |
| ATOM | 3211 | C | LEU B 223 | 41.094 | 18.350 | 87.300 | 1.00 | 17.11 | B | | | |
| ATOM | 3212 | O | LEU B 223 | 40.436 | 18.710 | 88.261 | 1.00 | 19.12 | B | | | |
| ATOM | 3213 | N | MET B 224 | 40.553 | 18.211 | 86.095 | 1.00 | 13.82 | B | | | |
| ATOM | 3214 | CA | MET B 224 | 39.131 | 18.497 | 85.923 | 1.00 | 15.04 | B | | | |
| ATOM | 3215 | CB | MET B 224 | 38.796 | 18.553 | 84.441 | 1.00 | 14.02 | B | | | |
| ATOM | 3216 | CG | MET B 224 | 39.389 | 19.815 | 83.772 | 1.00 | 12.91 | B | | | |
| ATOM | 3217 | SD | MET B 224 | 38.898 | 19.973 | 82.022 | 1.00 | 16.54 | B | | | |
| ATOM | 3218 | CE | MET B 224 | 39.742 | 18.509 | 81.262 | 1.00 | 15.83 | B | | | |
| ATOM | 3219 | C | MET B 224 | 38.238 | 17.470 | 86.646 | 1.00 | 18.90 | B | | | |
| ATOM | 3220 | O | MET B 224 | 37.147 | 17.807 | 87.072 | 1.00 | 19.15 | B | | | |
| ATOM | 3221 | N | MET B 225 | 38.715 | 16.243 | 86.791 | 1.00 | 17.03 | B | | | |
| ATOM | 3222 | CA | MET B 225 | 37.929 | 15.196 | 87.466 | 1.00 | 23.78 | B | | | |
| ATOM | 3223 | CB | MET B 225 | 38.539 | 13.821 | 87.237 | 1.00 | 19.99 | B | | | |
| ATOM | 3224 | CG | MET B 225 | 38.251 | 13.260 | 85.870 | 1.00 | 29.61 | B | | | |
| ATOM | 3225 | SD | MET B 225 | 36.479 | 13.167 | 85.684 | 1.00 | 30.44 | B | | | |
| ATOM | 3226 | CE | MET B 225 | 36.024 | 11.674 | 86.753 | 1.00 | 27.05 | B | | | |
| ATOM | 3227 | C | MET B 225 | 37.856 | 15.436 | 88.955 | 1.00 | 32.21 | B | | | |
| ATOM | 3228 | O | MET B 225 | 36.922 | 14.988 | 89.615 | 1.00 | 38.70 | B | | | |
| ATOM | 3229 | N | LYS B 226 | 38.833 | 16.136 | 89.505 | 1.00 | 32.94 | B | | | |
| ATOM | 3230 | CA | LYS B 226 | 38.796 | 16.379 | 90.931 | 1.00 | 39.13 | B | | | |
| ATOM | 3231 | CB | LYS B 226 | 40.164 | 16.106 | 91.538 | 1.00 | 40.08 | B | | | |
| ATOM | 3232 | CG | LYS B 226 | 41.221 | 17.083 | 91.173 | 1.00 | 45.26 | B | | | |
| ATOM | 3233 | CD | LYS B 226 | 42.475 | 16.813 | 91.996 | 1.00 | 48.87 | B | | | |
| ATOM | 3234 | CE | LYS B 226 | 43.257 | 18.096 | 92.228 | 1.00 | 52.94 | B | | | |
| ATOM | 3235 | NZ | LYS B 226 | 42.412 | 19.195 | 92.836 | 1.00 | 53.34 | B | | | |
| ATOM | 3236 | C | LYS B 226 | 38.308 | 17.789 | 91.234 | 1.00 | 42.41 | B | | | |
| ATOM | 3237 | O | LYS B 226 | 38.230 | 18.197 | 92.397 | 1.00 | 44.09 | B | | | |
| ATOM | 3238 | N | ASN B 227 | 37.955 | 18.512 | 90.168 | 1.00 | 41.51 | B | | | |
| ATOM | 3239 | CA | ASN B 227 | 37.444 | 19.891 | 90.237 | 1.00 | 47.42 | B | | | |
| ATOM | 3240 | CB | ASN B 227 | 37.453 | 20.557 | 88.841 | 1.00 | 44.14 | B | | | |
| ATOM | 3241 | CG | ASN B 227 | 36.758 | 21.946 | 88.822 | 1.00 | 43.29 | B | | | |
| ATOM | 3242 | OD1 | ASN B 227 | 37.341 | 22.955 | 89.223 | 1.00 | 38.08 | B | | | |
| ATOM | 3243 | ND2 | ASN B 227 | 35.507 | 21.984 | 88.358 | 1.00 | 42.21 | B | | | |
| ATOM | 3244 | C | ASN B 227 | 36.002 | 19.877 | 90.712 | 1.00 | 50.22 | B | | | |
| ATOM | 3245 | O | ASN B 227 | 35.657 | 20.468 | 91.743 | 1.00 | 49.75 | B | | | |
| ATOM | 3246 | N | LYS B 228 | 35.186 | 19.201 | 89.903 | 1.00 | 54.08 | B | | | |
| ATOM | 3247 | CA | LYS B 228 | 33.739 | 19.048 | 90.059 | 1.00 | 59.69 | B | | | |
| ATOM | 3248 | CB | LYS B 228 | 33.202 | 19.774 | 91.312 | 1.00 | 56.52 | B | | | |
| ATOM | 3249 | CG | LYS B 228 | 33.575 | 19.080 | 92.639 | 1.00 | 56.77 | B | | | |
| ATOM | 3250 | CD | LYS B 228 | 33.160 | 19.905 | 93.862 | 1.00 | 59.87 | B | | | |
| ATOM | 3251 | CE | LYS B 228 | 31.740 | 19.565 | 94.344 | 1.00 | 56.59 | B | | | |
| ATOM | 3252 | NZ | LYS B 228 | 30.689 | 19.672 | 93.285 | 1.00 | 58.10 | B | | | |
| ATOM | 3253 | C | LYS B 228 | 33.092 | 19.626 | 88.782 | 1.00 | 64.05 | B | | | |
| ATOM | 3254 | O | LYS B 228 | 31.839 | 19.632 | 88.682 | 1.00 | 67.93 | B | | | |
| ATOM | 3255 | OXT | LYS B 228 | 33.855 | 20.046 | 87.871 | 1.00 | 70.92 | B | | | |
| ATOM | 3256 | OH2 | TIP S 1 | 51.854 | 39.696 | 79.590 | 1.00 | 12.70 | S | | | |
| ATOM | 3257 | OH2 | TIP S 2 | 60.181 | 25.656 | 86.745 | 1.00 | 11.90 | S | | | |
| ATOM | 3258 | OH2 | TIP S 3 | 45.817 | 40.480 | 67.385 | 1.00 | 15.74 | S | | | |
| ATOM | 3259 | OH2 | TIP S 4 | 36.137 | 22.651 | 36.398 | 1.00 | 14.93 | S | | | |
| ATOM | 3260 | OH2 | TIP S 5 | 57.991 | 47.723 | 74.232 | 1.00 | 14.19 | S | | | |
| ATOM | 3261 | OH2 | TIP S 6 | 36.666 | 8.424 | 47.065 | 1.00 | 15.43 | S | | | |
| ATOM | 3262 | OH2 | TIP S 7 | 68.267 | 25.222 | 83.245 | 1.00 | 15.49 | S | | | |
| ATOM | 3263 | OH2 | TIP S 8 | 58.435 | 13.769 | 86.837 | 1.00 | 15.71 | S | | | |
| ATOM | 3264 | OH2 | TIP S 9 | 47.596 | 33.296 | 66.468 | 1.00 | 15.16 | S | | | |
| ATOM | 3265 | OH2 | TIP S 10 | 62.369 | 24.719 | 85.556 | 1.00 | 12.11 | S | | | |
| ATOM | 3266 | OH2 | TIP S 11 | 42.454 | 7.378 | 59.448 | 1.00 | 13.36 | S | | | |
| ATOM | 3267 | OH2 | TIP S 12 | 44.543 | 22.522 | 69.203 | 1.00 | 16.97 | S | | | |
| ATOM | 3268 | OH2 | TIP S 13 | 54.636 | 13.804 | 77.543 | 1.00 | 15.98 | S | | | |
| ATOM | 3269 | OH2 | TIP S 14 | 39.308 | 34.384 | 46.838 | 1.00 | 17.86 | S | | | |
| ATOM | 3270 | OH2 | TIP S 15 | 50.542 | 14.545 | 71.799 | 1.00 | 14.14 | S | | | |
| ATOM | 3271 | OH2 | TIP S 16 | 41.249 | 33.446 | 53.492 | 1.00 | 16.75 | S | | | |
| ATOM | 3272 | OH2 | TIP S 17 | 40.388 | 32.419 | 34.091 | 1.00 | 17.35 | S | | | |
| ATOM | 3273 | OH2 | TIP S 18 | 65.326 | 37.919 | 65.539 | 1.00 | 17.62 | S | | | |
| ATOM | 3274 | OH2 | TIP S 19 | 38.590 | 15.078 | 82.598 | 1.00 | 16.86 | S | | | |
| ATOM | 3275 | OH2 | TIP S 20 | 61.528 | 27.675 | 88.059 | 1.00 | 15.04 | S | | | |
| ATOM | 3276 | OH2 | TIP S 21 | 34.362 | 9.793 | 46.787 | 1.00 | 15.53 | S | | | |
| ATOM | 3277 | OH2 | TIP S 22 | 41.029 | 28.663 | 79.019 | 1.00 | 17.05 | S | | | |
| ATOM | 3278 | OH2 | TIP S 23 | 58.165 | 15.611 | 75.130 | 1.00 | 19.42 | S | | | |
| ATOM | 3279 | OH2 | TIP S 24 | 53.508 | 46.226 | 71.438 | 1.00 | 18.83 | S | | | |
| ATOM | 3280 | OH2 | TIP S 25 | 50.551 | 38.228 | 81.564 | 1.00 | 15.96 | S | | | |
| ATOM | 3281 | OH2 | TIP S 26 | 53.538 | 14.698 | 81.947 | 1.00 | 16.18 | S | | | |
| ATOM | 3282 | OH2 | TIP S 27 | 43.480 | 32.705 | 45.375 | 1.00 | 19.34 | S | | | |
| ATOM | 3283 | OH2 | TIP S 28 | 38.401 | 23.598 | 35.524 | 1.00 | 14.44 | S | | | |
| ATOM | 3284 | OH2 | TIP S 29 | 37.554 | 25.908 | 71.514 | 1.00 | 19.22 | S | | | |
| ATOM | 3285 | OH2 | TIP S 30 | 70.773 | 36.288 | 67.813 | 1.00 | 17.06 | S | | | |
| ATOM | 3286 | OH2 | TIP S 31 | 44.644 | 38.647 | 56.050 | 1.00 | 21.99 | S | | | |
| ATOM | 3287 | OH2 | TIP S 32 | 57.844 | 15.967 | 72.052 | 1.00 | 17.70 | S | | | |
| ATOM | 3288 | OH2 | TIP S 33 | 35.739 | 12.837 | 53.333 | 1.00 | 19.05 | S | | | |
| ATOM | 3289 | OH2 | TIP S 34 | 29.061 | 79.795 | 1.00 | 17.00 | S | | | | |
| ATOM | 3290 | OH2 | TIP S 35 | 44.406 | 7.254 | 64.150 | 1.00 | 16.76 | S | | | |
| ATOM | 3291 | OH2 | TIP S 36 | 57.021 | 42.898 | 82.998 | 1.00 | 18.82 | S | | | |
| ATOM | 3292 | OH2 | TIP S 37 | 35.310 | 10.396 | 78.482 | 1.00 | 21.82 | S | | | |
| ATOM | 3293 | OH2 | TIP S 38 | 33.739 | 21.604 | 63.672 | 1.00 | 18.61 | S | | | |
| ATOM | 3294 | OH2 | TIP S 39 | 56.025 | 10.616 | 45.447 | 1.00 | 19.99 | S | | | |
| ATOM | 3295 | OH2 | TIP S 40 | 38.067 | 28.099 | 79.542 | 1.00 | 21.17 | S | | | |
| ATOM | 3296 | OH2 | TIP S 41 | 45.213 | 32.342 | 67.811 | 1.00 | 23.00 | S | | | |
| ATOM | 3297 | OH2 | TIP S 42 | 45.435 | 29.625 | 81.983 | 1.00 | 14.87 | S | | | |
| ATOM | 3298 | OH2 | TIP S 43 | 64.832 | 39.093 | 81.664 | 1.00 | 15.72 | S | | | |
| ATOM | 3299 | OH2 | TIP S 44 | 43.271 | 40.588 | 62.955 | 1.00 | 19.08 | S | | | |
| ATOM | 3300 | OH2 | TIP S 45 | 44.385 | 42.686 | 64.530 | 1.00 | 20.42 | S | | | |
| ATOM | 3301 | OH2 | TIP S 46 | 50.417 | 9.237 | 67.562 | 1.00 | 21.60 | S | | | |
| ATOM | 3302 | OH2 | TIP S 47 | 60.421 | 45.278 | 83.361 | 1.00 | 20.48 | S | | | |
| ATOM | 3303 | OH2 | TIP S 48 | 56.556 | 41.879 | 60.065 | 1.00 | 20.65 | S | | | |
| ATOM | 3304 | OH2 | TIP S 49 | 65.788 | 35.221 | 86.870 | 1.00 | 20.25 | S | | | |
| ATOM | 3305 | OH2 | TIP S 50 | 47.382 | 42.536 | 79.638 | 1.00 | 22.26 | S | | | |
| ATOM | 3306 | OH2 | TIP S 51 | 44.104 | 14.564 | 58.849 | 1.00 | 18.90 | S | | | |
| ATOM | 3307 | OH2 | TIP S 52 | 44.147 | 1.990 | 50.767 | 1.00 | 19.22 | S | | | |
| ATOM | 3308 | OH2 | TIP S 53 | 71.635 | 32.604 | 64.102 | 1.00 | 22.93 | S | | | |
| ATOM | 3309 | OH2 | TIP S 54 | 44.690 | 35.648 | 74.410 | 1.00 | 21.09 | S | | | |
| ATOM | 3310 | OH2 | TIP S 55 | 41.584 | 15.313 | 59.780 | 1.00 | 19.75 | S | | | |
| ATOM | 3311 | OH2 | TIP S 56 | 45.455 | 23.960 | 67.017 | 1.00 | 23.14 | S | | | |
| ATOM | 3312 | OH2 | TIP S 57 | 66.232 | 21.880 | 86.209 | 1.00 | 19.92 | S | | | |
| ATOM | 3313 | OH2 | TIP S 58 | 36.825 | 17.877 | 70.856 | 1.00 | 21.46 | S | | | |
| ATOM | 3314 | OH2 | TIP S 59 | 46.542 | 35.004 | 76.306 | 1.00 | 19.38 | S | | | |
| ATOM | 3315 | OH2 | TIP S 60 | 55.369 | 33.645 | 59.732 | 1.00 | 24.04 | S | | | |
| ATOM | 3316 | OH2 | TIP S 61 | 25.234 | 32.168 | 56.071 | 1.00 | 18.02 | S | | | |
| ATOM | 3317 | OH2 | TIP S 62 | 42.576 | 9.477 | 80.880 | 1.00 | 22.23 | S | | | |
| ATOM | 3318 | OH2 | TIP S 63 | 64.079 | 30.401 | 83.749 | 1.00 | 20.50 | S | | | |
| ATOM | 3319 | OH2 | TIP S 64 | 39.792 | 25.337 | 59.676 | 1.00 | 17.79 | S | | | |
| ATOM | 3320 | OH2 | TIP S 65 | 50.124 | 27.561 | 91.492 | 1.00 | 25.32 | S | | | |

Fig. 4 cont.

| | | | | | | | | | | | | |
|---|---|---|---|---|---|---|---|---|---|---|---|---|
| ATOM | 3321 | OH2 TIP S | 66 | 39.966 | 20.889 | 29.112 | 1.00 23.58 | S | ATOM | 3401 | OH2 TIP S 146 | 42.180 34.140 68.789 1.00 25.93 | S |
| ATOM | 3322 | OH2 TIP S | 67 | 37.688 | 32.695 | 78.675 | 1.00 23.98 | S | ATOM | 3402 | OH2 TIP S 147 | 37.087 30.270 86.615 1.00 29.11 | S |
| ATOM | 3323 | OH2 TIP S | 68 | 45.583 | 32.307 | 47.721 | 1.00 22.01 | S | ATOM | 3403 | OH2 TIP S 148 | 59.220 41.013 60.314 1.00 28.45 | S |
| ATOM | 3324 | OH2 TIP S | 69 | 36.855 | 9.840 | 82.376 | 1.00 23.79 | S | ATOM | 3404 | OH2 TIP S 149 | 65.471 38.201 62.837 1.00 30.02 | S |
| ATOM | 3325 | OH2 TIP S | 70 | 33.496 | 29.622 | 64.666 | 1.00 20.07 | S | ATOM | 3405 | OH2 TIP S 150 | 48.954 25.037 65.586 1.00 39.52 | S |
| ATOM | 3326 | OH2 TIP S | 71 | 62.491 | 31.429 | 90.415 | 1.00 18.92 | S | ATOM | 3406 | OH2 TIP S 151 | 53.743 6.661 39.901 1.00 24.99 | S |
| ATOM | 3327 | OH2 TIP S | 72 | 68.119 | 41.721 | 70.633 | 1.00 22.58 | S | ATOM | 3407 | OH2 TIP S 152 | 69.566 15.347 72.332 1.00 26.31 | S |
| ATOM | 3328 | OH2 TIP S | 73 | 36.952 | 5.424 | 43.484 | 1.00 20.58 | S | ATOM | 3408 | OH2 TIP S 153 | 39.806 7.579 75.648 1.00 27.84 | S |
| ATOM | 3329 | OH2 TIP S | 74 | 59.387 | 17.345 | 69.613 | 1.00 18.39 | S | ATOM | 3409 | OH2 TIP S 154 | 51.948 14.387 85.201 1.00 28.39 | S |
| ATOM | 3330 | OH2 TIP S | 75 | 56.928 | 25.702 | 93.062 | 1.00 20.14 | S | ATOM | 3410 | OH2 TIP S 155 | 40.970 7.523 35.424 1.00 35.59 | S |
| ATOM | 3331 | OH2 TIP S | 76 | 43.933 | 2.954 | 56.507 | 1.00 19.48 | S | ATOM | 3411 | OH2 TIP S 156 | 48.798 30.893 48.015 1.00 23.54 | S |
| ATOM | 3332 | OH2 TIP S | 77 | 60.405 | 32.804 | 60.487 | 1.00 24.44 | S | ATOM | 3412 | OH2 TIP S 157 | 36.596 36.979 54.862 1.00 28.35 | S |
| ATOM | 3333 | OH2 TIP S | 78 | 44.178 | 36.846 | 53.796 | 1.00 24.17 | S | ATOM | 3413 | OH2 TIP S 158 | 56.971 39.348 89.656 1.00 31.51 | S |
| ATOM | 3334 | OH2 TIP S | 79 | 54.866 | 6.195 | 55.563 | 1.00 26.83 | S | ATOM | 3414 | OH2 TIP S 159 | 33.905 18.937 62.802 1.00 28.16 | S |
| ATOM | 3335 | OH2 TIP S | 80 | 44.877 | 11.095 | 71.155 | 1.00 23.28 | S | ATOM | 3415 | OH2 TIP S 160 | 31.064 22.468 64.059 1.00 25.58 | S |
| ATOM | 3336 | OH2 TIP S | 81 | 44.046 | 23.298 | 32.261 | 1.00 20.04 | S | ATOM | 3416 | OH2 TIP S 161 | 56.724 15.476 52.529 1.00 33.80 | S |
| ATOM | 3337 | OH2 TIP S | 82 | 54.340 | 14.510 | 56.933 | 1.00 21.77 | S | ATOM | 3417 | OH2 TIP S 162 | 35.650 24.974 73.404 1.00 26.16 | S |
| ATOM | 3338 | OH2 TIP S | 83 | 40.268 | 33.017 | 44.934 | 1.00 24.07 | S | ATOM | 3418 | OH2 TIP S 163 | 30.740 5.569 40.051 1.00 25.07 | S |
| ATOM | 3339 | OH2 TIP S | 84 | 58.597 | 31.646 | 90.480 | 1.00 19.49 | S | ATOM | 3419 | OH2 TIP S 164 | 67.443 44.477 68.600 1.00 24.90 | S |
| ATOM | 3340 | OH2 TIP S | 85 | 70.562 | 17.802 | 72.375 | 1.00 24.81 | S | ATOM | 3420 | OH2 TIP S 165 | 46.668 7.692 78.858 1.00 41.89 | S |
| ATOM | 3341 | OH2 TIP S | 86 | 40.076 | 26.555 | 31.964 | 1.00 22.65 | S | ATOM | 3421 | OH2 TIP S 166 | 66.610 36.706 84.758 1.00 26.37 | S |
| ATOM | 3342 | OH2 TIP S | 87 | 38.305 | 14.174 | 71.374 | 1.00 22.58 | S | ATOM | 3422 | OH2 TIP S 167 | 57.917 26.647 65.759 1.00 22.83 | S |
| ATOM | 3343 | OH2 TIP S | 88 | 39.106 | 3.003 | 37.867 | 1.00 24.90 | S | ATOM | 3423 | OH2 TIP S 168 | 56.775 15.016 78.828 1.00 24.47 | S |
| ATOM | 3344 | OH2 TIP S | 89 | 33.674 | 11.838 | 56.903 | 1.00 21.14 | S | ATOM | 3424 | OH2 TIP S 169 | 29.001 22.530 34.992 1.00 22.91 | S |
| ATOM | 3345 | OH2 TIP S | 90 | 40.424 | 37.984 | 75.768 | 1.00 25.56 | S | ATOM | 3425 | OH2 TIP S 170 | 50.790 21.526 51.474 1.00 27.56 | S |
| ATOM | 3346 | OH2 TIP S | 91 | 57.403 | 14.214 | 89.356 | 1.00 21.01 | S | ATOM | 3426 | OH2 TIP S 171 | 57.916 14.158 83.398 1.00 27.13 | S |
| ATOM | 3347 | OH2 TIP S | 92 | 41.000 | 18.071 | 35.158 | 1.00 24.72 | S | ATOM | 3427 | OH2 TIP S 172 | 28.120 30.285 35.684 1.00 32.98 | S |
| ATOM | 3348 | OH2 TIP S | 93 | 35.274 | 33.353 | 44.783 | 1.00 18.38 | S | ATOM | 3428 | OH2 TIP S 173 | 45.370 41.570 80.575 1.00 32.46 | S |
| ATOM | 3349 | OH2 TIP S | 94 | 51.369 | 45.744 | 67.016 | 1.00 23.93 | S | ATOM | 3429 | OH2 TIP S 174 | 41.370 11.466 83.959 1.00 28.63 | S |
| ATOM | 3350 | OH2 TIP S | 95 | 43.917 | 5.163 | 62.353 | 1.00 21.42 | S | ATOM | 3430 | OH2 TIP S 175 | 34.975 4.845 39.559 1.00 28.07 | S |
| ATOM | 3351 | OH2 TIP S | 96 | 68.259 | 27.546 | 88.339 | 1.00 20.50 | S | ATOM | 3431 | OH2 TIP S 176 | 29.613 22.643 73.342 1.00 36.14 | S |
| ATOM | 3352 | OH2 TIP S | 97 | 36.089 | 12.104 | 55.969 | 1.00 23.22 | S | ATOM | 3432 | OH2 TIP S 177 | 57.111 46.993 65.463 1.00 24.36 | S |
| ATOM | 3353 | OH2 TIP S | 98 | 57.999 | 12.366 | 40.259 | 1.00 26.68 | S | ATOM | 3433 | OH2 TIP S 178 | 38.962 13.555 61.597 1.00 28.18 | S |
| ATOM | 3354 | OH2 TIP S | 99 | 49.110 | 44.922 | 68.092 | 1.00 22.21 | S | ATOM | 3434 | OH2 TIP S 179 | 58.384 36.320 88.964 1.00 25.48 | S |
| ATOM | 3355 | OH2 TIP S | 100 | 39.484 | 17.996 | 67.023 | 1.00 20.31 | S | ATOM | 3435 | OH2 TIP S 180 | 73.340 27.835 67.174 1.00 28.92 | S |
| ATOM | 3356 | OH2 TIP S | 101 | 54.674 | 42.674 | 81.605 | 1.00 20.62 | S | ATOM | 3436 | OH2 TIP S 181 | 43.151 32.891 65.648 1.00 36.99 | S |
| ATOM | 3357 | OH2 TIP S | 102 | 64.080 | 23.586 | 88.911 | 1.00 19.61 | S | ATOM | 3437 | OH2 TIP S 182 | 32.232 16.300 35.096 1.00 22.51 | S |
| ATOM | 3358 | OH2 TIP S | 103 | 42.363 | 35.890 | 75.692 | 1.00 19.70 | S | ATOM | 3438 | OH2 TIP S 183 | 73.264 30.720 81.099 1.00 26.75 | S |
| ATOM | 3359 | OH2 TIP S | 104 | 63.743 | 40.893 | 83.596 | 1.00 22.69 | S | ATOM | 3439 | OH2 TIP S 184 | 69.065 13.528 77.059 1.00 35.09 | S |
| ATOM | 3360 | OH2 TIP S | 105 | 48.828 | 21.226 | 49.552 | 1.00 22.29 | S | ATOM | 3440 | OH2 TIP S 185 | 52.595 11.717 34.462 1.00 35.05 | S |
| ATOM | 3361 | OH2 TIP S | 106 | 36.005 | 20.652 | 34.465 | 1.00 17.60 | S | ATOM | 3441 | OH2 TIP S 186 | 32.110 34.043 37.098 1.00 30.16 | S |
| ATOM | 3362 | OH2 TIP S | 107 | 41.892 | 23.750 | 60.256 | 1.00 21.01 | S | ATOM | 3442 | OH2 TIP S 187 | 36.793 24.831 32.004 1.00 22.10 | S |
| ATOM | 3363 | OH2 TIP S | 108 | 34.833 | 34.453 | 38.052 | 1.00 23.69 | S | ATOM | 3443 | OH2 TIP S 188 | 25.962 20.255 41.244 1.00 33.11 | S |
| ATOM | 3364 | OH2 TIP S | 109 | 46.912 | 30.144 | 89.666 | 1.00 20.97 | S | ATOM | 3444 | OH2 TIP S 189 | 48.320 28.535 56.700 1.00 26.40 | S |
| ATOM | 3365 | OH2 TIP S | 110 | 72.161 | 27.490 | 83.623 | 1.00 22.23 | S | ATOM | 3445 | OH2 TIP S 190 | 47.327 35.934 86.370 1.00 25.27 | S |
| ATOM | 3366 | OH2 TIP S | 111 | 51.597 | 29.352 | 65.774 | 1.00 27.32 | S | ATOM | 3446 | OH2 TIP S 191 | 48.165 30.751 54.012 1.00 25.42 | S |
| ATOM | 3367 | OH2 TIP S | 112 | 50.206 | 1.338 | 64.653 | 1.00 26.97 | S | ATOM | 3447 | OH2 TIP S 192 | 31.778 33.577 43.914 1.00 31.30 | S |
| ATOM | 3368 | OH2 TIP S | 113 | 55.812 | 13.188 | 52.834 | 1.00 25.89 | S | ATOM | 3448 | OH2 TIP S 193 | 69.124 28.403 62.147 1.00 30.98 | S |
| ATOM | 3369 | OH2 TIP S | 114 | 59.434 | 35.247 | 61.140 | 1.00 21.76 | S | ATOM | 3449 | OH2 TIP S 194 | 56.281 5.360 48.984 1.00 27.25 | S |
| ATOM | 3370 | OH2 TIP S | 115 | 45.581 | 42.449 | 69.549 | 1.00 25.05 | S | ATOM | 3450 | OH2 TIP S 195 | 27.504 28.727 65.138 1.00 30.89 | S |
| ATOM | 3371 | OH2 TIP S | 116 | 62.415 | 43.072 | 63.054 | 1.00 23.04 | S | ATOM | 3451 | OH2 TIP S 196 | 46.023 35.060 38.710 1.00 28.35 | S |
| ATOM | 3372 | OH2 TIP S | 117 | 46.332 | 21.107 | 29.236 | 1.00 24.66 | S | ATOM | 3452 | OH2 TIP S 197 | 23.711 18.986 60.438 1.00 26.59 | S |
| ATOM | 3373 | OH2 TIP S | 118 | 55.258 | 39.815 | 59.507 | 1.00 26.19 | S | ATOM | 3453 | OH2 TIP S 198 | 69.327 22.315 79.646 1.00 27.13 | S |
| ATOM | 3374 | OH2 TIP S | 119 | 52.352 | 11.244 | 69.296 | 1.00 20.68 | S | ATOM | 3454 | OH2 TIP S 199 | 37.342 5.367 40.760 1.00 23.20 | S |
| ATOM | 3375 | OH2 TIP S | 120 | 43.246 | 9.326 | 35.622 | 1.00 22.72 | S | ATOM | 3455 | OH2 TIP S 200 | 38.115 35.117 82.476 1.00 30.60 | S |
| ATOM | 3376 | OH2 TIP S | 121 | 66.109 | 41.798 | 74.353 | 1.00 21.48 | S | ATOM | 3456 | OH2 TIP S 201 | 69.066 35.294 85.022 1.00 25.25 | S |
| ATOM | 3377 | OH2 TIP S | 122 | 72.948 | 25.041 | 68.011 | 1.00 23.23 | S | ATOM | 3457 | OH2 TIP S 202 | 50.428 17.914 54.937 1.00 26.29 | S |
| ATOM | 3378 | OH2 TIP S | 123 | 34.838 | 16.865 | 32.153 | 1.00 23.21 | S | ATOM | 3458 | OH2 TIP S 203 | 38.497 30.310 75.414 1.00 34.85 | S |
| ATOM | 3379 | OH2 TIP S | 124 | 27.987 | 19.338 | 58.317 | 1.00 26.48 | S | ATOM | 3459 | OH2 TIP S 204 | 41.083 15.763 66.110 1.00 32.71 | S |
| ATOM | 3380 | OH2 TIP S | 125 | 54.598 | 30.285 | 64.016 | 1.00 25.23 | S | ATOM | 3460 | OH2 TIP S 205 | 25.612 12.021 54.866 1.00 47.58 | S |
| ATOM | 3381 | OH2 TIP S | 126 | 54.377 | 8.383 | 57.026 | 1.00 24.98 | S | ATOM | 3461 | OH2 TIP S 206 | 38.193 28.589 71.966 1.00 28.01 | S |
| ATOM | 3382 | OH2 TIP S | 127 | 45.496 | 25.201 | 70.335 | 1.00 22.94 | S | ATOM | 3462 | OH2 TIP S 207 | 55.108 15.324 58.968 1.00 25.31 | S |
| ATOM | 3383 | OH2 TIP S | 128 | 54.240 | 32.132 | 57.575 | 1.00 21.92 | S | ATOM | 3463 | OH2 TIP S 208 | 56.489 43.363 85.722 1.00 28.36 | S |
| ATOM | 3384 | OH2 TIP S | 129 | 42.737 | 41.934 | 73.638 | 1.00 22.34 | S | ATOM | 3464 | OH2 TIP S 209 | 35.509 10.259 71.683 1.00 44.48 | S |
| ATOM | 3385 | OH2 TIP S | 130 | 46.172 | 2.270 | 55.341 | 1.00 26.82 | S | ATOM | 3465 | OH2 TIP S 210 | 49.891 16.786 89.249 1.00 28.24 | S |
| ATOM | 3386 | OH2 TIP S | 131 | 24.787 | 30.434 | 62.550 | 1.00 25.57 | S | ATOM | 3466 | OH2 TIP S 211 | 21.767 33.988 50.020 1.00 34.12 | S |
| ATOM | 3387 | OH2 TIP S | 132 | 55.939 | 17.467 | 93.325 | 1.00 27.38 | S | ATOM | 3467 | OH2 TIP S 212 | 41.582 13.007 89.060 1.00 30.23 | S |
| ATOM | 3388 | OH2 TIP S | 133 | 38.256 | 29.706 | 65.077 | 1.00 23.91 | S | ATOM | 3468 | OH2 TIP S 213 | 39.630 22.488 58.155 1.00 25.96 | S |
| ATOM | 3389 | OH2 TIP S | 134 | 46.580 | 2.300 | 52.439 | 1.00 23.36 | S | ATOM | 3469 | OH2 TIP S 214 | 65.048 13.243 77.611 1.00 25.21 | S |
| ATOM | 3390 | OH2 TIP S | 135 | 57.846 | 27.056 | 68.637 | 1.00 19.98 | S | ATOM | 3470 | OH2 TIP S 215 | 61.174 15.411 41.624 1.00 33.91 | S |
| ATOM | 3391 | OH2 TIP S | 136 | 52.325 | 19.351 | 64.445 | 1.00 23.61 | S | ATOM | 3471 | OH2 TIP S 216 | 33.424 11.854 36.228 1.00 27.42 | S |
| ATOM | 3392 | OH2 TIP S | 137 | 47.312 | 18.449 | 56.028 | 1.00 30.77 | S | ATOM | 3472 | OH2 TIP S 217 | 55.456 19.566 59.743 1.00 42.76 | S |
| ATOM | 3393 | OH2 TIP S | 138 | 28.678 | 11.543 | 46.452 | 1.00 26.83 | S | ATOM | 3473 | OH2 TIP S 218 | 41.761 41.280 58.532 1.00 25.39 | S |
| ATOM | 3394 | OH2 TIP S | 139 | 34.016 | 33.178 | 63.312 | 1.00 23.70 | S | ATOM | 3474 | OH2 TIP S 219 | 41.789 37.171 68.457 1.00 29.26 | S |
| ATOM | 3395 | OH2 TIP S | 140 | 40.973 | 5.187 | 58.196 | 1.00 24.80 | S | ATOM | 3475 | OH2 TIP S 220 | 38.494 36.758 58.004 1.00 29.48 | S |
| ATOM | 3396 | OH2 TIP S | 141 | 28.795 | 37.979 | 54.145 | 1.00 26.71 | S | ATOM | 3476 | OH2 TIP S 221 | 31.504 6.484 51.442 1.00 37.36 | S |
| ATOM | 3397 | OH2 TIP S | 142 | 21.621 | 25.493 | 65.475 | 1.00 34.15 | S | ATOM | 3477 | OH2 TIP S 222 | 69.785 10.687 70.591 1.00 28.39 | S |
| ATOM | 3398 | OH2 TIP S | 143 | 49.675 | 6.552 | 39.262 | 1.00 23.78 | S | ATOM | 3478 | OH2 TIP S 223 | 43.153 2.301 37.691 1.00 27.90 | S |
| ATOM | 3399 | OH2 TIP S | 144 | 63.384 | 45.911 | 80.398 | 1.00 21.90 | S | ATOM | 3479 | OH2 TIP S 224 | 46.274 42.990 75.697 1.00 31.30 | S |
| ATOM | 3400 | OH2 TIP S | 145 | 46.738 | 6.436 | 68.155 | 1.00 30.01 | S | ATOM | 3480 | OH2 TIP S 225 | 57.929 25.033 63.522 1.00 31.27 | S |

Fig. 4 cont.

```
ATOM 3481 OH2 TIP S 226   63.471 21.724 66.041 1.00 29.35   S
ATOM 3482 OH2 TIP S 227   39.637 13.342 31.837 1.00 30.84   S
ATOM 3483 OH2 TIP S 228   43.311 13.395 30.331 1.00 25.88   S
ATOM 3484 OH2 TIP S 229   32.022  8.936 36.558 1.00 36.20   S
ATOM 3485 OH2 TIP S 230   25.336 16.942 44.768 1.00 37.05   S
ATOM 3486 OH2 TIP S 231   42.211 22.585 62.705 1.00 43.04   S
ATOM 3487 OH2 TIP S 232   54.443 30.527 92.694 1.00 30.60   S
ATOM 3488 OH2 TIP S 233   57.592 38.228 35.821 1.00 35.40   S
ATOM 3489 OH2 TIP S 234   31.455 38.289 50.682 1.00 42.17   S
ATOM 3490 OH2 TIP S 235   35.293 30.663 82.088 1.00 41.49   S
ATOM 3491 OH2 TIP S 236   64.428 39.413 89.175 1.00 34.03   S
ATOM 3492 OH2 TIP S 237   38.055 19.595 64.950 1.00 34.36   S
ATOM 3493 OH2 TIP S 238   57.874 19.200 47.528 1.00 27.77   S
ATOM 3494 OH2 TIP S 239   41.885 11.985 32.508 1.00 33.91   S
ATOM 3495 OH2 TIP S 240   26.457 11.630 51.587 1.00 40.38   S
ATOM 3496 OH2 TIP S 241   66.697 18.144 87.118 1.00 33.20   S
ATOM 3497 OH2 TIP S 242   42.789 -0.460 50.131 1.00 32.05   S
ATOM 3498 OH2 TIP S 243   63.402 45.506 62.429 1.00 32.20   S
ATOM 3499 OH2 TIP S 244   44.542  2.506 63.013 1.00 35.11   S
ATOM 3500 OH2 TIP S 245   44.125 31.613 89.065 1.00 31.86   S
ATOM 3501 OH2 TIP S 246   69.367 15.327 59.416 1.00 64.98   S
ATOM 3502 OH2 TIP S 247   63.462 44.208 89.120 1.00 41.33   S
ATOM 3503 OH2 TIP S 248   25.759 22.108 60.950 1.00 17.52   S
ATOM 3504 OH2 TIP S 249   34.764 24.938 79.199 1.00 19.96   S
ATOM 3505 OH2 TIP S 250   63.477 26.249 89.548 1.00 20.23   S
ATOM 3506 OH2 TIP S 251   37.451 30.058 77.739 1.00 21.61   S
ATOM 3507 OH2 TIP S 252   51.475 11.957 71.809 1.00 20.81   S
ATOM 3508 OH2 TIP S 253   41.699 36.083 52.858 1.00 19.11   S
ATOM 3509 OH2 TIP S 254   56.559 12.444 85.114 1.00 27.34   S
ATOM 3510 OH2 TIP S 255   53.650 45.787 68.638 1.00 21.57   S
ATOM 3511 OH2 TIP S 256   35.420  7.640 78.842 1.00 19.89   S
ATOM 3512 OH2 TIP S 257   43.864 23.991 63.835 1.00 34.40   S
ATOM 3513 OH2 TIP S 258   36.744  7.269 81.236 1.00 25.11   S
ATOM 3514 OH2 TIP S 259   60.466 29.335 90.169 1.00 21.50   S
ATOM 3515 OH2 TIP S 260   41.937 39.498 65.149 1.00 23.14   S
ATOM 3516 OH2 TIP S 261   38.523 24.903 67.265 1.00 31.11   S
ATOM 3517 OH2 TIP S 262   41.818  8.397 63.955 1.00 24.41   S
ATOM 3518 OH2 TIP S 263   69.366 22.823 82.171 1.00 24.20   S
ATOM 3519 OH2 TIP S 264   44.397  6.319 66.739 1.00 26.57   S
ATOM 3520 OH2 TIP S 265   43.250 42.585 70.951 1.00 25.79   S
ATOM 3521 OH2 TIP S 266   35.993 22.153 32.094 1.00 24.01   S
ATOM 3522 OH2 TIP S 267   47.915 27.925 91.033 1.00 28.85   S
ATOM 3523 OH2 TIP S 268   43.233 39.740 67.490 1.00 24.02   S
ATOM 3524 OH2 TIP S 269   70.476 25.777 84.993 1.00 26.47   S
ATOM 3525 OH2 TIP S 270   45.462 25.769 32.251 1.00 27.98   S
ATOM 3526 OH2 TIP S 271   34.991 21.837 66.097 1.00 24.19   S
ATOM 3527 OH2 TIP S 272   41.389 36.097 47.316 1.00 28.30   S
ATOM 3528 OH2 TIP S 273   31.938  8.197 47.234 1.00 28.78   S
ATOM 3529 OH2 TIP S 274   49.192 40.077 83.135 1.00 29.29   'S
ATOM 3530 OH2 TIP S 275   33.932 18.984 33.634 1.00 26.64   S
ATOM 3531 OH2 TIP S 276   42.871 44.910 74.190 1.00 30.27   S
ATOM 3532 OH2 TIP S 277   40.613  8.049 61.423 1.00 25.94   S
ATOM 3533 OH2 TIP S 278   73.910 30.219 71.875 1.00 30.33   S
ATOM 3534 OH2 TIP S 279   41.166 41.563 61.465 1.00 24.45   S
ATOM 3535 OH2 TIP S 280   61.405 42.215 60.742 1.00 28.52   S
ATOM 3536 OH2 TIP S 281   24.916 20.387 62.759 1.00 27.73   S
ATOM 3537 OH2 TIP S 282   56.342 10.111 56.331 1.00 27.39   S
ATOM 3538 OH2 TIP S 283   55.481 11.897 75.712 1.00 27.38   S
ATOM 3539 OH2 TIP S 284   56.801 37.995 58.425 1.00 27.13   S
ATOM 3540 OH2 TIP S 285   53.338 12.689 79.656 1.00 26.39   S
ATOM 3541 OH2 TIP S 286   60.193 33.616 91.066 1.00 26.52   S
ATOM 3542 OH2 TIP S 287   37.742 22.526 65.293 1.00 28.96   S
ATOM 3543 OH2 TIP S 288   53.481 30.791 37.717 1.00 25.62   S
ATOM 3544 OH2 TIP S 289   63.084 45.643 83.184 1.00 25.46   S
ATOM 3545 OH2 TIP S 290   35.146 35.690 40.505 1.00 32.04   S
ATOM 3546 OH2 TIP S 291   50.811 42.292 80.299 1.00 28.52   S
ATOM 3547 OH2 TIP S 292   48.624 30.682 65.633 1.00 30.86   S
ATOM 3548 OH2 TIP S 293   57.408  5.916 51.383 1.00 30.14   S
ATOM 3549 OH2 TIP S 294   37.381 17.395 68.048 1.00 29.47   S
ATOM 3550 OH2 TIP S 295   35.228  5.930 47.362 1.00 27.26   S
ATOM 3551 OH2 TIP S 296   39.449 28.281 67.319 1.00 30.64   S
ATOM 3552 OH2 TIP S 297   63.894 22.336 91.513 1.00 31.15   S
ATOM 3553 OH2 TIP S 298   64.848 43.669 83.807 1.00 33.42   S
ATOM 3554 OH2 TIP S 299   36.429 25.656 68.929 1.00 29.75   S
ATOM 3555 OH2 TIP S 300   64.894 42.030 63.566 1.00 29.86   S
ATOM 3556 OH2 TIP S 301   23.844 24.103 66.020 1.00 26.68   S
ATOM 3557 OH2 TIP S 302   35.615 37.096 80.125 1.00 32.73   S
ATOM 3558 OH2 TIP S 303   36.217  4.860 53.855 1.00 35.57   S
ATOM 3559 OH2 TIP S 304   54.311 12.766 86.021 1.00 29.48   S
ATOM 3560 OH2 TIP S 305   54.480 12.257 72.952 1.00 32.31   S
ATOM 3561 OH2 TIP S 306   59.843 19.328 67.041 1.00 27.08   S
ATOM 3562 OH2 TIP S 307   42.201 14.966 62.852 1.00 32.27   S
ATOM 3563 OH2 TIP S 308   59.537 47.755 65.768 1.00 35.94   S
ATOM 3564 OH2 TIP S 309   32.254 27.804 66.833 1.00 34.09   S
ATOM 3565 OH2 TIP S 310   72.934 33.185 79.777 1.00 34.12   S
ATOM 3566 OH2 TIP S 311   68.809 17.775 59.314 1.00 32.29   S
ATOM 3567 OH2 TIP S 312   27.898 17.516 36.653 1.00 32.36   S
ATOM 3568 OH2 TIP S 313   44.041 22.927 29.617 1.00 32.37   S
ATOM 3569 OH2 TIP S 314   30.015 35.645 37.692 1.00 28.88   S
ATOM 3570 OH2 TIP S 315   69.446 41.692 72.806 1.00 30.88   S
ATOM 3571 OH2 TIP S 316   32.526 26.324 78.571 1.00 35.39   S
ATOM 3572 OH2 TIP S 317   35.976 30.321 65.993 1.00 34.04   S
ATOM 3573 OH2 TIP S 318   28.928 17.262 59.553 1.00 31.92   S
ATOM 3574 OH2 TIP S 319   56.332  7.098 53.341 1.00 29.21   S
ATOM 3575 OH2 TIP S 320   48.621 17.984 29.729 1.00 29.56   S
ATOM 3576 OH2 TIP S 321   36.415 17.602 63.908 1.00 35.97   S
ATOM 3577 OH2 TIP S 322   41.611 40.931 69.120 1.00 30.94   S
ATOM 3578 OH2 TIP S 323   46.474 36.478 51.530 1.00 35.47   S
ATOM 3579 OH2 TIP S 324   34.651 25.952 30.435 1.00 33.76   S
ATOM 3580 OH2 TIP S 325   57.870 36.540 80.796 1.00 28.15   S
ATOM 3581 OH2 TIP S 326   36.751  6.692 76.561 1.00 31.73   S
ATOM 3582 OH2 TIP S 327   60.847 21.306 65.678 1.00 35.24   S
ATOM 3583 OH2 TIP S 328   55.860 12.794 55.577 1.00 30.43   S
ATOM 3584 OH2 TIP S 329   40.614 40.613 74.511 1.00 30.56   S
ATOM 3585 OH2 TIP S 330   24.684 13.227 45.681 1.00 36.15   S
ATOM 3586 OH2 TIP S 331   75.849 29.971 73.430 1.00 41.35   S
ATOM 3587 OH2 TIP S 332   20.734 19.113 42.507 1.00 39.92   S
ATOM 3588 OH2 TIP S 333   36.888 37.783 77.966 1.00 29.97   S
ATOM 3589 OH2 TIP S 334   26.166 36.528 61.627 1.00 33.27   S
ATOM 3590 OH2 TIP S 335   28.029 27.276 33.161 1.00 33.21   S
ATOM 3591 OH2 TIP S 336   54.396 17.376 66.045 1.00 36.44   S
ATOM 3592 OH2 TIP S 337   19.302 22.431 57.285 1.00 30.54   S
ATOM 3593 OH2 TIP S 338   58.199  9.506 47.009 1.00 34.23   S
ATOM 3594 OH2 TIP S 339   64.822 30.203 91.519 1.00 33.78   S
ATOM 3595 OH2 TIP S 340   65.513 27.784 89.961 1.00 32.73   S
ATOM 3596 OH2 TIP S 341   33.327 24.601 86.711 1.00 34.18   S
ATOM 3597 OH2 TIP S 342   34.355 23.635 68.053 1.00 31.48   S
ATOM 3598 OH2 TIP S 343   36.924 35.406 46.610 1.00 27.46   S
ATOM 3599 OH2 TIP S 344   51.128  1.159 51.719 1.00 29.56   S
ATOM 3600 OH2 TIP S 345   46.864 10.797 74.433 1.00 31.38   S
ATOM 3601 OH2 TIP S 346   33.953  5.291 50.450 1.00 31.37   S
ATOM 3602 OH2 TIP S 347   51.135 28.985 49.434 1.00 35.48   S
ATOM 3603 OH2 TIP S 348   72.122 37.185 75.072 1.00 29.27   S
ATOM 3604 OH2 TIP S 349   64.466  9.912 65.719 1.00 32.66   S
ATOM 3605 OH2 TIP S 350   45.388 17.294 58.562 1.00 30.21   S
ATOM 3606 OH2 TIP S 351   59.145 24.651 94.235 1.00 38.49   S
ATOM 3607 OH2 TIP S 352   49.757 45.186 77.953 1.00 35.04   S
ATOM 3608 OH2 TIP S 353   53.201 46.981 74.813 1.00 30.18   S
ATOM 3609 OH2 TIP S 354   33.461 21.937 70.437 1.00 32.89   S
ATOM 3610 OH2 TIP S 355   41.613  4.954 34.666 1.00 41.39   S
ATOM 3611 OH2 TIP S 356   75.770 14.987 58.529 1.00 39.60   S
ATOM 3612 OH2 TIP S 357   37.056  8.101 86.532 1.00 34.86   S
ATOM 3613 OH2 TIP S 358   24.273 21.434 65.285 1.00 34.70   S
ATOM 3614 OH2 TIP S 359   57.902 11.808 52.105 1.00 29.64   S
ATOM 3615 OH2 TIP S 360   67.954 19.300 79.377 1.00 38.42   S
ATOM 3616 OH2 TIP S 361   31.070 39.660 59.978 1.00 31.88   S
ATOM 3617 OH2 TIP S 362   43.999 34.598 43.617 1.00 27.22   S
ATOM 3618 OH2 TIP S 363   74.780 22.748 68.291 1.00 30.71   S
ATOM 3619 OH2 TIP S 364   32.682 35.497 41.746 1.00 33.82   S
ATOM 3620 OH2 TIP S 365   32.195 25.236 67.363 1.00 31.57   S
ATOM 3621 OH2 TIP S 366   45.229 23.023 58.550 1.00 34.18   S
ATOM 3622 OH2 TIP S 367   34.382 19.437 70.333 1.00 33.75   S
ATOM 3623 OH2 TIP S 368   65.243 29.118 62.795 1.00 26.69   S
ATOM 3624 OH2 TIP S 369   36.532  2.716 50.210 1.00 34.22   S
ATOM 3625 OH2 TIP S 370   46.759 42.659 73.446 1.00 35.34   S
ATOM 3626 OH2 TIP S 371   52.225  0.491 49.463 1.00 32.07   S
ATOM 3627 OH2 TIP S 372   74.503 29.257 68.998 1.00 34.40   S
ATOM 3628 OH2 TIP S 373   21.446 22.979 44.855 1.00 42.87   S
ATOM 3629 OH2 TIP S 374   49.569 15.538 30.770 1.00 37.44   S
ATOM 3630 OH2 TIP S 375   52.593 33.537 38.623 1.00 37.56   S
ATOM 3631 OH2 TIP S 376   46.732  9.057 80.818 1.00 29.27   S
ATOM 3632 OH2 TIP S 377   49.744 32.485 52.585 1.00 32.52   S
ATOM 3633 OH2 TIP S 378   29.338  8.970 47.658 1.00 39.79   S
ATOM 3634 OH2 TIP S 379   59.088 19.103 36.066 1.00 39.08   S
ATOM 3635 OH2 TIP S 380   68.745 33.015 61.743 1.00 38.39   S
ATOM 3636 OH2 TIP S 381   26.063 34.535 64.237 1.00 38.23   S
ATOM 3637 OH2 TIP S 382   42.098  7.424 68.387 1.00 31.10   S
ATOM 3638 OH2 TIP S 383   66.091 36.485 89.059 1.00 35.89   S
ATOM 3639 OH2 TIP S 384   22.443 22.519 47.541 1.00 39.22   S
ATOM 3640 OH2 TIP S 385   54.346 29.183 56.780 1.00 36.52   S
```

Fig. 4 cont.

```
ATOM 3641 OH2 TIP S 386   64.284 22.873 63.678 1.00 36.48   S
ATOM 3642 OH2 TIP S 387   53.589 43.383 55.951 1.00 42.41   S
ATOM 3643 OH2 TIP S 388   61.785 20.617 92.769 1.00 37.50   S
ATOM 3644 OH2 TIP S 389   41.292 20.473 90.202 1.00 34.67   S
ATOM 3645 OH2 TIP S 390   62.989 29.240 60.994 1.00 31.68   S
ATOM 3646 OH2 TIP S 391   35.102 28.365 68.721 1.00 36.84   S
ATOM 3647 OH2 TIP S 392   56.214 13.846 81.526 1.00 30.94   S
ATOM 3648 OH2 TIP S 393   54.908 11.133 68.917 1.00 44.40   S
ATOM 3649 OH2 TIP S 394   59.370 21.852 93.650 1.00 35.08   S
ATOM 3650 OH2 TIP S 395   46.469 46.550 58.080 1.00 32.23   S
ATOM 3651 OH2 TIP S 396   30.449 18.301 50.190 1.00 42.94   S
ATOM 3652 OH2 TIP S 397   55.605  4.498 60.833 1.00 43.43   S
ATOM 3653 OH2 TIP S 398   33.131 14.561 33.518 1.00 37.46   S
ATOM 3654 OH2 TIP S 399   38.044 40.850 56.567 1.00 47.57   S
ATOM 3655 OH2 TIP S 400   52.616 26.739 49.125 1.00 42.49   S
ATOM 3656 OH2 TIP S 401   17.928 31.346 45.037 1.00 40.07   S
ATOM 3657 OH2 TIP S 402   57.560  6.567 46.741 1.00 34.51   S
ATOM 3658 OH2 TIP S 403   73.883 20.750 66.722 1.00 38.48   S
ATOM 3659 OH2 TIP S 404   30.687 26.590 32.768 1.00 34.21   S
ATOM 3660 OH2 TIP S 405   35.487 18.432 29.713 1.00 39.73   S
ATOM 3661 OH2 TIP S 406   24.433 16.782 58.950 1.00 37.23   S
ATOM 3662 OH2 TIP S 407   39.682  7.609 73.029 1.00 34.21   S
ATOM 3663 OH2 TIP S 408   41.824 35.898 84.247 1.00 41.47   S
ATOM 3664 OH2 TIP S 409   66.551 44.088 63.722 1.00 33.53   S
ATOM 3665 OH2 TIP S 410   42.392 35.999 50.190 1.00 32.48   S
ATOM 3666 OH2 TIP S 411   52.489  7.781 75.847 1.00 39.36   S
ATOM 3667 OH2 TIP S 412   66.412 20.468 39.964 1.00 40.98   S
ATOM 3668 OH2 TIP S 413   16.276 24.982 45.239 1.00 51.35   S
ATOM 3669 OH2 TIP S 414   24.914 19.994 43.451 1.00 44.47   S
ATOM 3670 OH2 TIP S 415   30.857 17.610 91.341 1.00 53.65   S
ATOM 3671 OH2 TIP S 416   56.389  3.775 56.737 1.00 46.95   S
ATOM 3672 OH2 TIP S 417   39.680 30.174 30.958 1.00 38.57   S
ATOM 3673 OH2 TIP S 418   43.906  3.496 66.145 1.00 41.62   S
ATOM 3674 OH2 TIP S 419   36.689 34.770 77.131 1.00 38.64   S
ATOM 3675 OH2 TIP S 420   69.208 36.327 81.043 1.00 36.76   S
ATOM 3676 OH2 TIP S 421   15.172 25.725 50.698 1.00 54.64   S
ATOM 3677 OH2 TIP S 422   48.716 41.384 88.983 1.00 36.29   S
ATOM 3678 OH2 TIP S 423   59.539 20.483 38.466 1.00 38.95   S
ATOM 3679 OH2 TIP S 424   55.120 27.635 64.251 1.00 38.22   S
ATOM 3680 OH2 TIP S 425   38.453 11.670 30.319 1.00 33.85   S
ATOM 3681 OH2 TIP S 426   67.360 21.880 78.014 1.00 40.91   S
ATOM 3682 OH2 TIP S 427   37.343 34.040 40.764 1.00 31.65   S
ATOM 3683 OH2 TIP S 428   38.687 29.971 69.426 1.00 35.14   S
ATOM 3684 OH2 TIP S 429   33.596 21.207 30.945 1.00 34.85   S
ATOM 3685 OH2 TIP S 430   56.371 15.394 66.022 1.00 36.62   S
ATOM 3686 OH2 TIP S 431   66.689 24.061 88.794 1.00 35.81   S
ATOM 3687 OH2 TIP S 432   55.498 20.745 29.302 1.00 44.11   S
ATOM 3688 OH2 TIP S 433   21.153 18.281 56.655 1.00 33.44   S
ATOM 3689 OH2 TIP S 434   37.247 20.595 30.163 1.00 29.36   S
ATOM 3690 OH2 TIP S 435   54.782 25.139 94.944 1.00 37.20   S
ATOM 3691 OH2 TIP S 436   73.213 35.646 66.549 1.00 39.42   S
ATOM 3692 OH2 TIP S 437   77.081 28.986 79.075 1.00 34.66   S
ATOM 3693 OH2 TIP S 438   57.589 18.773 64.891 1.00 45.05   S
ATOM 3694 OH2 TIP S 439   57.172 39.948 92.701 1.00 42.42   S
ATOM 3695 OH2 TIP S 440   55.313 36.347 96.390 1.00 50.77   S
ATOM 3696 OH2 TIP S 441   35.813 39.062 53.079 1.00 36.73   S
ATOM 3697 OH2 TIP S 442   26.870 36.202 52.590 1.00 36.59   S
ATOM 3698 OH2 TIP S 443   38.989 10.304 61.955 1.00 31.77   S
ATOM 3699 OH2 TIP S 444   64.748 45.120 86.671 1.00 45.67   S
ATOM 3700 OH2 TIP S 445   57.651  9.521 53.768 1.00 37.45   S
ATOM 3701 OH2 TIP S 446   57.263 20.501 94.798 1.00 39.44   S
ATOM 3702 OH2 TIP S 447   37.392  9.124 31.308 1.00 34.17   S
ATOM 3703 OH2 TIP S 448   65.885 20.286 91.083 1.00 40.59   S
ATOM 3704 OH2 TIP S 449   60.447 26.636 93.785 1.00 38.87   S
ATOM 3705 OH2 TIP S 450   48.356 14.031 32.942 1.00 40.97   S
ATOM 3706 OH2 TIP S 451   42.342 17.568 63.176 1.00 47.87   S
ATOM 3707 OH2 TIP S 452   53.491  4.488 62.546 1.00 39.40   S
ATOM 3708 OH2 TIP S 453   52.588 34.392 34.601 1.00 40.67   S
ATOM 3709 OH2 TIP S 454   25.961 15.906 54.784 1.00 41.49   S
ATOM 3710 OH2 TIP S 455   72.635 40.142 84.584 1.00 33.81   S
ATOM 3711 OH2 TIP S 456   34.738 19.235 67.199 1.00 38.43   S
ATOM 3712 OH2 TIP S 457   31.559 39.638 46.925 1.00 41.24   S
ATOM 3713 OH2 TIP S 458   57.016  3.147 36.937 1.00 59.51   S
ATOM 3714 OH2 TIP S 459   65.226 19.854 59.708 1.00 49.91   S
ATOM 3715 OH2 TIP S 460   61.374 36.435 59.895 1.00 34.49   S
ATOM 3716 OH2 TIP S 461   65.327 20.442 43.375 1.00 39.80   S
ATOM 3717 OH2 TIP S 462   40.433 10.826 64.485 1.00 39.29   S
ATOM 3718 OH2 TIP S 463   22.398 28.436 43.591 1.00 50.52   S
ATOM 3719 OH2 TIP S 464   13.366 27.349 47.291 1.00 41.77   S
ATOM 3720 OH2 TIP S 465   70.276 44.556 64.910 1.00 41.15   S
ATOM 3721 OH2 TIP S 466   58.179 14.018 56.224 1.00 38.67   S
ATOM 3722 OH2 TIP S 467   53.389 33.038 93.822 1.00 41.10   S
ATOM 3723 OH2 TIP S 468   54.898  9.338 76.213 1.00 29.99   S
ATOM 3724 OH2 TIP S 469   20.697 17.249 40.311 1.00 50.24   S
ATOM 3725 OH2 TIP S 470   47.046 39.749 54.170 1.00 44.93   S
ATOM 3726 OH2 TIP S 471   40.073 34.851 73.009 1.00 31.50   S
ATOM 3727 OH2 TIP S 472   71.848 38.579 64.730 1.00 43.17   S
ATOM 3728 OH2 TIP S 473   36.278 33.468 81.026 1.00 39.34   S
ATOM 3729 OH2 TIP S 474   51.774 43.025 83.000 1.00 39.99   S
ATOM 3730 OH2 TIP S 475   74.399 34.557 76.642 1.00 44.44   S
ATOM 3731 OH2 TIP S 476   53.373 13.171 88.886 1.00 41.97   S
ATOM 3732 OH2 TIP S 477   52.356 35.948 93.930 1.00 38.12   S
ATOM 3733 OH2 TIP S 478   69.502 20.557 83.525 1.00 41.85   S
ATOM 3734 OH2 TIP S 479   62.750 26.702 92.252 1.00 36.69   S
ATOM 3735 OH2 TIP S 480   48.292 -0.047 51.507 1.00 39.07   S
ATOM 3736 OH2 TIP S 481   45.237 23.809 89.900 1.00 39.94   S
ATOM 3737 OH2 TIP S 482   66.822 39.417 85.349 1.00 50.58   S
ATOM 3738 OH2 TIP S 483   47.819 23.196 102.092 1.00 48.36   S
ATOM 3739 OH2 TIP S 484   48.963 42.903 86.293 1.00 39.32   S
ATOM 3740 OH2 TIP S 485   38.456  6.593 61.679 1.00 37.96   S
ATOM 3741 OH2 TIP S 486   72.988 18.595 73.751 1.00 41.37   S
ATOM 3742 OH2 TIP S 487   57.095 16.359 55.397 1.00 40.22   S
ATOM 3743 OH2 TIP S 488   59.459 38.482 59.409 1.00 39.22   S
ATOM 3744 OH2 TIP S 489   40.600 37.040 65.862 1.00 42.68   S
ATOM 3745 OH2 TIP S 490   31.501 17.967 63.334 1.00 50.72   S
ATOM 3746 OH2 TIP S 491   64.110 24.056 93.483 1.00 48.42   S
ATOM 3747 OH2 TIP S 492   28.715 30.709 66.530 1.00 44.58   S
ATOM 3748 OH2 TIP S 493   46.943  9.506 72.007 1.00 44.69   S
ATOM 3749 OH2 TIP S 494   42.541  1.706 58.651 1.00 48.86   S
ATOM 3750 OH2 TIP S 495   20.075 25.389 44.275 1.00 46.48   S
ATOM 3751 OH2 TIP S 496   40.050 38.123 53.764 1.00 32.45   S
ATOM 3752 OH2 TIP S 497   39.566 23.871 29.363 1.00 47.39   S
ATOM 3753 OH2 TIP S 498   31.353 19.100 34.380 1.00 31.68   S
ATOM 3754 OH2 TIP S 499   75.600 33.976 67.752 1.00 44.08   S
ATOM 3755 OH2 TIP S 500   28.987 22.935 78.776 1.00 38.23   S
ATOM 3756 OH2 TIP S 501   72.803 29.803 87.864 1.00 38.56   S
ATOM 3757 OH2 TIP S 502   73.999 28.795 85.494 1.00 41.17   S
ATOM 3758 OH2 TIP S 503   60.853 35.044 40.979 1.00 40.95   S
ATOM 3759 OH2 TIP S 504   24.612  7.720 45.128 1.00 51.97   S
ATOM 3760 OH2 TIP S 505   57.347 35.335 59.278 1.00 33.17   S
ATOM 3761 OH2 TIP S 506   45.879 38.954 85.022 1.00 39.11   S
ATOM 3762 OH2 TIP S 507   57.168 14.118 59.524 1.00 41.53   S
ATOM 3763 OH2 TIP S 508   45.515 20.213 26.327 1.00 43.82   S
ATOM 3764 OH2 TIP S 509   63.288  9.350 46.424 1.00 46.19   S
ATOM 3765 OH2 TIP S 510   63.380 18.419 92.439 1.00 38.49   S
ATOM 3766 OH2 TIP S 511   44.182 45.271 63.507 1.00 39.21   S
ATOM 3767 OH2 TIP S 512   48.633 -1.765 60.036 1.00 44.52   S
ATOM 3768 OH2 TIP S 513   29.366 22.783 70.316 1.00 45.95   S
ATOM 3769 OH2 TIP S 514   58.679 24.538 49.146 1.00 59.79   S
ATOM 3770 OH2 TIP S 515   38.843 20.995 86.607 1.00 82.81   S
ATOM 3771 OH2 TIP S 516   22.065 15.119 43.478 1.00 55.53   S
ATOM 3772 OH2 TIP S 517   54.591 34.103 55.527 1.00 44.64   S
ATOM 3773 OH2 TIP S 518   44.693 36.683 89.845 1.00 47.16   S
ATOM 3774 OH2 TIP S 519   39.632 34.224 70.191 1.00 43.05   S
ATOM 3775 OH2 TIP S 520   25.464 11.572 37.853 1.00 43.86   S
ATOM 3776 OH2 TIP S 521   67.410 14.064 58.600 1.00 45.41   S
ATOM 3777 OH2 TIP S 522   75.372 30.934 83.554 1.00 48.40   S
ATOM 3778 OH2 TIP S 523   35.238 38.447 50.240 1.00 52.82   S
ATOM 3779 OH2 TIP S 524   63.503 40.603 59.680 1.00 41.95   S
ATOM 3780 OH2 TIP S 525   39.547 11.639 41.593 1.00 32.66   S
ATOM 3781 OH2 TIP S 526   32.974 12.194 77.562 1.00 40.24   S
ATOM 3782 OH2 TIP S 527   50.605 27.027 58.713 1.00 47.39   S
ATOM 3783 OH2 TIP S 528   55.487 22.779 63.696 1.00 44.29   S
ATOM 3784 OH2 TIP S 529   56.770 43.848 58.171 1.00 35.25   S
ATOM 3785 OH2 TIP S 530   41.977 -1.923 60.232 1.00 51.63   S
ATOM 3786 OH2 TIP S 531   21.082 21.516 38.274 1.00 50.24   S
ATOM 3787 OH2 TIP S 532   39.836 32.105 64.435 1.00 38.69   S
ATOM 3788 OH2 TIP S 533   53.483 19.268 94.809 1.00 39.48   S
ATOM 3789 OH2 TIP S 534   69.691 17.051 86.174 1.00 36.64   S
ATOM 3790 OH2 TIP S 535   69.045 13.182 74.150 1.00 43.58   S
ATOM 3791 OH2 TIP S 536   72.914 33.764 86.534 1.00 40.82   S
ATOM 3792 OH2 TIP S 537   58.989 23.917 39.002 1.00 47.55   S
ATOM 3793 OH2 TIP S 538   60.563 37.888 92.479 1.00 37.76   S
ATOM 3794 OH2 TIP S 539   37.354 17.216 27.164 1.00 47.96   S
ATOM 3795 OH2 TIP S 540   46.307 17.979 92.407 1.00 67.78   S
ATOM 3796 OH2 TIP S 541   32.866 16.632 79.012 1.00 38.96   S
ATOM 3797 OH2 TIP S 542   47.072 33.600 88.529 1.00 42.24   S
ATOM 3798 OH2 TIP S 543   47.078 21.203 57.037 1.00 43.62   S
ATOM 3799 OH2 TIP S 544   34.568 28.890 85.813 1.00 40.09   S
ATOM 3800 OH2 TIP S 545   37.985  5.411 59.374 1.00 38.55   S
```

Fig. 4 cont.

```
ATOM 3801 OH2 TIP S 546    31.621 16.899 60.366 1.00 39.55    S
ATOM 3802 OH2 TIP S 547    65.678 40.529 61.691 1.00 46.31    S
ATOM 3803 OH2 TIP S 548    23.183 19.969 39.479 1.00 46.29    S
ATOM 3804 OH2 TIP S 549    26.511 41.018 59.895 1.00 48.44    S
ATOM 3805 OH2 TIP S 550    47.461 28.710 35.463 1.00 43.94    S
ATOM 3806 N   NO3 I  1    48.240 22.288 46.313 1.00 32.22    I
ATOM 3807 O1  NO3 I  1    48.447 22.861 47.578 1.00 38.76    I
ATOM 3808 O2  NO3 I  1    48.757 22.586 45.006 1.00 23.04    I
ATOM 3809 O3  NO3 I  1    47.254 21.090 46.322 1.00 25.07    I
ATOM 3810 N   NO3 I  2    55.297 21.718 44.821 1.00 27.95    I
ATOM 3811 O1  NO3 I  2    55.312 23.086 45.267 1.00 38.29    I
ATOM 3812 O2  NO3 I  2    56.354 20.735 44.574 1.00 40.07    I
ATOM 3813 O3  NO3 I  2    53.870 21.094 44.630 1.00 25.93    I
ATOM 3814 N   NO3 I  3    65.841 26.978 66.669 1.00 23.84    I
ATOM 3815 O1  NO3 I  3    65.051 27.415 67.755 1.00 23.18    I
ATOM 3816 O2  NO3 I  3    66.747 27.604 65.803 1.00 30.25    I
ATOM 3817 O3  NO3 I  3    65.712 25.503 66.286 1.00 29.12    I
ATOM 3818 N   NO3 I  4    60.269 26.244 71.280 1.00 23.03    I
ATOM 3819 O1  NO3 I  4    59.531 27.321 71.838 1.00 21.31    I
ATOM 3820 O2  NO3 I  4    61.542 25.674 71.540 1.00 19.03    I
ATOM 3821 O3  NO3 I  4    59.557 25.514 70.140 1.00 28.00    I
END
```

Fig. 4 cont.

PDB AT279
```
HEADER    ----             XX-XXX-9-  xxxx
COMPND    ---
REMARK   3
REMARK   3 REFINEMENT.
REMARK   3   PROGRAM     : REFMAC 5.2.0019
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) : 1.90
REMARK   3   RESOLUTION RANGE LOW  (ANGSTROMS) : 43.85
REMARK   3   DATA CUTOFF         (SIGMA(F)) : NONE
REMARK   3   COMPLETENESS FOR RANGE     (%) : 100.00
REMARK   3   NUMBER OF REFLECTIONS          : 34285
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE    (WORKING + TEST SET) : 0.20983
REMARK   3   R VALUE            (WORKING SET) : 0.20698
REMARK   3   FREE R VALUE                     : 0.26211
REMARK   3   FREE R VALUE TEST SET SIZE   (%) : 5.0
REMARK   3   FREE R VALUE TEST SET COUNT      : 1799
REMARK   3
REMARK   3  FIT IN THE HIGHEST RESOLUTION BIN.
REMARK   3   TOTAL NUMBER OF BINS USED        :  20
REMARK   3   BIN RESOLUTION RANGE HIGH        :  1.900
REMARK   3   BIN RESOLUTION RANGE LOW         :  1.949
REMARK   3   REFLECTION IN BIN   (WORKING SET) :  2499
REMARK   3   BIN COMPLETENESS (WORKING+TEST) (%) : 100.00
REMARK   3   BIN R VALUE          (WORKING SET) : 0.208
REMARK   3   BIN FREE R VALUE SET COUNT         :  111
REMARK   3   BIN FREE R VALUE                   :  0.244
REMARK   3
REMARK   3  NUMBER OF NON-HYDROGEN ATOMS USED IN
REFINEMENT.
REMARK   3   ALL ATOMS         :  3528
REMARK   3
REMARK   3  B VALUES.
REMARK   3   FROM WILSON PLOT      (A**2) : NULL
REMARK   3   MEAN B VALUE     (OVERALL, A**2) : 21.792
REMARK   3   OVERALL ANISOTROPIC B VALUE.
REMARK   3    B11 (A**2) :  -0.13
REMARK   3    B22 (A**2) :  -0.22
REMARK   3    B33 (A**2) :   0.35
REMARK   3    B12 (A**2) :   0.00
REMARK   3    B13 (A**2) :   0.00
REMARK   3    B23 (A**2) :   0.00
REMARK   3
REMARK   3  ESTIMATED OVERALL COORDINATE ERROR.
REMARK   3   ESU BASED ON R VALUE        (A):  0.167
REMARK   3   ESU BASED ON FREE R VALUE   (A):  0.163
REMARK   3   ESU BASED ON MAXIMUM LIKELIHOOD   (A):  0.108
REMARK   3   ESU FOR B VALUES BASED ON MAXIMUM LIKELIHOOD
(A**2): 3.531
REMARK   3
REMARK   3 CORRELATION COEFFICIENTS.
REMARK   3   CORRELATION COEFFICIENT FO-FC       : 0.937
REMARK   3   CORRELATION COEFFICIENT FO-FC FREE : 0.899
REMARK   3
REMARK   3  RMS DEVIATIONS FROM IDEAL VALUES         COUNT    RMS
WEIGHT
REMARK   3   BOND LENGTHS REFINED ATOMS       (A):  3232 ; 0.017 ; 0.022
REMARK   3   BOND ANGLES REFINED ATOMS   (DEGREES):  4328 ; 1.678 ;
1.990
REMARK   3   TORSION ANGLES, PERIOD 1  (DEGREES):  400 ; 5.928 ; 5.000
REMARK   3   TORSION ANGLES, PERIOD 2  (DEGREES):  146 ; 40.076
; 24.247
REMARK   3   TORSION ANGLES, PERIOD 3  (DEGREES):  588 ; 16.355
; 15.000
REMARK   3   TORSION ANGLES, PERIOD 4  (DEGREES):  22 ; 17.220
; 15.000
REMARK   3   CHIRAL-CENTER RESTRAINTS    (A**3):  478 ; 0.136 ; 0.200
REMARK   3   GENERAL PLANES REFINED ATOMS    (A):  2388 ; 0.007 ;
0.020
REMARK   3   NON-BONDED CONTACTS REFINED ATOMS (A):  1501 ; 0.238
; 0.200
REMARK   3   NON-BONDED TORSION REFINED ATOMS (A):  2208 ; 0.310 ;
0.200
REMARK   3   H-BOND (X...Y) REFINED ATOMS     (A):  311 ; 0.349 ; 0.200
REMARK   3   SYMMETRY VDW REFINED ATOMS      (A):  45 ; 0.149 ;
0.200
REMARK   3   SYMMETRY H-BOND REFINED ATOMS   (A):  25 ; 0.267 ;
0.200
REMARK   3
REMARK   3  ISOTROPIC THERMAL FACTOR RESTRAINTS.    COUNT
RMS   WEIGHT
REMARK   3   MAIN-CHAIN BOND REFINED ATOMS (A**2):  2044 ; 1.182 ;
1.500
REMARK   3   MAIN-CHAIN ANGLE REFINED ATOMS (A**2):  3188 ; 1.967 ;
2.000
REMARK   3   SIDE-CHAIN BOND REFINED ATOMS (A**2):  1308 ; 3.112 ;
3.000
REMARK   3   SIDE-CHAIN ANGLE REFINED ATOMS (A**2):  1140 ; 4.815 ;
4.500
REMARK   3
REMARK   3  NCS RESTRAINTS STATISTICS
REMARK   3   NUMBER OF NCS GROUPS : NULL
REMARK   3
REMARK   3
REMARK   3  TLS DETAILS
REMARK   3   NUMBER OF TLS GROUPS : NULL
REMARK   3
REMARK   3
REMARK   3  BULK SOLVENT MODELLING.
REMARK   3   METHOD USED : MASK
REMARK   3   PARAMETERS FOR MASK CALCULATION
REMARK   3   VDW PROBE RADIUS  :  1.40
REMARK   3   ION PROBE RADIUS  :  0.80
REMARK   3   SHRINKAGE RADIUS  :  0.80
REMARK   3
REMARK   3  OTHER REFINEMENT REMARKS:
REMARK   3  HYDROGENS HAVE BEEN ADDED IN THE RIDING POSITIONS
REMARK   3
CRYST1   56.489  56.901  139.608  90.00  90.00  90.00 P 21 21 21
SCALE1    0.017703  0.000000  0.000000     0.00000
SCALE2    0.000000  0.017574  0.000000     0.00000
SCALE3    0.000000  0.000000  0.007163     0.00000
ATOM   1  N   SER A   4    -22.480  -6.638  10.683  1.00 28.06     N
ATOM   2  CA  SER A   4    -21.118  -6.315  10.181  1.00 27.54     C
ATOM   3  CB  SER A   4    -20.222  -5.770  11.292  1.00 28.14     C
ATOM   4  OG  SER A   4    -20.615  -4.463  11.634  1.00 31.85     O
ATOM   5  C   SER A   4    -20.471  -7.562   9.698  1.00 27.11     C
ATOM   6  O   SER A   4    -20.692  -8.642  10.254  1.00 26.56     O
ATOM   7  N   VAL A   5    -19.627  -7.394   8.685  1.00 25.00     N
ATOM   8  CA  VAL A   5    -18.948  -8.475   8.055  1.00 25.15     C
ATOM   9  CB  VAL A   5    -19.271  -8.516   6.548  1.00 24.83     C
ATOM  10  CG1 VAL A   5    -18.428  -9.525   5.858  1.00 25.38     C
ATOM  11  CG2 VAL A   5    -20.754  -8.842   6.345  1.00 25.87     C
ATOM  12  C   VAL A   5    -17.458  -8.239   8.259  1.00 25.61     C
ATOM  13  O   VAL A   5    -16.952  -7.163   7.972  1.00 23.90     O
ATOM  14  N   VAL A   6    -16.770  -9.258   8.751  1.00 25.94     N
ATOM  15  CA  VAL A   6    -15.334  -9.164   9.001  1.00 26.58     C
ATOM  16  CB  VAL A   6    -14.943  -9.955  10.281  1.00 27.01     C
ATOM  17  CG1 VAL A   6    -13.441  -9.935  10.515  1.00 26.46     C
ATOM  18  CG2 VAL A   6    -15.672  -9.418  11.488  1.00 27.15     C
ATOM  19  C   VAL A   6    -14.594  -9.723   7.806  1.00 26.66     C
ATOM  20  O   VAL A   6    -14.975 -10.757   7.237  1.00 28.35     O
ATOM  21  N   GLU A   7    -13.532  -9.060   7.385  1.00 24.77     N
ATOM  22  CA  GLU A   7    -12.657  -9.712   6.443  1.00 24.39     C
ATOM  23  CB  GLU A   7    -11.896  -8.669   5.637  1.00 23.47     C
ATOM  24  CG  GLU A   7    -11.206  -9.189   4.442  1.00 24.17     C
ATOM  25  CD  GLU A   7     -9.998 -10.022   4.771  1.00 27.44     C
ATOM  26  OE1 GLU A   7     -9.940 -11.167   4.290  1.00 25.91     O
ATOM  27  OE2 GLU A   7     -9.101  -9.524   5.505  1.00 23.18     O
ATOM  28  C   GLU A   7    -11.732 -10.545   7.346  1.00 24.68     C
ATOM  29  O   GLU A   7    -11.050  -9.973   8.176  1.00 24.24     O
ATOM  30  N   PRO A   8    -11.751 -11.894   7.231  1.00 24.70     N
ATOM  31  CA  PRO A   8    -11.036 -12.640   8.284  1.00 23.84     C
ATOM  32  CB  PRO A   8    -11.492 -14.098   8.061  1.00 25.26     C
ATOM  33  CG  PRO A   8    -11.788 -14.158   6.609  1.00 24.69     C
ATOM  34  CD  PRO A   8    -12.401 -12.799   6.264  1.00 25.20     C
ATOM  35  C   PRO A   8     -9.511 -12.524   8.271  1.00 22.53     C
ATOM  36  O   PRO A   8     -8.930 -12.473   9.350  1.00 22.80     O
ATOM  37  N   LYS A   9     -8.884 -12.460   7.093  1.00 21.56     N
ATOM  38  CA  LYS A   9     -7.418 -12.355   6.997  1.00 20.07     C
ATOM  39  CB  LYS A   9     -6.881 -12.287   5.577  1.00 20.15     C
ATOM  40  CG  LYS A   9     -5.338 -12.371   5.534  1.00 21.63     C
ATOM  41  CD  LYS A   9     -4.768 -12.445   4.175  1.00 25.33     C
ATOM  42  CE  LYS A   9     -3.284 -12.731   4.267  1.00 26.93     C
ATOM  43  NZ  LYS A   9     -2.647 -12.548   2.931  1.00 28.90     N
ATOM  44  C   LYS A   9     -6.878 -11.157   7.736  1.00 19.90     C
ATOM  45  O   LYS A   9     -5.857 -11.278   8.405  1.00 17.15     O
ATOM  46  N   THR A  10     -7.555 -10.014   7.584  1.00 18.25     N
ATOM  47  CA  THR A  10     -7.157  -8.758   8.249  1.00 18.57     C
```

Fig. 5

| | | | | | | | | | | | | | | |
|---|---|---|---|---|---|---|---|---|---|---|---|---|---|---|
| ATOM | 48 | CB | THR A 10 | -7.360 | -7.528 | 7.320 | 1.00 | 18.01 | C | ATOM | 133 | CD ARG A 22 | -25.125 3.529 -0.966 1.00 28.60 | C |
| ATOM | 49 | OG1 | THR A 10 | -8.749 | -7.359 | 7.076 | 1.00 | 20.31 | O | ATOM | 134 | NE ARG A 22 | -24.048 4.152 -1.662 1.00 31.72 | N |
| ATOM | 50 | CG2 | THR A 10 | -6.690 | -7.735 | 5.998 | 1.00 | 19.32 | C | ATOM | 135 | CZ ARG A 22 | -24.116 5.307 -2.257 1.00 30.42 | C |
| ATOM | 51 | C | THR A 10 | -7.872 | -8.488 | 9.583 | 1.00 | 17.91 | C | ATOM | 136 | NH1 ARG A 22 | -25.266 6.014 -2.258 1.00 27.59 | N |
| ATOM | 52 | O | THR A 10 | -7.319 | -7.831 | 10.444 | 1.00 | 17.38 | O | ATOM | 137 | NH2 ARG A 22 | -23.022 5.726 -2.858 1.00 30.63 | N |
| ATOM | 53 | N | GLY A 11 | -9.074 | -9.019 | 9.775 | 1.00 | 16.38 | N | ATOM | 138 | C ARG A 22 | -26.134 -0.562 0.878 1.00 19.79 | C |
| ATOM | 54 | CA | GLY A 11 | -9.884 | -8.686 | 10.937 | 1.00 | 18.05 | C | ATOM | 139 | O ARG A 22 | -25.634 -0.524 2.000 1.00 19.87 | O |
| ATOM | 55 | C | GLY A 11 | -10.708 | -7.421 | 10.785 | 1.00 | 18.80 | C | ATOM | 140 | N ARG A 23 | -26.256 -1.686 0.176 1.00 17.61 | N |
| ATOM | 56 | O | GLY A 11 | -11.471 | -7.042 | 11.701 | 1.00 | 19.98 | O | ATOM | 141 | CA ARG A 23 | -25.943 -2.997 0.769 1.00 17.33 | C |
| ATOM | 57 | N | PHE A 12 | -10.582 | -6.738 | 9.643 | 1.00 | 18.73 | N | ATOM | 142 | CB ARG A 23 | -26.929 -4.056 0.257 1.00 18.31 | C |
| ATOM | 58 | CA | PHE A 12 | -11.231 | -5.424 | 9.496 | 1.00 | 19.56 | C | ATOM | 143 | CG ARG A 23 | -28.378 -3.790 0.680 1.00 24.84 | C |
| ATOM | 59 | CB | PHE A 12 | -10.604 | -4.665 | 8.327 | 1.00 | 20.11 | C | ATOM | 144 | CD ARG A 23 | -28.592 -4.094 2.168 1.00 34.04 | C |
| ATOM | 60 | CG | PHE A 12 | -9.252 | -4.079 | 8.646 | 1.00 | 20.85 | C | ATOM | 145 | NE ARG A 23 | -30.005 -4.011 2.526 1.00 41.97 | N |
| ATOM | 61 | CD1 | PHE A 12 | -8.884 | -2.865 | 8.153 | 1.00 | 25.50 | C | ATOM | 146 | CZ ARG A 23 | -30.619 -2.889 2.882 1.00 45.00 | C |
| ATOM | 62 | CE1 | PHE A 12 | -7.632 | -2.318 | 8.452 | 1.00 | 25.16 | C | ATOM | 147 | NH1 ARG A 23 | -29.937 -1.755 2.935 1.00 46.50 | N |
| ATOM | 63 | CZ | PHE A 12 | -6.749 | -3.002 | 9.221 | 1.00 | 20.00 | C | ATOM | 148 | NH2 ARG A 23 | -31.916 -2.906 3.190 1.00 47.13 | N |
| ATOM | 64 | CE2 | PHE A 12 | -7.084 | -4.208 | 9.731 | 1.00 | 22.31 | C | ATOM | 149 | C ARG A 23 | -24.519 -3.469 0.456 1.00 16.11 | C |
| ATOM | 65 | CD2 | PHE A 12 | -8.329 | -4.766 | 9.440 | 1.00 | 24.60 | C | ATOM | 150 | O ARG A 23 | -24.122 -3.470 -0.701 1.00 15.07 | O |
| ATOM | 66 | C | PHE A 12 | -12.714 | -5.623 | 9.240 | 1.00 | 20.49 | C | ATOM | 151 | N LEU A 24 | -23.783 -3.931 1.467 1.00 14.10 | N |
| ATOM | 67 | O | PHE A 12 | -13.094 | -6.555 | 8.531 | 1.00 | 19.83 | O | ATOM | 152 | CA LEU A 24 | -22.482 -4.592 1.207 1.00 12.74 | C |
| ATOM | 68 | N | SER A 13 | -13.543 | -4.771 | 9.834 | 1.00 | 20.32 | N | ATOM | 153 | CB LEU A 24 | -21.796 -4.948 2.516 1.00 12.90 | C |
| ATOM | 69 | CA | SER A 13 | -14.982 | -4.982 | 9.788 | 1.00 | 20.43 | C | ATOM | 154 | CG LEU A 24 | -20.413 -5.571 2.437 1.00 13.58 | C |
| ATOM | 70 | CB | SER A 13 | -15.547 | -5.046 | 11.211 | 1.00 | 21.25 | C | ATOM | 155 | CD1 LEU A 24 | -19.460 -4.572 1.739 1.00 13.14 | C |
| ATOM | 71 | OG | SER A 13 | -16.781 | -4.388 | 11.332 | 1.00 | 26.70 | O | ATOM | 156 | CD2 LEU A 24 | -19.988 -5.848 3.892 1.00 11.99 | C |
| ATOM | 72 | C | SER A 13 | -15.668 | -3.937 | 8.907 | 1.00 | 18.24 | C | ATOM | 157 | C LEU A 24 | -22.696 -5.899 0.465 1.00 12.76 | C |
| ATOM | 73 | O | SER A 13 | -15.235 | -2.769 | 8.836 | 1.00 | 17.32 | O | ATOM | 158 | O LEU A 24 | -23.399 -6.830 0.984 1.00 11.75 | O |
| ATOM | 74 | N | PHE A 14 | -16.694 | -4.394 | 8.196 | 1.00 | 16.46 | N | ATOM | 159 | N LEU A 25 | -22.057 -6.010 -0.698 1.00 11.03 | N |
| ATOM | 75 | CA | PHE A 14 | -17.483 | -3.541 | 7.278 | 1.00 | 15.90 | C | ATOM | 160 | CA LEU A 25 | -22.216 -7.206 -1.528 1.00 11.74 | C |
| ATOM | 76 | CB | PHE A 14 | -17.319 | -3.955 | 5.805 | 1.00 | 15.56 | C | ATOM | 161 | CB LEU A 25 | -22.695 -6.770 -2.913 1.00 10.67 | C |
| ATOM | 77 | CG | PHE A 14 | -15.942 | -3.743 | 5.262 | 1.00 | 15.36 | C | ATOM | 162 | CG LEU A 25 | -24.163 -6.690 -3.311 1.00 17.77 | C |
| ATOM | 78 | CD1 | PHE A 14 | -15.625 | -2.584 | 4.546 | 1.00 | 15.49 | C | ATOM | 163 | CD1 LEU A 25 | -25.241 -6.655 -2.205 1.00 16.31 | C |
| ATOM | 79 | CE1 | PHE A 14 | -14.321 | -2.383 | 4.065 | 1.00 | 11.90 | C | ATOM | 164 | CD2 LEU A 25 | -24.384 -5.676 -4.425 1.00 14.51 | C |
| ATOM | 80 | CZ | PHE A 14 | -13.327 | -3.335 | 4.317 | 1.00 | 13.71 | C | ATOM | 165 | C LEU A 25 | -20.974 -8.053 -1.653 1.00 10.10 | C |
| ATOM | 81 | CE2 | PHE A 14 | -13.627 | -4.477 | 5.032 | 1.00 | 12.36 | C | ATOM | 166 | O LEU A 25 | -21.034 -9.252 -1.961 1.00 11.18 | O |
| ATOM | 82 | CD2 | PHE A 14 | -14.912 | -4.689 | 5.511 | 1.00 | 13.82 | C | ATOM | 167 | N GLY A 26 | -19.821 -7.459 -1.402 1.00 10.90 | N |
| ATOM | 83 | C | PHE A 14 | -18.968 | -3.658 | 7.649 | 1.00 | 15.41 | C | ATOM | 168 | CA GLY A 26 | -18.558 -8.218 -1.543 1.00 11.41 | C |
| ATOM | 84 | O | PHE A 14 | -19.474 | -4.761 | 7.812 | 1.00 | 18.73 | O | ATOM | 169 | C GLY A 26 | -17.466 -7.548 -0.731 1.00 12.04 | C |
| ATOM | 85 | N | PRO A 15 | -19.676 | -2.523 | 7.743 | 1.00 | 15.80 | N | ATOM | 170 | O GLY A 26 | -17.425 -6.308 -0.629 1.00 10.47 | O |
| ATOM | 86 | CA | PRO A 15 | -21.092 | -2.648 | 8.066 | 1.00 | 16.78 | C | ATOM | 171 | N VAL A 27 | -16.600 -8.375 -0.146 1.00 12.03 | N |
| ATOM | 87 | CB | PRO A 15 | -21.548 | -1.192 | 8.242 | 1.00 | 17.34 | C | ATOM | 172 | CA VAL A 27 | -15.433 -7.854 0.584 1.00 11.66 | C |
| ATOM | 88 | CG | PRO A 15 | -20.554 | -0.353 | 7.479 | 1.00 | 18.21 | C | ATOM | 173 | CB VAL A 27 | -15.604 -8.106 2.093 1.00 13.38 | C |
| ATOM | 89 | CD | PRO A 15 | -19.239 | -1.121 | 7.569 | 1.00 | 16.32 | C | ATOM | 174 | CG1 VAL A 27 | -14.279 -7.768 2.872 1.00 13.55 | C |
| ATOM | 90 | C | PRO A 15 | -21.853 | -3.302 | 6.923 | 1.00 | 17.40 | C | ATOM | 175 | CG2 VAL A 27 | -16.734 -7.282 2.637 1.00 9.86 | C |
| ATOM | 91 | O | PRO A 15 | -21.461 | -3.144 | 5.755 | 1.00 | 16.66 | O | ATOM | 176 | C VAL A 27 | -14.186 -8.559 0.083 1.00 12.83 | C |
| ATOM | 92 | N | ALA A 16 | -22.918 | -4.023 | 7.252 | 1.00 | 16.66 | N | ATOM | 177 | O VAL A 27 | -14.203 -9.782 -0.112 1.00 11.15 | O |
| ATOM | 93 | CA | ALA A 16 | -23.705 | -4.766 | 6.259 | 1.00 | 18.21 | C | ATOM | 178 | N GLY A 28 | -13.103 -7.805 -0.103 1.00 12.96 | N |
| ATOM | 94 | CB | ALA A 16 | -24.704 | -5.667 | 6.963 | 1.00 | 19.11 | C | ATOM | 179 | CA GLY A 28 | -11.866 -8.372 -0.612 1.00 13.73 | C |
| ATOM | 95 | C | ALA A 16 | -24.432 | -3.810 | 5.318 | 1.00 | 18.90 | C | ATOM | 180 | C GLY A 28 | -10.618 -7.657 -0.124 1.00 14.06 | C |
| ATOM | 96 | O | ALA A 16 | -24.854 | -4.180 | 4.199 | 1.00 | 17.76 | O | ATOM | 181 | O GLY A 28 | -10.708 -6.761 0.736 1.00 13.81 | O |
| ATOM | 97 | N | SER A 17 | -24.556 | -2.562 | 5.769 | 1.00 | 19.77 | N | ATOM | 182 | N LEU A 29 | -9.461 -8.048 -0.682 1.00 13.48 | N |
| ATOM | 98 | CA | SER A 17 | -25.299 | -1.565 | 5.021 | 1.00 | 22.45 | C | ATOM | 183 | CA LEU A 29 | -8.168 -7.497 -0.288 1.00 14.33 | C |
| ATOM | 99 | CB | SER A 17 | -26.773 | -1.656 | 5.403 | 1.00 | 22.41 | C | ATOM | 184 | CB LEU A 29 | -7.325 -8.578 0.437 1.00 14.11 | C |
| ATOM | 100 | OG | SER A 17 | -27.541 | -1.028 | 4.415 | 1.00 | 30.13 | O | ATOM | 185 | CG LEU A 29 | -7.782 -9.116 1.787 1.00 17.63 | C |
| ATOM | 101 | C | SER A 17 | -24.783 | -0.195 | 5.355 | 1.00 | 22.18 | C | ATOM | 186 | CD1 LEU A 29 | -6.680 -10.010 2.291 1.00 20.91 | C |
| ATOM | 102 | O | SER A 17 | -24.350 | 0.025 | 6.493 | 1.00 | 22.04 | O | ATOM | 187 | CD2 LEU A 29 | -8.000 -7.941 2.767 1.00 22.86 | C |
| ATOM | 103 | N | ILE A 18 | -24.811 | 0.713 | 4.380 | 1.00 | 23.08 | N | ATOM | 188 | C LEU A 29 | -7.447 -7.090 -1.538 1.00 14.00 | C |
| ATOM | 104 | CA | ILE A 18 | -24.617 | 2.148 | 4.643 | 1.00 | 25.00 | C | ATOM | 189 | O LEU A 29 | -7.462 -7.824 -2.551 1.00 13.89 | O |
| ATOM | 105 | CB | ILE A 18 | -23.416 | 2.735 | 3.865 | 1.00 | 24.49 | C | ATOM | 190 | N ARG A 30 | -6.850 -5.913 -1.501 1.00 12.98 | N |
| ATOM | 106 | CG1 | ILE A 18 | -22.124 | 1.976 | 4.187 | 1.00 | 23.04 | C | ATOM | 191 | CA ARG A 30 | -5.990 -5.447 -2.556 1.00 12.88 | C |
| ATOM | 107 | CD1 | ILE A 18 | -20.931 | 2.454 | 3.400 | 1.00 | 24.42 | C | ATOM | 192 | CB ARG A 30 | -6.176 -3.943 -2.772 1.00 12.24 | C |
| ATOM | 108 | CG2 | ILE A 18 | -23.253 | 4.229 | 4.183 | 1.00 | 25.41 | C | ATOM | 193 | CG ARG A 30 | -5.600 -3.368 -4.068 1.00 15.22 | C |
| ATOM | 109 | C | ILE A 18 | -25.924 | 2.950 | 4.343 | 1.00 | 26.70 | C | ATOM | 194 | CD ARG A 30 | -4.161 -2.883 -3.909 1.00 13.93 | C |
| ATOM | 110 | O | ILE A 18 | -26.485 | 2.850 | 3.263 | 1.00 | 27.14 | O | ATOM | 195 | NE ARG A 30 | -3.836 -1.916 -4.977 1.00 13.30 | N |
| ATOM | 111 | N | GLY A 19 | -26.410 | 3.708 | 5.319 | 1.00 | 28.45 | N | ATOM | 196 | CZ ARG A 30 | -2.842 -2.083 -5.831 1.00 15.61 | C |
| ATOM | 112 | CA | GLY A 19 | -27.572 | 4.587 | 5.116 | 1.00 | 29.92 | C | ATOM | 197 | NH1 ARG A 30 | -2.068 -3.168 -5.729 1.00 18.49 | N |
| ATOM | 113 | C | GLY A 19 | -28.896 | 3.885 | 4.861 | 1.00 | 31.06 | C | ATOM | 198 | NH2 ARG A 30 | -2.613 -1.165 -6.776 1.00 18.43 | N |
| ATOM | 114 | O | GLY A 19 | -29.839 | 4.502 | 4.334 | 1.00 | 32.34 | O | ATOM | 199 | C ARG A 30 | -4.594 -5.741 -2.073 1.00 14.87 | C |
| ATOM | 115 | N | ASP A 20 | -28.981 | 2.608 | 5.231 | 1.00 | 31.79 | N | ATOM | 200 | O ARG A 30 | -4.162 -5.172 -1.045 1.00 14.62 | O |
| ATOM | 116 | CA | ASP A 20 | -30.184 | 1.790 | 5.001 | 1.00 | 32.67 | C | ATOM | 201 | N LYS A 31 | -3.901 -6.618 -2.805 1.00 14.99 | N |
| ATOM | 117 | CB | ASP A 20 | -31.453 | 2.553 | 5.381 | 1.00 | 34.44 | C | ATOM | 202 | CA LYS A 31 | -2.514 -6.988 -2.501 1.00 16.36 | C |
| ATOM | 118 | CG | ASP A 20 | -31.533 | 2.850 | 6.863 | 1.00 | 38.13 | C | ATOM | 203 | CB LYS A 31 | -2.363 -8.506 -2.609 1.00 18.53 | C |
| ATOM | 119 | OD1 | ASP A 20 | -31.216 | 1.941 | 7.678 | 1.00 | 41.50 | O | ATOM | 204 | CG LYS A 31 | -3.069 -9.251 -1.506 1.00 18.52 | C |
| ATOM | 120 | OD2 | ASP A 20 | -31.910 | 4.001 | 7.192 | 1.00 | 43.20 | O | ATOM | 205 | CD LYS A 31 | -3.275 -10.726 -1.851 1.00 25.36 | C |
| ATOM | 121 | C | ASP A 20 | -30.370 | 1.266 | 3.577 | 1.00 | 31.79 | C | ATOM | 206 | CE LYS A 31 | -4.348 -11.296 -0.900 1.00 23.81 | C |
| ATOM | 122 | O | ASP A 20 | -30.209 | 0.255 | 3.374 | 1.00 | 32.71 | O | ATOM | 207 | NZ LYS A 31 | -4.303 -12.789 -0.879 1.00 33.10 | N |
| ATOM | 123 | N | SER A 21 | -29.810 | 1.963 | 2.598 | 1.00 | 29.79 | N | ATOM | 208 | C LYS A 31 | -1.526 -6.334 -3.465 1.00 17.74 | C |
| ATOM | 124 | CA | SER A 21 | -30.141 | 1.721 | 1.204 | 1.00 | 27.91 | C | ATOM | 209 | O LYS A 31 | -1.909 -5.837 -4.548 1.00 15.71 | O |
| ATOM | 125 | CB | SER A 21 | -30.554 | 3.061 | 0.572 | 1.00 | 28.88 | C | ATOM | 210 | N LYS A 32 | -0.254 -6.338 -3.057 1.00 17.62 | N |
| ATOM | 126 | OG | SER A 21 | -29.661 | 4.102 | 0.971 | 1.00 | 28.48 | O | ATOM | 211 | CA LYS A 32 | 0.853 -6.012 -3.933 1.00 19.83 | C |
| ATOM | 127 | C | SER A 21 | -29.000 | 1.074 | 0.400 | 1.00 | 26.21 | C | ATOM | 212 | CB LYS A 32 | 1.617 -4.794 -3.385 1.00 20.71 | C |
| ATOM | 128 | O | SER A 21 | -29.227 | 0.499 | -0.658 | 1.00 | 26.12 | O | ATOM | 213 | CG LYS A 32 | 2.899 -4.415 -4.118 1.00 23.97 | C |
| ATOM | 129 | N | ARG A 22 | -27.787 | 1.167 | 0.928 | 1.00 | 23.54 | N | ATOM | 214 | CD LYS A 32 | 2.680 -4.065 -5.570 1.00 29.42 | C |
| ATOM | 130 | CA | ARG A 22 | -26.556 | 0.737 | 0.246 | 1.00 | 22.15 | C | ATOM | 215 | CE LYS A 32 | 4.011 -3.801 -6.287 1.00 33.60 | C |
| ATOM | 131 | CB | ARG A 22 | -25.456 | 1.744 | 0.603 | 1.00 | 22.07 | C | ATOM | 216 | NZ LYS A 32 | 4.518 -2.410 -6.080 1.00 35.43 | N |
| ATOM | 132 | CG | ARG A 22 | -24.605 | 2.195 | -0.489 | 1.00 | 25.28 | C | ATOM | 217 | C LYS A 32 | 1.770 -7.228 -3.992 1.00 21.26 | C |

Fig. 5 cont.

```
ATOM  218  O   LYS A 32    2.186  -7.769  -2.938 1.00 21.13   O      ATOM  303  C   TYR A 43   -7.122  -3.620  1.908 1.00 11.10   C
ATOM  219  N   SER A 33    2.056  -7.674  -5.213 1.00 21.51   N      ATOM  304  O   TYR A 43   -7.081  -4.411  0.966 1.00 11.20   O
ATOM  220  CA  SER A 33    2.971  -8.799  -5.421 1.00 22.97   C      ATOM  305  N   ALA A 44   -8.114  -3.605  2.818 1.00 10.43   N
ATOM  221  CB  SER A 33    2.697  -9.529  -6.736 1.00 23.81   C      ATOM  306  CA  ALA A 44   -9.299  -4.422  2.653 1.00 10.65   C
ATOM  222  OG  SER A 33    3.343 -10.806  -6.735 1.00 26.21   O      ATOM  307  CB  ALA A 44   -9.812  -4.873  3.989 1.00  9.94   C
ATOM  223  C   SER A 33    4.401  -8.279  -5.415 1.00 23.68   C      ATOM  308  C   ALA A 44  -10.329  -3.493  2.032 1.00 10.88   C
ATOM  224  O   SER A 33    4.764  -7.385  -6.197 1.00 22.36   O      ATOM  309  O   ALA A 44  -10.293  -2.287  2.283 1.00  9.99   O
ATOM  225  N   LEU A 34    5.181  -8.803  -4.483 1.00 23.41   N      ATOM  310  N   PHE A 45  -11.241  -4.034  1.226 1.00 10.51   N
ATOM  226  CA  LEU A 34    6.577  -8.472  -4.410 1.00 24.68   C      ATOM  311  CA  PHE A 45  -12.285  -3.144  0.654 1.00 10.72   C
ATOM  227  CB  LEU A 34    6.963  -8.240  -2.952 1.00 24.19   C      ATOM  312  CB  PHE A 45  -11.939  -2.680 -0.783 1.00 11.68   C
ATOM  228  CG  LEU A 34    6.321  -6.993  -2.312 1.00 26.08   C      ATOM  313  CG  PHE A 45  -11.784  -3.806 -1.766 1.00 12.71   C
ATOM  229  CD1 LEU A 34    6.847  -6.823  -0.883 1.00 27.09   C      ATOM  314  CD1 PHE A 45  -12.903  -4.334 -2.430 1.00 12.89   C
ATOM  230  CD2 LEU A 34    6.618  -5.760  -3.145 1.00 29.75   C      ATOM  315  CE1 PHE A 45  -12.767  -5.393 -3.352 1.00 13.11   C
ATOM  231  C   LEU A 34    7.352  -9.621  -5.082 1.00 25.51   C      ATOM  316  CZ  PHE A 45  -11.459  -5.918 -3.611 1.00 11.22   C
ATOM  232  O   LEU A 34    6.759 -10.484  -5.716 1.00 26.26   O      ATOM  317  CE2 PHE A 45  -10.339  -5.350 -2.945 1.00 14.33   C
ATOM  233  N   LEU A 35    8.665  -9.622  -4.961 1.00 26.73   N      ATOM  318  CD2 PHE A 45  -10.513  -4.316 -2.046 1.00 13.15   C
ATOM  234  CA  LEU A 35    9.447 -10.589  -5.713 1.00 27.80   C      ATOM  319  C   PHE A 45  -13.638  -3.819  0.719 1.00 10.37   C
ATOM  235  CB  LEU A 35   10.904 -10.178  -5.750 1.00 29.14   C      ATOM  320  O   PHE A 45  -13.722  -5.053  0.791 1.00  9.22   O
ATOM  236  CG  LEU A 35   11.284  -8.952  -6.577 1.00 31.78   C      ATOM  321  N   GLY A 46  -14.719  -3.029  0.711 1.00 10.52   N
ATOM  237  CD1 LEU A 35   12.791  -8.976  -6.774 1.00 32.61   C      ATOM  322  CA  GLY A 46  -16.049  -3.588  0.715 1.00  9.63   C
ATOM  238  CD2 LEU A 35   10.537  -8.947  -7.930 1.00 34.05   C      ATOM  323  C   GLY A 46  -16.808  -2.845 -0.382 1.00 10.00   C
ATOM  239  C   LEU A 35    9.317 -11.964  -5.078 1.00 26.99   C      ATOM  324  O   GLY A 46  -16.666  -1.615 -0.506 1.00  8.89   O
ATOM  240  O   LEU A 35    9.328 -12.071  -3.862 1.00 27.17   O      ATOM  325  N   VAL A 47  -17.578  -3.587 -1.169 1.00  9.81   N
ATOM  241  N   GLY A 36    9.176 -12.984  -5.923 1.00 26.71   N      ATOM  326  CA  VAL A 47  -18.285  -2.986 -2.317 1.00 11.22   C
ATOM  242  CA  GLY A 36    9.151 -14.377  -5.487 1.00 26.34   C      ATOM  327  CB  VAL A 47  -18.022  -3.746 -3.625 1.00 12.64   C
ATOM  243  C   GLY A 36    7.920 -14.623  -4.638 1.00 25.39   C      ATOM  328  CG1 VAL A 47  -18.782  -3.032 -4.798 1.00 13.25   C
ATOM  244  O   GLY A 36    6.829 -14.247  -5.037 1.00 25.35   O      ATOM  329  CG2 VAL A 47  -16.487  -3.819 -3.916 1.00 13.97   C
ATOM  245  N   LEU A 37    8.112 -15.209  -3.455 1.00 25.27   N      ATOM  330  C   VAL A 47  -19.786  -2.998 -1.995 1.00 10.49   C
ATOM  246  CA  LEU A 37    6.990 -15.617  -2.577 1.00 23.39   C      ATOM  331  O   VAL A 47  -20.345  -4.058 -1.719 1.00 10.19   O
ATOM  247  CB  LEU A 37    7.397 -16.839  -1.730 1.00 23.78   C      ATOM  332  N   TYR A 48  -20.406  -1.805 -2.043 1.00 11.53   N
ATOM  248  CG  LEU A 37    7.491 -18.128  -2.542 1.00 22.95   C      ATOM  333  CA  TYR A 48  -21.808  -1.582 -1.659 1.00 11.13   C
ATOM  249  CD1 LEU A 37    8.347 -19.160  -1.831 1.00 25.53   C      ATOM  334  CB  TYR A 48  -21.897  -0.458 -0.622 1.00 12.05   C
ATOM  250  CD2 LEU A 37    6.094 -18.699  -2.807 1.00 26.51   C      ATOM  335  CG  TYR A 48  -21.315  -0.787  0.736 1.00 10.84   C
ATOM  251  C   LEU A 37    6.479 -14.522  -1.662 1.00 23.05   C      ATOM  336  CD1 TYR A 48  -19.920  -0.651  0.987 1.00  9.84   C
ATOM  252  O   LEU A 37    5.614 -14.776  -0.823 1.00 22.67   O      ATOM  337  CE1 TYR A 48  -19.378  -0.932  2.196 1.00 10.45   C
ATOM  253  N   LYS A 38    6.991 -13.303  -1.841 1.00 21.79   N      ATOM  338  CZ  TYR A 48  -20.220  -1.346  3.226 1.00 10.68   C
ATOM  254  CA  LYS A 38    6.606 -12.184  -1.008 1.00 22.01   C      ATOM  339  OH  TYR A 48  -19.662  -1.682  4.459 1.00 12.23   O
ATOM  255  CB  LYS A 38    7.753 -11.189  -0.873 1.00 23.05   C      ATOM  340  CE2 TYR A 48  -21.601  -1.535  2.993 1.00 10.19   C
ATOM  256  CG  LYS A 38    9.043 -11.826  -0.369 1.00 23.90   C      ATOM  341  CD2 TYR A 48  -22.126  -1.228  1.740 1.00  9.81   C
ATOM  257  CD  LYS A 38   10.065 -10.740  -0.121 1.00 29.72   C      ATOM  342  C   TYR A 48  -22.588  -1.107 -2.899 1.00 11.99   C
ATOM  258  CE  LYS A 38    9.941 -10.210   1.300 1.00 34.14   C      ATOM  343  O   TYR A 48  -22.049  -0.367 -3.698 1.00 13.43   O
ATOM  259  NZ  LYS A 38   11.021 -10.796   2.198 1.00 36.13   N      ATOM  344  N   ALA A 49  -23.826  -1.543 -3.043 1.00 12.03   N
ATOM  260  C   LYS A 38    5.390 -11.449  -1.553 1.00 21.63   C      ATOM  345  CA  ALA A 49  -24.693  -1.065 -4.137 1.00 12.23   C
ATOM  261  O   LYS A 38    5.277 -11.188  -2.766 1.00 21.73   O      ATOM  346  CB  ALA A 49  -24.789  -2.098 -5.270 1.00 11.48   C
ATOM  262  N   ASN A 39    4.497 -11.088  -0.641 1.00 21.78   N      ATOM  347  C   ALA A 49  -26.088  -0.736 -3.567 1.00 12.99   C
ATOM  263  CA  ASN A 39    3.301 -10.347  -1.012 1.00 21.98   C      ATOM  348  O   ALA A 49  -26.597  -1.409 -2.708 1.00 13.45   O
ATOM  264  CB  ASN A 39    2.145 -11.292  -1.344 1.00 23.28   C      ATOM  349  N   ASP A 50  -26.675   0.334 -4.064 1.00 14.67   N
ATOM  265  CG  ASN A 39    2.389 -12.114  -2.619 1.00 27.32   C      ATOM  350  CA  ASP A 50  -28.026   0.743 -3.677 1.00 15.42   C
ATOM  266  OD1 ASN A 39    2.609 -13.324  -2.555 1.00 33.67   O      ATOM  351  CB  ASP A 50  -28.336   2.104 -4.315 1.00 15.73   C
ATOM  267  ND2 ASN A 39    2.357 -11.456  -3.772 1.00 28.11   N      ATOM  352  CG  ASP A 50  -29.724   2.589 -3.957 1.00 19.05   C
ATOM  268  C   ASN A 39    2.922  -9.496   0.179 1.00 21.67   C      ATOM  353  OD1 ASP A 50  -30.690   2.190 -4.622 1.00 18.27   O
ATOM  269  O   ASN A 39    3.223  -9.857   1.325 1.00 20.78   O      ATOM  354  OD2 ASP A 50  -29.848   3.326 -2.973 1.00 20.60   O
ATOM  270  N   ILE A 40    2.236  -8.386  -0.080 1.00 20.38   N      ATOM  355  C   ASP A 50  -29.018  -0.303 -4.168 1.00 15.02   C
ATOM  271  CA  ILE A 40    1.767  -7.531   0.988 1.00 21.79   C      ATOM  356  O   ASP A 50  -29.046  -0.645 -5.370 1.00 14.92   O
ATOM  272  CB  ILE A 40    2.564  -6.215   0.973 1.00 22.59   C      ATOM  357  N   CYS A 51  -29.824  -0.804 -3.239 1.00 14.42   N
ATOM  273  CG1 ILE A 40    3.942  -6.467   1.614 1.00 25.28   C      ATOM  358  CA  CYS A 51  -30.752  -1.908 -3.467 1.00 17.21   C
ATOM  274  CD1 ILE A 40    4.805  -5.196   1.770 1.00 24.90   C      ATOM  359  CB  CYS A 51  -31.457  -2.246 -2.129 1.00 17.69   C
ATOM  275  CG2 ILE A 40    1.798  -5.144   1.701 1.00 24.74   C      ATOM  360  SG  CYS A 51  -30.259  -2.989 -1.004 1.00 29.41   S
ATOM  276  C   ILE A 40    0.268  -7.286   0.847 1.00 20.30   C      ATOM  361  C   CYS A 51  -31.766  -1.525 -4.520 1.00 15.84   C
ATOM  277  O   ILE A 40   -0.192  -7.072  -0.261 1.00 18.41   O      ATOM  362  O   CYS A 51  -32.056  -2.313 -5.421 1.00 17.27   O
ATOM  278  N   ASP A 41   -0.488  -7.358   1.954 1.00 19.43   N      ATOM  363  N   ASP A 52  -32.305  -0.304 -4.425 1.00 16.01   N
ATOM  279  CA  ASP A 41   -1.902  -6.965   1.939 1.00 18.70   C      ATOM  364  CA  ASP A 52  -33.382   0.095 -5.375 1.00 16.30   C
ATOM  280  CB  ASP A 41   -2.637  -7.569   3.140 1.00 19.84   C      ATOM  365  CB  ASP A 52  -34.010   1.446 -4.978 1.00 17.27   C
ATOM  281  CG  ASP A 41   -2.618  -9.109   3.149 1.00 23.15   C      ATOM  366  CG  ASP A 52  -34.902   1.361 -3.707 1.00 22.81   C
ATOM  282  OD1 ASP A 41   -2.715  -9.717   2.071 1.00 23.43   O      ATOM  367  OD1 ASP A 52  -35.466   0.290 -3.347 1.00 24.71   O
ATOM  283  OD2 ASP A 41   -2.479  -9.691   4.252 1.00 30.54   O      ATOM  368  OD2 ASP A 52  -35.046   2.426 -3.055 1.00 29.09   O
ATOM  284  C   ASP A 41   -1.945  -5.484   2.118 1.00 16.94   C      ATOM  369  C   ASP A 52  -32.851   0.189 -6.808 1.00 14.90   C
ATOM  285  O   ASP A 41   -1.526  -4.993   3.190 1.00 17.45   O      ATOM  370  O   ASP A 52  -33.513  -0.212 -7.754 1.00 15.62   O
ATOM  286  N   VAL A 42   -2.458  -4.760   1.122 1.00 14.54   N      ATOM  371  N   ASP A 53  -31.658   0.747 -6.961 1.00 13.54   N
ATOM  287  CA  VAL A 42   -2.374  -3.289   1.160 1.00 14.40   C      ATOM  372  CA  ASP A 53  -31.008   0.908 -8.255 1.00 14.26   C
ATOM  288  CB  VAL A 42   -2.179  -2.642  -0.224 1.00 13.69   C      ATOM  373  CB  ASP A 53  -29.704   1.686 -8.070 1.00 13.83   C
ATOM  289  CG1 VAL A 42   -1.905  -1.111  -0.068 1.00 14.96   C      ATOM  374  CG  ASP A 53  -29.920   3.162 -7.808 1.00 18.61   C
ATOM  290  CG2 VAL A 42   -0.947  -3.234  -0.910 1.00 14.75   C      ATOM  375  OD1 ASP A 53  -28.943   3.823 -7.420 1.00 15.39   O
ATOM  291  C   VAL A 42   -3.565  -2.682   1.878 1.00 14.54   C      ATOM  376  OD2 ASP A 53  -31.061   3.679 -7.998 1.00 19.58   O
ATOM  292  O   VAL A 42   -3.390  -1.872   2.794 1.00 15.45   O      ATOM  377  C   ASP A 53  -30.725  -0.458 -8.901 1.00 13.60   C
ATOM  293  N   TYR A 43   -4.770  -3.060   1.443 1.00 12.65   N      ATOM  378  O   ASP A 53  -30.940  -0.644 -10.113 1.00 12.08   O
ATOM  294  CA  TYR A 43   -5.991  -2.629   2.109 1.00 11.44   C      ATOM  379  N   VAL A 54  -30.232  -1.408 -8.108 1.00 13.98   N
ATOM  295  CB  TYR A 43   -6.422  -1.236   1.619 1.00 11.73   C      ATOM  380  CA  VAL A 54  -30.018  -2.774 -8.625 1.00 13.66   C
ATOM  296  CG  TYR A 43   -6.738  -1.037   0.118 1.00 10.10   C      ATOM  381  CB  VAL A 54  -29.272  -3.651 -7.627 1.00 15.00   C
ATOM  297  CD1 TYR A 43   -5.775  -0.500  -0.732 1.00  9.32   C      ATOM  382  CG1 VAL A 54  -29.184  -5.077 -8.154 1.00 13.95   C
ATOM  298  CE1 TYR A 43   -6.046  -0.282  -2.084 1.00 11.63   C      ATOM  383  CG2 VAL A 54  -27.861  -3.128 -7.384 1.00 13.80   C
ATOM  299  CZ  TYR A 43   -7.288  -0.658  -2.604 1.00 12.10   C      ATOM  384  C   VAL A 54  -31.346  -3.447 -9.006 1.00 14.94   C
ATOM  300  OH  TYR A 43   -7.559  -0.414  -3.948 1.00 12.55   O      ATOM  385  O   VAL A 54  -31.443  -4.059 -10.055 1.00 15.55   O
ATOM  301  CE2 TYR A 43   -8.257  -1.226  -1.774 1.00 10.76   C      ATOM  386  N   LYS A 55  -32.375  -3.351 -8.161 1.00 15.64   N
ATOM  302  CD2 TYR A 43   -7.980  -1.412  -0.433 1.00  9.11   C      ATOM  387  CA  LYS A 55  -33.701  -3.923 -8.496 1.00 18.03   C
```

Fig. 5 cont.

```
ATOM  388 CB  LYS A 55   -34.745  -3.628  -7.392 1.00 18.05    C
ATOM  389 CG  LYS A 55   -34.556  -4.378  -6.135 1.00 20.11    C
ATOM  390 CD  LYS A 55   -35.533  -3.927  -5.016 1.00 21.97    C
ATOM  391 CE  LYS A 55   -35.339  -4.856  -3.815 1.00 28.49    C
ATOM  392 NZ  LYS A 55   -35.531  -4.170  -2.516 1.00 31.71    N
ATOM  393 C   LYS A 55   -34.250  -3.383  -9.816 1.00 17.84    C
ATOM  394 O   LYS A 55   -34.818  -4.128 -10.599 1.00 18.19    O
ATOM  395 N   LYS A 56   -34.076  -2.090 -10.052 1.00 17.91    N
ATOM  396 CA  LYS A 56   -34.554  -1.445 -11.262 1.00 19.28    C
ATOM  397 CB  LYS A 56   -34.461   0.077 -11.126 1.00 20.39    C
ATOM  398 CG  LYS A 56   -35.066   0.845 -12.291 1.00 22.61    C
ATOM  399 CD  LYS A 56   -34.786   2.332 -12.191 1.00 31.06    C
ATOM  400 CE  LYS A 56   -35.704   3.029 -11.168 1.00 36.05    C
ATOM  401 NZ  LYS A 56   -35.302   4.467 -10.894 1.00 40.70    N
ATOM  402 C   LYS A 56   -33.806  -1.941 -12.513 1.00 19.08    C
ATOM  403 O   LYS A 56   -34.420  -2.245 -13.523 1.00 19.78    O
ATOM  404 N   LEU A 57   -32.482  -2.064 -12.430 1.00 18.41    N
ATOM  405 CA  LEU A 57   -31.692  -2.631 -13.522 1.00 17.31    C
ATOM  406 CB  LEU A 57   -30.205  -2.560 -13.154 1.00 17.25    C
ATOM  407 CG  LEU A 57   -29.099  -2.995 -14.117 1.00 17.21    C
ATOM  408 CD1 LEU A 57   -28.698  -4.443 -13.939 1.00 18.18    C
ATOM  409 CD2 LEU A 57   -29.417  -2.674 -15.591 1.00 19.98    C
ATOM  410 C   LEU A 57   -32.143  -4.057 -13.879 1.00 17.40    C
ATOM  411 O   LEU A 57   -32.416  -4.354 -15.049 1.00 17.10    O
ATOM  412 N   VAL A 58   -32.254  -4.929 -12.878 1.00 17.47    N
ATOM  413 CA  VAL A 58   -32.723  -6.291 -13.100 1.00 18.40    C
ATOM  414 CB  VAL A 58   -32.693  -7.117 -11.778 1.00 18.74    C
ATOM  415 CG1 VAL A 58   -33.331  -8.446 -11.999 1.00 19.24    C
ATOM  416 CG2 VAL A 58   -31.244  -7.289 -11.292 1.00 16.52    C
ATOM  417 C   VAL A 58   -34.130  -6.335 -13.712 1.00 19.96    C
ATOM  418 O   VAL A 58   -34.379  -7.062 -14.675 1.00 17.10    O
ATOM  419 N   GLY A 59   -35.061  -5.575 -13.153 1.00 20.80    N
ATOM  420 CA  GLY A 59   -36.431  -5.592 -13.674 1.00 23.00    C
ATOM  421 C   GLY A 59   -36.528  -5.035 -15.084 1.00 24.00    C
ATOM  422 O   GLY A 59   -37.424  -5.419 -15.858 1.00 24.75    O
ATOM  423 N   ASP A 60   -35.641  -4.109 -15.415 1.00 24.31    N
ATOM  424 CA  ASP A 60   -35.576  -3.571 -16.773 1.00 25.59    C
ATOM  425 CB  ASP A 60   -34.985  -2.161 -16.783 1.00 27.14    C
ATOM  426 CG  ASP A 60   -35.878  -1.151 -16.057 1.00 31.07    C
ATOM  427 OD1 ASP A 60   -37.005  -1.518 -15.620 1.00 35.86    O
ATOM  428 OD2 ASP A 60   -35.446   0.011 -15.906 1.00 35.91    O
ATOM  429 C   ASP A 60   -34.869  -4.462 -17.786 1.00 24.96    C
ATOM  430 O   ASP A 60   -35.381  -4.655 -18.891 1.00 25.31    O
ATOM  431 N   LYS A 61   -33.716  -5.016 -17.430 1.00 22.28    N
ATOM  432 CA  LYS A 61   -32.930  -5.791 -18.396 1.00 21.27    C
ATOM  433 CB  LYS A 61   -31.449  -5.433 -18.278 1.00 20.97    C
ATOM  434 CG  LYS A 61   -31.089  -4.169 -19.071 1.00 25.32    C
ATOM  435 CD  LYS A 61   -29.609  -3.863 -19.056 1.00 25.82    C
ATOM  436 CE  LYS A 61   -29.337  -2.742 -20.026 1.00 29.46    C
ATOM  437 NZ  LYS A 61   -29.857  -3.179 -21.346 1.00 32.10    N
ATOM  438 C   LYS A 61   -33.087  -7.325 -18.298 1.00 20.24    C
ATOM  439 O   LYS A 61   -32.720  -8.039 -19.246 1.00 18.68    O
ATOM  440 N   TYR A 62   -33.527  -7.800 -17.121 1.00 17.96    N
ATOM  441 CA  TYR A 62   -33.619  -9.237 -16.770 1.00 17.62    C
ATOM  442 CB  TYR A 62   -32.528  -9.595 -15.727 1.00 16.91    C
ATOM  443 CG  TYR A 62   -31.151  -9.346 -16.278 1.00 15.11    C
ATOM  444 CD1 TYR A 62   -30.514  -8.114 -16.106 1.00 16.11    C
ATOM  445 CE1 TYR A 62   -29.224  -7.882 -16.684 1.00 15.14    C
ATOM  446 CZ  TYR A 62   -28.594  -8.894 -17.379 1.00 16.88    C
ATOM  447 OH  TYR A 62   -27.339  -8.712 -17.965 1.00 17.79    O
ATOM  448 CE2 TYR A 62   -29.203 -10.125 -17.534 1.00 17.16    C
ATOM  449 CD2 TYR A 62   -30.477 -10.344 -16.991 1.00 17.28    C
ATOM  450 C   TYR A 62   -34.995  -9.594 -16.212 1.00 18.60    C
ATOM  451 O   TYR A 62   -35.114 -10.416 -15.322 1.00 18.15    O
ATOM  452 N   ALA A 63   -36.052  -8.990 -16.765 1.00 18.55    N
ATOM  453 CA  ALA A 63   -37.404  -9.204 -16.261 1.00 19.24    C
ATOM  454 CB  ALA A 63   -38.434  -8.370 -17.070 1.00 19.23    C
ATOM  455 C   ALA A 63   -37.770 -10.679 -16.269 1.00 19.86    C
ATOM  456 O   ALA A 63   -37.453 -11.419 -17.216 1.00 18.97    O
ATOM  457 N   ASN A 64   -38.394 -11.101 -15.175 1.00 20.48    N
ATOM  458 CA  ASN A 64   -38.861 -12.487 -14.969 1.00 21.82    C
ATOM  459 CB  ASN A 64   -39.945 -12.909 -15.969 1.00 22.66    C
ATOM  460 CG  ASN A 64   -41.053 -11.914 -16.063 1.00 25.85    C
ATOM  461 OD1 ASN A 64   -41.447 -11.294 -15.054 1.00 27.43    O
ATOM  462 ND2 ASN A 64   -41.582 -11.740 -17.275 1.00 27.85    N
ATOM  463 C   ASN A 64   -37.814 -13.576 -14.868 1.00 21.78    C
ATOM  464 O   ASN A 64   -38.181 -14.766 -14.790 1.00 23.52    O
ATOM  465 N   LEU A 65   -36.531 -13.215 -14.823 1.00 19.34    N
ATOM  466 CA  LEU A 65   -35.509 -14.251 -14.762 1.00 18.53    C
ATOM  467 CB  LEU A 65   -34.272 -13.902 -15.605 1.00 18.11    C
ATOM  468 CG  LEU A 65   -34.606 -13.508 -17.042 1.00 20.25    C
ATOM  469 CD1 LEU A 65   -33.336 -12.918 -17.663 1.00 21.37    C
ATOM  470 CD2 LEU A 65   -35.107 -14.700 -17.825 1.00 22.39    C
ATOM  471 C   LEU A 65   -35.111 -14.514 -13.321 1.00 17.38    C
ATOM  472 O   LEU A 65   -35.077 -13.587 -12.526 1.00 15.91    O
ATOM  473 N   PRO A 66   -34.878 -15.793 -12.980 1.00 17.05    N
ATOM  474 CA  PRO A 66   -34.353 -16.169 -11.684 1.00 15.99    C
ATOM  475 CB  PRO A 66   -34.430 -17.708 -11.704 1.00 15.92    C
ATOM  476 CG  PRO A 66   -34.418 -18.097 -13.136 1.00 17.00    C
ATOM  477 CD  PRO A 66   -35.176 -16.964 -13.821 1.00 18.57    C
ATOM  478 C   PRO A 66   -32.896 -15.701 -11.516 1.00 15.11    C
ATOM  479 O   PRO A 66   -32.199 -15.516 -12.516 1.00 14.21    O
ATOM  480 N   ALA A 67   -32.454 -15.547 -10.281 1.00 14.07    N
ATOM  481 CA  ALA A 67   -31.080 -15.103  -9.972 1.00 14.30    C
ATOM  482 CB  ALA A 67   -30.836 -15.182  -8.417 1.00 13.56    C
ATOM  483 C   ALA A 67   -30.040 -15.916 -10.733 1.00 14.34    C
ATOM  484 O   ALA A 67   -29.117 -15.372 -11.339 1.00 15.55    O
ATOM  485 N   SER A 68   -30.195 -17.242 -10.735 1.00 14.55    N
ATOM  486 CA  SER A 68   -29.243 -18.106 -11.403 1.00 14.27    C
ATOM  487 CB  SER A 68   -29.685 -19.585 -11.239 1.00 14.72    C
ATOM  488 OG  SER A 68   -30.906 -19.808 -11.949 1.00 19.50    O
ATOM  489 C   SER A 68   -29.101 -17.740 -12.882 1.00 14.16    C
ATOM  490 O   SER A 68   -28.007 -17.816 -13.451 1.00 12.31    O
ATOM  491 N   GLU A 69   -30.201 -17.382 -13.540 1.00 15.14    N
ATOM  492 CA  GLU A 69   -30.081 -17.047 -14.940 1.00 16.17    C
ATOM  493 CB  GLU A 69   -31.379 -17.318 -15.692 1.00 18.56    C
ATOM  494 CG  GLU A 69   -31.913 -18.768 -15.448 1.00 24.43    C
ATOM  495 CD  GLU A 69   -30.840 -19.892 -15.550 1.00 35.70    C
ATOM  496 OE1 GLU A 69   -30.523 -20.554 -14.509 1.00 37.56    O
ATOM  497 OE2 GLU A 69   -30.331 -20.119 -16.677 1.00 41.01    O
ATOM  498 C   GLU A 69   -29.590 -15.640 -15.147 1.00 15.33    C
ATOM  499 O   GLU A 69   -28.937 -15.342 -16.144 1.00 15.65    O
ATOM  500 N   ILE A 70   -29.877 -14.770 -14.201 1.00 13.99    N
ATOM  501 CA  ILE A 70   -29.307 -13.397 -14.282 1.00 13.47    C
ATOM  502 CB  ILE A 70   -29.854 -12.519 -13.169 1.00 11.81    C
ATOM  503 CG1 ILE A 70   -31.370 -12.257 -13.367 1.00 13.00    C
ATOM  504 CD1 ILE A 70   -32.077 -11.745 -12.068 1.00 13.89    C
ATOM  505 CG2 ILE A 70   -29.044 -11.199 -13.065 1.00 14.91    C
ATOM  506 C   ILE A 70   -27.792 -13.524 -14.164 1.00 13.82    C
ATOM  507 O   ILE A 70   -27.011 -12.953 -14.979 1.00 12.68    O
ATOM  508 N   ARG A 71   -27.376 -14.246 -13.136 1.00 13.23    N
ATOM  509 CA  ARG A 71   -25.936 -14.469 -12.853 1.00 14.45    C
ATOM  510 CB  ARG A 71   -25.782 -15.217 -11.523 1.00 13.00    C
ATOM  511 CG  ARG A 71   -24.359 -15.468 -11.088 1.00 15.44    C
ATOM  512 CD  ARG A 71   -23.595 -14.149 -10.805 1.00 15.23    C
ATOM  513 NE  ARG A 71   -22.378 -14.498 -10.081 1.00 17.11    N
ATOM  514 CZ  ARG A 71   -21.171 -14.594 -10.622 1.00 17.34    C
ATOM  515 NH1 ARG A 71   -21.007 -14.343 -11.913 1.00 18.54    N
ATOM  516 NH2 ARG A 71   -20.128 -14.969  -9.866 1.00 15.81    N
ATOM  517 C   ARG A 71   -25.235 -15.217 -13.988 1.00 14.61    C
ATOM  518 O   ARG A 71   -24.057 -14.933 -14.342 1.00 14.40    O
ATOM  519 N   GLY A 72   -25.984 -16.132 -14.605 1.00 14.95    N
ATOM  520 CA  GLY A 72   -25.470 -16.893 -15.731 1.00 15.59    C
ATOM  521 C   GLY A 72   -25.256 -16.074 -16.997 1.00 15.72    C
ATOM  522 O   GLY A 72   -24.652 -16.567 -17.926 1.00 16.54    O
ATOM  523 N   ASN A 73   -25.712 -14.820 -17.028 1.00 15.31    N
ATOM  524 CA  ASN A 73   -25.587 -14.031 -18.237 1.00 14.60    C
ATOM  525 CB  ASN A 73   -26.686 -12.958 -18.322 1.00 14.03    C
ATOM  526 CG  ASN A 73   -27.867 -13.417 -19.141 1.00 20.36    C
ATOM  527 OD1 ASN A 73   -28.867 -13.925 -18.607 1.00 25.94    O
ATOM  528 ND2 ASN A 73   -27.768 -13.247 -20.447 1.00 17.75    N
ATOM  529 C   ASN A 73   -24.236 -13.372 -18.235 1.00 13.27    C
ATOM  530 O   ASN A 73   -23.917 -12.655 -17.316 1.00 11.31    O
ATOM  531 N   LYS A 74   -23.430 -13.619 -19.260 1.00 13.93    N
ATOM  532 CA  LYS A 74   -22.106 -12.966 -19.318 1.00 15.07    C
ATOM  533 CB  LYS A 74   -21.270 -13.462 -20.515 1.00 16.00    C
ATOM  534 CG  LYS A 74   -22.073 -14.152 -21.517 1.00 21.08    C
ATOM  535 CD  LYS A 74   -22.192 -15.642 -21.273 1.00 27.00    C
ATOM  536 CE  LYS A 74   -23.603 -16.077 -20.746 1.00 15.50    C
ATOM  537 NZ  LYS A 74   -24.667 -15.561 -21.427 1.00 14.33    N
ATOM  538 C   LYS A 74   -22.205 -11.468 -19.357 1.00 13.97    C
ATOM  539 O   LYS A 74   -21.263 -10.806 -18.980 1.00 15.42    O
ATOM  540 N   SER A 75   -23.326 -10.932 -19.828 1.00 14.13    N
ATOM  541 CA  SER A 75   -23.548  -9.465 -19.894 1.00 13.95    C
ATOM  542 CB  SER A 75   -24.780  -9.176 -20.779 1.00 14.73    C
ATOM  543 OG  SER A 75   -25.899  -9.883 -20.233 1.00 20.02    O
ATOM  544 C   SER A 75   -23.792  -8.803 -18.531 1.00 12.79    C
ATOM  545 O   SER A 75   -23.751  -7.576 -18.429 1.00 12.59    O
ATOM  546 N   PHE A 76   -24.052  -9.596 -17.487 1.00 12.77    N
ATOM  547 CA  PHE A 76   -24.604  -9.024 -16.226 1.00 11.88    C
ATOM  548 CB  PHE A 76   -25.042 -10.154 -15.292 1.00 11.83    C
ATOM  549 CG  PHE A 76   -25.577  -9.701 -13.941 1.00 11.89    C
ATOM  550 CD1 PHE A 76   -26.676  -8.853 -13.844 1.00 10.84    C
ATOM  551 CE1 PHE A 76   -27.187  -8.486 -12.602 1.00  9.07    C
ATOM  552 CZ  PHE A 76   -26.580  -8.973 -11.454 1.00 11.50    C
ATOM  553 CE2 PHE A 76   -25.499  -9.798 -11.538 1.00 11.95    C
ATOM  554 CD2 PHE A 76   -24.994 -10.168 -12.769 1.00 10.57    C
ATOM  555 C   PHE A 76   -23.590  -8.095 -15.597 1.00 12.76    C
ATOM  556 O   PHE A 76   -23.938  -6.981 -15.199 1.00 13.29    O
ATOM  557 N   MET A 77   -22.332  -8.528 -15.559 1.00 13.20    N
```

Fig. 5 cont.

| | | | | | | | | | | | | | | | |
|---|---|---|---|---|---|---|---|---|---|---|---|---|---|---|---|
| ATOM | 558 | CA | MET A 77 | -21.295 | -7.740 | -14.901 | 1.00 17.09 | C | ATOM | 643 | O | MET A 87 | -20.982 | 4.285 -4.418 1.00 14.09 | O |
| ATOM | 559 | CB | MET A 77 | -19.959 | -8.513 | -14.878 | 1.00 14.37 | C | ATOM | 644 | N | THR A 88 | -20.708 | 2.303 -3.337 1.00 13.62 | N |
| ATOM | 560 | CG | MET A 77 | -18.738 | -7.663 | -14.357 | 1.00 20.63 | C | ATOM | 645 | CA | THR A 88 | -19.616 | 2.809 -2.484 1.00 13.91 | C |
| ATOM | 561 | SD | MET A 77 | -17.212 | -8.605 | -14.244 | 1.00 24.37 | S | ATOM | 646 | CB | THR A 88 | -20.092 | 3.059 -0.997 1.00 14.79 | C |
| ATOM | 562 | CE | MET A 77 | -16.699 | -8.920 | -15.909 | 1.00 23.77 | C | ATOM | 647 | OG1 | THR A 88 | -21.037 | 4.121 -0.975 1.00 17.79 | O |
| ATOM | 563 | C | MET A 77 | -21.173 | -6.352 | -15.565 | 1.00 15.50 | C | ATOM | 648 | CG2 | THR A 88 | -18.923 | 3.564 -0.086 1.00 15.14 | C |
| ATOM | 564 | O | MET A 77 | -21.210 | -5.330 | -14.889 | 1.00 16.48 | O | ATOM | 649 | C | THR A 88 | -18.547 | 1.729 -2.469 1.00 12.65 | C |
| ATOM | 565 | N | ASP A 78 | -21.094 | -6.306 | -16.889 | 1.00 16.44 | N | ATOM | 650 | O | THR A 88 | -18.899 | 0.553 -2.347 1.00 12.72 | O |
| ATOM | 566 | CA | ASP A 78 | -20.983 | -4.992 | -17.601 | 1.00 16.04 | C | ATOM | 651 | N | ILE A 89 | -17.278 | 2.125 -2.624 1.00 12.39 | N |
| ATOM | 567 | CB | ASP A 78 | -20.582 | -5.178 | -19.071 | 1.00 15.86 | C | ATOM | 652 | CA | ILE A 89 | -16.151 | 1.251 -2.312 1.00 11.52 | C |
| ATOM | 568 | CG | ASP A 78 | -20.096 | -3.872 | -19.720 | 1.00 19.74 | C | ATOM | 653 | CB | ILE A 89 | -15.047 | 1.255 -3.438 1.00 10.99 | C |
| ATOM | 569 | OD1 | ASP A 78 | -18.903 | -3.555 | -19.552 | 1.00 23.07 | O | ATOM | 654 | CG1 | ILE A 89 | -15.645 | 0.975 -4.807 1.00 13.91 | C |
| ATOM | 570 | OD2 | ASP A 78 | -20.900 | -3.187 | -20.389 | 1.00 20.19 | O | ATOM | 655 | CD1 | ILE A 89 | -16.202 | -0.416 -4.876 1.00 18.95 | C |
| ATOM | 571 | C | ASP A 78 | -22.285 | -4.198 | -17.501 | 1.00 16.64 | C | ATOM | 656 | CG2 | ILE A 89 | -13.884 | 0.311 -3.076 1.00 12.55 | C |
| ATOM | 572 | O | ASP A 78 | -22.273 | -2.961 | -17.452 | 1.00 15.81 | O | ATOM | 657 | C | ILE A 89 | -15.517 | 1.840 -1.053 1.00 11.14 | C |
| ATOM | 573 | N | ASP A 79 | -23.413 | -4.897 | -17.459 | 1.00 15.85 | N | ATOM | 658 | O | ILE A 89 | -15.048 | 3.004 -1.059 1.00 11.77 | O |
| ATOM | 574 | CA | ASP A 79 | -24.711 | -4.202 | -17.347 | 1.00 16.58 | C | ATOM | 659 | N | ARG A 90 | -15.538 | 1.079 0.021 1.00 9.91 | N |
| ATOM | 575 | CB | ASP A 79 | -25.915 | -5.155 | -17.520 | 1.00 16.77 | C | ATOM | 660 | CA | ARG A 90 | -14.883 | 1.517 1.262 1.00 11.47 | C |
| ATOM | 576 | CG | ASP A 79 | -26.220 | -5.504 | -18.993 | 1.00 21.04 | C | ATOM | 661 | CB | ARG A 90 | -15.795 | 1.259 2.471 1.00 10.64 | C |
| ATOM | 577 | OD1 | ASP A 79 | -25.717 | -4.856 | -19.945 | 1.00 19.43 | O | ATOM | 662 | CG | ARG A 90 | -15.065 | 1.385 3.829 1.00 14.38 | C |
| ATOM | 578 | OD2 | ASP A 79 | -26.970 | -6.471 | -19.198 | 1.00 20.56 | O | ATOM | 663 | CD | ARG A 90 | -16.072 | 1.354 4.979 1.00 14.29 | C |
| ATOM | 579 | C | ASP A 79 | -24.822 | -3.439 | -16.023 | 1.00 17.01 | C | ATOM | 664 | NE | ARG A 90 | -16.934 | 2.542 4.896 1.00 21.68 | N |
| ATOM | 580 | O | ASP A 79 | -25.314 | -2.297 | -16.015 | 1.00 16.65 | O | ATOM | 665 | CZ | ARG A 90 | -17.856 | 2.873 5.797 1.00 21.50 | C |
| ATOM | 581 | N | LEU A 80 | -24.339 | -4.050 | -14.928 | 1.00 16.90 | N | ATOM | 666 | NH1 | ARG A 90 | -18.029 | 2.114 6.871 1.00 20.62 | N |
| ATOM | 582 | CA | LEU A 80 | -24.298 | -3.397 | -13.612 | 1.00 19.37 | C | ATOM | 667 | NH2 | ARG A 90 | -18.591 | 3.968 5.621 1.00 22.79 | N |
| ATOM | 583 | CB | LEU A 80 | -23.842 | -4.348 | -12.503 | 1.00 18.05 | C | ATOM | 668 | C | ARG A 90 | -13.552 | 0.797 1.426 1.00 11.22 | C |
| ATOM | 584 | CG | LEU A 80 | -24.762 | -5.444 | -12.024 | 1.00 18.21 | C | ATOM | 669 | O | ARG A 90 | -13.508 | -0.454 1.399 1.00 10.99 | O |
| ATOM | 585 | CD1 | LEU A 80 | -23.904 | -6.361 | -11.191 | 1.00 17.93 | C | ATOM | 670 | N | LEU A 91 | -12.466 | 1.577 1.557 1.00 10.88 | N |
| ATOM | 586 | CD2 | LEU A 80 | -25.943 | -4.854 | -11.198 | 1.00 15.72 | C | ATOM | 671 | CA | LEU A 91 | -11.127 | 1.028 1.650 1.00 12.00 | C |
| ATOM | 587 | C | LEU A 80 | -23.368 | -2.212 | -13.565 | 1.00 20.46 | C | ATOM | 672 | CB | LEU A 91 | -10.119 | 1.804 0.771 1.00 10.21 | C |
| ATOM | 588 | O | LEU A 80 | -23.728 | -1.180 | -13.003 | 1.00 21.51 | O | ATOM | 673 | CG | LEU A 91 | -10.187 | 1.807 -0.735 1.00 13.27 | C |
| ATOM | 589 | N | MET A 81 | -22.151 | -2.385 | -14.087 | 1.00 21.63 | N | ATOM | 674 | CD1 | LEU A 91 | -11.289 | 2.700 -1.192 1.00 16.29 | C |
| ATOM | 590 | CA | MET A 81 | -21.141 | -1.335 | -14.067 | 1.00 24.23 | C | ATOM | 675 | CD2 | LEU A 91 | -8.865 | 2.313 -1.325 1.00 12.78 | C |
| ATOM | 591 | CB | MET A 81 | -19.789 | -1.853 | -14.565 | 1.00 23.65 | C | ATOM | 676 | C | LEU A 91 | -10.727 | 1.236 3.085 1.00 11.68 | C |
| ATOM | 592 | CG | MET A 81 | -18.906 | -2.616 | -13.554 | 1.00 27.03 | C | ATOM | 677 | O | LEU A 91 | -11.000 | 2.313 3.630 1.00 12.10 | O |
| ATOM | 593 | SD | MET A 81 | -17.086 | -2.628 | -13.932 | 1.00 31.33 | S | ATOM | 678 | N | GLN A 92 | -10.086 | 0.236 3.679 1.00 11.57 | N |
| ATOM | 594 | CE | MET A 81 | -17.073 | -3.685 | -15.394 | 1.00 32.84 | C | ATOM | 679 | CA | GLN A 92 | -9.489 | 0.385 5.024 1.00 12.93 | C |
| ATOM | 595 | C | MET A 81 | -21.585 | -0.139 | -14.921 | 1.00 23.88 | C | ATOM | 680 | CB | GLN A 92 | -10.250 | -0.434 6.074 1.00 12.47 | C |
| ATOM | 596 | O | MET A 81 | -21.248 | 0.986 | -14.606 | 1.00 24.47 | O | ATOM | 681 | CG | GLN A 92 | -11.687 | 0.042 6.308 1.00 13.11 | C |
| ATOM | 597 | N | GLU A 82 | -22.328 | -0.381 | -16.004 | 1.00 23.50 | N | ATOM | 682 | CD | GLN A 92 | -12.372 | -0.762 7.363 1.00 18.85 | C |
| ATOM | 598 | CA | GLU A 82 | -22.720 | 0.702 | -16.898 | 1.00 22.74 | C | ATOM | 683 | OE1 | GLN A 92 | -13.363 | -1.439 7.104 1.00 24.30 | O |
| ATOM | 599 | CB | GLU A 82 | -22.815 | 0.214 | -18.360 | 1.00 24.90 | C | ATOM | 684 | NE2 | GLN A 92 | -11.840 | -0.713 8.563 1.00 18.27 | N |
| ATOM | 600 | CG | GLU A 82 | -21.451 | -0.270 | -18.917 | 1.00 28.77 | C | ATOM | 685 | C | GLN A 92 | -8.048 | -0.065 4.948 1.00 13.31 | C |
| ATOM | 601 | CD | GLU A 82 | -21.286 | -0.223 | -20.469 | 1.00 29.94 | C | ATOM | 686 | O | GLN A 92 | -7.771 | -1.219 4.575 1.00 11.91 | O |
| ATOM | 602 | OE1 | GLU A 82 | -22.130 | 0.433 | -21.139 | 1.00 37.31 | O | ATOM | 687 | N | ILE A 93 | -7.126 | 0.838 5.275 1.00 12.73 | N |
| ATOM | 603 | OE2 | GLU A 82 | -20.287 | -0.830 | -21.012 | 1.00 31.96 | O | ATOM | 688 | CA | ILE A 93 | -5.713 | 0.578 5.046 1.00 12.94 | C |
| ATOM | 604 | C | GLU A 82 | -23.998 | 1.426 | -16.421 | 1.00 23.23 | C | ATOM | 689 | CB | ILE A 93 | -4.830 | 1.917 5.095 1.00 13.41 | C |
| ATOM | 605 | O | GLU A 82 | -24.271 | 2.551 | -16.817 | 1.00 22.48 | O | ATOM | 690 | CG1 | ILE A 93 | -5.330 | 2.948 4.071 1.00 16.79 | C |
| ATOM | 606 | N | ALA A 83 | -24.752 | 0.797 | -15.523 | 1.00 21.89 | N | ATOM | 691 | CD1 | ILE A 93 | -5.258 | 2.489 2.606 1.00 19.62 | C |
| ATOM | 607 | CA | ALA A 83 | -26.057 | 1.323 | -15.137 | 1.00 22.10 | C | ATOM | 692 | CG2 | ILE A 93 | -3.317 | 1.600 4.908 1.00 12.98 | C |
| ATOM | 608 | CB | ALA A 83 | -26.882 | 0.243 | -14.545 | 1.00 20.90 | C | ATOM | 693 | C | ILE A 93 | -5.193 | -0.456 6.011 1.00 13.03 | C |
| ATOM | 609 | C | ALA A 83 | -25.892 | 2.472 | -14.149 | 1.00 22.10 | C | ATOM | 694 | O | ILE A 93 | -5.362 | -0.319 7.229 1.00 11.77 | O |
| ATOM | 610 | O | ALA A 83 | -24.859 | 2.601 | -13.524 | 1.00 21.93 | O | ATOM | 695 | N | VAL A 94 | -4.543 | -1.488 5.463 1.00 13.52 | N |
| ATOM | 611 | N | ASP A 84 | -26.919 | 3.301 | -14.003 | 1.00 21.82 | N | ATOM | 696 | CA | VAL A 94 | -3.980 | -2.573 6.251 1.00 14.75 | C |
| ATOM | 612 | CA | ASP A 84 | -26.858 | 4.390 | -13.035 | 1.00 21.99 | C | ATOM | 697 | CB | VAL A 94 | -4.289 | -3.970 5.570 1.00 14.33 | C |
| ATOM | 613 | CB | ASP A 84 | -27.816 | 5.539 | -13.408 | 1.00 23.63 | C | ATOM | 698 | CG1 | VAL A 94 | -3.621 | -5.131 6.306 1.00 17.32 | C |
| ATOM | 614 | CG | ASP A 84 | -27.492 | 6.834 | -12.652 | 1.00 28.95 | C | ATOM | 699 | CG2 | VAL A 94 | -5.813 | -4.210 5.536 1.00 15.48 | C |
| ATOM | 615 | OD1 | ASP A 84 | -26.559 | 6.834 | -11.795 | 1.00 34.55 | O | ATOM | 700 | C | VAL A 94 | -2.451 | -2.410 6.471 1.00 15.59 | C |
| ATOM | 616 | OD2 | ASP A 84 | -28.166 | 7.855 | -12.915 | 1.00 34.27 | O | ATOM | 701 | O | VAL A 94 | -1.978 | -2.535 7.623 1.00 14.52 | O |
| ATOM | 617 | C | ASP A 84 | -27.249 | 3.759 | -11.720 | 1.00 20.29 | C | ATOM | 702 | N | TYR A 95 | -1.699 | -2.197 5.381 1.00 16.27 | N |
| ATOM | 618 | O | ASP A 84 | -28.414 | 3.758 | -11.318 | 1.00 20.67 | O | ATOM | 703 | CA | TYR A 95 | -0.255 | -2.072 5.430 1.00 18.23 | C |
| ATOM | 619 | N | ILE A 85 | -26.260 | 3.157 | -11.071 | 1.00 17.72 | N | ATOM | 704 | CB | TYR A 95 | 0.388 | -2.060 4.021 1.00 20.56 | C |
| ATOM | 620 | CA | ILE A 85 | -26.469 | 2.505 | -9.795 | 1.00 15.32 | C | ATOM | 705 | CG | TYR A 95 | 1.914 | -2.151 4.006 1.00 22.97 | C |
| ATOM | 621 | CB | ILE A 85 | -26.178 | 0.959 | -9.898 | 1.00 14.39 | C | ATOM | 706 | CD1 | TYR A 95 | 2.583 | -3.227 4.611 1.00 26.00 | C |
| ATOM | 622 | CG1 | ILE A 85 | -27.255 | 0.276 | -10.776 | 1.00 15.19 | C | ATOM | 707 | CE1 | TYR A 95 | 3.989 | -3.316 4.588 1.00 27.44 | C |
| ATOM | 623 | CD1 | ILE A 85 | -27.024 | -1.237 | -11.129 | 1.00 14.63 | C | ATOM | 708 | CZ | TYR A 95 | 4.711 | -2.322 3.963 1.00 26.69 | C |
| ATOM | 624 | CG2 | ILE A 85 | -26.105 | 0.370 | -8.491 | 1.00 12.58 | C | ATOM | 709 | OH | TYR A 95 | 6.081 | -2.366 3.940 1.00 27.85 | O |
| ATOM | 625 | C | ILE A 85 | -25.480 | 3.176 | -8.830 | 1.00 14.52 | C | ATOM | 710 | CE2 | TYR A 95 | 4.065 | -1.245 3.361 1.00 28.65 | C |
| ATOM | 626 | O | ILE A 85 | -24.284 | 3.198 | -9.102 | 1.00 14.43 | O | ATOM | 711 | CD2 | TYR A 95 | 2.676 | -1.176 3.376 1.00 25.60 | C |
| ATOM | 627 | N | LYS A 86 | -25.997 | 3.744 | -7.753 | 1.00 14.23 | N | ATOM | 712 | C | TYR A 95 | 0.121 | -0.815 6.229 1.00 18.43 | C |
| ATOM | 628 | CA | LYS A 86 | -25.180 | 4.329 | -6.685 | 1.00 14.15 | C | ATOM | 713 | O | TYR A 95 | -0.433 | 0.271 6.003 1.00 16.89 | O |
| ATOM | 629 | CB | LYS A 86 | -26.060 | 5.026 | -5.681 | 1.00 15.74 | C | ATOM | 714 | N | GLY A 96 | 1.101 | -0.967 7.129 1.00 18.90 | N |
| ATOM | 630 | CG | LYS A 86 | -26.631 | 6.342 | -6.286 | 1.00 17.61 | C | ATOM | 715 | CA | GLY A 96 | 1.432 | 0.090 8.121 1.00 20.04 | C |
| ATOM | 631 | CD | LYS A 86 | -27.560 | 7.086 | -5.312 | 1.00 17.93 | C | ATOM | 716 | C | GLY A 96 | 2.505 | 1.075 7.673 1.00 22.01 | C |
| ATOM | 632 | CE | LYS A 86 | -28.784 | 6.312 | -4.844 | 1.00 21.29 | C | ATOM | 717 | O | GLY A 96 | 2.715 | 2.117 8.314 1.00 21.43 | O |
| ATOM | 633 | NZ | LYS A 86 | -29.770 | 6.066 | -5.956 | 1.00 20.05 | N | ATOM | 718 | N | LYS A 97 | 3.164 | 0.770 6.561 1.00 22.00 | N |
| ATOM | 634 | C | LYS A 86 | -24.420 | 3.192 | -5.999 | 1.00 13.61 | C | ATOM | 719 | CA | LYS A 97 | 4.311 | 1.571 6.110 1.00 25.08 | C |
| ATOM | 635 | O | LYS A 86 | -25.017 | 2.205 | -5.607 | 1.00 11.64 | O | ATOM | 720 | CB | LYS A 97 | 5.612 | 0.751 6.240 1.00 25.58 | C |
| ATOM | 636 | N | MET A 87 | -23.121 | 3.389 | -5.846 | 1.00 13.21 | N | ATOM | 721 | CG | LYS A 97 | 6.024 | 0.494 7.714 1.00 29.56 | C |
| ATOM | 637 | CA | MET A 87 | -22.271 | 2.414 | -5.198 | 1.00 13.80 | C | ATOM | 722 | CD | LYS A 97 | 6.691 | -0.881 7.914 1.00 34.25 | C |
| ATOM | 638 | CB | MET A 87 | -21.526 | 1.633 | -6.272 | 1.00 13.55 | C | ATOM | 723 | CE | LYS A 97 | 5.646 | -2.034 7.921 1.00 37.27 | C |
| ATOM | 639 | CG | MET A 87 | -22.445 | 0.876 | -7.241 | 1.00 17.02 | C | ATOM | 724 | NZ | LYS A 97 | 6.210 | -3.436 8.102 1.00 33.52 | N |
| ATOM | 640 | SD | MET A 87 | -21.409 | -0.211 | -8.231 | 1.00 18.02 | S | ATOM | 725 | C | LYS A 97 | 4.182 | 2.181 4.720 1.00 24.78 | C |
| ATOM | 641 | CE | MET A 87 | -22.622 | -1.198 | -9.118 | 1.00 19.25 | C | ATOM | 726 | O | LYS A 97 | 5.189 | 2.324 3.995 1.00 26.46 | O |
| ATOM | 642 | C | MET A 87 | -21.274 | 3.082 | -4.271 | 1.00 13.81 | C | ATOM | 727 | N | LEU A 98 | 2.974 | 2.603 4.346 1.00 24.24 | N |

Fig. 5 cont.

| | | | | | | | | | | | | | | |
|---|---|---|---|---|---|---|---|---|---|---|---|---|---|---|
| ATOM | 728 | CA | LEU A 98 | 2.775 | 3.209 | 3.020 | 1.00 | 23.90 | C | ATOM | 813 | CG GLN A 108 | -1.309 9.034 -10.606 1.00 22.96 | C |
| ATOM | 729 | CB | LEU A 98 | 1.279 | 3.316 | 2.672 | 1.00 | 23.57 | C | ATOM | 814 | CD GLN A 108 | -0.116 9.844 -10.096 1.00 27.16 | C |
| ATOM | 730 | CG | LEU A 98 | 0.549 | 1.962 | 2.475 | 1.00 | 20.11 | C | ATOM | 815 | OE1 GLN A 108 | 1.035 9.395 -10.154 1.00 28.64 | O |
| ATOM | 731 | CD1 | LEU A 98 | -0.940 | 2.180 | 2.269 | 1.00 | 17.74 | C | ATOM | 816 | NE2 GLN A 108 | -0.395 11.005 -9.560 1.00 25.37 | N |
| ATOM | 732 | CD2 | LEU A 98 | 1.152 | 1.275 | 1.237 | 1.00 | 20.33 | C | ATOM | 817 | C GLN A 108 | -1.829 5.587 -12.198 1.00 20.17 | C |
| ATOM | 733 | C | LEU A 98 | 3.392 | 4.611 | 3.012 | 1.00 | 25.78 | C | ATOM | 818 | O GLN A 108 | -2.454 5.674 -13.266 1.00 20.30 | O |
| ATOM | 734 | O | LEU A 98 | 3.321 | 5.322 | 4.007 | 1.00 | 25.99 | O | ATOM | 819 | N GLU A 109 | -1.032 4.567 -11.886 1.00 18.70 | N |
| ATOM | 735 | N | ASN A 99 | 4.018 | 4.998 | 1.913 | 1.00 | 27.36 | N | ATOM | 820 | CA GLU A 109 | -0.904 3.386 -12.731 1.00 20.88 | C |
| ATOM | 736 | CA | ASN A 99 | 4.270 | 6.418 | 1.725 | 1.00 | 29.55 | C | ATOM | 821 | CB GLU A 109 | 0.168 2.433 -12.189 1.00 21.29 | C |
| ATOM | 737 | CB | ASN A 99 | 5.757 | 6.744 | 1.550 | 1.00 | 29.94 | C | ATOM | 822 | CG GLU A 109 | 0.508 1.310 -13.158 1.00 24.62 | C |
| ATOM | 738 | CG | ASN A 99 | 6.308 | 6.297 | 0.245 | 1.00 | 31.27 | C | ATOM | 823 | CD GLU A 109 | 1.770 0.558 -12.777 1.00 29.54 | C |
| ATOM | 739 | OD1 | ASN A 99 | 6.313 | 7.058 | -0.727 | 1.00 | 34.42 | O | ATOM | 824 | OE1 GLU A 109 | 1.632 -0.486 -12.109 1.00 34.40 | O |
| ATOM | 740 | ND2 | ASN A 99 | 6.789 | 5.054 | 0.197 | 1.00 | 32.82 | N | ATOM | 825 | OE2 GLU A 109 | 2.884 0.995 -13.154 1.00 29.34 | O |
| ATOM | 741 | C | ASN A 99 | 3.420 | 7.002 | 0.619 | 1.00 | 29.94 | C | ATOM | 826 | C GLU A 109 | -2.214 2.587 -12.867 1.00 20.81 | C |
| ATOM | 742 | O | ASN A 99 | 3.088 | 6.322 | -0.355 | 1.00 | 29.89 | O | ATOM | 827 | O GLU A 109 | -2.667 2.342 -13.987 1.00 20.79 | O |
| ATOM | 743 | N | ILE A 100 | 3.093 | 8.276 | 0.794 | 1.00 | 29.99 | N | ATOM | 828 | N SER A 110 | -2.787 2.155 -11.739 1.00 20.27 | N |
| ATOM | 744 | CA | ILE A 100 | 2.206 | 9.017 | -0.075 | 1.00 | 30.47 | C | ATOM | 829 | CA SER A 110 | -4.006 1.316 -11.800 1.00 20.75 | C |
| ATOM | 745 | CB | ILE A 100 | 1.976 | 10.453 | 0.530 | 1.00 | 31.42 | C | ATOM | 830 | CB SER A 110 | -4.388 0.825 -10.389 1.00 21.77 | C |
| ATOM | 746 | CG1 | ILE A 100 | 0.609 | 11.058 | 0.155 | 1.00 | 34.14 | C | ATOM | 831 | OG SER A 110 | -4.604 1.924 -9.553 1.00 23.56 | O |
| ATOM | 747 | CD1 | ILE A 100 | -0.202 | 10.310 | -0.901 | 1.00 | 39.97 | C | ATOM | 832 | C SER A 110 | -5.162 2.073 -12.453 1.00 20.15 | C |
| ATOM | 748 | CG2 | ILE A 100 | 3.179 | 11.364 | 0.276 | 1.00 | 31.60 | C | ATOM | 833 | O SER A 110 | -5.759 1.596 -13.406 1.00 20.50 | O |
| ATOM | 749 | C | ILE A 100 | 2.681 | 9.060 | -1.537 | 1.00 | 29.15 | C | ATOM | 834 | N VAL A 111 | -5.477 3.261 -11.960 1.00 20.17 | N |
| ATOM | 750 | O | ILE A 100 | 1.852 | 9.038 | -2.441 | 1.00 | 27.86 | O | ATOM | 835 | CA VAL A 111 | -6.569 4.033 -12.542 1.00 20.94 | C |
| ATOM | 751 | N | ARG A 101 | 3.995 | 9.112 | -1.779 | 1.00 | 29.04 | N | ATOM | 836 | CB VAL A 111 | -6.926 5.238 -11.664 1.00 21.05 | C |
| ATOM | 752 | CA | ARG A 101 | 4.517 | 9.154 | -3.155 | 1.00 | 27.87 | C | ATOM | 837 | CG1 VAL A 111 | -7.980 6.113 -12.355 1.00 21.04 | C |
| ATOM | 753 | CB | ARG A 101 | 6.012 | 9.521 | -3.204 | 1.00 | 28.14 | C | ATOM | 838 | CG2 VAL A 111 | -7.420 4.761 -10.266 1.00 16.85 | C |
| ATOM | 754 | CG | ARG A 101 | 6.319 | 10.934 | -2.680 | 1.00 | 29.43 | C | ATOM | 839 | C VAL A 111 | -6.220 4.448 -13.989 1.00 22.59 | C |
| ATOM | 755 | CD | ARG A 101 | 7.813 | 11.148 | -2.354 | 1.00 | 28.51 | C | ATOM | 840 | O VAL A 111 | -7.043 4.302 -14.899 1.00 22.82 | O |
| ATOM | 756 | NE | ARG A 101 | 8.313 | 10.179 | -1.377 | 1.00 | 30.83 | N | ATOM | 841 | N GLY A 112 | -4.996 4.944 -14.192 1.00 23.08 | N |
| ATOM | 757 | CZ | ARG A 101 | 8.155 | 10.257 | -0.053 | 1.00 | 30.05 | C | ATOM | 842 | CA GLY A 112 | -4.427 5.177 -15.541 1.00 23.43 | C |
| ATOM | 758 | NH1 | ARG A 101 | 7.505 | 11.271 | 0.506 | 1.00 | 32.36 | N | ATOM | 843 | C GLY A 112 | -4.469 4.075 -16.568 1.00 23.80 | C |
| ATOM | 759 | NH2 | ARG A 101 | 8.667 | 9.307 | 0.724 | 1.00 | 31.98 | N | ATOM | 844 | O GLY A 112 | -5.125 4.364 -17.658 1.00 25.74 | O |
| ATOM | 760 | C | ARG A 101 | 4.312 | 7.812 | -3.823 | 1.00 | 27.58 | C | ATOM | 845 | N ASN A 113 | -4.217 2.845 -16.243 1.00 23.54 | N |
| ATOM | 761 | O | ARG A 101 | 3.899 | 7.748 | -4.977 | 1.00 | 27.18 | O | ATOM | 846 | CA ASN A 113 | -4.414 1.622 -17.071 1.00 23.79 | C |
| ATOM | 762 | N | SER A 102 | 4.621 | 6.752 | -3.087 | 1.00 | 26.85 | N | ATOM | 847 | CB ASN A 113 | -4.057 0.340 -16.253 1.00 23.61 | C |
| ATOM | 763 | CA | SER A 102 | 4.414 | 5.384 | -3.537 | 1.00 | 26.68 | C | ATOM | 848 | CG ASN A 113 | -4.307 -1.034 -17.013 1.00 25.91 | C |
| ATOM | 764 | CB | SER A 102 | 4.917 | 4.405 | -2.488 | 1.00 | 27.36 | C | ATOM | 849 | OD1 ASN A 113 | -5.432 -1.610 -17.003 1.00 24.02 | O |
| ATOM | 765 | OG | SER A 102 | 4.747 | 3.068 | -2.906 | 1.00 | 33.06 | O | ATOM | 850 | ND2 ASN A 113 | -3.223 -1.596 -17.589 1.00 28.23 | N |
| ATOM | 766 | C | SER A 102 | 2.952 | 5.125 | -3.871 | 1.00 | 25.23 | C | ATOM | 851 | C ASN A 113 | -5.859 1.570 -17.550 1.00 24.00 | C |
| ATOM | 767 | O | SER A 102 | 2.649 | 4.563 | -4.926 | 1.00 | 24.56 | O | ATOM | 852 | O ASN A 113 | -6.147 1.364 -18.748 1.00 23.38 | O |
| ATOM | 768 | N | VAL A 103 | 2.064 | 5.557 | -2.974 | 1.00 | 22.78 | N | ATOM | 853 | N ARG A 114 | -6.781 1.811 -16.619 1.00 23.30 | N |
| ATOM | 769 | CA | VAL A 103 | 0.639 | 5.396 | -3.152 | 1.00 | 21.81 | C | ATOM | 854 | CA ARG A 114 | -8.201 1.628 -16.933 1.00 23.78 | C |
| ATOM | 770 | CB | VAL A 103 | -0.126 | 5.791 | -1.870 | 1.00 | 21.23 | C | ATOM | 855 | CB ARG A 114 | -9.033 1.392 -15.661 1.00 24.20 | C |
| ATOM | 771 | CG1 | VAL A 103 | -1.600 | 6.040 | -2.148 | 1.00 | 19.57 | C | ATOM | 856 | CG ARG A 114 | -8.764 0.062 -14.970 1.00 23.94 | C |
| ATOM | 772 | CG2 | VAL A 103 | 0.086 | 4.710 | -0.805 | 1.00 | 20.91 | C | ATOM | 857 | CD ARG A 114 | -9.000 -1.153 -15.855 1.00 25.83 | C |
| ATOM | 773 | C | VAL A 103 | 0.130 | 6.142 | -4.382 | 1.00 | 22.08 | C | ATOM | 858 | NE ARG A 114 | -9.079 -2.429 -15.123 1.00 27.37 | N |
| ATOM | 774 | O | VAL A 103 | -0.597 | 5.559 | -5.193 | 1.00 | 21.04 | O | ATOM | 859 | CZ ARG A 114 | -8.033 -3.166 -14.730 1.00 26.96 | C |
| ATOM | 775 | N | ARG A 104 | 0.511 | 7.418 | -4.517 | 1.00 | 22.54 | N | ATOM | 860 | NH1 ARG A 114 | -6.786 -2.766 -14.931 1.00 28.05 | N |
| ATOM | 776 | CA | ARG A 104 | 0.170 | 8.210 | -5.698 | 1.00 | 23.86 | C | ATOM | 861 | NH2 ARG A 114 | -8.247 -4.307 -14.108 1.00 28.02 | N |
| ATOM | 777 | CB | ARG A 104 | 0.774 | 9.623 | -5.612 | 1.00 | 24.08 | C | ATOM | 862 | C ARG A 114 | -8.757 2.738 -17.787 1.00 24.32 | C |
| ATOM | 778 | CG | ARG A 104 | 0.020 | 10.547 | -4.706 | 1.00 | 24.88 | C | ATOM | 863 | O ARG A 114 | -9.502 2.468 -18.731 1.00 24.31 | O |
| ATOM | 779 | CD | ARG A 104 | 0.679 | 11.942 | -4.574 | 1.00 | 26.28 | C | ATOM | 864 | N LEU A 115 | -8.362 3.978 -17.481 1.00 24.75 | N |
| ATOM | 780 | NE | ARG A 104 | -0.156 | 12.755 | -3.692 | 1.00 | 31.89 | N | ATOM | 865 | CA LEU A 115 | -8.721 5.144 -18.267 1.00 26.48 | C |
| ATOM | 781 | CZ | ARG A 104 | 0.225 | 13.336 | -2.551 | 1.00 | 34.35 | C | ATOM | 866 | CB LEU A 115 | -8.053 6.377 -17.686 1.00 26.29 | C |
| ATOM | 782 | NH1 | ARG A 104 | 1.492 | 13.265 | -2.115 | 1.00 | 33.73 | N | ATOM | 867 | CG LEU A 115 | -8.802 7.441 -16.908 1.00 27.58 | C |
| ATOM | 783 | NH2 | ARG A 104 | -0.683 | 14.015 | -1.850 | 1.00 | 32.46 | N | ATOM | 868 | CD1 LEU A 115 | -10.231 7.078 -16.469 1.00 27.17 | C |
| ATOM | 784 | C | ARG A 104 | 0.622 | 7.538 | -6.985 | 1.00 | 23.65 | C | ATOM | 869 | CD2 LEU A 115 | -7.967 7.973 -15.745 1.00 26.29 | C |
| ATOM | 785 | O | ARG A 104 | -0.151 | 7.444 | -7.951 | 1.00 | 22.84 | O | ATOM | 870 | C LEU A 115 | -8.328 5.004 -19.743 1.00 28.63 | C |
| ATOM | 786 | N | ASN A 105 | 1.871 | 7.082 | -7.007 | 1.00 | 23.13 | N | ATOM | 871 | O LEU A 115 | -9.103 5.380 -20.624 1.00 28.25 | O |
| ATOM | 787 | CA | ASN A 105 | 2.360 | 6.359 | -8.201 | 1.00 | 23.56 | C | ATOM | 872 | N LYS A 116 | -7.144 4.447 -20.004 1.00 30.42 | N |
| ATOM | 788 | CB | ASN A 105 | 3.848 | 5.991 | -8.079 | 1.00 | 24.19 | C | ATOM | 873 | CA LYS A 116 | -6.713 4.217 -21.379 1.00 32.86 | C |
| ATOM | 789 | CG | ASN A 105 | 4.783 | 7.166 | -8.395 | 1.00 | 29.21 | C | ATOM | 874 | CB LYS A 116 | -5.218 3.942 -21.460 1.00 32.54 | C |
| ATOM | 790 | OD1 | ASN A 105 | 4.348 | 8.300 | -8.624 | 1.00 | 33.91 | O | ATOM | 875 | CG LYS A 116 | -4.691 4.167 -22.866 1.00 34.82 | C |
| ATOM | 791 | ND2 | ASN A 105 | 6.095 | 6.888 | -8.394 | 1.00 | 33.76 | N | ATOM | 876 | CD LYS A 116 | -3.461 3.363 -23.155 1.00 36.12 | C |
| ATOM | 792 | C | ASN A 105 | 1.509 | 5.110 | -8.513 | 1.00 | 22.39 | C | ATOM | 877 | CE LYS A 116 | -3.012 3.646 -24.579 1.00 35.85 | C |
| ATOM | 793 | O | ASN A 105 | 1.178 | 4.848 | -9.687 | 1.00 | 22.78 | O | ATOM | 878 | NZ LYS A 116 | -2.125 2.563 -25.062 1.00 32.82 | N |
| ATOM | 794 | N | ALA A 106 | 1.103 | 4.397 | -7.464 | 1.00 | 20.69 | N | ATOM | 879 | C LYS A 116 | -7.462 3.056 -22.012 1.00 33.76 | C |
| ATOM | 795 | CA | ALA A 106 | 0.336 | 3.141 | -7.628 | 1.00 | 20.01 | C | ATOM | 880 | O LYS A 116 | -7.719 3.065 -23.215 1.00 34.48 | O |
| ATOM | 796 | CB | ALA A 106 | 0.299 | 2.328 | -6.325 | 1.00 | 20.43 | C | ATOM | 881 | N LYS A 117 | -7.785 2.060 -21.202 1.00 34.73 | N |
| ATOM | 797 | C | ALA A 106 | -1.066 | 3.349 | -8.147 | 1.00 | 20.10 | C | ATOM | 882 | CA LYS A 117 | -8.512 0.879 -21.650 1.00 37.08 | C |
| ATOM | 798 | O | ALA A 106 | -1.495 | 2.600 | -9.047 | 1.00 | 19.28 | O | ATOM | 883 | CB LYS A 117 | -8.511 -0.192 -20.542 1.00 36.71 | C |
| ATOM | 799 | N | PHE A 107 | -1.807 | 4.320 | -7.574 | 1.00 | 19.39 | N | ATOM | 884 | CG LYS A 117 | -9.433 -1.409 -20.701 1.00 38.38 | C |
| ATOM | 800 | CA | PHE A 107 | -3.163 | 4.618 | -8.098 | 1.00 | 18.77 | C | ATOM | 885 | CD LYS A 117 | -9.350 -2.329 -19.443 1.00 38.60 | C |
| ATOM | 801 | CB | PHE A 107 | -4.133 | 5.247 | -7.044 | 1.00 | 20.03 | C | ATOM | 886 | CE LYS A 117 | -10.625 -3.168 -19.214 1.00 41.44 | C |
| ATOM | 802 | CG | PHE A 107 | -3.923 | 6.716 | -6.762 | 1.00 | 19.58 | C | ATOM | 887 | NZ LYS A 117 | -10.508 -4.209 -18.136 1.00 39.72 | N |
| ATOM | 803 | CD1 | PHE A 107 | -4.131 | 7.685 | -7.757 | 1.00 | 20.71 | C | ATOM | 888 | C LYS A 117 | -9.928 1.241 -22.081 1.00 37.94 | C |
| ATOM | 804 | CE1 | PHE A 107 | -3.965 | 9.033 | -7.492 | 1.00 | 22.92 | C | ATOM | 889 | O LYS A 117 | -10.416 0.681 -23.062 1.00 38.74 | O |
| ATOM | 805 | CZ | PHE A 107 | -3.608 | 9.449 | -6.201 | 1.00 | 22.80 | C | ATOM | 890 | N PHE A 118 | -10.570 2.186 -21.395 1.00 38.84 | N |
| ATOM | 806 | CE2 | PHE A 107 | -3.440 | 8.519 | -5.192 | 1.00 | 22.83 | C | ATOM | 891 | CA PHE A 118 | -12.000 2.398 -21.612 1.00 40.89 | C |
| ATOM | 807 | CD2 | PHE A 107 | -3.603 | 7.138 | -5.475 | 1.00 | 21.64 | C | ATOM | 892 | CB PHE A 118 | -12.765 2.579 -20.312 1.00 40.44 | C |
| ATOM | 808 | C | PHE A 107 | -3.134 | 5.319 | -9.479 | 1.00 | 19.03 | C | ATOM | 893 | CG PHE A 118 | -12.998 1.297 -19.621 1.00 41.09 | C |
| ATOM | 809 | O | PHE A 107 | -4.029 | 5.137 | -10.271 | 1.00 | 18.13 | O | ATOM | 894 | CD1 PHE A 118 | -13.035 1.230 -18.253 1.00 41.57 | C |
| ATOM | 810 | N | GLN A 108 | -2.083 | 6.076 | -9.792 | 1.00 | 19.02 | N | ATOM | 895 | CE1 PHE A 118 | -13.219 0.013 -17.627 1.00 43.05 | C |
| ATOM | 811 | CA | GLN A 108 | -1.992 | 6.671 | -11.141 | 1.00 | 19.98 | C | ATOM | 896 | CZ PHE A 118 | -13.358 -1.163 -18.385 1.00 42.69 | C |
| ATOM | 812 | CB | GLN A 108 | -0.893 | 7.726 | -11.246 | 1.00 | 20.03 | C | ATOM | 897 | CE2 PHE A 118 | -13.301 -1.104 -19.766 1.00 42.42 | C |

Fig. 5 cont.

| | | | | | | | |
|---|---|---|---|---|---|---|---|
| ATOM | 898 | CD2 PHE A 118 | -13.118 0.119 -20.372 1.00 41.93 | C | ATOM | 983 | CD1 PHE A 130 | -9.877 9.894 -8.371 1.00 21.73 | C |
| ATOM | 899 | C PHE A 118 | -12.463 3.352 -22.686 1.00 42.54 | C | ATOM | 984 | CE1 PHE A 130 | -10.030 8.885 -7.390 1.00 20.87 | C |
| ATOM | 900 | O PHE A 118 | -12.126 3.167 -23.835 1.00 44.67 | O | ATOM | 985 | CZ PHE A 130 | -9.001 7.995 -7.172 1.00 21.57 | C |
| ATOM | 901 | N GLY A 119 | -13.315 4.297 -22.330 1.00 43.57 | N | ATOM | 986 | CE2 PHE A 130 | -7.808 8.087 -7.906 1.00 20.78 | C |
| ATOM | 902 | CA GLY A 119 | -13.856 5.239 -23.285 1.00 45.66 | C | ATOM | 987 | CD2 PHE A 130 | -7.659 9.093 -8.868 1.00 19.61 | C |
| ATOM | 903 | C GLY A 119 | -12.898 6.397 -23.281 1.00 46.74 | C | ATOM | 988 | C PHE A 130 | -7.389 12.622 -8.532 1.00 21.90 | C |
| ATOM | 904 | O GLY A 119 | -13.214 7.512 -23.755 1.00 47.03 | O | ATOM | 989 | O PHE A 130 | -7.613 12.766 -7.338 1.00 21.06 | O |
| ATOM | 905 | N GLY A 120 | -11.725 6.109 -22.716 1.00 47.10 | N | ATOM | 990 | N THR A 131 | -6.165 12.592 -9.028 1.00 22.96 | N |
| ATOM | 906 | CA GLY A 120 | -10.684 7.078 -22.610 1.00 48.58 | C | ATOM | 991 | CA THR A 131 | -4.980 12.858 -8.204 1.00 22.33 | C |
| ATOM | 907 | C GLY A 120 | -10.043 7.319 -23.948 1.00 48.99 | C | ATOM | 992 | CB THR A 131 | -3.751 13.066 -9.111 1.00 22.68 | C |
| ATOM | 908 | O GLY A 120 | -9.453 6.401 -24.530 1.00 49.39 | O | ATOM | 993 | OG1 THR A 131 | -3.488 11.867 -9.835 1.00 22.43 | O |
| ATOM | 909 | N SER A 121 | -10.202 8.559 -24.420 1.00 49.73 | N | ATOM | 994 | CG2 THR A 131 | -2.497 13.394 -8.261 1.00 20.84 | C |
| ATOM | 910 | CA SER A 121 | -9.407 9.147 -25.499 1.00 50.08 | C | ATOM | 995 | C THR A 131 | -5.120 14.071 -7.248 1.00 23.31 | C |
| ATOM | 911 | CB SER A 121 | -9.912 10.560 -25.838 1.00 50.38 | C | ATOM | 996 | O THR A 131 | -4.836 13.954 -6.050 1.00 22.15 | O |
| ATOM | 912 | OG SER A 121 | -11.223 10.814 -25.339 1.00 51.22 | O | ATOM | 997 | N SER A 132 | -5.543 15.226 -7.781 1.00 23.05 | N |
| ATOM | 913 | C SER A 121 | -7.977 9.243 -24.973 1.00 50.11 | C | ATOM | 998 | CA SER A 132 | -5.718 16.441 -6.981 1.00 24.84 | C |
| ATOM | 914 | O SER A 121 | -7.239 8.254 -25.008 1.00 50.47 | O | ATOM | 999 | CB SER A 132 | -6.141 17.645 -7.834 1.00 25.37 | C |
| ATOM | 915 | N ASP A 122 | -7.598 10.430 -24.488 1.00 49.88 | N | ATOM | 1000 | OG SER A 132 | -5.125 17.959 -8.767 1.00 28.47 | O |
| ATOM | 916 | CA ASP A 122 | -6.404 10.594 -23.634 1.00 49.14 | C | ATOM | 1001 | C SER A 132 | -6.652 16.317 -5.773 1.00 24.62 | C |
| ATOM | 917 | CB ASP A 122 | -5.153 10.924 -24.429 1.00 49.40 | C | ATOM | 1002 | O SER A 132 | -6.534 17.090 -4.838 1.00 24.90 | O |
| ATOM | 918 | CG ASP A 122 | -4.473 9.673 -24.972 1.00 51.06 | C | ATOM | 1003 | N LEU A 133 | -7.581 15.368 -5.780 1.00 24.16 | N |
| ATOM | 919 | OD1 ASP A 122 | -4.473 8.620 -24.277 1.00 52.39 | O | ATOM | 1004 | CA LEU A 133 | -8.405 15.112 -4.594 1.00 23.34 | C |
| ATOM | 920 | OD2 ASP A 122 | -3.935 9.737 -26.100 1.00 52.13 | O | ATOM | 1005 | CB LEU A 133 | -9.417 13.976 -4.862 1.00 24.55 | C |
| ATOM | 921 | C ASP A 122 | -6.632 11.537 -22.449 1.00 47.91 | C | ATOM | 1006 | CG LEU A 133 | -10.453 14.138 -6.002 1.00 23.24 | C |
| ATOM | 922 | O ASP A 122 | -7.076 12.682 -22.600 1.00 48.22 | O | ATOM | 1007 | CD1 LEU A 133 | -11.361 12.873 -6.132 1.00 21.33 | C |
| ATOM | 923 | N ASN A 123 | -6.316 11.020 -21.266 1.00 46.23 | N | ATOM | 1008 | CD2 LEU A 133 | -11.299 15.404 -5.867 1.00 25.79 | C |
| ATOM | 924 | CA ASN A 123 | -7.027 11.388 -20.053 1.00 44.46 | C | ATOM | 1009 | C LEU A 133 | -7.565 14.812 -3.336 1.00 23.68 | C |
| ATOM | 925 | CB ASN A 123 | -7.832 10.174 -19.571 1.00 44.50 | C | ATOM | 1010 | O LEU A 133 | -7.993 15.072 -2.196 1.00 23.01 | O |
| ATOM | 926 | CG ASN A 123 | -8.488 9.424 -20.711 1.00 43.78 | C | ATOM | 1011 | N PHE A 134 | -6.363 14.296 -3.540 1.00 23.05 | N |
| ATOM | 927 | OD1 ASN A 123 | -9.528 9.842 -21.221 1.00 42.74 | O | ATOM | 1012 | CA PHE A 134 | -5.522 13.846 -2.422 1.00 24.20 | C |
| ATOM | 928 | ND2 ASN A 123 | -7.870 8.318 -21.136 1.00 42.93 | N | ATOM | 1013 | CB PHE A 134 | -5.102 12.391 -2.625 1.00 23.33 | C |
| ATOM | 929 | C ASN A 123 | -6.145 11.900 -18.919 1.00 43.26 | C | ATOM | 1014 | CG PHE A 134 | -6.229 11.496 -3.015 1.00 23.10 | C |
| ATOM | 930 | O ASN A 123 | -6.477 11.723 -17.758 1.00 42.50 | O | ATOM | 1015 | CD1 PHE A 134 | -6.527 11.285 -4.365 1.00 24.36 | C |
| ATOM | 931 | N ASP A 124 | -5.036 12.543 -19.269 1.00 41.93 | N | ATOM | 1016 | CE1 PHE A 134 | -7.598 10.473 -4.750 1.00 22.08 | C |
| ATOM | 932 | CA ASP A 124 | -4.100 13.073 -18.289 1.00 41.08 | C | ATOM | 1017 | CZ PHE A 134 | -8.362 9.846 -3.779 1.00 23.06 | C |
| ATOM | 933 | CB ASP A 124 | -2.871 13.698 -18.967 1.00 41.93 | C | ATOM | 1018 | CE2 PHE A 134 | -8.070 10.046 -2.434 1.00 23.57 | C |
| ATOM | 934 | CG ASP A 124 | -2.305 12.828 -20.067 1.00 44.66 | C | ATOM | 1019 | CD2 PHE A 134 | -6.998 10.872 -2.058 1.00 22.86 | C |
| ATOM | 935 | OD1 ASP A 124 | -2.077 11.613 -19.825 1.00 47.45 | O | ATOM | 1020 | C PHE A 134 | -4.282 14.725 -2.230 1.00 25.38 | C |
| ATOM | 936 | OD2 ASP A 124 | -2.092 13.362 -21.183 1.00 48.59 | O | ATOM | 1021 | O PHE A 134 | -3.334 14.327 -1.542 1.00 24.69 | O |
| ATOM | 937 | C ASP A 124 | -4.757 14.095 -17.380 1.00 39.56 | C | ATOM | 1022 | N LYS A 135 | -4.312 15.916 -2.832 1.00 26.84 | N |
| ATOM | 938 | O ASP A 124 | -4.581 14.025 -16.169 1.00 39.11 | O | ATOM | 1023 | CA LYS A 135 | -3.164 16.835 -2.830 1.00 28.88 | C |
| ATOM | 939 | N GLU A 125 | -5.495 15.043 -17.965 1.00 37.61 | N | ATOM | 1024 | CB LYS A 135 | -3.472 18.058 -3.702 1.00 28.34 | C |
| ATOM | 940 | CA GLU A 125 | -6.236 16.043 -17.188 1.00 36.49 | C | ATOM | 1025 | CG LYS A 135 | -4.727 18.800 -3.248 1.00 29.80 | C |
| ATOM | 941 | CB GLU A 125 | -6.944 17.068 -18.093 1.00 36.62 | C | ATOM | 1026 | CD LYS A 135 | -5.080 19.971 -4.164 1.00 31.35 | C |
| ATOM | 942 | CG GLU A 125 | -6.187 18.412 -18.272 1.00 38.65 | C | ATOM | 1027 | CE LYS A 135 | -4.086 21.116 -4.022 1.00 35.96 | C |
| ATOM | 943 | CD GLU A 125 | -6.844 19.340 -19.305 1.00 40.10 | C | ATOM | 1028 | NZ LYS A 135 | -3.888 21.532 -2.588 1.00 39.34 | N |
| ATOM | 944 | OE1 GLU A 125 | -6.313 19.438 -20.455 1.00 45.16 | O | ATOM | 1029 | C LYS A 135 | -2.770 17.273 -1.412 1.00 28.68 | C |
| ATOM | 945 | OE2 GLU A 125 | -7.886 19.972 -18.972 1.00 43.21 | O | ATOM | 1030 | O LYS A 135 | -1.621 17.652 -1.176 1.00 29.54 | O |
| ATOM | 946 | C GLU A 125 | -7.251 15.367 -16.255 1.00 33.81 | C | ATOM | 1031 | N ASP A 136 | -3.719 17.189 -0.478 1.00 29.04 | N |
| ATOM | 947 | O GLU A 125 | -7.358 15.734 -15.100 1.00 33.00 | O | ATOM | 1032 | CA ASP A 136 | -3.537 17.692 0.891 1.00 29.70 | C |
| ATOM | 948 | N LEU A 126 | -7.982 14.386 -16.778 1.00 31.21 | N | ATOM | 1033 | CB ASP A 136 | -4.795 18.454 1.361 1.00 30.29 | C |
| ATOM | 949 | CA LEU A 126 | -8.944 13.622 -15.982 1.00 29.23 | C | ATOM | 1034 | CG ASP A 136 | -5.012 19.781 0.618 1.00 32.82 | C |
| ATOM | 950 | CB LEU A 126 | -9.680 12.596 -16.853 1.00 29.55 | C | ATOM | 1035 | OD1 ASP A 136 | -4.021 20.447 0.244 1.00 34.17 | O |
| ATOM | 951 | CG LEU A 126 | -10.717 11.745 -16.114 1.00 28.28 | C | ATOM | 1036 | OD2 ASP A 136 | -6.190 20.156 0.407 1.00 36.15 | O |
| ATOM | 952 | CD1 LEU A 126 | -11.732 12.648 -15.369 1.00 26.13 | C | ATOM | 1037 | C ASP A 136 | -3.165 16.611 1.915 1.00 29.00 | C |
| ATOM | 953 | CD2 LEU A 126 | -11.392 10.807 -17.100 1.00 29.26 | C | ATOM | 1038 | O ASP A 136 | -3.067 16.881 3.117 1.00 28.95 | O |
| ATOM | 954 | C LEU A 126 | -8.267 12.913 -14.807 1.00 28.02 | C | ATOM | 1039 | N GLU A 137 | -2.980 15.387 1.440 1.00 27.78 | N |
| ATOM | 955 | O LEU A 126 | -8.721 13.043 -13.655 1.00 26.87 | O | ATOM | 1040 | CA GLU A 137 | -2.684 14.263 2.302 1.00 27.04 | C |
| ATOM | 956 | N LEU A 127 | -7.201 12.169 -15.102 1.00 26.94 | N | ATOM | 1041 | CB GLU A 137 | -3.323 12.970 1.749 1.00 26.80 | C |
| ATOM | 957 | CA LEU A 127 | -6.390 11.520 -14.055 1.00 26.31 | C | ATOM | 1042 | CG GLU A 137 | -4.813 13.128 1.400 1.00 28.30 | C |
| ATOM | 958 | CB LEU A 127 | -5.256 10.662 -14.640 1.00 26.31 | C | ATOM | 1043 | CD GLU A 137 | -5.651 13.546 2.612 1.00 30.57 | C |
| ATOM | 959 | CG LEU A 127 | -4.422 9.846 -13.636 1.00 26.03 | C | ATOM | 1044 | OE1 GLU A 137 | -4.567 14.376 2.468 1.00 29.62 | O |
| ATOM | 960 | CD1 LEU A 127 | -5.303 8.868 -12.786 1.00 23.40 | C | ATOM | 1045 | OE2 GLU A 137 | -5.376 13.029 3.717 1.00 33.81 | O |
| ATOM | 961 | CD2 LEU A 127 | -3.280 9.106 -14.330 1.00 25.09 | C | ATOM | 1046 | C GLU A 137 | -1.200 14.096 2.417 1.00 26.32 | C |
| ATOM | 962 | C LEU A 127 | -5.835 12.518 -13.062 1.00 26.60 | C | ATOM | 1047 | O GLU A 137 | -0.503 14.062 1.409 1.00 25.84 | O |
| ATOM | 963 | O LEU A 127 | -5.753 12.229 -11.885 1.00 25.56 | O | ATOM | 1048 | N TYR A 138 | -0.709 14.007 3.648 1.00 25.72 | N |
| ATOM | 964 | N GLN A 128 | -5.460 13.705 -13.532 1.00 26.82 | N | ATOM | 1049 | CA TYR A 138 | 0.714 13.801 3.868 1.00 26.11 | C |
| ATOM | 965 | CA GLN A 128 | -4.912 14.710 -12.626 1.00 27.78 | C | ATOM | 1050 | CB TYR A 138 | 1.273 14.858 4.829 1.00 26.77 | C |
| ATOM | 966 | CB GLN A 128 | -4.184 15.828 -13.422 1.00 27.84 | C | ATOM | 1051 | CG TYR A 138 | 1.458 16.155 4.115 1.00 26.92 | C |
| ATOM | 967 | CG GLN A 128 | -3.316 16.792 -12.591 1.00 30.80 | C | ATOM | 1052 | CD1 TYR A 138 | 0.372 17.022 3.887 1.00 28.26 | C |
| ATOM | 968 | CD GLN A 128 | -2.517 16.123 -11.464 1.00 34.36 | C | ATOM | 1053 | CE1 TYR A 138 | 0.553 18.234 3.171 1.00 27.21 | C |
| ATOM | 969 | OE1 GLN A 128 | -1.638 15.286 -11.702 1.00 35.51 | O | ATOM | 1054 | CZ TYR A 138 | 1.828 18.540 2.689 1.00 27.98 | C |
| ATOM | 970 | NE2 GLN A 128 | -2.823 16.504 -10.228 1.00 34.67 | N | ATOM | 1055 | OH TYR A 138 | 2.085 19.706 2.001 1.00 29.40 | O |
| ATOM | 971 | C GLN A 128 | -6.021 15.283 -11.745 1.00 26.95 | C | ATOM | 1056 | CE2 TYR A 138 | 2.897 17.689 2.908 1.00 29.96 | C |
| ATOM | 972 | O GLN A 128 | -5.783 15.658 -10.609 1.00 27.22 | O | ATOM | 1057 | CD2 TYR A 138 | 2.706 16.500 3.605 1.00 26.85 | C |
| ATOM | 973 | N SER A 129 | -7.247 15.334 -12.256 1.00 26.23 | N | ATOM | 1058 | C TYR A 138 | 1.070 12.391 4.313 1.00 26.67 | C |
| ATOM | 974 | CA SER A 129 | -8.383 15.787 -11.431 1.00 25.76 | C | ATOM | 1059 | O TYR A 138 | 2.212 11.922 4.072 1.00 27.38 | O |
| ATOM | 975 | CB SER A 129 | -9.646 15.968 -12.294 1.00 26.36 | C | ATOM | 1060 | N LYS A 139 | 0.084 11.709 4.895 1.00 25.98 | N |
| ATOM | 976 | OG SER A 129 | -10.177 14.717 -12.728 1.00 30.05 | O | ATOM | 1061 | CA LYS A 139 | 0.277 10.372 5.464 1.00 26.30 | C |
| ATOM | 977 | C SER A 129 | -8.646 14.804 -10.284 1.00 24.80 | C | ATOM | 1062 | CB LYS A 139 | 0.438 10.459 6.988 1.00 25.42 | C |
| ATOM | 978 | O SER A 129 | -9.036 15.196 -9.160 1.00 24.13 | O | ATOM | 1063 | CG LYS A 139 | -0.805 11.006 7.694 1.00 28.42 | C |
| ATOM | 979 | N PHE A 130 | -8.445 13.515 -10.577 1.00 23.56 | N | ATOM | 1064 | CD LYS A 139 | -0.749 10.907 9.215 1.00 30.43 | C |
| ATOM | 980 | CA PHE A 130 | -8.528 12.486 -9.541 1.00 22.96 | C | ATOM | 1065 | CE LYS A 139 | -2.132 11.160 9.774 1.00 34.31 | C |
| ATOM | 981 | CB PHE A 130 | -8.525 11.080 -10.142 1.00 22.15 | C | ATOM | 1066 | NZ LYS A 139 | -2.109 11.802 11.127 1.00 38.32 | N |
| ATOM | 982 | CG PHE A 130 | -8.693 9.997 -9.112 1.00 22.23 | C | ATOM | 1067 | C LYS A 139 | -0.942 9.510 5.136 1.00 24.62 | C |

Fig. 5 cont.

```
ATOM 1068 O   LYS A 139   -2.018 10.045  4.895 1.00 24.89   O
ATOM 1069 N   ILE A 140   -0.776  8.184  5.137 1.00 22.84   N
ATOM 1070 CA  ILE A 140   -1.906  7.275  4.896 1.00 22.68   C
ATOM 1071 CB  ILE A 140   -1.911  6.599  3.465 1.00 23.23   C
ATOM 1072 CG1 ILE A 140   -1.014  7.304  2.463 1.00 25.12   C
ATOM 1073 CD1 ILE A 140   -1.548  8.627  1.970 1.00 31.60   C
ATOM 1074 CG2 ILE A 140   -3.362  6.215  3.005 1.00 23.15   C
ATOM 1075 C   ILE A 140   -1.688  6.123  5.841 1.00 21.14   C
ATOM 1076 O   ILE A 140   -1.215  5.060  5.406 1.00 19.83   O
ATOM 1077 N   PRO A 141   -2.000  6.321  7.140 1.00 19.61   N
ATOM 1078 CA  PRO A 141   -1.624  5.235  8.023 1.00 18.57   C
ATOM 1079 CB  PRO A 141   -1.610  5.903  9.417 1.00 18.65   C
ATOM 1080 CG  PRO A 141   -2.680  6.973  9.314 1.00 20.23   C
ATOM 1081 CD  PRO A 141   -2.641  7.453  7.858 1.00 20.28   C
ATOM 1082 C   PRO A 141   -2.589  4.039  8.009 1.00 17.28   C
ATOM 1083 O   PRO A 141   -3.735  4.153  7.569 1.00 15.36   O
ATOM 1084 N   ARG A 142   -2.104  2.917  8.527 1.00 16.14   N
ATOM 1085 CA  ARG A 142   -2.978  1.801  8.899 1.00 16.67   C
ATOM 1086 CB  ARG A 142   -2.189  0.753  9.688 1.00 15.75   C
ATOM 1087 CG  ARG A 142   -3.039 -0.467 10.071 1.00 17.67   C
ATOM 1088 CD  ARG A 142   -2.212 -1.462 10.802 1.00 19.29   C
ATOM 1089 NE  ARG A 142   -2.983 -2.522 11.470 1.00 21.98   N
ATOM 1090 CZ  ARG A 142   -3.288 -3.694 10.914 1.00 22.69   C
ATOM 1091 NH1 ARG A 142   -2.923 -3.942  9.667 1.00 21.65   N
ATOM 1092 NH2 ARG A 142   -3.940 -4.630 11.609 1.00 23.19   N
ATOM 1093 C   ARG A 142   -4.230  2.249  9.671 1.00 17.44   C
ATOM 1094 O   ARG A 142   -4.163  3.142 10.550 1.00 16.01   O
ATOM 1095 N   ASN A 143   -5.359  1.640  9.290 1.00 17.55   N
ATOM 1096 CA  ASN A 143   -6.718  1.857  9.823 1.00 18.86   C
ATOM 1097 CB  ASN A 143   -6.782  1.796 11.377 1.00 19.11   C
ATOM 1098 CG  ASN A 143   -6.167  0.523 11.958 1.00 22.86   C
ATOM 1099 OD1 ASN A 143   -6.475 -0.589 11.530 1.00 28.17   O
ATOM 1100 ND2 ASN A 143   -5.285  0.687 12.936 1.00 28.04   N
ATOM 1101 C   ASN A 143   -7.421  3.104  9.264 1.00 18.97   C
ATOM 1102 O   ASN A 143   -8.528  3.433  9.716 1.00 21.07   O
ATOM 1103 N   SER A 144   -6.782  3.809  8.310 1.00 18.34   N
ATOM 1104 CA  SER A 144   -7.433  4.933  7.589 1.00 18.35   C
ATOM 1105 CB  SER A 144   -6.450  5.648  6.651 1.00 18.33   C
ATOM 1106 OG  SER A 144   -5.330  6.171  7.361 1.00 20.13   O
ATOM 1107 C   SER A 144   -8.564  4.359  6.729 1.00 18.91   C
ATOM 1108 O   SER A 144   -8.434  3.224  6.242 1.00 17.43   O
ATOM 1109 N   THR A 145   -9.670  5.091  6.579 1.00 18.07   N
ATOM 1110 CA  THR A 145  -10.824  4.605  5.793 1.00 19.45   C
ATOM 1111 CB  THR A 145  -12.136  4.515  6.631 1.00 20.87   C
ATOM 1112 OG1 THR A 145  -12.010  3.530  7.662 1.00 22.19   O
ATOM 1113 CG2 THR A 145  -13.321  4.108  5.782 1.00 20.87   C
ATOM 1114 C   THR A 145  -11.036  5.635  4.700 1.00 20.00   C
ATOM 1115 O   THR A 145  -11.041  6.842  4.992 1.00 20.66   O
ATOM 1116 N   ILE A 146  -11.175  5.180  3.457 1.00 18.69   N
ATOM 1117 CA  ILE A 146  -11.447  6.054  2.314 1.00 18.55   C
ATOM 1118 CB  ILE A 146  -10.294  6.033  1.283 1.00 18.42   C
ATOM 1119 CG1 ILE A 146   -8.975  6.536  1.899 1.00 20.74   C
ATOM 1120 CD1 ILE A 146   -8.019  5.405  2.261 1.00 23.09   C
ATOM 1121 CG2 ILE A 146  -10.636  6.791 -0.012 1.00 17.76   C
ATOM 1122 C   ILE A 146  -12.702  5.500  1.675 1.00 18.90   C
ATOM 1123 O   ILE A 146  -12.807  4.286  1.427 1.00 18.45   O
ATOM 1124 N   ASP A 147  -13.671  6.374  1.432 1.00 18.08   N
ATOM 1125 CA  ASP A 147  -14.908  5.952  0.774 1.00 19.01   C
ATOM 1126 CB  ASP A 147  -16.126  6.438  1.565 1.00 19.35   C
ATOM 1127 CG  ASP A 147  -16.501  5.501  2.677 1.00 22.85   C
ATOM 1128 OD1 ASP A 147  -15.796  4.472  2.834 1.00 22.81   O
ATOM 1129 OD2 ASP A 147  -17.515  5.773  3.391 1.00 24.65   O
ATOM 1130 C   ASP A 147  -14.912  6.576 -0.601 1.00 18.24   C
ATOM 1131 O   ASP A 147  -14.838  7.810 -0.706 1.00 18.12   O
ATOM 1132 N   LEU A 148  -14.956  5.727 -1.633 1.00 16.06   N
ATOM 1133 CA  LEU A 148  -15.168  6.178 -3.001 1.00 15.89   C
ATOM 1134 CB  LEU A 148  -14.284  5.407 -4.001 1.00 15.68   C
ATOM 1135 CG  LEU A 148  -12.807  5.210 -3.679 1.00 16.93   C
ATOM 1136 CD1 LEU A 148  -12.228  4.164 -4.675 1.00 16.92   C
ATOM 1137 CD2 LEU A 148  -12.065  6.536 -3.748 1.00 18.44   C
ATOM 1138 C   LEU A 148  -16.605  5.925 -3.343 1.00 16.65   C
ATOM 1139 O   LEU A 148  -17.122  4.799 -3.239 1.00 15.11   O
ATOM 1140 N   THR A 149  -17.285  6.981 -3.754 1.00 17.72   N
ATOM 1141 CA  THR A 149  -18.721  6.875 -3.988 1.00 19.78   C
ATOM 1142 CB  THR A 149  -19.435  7.796 -2.974 1.00 20.50   C
ATOM 1143 OG1 THR A 149  -19.395  7.154 -1.673 1.00 24.22   O
ATOM 1144 CG2 THR A 149  -20.809  7.971 -3.354 1.00 23.88   C
ATOM 1145 C   THR A 149  -19.129  7.216 -5.442 1.00 18.68   C
ATOM 1146 O   THR A 149  -18.688  8.221 -5.987 1.00 18.95   O
ATOM 1147 N   LYS A 150  -19.929  6.352 -6.062 1.00 18.47   N
ATOM 1148 CA  LYS A 150  -20.580  6.647 -7.333 1.00 19.21   C
ATOM 1149 CB  LYS A 150  -20.776  5.368 -8.174 1.00 19.18   C
ATOM 1150 CG  LYS A 150  -21.376  5.584 -9.582 1.00 21.01   C
ATOM 1151 CD  LYS A 150  -21.271  4.316-10.450 1.00 21.95   C
ATOM 1152 CE  LYS A 150  -22.333  4.305-11.533 1.00 24.48   C
ATOM 1153 NZ  LYS A 150  -22.163  3.076-12.338 1.00 27.35   N
ATOM 1154 C   LYS A 150  -21.914  7.315 -6.987 1.00 18.31   C
ATOM 1155 O   LYS A 150  -22.848  6.664 -6.551 1.00 17.26   O
ATOM 1156 N   ASP A 151  -21.974  8.626 -7.166 1.00 19.41   N
ATOM 1157 CA  ASP A 151  -23.161  9.410 -6.855 1.00 21.10   C
ATOM 1158 CB  ASP A 151  -22.738 10.798 -6.361 1.00 21.06   C
ATOM 1159 CG  ASP A 151  -22.084 10.762 -4.980 1.00 25.64   C
ATOM 1160 OD1 ASP A 151  -21.434 11.785 -4.585 1.00 28.13   O
ATOM 1161 OD2 ASP A 151  -22.213  9.700 -4.300 1.00 25.97   O
ATOM 1162 C   ASP A 151  -24.013  9.505 -8.131 1.00 21.85   C
ATOM 1163 O   ASP A 151  -23.514  9.192 -9.223 1.00 22.01   O
ATOM 1164 N   PRO A 152  -25.295  9.917 -8.015 1.00 22.60   N
ATOM 1165 CA  PRO A 152  -26.079  9.988 -9.274 1.00 24.09   C
ATOM 1166 CB  PRO A 152  -27.452 10.547 -8.828 1.00 23.75   C
ATOM 1167 CG  PRO A 152  -27.522 10.351 -7.374 1.00 23.58   C
ATOM 1168 CD  PRO A 152  -26.095 10.277 -6.828 1.00 22.19   C
ATOM 1169 C   PRO A 152  -25.418 10.888-10.322 1.00 25.09   C
ATOM 1170 O   PRO A 152  -24.662 11.823 -9.981 1.00 25.62   O
ATOM 1171 N   GLY A 153  -25.696 10.602-11.595 1.00 27.65   N
ATOM 1172 CA  GLY A 153  -25.092 11.337-12.704 1.00 28.29   C
ATOM 1173 C   GLY A 153  -23.638 10.934-12.891 1.00 29.47   C
ATOM 1174 O   GLY A 153  -22.802 11.754-13.272 1.00 30.48   O
ATOM 1175 N   HIS A 154  -23.319  9.678-12.565 1.00 29.99   N
ATOM 1176 CA  HIS A 154  -21.924  9.208-12.657 1.00 30.67   C
ATOM 1177 CB  HIS A 154  -21.613  8.762-14.109 1.00 31.01   C
ATOM 1178 CG  HIS A 154  -22.506  7.659-14.605 1.00 32.41   C
ATOM 1179 ND1 HIS A 154  -22.164  6.326-14.512 1.00 33.27   N
ATOM 1180 CE1 HIS A 154  -23.141  5.581-15.005 1.00 34.79   C
ATOM 1181 NE2 HIS A 154  -24.109  6.383-15.413 1.00 35.29   N
ATOM 1182 CD2 HIS A 154  -23.735  7.688-15.175 1.00 35.52   C
ATOM 1183 C   HIS A 154  -20.911 10.269-12.102 1.00 30.16   C
ATOM 1184 O   HIS A 154  -19.931 10.664-12.776 1.00 31.29   O
ATOM 1185 N   VAL A 155  -21.172 10.738-10.872 1.00 28.54   N
ATOM 1186 CA  VAL A 155  -20.278 11.647-10.179 1.00 26.45   C
ATOM 1187 CB  VAL A 155  -21.032 12.789 -9.428 1.00 27.27   C
ATOM 1188 CG1 VAL A 155  -20.105 13.551 -8.433 1.00 26.48   C
ATOM 1189 CG2 VAL A 155  -21.656 13.764-10.423 1.00 27.28   C
ATOM 1190 C   VAL A 155  -19.465 10.830 -9.174 1.00 25.84   C
ATOM 1191 O   VAL A 155  -20.057 10.180 -8.326 1.00 23.94   O
ATOM 1192 N   LEU A 156  -18.127 10.900 -9.269 1.00 23.85   N
ATOM 1193 CA  LEU A 156  -17.247 10.220 -8.296 1.00 23.21   C
ATOM 1194 CB  LEU A 156  -15.941  9.777 -8.951 1.00 22.91   C
ATOM 1195 CG  LEU A 156  -15.059  9.079 -7.893 1.00 25.01   C
ATOM 1196 CD1 LEU A 156  -15.278  7.595 -8.017 1.00 21.66   C
ATOM 1197 CD2 LEU A 156  -13.605  9.471 -8.040 1.00 26.08   C
ATOM 1198 C   LEU A 156  -16.921 11.146 -7.129 1.00 22.89   C
ATOM 1199 O   LEU A 156  -16.315 12.189 -7.328 1.00 23.64   O
ATOM 1200 N   SER A 157  -17.324 10.770 -5.918 1.00 21.76   N
ATOM 1201 CA  SER A 157  -16.947 11.508 -4.729 1.00 20.79   C
ATOM 1202 CB  SER A 157  -18.192 11.949 -3.965 1.00 22.44   C
ATOM 1203 OG  SER A 157  -18.994 12.775 -4.791 1.00 24.54   O
ATOM 1204 C   SER A 157  -16.061 10.709 -3.790 1.00 20.36   C
ATOM 1205 O   SER A 157  -16.215  9.485 -3.668 1.00 18.58   O
ATOM 1206 N   VAL A 158  -15.173 11.413 -3.105 1.00 17.76   N
ATOM 1207 CA  VAL A 158  -14.209 10.783 -2.213 1.00 17.96   C
ATOM 1208 CB  VAL A 158  -12.766 10.893 -2.759 1.00 17.68   C
ATOM 1209 CG1 VAL A 158  -11.744 10.227 -1.785 1.00 18.78   C
ATOM 1210 CG2 VAL A 158  -12.689 10.275 -4.157 1.00 14.77   C
ATOM 1211 C   VAL A 158  -14.260 11.409 -0.835 1.00 18.08   C
ATOM 1212 O   VAL A 158  -14.206 12.649 -0.698 1.00 18.91   O
ATOM 1213 N   ALA A 159  -14.353 10.547  0.177 1.00 18.81   N
ATOM 1214 CA  ALA A 159  -14.246 10.963  1.577 1.00 19.51   C
ATOM 1215 CB  ALA A 159  -15.560 10.732  2.288 1.00 18.79   C
ATOM 1216 C   ALA A 159  -13.102 10.203  2.247 1.00 20.12   C
ATOM 1217 O   ALA A 159  -12.888  8.988  1.994 1.00 19.35   O
ATOM 1218 N   ILE A 160  -12.346 10.909  3.070 1.00 20.62   N
ATOM 1219 CA  ILE A 160  -11.198 10.326  3.774 1.00 21.04   C
ATOM 1220 CB  ILE A 160   -9.863 10.978  3.325 1.00 20.73   C
ATOM 1221 CG1 ILE A 160   -9.597 10.705  1.840 1.00 20.43   C
ATOM 1222 CD1 ILE A 160   -8.366 11.432  1.301 1.00 20.44   C
ATOM 1223 CG2 ILE A 160   -8.701 10.469  4.141 1.00 19.85   C
ATOM 1224 C   ILE A 160  -11.440 10.575  5.261 1.00 23.42   C
ATOM 1225 O   ILE A 160  -11.673 11.726  5.669 1.00 23.38   O
ATOM 1226 N   GLU A 161  -11.447  9.495  6.043 1.00 24.20   N
ATOM 1227 CA  GLU A 161  -11.743  9.513  7.485 1.00 25.89   C
ATOM 1228 CB  GLU A 161  -10.545 10.062  8.280 1.00 26.16   C
ATOM 1229 CG  GLU A 161   -9.229  9.288  8.124 1.00 29.09   C
ATOM 1230 CD  GLU A 161   -9.166  7.960  8.901 1.00 32.08   C
ATOM 1231 OE1 GLU A 161  -10.131  7.162  8.911 1.00 32.00   O
ATOM 1232 OE2 GLU A 161   -8.110  7.710  9.516 1.00 39.13   O
ATOM 1233 C   GLU A 161  -13.015 10.289  7.820 1.00 26.67   C
ATOM 1234 O   GLU A 161  -13.061 11.034  8.811 1.00 27.66   O
ATOM 1235 N   GLY A 162  -14.042 10.120  6.998 1.00 27.05   N
ATOM 1236 CA  GLY A 162  -15.350 10.748  7.230 1.00 27.85   C
ATOM 1237 C   GLY A 162  -15.556 12.095  6.574 1.00 28.41   C
```

Fig. 5 cont.

```
ATOM   1238  O   GLY A 162     -16.679  12.584   6.513  1.00 29.30           O
ATOM   1239  N   ASN A 163     -14.473  12.679   6.074  1.00 28.06           N
ATOM   1240  CA  ASN A 163     -14.465  14.033   5.534  1.00 28.08           C
ATOM   1241  CB  ASN A 163     -13.227  14.777   6.050  1.00 28.23           C
ATOM   1242  CG  ASN A 163     -13.164  14.825   7.582  1.00 30.62           C
ATOM   1243  OD1 ASN A 163     -14.191  14.974   8.260  1.00 30.98           O
ATOM   1244  ND2 ASN A 163     -11.959  14.672   8.131  1.00 32.93           N
ATOM   1245  C   ASN A 163     -14.469  14.050   4.008  1.00 27.23           C
ATOM   1246  O   ASN A 163     -13.551  13.542   3.382  1.00 25.05           O
ATOM   1247  N   HIS A 164     -15.514  14.622   3.417  1.00 27.56           N
ATOM   1248  CA  HIS A 164     -15.560  14.816   1.959  1.00 27.00           C
ATOM   1249  CB  HIS A 164     -16.864  15.514   1.590  1.00 28.05           C
ATOM   1250  CG  HIS A 164     -17.056  15.708   0.124  1.00 27.30           C
ATOM   1251  ND1 HIS A 164     -16.865  16.929  -0.491  1.00 28.12           N
ATOM   1252  CE1 HIS A 164     -17.133  16.820  -1.776  1.00 22.79           C
ATOM   1253  NE2 HIS A 164     -17.484  15.570  -2.021  1.00 27.05           N
ATOM   1254  CD2 HIS A 164     -17.441  14.850  -0.849  1.00 25.52           C
ATOM   1255  C   HIS A 164     -14.378  15.641   1.464  1.00 27.25           C
ATOM   1256  O   HIS A 164     -14.102  16.727   1.976  1.00 26.99           O
ATOM   1257  N   VAL A 165     -13.675  15.135   0.462  1.00 27.14           N
ATOM   1258  CA  VAL A 165     -12.530  15.851  -0.079  1.00 27.57           C
ATOM   1259  CB  VAL A 165     -11.210  15.035  -0.047  1.00 27.44           C
ATOM   1260  CG1 VAL A 165     -10.705  14.840   1.389  1.00 29.24           C
ATOM   1261  CG2 VAL A 165     -11.370  13.715  -0.788  1.00 27.22           C
ATOM   1262  C   VAL A 165     -12.761  16.358  -1.492  1.00 27.50           C
ATOM   1263  O   VAL A 165     -11.999  17.198  -1.970  1.00 29.22           O
ATOM   1264  N   GLY A 166     -13.779  15.848  -2.170  1.00 27.35           N
ATOM   1265  CA  GLY A 166     -14.123  16.361  -3.492  1.00 27.06           C
ATOM   1266  C   GLY A 166     -14.810  15.374  -4.400  1.00 26.99           C
ATOM   1267  O   GLY A 166     -15.019  14.220  -4.020  1.00 26.80           O
ATOM   1268  N   SER A 167     -15.168  15.842  -5.601  1.00 26.05           N
ATOM   1269  CA  SER A 167     -15.888  15.060  -6.584  1.00 26.36           C
ATOM   1270  CB  SER A 167     -17.369  15.438  -6.630  1.00 26.29           C
ATOM   1271  OG  SER A 167     -18.016  15.284  -5.383  1.00 28.97           O
ATOM   1272  C   SER A 167     -15.318  15.348  -7.960  1.00 26.57           C
ATOM   1273  O   SER A 167     -14.742  16.424  -8.204  1.00 26.38           O
ATOM   1274  N   VAL A 168     -15.502  14.387  -8.859  1.00 26.60           N
ATOM   1275  CA  VAL A 168     -15.261  14.542 -10.290  1.00 26.44           C
ATOM   1276  CB  VAL A 168     -13.967  13.791 -10.742  1.00 25.84           C
ATOM   1277  CG1 VAL A 168     -13.788  13.816 -12.266  1.00 26.41           C
ATOM   1278  CG2 VAL A 168     -12.679  14.350 -10.027  1.00 26.53           C
ATOM   1279  C   VAL A 168     -16.503  13.961 -10.979  1.00 27.31           C
ATOM   1280  O   VAL A 168     -16.856  12.806 -10.739  1.00 26.58           O
ATOM   1281  N   LYS A 169     -17.188  14.772 -11.798  1.00 27.91           N
ATOM   1282  CA  LYS A 169     -18.254  14.248 -12.663  1.00 28.34           C
ATOM   1283  CB  LYS A 169     -19.301  15.317 -13.055  1.00 28.83           C
ATOM   1284  CG  LYS A 169     -20.496  14.698 -13.807  1.00 29.46           C
ATOM   1285  CD  LYS A 169     -21.589  15.703 -14.233  1.00 31.36           C
ATOM   1286  CE  LYS A 169     -22.490  15.031 -15.281  1.00 35.04           C
ATOM   1287  NZ  LYS A 169     -23.977  15.224 -15.070  1.00 38.58           N
ATOM   1288  C   LYS A 169     -17.573  13.658 -13.898  1.00 28.10           C
ATOM   1289  O   LYS A 169     -16.997  14.400 -14.700  1.00 28.16           O
ATOM   1290  N   SER A 170     -17.595  12.327 -14.016  1.00 27.06           N
ATOM   1291  CA  SER A 170     -16.993  11.644 -15.164  1.00 25.65           C
ATOM   1292  CB  SER A 170     -15.445  11.751 -15.140  1.00 26.05           C
ATOM   1293  OG  SER A 170     -14.801  10.918 -16.115  1.00 22.48           O
ATOM   1294  C   SER A 170     -17.474  10.198 -15.213  1.00 25.59           C
ATOM   1295  O   SER A 170     -17.164   9.413 -14.332  1.00 24.40           O
ATOM   1296  N   HIS A 171     -18.269   9.874 -16.234  1.00 24.81           N
ATOM   1297  CA  HIS A 171     -18.683   8.499 -16.492  1.00 24.53           C
ATOM   1298  CB  HIS A 171     -19.503   8.454 -17.789  1.00 25.89           C
ATOM   1299  CG  HIS A 171     -20.379   7.251 -17.912  1.00 31.21           C
ATOM   1300  ND1 HIS A 171     -19.889   5.998 -18.221  1.00 37.13           N
ATOM   1301  CE1 HIS A 171     -20.888   5.136 -18.283  1.00 37.90           C
ATOM   1302  NE2 HIS A 171     -22.012   5.790 -18.039  1.00 38.55           N
ATOM   1303  CD2 HIS A 171     -21.723   7.115 -17.815  1.00 34.99           C
ATOM   1304  C   HIS A 171     -17.443   7.615 -16.656  1.00 22.55           C
ATOM   1305  O   HIS A 171     -17.360   6.511 -16.119  1.00 20.45           O
ATOM   1306  N   LEU A 172     -16.469   8.119 -17.404  1.00 20.03           N
ATOM   1307  CA  LEU A 172     -15.254   7.348 -17.652  1.00 19.52           C
ATOM   1308  CB  LEU A 172     -14.348   8.097 -18.634  1.00 19.98           C
ATOM   1309  CG  LEU A 172     -12.943   7.584 -18.878  1.00 20.72           C
ATOM   1310  CD1 LEU A 172     -12.957   6.164 -19.405  1.00 21.91           C
ATOM   1311  CD2 LEU A 172     -12.304   8.536 -19.882  1.00 23.27           C
ATOM   1312  C   LEU A 172     -14.488   7.040 -16.361  1.00 17.94           C
ATOM   1313  O   LEU A 172     -14.129   5.886 -16.114  1.00 16.89           O
ATOM   1314  N   LEU A 173     -14.241   8.059 -15.558  1.00 17.63           N
ATOM   1315  CA  LEU A 173     -13.563   7.832 -14.264  1.00 17.98           C
ATOM   1316  CB  LEU A 173     -13.334   9.140 -13.512  1.00 16.92           C
ATOM   1317  CG  LEU A 173     -12.361   9.026 -12.323  1.00 16.48           C
ATOM   1318  CD1 LEU A 173     -10.914   8.583 -12.695  1.00 18.59           C
ATOM   1319  CD2 LEU A 173     -12.334  10.389 -11.632  1.00 18.96           C
ATOM   1320  C   LEU A 173     -14.325   6.859 -13.367  1.00 18.07           C
ATOM   1321  O   LEU A 173     -13.706   5.971 -12.797  1.00 18.41           O
ATOM   1322  N   CYS A 174     -15.647   7.034 -13.229  1.00 19.40           N
ATOM   1323  CA  CYS A 174     -16.440   6.096 -12.403  1.00 19.56           C
ATOM   1324  CB  CYS A 174     -17.916   6.453 -12.394  1.00 20.83           C
ATOM   1325  SG  CYS A 174     -18.276   7.875 -11.435  1.00 22.53           S
ATOM   1326  C   CYS A 174     -16.264   4.661 -12.860  1.00 19.87           C
ATOM   1327  O   CYS A 174     -15.970.  3.774 -12.049  1.00 18.86           O
ATOM   1328  N   ARG A 175     -16.420   4.437 -14.165  1.00 19.79           N
ATOM   1329  CA  ARG A 175     -16.269   3.095 -14.752  1.00 20.18           C
ATOM   1330  CB  ARG A 175     -16.535   3.157 -16.266  1.00 20.11           C
ATOM   1331  CG  ARG A 175     -16.642   1.830 -16.936  1.00 25.96           C
ATOM   1332  CD  ARG A 175     -17.982   1.165 -16.588  1.00 33.04           C
ATOM   1333  NE  ARG A 175     -18.484   0.312 -17.657  1.00 38.64           N
ATOM   1334  CZ  ARG A 175     -17.936  -0.833 -18.050  1.00 40.16           C
ATOM   1335  NH1 ARG A 175     -16.826  -1.306 -17.497  1.00 41.91           N
ATOM   1336  NH2 ARG A 175     -18.496  -1.494 -19.039  1.00 43.26           N
ATOM   1337  C   ARG A 175     -14.883   2.525 -14.534  1.00 19.28           C
ATOM   1338  O   ARG A 175     -14.723   1.344 -14.165  1.00 19.50           O
ATOM   1339  N   SER A 176     -13.869   3.340 -14.797  1.00 18.25           N
ATOM   1340  CA  SER A 176     -12.488   2.884 -14.644  1.00 18.23           C
ATOM   1341  CB  SER A 176     -11.528   3.983 -15.087  1.00 17.83           C
ATOM   1342  OG  SER A 176     -11.796   4.353 -16.443  1.00 20.75           O
ATOM   1343  C   SER A 176     -12.157   2.463 -13.214  1.00 17.95           C
ATOM   1344  O   SER A 176     -11.544   1.417 -12.981  1.00 17.91           O
ATOM   1345  N   ILE A 177     -12.562   3.275 -12.246  1.00 18.35           N
ATOM   1346  CA  ILE A 177     -12.294   2.915 -10.833  1.00 18.95           C
ATOM   1347  CB  ILE A 177     -12.579   4.109  -9.888  1.00 19.45           C
ATOM   1348  CG1 ILE A 177     -11.499   5.195 -10.104  1.00 19.54           C
ATOM   1349  CD1 ILE A 177     -11.836   6.524  -9.491  1.00 24.26           C
ATOM   1350  CG2 ILE A 177     -12.525   3.669  -8.459  1.00 19.40           C
ATOM   1351  C   ILE A 177     -13.051   1.629 -10.436  1.00 18.04           C
ATOM   1352  O   ILE A 177     -12.450   0.687  -9.945  1.00 17.88           O
ATOM   1353  N   LEU A 178     -14.365   1.599 -10.645  1.00 18.70           N
ATOM   1354  CA  LEU A 178     -15.161   0.400 -10.360  1.00 17.32           C
ATOM   1355  CB  LEU A 178     -16.596   0.594 -10.790  1.00 18.25           C
ATOM   1356  CG  LEU A 178     -17.552   1.393  -9.918  1.00 20.92           C
ATOM   1357  CD1 LEU A 178     -18.950   1.331 -10.573  1.00 25.17           C
ATOM   1358  CD2 LEU A 178     -17.586   0.749  -8.519  1.00 24.09           C
ATOM   1359  C   LEU A 178     -14.634  -0.837 -11.054  1.00 16.36           C
ATOM   1360  O   LEU A 178     -14.730  -1.916 -10.505  1.00 16.51           O
ATOM   1361  N   ASP A 179     -14.086  -0.692 -12.262  1.00 15.84           N
ATOM   1362  CA  ASP A 179     -13.545  -1.846 -13.017  1.00 16.07           C
ATOM   1363  CB  ASP A 179     -13.035  -1.447 -14.417  1.00 17.07           C
ATOM   1364  CG  ASP A 179     -12.873  -2.657 -15.338  1.00 21.01           C
ATOM   1365  OD1 ASP A 179     -11.711  -3.078 -15.589  1.00 22.53           O
ATOM   1366  OD2 ASP A 179     -13.910  -3.227 -15.754  1.00 21.70           O
ATOM   1367  C   ASP A 179     -12.441  -2.555 -12.252  1.00 15.17           C
ATOM   1368  O   ASP A 179     -12.237  -3.768 -12.418  1.00 15.14           O
ATOM   1369  N   LEU A 180     -11.721  -1.805 -11.415  1.00 13.42           N
ATOM   1370  CA  LEU A 180     -10.612  -2.392 -10.646  1.00 13.47           C
ATOM   1371  CB  LEU A 180      -9.842  -1.288  -9.870  1.00 12.12           C
ATOM   1372  CG  LEU A 180      -9.122  -0.263 -10.772  1.00 14.32           C
ATOM   1373  CD1 LEU A 180      -8.565   0.931  -9.919  1.00 14.09           C
ATOM   1374  CD2 LEU A 180      -8.018  -0.959 -11.554  1.00 16.05           C
ATOM   1375  C   LEU A 180     -11.122  -3.407  -9.653  1.00 12.97           C
ATOM   1376  O   LEU A 180     -10.399  -4.316  -9.278  1.00 13.68           O
ATOM   1377  N   TYR A 181     -12.326  -3.150  -9.121  1.00 13.47           N
ATOM   1378  CA  TYR A 181     -12.906  -3.990  -8.064  1.00 12.71           C
ATOM   1379  CB  TYR A 181     -13.595  -3.073  -7.024  1.00 12.64           C
ATOM   1380  CG  TYR A 181     -12.605  -2.082  -6.424  1.00  9.90           C
ATOM   1381  CD1 TYR A 181     -11.685  -2.496  -5.448  1.00 12.39           C
ATOM   1382  CE1 TYR A 181     -10.734  -1.594  -4.920  1.00 10.64           C
ATOM   1383  CZ  TYR A 181     -10.715  -0.265  -5.411  1.00 13.61           C
ATOM   1384  OH  TYR A 181      -9.789   0.662  -4.932  1.00 14.22           O
ATOM   1385  CE2 TYR A 181     -11.594   0.143  -6.402  1.00 12.51           C
ATOM   1386  CD2 TYR A 181     -12.541  -0.779  -6.892  1.00 11.76           C
ATOM   1387  C   TYR A 181     -13.874  -5.090  -8.563  1.00 14.87           C
ATOM   1388  O   TYR A 181     -13.893  -6.216  -8.051  1.00 14.42           O
ATOM   1389  N   ILE A 182     -14.659  -4.754  -9.565  1.00 16.54           N
ATOM   1390  CA  ILE A 182     -15.715  -5.675 -10.032  1.00 18.71           C
ATOM   1391  CB  ILE A 182     -17.130  -5.136  -9.609  1.00 18.76           C
ATOM   1392  CG1 ILE A 182     -17.398  -3.764 -10.209  1.00 22.54           C
ATOM   1393  CD1 ILE A 182     -18.801  -3.164  -9.845  1.00 22.31           C
ATOM   1394  CG2 ILE A 182     -17.206  -5.030  -8.079  1.00 18.57           C
ATOM   1395  C   ILE A 182     -15.694  -6.017 -11.529  1.00 19.47           C
ATOM   1396  O   ILE A 182     -16.678  -6.604 -12.028  1.00 21.69           O
ATOM   1397  N   GLY A 183     -14.573  -5.771 -12.210  1.00 18.34           N
ATOM   1398  CA  GLY A 183     -14.445  -5.965 -13.657  1.00 19.03           C
ATOM   1399  C   GLY A 183     -13.760  -7.278 -14.017  1.00 19.85           C
ATOM   1400  O   GLY A 183     -13.578  -8.149 -13.145  1.00 19.09           O
ATOM   1401  N   GLU A 184     -13.374  -7.451 -15.283  1.00 20.53           N
ATOM   1402  CA  GLU A 184     -12.832  -8.758 -15.688  1.00 21.69           C
ATOM   1403  CB  GLU A 184     -12.760  -8.926 -17.220  1.00 24.11           C
ATOM   1404  CG  GLU A 184     -13.497 -10.229 -17.726  1.00 30.51           C
ATOM   1405  CD  GLU A 184     -12.577 -11.449 -17.876  1.00 38.60           C
ATOM   1406  OE1 GLU A 184     -11.831 -11.794 -16.930  1.00 40.62           O
ATOM   1407  OE2 GLU A 184     -12.613 -12.088 -18.955  1.00 41.42           O
```

Fig. 5 cont.

```
ATOM   1408  C   GLU A 184     -11.507  -9.133 -15.028  1.00 22.13           C
ATOM   1409  O   GLU A 184     -11.232 -10.327 -14.807  1.00 21.56           O
ATOM   1410  N   GLU A 185     -10.680  -8.138 -14.711  1.00 21.19           N
ATOM   1411  CA  GLU A 185      -9.390  -8.400 -14.075  1.00 21.88           C
ATOM   1412  CB  GLU A 185      -8.255  -7.998 -15.007  1.00 23.56           C
ATOM   1413  CG  GLU A 185      -7.958  -9.018 -16.114  1.00 27.23           C
ATOM   1414  CD  GLU A 185      -7.508  -8.366 -17.408  1.00 34.84           C
ATOM   1415  OE1 GLU A 185      -8.121  -7.362 -17.826  1.00 38.43           O
ATOM   1416  OE2 GLU A 185      -6.543  -8.860 -18.025  1.00 37.78           O
ATOM   1417  C   GLU A 185      -9.297  -7.622 -12.733  1.00 21.47           C
ATOM   1418  O   GLU A 185      -8.650  -6.565 -12.659  1.00 21.92           O
ATOM   1419  N   PRO A 186      -9.968  -8.140 -11.689  1.00 20.45           N
ATOM   1420  CA  PRO A 186     -10.185  -7.390 -10.460  1.00 20.07           C
ATOM   1421  CB  PRO A 186     -11.515  -7.946  -9.973  1.00 19.54           C
ATOM   1422  CG  PRO A 186     -11.427  -9.406 -10.323  1.00 21.15           C
ATOM   1423  CD  PRO A 186     -10.580  -9.476 -11.601  1.00 20.80           C
ATOM   1424  C   PRO A 186      -9.091  -7.654  -9.422  1.00 18.58           C
ATOM   1425  O   PRO A 186      -8.342  -8.618  -9.539  1.00 17.68           O
ATOM   1426  N   PHE A 187      -9.024  -6.821  -8.389  1.00 18.02           N
ATOM   1427  CA  PHE A 187      -7.990  -7.017  -7.379  1.00 18.46           C
ATOM   1428  CB  PHE A 187      -7.993  -5.878  -6.359  1.00 18.93           C
ATOM   1429  CG  PHE A 187      -7.479  -4.574  -6.883  1.00 19.25           C
ATOM   1430  CD1 PHE A 187      -8.235  -3.415  -6.721  1.00 21.88           C
ATOM   1431  CE1 PHE A 187      -7.786  -2.181  -7.187  1.00 19.63           C
ATOM   1432  CZ  PHE A 187      -6.567  -2.104  -7.813  1.00 18.52           C
ATOM   1433  CE2 PHE A 187      -5.790  -3.259  -7.976  1.00 20.89           C
ATOM   1434  CD2 PHE A 187      -6.246  -4.489  -7.503  1.00 20.75           C
ATOM   1435  C   PHE A 187      -8.180  -8.338  -6.628  1.00 18.37           C
ATOM   1436  O   PHE A 187      -7.213  -8.930  -6.150  1.00 17.97           O
ATOM   1437  N   ASP A 188      -9.432  -8.792  -6.510  1.00 16.56           N
ATOM   1438  CA  ASP A 188      -9.761  -9.930  -5.679  1.00 17.02           C
ATOM   1439  CB  ASP A 188     -10.205  -9.474  -4.269  1.00 17.08           C
ATOM   1440  CG  ASP A 188     -10.397 -10.627  -3.285  1.00 19.44           C
ATOM   1441  OD1 ASP A 188      -9.906 -10.537  -2.128  1.00 16.31           O
ATOM   1442  OD2 ASP A 188     -11.053 -11.637  -3.632  1.00 21.90           O
ATOM   1443  C   ASP A 188     -10.900 -10.655  -6.391  1.00 17.92           C
ATOM   1444  O   ASP A 188     -12.082 -10.236  -6.322  1.00 15.57           O
ATOM   1445  N   LYS A 189     -10.552 -11.754  -7.059  1.00 17.91           N
ATOM   1446  CA  LYS A 189     -11.582 -12.467  -7.815  1.00 19.08           C
ATOM   1447  CB  LYS A 189     -10.984 -13.577  -8.675  1.00 19.81           C
ATOM   1448  CG  LYS A 189     -10.107 -12.996  -9.769  1.00 22.56           C
ATOM   1449  CD  LYS A 189     -10.319 -13.700 -11.141  1.00 29.01           C
ATOM   1450  CE  LYS A 189      -9.211 -13.300 -12.127  1.00 33.66           C
ATOM   1451  NZ  LYS A 189      -9.645 -13.293 -13.561  1.00 35.96           N
ATOM   1452  C   LYS A 189     -12.699 -12.961  -6.923  1.00 19.08           C
ATOM   1453  O   LYS A 189     -13.869 -12.884  -7.316  1.00 18.39           O
ATOM   1454  N   ASN A 190     -12.364 -13.418  -5.717  1.00 19.33           N
ATOM   1455  CA  ASN A 190     -13.386 -13.919  -4.808  1.00 20.11           C
ATOM   1456  CB  ASN A 190     -12.750 -14.603  -3.565  1.00 21.43           C
ATOM   1457  CG  ASN A 190     -13.794 -15.140  -2.571  1.00 25.33           C
ATOM   1458  OD1 ASN A 190     -14.493 -16.125  -2.845  1.00 32.08           O
ATOM   1459  ND2 ASN A 190     -13.888 -14.510  -1.405  1.00 28.30           N
ATOM   1460  C   ASN A 190     -14.403 -12.818  -4.417  1.00 18.45           C
ATOM   1461  O   ASN A 190     -15.602 -13.093  -4.300  1.00 18.44           O
ATOM   1462  N   ALA A 191     -13.929 -11.574  -4.243  1.00 16.27           N
ATOM   1463  CA  ALA A 191     -14.801 -10.481  -3.889  1.00 15.11           C
ATOM   1464  CB  ALA A 191     -14.023  -9.193  -3.554  1.00 15.25           C
ATOM   1465  C   ALA A 191     -15.727 -10.202  -5.026  1.00 13.77           C
ATOM   1466  O   ALA A 191     -16.861  -9.818  -4.805  1.00 13.71           O
ATOM   1467  N   ARG A 192     -15.216 -10.307  -6.243  1.00 13.80           N
ATOM   1468  CA  ARG A 192     -16.012  -9.990  -7.415  1.00 13.29           C
ATOM   1469  CB  ARG A 192     -15.161  -9.963  -8.689  1.00 12.71           C
ATOM   1470  CG  ARG A 192     -16.053  -9.643  -9.937  1.00 13.53           C
ATOM   1471  CD  ARG A 192     -15.407 -10.021 -11.267  1.00 15.22           C
ATOM   1472  NE  ARG A 192     -15.093 -11.442 -11.389  1.00 16.79           N
ATOM   1473  CZ  ARG A 192     -14.255 -11.926 -12.301  1.00 20.87           C
ATOM   1474  NH1 ARG A 192     -13.648 -11.090 -13.149  1.00 15.33           N
ATOM   1475  NH2 ARG A 192     -14.016 -13.235 -12.361  1.00 21.20           N
ATOM   1476  C   ARG A 192     -17.136 -11.017  -7.559  1.00 13.56           C
ATOM   1477  O   ARG A 192     -18.282 -10.653  -7.870  1.00 13.36           O
ATOM   1478  N   GLU A 193     -16.801 -12.297  -7.341  1.00 13.84           N
ATOM   1479  CA  GLU A 193     -17.784 -13.351  -7.482  1.00 14.44           C
ATOM   1480  CB  GLU A 193     -17.115 -14.724  -7.422  1.00 15.53           C
ATOM   1481  CG  GLU A 193     -16.099 -14.948  -8.588  1.00 18.42           C
ATOM   1482  CD  GLU A 193     -16.760 -14.926  -9.970  1.00 23.54           C
ATOM   1483  OE1 GLU A 193     -17.521 -15.884 -10.293  1.00 23.43           O
ATOM   1484  OE2 GLU A 193     -16.561 -13.951 -10.731  1.00 22.39           O
ATOM   1485  C   GLU A 193     -18.888 -13.221  -6.443  1.00 15.05           C
ATOM   1486  O   GLU A 193     -20.063 -13.396  -6.777  1.00 14.30           O
ATOM   1487  N   ASP A 194     -18.517 -12.920  -5.191  1.00 13.85           N
ATOM   1488  CA  ASP A 194     -19.506 -12.648  -4.137  1.00 13.84           C
ATOM   1489  CB  ASP A 194     -18.852 -12.397  -2.757  1.00 14.36           C
ATOM   1490  CG  ASP A 194     -18.197 -13.645  -2.174  1.00 20.74           C
ATOM   1491  OD1 ASP A 194     -17.425 -13.504  -1.175  1.00 21.21           O
ATOM   1492  OD2 ASP A 194     -18.468 -14.769  -2.709  1.00 24.18           O
ATOM   1493  C   ASP A 194     -20.362 -11.449  -4.534  1.00 12.65           C
ATOM   1494  O   ASP A 194     -21.566 -11.479  -4.354  1.00 12.64           O
ATOM   1495  N   PHE A 195     -19.749 -10.384  -5.032  1.00 10.79           N
ATOM   1496  CA  PHE A 195     -20.513  -9.194  -5.413  1.00 11.01           C
ATOM   1497  CB  PHE A 195     -19.542  -8.097  -5.969  1.00 11.19           C
ATOM   1498  CG  PHE A 195     -20.256  -6.916  -6.589  1.00 12.87           C
ATOM   1499  CD1 PHE A 195     -20.572  -6.909  -7.949  1.00 18.24           C
ATOM   1500  CE1 PHE A 195     -21.258  -5.809  -8.524  1.00 15.31           C
ATOM   1501  CZ  PHE A 195     -21.622  -4.745  -7.728  1.00 16.11           C
ATOM   1502  CE2 PHE A 195     -21.326  -4.742  -6.385  1.00 13.27           C
ATOM   1503  CD2 PHE A 195     -20.655  -5.837  -5.808  1.00 14.53           C
ATOM   1504  C   PHE A 195     -21.602  -9.540  -6.441  1.00 11.13           C
ATOM   1505  O   PHE A 195     -22.744  -9.092  -6.319  1.00 10.64           O
ATOM   1506  N   LEU A 196     -21.229 -10.298  -7.474  1.00 11.48           N
ATOM   1507  CA  LEU A 196     -22.126 -10.610  -8.592  1.00 11.98           C
ATOM   1508  CB  LEU A 196     -21.329 -11.178  -9.762  1.00 12.52           C
ATOM   1509  CG  LEU A 196     -20.391 -10.188 -10.464  1.00 11.39           C
ATOM   1510  CD1 LEU A 196     -19.563 -10.963 -11.534  1.00 12.36           C
ATOM   1511  CD2 LEU A 196     -21.243  -9.133 -11.116  1.00 13.09           C
ATOM   1512  C   LEU A 196     -23.217 -11.585  -8.140  1.00 12.38           C
ATOM   1513  O   LEU A 196     -24.400 -11.422  -8.493  1.00 11.21           O
ATOM   1514  N   ASP A 197     -22.820 -12.558  -7.324  1.00 13.43           N
ATOM   1515  CA  ASP A 197     -23.768 -13.519  -6.721  1.00 14.10           C
ATOM   1516  CB  ASP A 197     -23.078 -14.516  -5.783  1.00 14.31           C
ATOM   1517  CG  ASP A 197     -22.328 -15.653  -6.496  1.00 17.99           C
ATOM   1518  OD1 ASP A 197     -22.412 -15.798  -7.722  1.00 18.03           O
ATOM   1519  OD2 ASP A 197     -21.623 -16.426  -5.777  1.00 19.41           O
ATOM   1520  C   ASP A 197     -24.791 -12.759  -5.910  1.00 13.52           C
ATOM   1521  O   ASP A 197     -25.979 -13.022  -6.031  1.00 13.80           O
ATOM   1522  N   ASN A 198     -24.350 -11.808  -5.075  1.00 13.42           N
ATOM   1523  CA  ASN A 198     -25.254 -11.113  -4.172  1.00 13.78           C
ATOM   1524  CB  ASN A 198     -24.525 -10.598  -2.892  1.00 13.60           C
ATOM   1525  CG  ASN A 198     -23.974 -11.748  -2.040  1.00 17.61           C
ATOM   1526  OD1 ASN A 198     -24.625 -12.805  -1.893  1.00 16.17           O
ATOM   1527  ND2 ASN A 198     -22.751 -11.570  -1.515  1.00 15.25           N
ATOM   1528  C   ASN A 198     -26.041 -10.008  -4.870  1.00 13.39           C
ATOM   1529  O   ASN A 198     -27.200  -9.703  -4.497  1.00 13.21           O
ATOM   1530  N   ALA A 199     -25.426  -9.407  -5.892  1.00 11.49           N
ATOM   1531  CA  ALA A 199     -26.162  -8.440  -6.725  1.00 11.60           C
ATOM   1532  CB  ALA A 199     -25.236  -7.758  -7.745  1.00  9.91           C
ATOM   1533  C   ALA A 199     -27.310  -9.139  -7.463  1.00 11.78           C
ATOM   1534  O   ALA A 199     -28.392  -8.561  -7.588  1.00 13.52           O
ATOM   1535  N   ALA A 200     -27.081 -10.365  -7.923  1.00 12.17           N
ATOM   1536  CA  ALA A 200     -28.120 -11.133  -8.655  1.00 13.40           C
ATOM   1537  CB  ALA A 200     -27.517 -12.362  -9.350  1.00 13.95           C
ATOM   1538  C   ALA A 200     -29.275 -11.534  -7.685  1.00 14.32           C
ATOM   1539  O   ALA A 200     -30.436 -11.565  -8.101  1.00 14.63           O
ATOM   1540  N   SER A 201     -28.966 -11.770  -6.408  1.00 15.33           N
ATOM   1541  CA  SER A 201     -29.988 -12.094  -5.380  1.00 15.62           C
ATOM   1542  CB  SER A 201     -29.332 -12.782  -4.164  1.00 16.81           C
ATOM   1543  OG  SER A 201     -28.631 -13.944  -4.556  1.00 22.49           O
ATOM   1544  C   SER A 201     -30.735 -10.891  -4.839  1.00 16.11           C
ATOM   1545  O   SER A 201     -31.858 -11.013  -4.369  1.00 14.39           O
ATOM   1546  N   LEU A 202     -30.092  -9.723  -4.878  1.00 16.64           N
ATOM   1547  CA  LEU A 202     -30.587  -8.515  -4.219  1.00 19.29           C
ATOM   1548  CB  LEU A 202     -29.623  -7.349  -4.478  1.00 18.07           C
ATOM   1549  CG  LEU A 202     -29.145  -6.444  -3.365  1.00 19.21           C
ATOM   1550  CD1 LEU A 202     -28.629  -5.127  -3.940  1.00 18.50           C
ATOM   1551  CD2 LEU A 202     -30.150  -6.245  -2.233  1.00 24.67           C
ATOM   1552  C   LEU A 202     -31.974  -8.118  -4.679  1.00 20.31           C
ATOM   1553  O   LEU A 202     -32.767  -7.601  -3.880  1.00 22.18           O
ATOM   1554  N   ALA A 203     -32.311  -8.361  -5.948  1.00 21.75           N
ATOM   1555  CA  ALA A 203     -33.643  -7.989  -6.427  1.00 22.33           C
ATOM   1556  CB  ALA A 203     -33.723  -7.963  -7.965  1.00 23.22           C
ATOM   1557  C   ALA A 203     -34.780  -8.801  -5.833  1.00 23.34           C
ATOM   1558  O   ALA A 203     -35.933  -8.353  -5.889  1.00 25.27           O
ATOM   1559  N   PHE A 204     -34.474  -9.955  -5.233  1.00 20.96           N
ATOM   1560  CA  PHE A 204     -35.478 -10.870  -4.676  1.00 20.39           C
ATOM   1561  CB  PHE A 204     -35.146 -12.297  -5.090  1.00 17.98           C
ATOM   1562  CG  PHE A 204     -35.006 -12.445  -6.567  1.00 17.26           C
ATOM   1563  CD1 PHE A 204     -33.747 -12.482  -7.164  1.00 16.50           C
ATOM   1564  CE1 PHE A 204     -33.633 -12.588  -8.546  1.00 14.61           C
ATOM   1565  CZ  PHE A 204     -34.761 -12.618  -9.346  1.00 16.36           C
ATOM   1566  CE2 PHE A 204     -36.019 -12.538  -8.754  1.00 15.67           C
ATOM   1567  CD2 PHE A 204     -36.137 -12.445  -7.390  1.00 13.11           C
ATOM   1568  C   PHE A 204     -35.620 -10.762  -3.159  1.00 22.24           C
ATOM   1569  O   PHE A 204     -35.115  -9.780  -2.579  1.00 25.10           O
ATOM   1570  N   SER B   4      -6.758 -25.010 -22.991  1.00 20.91           N
ATOM   1571  CA  SER B   4      -7.146 -23.628 -23.473  1.00 24.35           C
ATOM   1572  CB  SER B   4      -7.659 -22.737 -22.324  1.00 25.48           C
ATOM   1573  OG  SER B   4      -9.023 -23.002 -22.008  1.00 28.50           O
ATOM   1574  C   SER B   4      -5.939 -22.982 -24.116  1.00 24.01           C
ATOM   1575  O   SER B   4      -4.803 -23.282 -23.730  1.00 23.71           O
ATOM   1576  N   VAL B   5      -6.162 -22.065 -25.059  1.00 20.60           N
ATOM   1577  CA  VAL B   5      -5.072 -21.498 -25.826  1.00 19.94           C
```

Fig. 5 cont.

| | | | | | |
|---|---|---|---|---|---|
| ATOM | 1578 CB VAL B 5 | -5.189 -21.824 -27.350 | 1.00 19.56 | | C |
| ATOM | 1579 CG1 VAL B 5 | -4.199 -20.992 -28.145 | 1.00 21.04 | | C |
| ATOM | 1580 CG2 VAL B 5 | -4.981 -23.340 -27.631 | 1.00 19.09 | | C |
| ATOM | 1581 C VAL B 5 | -5.109 -19.997 -25.643 | 1.00 20.62 | | C |
| ATOM | 1582 O VAL B 5 | -6.157 -19.397 -25.790 | 1.00 17.79 | | O |
| ATOM | 1583 N VAL B 6 | -3.957 -19.389 -25.353 | 1.00 20.77 | | N |
| ATOM | 1584 CA VAL B 6 | -3.931 -17.972 -25.037 | 1.00 22.20 | | C |
| ATOM | 1585 CB VAL B 6 | -3.076 -17.691 -23.769 | 1.00 22.35 | | C |
| ATOM | 1586 CG1 VAL B 6 | -2.712 -16.159 -23.616 | 1.00 23.44 | | C |
| ATOM | 1587 CG2 VAL B 6 | -3.786 -18.215 -22.517 | 1.00 24.30 | | C |
| ATOM | 1588 C VAL B 6 | -3.421 -17.215 -26.253 | 1.00 22.71 | | C |
| ATOM | 1589 O VAL B 6 | -2.461 -17.624 -26.910 | 1.00 23.99 | | O |
| ATOM | 1590 N GLU B 7 | -4.074 -16.106 -26.579 | 1.00 21.73 | | N |
| ATOM | 1591 CA GLU B 7 | -3.524 -15.244 -27.589 | 1.00 20.63 | | C |
| ATOM | 1592 CB GLU B 7 | -4.648 -14.433 -28.240 | 1.00 20.52 | | C |
| ATOM | 1593 CG GLU B 7 | -4.247 -13.768 -29.558 | 1.00 22.33 | | C |
| ATOM | 1594 CD GLU B 7 | -3.248 -12.623 -29.320 | 1.00 23.24 | | C |
| ATOM | 1595 OE1 GLU B 7 | -2.175 -12.634 -29.927 | 1.00 24.43 | | O |
| ATOM | 1596 OE2 GLU B 7 | -3.541 -11.735 -28.496 | 1.00 22.75 | | O |
| ATOM | 1597 C GLU B 7 | -2.479 -14.361 -26.831 | 1.00 20.25 | | C |
| ATOM | 1598 O GLU B 7 | -2.848 -13.642 -25.912 | 1.00 20.37 | | O |
| ATOM | 1599 N PRO B 8 | -1.176 -14.448 -27.189 | 1.00 20.33 | | N |
| ATOM | 1600 CA PRO B 8 | -0.161 -13.832 -26.272 | 1.00 20.62 | | C |
| ATOM | 1601 CB PRO B 8 | 1.185 -14.308 -26.832 | 1.00 21.18 | | C |
| ATOM | 1602 CG PRO B 8 | 0.903 -14.763 -28.255 | 1.00 22.11 | | C |
| ATOM | 1603 CD PRO B 8 | -0.580 -15.055 -28.397 | 1.00 21.19 | | C |
| ATOM | 1604 C PRO B 8 | -0.186 -12.302 -26.208 | 1.00 20.08 | | C |
| ATOM | 1605 O PRO B 8 | 0.100 -11.718 -25.150 | 1.00 19.12 | | O |
| ATOM | 1606 N LYS B 9 | -0.531 -11.664 -27.326 | 1.00 19.80 | | N |
| ATOM | 1607 CA LYS B 9 | -0.481 -10.197 -27.376 | 1.00 19.04 | | C |
| ATOM | 1608 CB LYS B 9 | -0.651 -9.678 -28.796 | 1.00 18.14 | | C |
| ATOM | 1609 CG LYS B 9 | -0.448 -8.134 -28.874 | 1.00 19.75 | | C |
| ATOM | 1610 CD LYS B 9 | -0.435 -7.581 -30.283 | 1.00 19.57 | | C |
| ATOM | 1611 CE LYS B 9 | -0.250 -6.057 -30.217 | 1.00 21.83 | | C |
| ATOM | 1612 NZ LYS B 9 | -0.570 -5.481 -31.547 | 1.00 21.93 | | N |
| ATOM | 1613 C LYS B 9 | -1.514 -9.575 -26.419 | 1.00 17.83 | | C |
| ATOM | 1614 O LYS B 9 | -1.235 -8.585 -25.744 | 1.00 18.29 | | O |
| ATOM | 1615 N THR B 10 | -2.705 -10.181 -26.353 | 1.00 16.54 | | N |
| ATOM | 1616 CA THR B 10 | -3.813 -9.638 -25.579 | 1.00 14.80 | | C |
| ATOM | 1617 CB THR B 10 | -5.160 -9.823 -26.380 | 1.00 15.02 | | C |
| ATOM | 1618 OG1 THR B 10 | -5.347 -11.215 -26.606 | 1.00 13.15 | | O |
| ATOM | 1619 CG2 THR B 10 | -5.047 -9.185 -27.725 | 1.00 15.73 | | C |
| ATOM | 1620 C THR B 10 | -3.992 -10.380 -24.282 | 1.00 15.45 | | C |
| ATOM | 1621 O THR B 10 | -4.650 -9.896 -23.341 | 1.00 15.45 | | O |
| ATOM | 1622 N GLY B 11 | -3.460 -11.588 -24.216 | 1.00 15.01 | | N |
| ATOM | 1623 CA GLY B 11 | -3.686 -12.396 -23.033 | 1.00 15.64 | | C |
| ATOM | 1624 C GLY B 11 | -5.012 -13.135 -23.005 | 1.00 15.58 | | C |
| ATOM | 1625 O GLY B 11 | -5.275 -13.858 -22.058 | 1.00 16.11 | | O |
| ATOM | 1626 N PHE B 12 | -5.853 -12.957 -24.028 | 1.00 15.28 | | N |
| ATOM | 1627 CA PHE B 12 | -7.189 -13.593 -24.085 | 1.00 13.60 | | C |
| ATOM | 1628 CB PHE B 12 | -8.026 -12.963 -25.199 | 1.00 13.70 | | C |
| ATOM | 1629 CG PHE B 12 | -8.538 -11.548 -24.873 | 1.00 16.95 | | C |
| ATOM | 1630 CD1 PHE B 12 | -9.580 -10.987 -25.590 | 1.00 17.79 | | C |
| ATOM | 1631 CE1 PHE B 12 | -10.050 -9.661 -25.297 | 1.00 15.57 | | C |
| ATOM | 1632 CZ PHE B 12 | -9.504 -8.947 -24.296 | 1.00 16.82 | | C |
| ATOM | 1633 CE2 PHE B 12 | -8.437 -9.479 -23.571 | 1.00 16.82 | | C |
| ATOM | 1634 CD2 PHE B 12 | -7.964 -10.772 -23.854 | 1.00 18.47 | | C |
| ATOM | 1635 C PHE B 12 | -7.116 -15.103 -24.309 | 1.00 13.60 | | C |
| ATOM | 1636 O PHE B 12 | -6.295 -15.570 -25.080 | 1.00 13.65 | | O |
| ATOM | 1637 N SER B 13 | -7.991 -15.851 -23.640 | 1.00 12.45 | | N |
| ATOM | 1638 CA SER B 13 | -7.961 -17.315 -23.672 | 1.00 14.17 | | C |
| ATOM | 1639 CB SER B 13 | -8.086 -17.886 -22.245 | 1.00 14.28 | | C |
| ATOM | 1640 OG SER B 13 | -7.881 -19.297 -22.310 | 1.00 15.15 | | O |
| ATOM | 1641 C SER B 13 | -9.142 -17.847 -24.467 | 1.00 13.47 | | C |
| ATOM | 1642 O SER B 13 | -10.260 -17.296 -24.361 | 1.00 14.95 | | O |
| ATOM | 1643 N PHE B 14 | -8.909 -18.921 -25.222 | 1.00 12.17 | | N |
| ATOM | 1644 CA PHE B 14 | -9.942 -19.598 -26.016 | 1.00 12.29 | | C |
| ATOM | 1645 CB PHE B 14 | -9.579 -19.480 -27.531 | 1.00 11.69 | | C |
| ATOM | 1646 CG PHE B 14 | -9.767 -18.115 -28.079 | 1.00 12.47 | | C |
| ATOM | 1647 CD1 PHE B 14 | -10.957 -17.758 -28.738 | 1.00 12.45 | | C |
| ATOM | 1648 CE1 PHE B 14 | -11.147 -16.426 -29.202 | 1.00 10.55 | | C |
| ATOM | 1649 CZ PHE B 14 | -10.135 -15.463 -28.997 | 1.00 10.40 | | C |
| ATOM | 1650 CE2 PHE B 14 | -8.958 -15.831 -28.331 | 1.00 9.98 | | C |
| ATOM | 1651 CD2 PHE B 14 | -8.765 -17.133 -27.899 | 1.00 8.21 | | C |
| ATOM | 1652 C PHE B 14 | -10.011 -21.076 -25.611 | 1.00 13.00 | | C |
| ATOM | 1653 O PHE B 14 | -8.947 -21.751 -25.510 | 1.00 13.47 | | O |
| ATOM | 1654 N PRO B 15 | -11.232 -21.616 -25.413 | 1.00 14.61 | | N |
| ATOM | 1655 CA PRO B 15 | -11.276 -23.066 -25.097 | 1.00 15.97 | | C |
| ATOM | 1656 CB PRO B 15 | -12.735 -23.307 -24.693 | 1.00 16.35 | | C |
| ATOM | 1657 CG PRO B 15 | -13.509 -22.222 -25.340 | 1.00 16.32 | | C |
| ATOM | 1658 CD PRO B 15 | -12.574 -21.010 -25.439 | 1.00 14.34 | | C |
| ATOM | 1659 C PRO B 15 | -10.859 -23.968 -26.244 | 1.00 17.16 | | C |
| ATOM | 1660 O PRO B 15 | -10.951 -23.600 -27.433 | 1.00 16.70 | | O |
| ATOM | 1661 N ALA B 16 | -10.399 -25.156 -25.866 | 1.00 18.48 | | N |
| ATOM | 1662 CA ALA B 16 | -9.980 -26.168 -26.797 | 1.00 20.80 | | C |
| ATOM | 1663 CB ALA B 16 | -9.396 -27.361 -26.014 | 1.00 21.72 | | C |
| ATOM | 1664 C ALA B 16 | -11.108 -26.635 -27.740 | 1.00 20.32 | | C |
| ATOM | 1665 O ALA B 16 | -10.839 -26.935 -28.890 | 1.00 21.07 | | O |
| ATOM | 1666 N SER B 17 | -12.340 -26.673 -27.242 | 1.00 22.87 | | N |
| ATOM | 1667 CA SER B 17 | -13.523 -27.133 -27.992 | 1.00 24.42 | | C |
| ATOM | 1668 CB SER B 17 | -13.845 -28.596 -27.641 | 1.00 24.95 | | C |
| ATOM | 1669 OG SER B 17 | -12.664 -29.369 -27.663 | 1.00 27.07 | | O |
| ATOM | 1670 C SER B 17 | -14.709 -26.303 -27.575 | 1.00 25.69 | | C |
| ATOM | 1671 O SER B 17 | -14.721 -25.765 -26.459 | 1.00 26.37 | | O |
| ATOM | 1672 N ILE B 18 | -15.707 -26.194 -28.446 | 1.00 26.68 | | N |
| ATOM | 1673 CA ILE B 18 | -16.985 -25.554 -28.110 | 1.00 29.02 | | C |
| ATOM | 1674 CB ILE B 18 | -17.076 -24.034 -28.466 | 1.00 29.53 | | C |
| ATOM | 1675 CG1 ILE B 18 | -16.910 -23.749 -29.956 | 1.00 30.74 | | C |
| ATOM | 1676 CD1 ILE B 18 | -16.900 -22.263 -30.220 | 1.00 27.89 | | C |
| ATOM | 1677 CG2 ILE B 18 | -16.064 -23.209 -27.683 | 1.00 28.70 | | C |
| ATOM | 1678 C ILE B 18 | -18.210 -26.276 -28.693 | 1.00 30.98 | | C |
| ATOM | 1679 O ILE B 18 | -18.064 -27.176 -29.532 | 1.00 30.48 | | O |
| ATOM | 1680 N GLY B 19 | -19.393 -25.840 -28.245 | 1.00 32.82 | | N |
| ATOM | 1681 CA GLY B 19 | -20.698 -26.440 -28.606 | 1.00 35.63 | | C |
| ATOM | 1682 C GLY B 19 | -20.558 -27.943 -28.723 | 1.00 36.95 | | C |
| ATOM | 1683 O GLY B 19 | -21.207 -28.560 -29.583 | 1.00 37.64 | | O |
| ATOM | 1684 N ASP B 20 | -19.709 -28.506 -27.847 | 1.00 38.37 | | N |
| ATOM | 1685 CA ASP B 20 | -19.056 -29.836 -27.988 | 1.00 39.32 | | C |
| ATOM | 1686 CB ASP B 20 | -19.753 -30.899 -27.110 | 1.00 40.62 | | C |
| ATOM | 1687 CG ASP B 20 | -19.209 -30.940 -25.660 | 1.00 43.61 | | C |
| ATOM | 1688 OD1 ASP B 20 | -18.071 -30.462 -25.415 | 1.00 46.56 | | O |
| ATOM | 1689 OD2 ASP B 20 | -19.918 -31.471 -24.764 | 1.00 46.35 | | O |
| ATOM | 1690 C ASP B 20 | -18.909 -30.346 -29.437 | 1.00 38.87 | | C |
| ATOM | 1691 O ASP B 20 | -19.924 -30.482 -30.153 | 1.00 39.53 | | O |
| ATOM | 1692 N SER B 21 | -17.669 -30.639 -29.863 | 1.00 37.22 | | N |
| ATOM | 1693 CA SER B 21 | -17.398 -31.313 -31.159 | 1.00 34.35 | | C |
| ATOM | 1694 CB SER B 21 | -18.720 -31.715 -31.816 | 1.00 35.33 | | C |
| ATOM | 1695 OG SER B 21 | -19.576 -30.593 -32.002 | 1.00 32.57 | | O |
| ATOM | 1696 C SER B 21 | -16.574 -30.437 -32.129 | 1.00 32.64 | | C |
| ATOM | 1697 O SER B 21 | -15.853 -30.941 -33.044 | 1.00 31.80 | | O |
| ATOM | 1698 N ARG B 22 | -16.692 -29.125 -31.913 | 1.00 29.39 | | N |
| ATOM | 1699 CA ARG B 22 | -15.947 -28.133 -32.674 | 1.00 26.78 | | C |
| ATOM | 1700 CB ARG B 22 | -16.726 -26.828 -32.669 | 1.00 26.89 | | C |
| ATOM | 1701 CG ARG B 22 | -17.706 -26.790 -33.794 | 1.00 30.39 | | C |
| ATOM | 1702 CD ARG B 22 | -18.958 -26.145 -33.372 | 1.00 33.13 | | C |
| ATOM | 1703 NE ARG B 22 | -19.401 -25.353 -34.498 | 1.00 36.21 | | N |
| ATOM | 1704 CZ ARG B 22 | -20.576 -25.462 -35.097 | 1.00 36.59 | | C |
| ATOM | 1705 NH1 ARG B 22 | -21.465 -26.340 -34.681 | 1.00 39.50 | | N |
| ATOM | 1706 NH2 ARG B 22 | -20.846 -24.677 -36.124 | 1.00 34.93 | | N |
| ATOM | 1707 C ARG B 22 | -14.612 -27.916 -32.009 | 1.00 24.61 | | C |
| ATOM | 1708 O ARG B 22 | -14.576 -27.547 -30.858 | 1.00 24.48 | | O |
| ATOM | 1709 N ARG B 23 | -13.532 -28.134 -32.738 | 1.00 22.50 | | N |
| ATOM | 1710 CA ARG B 23 | -12.193 -28.056 -32.165 | 1.00 21.39 | | C |
| ATOM | 1711 CB ARG B 23 | -11.300 -29.181 -32.693 | 1.00 22.14 | | C |
| ATOM | 1712 CG ARG B 23 | -11.800 -30.553 -32.302 | 1.00 28.19 | | C |
| ATOM | 1713 CD ARG B 23 | -11.205 -31.083 -30.965 | 1.00 33.61 | | C |
| ATOM | 1714 NE ARG B 23 | -11.903 -32.307 -30.561 | 1.00 40.85 | | N |
| ATOM | 1715 CZ ARG B 23 | -13.164 -32.355 -30.118 | 1.00 42.06 | | C |
| ATOM | 1716 NH1 ARG B 23 | -13.894 -31.250 -30.015 | 1.00 42.18 | | N |
| ATOM | 1717 NH2 ARG B 23 | -13.705 -33.521 -29.795 | 1.00 43.81 | | N |
| ATOM | 1718 C ARG B 23 | -11.563 -26.754 -32.563 | 1.00 18.07 | | C |
| ATOM | 1719 O ARG B 23 | -11.643 -26.341 -33.711 | 1.00 15.80 | | O |
| ATOM | 1720 N LEU B 24 | -10.867 -26.140 -31.616 | 1.00 16.61 | | N |
| ATOM | 1721 CA LEU B 24 | -10.089 -24.950 -31.943 | 1.00 15.16 | | C |
| ATOM | 1722 CB LEU B 24 | -9.688 -24.239 -30.638 | 1.00 15.16 | | C |
| ATOM | 1723 CG LEU B 24 | -8.797 -23.025 -30.798 | 1.00 14.74 | | C |
| ATOM | 1724 CD1 LEU B 24 | -9.569 -21.869 -31.456 | 1.00 9.37 | | C |
| ATOM | 1725 CD2 LEU B 24 | -8.152 -22.601 -29.430 | 1.00 14.55 | | C |
| ATOM | 1726 C LEU B 24 | -8.856 -25.288 -32.788 | 1.00 17.10 | | C |
| ATOM | 1727 O LEU B 24 | -7.974 -26.069 -32.377 | 1.00 17.15 | | O |
| ATOM | 1728 N LEU B 25 | -8.764 -24.655 -33.948 | 1.00 17.01 | | N |
| ATOM | 1729 CA LEU B 25 | -7.717 -24.935 -34.904 | 1.00 17.77 | | C |
| ATOM | 1730 CB LEU B 25 | -8.351 -25.427 -36.202 | 1.00 16.74 | | C |
| ATOM | 1731 CG LEU B 25 | -8.648 -26.901 -36.466 | 1.00 19.47 | | C |
| ATOM | 1732 CD1 LEU B 25 | -8.663 -27.905 -35.323 | 1.00 21.03 | | C |
| ATOM | 1733 CD2 LEU B 25 | -9.867 -27.041 -37.396 | 1.00 19.60 | | C |
| ATOM | 1734 C LEU B 25 | -6.792 -23.770 -35.199 | 1.00 15.76 | | C |
| ATOM | 1735 O LEU B 25 | -5.683 -23.970 -35.665 | 1.00 15.89 | | O |
| ATOM | 1736 N GLY B 26 | -7.236 -22.541 -34.943 | 1.00 16.21 | | N |
| ATOM | 1737 CA GLY B 26 | -6.416 -21.370 -35.239 | 1.00 14.98 | | C |
| ATOM | 1738 C GLY B 26 | -6.859 -20.228 -34.317 | 1.00 16.47 | | C |
| ATOM | 1739 O GLY B 26 | -8.043 -20.115 -34.000 | 1.00 14.87 | | O |
| ATOM | 1740 N VAL B 27 | -5.921 -19.359 -33.922 | 1.00 14.93 | | N |
| ATOM | 1741 CA VAL B 27 | -6.276 -18.170 -33.113 | 1.00 14.88 | | C |
| ATOM | 1742 CB VAL B 27 | -5.863 -18.345 -31.623 | 1.00 15.21 | | C |
| ATOM | 1743 CG1 VAL B 27 | -5.904 -16.986 -30.888 | 1.00 15.40 | | C |
| ATOM | 1744 CG2 VAL B 27 | -6.734 -19.372 -30.904 | 1.00 14.61 | | C |
| ATOM | 1745 C VAL B 27 | -5.530 -16.984 -33.711 | 1.00 15.12 | | C |
| ATOM | 1746 O VAL B 27 | -4.338 -17.103 -34.038 | 1.00 15.18 | | O |
| ATOM | 1747 N GLY B 28 | -6.203 -15.847 -33.892 | 1.00 13.78 | | N |

Fig. 5 cont.

| ATOM | 1748 | CA  | GLY | B | 28 | -5.567 -14.663 -34.386 1.00 13.37 | C |
|------|------|-----|-----|---|----|-----------------------------------|---|
| ATOM | 1749 | C   | GLY | B | 28 | -6.110 -13.344 -33.855 1.00 13.68 | C |
| ATOM | 1750 | O   | GLY | B | 28 | -6.913 -13.314 -32.934 1.00 15.21 | O |
| ATOM | 1751 | N   | LEU | B | 29 | -5.590 -12.268 -34.397 1.00 13.97 | N |
| ATOM | 1752 | CA  | LEU | B | 29 | -6.019 -10.893 -34.099 1.00 15.38 | C |
| ATOM | 1753 | CB  | LEU | B | 29 | -4.851 -10.051 -33.588 1.00 16.28 | C |
| ATOM | 1754 | CG  | LEU | B | 29 | -4.573 -10.015 -32.115 1.00 20.46 | C |
| ATOM | 1755 | CD1 | LEU | B | 29 | -3.329 -9.066 -31.951 1.00 22.51  | C |
| ATOM | 1756 | CD2 | LEU | B | 29 | -5.782 -9.510 -31.304 1.00 21.60  | C |
| ATOM | 1757 | C   | LEU | B | 29 | -6.520 -10.174 -35.316 1.00 15.56 | C |
| ATOM | 1758 | O   | LEU | B | 29 | -5.917 -10.227 -36.415 1.00 15.98 | O |
| ATOM | 1759 | N   | ARG | B | 30 | -7.592 -9.429 -35.120 1.00 13.87  | N |
| ATOM | 1760 | CA  | ARG | B | 30 | -8.073 -8.593 -36.159 1.00 13.46  | C |
| ATOM | 1761 | CB  | ARG | B | 30 | -9.574 -8.707 -36.293 1.00 13.49  | C |
| ATOM | 1762 | CG  | ARG | B | 30 | -10.155 -8.046 -37.556 1.00 9.90  | C |
| ATOM | 1763 | CD  | ARG | B | 30 | -10.596 -6.607 -37.347 1.00 14.26 | C |
| ATOM | 1764 | NE  | ARG | B | 30 | -11.569 -6.251 -38.379 1.00 14.25 | N |
| ATOM | 1765 | CZ  | ARG | B | 30 | -11.467 -5.288 -39.293 1.00 17.77 | C |
| ATOM | 1766 | NH1 | ARG | B | 30 | -10.418 -4.483 -39.363 1.00 20.20 | N |
| ATOM | 1767 | NH2 | ARG | B | 30 | -12.473 -5.107 -40.154 1.00 16.21 | N |
| ATOM | 1768 | C   | ARG | B | 30 | -7.673 -7.183 -35.746 1.00 14.79  | C |
| ATOM | 1769 | O   | ARG | B | 30 | -8.143 -6.656 -34.740 1.00 13.89  | O |
| ATOM | 1770 | N   | LYS | B | 31 | -6.785 -6.616 -36.546 1.00 15.83  | N |
| ATOM | 1771 | CA  | LYS | B | 31 | -6.273 -5.273 -36.317 1.00 19.16  | C |
| ATOM | 1772 | CB  | LYS | B | 31 | -4.751 -5.256 -36.540 1.00 19.47  | C |
| ATOM | 1773 | CG  | LYS | B | 31 | -3.995 -6.313 -35.791 1.00 21.77  | C |
| ATOM | 1774 | CD  | LYS | B | 31 | -2.577 -5.836 -35.590 1.00 28.77  | C |
| ATOM | 1775 | CE  | LYS | B | 31 | -1.538 -6.845 -36.000 1.00 31.11  | C |
| ATOM | 1776 | NZ  | LYS | B | 31 | -0.249 -6.060 -36.076 1.00 33.26  | N |
| ATOM | 1777 | C   | LYS | B | 31 | -6.976 -4.301 -37.266 1.00 20.10  | C |
| ATOM | 1778 | O   | LYS | B | 31 | -7.642 -4.713 -38.240 1.00 21.42  | O |
| ATOM | 1779 | N   | LYS | B | 32 | -6.883 -3.005 -36.964 1.00 20.22  | N |
| ATOM | 1780 | CA  | LYS | B | 32 | -7.426 -1.964 -37.836 1.00 21.47  | C |
| ATOM | 1781 | CB  | LYS | B | 32 | -8.574 -1.235 -37.158 1.00 22.21  | C |
| ATOM | 1782 | CG  | LYS | B | 32 | -9.127 -0.014 -37.921 1.00 25.14  | C |
| ATOM | 1783 | CD  | LYS | B | 32 | -10.037 -0.425 -39.094 1.00 29.47 | C |
| ATOM | 1784 | CE  | LYS | B | 32 | -10.275 0.728 -40.057 1.00 34.62  | C |
| ATOM | 1785 | NZ  | LYS | B | 32 | -10.580 2.011 -39.323 1.00 36.81  | N |
| ATOM | 1786 | C   | LYS | B | 32 | -6.307 -0.966 -38.009 1.00 22.88  | C |
| ATOM | 1787 | O   | LYS | B | 32 | -5.878 -0.389 -37.023 1.00 21.78  | O |
| ATOM | 1788 | N   | SER | B | 33 | -5.823 -0.798 -39.241 1.00 24.43  | N |
| ATOM | 1789 | CA  | SER | B | 33 | -4.764 0.171 -39.518 1.00 26.12   | C |
| ATOM | 1790 | CB  | SER | B | 33 | -4.043 -0.208 -40.810 1.00 27.08  | C |
| ATOM | 1791 | OG  | SER | B | 33 | -3.078 0.759 -41.199 1.00 28.37   | O |
| ATOM | 1792 | C   | SER | B | 33 | -5.442 1.533 -39.600 1.00 26.93   | C |
| ATOM | 1793 | O   | SER | B | 33 | -6.390 1.718 -40.373 1.00 27.65   | O |
| ATOM | 1794 | N   | LEU | B | 34 | -5.031 2.459 -38.738 1.00 26.57   | N |
| ATOM | 1795 | CA  | LEU | B | 34 | -5.574 3.800 -38.750 1.00 27.20   | C |
| ATOM | 1796 | CB  | LEU | B | 34 | -5.892 4.281 -37.321 1.00 29.16   | C |
| ATOM | 1797 | CG  | LEU | B | 34 | -6.925 3.408 -36.592 1.00 27.42   | C |
| ATOM | 1798 | CD1 | LEU | B | 34 | -7.181 3.793 -35.163 1.00 25.88   | C |
| ATOM | 1799 | CD2 | LEU | B | 34 | -8.258 3.453 -37.351 1.00 28.16   | C |
| ATOM | 1800 | C   | LEU | B | 34 | -4.576 4.688 -39.526 1.00 28.50   | C |
| ATOM | 1801 | O   | LEU | B | 34 | -3.710 4.174 -40.243 1.00 28.68   | O |
| ATOM | 1802 | N   | LEU | B | 35 | -4.694 5.997 -39.405 1.00 29.88   | N |
| ATOM | 1803 | CA  | LEU | B | 35 | -3.869 6.886 -40.224 1.00 31.34   | C |
| ATOM | 1804 | CB  | LEU | B | 35 | -4.297 8.342 -40.015 1.00 32.30   | C |
| ATOM | 1805 | CG  | LEU | B | 35 | -5.671 8.823 -40.524 1.00 34.30   | C |
| ATOM | 1806 | CD1 | LEU | B | 35 | -5.863 10.329 -40.198 1.00 36.09  | C |
| ATOM | 1807 | CD2 | LEU | B | 35 | -5.887 8.550 -42.032 1.00 35.34   | C |
| ATOM | 1808 | C   | LEU | B | 35 | -2.390 6.692 -39.863 1.00 30.91   | C |
| ATOM | 1809 | O   | LEU | B | 35 | -2.064 6.617 -38.674 1.00 31.13   | O |
| ATOM | 1810 | N   | GLY | B | 36 | -1.527 6.543 -40.881 1.00 30.72   | N |
| ATOM | 1811 | CA  | GLY | B | 36 | -0.056 6.515 -40.685 1.00 29.47   | C |
| ATOM | 1812 | C   | GLY | B | 36 | 0.430 5.302 -39.900 1.00 28.09    | C |
| ATOM | 1813 | O   | GLY | B | 36 | 0.235 4.183 -40.347 1.00 28.10    | O |
| ATOM | 1814 | N   | LEU | B | 37 | 1.039 5.533 -38.727 1.00 26.43    | N |
| ATOM | 1815 | CA  | LEU | B | 37 | 1.611 4.461 -37.888 1.00 24.71    | C |
| ATOM | 1816 | CB  | LEU | B | 37 | 2.981 4.895 -37.312 1.00 24.75    | C |
| ATOM | 1817 | CG  | LEU | B | 37 | 4.166 4.897 -38.300 1.00 23.10    | C |
| ATOM | 1818 | CD1 | LEU | B | 37 | 5.195 5.980 -37.877 1.00 20.43    | C |
| ATOM | 1819 | CD2 | LEU | B | 37 | 4.819 3.530 -38.468 1.00 26.44    | C |
| ATOM | 1820 | C   | LEU | B | 37 | 0.704 4.024 -36.728 1.00 24.28    | C |
| ATOM | 1821 | O   | LEU | B | 37 | 1.138 3.258 -35.861 1.00 23.01    | O |
| ATOM | 1822 | N   | LYS | B | 38 | -0.537 4.527 -36.708 1.00 23.04   | N |
| ATOM | 1823 | CA  | LYS | B | 38 | -1.484 4.156 -35.664 1.00 23.05   | C |
| ATOM | 1824 | CB  | LYS | B | 38 | -2.532 5.253 -35.497 1.00 22.62   | C |
| ATOM | 1825 | CG  | LYS | B | 38 | -3.194 5.265 -34.123 1.00 24.62   | C |
| ATOM | 1826 | CD  | LYS | B | 38 | -4.073 6.518 -33.912 1.00 25.80   | C |
| ATOM | 1827 | CE  | LYS | B | 38 | -3.269 7.834 -33.919 1.00 31.43   | C |
| ATOM | 1828 | NZ  | LYS | B | 38 | -2.314 7.957 -32.742 1.00 30.66   | N |
| ATOM | 1829 | C   | LYS | B | 38 | -2.181 2.843 -36.065 1.00 22.45   | C |
| ATOM | 1830 | O   | LYS | B | 38 | -2.663 2.713 -37.196 1.00 22.42   | O |
| ATOM | 1831 | N   | ASN | B | 39 | -2.222 1.893 -35.144 1.00 22.48   | N |
| ATOM | 1832 | CA  | ASN | B | 39 | -2.946 0.641 -35.363 1.00 21.91   | C |
| ATOM | 1833 | CB  | ASN | B | 39 | -1.957 -0.456 -35.705 1.00 23.46  | C |
| ATOM | 1834 | CG  | ASN | B | 39 | -1.086 -0.097 -36.906 1.00 27.47  | C |
| ATOM | 1835 | OD1 | ASN | B | 39 | 0.063 0.350 -36.745 1.00 33.11    | O |
| ATOM | 1836 | ND2 | ASN | B | 39 | -1.641 -0.240 -38.116 1.00 28.80  | N |
| ATOM | 1837 | C   | ASN | B | 39 | -3.711 0.321 -34.085 1.00 21.29   | C |
| ATOM | 1838 | O   | ASN | B | 39 | -3.326 0.783 -32.991 1.00 20.09   | O |
| ATOM | 1839 | N   | ILE | B | 40 | -4.810 -0.417 -34.196 1.00 18.03  | N |
| ATOM | 1840 | CA  | ILE | B | 40 | -5.421 -0.916 -32.976 1.00 18.08  | C |
| ATOM | 1841 | CB  | ILE | B | 40 | -6.721 -0.174 -32.577 1.00 18.66  | C |
| ATOM | 1842 | CG1 | ILE | B | 40 | -7.773 -0.201 -33.685 1.00 17.80  | C |
| ATOM | 1843 | CD1 | ILE | B | 40 | -9.105 0.468 -33.227 1.00 18.98   | C |
| ATOM | 1844 | CG2 | ILE | B | 40 | -6.455 1.308 -32.231 1.00 19.44   | C |
| ATOM | 1845 | C   | ILE | B | 40 | -5.702 -2.391 -33.135 1.00 17.06  | C |
| ATOM | 1846 | O   | ILE | B | 40 | -5.957 -2.860 -34.254 1.00 16.03  | O |
| ATOM | 1847 | N   | ASP | B | 41 | -5.674 -3.108 -32.024 1.00 17.15  | N |
| ATOM | 1848 | CA  | ASP | B | 41 | -6.134 -4.515 -31.999 1.00 16.32  | C |
| ATOM | 1849 | CB  | ASP | B | 41 | -5.407 -5.252 -30.882 1.00 16.58  | C |
| ATOM | 1850 | CG  | ASP | B | 41 | -3.896 -5.236 -31.055 1.00 21.00  | C |
| ATOM | 1851 | OD1 | ASP | B | 41 | -3.403 -5.318 -32.199 1.00 23.90  | O |
| ATOM | 1852 | OD2 | ASP | B | 41 | -3.212 -5.131 -30.019 1.00 25.69  | O |
| ATOM | 1853 | C   | ASP | B | 41 | -7.606 -4.476 -31.668 1.00 14.76  | C |
| ATOM | 1854 | O   | ASP | B | 41 | -7.964 -4.051 -30.584 1.00 14.62  | O |
| ATOM | 1855 | N   | VAL | B | 42 | -8.459 -4.880 -32.604 1.00 13.37  | N |
| ATOM | 1856 | CA  | VAL | B | 42 | -9.880 -4.681 -32.419 1.00 11.65  | C |
| ATOM | 1857 | CB  | VAL | B | 42 | -10.644 -4.611 -33.792 1.00 12.08 | C |
| ATOM | 1858 | CG1 | VAL | B | 42 | -12.127 -4.320 -33.523 1.00 11.34 | C |
| ATOM | 1859 | CG2 | VAL | B | 42 | -10.112 -3.493 -34.656 1.00 13.58 | C |
| ATOM | 1860 | C   | VAL | B | 42 | -10.426 -5.848 -31.587 1.00 10.85 | C |
| ATOM | 1861 | O   | VAL | B | 42 | -11.145 -5.633 -30.621 1.00 10.31 | O |
| ATOM | 1862 | N   | TYR | B | 43 | -10.089 -7.086 -31.978 1.00 8.37  | N |
| ATOM | 1863 | CA  | TYR | B | 43 | -10.563 -8.272 -31.271 1.00 9.24  | C |
| ATOM | 1864 | CB  | TYR | B | 43 | -12.035 -8.635 -31.616 1.00 8.66  | C |
| ATOM | 1865 | CG  | TYR | B | 43 | -12.365 -8.955 -33.092 1.00 7.45  | C |
| ATOM | 1866 | CD1 | TYR | B | 43 | -12.959 -8.011 -33.910 1.00 8.76  | C |
| ATOM | 1867 | CE1 | TYR | B | 43 | -13.288 -8.299 -35.275 1.00 9.69  | C |
| ATOM | 1868 | CZ  | TYR | B | 43 | -13.007 -9.551 -35.806 1.00 10.80 | C |
| ATOM | 1869 | OH  | TYR | B | 43 | -13.367 -9.870 -37.131 1.00 10.50 | O |
| ATOM | 1870 | CE2 | TYR | B | 43 | -12.417 -10.518 -35.004 1.00 8.20 | C |
| ATOM | 1871 | CD2 | TYR | B | 43 | -12.102 -10.222 -33.644 1.00 10.85| C |
| ATOM | 1872 | C   | TYR | B | 43 | -9.648 -9.455 -31.585 1.00 9.06   | C |
| ATOM | 1873 | O   | TYR | B | 43 | -8.999 -9.500 -32.631 1.00 10.65  | O |
| ATOM | 1874 | N   | ALA | B | 44 | -9.620 -10.393 -30.678 1.00 8.85  | N |
| ATOM | 1875 | CA  | ALA | B | 44 | -8.966 -11.686 -30.929 1.00 9.08  | C |
| ATOM | 1876 | CB  | ALA | B | 44 | -8.332 -12.193 -29.689 1.00 9.79  | C |
| ATOM | 1877 | C   | ALA | B | 44 | -10.047 -12.642 -31.393 1.00 10.07| C |
| ATOM | 1878 | O   | ALA | B | 44 | -11.226 -12.476 -31.052 1.00 8.72 | O |
| ATOM | 1879 | N   | PHE | B | 45 | -9.650 -13.650 -32.153 1.00 9.92  | N |
| ATOM | 1880 | CA  | PHE | B | 45 | -10.608 -14.630 -32.593 1.00 9.21 | C |
| ATOM | 1881 | CB  | PHE | B | 45 | -11.194 -14.251 -33.984 1.00 8.41 | C |
| ATOM | 1882 | CG  | PHE | B | 45 | -10.169 -14.207 -35.119 1.00 9.61 | C |
| ATOM | 1883 | CD1 | PHE | B | 45 | -9.819 -15.364 -35.795 1.00 10.90 | C |
| ATOM | 1884 | CE1 | PHE | B | 45 | -8.900 -15.318 -36.807 1.00 9.72  | C |
| ATOM | 1885 | CZ  | PHE | B | 45 | -8.290 -14.115 -37.193 1.00 9.11  | C |
| ATOM | 1886 | CE2 | PHE | B | 45 | -8.654 -12.939 -36.564 1.00 11.65 | C |
| ATOM | 1887 | CD2 | PHE | B | 45 | -9.602 -12.997 -35.525 1.00 8.53  | C |
| ATOM | 1888 | C   | PHE | B | 45 | -10.042 -16.040 -32.580 1.00 9.20 | C |
| ATOM | 1889 | O   | PHE | B | 45 | -8.830 -16.225 -32.682 1.00 8.67  | O |
| ATOM | 1890 | N   | GLY | B | 46 | -10.948 -17.024 -32.489 1.00 8.77 | N |
| ATOM | 1891 | CA  | GLY | B | 46 | -10.614 -18.433 -32.435 1.00 8.40 | C |
| ATOM | 1892 | C   | GLY | B | 46 | -11.443 -19.050 -33.533 1.00 8.97 | C |
| ATOM | 1893 | O   | GLY | B | 46 | -12.610 -18.696 -33.683 1.00 8.70 | O |
| ATOM | 1894 | N   | VAL | B | 47 | -10.839 -19.917 -34.332 1.00 9.69 | N |
| ATOM | 1895 | CA  | VAL | B | 47 | -11.542 -20.534 -35.482 1.00 10.78| C |
| ATOM | 1896 | CB  | VAL | B | 47 | -10.776 -20.385 -36.836 1.00 11.91| C |
| ATOM | 1897 | CG1 | VAL | B | 47 | -11.661 -20.937 -38.026 1.00 11.79| C |
| ATOM | 1898 | CG2 | VAL | B | 47 | -10.401 -18.907 -37.231 1.00 11.11| C |
| ATOM | 1899 | C   | VAL | B | 47 | -11.697 -22.026 -35.115 1.00 10.97| C |
| ATOM | 1900 | O   | VAL | B | 47 | -10.691 -22.727 -34.890 1.00 11.46| O |
| ATOM | 1901 | N   | TYR | B | 48 | -12.936 -22.504 -35.077 1.00 11.58| N |
| ATOM | 1902 | CA  | TYR | B | 48 | -13.290 -23.866 -34.596 1.00 9.83 | C |
| ATOM | 1903 | CB  | TYR | B | 48 | -14.350 -23.781 -33.482 1.00 11.06| C |
| ATOM | 1904 | CG  | TYR | B | 48 | -13.833 -23.179 -32.194 1.00 9.49 | C |
| ATOM | 1905 | CD1 | TYR | B | 48 | -13.661 -21.817 -32.063 1.00 8.29 | C |
| ATOM | 1906 | CE1 | TYR | B | 48 | -13.177 -21.258 -30.857 1.00 6.82 | C |
| ATOM | 1907 | CZ  | TYR | B | 48 | -12.830 -22.097 -29.812 1.00 10.45| C |
| ATOM | 1908 | OH  | TYR | B | 48 | -12.318 -21.551 -28.661 1.00 11.90| O |
| ATOM | 1909 | CE2 | TYR | B | 48 | -12.978 -23.472 -29.937 1.00 9.80 | C |
| ATOM | 1910 | CD2 | TYR | B | 48 | -13.468 -23.998 -31.135 1.00 9.71 | C |
| ATOM | 1911 | C   | TYR | B | 48 | -13.963 -24.597 -35.747 1.00 11.92| C |
| ATOM | 1912 | O   | TYR | B | 48 | -14.768 -24.015 -36.478 1.00 10.83| O |
| ATOM | 1913 | N   | ALA | B | 49 | -13.679 -25.891 -35.901 1.00 12.45| N |
| ATOM | 1914 | CA  | ALA | B | 49 | -14.381 -26.644 -36.937 1.00 12.60| C |
| ATOM | 1915 | CB  | ALA | B | 49 | -13.501 -26.784 -38.187 1.00 13.45| C |
| ATOM | 1916 | C   | ALA | B | 49 | -14.784 -28.010 -36.386 1.00 14.48| C |
| ATOM | 1917 | O   | ALA | B | 49 | -14.108 -28.559 -35.502 1.00 15.09| O |

Fig. 5 cont.

```
ATOM 1918 N   ASP B 50   -15.895 -28.538 -36.890 1.00 13.55           N
ATOM 1919 CA  ASP B 50   -16.373 -29.868 -36.502 1.00 14.56           C
ATOM 1920 CB  ASP B 50   -17.781 -30.055 -37.075 1.00 14.79           C
ATOM 1921 CG  ASP B 50   -18.381 -31.435 -36.778 1.00 17.56           C
ATOM 1922 OD1 ASP B 50   -17.766 -32.426 -37.142 1.00 18.17           O
ATOM 1923 OD2 ASP B 50   -19.469 -31.545 -36.177 1.00 20.40           O
ATOM 1924 C   ASP B 50   -15.374 -30.856 -37.125 1.00 14.79           C
ATOM 1925 O   ASP B 50   -15.209 -30.870 -38.334 1.00 15.04           O
ATOM 1926 N   CYS B 51   -14.714 -31.671 -36.316 1.00 15.58           N
ATOM 1927 CA  CYS B 51   -13.643 -32.530 -36.822 1.00 17.91           C
ATOM 1928 CB  CYS B 51   -12.867 -33.160 -35.669 1.00 18.79           C
ATOM 1929 SG  CYS B 51   -12.050 -31.872 -34.776 1.00 30.23           S
ATOM 1930 C   CYS B 51   -14.171 -33.630 -37.716 1.00 16.11           C
ATOM 1931 O   CYS B 51   -13.528 -33.986 -38.697 1.00 16.78           O
ATOM 1932 N   ASP B 52   -15.338 -34.150 -37.379 1.00 16.05           N
ATOM 1933 CA  ASP B 52   -16.020 -35.149 -38.235 1.00 16.51           C
ATOM 1934 CB  ASP B 52   -17.345 -35.572 -37.593 1.00 17.74           C
ATOM 1935 CG  ASP B 52   -17.158 -36.267 -36.247 1.00 21.09           C
ATOM 1936 OD1 ASP B 52   -16.238 -37.061 -36.113 1.00 23.82           O
ATOM 1937 OD2 ASP B 52   -17.952 -36.015 -35.303 1.00 26.98           O
ATOM 1938 C   ASP B 52   -16.254 -34.615 -39.669 1.00 15.56           C
ATOM 1939 O   ASP B 52   -16.108 -35.351 -40.653 1.00 13.46           O
ATOM 1940 N   ASP B 53   -16.616 -33.328 -39.787 1.00 13.68           N
ATOM 1941 CA  ASP B 53   -16.967 -32.778 -41.084 1.00 13.75           C
ATOM 1942 CB  ASP B 53   -17.659 -31.384 -40.962 1.00 12.79           C
ATOM 1943 CG  ASP B 53   -19.100 -31.455 -40.432 1.00 19.12           C
ATOM 1944 OD1 ASP B 53   -19.675 -30.373 -40.085 1.00 14.89           O
ATOM 1945 OD2 ASP B 53   -19.680 -32.591 -40.351 1.00 17.73           O
ATOM 1946 C   ASP B 53   -15.688 -32.631 -41.907 1.00 14.20           C
ATOM 1947 O   ASP B 53   -15.689 -32.864 -43.142 1.00 14.05           O
ATOM 1948 N   VAL B 54   -14.599 -32.219 -41.232 1.00 13.29           N
ATOM 1949 CA  VAL B 54   -13.332 -32.030 -41.934 1.00 12.63           C
ATOM 1950 CB  VAL B 54   -12.280 -31.342 -41.053 1.00 11.67           C
ATOM 1951 CG1 VAL B 54   -10.958 -31.304 -41.755 1.00 13.04           C
ATOM 1952 CG2 VAL B 54   -12.708 -29.830 -40.726 1.00 10.79           C
ATOM 1953 C   VAL B 54   -12.847 -33.420 -42.363 1.00 12.80           C
ATOM 1954 O   VAL B 54   -12.306 -33.606 -43.465 1.00 12.46           O
ATOM 1955 N   LYS B 55   -13.037 -34.397 -41.494 1.00 13.47           N
ATOM 1956 CA  LYS B 55   -12.597 -35.754 -41.863 1.00 15.61           C
ATOM 1957 CB  LYS B 55   -12.685 -36.710 -40.697 1.00 15.57           C
ATOM 1958 CG  LYS B 55   -11.596 -36.472 -39.641 1.00 20.01           C
ATOM 1959 CD  LYS B 55   -11.904 -37.285 -38.400 1.00 19.86           C
ATOM 1960 CE  LYS B 55   -11.021 -36.869 -37.260 1.00 27.37           C
ATOM 1961 NZ  LYS B 55   -11.470 -37.557 -36.035 1.00 31.36           N
ATOM 1962 C   LYS B 55   -13.369 -36.292 -43.070 1.00 16.08           C
ATOM 1963 O   LYS B 55   -12.795 -36.963 -43.938 1.00 16.17           O
ATOM 1964 N   LYS B 56   -14.668 -36.426 -46.593 1.00 17.29           N
ATOM 1965 CA  LYS B 56   -15.501 -36.419 -44.250 1.00 17.68           C
ATOM 1966 CB  LYS B 56   -16.950 -36.083 -43.959 1.00 18.16           C
ATOM 1967 CG  LYS B 56   -17.892 -36.391 -45.117 1.00 21.88           C
ATOM 1968 CD  LYS B 56   -19.320 -36.046 -44.694 1.00 26.55           C
ATOM 1969 CE  LYS B 56   -20.125 -35.622 -45.921 1.00 29.09           C
ATOM 1970 NZ  LYS B 56   -20.318 -36.781 -46.816 1.00 28.87           N
ATOM 1971 C   LYS B 56   -15.051 -35.770 -45.557 1.00 17.16           C
ATOM 1972 O   LYS B 56   -14.989 -36.426 -46.593 1.00 15.46           O
ATOM 1973 N   LEU B 57   -14.725 -34.470 -45.507 1.00 17.65           N
ATOM 1974 CA  LEU B 57   -14.223 -33.785 -46.686 1.00 16.94           C
ATOM 1975 CB  LEU B 57   -13.972 -32.303 -46.353 1.00 16.94           C
ATOM 1976 CG  LEU B 57   -13.568 -31.254 -47.398 1.00 20.55           C
ATOM 1977 CD1 LEU B 57   -12.083 -31.256 -47.624 1.00 27.56           C
ATOM 1978 CD2 LEU B 57   -14.368 -31.337 -48.714 1.00 22.52           C
ATOM 1979 C   LEU B 57   -12.928 -34.420 -47.211 1.00 16.67           C
ATOM 1980 O   LEU B 57   -12.769 -34.596 -48.414 1.00 15.46           O
ATOM 1981 N   VAL B 58   -11.993 -34.703 -46.309 1.00 16.94           N
ATOM 1982 CA  VAL B 58   -10.721 -35.329 -46.696 1.00 18.47           C
ATOM 1983 CB  VAL B 58    -9.726 -35.447 -45.507 1.00 18.87           C
ATOM 1984 CG1 VAL B 58    -8.478 -36.275 -45.917 1.00 19.88           C
ATOM 1985 CG2 VAL B 58    -9.254 -34.079 -45.067 1.00 19.22           C
ATOM 1986 C   VAL B 58   -10.985 -36.719 -47.335 1.00 19.27           C
ATOM 1987 O   VAL B 58   -10.431 -37.052 -48.395 1.00 18.85           O
ATOM 1988 N   GLY B 59   -11.872 -37.483 -46.726 1.00 20.10           N
ATOM 1989 CA  GLY B 59   -12.275 -38.787 -47.276 1.00 22.26           C
ATOM 1990 C   GLY B 59   -12.946 -38.698 -48.646 1.00 23.96           C
ATOM 1991 O   GLY B 59   -12.773 -39.582 -49.491 1.00 25.18           O
ATOM 1992 N   ASP B 60   -13.718 -37.642 -48.877 1.00 24.05           N
ATOM 1993 CA  ASP B 60   -14.483 -37.511 -50.116 1.00 23.44           C
ATOM 1994 CB  ASP B 60   -15.638 -36.501 -49.968 1.00 24.22           C
ATOM 1995 CG  ASP B 60   -16.835 -37.030 -49.154 1.00 24.00           C
ATOM 1996 OD1 ASP B 60   -16.881 -38.233 -48.822 1.00 28.48           O
ATOM 1997 OD2 ASP B 60   -17.749 -36.210 -48.844 1.00 25.56           O
ATOM 1998 C   ASP B 60   -13.614 -37.018 -51.272 1.00 23.41           C
ATOM 1999 O   ASP B 60   -13.807 -37.436 -52.410 1.00 22.58           O
ATOM 2000 N   LYS B 61   -12.691 -36.098 -50.988 1.00 21.58           N
ATOM 2001 CA  LYS B 61   -12.038 -35.342 -52.032 1.00 22.26           C
ATOM 2002 CB  LYS B 61   -12.576 -33.900 -52.044 1.00 22.46           C
ATOM 2003 CG  LYS B 61   -14.035 -33.802 -52.533 1.00 24.39           C
ATOM 2004 CD  LYS B 61   -14.677 -32.430 -52.290 1.00 26.21           C
ATOM 2005 CE  LYS B 61   -14.348 -31.417 -53.356 1.00 30.70           C
ATOM 2006 NZ  LYS B 61   -15.470 -30.420 -53.569 1.00 33.39           N
ATOM 2007 C   LYS B 61   -10.492 -35.362 -51.966 1.00 21.19           C
ATOM 2008 O   LYS B 61    -9.828 -34.994 -52.936 1.00 20.38           O
ATOM 2009 N   TYR B 62    -9.940 -35.788 -50.830 1.00 20.21           N
ATOM 2010 CA  TYR B 62    -8.474 -35.766 -50.611 1.00 21.23           C
ATOM 2011 CB  TYR B 62    -8.090 -34.583 -49.685 1.00 21.48           C
ATOM 2012 CG  TYR B 62    -8.494 -33.231 -50.266 1.00 19.30           C
ATOM 2013 CD1 TYR B 62    -9.735 -32.658 -49.962 1.00 21.17           C
ATOM 2014 CE1 TYR B 62   -10.138 -31.402 -50.526 1.00 19.51           C
ATOM 2015 CZ  TYR B 62    -9.263 -30.721 -51.362 1.00 23.04           C
ATOM 2016 OH  TYR B 62    -9.650 -29.514 -51.931 1.00 24.56           O
ATOM 2017 CE2 TYR B 62    -8.016 -31.287 -51.692 1.00 20.07           C
ATOM 2018 CD2 TYR B 62    -7.634 -32.531 -51.129 1.00 21.87           C
ATOM 2019 C   TYR B 62    -7.952 -37.111 -50.084 1.00 21.02           C
ATOM 2020 O   TYR B 62    -6.970 -37.154 -49.352 1.00 21.28           O
ATOM 2021 N   ALA B 63    -8.606 -38.217 -50.479 1.00 20.81           N
ATOM 2022 CA  ALA B 63    -8.267 -39.548 -49.958 1.00 21.32           C
ATOM 2023 CB  ALA B 63    -9.326 -40.547 -50.389 1.00 21.12           C
ATOM 2024 C   ALA B 63    -6.864 -40.046 -50.374 1.00 20.85           C
ATOM 2025 O   ALA B 63    -6.409 -39.713 -51.441 1.00 21.05           O
ATOM 2026 N   ASN B 64    -6.201 -40.852 -49.535 1.00 22.50           N
ATOM 2027 CA  ASN B 64    -4.892 -41.457 -49.873 1.00 22.50           C
ATOM 2028 CB  ASN B 64    -5.066 -42.434 -51.054 1.00 24.25           C
ATOM 2029 CG  ASN B 64    -6.107 -43.480 -50.771 1.00 25.86           C
ATOM 2030 OD1 ASN B 64    -6.152 -44.026 -49.659 1.00 30.29           O
ATOM 2031 ND2 ASN B 64    -6.974 -43.764 -51.760 1.00 30.01           N
ATOM 2032 C   ASN B 64    -3.808 -40.420 -50.176 1.00 22.23           C
ATOM 2033 O   ASN B 64    -2.993 -40.610 -51.093 1.00 22.72           O
ATOM 2034 N   LEU B 65    -3.830 -39.292 -49.448 1.00 19.47           N
ATOM 2035 CA  LEU B 65    -2.859 -38.212 -49.651 1.00 17.92           C
ATOM 2036 CB  LEU B 65    -3.537 -36.912 -50.140 1.00 17.18           C
ATOM 2037 CG  LEU B 65    -4.182 -36.879 -51.535 1.00 18.46           C
ATOM 2038 CD1 LEU B 65    -4.741 -35.492 -51.869 1.00 19.53           C
ATOM 2039 CD2 LEU B 65    -3.175 -37.318 -52.594 1.00 20.49           C
ATOM 2040 C   LEU B 65    -2.221 -37.907 -48.316 1.00 17.12           C
ATOM 2041 O   LEU B 65    -2.906 -37.798 -47.329 1.00 16.91           O
ATOM 2042 N   PRO B 66    -0.910 -37.766 -48.276 1.00 16.14           N
ATOM 2043 CA  PRO B 66    -0.348 -37.262 -47.003 1.00 16.29           C
ATOM 2044 CB  PRO B 66     1.163 -37.333 -47.260 1.00 16.07           C
ATOM 2045 CG  PRO B 66     1.348 -37.400 -48.642 1.00 15.81           C
ATOM 2046 CD  PRO B 66     0.151 -38.091 -49.243 1.00 17.37           C
ATOM 2047 C   PRO B 66    -0.761 -35.812 -46.698 1.00 14.45           C
ATOM 2048 O   PRO B 66    -1.172 -35.106 -47.607 1.00 13.91           O
ATOM 2049 N   ALA B 67    -0.621 -35.379 -45.444 1.00 15.24           N
ATOM 2050 CA  ALA B 67    -1.069 -34.018 -45.018 1.00 16.39           C
ATOM 2051 CB  ALA B 67    -0.795 -33.788 -43.536 1.00 16.48           C
ATOM 2052 C   ALA B 67    -0.506 -32.897 -45.885 1.00 17.80           C
ATOM 2053 O   ALA B 67    -1.251 -31.998 -46.338 1.00 17.75           O
ATOM 2054 N   SER B 68     0.790 -32.972 -46.177 1.00 19.04           N
ATOM 2055 CA  SER B 68     1.444 -31.994 -47.030 1.00 19.96           C
ATOM 2056 CB  SER B 68     2.937 -32.330 -47.174 1.00 21.09           C
ATOM 2057 OG  SER B 68     3.091 -33.614 -47.776 1.00 24.27           O
ATOM 2058 C   SER B 68     0.809 -31.914 -48.435 1.00 19.70           C
ATOM 2059 O   SER B 68     0.775 -30.870 -49.048 1.00 19.35           O
ATOM 2060 N   GLU B 69     0.312 -33.027 -48.951 1.00 19.66           N
ATOM 2061 CA  GLU B 69    -0.255 -32.998 -50.283 1.00 19.74           C
ATOM 2062 CB  GLU B 69    -0.099 -34.369 -50.964 1.00 20.89           C
ATOM 2063 CG  GLU B 69     1.400 -34.880 -51.009 1.00 24.58           C
ATOM 2064 CD  GLU B 69     2.352 -33.909 -51.712 1.00 30.95           C
ATOM 2065 OE1 GLU B 69     3.251 -33.314 -51.061 1.00 32.30           O
ATOM 2066 OE2 GLU B 69     2.170 -33.718 -52.929 1.00 35.45           O
ATOM 2067 C   GLU B 69    -1.710 -32.479 -50.267 1.00 19.68           C
ATOM 2068 O   GLU B 69    -2.166 -31.801 -51.215 1.00 19.70           O
ATOM 2069 N   ILE B 70    -2.433 -32.778 -49.190 1.00 18.45           N
ATOM 2070 CA  ILE B 70    -3.734 -32.129 -48.945 1.00 18.44           C
ATOM 2071 CB  ILE B 70    -4.387 -32.638 -47.626 1.00 18.71           C
ATOM 2072 CG1 ILE B 70    -4.629 -34.151 -47.747 1.00 17.13           C
ATOM 2073 CD1 ILE B 70    -5.007 -34.853 -46.451 1.00 18.21           C
ATOM 2074 CG2 ILE B 70    -5.690 -31.853 -47.317 1.00 18.91           C
ATOM 2075 C   ILE B 70    -3.530 -30.624 -48.899 1.00 18.77           C
ATOM 2076 O   ILE B 70    -4.169 -29.870 -49.633 1.00 18.83           O
ATOM 2077 N   ARG B 71    -2.640 -30.190 -48.019 1.00 18.98           N
ATOM 2078 CA  ARG B 71    -2.346 -28.793 -47.834 1.00 21.60           C
ATOM 2079 CB  ARG B 71    -1.345 -28.671 -46.672 1.00 21.42           C
ATOM 2080 CG  ARG B 71    -1.012 -27.282 -46.262 1.00 25.01           C
ATOM 2081 CD  ARG B 71    -2.170 -26.640 -45.440 1.00 27.58           C
ATOM 2082 NE  ARG B 71    -1.612 -25.488 -44.758 1.00 25.84           N
ATOM 2083 CZ  ARG B 71    -1.538 -24.274 -45.265 1.00 27.36           C
ATOM 2084 NH1 ARG B 71    -2.029 -24.012 -46.477 1.00 27.84           N
ATOM 2085 NH2 ARG B 71    -0.952 -23.315 -44.542 1.00 28.39           N
ATOM 2086 C   ARG B 71    -1.877 -28.051 -49.103 1.00 22.69           C
ATOM 2087 O   ARG B 71    -2.215 -26.867 -49.307 1.00 22.93           O
```

Fig. 5 cont.

| | | | | | |
|---|---|---|---|---|---|
| ATOM | 2088 | N GLY B 72 | -1.097 -28.725 -49.953 1.00 23.84 | N |
| ATOM | 2089 | CA GLY B 72 | -0.611 -28.113 -51.201 1.00 25.29 | C |
| ATOM | 2090 | C GLY B 72 | -1.670 -27.952 -52.292 1.00 27.07 | C |
| ATOM | 2091 | O GLY B 72 | -1.346 -27.529 -53.414 1.00 26.99 | O |
| ATOM | 2092 | N ASN B 73 | -2.934 -28.272 -51.992 1.00 27.69 | N |
| ATOM | 2093 | CA ASN B 73 | -4.033 -28.058 -52.955 1.00 28.88 | C |
| ATOM | 2094 | CB ASN B 73 | -5.083 -29.144 -52.785 1.00 29.52 | C |
| ATOM | 2095 | CG ASN B 73 | -4.755 -30.393 -53.522 1.00 30.54 | C |
| ATOM | 2096 | OD1 ASN B 73 | -4.187 -31.326 -52.952 1.00 33.27 | O |
| ATOM | 2097 | ND2 ASN B 73 | -5.123 -30.444 -54.797 1.00 28.09 | N |
| ATOM | 2098 | C ASN B 73 | -4.717 -26.731 -52.666 1.00 29.76 | C |
| ATOM | 2099 | O ASN B 73 | -5.265 -26.577 -51.579 1.00 29.91 | O |
| ATOM | 2100 | N LYS B 74 | -4.702 -25.772 -53.604 1.00 31.36 | N |
| ATOM | 2101 | CA LYS B 74 | -5.407 -24.468 -53.377 1.00 32.14 | C |
| ATOM | 2102 | CB LYS B 74 | -5.239 -23.537 -54.574 1.00 33.12 | C |
| ATOM | 2103 | CG LYS B 74 | -4.821 -22.066 -54.219 1.00 36.19 | C |
| ATOM | 2104 | CD LYS B 74 | -5.987 -21.051 -54.364 1.00 41.44 | C |
| ATOM | 2105 | CE LYS B 74 | -6.517 -20.922 -55.810 1.00 44.09 | C |
| ATOM | 2106 | NZ LYS B 74 | -5.799 -19.977 -56.636 1.00 47.32 | N |
| ATOM | 2107 | C LYS B 74 | -6.885 -24.686 -53.060 1.00 31.37 | C |
| ATOM | 2108 | O LYS B 74 | -7.504 -23.928 -52.275 1.00 32.12 | O |
| ATOM | 2109 | N SER B 75 | -7.419 -25.779 -53.614 1.00 28.95 | N |
| ATOM | 2110 | CA SER B 75 | -8.803 -26.149 -53.431 1.00 26.54 | C |
| ATOM | 2111 | CB SER B 75 | -9.194 -27.246 -54.424 1.00 26.55 | C |
| ATOM | 2112 | OG SER B 75 | -8.519 -28.458 -54.137 1.00 25.92 | O |
| ATOM | 2113 | C SER B 75 | -9.142 -26.578 -52.009 1.00 25.27 | C |
| ATOM | 2114 | O SER B 75 | -10.304 -26.582 -51.654 1.00 24.77 | O |
| ATOM | 2115 | N PHE B 76 | -8.151 -26.938 -51.186 1.00 22.91 | N |
| ATOM | 2116 | CA PHE B 76 | -8.482 -27.407 -49.838 1.00 22.10 | C |
| ATOM | 2117 | CB PHE B 76 | -7.272 -28.094 -49.186 1.00 21.52 | C |
| ATOM | 2118 | CG PHE B 76 | -7.483 -28.550 -47.775 1.00 20.22 | C |
| ATOM | 2119 | CD1 PHE B 76 | -8.357 -29.590 -47.460 1.00 17.74 | C |
| ATOM | 2120 | CE1 PHE B 76 | -8.522 -30.039 -46.141 1.00 14.57 | C |
| ATOM | 2121 | CZ PHE B 76 | -7.776 -29.436 -45.132 1.00 16.86 | C |
| ATOM | 2122 | CE2 PHE B 76 | -6.879 -28.404 -45.468 1.00 15.63 | C |
| ATOM | 2123 | CD2 PHE B 76 | -6.724 -27.988 -46.759 1.00 18.15 | C |
| ATOM | 2124 | C PHE B 76 | -9.039 -26.239 -48.996 1.00 21.60 | C |
| ATOM | 2125 | O PHE B 76 | -10.096 -26.375 -48.360 1.00 21.49 | O |
| ATOM | 2126 | N MET B 77 | -8.324 -25.121 -49.001 1.00 21.15 | N |
| ATOM | 2127 | CA MET B 77 | -8.783 -23.885 -48.337 1.00 21.82 | C |
| ATOM | 2128 | CB MET B 77 | -7.824 -22.726 -48.630 1.00 21.35 | C |
| ATOM | 2129 | CG MET B 77 | -8.165 -21.397 -47.904 1.00 20.74 | C |
| ATOM | 2130 | SD MET B 77 | -7.123 -20.005 -48.453 1.00 23.19 | S |
| ATOM | 2131 | CE MET B 77 | -7.674 -19.797 -50.155 1.00 27.63 | C |
| ATOM | 2132 | C MET B 77 | -10.181 -23.484 -48.795 1.00 21.44 | C |
| ATOM | 2133 | O MET B 77 | -11.023 -23.194 -47.983 1.00 21.22 | O |
| ATOM | 2134 | N ASP B 78 | -10.403 -23.464 -50.100 1.00 21.57 | N |
| ATOM | 2135 | CA ASP B 78 | -11.714 -23.115 -50.685 1.00 23.07 | C |
| ATOM | 2136 | CB ASP B 78 | -11.646 -23.065 -52.210 1.00 24.41 | C |
| ATOM | 2137 | CG ASP B 78 | -10.689 -22.017 -52.722 1.00 30.69 | C |
| ATOM | 2138 | OD1 ASP B 78 | -10.554 -20.938 -52.083 1.00 36.73 | O |
| ATOM | 2139 | OD2 ASP B 78 | -10.086 -22.278 -53.790 1.00 37.85 | O |
| ATOM | 2140 | C ASP B 78 | -12.784 -24.116 -50.326 1.00 22.47 | C |
| ATOM | 2141 | O ASP B 78 | -13.899 -23.748 -49.948 1.00 21.38 | O |
| ATOM | 2142 | N ASP B 79 | -12.452 -25.395 -50.481 1.00 22.11 | N |
| ATOM | 2143 | CA ASP B 79 | -13.367 -26.463 -50.110 1.00 22.99 | C |
| ATOM | 2144 | CB ASP B 79 | -12.770 -27.829 -50.440 1.00 24.16 | C |
| ATOM | 2145 | CG ASP B 79 | -12.823 -28.162 -51.939 1.00 28.75 | C |
| ATOM | 2146 | OD1 ASP B 79 | -13.685 -27.599 -52.679 1.00 32.40 | O |
| ATOM | 2147 | OD2 ASP B 79 | -12.006 -29.016 -52.376 1.00 31.65 | O |
| ATOM | 2148 | C ASP B 79 | -13.804 -26.431 -48.660 1.00 22.40 | C |
| ATOM | 2149 | O ASP B 79 | -14.961 -26.724 -48.363 1.00 22.57 | O |
| ATOM | 2150 | N LEU B 80 | -12.891 -26.095 -47.740 1.00 20.18 | N |
| ATOM | 2151 | CA LEU B 80 | -13.262 -26.052 -46.340 1.00 19.52 | C |
| ATOM | 2152 | CB LEU B 80 | -12.073 -25.697 -45.482 1.00 17.77 | C |
| ATOM | 2153 | CG LEU B 80 | -11.084 -26.850 -45.224 1.00 20.30 | C |
| ATOM | 2154 | CD1 LEU B 80 | -9.807 -26.251 -44.688 1.00 19.42 | C |
| ATOM | 2155 | CD2 LEU B 80 | -11.657 -27.883 -44.266 1.00 18.22 | C |
| ATOM | 2156 | C LEU B 80 | -14.362 -25.028 -46.105 1.00 19.89 | C |
| ATOM | 2157 | O LEU B 80 | -15.236 -25.222 -45.241 1.00 20.59 | O |
| ATOM | 2158 | N MET B 81 | -14.299 -23.926 -46.854 1.00 18.27 | N |
| ATOM | 2159 | CA MET B 81 | -15.290 -22.862 -46.686 1.00 19.19 | C |
| ATOM | 2160 | CB MET B 81 | -14.701 -21.529 -47.056 1.00 18.17 | C |
| ATOM | 2161 | CG MET B 81 | -13.678 -21.039 -46.094 1.00 19.12 | C |
| ATOM | 2162 | SD MET B 81 | -13.026 -19.448 -46.595 1.00 21.69 | S |
| ATOM | 2163 | CE MET B 81 | -11.940 -19.805 -47.965 1.00 14.90 | C |
| ATOM | 2164 | C MET B 81 | -16.581 -23.094 -47.492 1.00 19.77 | C |
| ATOM | 2165 | O MET B 81 | -17.678 -22.689 -47.044 1.00 19.39 | O |
| ATOM | 2166 | N GLU B 82 | -16.445 -23.741 -48.648 1.00 19.85 | N |
| ATOM | 2167 | CA GLU B 82 | -17.581 -23.959 -49.572 1.00 22.21 | C |
| ATOM | 2168 | CB GLU B 82 | -17.095 -24.124 -51.022 1.00 21.99 | C |
| ATOM | 2169 | CG GLU B 82 | -16.664 -22.788 -51.634 1.00 26.66 | C |
| ATOM | 2170 | CD GLU B 82 | -15.904 -22.877 -52.962 1.00 28.97 | C |
| ATOM | 2171 | OE1 GLU B 82 | -15.650 -24.011 -53.470 1.00 35.09 | O |
| ATOM | 2172 | OE2 GLU B 82 | -15.551 -21.772 -53.493 1.00 34.06 | O |
| ATOM | 2173 | C GLU B 82 | -18.423 -25.169 -49.189 1.00 21.70 | C |
| ATOM | 2174 | O GLU B 82 | -19.621 -25.229 -49.511 1.00 21.90 | O |
| ATOM | 2175 | N ALA B 83 | -17.795 -26.139 -48.536 1.00 19.69 | N |
| ATOM | 2176 | CA ALA B 83 | -18.485 -27.370 -48.180 1.00 20.38 | C |
| ATOM | 2177 | CB ALA B 83 | -17.469 -28.466 -47.865 1.00 19.21 | C |
| ATOM | 2178 | C ALA B 83 | -19.436 -27.142 -46.988 1.00 20.44 | C |
| ATOM | 2179 | O ALA B 83 | -19.387 -26.099 -46.306 1.00 18.63 | O |
| ATOM | 2180 | N ASP B 84 | -20.313 -28.111 -46.744 1.00 20.34 | N |
| ATOM | 2181 | CA ASP B 84 | -21.178 -28.035 -45.579 1.00 21.98 | C |
| ATOM | 2182 | CB ASP B 84 | -22.482 -28.807 -45.804 1.00 23.28 | C |
| ATOM | 2183 | CG ASP B 84 | -23.535 -28.505 -44.723 1.00 29.45 | C |
| ATOM | 2184 | OD1 ASP B 84 | -23.133 -28.020 -43.635 1.00 32.64 | O |
| ATOM | 2185 | OD2 ASP B 84 | -24.754 -28.768 -44.952 1.00 34.48 | O |
| ATOM | 2186 | C ASP B 84 | -20.398 -28.541 -44.348 1.00 20.72 | C |
| ATOM | 2187 | O ASP B 84 | -20.640 -29.624 -43.823 1.00 21.71 | O |
| ATOM | 2188 | N ILE B 85 | -19.438 -27.737 -43.920 1.00 18.76 | N |
| ATOM | 2189 | CA ILE B 85 | -18.602 -28.044 -42.776 1.00 17.49 | C |
| ATOM | 2190 | CB ILE B 85 | -17.134 -27.918 -43.163 1.00 17.09 | C |
| ATOM | 2191 | CG1 ILE B 85 | -16.808 -28.966 -44.288 1.00 19.58 | C |
| ATOM | 2192 | CD1 ILE B 85 | -15.379 -28.845 -44.909 1.00 19.61 | C |
| ATOM | 2193 | CG2 ILE B 85 | -16.240 -28.086 -41.890 1.00 15.47 | C |
| ATOM | 2194 | C ILE B 85 | -18.911 -27.067 -41.641 1.00 16.12 | C |
| ATOM | 2195 | O ILE B 85 | -18.738 -25.850 -41.816 1.00 15.82 | O |
| ATOM | 2196 | N LYS B 86 | -19.376 -27.592 -40.508 1.00 13.69 | N |
| ATOM | 2197 | CA LYS B 86 | -19.706 -26.743 -39.360 1.00 12.84 | C |
| ATOM | 2198 | CB LYS B 86 | -20.436 -27.525 -38.264 1.00 14.26 | C |
| ATOM | 2199 | CG LYS B 86 | -21.948 -27.548 -38.488 1.00 18.89 | C |
| ATOM | 2200 | CD LYS B 86 | -22.368 -28.870 -38.869 1.00 24.78 | C |
| ATOM | 2201 | CE LYS B 86 | -22.376 -29.789 -37.675 1.00 23.25 | C |
| ATOM | 2202 | NZ LYS B 86 | -21.841 -31.053 -38.225 1.00 26.00 | N |
| ATOM | 2203 | C LYS B 86 | -18.466 -26.068 -38.764 1.00 12.68 | C |
| ATOM | 2204 | O LYS B 86 | -17.435 -26.720 -38.509 1.00 12.31 | O |
| ATOM | 2205 | N MET B 87 | -18.575 -24.757 -38.548 1.00 11.86 | N |
| ATOM | 2206 | CA MET B 87 | -17.447 -23.948 -38.022 1.00 13.42 | C |
| ATOM | 2207 | CB MET B 87 | -16.683 -23.299 -39.175 1.00 12.66 | C |
| ATOM | 2208 | CG MET B 87 | -15.837 -24.284 -39.980 1.00 16.91 | C |
| ATOM | 2209 | SD MET B 87 | -14.666 -23.421 -40.999 1.00 21.98 | S |
| ATOM | 2210 | CE MET B 87 | -14.172 -24.716 -42.113 1.00 20.52 | C |
| ATOM | 2211 | C MET B 87 | -17.974 -22.864 -37.131 1.00 12.31 | C |
| ATOM | 2212 | O MET B 87 | -19.148 -22.488 -37.254 1.00 11.93 | O |
| ATOM | 2213 | N THR B 88 | -17.119 -22.334 -36.241 1.00 11.41 | N |
| ATOM | 2214 | CA THR B 88 | -17.543 -21.229 -35.381 1.00 11.77 | C |
| ATOM | 2215 | CB THR B 88 | -17.875 -21.648 -33.940 1.00 11.53 | C |
| ATOM | 2216 | OG1 THR B 88 | -18.969 -22.560 -33.931 1.00 14.02 | O |
| ATOM | 2217 | CG2 THR B 88 | -18.268 -20.405 -33.080 1.00 13.95 | C |
| ATOM | 2218 | C THR B 88 | -16.364 -20.289 -35.341 1.00 11.01 | C |
| ATOM | 2219 | O THR B 88 | -15.207 -20.744 -35.177 1.00 10.34 | O |
| ATOM | 2220 | N ILE B 89 | -16.628 -19.008 -35.563 1.00 10.01 | N |
| ATOM | 2221 | CA ILE B 89 | -15.609 -18.009 -35.255 1.00 9.89 | C |
| ATOM | 2222 | CB ILE B 89 | -15.536 -16.905 -36.320 1.00 10.23 | C |
| ATOM | 2223 | CG1 ILE B 89 | -15.525 -17.487 -37.747 1.00 10.19 | C |
| ATOM | 2224 | CD1 ILE B 89 | -14.244 -18.214 -38.122 1.00 16.65 | C |
| ATOM | 2225 | CG2 ILE B 89 | -14.329 -15.998 -36.086 1.00 10.81 | C |
| ATOM | 2226 | C ILE B 89 | -15.994 -17.375 -33.931 1.00 9.67 | C |
| ATOM | 2227 | O ILE B 89 | -17.070 -16.792 -33.845 1.00 8.29 | O |
| ATOM | 2228 | N ARG B 90 | -15.143 -17.516 -32.895 1.00 8.74 | N |
| ATOM | 2229 | CA ARG B 90 | -15.381 -16.851 -31.612 1.00 8.72 | C |
| ATOM | 2230 | CB ARG B 90 | -15.013 -17.708 -30.392 1.00 10.08 | C |
| ATOM | 2231 | CG ARG B 90 | -15.093 -16.904 -29.047 1.00 11.69 | C |
| ATOM | 2232 | CD ARG B 90 | -15.162 -17.859 -27.870 1.00 18.23 | C |
| ATOM | 2233 | NE ARG B 90 | -16.427 -18.584 -27.870 1.00 15.59 | N |
| ATOM | 2234 | CZ ARG B 90 | -16.759 -19.480 -26.942 1.00 20.50 | C |
| ATOM | 2235 | NH1 ARG B 90 | -15.935 -19.736 -25.930 1.00 19.17 | N |
| ATOM | 2236 | NH2 ARG B 90 | -17.925 -20.099 -27.006 1.00 19.88 | N |
| ATOM | 2237 | C ARG B 90 | -14.567 -15.541 -31.602 1.00 9.67 | C |
| ATOM | 2238 | O ARG B 90 | -13.351 -15.555 -31.767 1.00 8.75 | O |
| ATOM | 2239 | N LEU B 91 | -15.259 -14.413 -31.455 1.00 8.75 | N |
| ATOM | 2240 | CA LEU B 91 | -14.613 -13.079 -31.318 1.00 9.61 | C |
| ATOM | 2241 | CB LEU B 91 | -15.399 -12.022 -32.119 1.00 9.70 | C |
| ATOM | 2242 | CG LEU B 91 | -15.443 -12.146 -33.636 1.00 10.25 | C |
| ATOM | 2243 | CD1 LEU B 91 | -16.414 -13.222 -34.026 1.00 14.62 | C |
| ATOM | 2244 | CD2 LEU B 91 | -15.902 -10.801 -34.216 1.00 10.86 | C |
| ATOM | 2245 | C LEU B 91 | -14.612 -12.683 -29.853 1.00 10.07 | C |
| ATOM | 2246 | O LEU B 91 | -15.626 -12.848 -29.168 1.00 10.69 | O |
| ATOM | 2247 | N GLN B 92 | -13.473 -12.212 -29.355 1.00 10.25 | N |
| ATOM | 2248 | CA GLN B 92 | -13.406 -11.660 -28.017 1.00 9.67 | C |
| ATOM | 2249 | CB GLN B 92 | -12.477 -12.459 -27.139 1.00 11.25 | C |
| ATOM | 2250 | CG GLN B 92 | -13.047 -13.795 -26.780 1.00 13.16 | C |
| ATOM | 2251 | CD GLN B 92 | -12.199 -14.490 -25.759 1.00 20.93 | C |
| ATOM | 2252 | OE1 GLN B 92 | -11.781 -15.623 -25.981 1.00 22.18 | O |
| ATOM | 2253 | NE2 GLN B 92 | -11.944 -13.829 -24.631 1.00 17.67 | N |
| ATOM | 2254 | C GLN B 92 | -12.885 -10.246 -28.139 1.00 10.56 | C |
| ATOM | 2255 | O GLN B 92 | -11.747 -10.024 -28.581 1.00 7.82 | O |
| ATOM | 2256 | N ILE B 93 | -13.718 -9.284 -27.747 1.00 9.35 | N |
| ATOM | 2257 | CA ILE B 93 | -13.397 -7.903 -28.030 1.00 9.29 | C |

Fig. 5 cont.

| ATOM | 2258 | CB  | ILE B 93  | -14.616 | -6.998  | -27.767 | 1.00 | 9.53  | C |
|------|------|-----|-----------|---------|---------|---------|------|-------|---|
| ATOM | 2259 | CG1 | ILE B 93  | -15.815 | -7.387  | -28.683 | 1.00 | 11.84 | C |
| ATOM | 2260 | CD1 | ILE B 93  | -15.481 | -7.411  | -30.162 | 1.00 | 10.78 | C |
| ATOM | 2261 | CG2 | ILE B 93  | -14.254 | -5.555  | -27.990 | 1.00 | 8.58  | C |
| ATOM | 2262 | C   | ILE B 93  | -12.223 | -7.356  | -27.190 | 1.00 | 9.73  | C |
| ATOM | 2263 | O   | ILE B 93  | -12.239 | -7.472  | -25.959 | 1.00 | 8.44  | O |
| ATOM | 2264 | N   | VAL B 94  | -11.254 | -6.723  | -27.871 | 1.00 | 9.52  | N |
| ATOM | 2265 | CA  | VAL B 94  | -10.028 | -6.194  | -27.199 | 1.00 | 11.81 | C |
| ATOM | 2266 | CB  | VAL B 94  | -8.739  | -6.557  | -28.028 | 1.00 | 11.82 | C |
| ATOM | 2267 | CG1 | VAL B 94  | -7.437  | -5.971  | -27.344 | 1.00 | 12.71 | C |
| ATOM | 2268 | CG2 | VAL B 94  | -8.648  | -8.093  | -28.168 | 1.00 | 14.10 | C |
| ATOM | 2269 | C   | VAL B 94  | -10.116 | -4.687  | -26.988 | 1.00 | 11.88 | C |
| ATOM | 2270 | O   | VAL B 94  | -9.815  | -4.191  | -25.899 | 1.00 | 13.55 | O |
| ATOM | 2271 | N   | TYR B 95  | -10.519 | -3.959  | -28.021 | 1.00 | 12.14 | N |
| ATOM | 2272 | CA  | TYR B 95  | -10.483 | -2.484  | -28.016 | 1.00 | 14.97 | C |
| ATOM | 2273 | CB  | TYR B 95  | -10.643 | -1.918  | -29.421 | 1.00 | 15.95 | C |
| ATOM | 2274 | CG  | TYR B 95  | -10.393 | -0.440  | -29.532 | 1.00 | 18.94 | C |
| ATOM | 2275 | CD1 | TYR B 95  | -9.134  | 0.091   | -29.262 | 1.00 | 21.52 | C |
| ATOM | 2276 | CE1 | TYR B 95  | -8.891  | 1.452   | -29.359 | 1.00 | 23.46 | C |
| ATOM | 2277 | CZ  | TYR B 95  | -9.900  | 2.295   | -29.738 | 1.00 | 22.44 | C |
| ATOM | 2278 | OH  | TYR B 95  | -9.623  | 3.650   | -29.836 | 1.00 | 25.27 | O |
| ATOM | 2279 | CE2 | TYR B 95  | -11.155 | 1.810   | -30.030 | 1.00 | 22.44 | C |
| ATOM | 2280 | CD2 | TYR B 95  | -11.406 | 0.433   | -29.918 | 1.00 | 21.05 | C |
| ATOM | 2281 | C   | TYR B 95  | -11.584 | -2.002  | -27.102 | 1.00 | 15.05 | C |
| ATOM | 2282 | O   | TYR B 95  | -12.667 | -2.557  | -27.132 | 1.00 | 17.22 | O |
| ATOM | 2283 | N   | GLY B 96  | -11.312 | -1.029  | -26.236 | 1.00 | 15.47 | N |
| ATOM | 2284 | CA  | GLY B 96  | -12.310 | -0.775  | -25.169 | 1.00 | 15.96 | C |
| ATOM | 2285 | C   | GLY B 96  | -13.254 | 0.379   | -25.481 | 1.00 | 17.55 | C |
| ATOM | 2286 | O   | GLY B 96  | -14.132 | 0.700   | -24.675 | 1.00 | 17.87 | O |
| ATOM | 2287 | N   | LYS B 97  | -13.088 | 0.997   | -26.643 | 1.00 | 17.61 | N |
| ATOM | 2288 | CA  | LYS B 97  | -13.904 | 2.171   | -26.964 | 1.00 | 19.93 | C |
| ATOM | 2289 | CB  | LYS B 97  | -13.114 | 3.476   | -26.776 | 1.00 | 20.77 | C |
| ATOM | 2290 | CG  | LYS B 97  | -11.616 | 3.353   | -27.091 | 1.00 | 25.43 | C |
| ATOM | 2291 | CD  | LYS B 97  | -10.699 | 3.425   | -25.861 | 1.00 | 30.67 | C |
| ATOM | 2292 | CE  | LYS B 97  | -9.302  | 2.787   | -26.075 | 1.00 | 29.76 | C |
| ATOM | 2293 | NZ  | LYS B 97  | -9.235  | 1.264   | -25.838 | 1.00 | 34.73 | N |
| ATOM | 2294 | C   | LYS B 97  | -14.507 | 2.135   | -28.351 | 1.00 | 19.07 | C |
| ATOM | 2295 | O   | LYS B 97  | -14.517 | 3.151   | -29.051 | 1.00 | 19.52 | O |
| ATOM | 2296 | N   | LEU B 98  | -15.004 | 0.972   | -28.758 | 1.00 | 18.13 | N |
| ATOM | 2297 | CA  | LEU B 98  | -15.658 | 0.841   | -30.071 | 1.00 | 17.53 | C |
| ATOM | 2298 | CB  | LEU B 98  | -16.002 | -0.613  | -30.352 | 1.00 | 17.07 | C |
| ATOM | 2299 | CG  | LEU B 98  | -14.799 | -1.512  | -30.605 | 1.00 | 17.31 | C |
| ATOM | 2300 | CD1 | LEU B 98  | -15.253 | -2.996  | -30.577 | 1.00 | 17.58 | C |
| ATOM | 2301 | CD2 | LEU B 98  | -14.106 | -1.126  | -31.909 | 1.00 | 17.56 | C |
| ATOM | 2302 | C   | LEU B 98  | -16.944 | 1.648   | -30.119 | 1.00 | 18.54 | C |
| ATOM | 2303 | O   | LEU B 98  | -17.702 | 1.680   | -29.143 | 1.00 | 18.92 | O |
| ATOM | 2304 | N   | ASN B 99  | -17.168 | 2.292   | -31.260 | 1.00 | 19.05 | N |
| ATOM | 2305 | CA  | ASN B 99  | -18.347 | 3.127   | -31.511 | 1.00 | 20.83 | C |
| ATOM | 2306 | CB  | ASN B 99  | -17.877 | 4.391   | -32.292 | 1.00 | 21.81 | C |
| ATOM | 2307 | CG  | ASN B 99  | -18.989 | 5.126   | -33.020 | 1.00 | 24.92 | C |
| ATOM | 2308 | OD1 | ASN B 99  | -20.073 | 4.625   | -33.206 | 1.00 | 30.20 | O |
| ATOM | 2309 | ND2 | ASN B 99  | -18.701 | 6.377   | -33.423 | 1.00 | 33.02 | N |
| ATOM | 2310 | C   | ASN B 99  | -19.223 | 2.222   | -32.357 | 1.00 | 19.89 | C |
| ATOM | 2311 | O   | ASN B 99  | -18.800 | 1.811   | -33.398 | 1.00 | 20.00 | O |
| ATOM | 2312 | N   | ILE B 100 | -20.428 | 1.903   | -31.918 | 1.00 | 19.35 | N |
| ATOM | 2313 | CA  | ILE B 100 | -21.221 | 0.940   | -32.667 | 1.00 | 20.51 | C |
| ATOM | 2314 | CB  | ILE B 100 | -22.420 | 0.464   | -31.876 | 1.00 | 21.96 | C |
| ATOM | 2315 | CG1 | ILE B 100 | -22.907 | -0.860  | -32.453 | 1.00 | 23.52 | C |
| ATOM | 2316 | CD1 | ILE B 100 | -23.566 | -1.723  | -31.416 | 1.00 | 27.96 | C |
| ATOM | 2317 | CG2 | ILE B 100 | -23.537 | 1.551   | -31.828 | 1.00 | 21.15 | C |
| ATOM | 2318 | C   | ILE B 100 | -21.596 | 1.391   | -34.113 | 1.00 | 20.25 | C |
| ATOM | 2319 | O   | ILE B 100 | -21.685 | 0.571   | -35.026 | 1.00 | 19.84 | O |
| ATOM | 2320 | N   | ARG B 101 | -21.773 | 2.694   | -34.319 | 1.00 | 19.30 | N |
| ATOM | 2321 | CA  | ARG B 101 | -22.006 | 3.219   | -35.663 | 1.00 | 19.19 | C |
| ATOM | 2322 | CB  | ARG B 101 | -22.350 | 4.725   | -35.615 | 1.00 | 19.10 | C |
| ATOM | 2323 | CG  | ARG B 101 | -22.759 | 5.338   | -36.967 | 1.00 | 22.27 | C |
| ATOM | 2324 | CD  | ARG B 101 | -23.151 | 6.822   | -36.842 | 1.00 | 21.95 | C |
| ATOM | 2325 | NE  | ARG B 101 | -24.468 | 7.004   | -36.216 | 1.00 | 27.98 | N |
| ATOM | 2326 | CZ  | ARG B 101 | -25.634 | 6.913   | -36.855 | 1.00 | 29.80 | C |
| ATOM | 2327 | NH1 | ARG B 101 | -25.682 | 6.665   | -38.160 | 1.00 | 32.68 | N |
| ATOM | 2328 | NH2 | ARG B 101 | -26.765 | 7.078   | -36.182 | 1.00 | 32.19 | N |
| ATOM | 2329 | C   | ARG B 101 | -20.808 | 2.917   | -36.560 | 1.00 | 18.22 | C |
| ATOM | 2330 | O   | ARG B 101 | -20.992 | 2.446   | -37.688 | 1.00 | 17.59 | O |
| ATOM | 2331 | N   | SER B 102 | -19.588 | 3.137   | -36.058 | 1.00 | 17.57 | N |
| ATOM | 2332 | CA  | SER B 102 | -18.374 | 2.850   | -36.836 | 1.00 | 18.99 | C |
| ATOM | 2333 | CB  | SER B 102 | -17.134 | 3.566   | -36.262 | 1.00 | 19.82 | C |
| ATOM | 2334 | OG  | SER B 102 | -16.596 | 2.801   | -35.194 | 1.00 | 27.52 | O |
| ATOM | 2335 | C   | SER B 102 | -18.123 | 1.337   | -37.003 | 1.00 | 18.30 | C |
| ATOM | 2336 | O   | SER B 102 | -17.610 | 0.910   | -38.046 | 1.00 | 18.65 | O |
| ATOM | 2337 | N   | VAL B 103 | -18.518 | 0.545   | -36.009 | 1.00 | 15.44 | N |
| ATOM | 2338 | CA  | VAL B 103 | -18.493 | -0.946  | -36.120 | 1.00 | 13.86 | C |
| ATOM | 2339 | CB  | VAL B 103 | -18.725 | -1.695  | -34.788 | 1.00 | 14.36 | C |
| ATOM | 2340 | CG1 | VAL B 103 | -18.911 | -3.256  | -35.010 | 1.00 | 12.36 | C |
| ATOM | 2341 | CG2 | VAL B 103 | -17.552 | -1.464  | -33.822 | 1.00 | 12.51 | C |
| ATOM | 2342 | C   | VAL B 103 | -19.410 | -1.452  | -37.228 | 1.00 | 14.59 | C |

| ATOM | 2343 | O   | VAL B 103 | -18.964 | -2.247  | -38.046 | 1.00 | 14.13 | O |
|------|------|-----|-----------|---------|---------|---------|------|-------|---|
| ATOM | 2344 | N   | ARG B 104 | -20.651 | -0.959  | -37.288 | 1.00 | 12.84 | N |
| ATOM | 2345 | CA  | ARG B 104 | -21.578 | -1.337  | -38.354 | 1.00 | 13.76 | C |
| ATOM | 2346 | CB  | ARG B 104 | -22.959 | -0.741  | -38.123 | 1.00 | 13.69 | C |
| ATOM | 2347 | CG  | ARG B 104 | -23.737 | -1.418  | -37.009 | 1.00 | 15.13 | C |
| ATOM | 2348 | CD  | ARG B 104 | -25.092 | -0.764  | -36.754 | 1.00 | 15.85 | C |
| ATOM | 2349 | NE  | ARG B 104 | -25.884 | -1.505  | -35.765 | 1.00 | 16.53 | N |
| ATOM | 2350 | CZ  | ARG B 104 | -26.239 | -1.038  | -34.561 | 1.00 | 18.50 | C |
| ATOM | 2351 | NH1 | ARG B 104 | -25.865 | 0.175   | -34.171 | 1.00 | 18.65 | N |
| ATOM | 2352 | NH2 | ARG B 104 | -26.990 | -1.793  | -33.737 | 1.00 | 14.54 | N |
| ATOM | 2353 | C   | ARG B 104 | -21.018 | -0.932  | -39.723 | 1.00 | 15.41 | C |
| ATOM | 2354 | O   | ARG B 104 | -21.005 | -1.708  | -40.663 | 1.00 | 14.20 | O |
| ATOM | 2355 | N   | ASN B 105 | -20.492 | 0.280   | -39.822 | 1.00 | 15.91 | N |
| ATOM | 2356 | CA  | ASN B 105 | -19.877 | 0.699   | -41.047 | 1.00 | 17.74 | C |
| ATOM | 2357 | CB  | ASN B 105 | -19.353 | 2.129   | -40.869 | 1.00 | 18.83 | C |
| ATOM | 2358 | CG  | ASN B 105 | -20.436 | 3.128   | -40.974 | 1.00 | 23.31 | C |
| ATOM | 2359 | OD1 | ASN B 105 | -21.490 | 2.854   | -41.570 | 1.00 | 32.46 | O |
| ATOM | 2360 | ND2 | ASN B 105 | -20.204 | 4.318   | -40.430 | 1.00 | 30.60 | N |
| ATOM | 2361 | C   | ASN B 105 | -18.754 | -0.234  | -41.486 | 1.00 | 17.67 | C |
| ATOM | 2362 | O   | ASN B 105 | -18.626 | -0.554  | -42.673 | 1.00 | 18.53 | O |
| ATOM | 2363 | N   | ALA B 106 | -17.950 | -0.670  | -40.521 | 1.00 | 17.58 | N |
| ATOM | 2364 | CA  | ALA B 106 | -16.774 | -1.479  | -40.778 | 1.00 | 17.32 | C |
| ATOM | 2365 | CB  | ALA B 106 | -15.905 | -1.553  | -39.524 | 1.00 | 18.40 | C |
| ATOM | 2366 | C   | ALA B 106 | -17.114 | -2.877  | -41.264 | 1.00 | 16.72 | C |
| ATOM | 2367 | O   | ALA B 106 | -16.458 | -3.400  | -42.183 | 1.00 | 16.73 | O |
| ATOM | 2368 | N   | PHE B 107 | -18.091 | -3.520  | -40.631 | 1.00 | 15.32 | N |
| ATOM | 2369 | CA  | PHE B 107 | -18.426 | -4.893  | -41.074 | 1.00 | 14.35 | C |
| ATOM | 2370 | CB  | PHE B 107 | -19.010 | -5.781  | -39.945 | 1.00 | 13.69 | C |
| ATOM | 2371 | CG  | PHE B 107 | -20.432 | -5.490  | -39.532 | 1.00 | 13.18 | C |
| ATOM | 2372 | CD1 | PHE B 107 | -21.513 | -5.612  | -40.429 | 1.00 | 12.79 | C |
| ATOM | 2373 | CE1 | PHE B 107 | -22.828 | -5.403  | -40.017 | 1.00 | 9.50  | C |
| ATOM | 2374 | CZ  | PHE B 107 | -23.089 | -5.119  | -38.712 | 1.00 | 12.14 | C |
| ATOM | 2375 | CE2 | PHE B 107 | -22.031 | -5.030  | -37.780 | 1.00 | 12.31 | C |
| ATOM | 2376 | CD2 | PHE B 107 | -20.710 | -5.226  | -38.206 | 1.00 | 14.20 | C |
| ATOM | 2377 | C   | PHE B 107 | -19.233 | -4.883  | -42.399 | 1.00 | 14.81 | C |
| ATOM | 2378 | O   | PHE B 107 | -19.163 | -5.808  | -43.205 | 1.00 | 14.11 | O |
| ATOM | 2379 | N   | GLN B 108 | -19.965 | -3.814  | -42.644 | 1.00 | 14.40 | N |
| ATOM | 2380 | CA  | GLN B 108 | -20.647 | -3.709  | -43.935 | 1.00 | 15.84 | C |
| ATOM | 2381 | CB  | GLN B 108 | -21.689 | -2.578  | -43.891 | 1.00 | 17.18 | C |
| ATOM | 2382 | CG  | GLN B 108 | -22.744 | -2.914  | -42.844 | 1.00 | 18.66 | C |
| ATOM | 2383 | CD  | GLN B 108 | -23.558 | -1.722  | -42.400 | 1.00 | 26.14 | C |
| ATOM | 2384 | OE1 | GLN B 108 | -23.322 | -0.600  | -42.840 | 1.00 | 26.74 | O |
| ATOM | 2385 | NE2 | GLN B 108 | -24.511 | -1.960  | -41.505 | 1.00 | 27.50 | N |
| ATOM | 2386 | C   | GLN B 108 | -19.634 | -3.625  | -45.097 | 1.00 | 15.88 | C |
| ATOM | 2387 | O   | GLN B 108 | -19.828 | -4.257  | -46.145 | 1.00 | 15.28 | O |
| ATOM | 2388 | N   | GLU B 109 | -18.535 | -2.907  | -44.864 | 1.00 | 16.56 | N |
| ATOM | 2389 | CA  | GLU B 109 | -17.395 | -2.831  | -45.764 | 1.00 | 17.34 | C |
| ATOM | 2390 | CB  | GLU B 109 | -16.389 | -1.810  | -45.230 | 1.00 | 17.72 | C |
| ATOM | 2391 | CG  | GLU B 109 | -15.092 | -1.675  | -46.043 | 1.00 | 21.29 | C |
| ATOM | 2392 | CD  | GLU B 109 | -14.172 | -0.583  | -45.467 | 1.00 | 24.17 | C |
| ATOM | 2393 | OE1 | GLU B 109 | -12.991 | -0.499  | -45.897 | 1.00 | 33.91 | O |
| ATOM | 2394 | OE2 | GLU B 109 | -14.628 | 0.182   | -44.569 | 1.00 | 31.34 | O |
| ATOM | 2395 | C   | GLU B 109 | -16.699 | -4.171  | -45.921 | 1.00 | 15.41 | C |
| ATOM | 2396 | O   | GLU B 109 | -16.455 | -4.621  | -47.034 | 1.00 | 16.56 | O |
| ATOM | 2397 | N   | SER B 110 | -16.369 | -4.831  | -44.826 | 1.00 | 14.07 | N |
| ATOM | 2398 | CA  | SER B 110 | -15.571 | -6.067  | -44.924 | 1.00 | 13.23 | C |
| ATOM | 2399 | CB  | SER B 110 | -14.965 | -6.411  | -43.568 | 1.00 | 13.85 | C |
| ATOM | 2400 | OG  | SER B 110 | -16.002 | -6.659  | -42.637 | 1.00 | 14.26 | O |
| ATOM | 2401 | C   | SER B 110 | -16.420 | -7.217  | -45.473 | 1.00 | 13.91 | C |
| ATOM | 2402 | O   | SER B 110 | -16.038 | -7.913  | -46.429 | 1.00 | 14.13 | O |
| ATOM | 2403 | N   | VAL B 111 | -17.584 | -7.430  | -44.864 | 1.00 | 14.10 | N |
| ATOM | 2404 | CA  | VAL B 111 | -18.480 | -8.484  | -45.329 | 1.00 | 13.98 | C |
| ATOM | 2405 | CB  | VAL B 111 | -19.626 | -8.737  | -44.301 | 1.00 | 13.60 | C |
| ATOM | 2406 | CG1 | VAL B 111 | -20.613 | -9.797  | -44.816 | 1.00 | 15.09 | C |
| ATOM | 2407 | CG2 | VAL B 111 | -19.043 | -9.206  | -42.981 | 1.00 | 13.14 | C |
| ATOM | 2408 | C   | VAL B 111 | -19.009 | -8.147  | -46.736 | 1.00 | 14.48 | C |
| ATOM | 2409 | O   | VAL B 111 | -19.087 | -9.023  | -47.618 | 1.00 | 13.54 | O |
| ATOM | 2410 | N   | GLY B 112 | -19.358 | -6.879  | -46.960 | 1.00 | 13.26 | N |
| ATOM | 2411 | CA  | GLY B 112 | -19.817 | -6.448  | -48.285 | 1.00 | 15.30 | C |
| ATOM | 2412 | C   | GLY B 112 | -18.786 | -6.720  | -49.387 | 1.00 | 16.23 | C |
| ATOM | 2413 | O   | GLY B 112 | -19.155 | -7.162  | -50.489 | 1.00 | 15.99 | O |
| ATOM | 2414 | N   | ASN B 113 | -17.520 | -6.398  | -49.110 | 1.00 | 17.27 | N |
| ATOM | 2415 | CA  | ASN B 113 | -16.370 | -6.667  | -50.020 | 1.00 | 18.11 | C |
| ATOM | 2416 | CB  | ASN B 113 | -15.043 | -6.327  | -49.336 | 1.00 | 20.77 | C |
| ATOM | 2417 | CG  | ASN B 113 | -13.799 | -6.778  | -50.113 | 1.00 | 26.18 | C |
| ATOM | 2418 | OD1 | ASN B 113 | -13.329 | -7.944  | -50.016 | 1.00 | 29.56 | O |
| ATOM | 2419 | ND2 | ASN B 113 | -13.192 | -5.819  | -50.823 | 1.00 | 32.15 | N |
| ATOM | 2420 | C   | ASN B 113 | -16.373 | -8.123  | -50.444 | 1.00 | 18.13 | C |
| ATOM | 2421 | O   | ASN B 113 | -16.272 | -8.397  | -51.633 | 1.00 | 16.62 | O |
| ATOM | 2422 | N   | ARG B 114 | -16.510 | -9.051  | -49.480 | 1.00 | 16.34 | N |
| ATOM | 2423 | CA  | ARG B 114 | -16.494 | -10.498 | -49.802 | 1.00 | 15.36 | C |
| ATOM | 2424 | CB  | ARG B 114 | -16.264 | -11.356 | -48.569 | 1.00 | 16.10 | C |
| ATOM | 2425 | CG  | ARG B 114 | -14.928 | -11.149 | -47.992 | 1.00 | 16.36 | C |
| ATOM | 2426 | CD  | ARG B 114 | -13.807 | -11.399 | -49.013 | 1.00 | 20.23 | C |
| ATOM | 2427 | NE  | ARG B 114 | -12.678 | -10.582 | -48.607 | 1.00 | 22.01 | N |

Fig. 5 cont.

```
ATOM 2428 CZ  ARG B 114   -11.603 -11.032 -48.016 1.00 20.46   C
ATOM 2429 NH1 ARG B 114   -11.452 -12.315 -47.787 1.00 25.32   N
ATOM 2430 NH2 ARG B 114   -10.676 -10.188 -47.649 1.00 22.50   N
ATOM 2431 C   ARG B 114   -17.716 -11.016 -50.491 1.00 16.59   C
ATOM 2432 O   ARG B 114   -17.605 -11.915 -51.320 1.00 17.01   O
ATOM 2433 N   LEU B 115   -18.889 -10.503 -50.133 1.00 15.33   N
ATOM 2434 CA  LEU B 115   -20.105 -10.871 -50.838 1.00 17.46   C
ATOM 2435 CB  LEU B 115   -21.280 -10.071 -50.279 1.00 16.20   C
ATOM 2436 CG  LEU B 115   -22.263 -10.623 -49.226 1.00 19.90   C
ATOM 2437 CD1 LEU B 115   -22.109 -12.119 -48.751 1.00 13.42   C
ATOM 2438 CD2 LEU B 115   -22.707  -9.691 -48.154 1.00 17.05   C
ATOM 2439 C   LEU B 115   -19.934 -10.606 -52.332 1.00 19.39   C
ATOM 2440 O   LEU B 115   -20.268 -11.447 -53.166 1.00 20.16   O
ATOM 2441 N   LYS B 116   -19.405  -9.428 -52.665 1.00 20.24   N
ATOM 2442 CA  LYS B 116   -19.146  -9.040 -54.050 1.00 21.53   C
ATOM 2443 CB  LYS B 116   -18.669  -7.573 -54.084 1.00 21.19   C
ATOM 2444 CG  LYS B 116   -18.406  -6.989 -55.456 1.00 24.54   C
ATOM 2445 CD  LYS B 116   -17.990  -5.521 -55.291 1.00 24.86   C
ATOM 2446 CE  LYS B 116   -17.517  -4.877 -56.618 1.00 31.15   C
ATOM 2447 NZ  LYS B 116   -18.013  -3.442 -56.682 1.00 33.46   N
ATOM 2448 C   LYS B 116   -18.139  -9.977 -54.714 1.00 20.83   C
ATOM 2449 O   LYS B 116   -18.313 -10.347 -55.864 1.00 21.04   O
ATOM 2450 N   LYS B 117   -17.099 -10.360 -53.993 1.00 20.47   N
ATOM 2451 CA  LYS B 117   -16.090 -11.283 -54.495 1.00 21.90   C
ATOM 2452 CB  LYS B 117   -15.031 -11.489 -53.432 1.00 21.94   C
ATOM 2453 CG  LYS B 117   -14.081 -12.600 -53.671 1.00 24.53   C
ATOM 2454 CD  LYS B 117   -12.726 -12.072 -54.083 1.00 30.18   C
ATOM 2455 CE  LYS B 117   -11.643 -12.997 -53.558 1.00 33.31   C
ATOM 2456 NZ  LYS B 117   -12.102 -13.502 -52.215 1.00 34.04   N
ATOM 2457 C   LYS B 117   -16.639 -12.652 -54.944 1.00 22.30   C
ATOM 2458 O   LYS B 117   -16.232 -13.193 -55.988 1.00 21.08   O
ATOM 2459 N   PHE B 118   -17.511 -13.225 -54.126 1.00 21.08   N
ATOM 2460 CA  PHE B 118   -18.065 -14.535 -54.413 1.00 22.77   C
ATOM 2461 CB  PHE B 118   -18.180 -15.329 -53.113 1.00 22.85   C
ATOM 2462 CG  PHE B 118   -16.860 -15.563 -52.466 1.00 24.10   C
ATOM 2463 CD1 PHE B 118   -16.511 -14.886 -51.315 1.00 22.65   C
ATOM 2464 CE1 PHE B 118   -15.266 -15.096 -50.713 1.00 23.94   C
ATOM 2465 CZ  PHE B 118   -14.352 -15.953 -51.294 1.00 27.06   C
ATOM 2466 CE2 PHE B 118   -14.683 -16.629 -52.473 1.00 28.58   C
ATOM 2467 CD2 PHE B 118   -15.942 -16.426 -53.050 1.00 26.04   C
ATOM 2468 C   PHE B 118   -19.408 -14.507 -55.102 1.00 23.03   C
ATOM 2469 O   PHE B 118   -19.808 -15.510 -55.651 1.00 23.41   O
ATOM 2470 N   GLY B 119   -20.122 -13.388 -55.049 1.00 23.78   N
ATOM 2471 CA  GLY B 119   -21.511 -13.368 -55.521 1.00 26.66   C
ATOM 2472 C   GLY B 119   -21.917 -12.221 -56.430 1.00 28.90   C
ATOM 2473 O   GLY B 119   -21.797  -9.160 -56.578 1.00 29.96   O
ATOM 2474 N   GLY B 120   -20.948 -11.547 -57.030 1.00 30.77   N
ATOM 2475 CA  GLY B 120   -21.255 -10.358 -57.822 1.00 32.24   C
ATOM 2476 C   GLY B 120   -21.791  -9.577 -57.056 1.00 33.21   C
ATOM 2477 O   GLY B 120   -21.801  -9.141 -55.817 1.00 32.37   O
ATOM 2478 N   SER B 121   -22.283  -8.173 -57.806 1.00 34.32   N
ATOM 2479 CA  SER B 121   -22.455  -6.802 -57.288 1.00 35.91   C
ATOM 2480 CB  SER B 121   -22.270  -5.773 -58.406 1.00 35.57   C
ATOM 2481 OG  SER B 121   -20.913  -5.371 -58.418 1.00 37.02   O
ATOM 2482 C   SER B 121   -23.711  -6.481 -56.487 1.00 36.49   C
ATOM 2483 O   SER B 121   -23.731  -5.495 -55.744 1.00 37.41   O
ATOM 2484 N   ASP B 122   -24.751  -7.283 -56.674 1.00 36.79   N
ATOM 2485 CA  ASP B 122   -25.985  -7.225 -55.882 1.00 37.63   C
ATOM 2486 CB  ASP B 122   -26.870  -8.412 -56.285 1.00 39.43   C
ATOM 2487 CG  ASP B 122   -26.041  -9.679 -56.693 1.00 42.87   C
ATOM 2488 OD1 ASP B 122   -26.390 -10.809 -56.227 1.00 45.96   O
ATOM 2489 OD2 ASP B 122   -25.054  -9.548 -57.482 1.00 44.39   O
ATOM 2490 C   ASP B 122   -25.727  -7.263 -54.364 1.00 36.44   C
ATOM 2491 O   ASP B 122   -24.979  -6.443 -53.818 1.00 37.59   O
ATOM 2492 N   ASN B 123   -26.351  -8.205 -53.674 1.00 34.55   N
ATOM 2493 CA  ASN B 123   -26.059  -8.458 -52.239 1.00 31.10   C
ATOM 2494 CB  ASN B 123   -24.563  -8.739 -52.007 1.00 31.64   C
ATOM 2495 CG  ASN B 123   -24.018  -9.734 -52.952 1.00 30.50   C
ATOM 2496 OD1 ASN B 123   -24.686 -10.704 -53.308 1.00 29.42   O
ATOM 2497 ND2 ASN B 123   -22.802  -9.486 -53.412 1.00 30.88   N
ATOM 2498 C   ASN B 123   -26.483  -7.436 -51.175 1.00 29.42   C
ATOM 2499 O   ASN B 123   -26.273  -7.699 -50.003 1.00 27.51   O
ATOM 2500 N   ASP B 124   -27.043  -6.282 -51.561 1.00 27.11   N
ATOM 2501 CA  ASP B 124   -27.481  -5.300 -50.567 1.00 25.75   C
ATOM 2502 CB  ASP B 124   -28.005  -4.026 -51.249 1.00 27.38   C
ATOM 2503 CG  ASP B 124   -26.894  -3.177 -51.832 1.00 30.82   C
ATOM 2504 OD1 ASP B 124   -25.763  -3.182 -51.275 1.00 35.67   O
ATOM 2505 OD2 ASP B 124   -27.152  -2.468 -52.830 1.00 37.24   O
ATOM 2506 C   ASP B 124   -28.527  -5.871 -49.588 1.00 23.29   C
ATOM 2507 O   ASP B 124   -28.441  -5.678 -48.368 1.00 21.51   O
ATOM 2508 N   GLU B 125   -29.493  -6.606 -50.119 1.00 21.07   N
ATOM 2509 CA  GLU B 125   -30.511  -7.226 -49.293 1.00 21.09   C
ATOM 2510 CB  GLU B 125   -31.541  -7.940 -50.173 1.00 20.86   C
ATOM 2511 CG  GLU B 125   -32.316  -6.977 -51.119 1.00 26.29   C
ATOM 2512 CD  GLU B 125   -33.537  -7.620 -51.761 1.00 27.37   C
ATOM 2513 OE1 GLU B 125   -34.352  -6.859 -52.339 1.00 35.02   O
ATOM 2514 OE2 GLU B 125   -33.696  -8.872 -51.663 1.00 35.98   O
ATOM 2515 C   GLU B 125   -29.890  -8.247 -48.338 1.00 18.21   C
ATOM 2516 O   GLU B 125   -30.292  -8.348 -47.192 1.00 16.05   O
ATOM 2517 N   LEU B 126   -28.978  -9.063 -48.868 1.00 15.69   N
ATOM 2518 CA  LEU B 126   -28.296 -10.064 -48.041 1.00 14.07   C
ATOM 2519 CB  LEU B 126   -27.412 -10.971 -48.912 1.00 14.01   C
ATOM 2520 CG  LEU B 126   -26.619 -12.044 -48.130 1.00 13.83   C
ATOM 2521 CD1 LEU B 126   -27.532 -12.926 -47.300 1.00 13.19   C
ATOM 2522 CD2 LEU B 126   -25.786 -12.875 -49.108 1.00 14.82   C
ATOM 2523 C   LEU B 126   -27.482  -9.409 -46.940 1.00 13.24   C
ATOM 2524 O   LEU B 126   -27.542  -9.826 -45.797 1.00 13.24   O
ATOM 2525 N   LEU B 127   -26.736  -8.352 -47.270 1.00 13.61   N
ATOM 2526 CA  LEU B 127   -25.908  -7.694 -46.264 1.00 13.76   C
ATOM 2527 CB  LEU B 127   -24.999  -6.657 -46.950 1.00 13.79   C
ATOM 2528 CG  LEU B 127   -24.067  -5.867 -46.045 1.00 15.96   C
ATOM 2529 CD1 LEU B 127   -23.059  -6.810 -45.433 1.00 11.38   C
ATOM 2530 CD2 LEU B 127   -23.439  -4.808 -46.869 1.00 15.41   C
ATOM 2531 C   LEU B 127   -26.800  -7.054 -45.208 1.00 14.38   C
ATOM 2532 O   LEU B 127   -26.490  -7.040 -44.013 1.00 12.11   O
ATOM 2533 N   GLN B 128   -27.939  -6.529 -45.638 1.00 14.59   N
ATOM 2534 CA  GLN B 128   -28.913  -6.014 -44.653 1.00 15.73   C
ATOM 2535 CB  GLN B 128   -30.054  -5.231 -45.320 1.00 16.65   C
ATOM 2536 CG  GLN B 128   -30.980  -4.521 -44.301 1.00 20.82   C
ATOM 2537 CD  GLN B 128   -30.238  -3.524 -43.353 1.00 28.38   C
ATOM 2538 OE1 GLN B 128   -29.423  -2.690 -43.799 1.00 32.98   O
ATOM 2539 NE2 GLN B 128   -30.518  -3.625 -42.040 1.00 27.01   N
ATOM 2540 C   GLN B 128   -29.494  -7.061 -43.711 1.00 14.88   C
ATOM 2541 O   GLN B 128   -29.675  -6.774 -42.557 1.00 15.35   O
ATOM 2542 N   SER B 129   -29.832  -8.270 -44.188 1.00 15.56   N
ATOM 2543 CA  SER B 129   -30.296  -9.307 -43.290 1.00 14.53   C
ATOM 2544 CB  SER B 129   -30.721 -10.590 -44.043 1.00 16.10   C
ATOM 2545 OG  SER B 129   -29.617 -11.173 -44.713 1.00 19.97   O
ATOM 2546 C   SER B 129   -29.225  -9.627 -42.217 1.00 13.71   C
ATOM 2547 O   SER B 129   -29.579  -9.991 -41.085 1.00 13.65   O
ATOM 2548 N   PHE B 130   -27.948  -9.539 -42.581 1.00 14.88   N
ATOM 2549 CA  PHE B 130   -26.855  -9.711 -41.585 1.00 11.02   C
ATOM 2550 CB  PHE B 130   -25.495  -9.862 -42.337 1.00 10.64   C
ATOM 2551 CG  PHE B 130   -24.305 -10.016 -41.411 1.00 11.51   C
ATOM 2552 CD1 PHE B 130   -24.128 -11.177 -40.700 1.00  9.78   C
ATOM 2553 CE1 PHE B 130   -23.038 -11.295 -39.792 1.00  8.89   C
ATOM 2554 CZ  PHE B 130   -22.131 -10.270 -39.708 1.00 11.35   C
ATOM 2555 CE2 PHE B 130   -22.312  -9.116 -40.389 1.00 13.46   C
ATOM 2556 CD2 PHE B 130   -23.371  -9.006 -41.288 1.00 11.47   C
ATOM 2557 C   PHE B 130   -26.820  -8.528 -40.612 1.00 11.64   C
ATOM 2558 O   PHE B 130   -26.873  -8.701 -39.377 1.00 13.19   O
ATOM 2559 N   THR B 131   -26.770  -7.311 -41.149 1.00 11.12   N
ATOM 2560 CA  THR B 131   -26.755  -6.105 -40.275 1.00 11.65   C
ATOM 2561 CB  THR B 131   -26.855  -4.856 -41.127 1.00 11.40   C
ATOM 2562 OG1 THR B 131   -25.691  -4.791 -41.958 1.00 13.69   O
ATOM 2563 CG2 THR B 131   -26.983  -3.605 -40.261 1.00 13.60   C
ATOM 2564 C   THR B 131   -27.929  -6.170 -39.299 1.00 11.96   C
ATOM 2565 O   THR B 131   -27.757  -5.882 -38.108 1.00 11.18   O
ATOM 2566 N   SER B 132   -29.115  -6.562 -39.793 1.00 12.41   N
ATOM 2567 CA  SER B 132   -30.334  -6.589 -38.940 1.00 14.15   C
ATOM 2568 CB  SER B 132   -31.609  -6.911 -39.726 1.00 16.25   C
ATOM 2569 OG  SER B 132   -31.886  -5.885 -40.647 1.00 21.58   O
ATOM 2570 C   SER B 132   -30.251  -7.511 -37.743 1.00 13.48   C
ATOM 2571 O   SER B 132   -30.928  -7.302 -36.767 1.00 12.31   O
ATOM 2572 N   LEU B 133   -29.409  -8.545 -37.802 1.00 13.61   N
ATOM 2573 CA  LEU B 133   -29.152  -9.374 -36.624 1.00 13.13   C
ATOM 2574 CB  LEU B 133   -28.008 -10.448 -36.955 1.00 13.05   C
ATOM 2575 CG  LEU B 133   -28.489 -11.492 -38.016 1.00 14.08   C
ATOM 2576 CD1 LEU B 133   -27.371 -12.571 -38.171 1.00 14.34   C
ATOM 2577 CD2 LEU B 133   -29.772 -12.143 -37.662 1.00 16.89   C
ATOM 2578 C   LEU B 133   -28.683  -8.604 -35.397 1.00 13.16   C
ATOM 2579 O   LEU B 133   -28.863  -9.058 -34.235 1.00 13.05   O
ATOM 2580 N   PHE B 134   -28.049  -7.468 -35.643 1.00 12.99   N
ATOM 2581 CA  PHE B 134   -27.478  -6.644 -34.573 1.00 13.22   C
ATOM 2582 CB  PHE B 134   -26.052  -6.238 -34.993 1.00 13.40   C
ATOM 2583 CG  PHE B 134   -25.189  -7.436 -35.416 1.00 11.62   C
ATOM 2584 CD1 PHE B 134   -25.042  -7.763 -36.753 1.00 12.42   C
ATOM 2585 CE1 PHE B 134   -24.306  -8.883 -37.149 1.00 14.21   C
ATOM 2586 CZ  PHE B 134   -23.701  -9.676 -36.169 1.00 11.89   C
ATOM 2587 CE2 PHE B 134   -23.859  -9.350 -34.812 1.00 11.12   C
ATOM 2588 CD2 PHE B 134   -24.624  -8.261 -34.445 1.00 10.37   C
ATOM 2589 C   PHE B 134   -28.313  -5.394 -34.198 1.00 13.26   C
ATOM 2590 O   PHE B 134   -27.827  -4.500 -33.494 1.00 13.31   O
ATOM 2591 N   LYS B 135   -29.553  -5.324 -34.690 1.00 14.13   N
ATOM 2592 CA  LYS B 135   -30.382  -4.126 -34.526 1.00 14.50   C
ATOM 2593 CB  LYS B 135   -31.743  -4.308 -35.214 1.00 15.32   C
ATOM 2594 CG  LYS B 135   -32.597  -5.378 -34.567 1.00 18.36   C
ATOM 2595 CD  LYS B 135   -33.733  -5.849 -35.470 1.00 24.31   C
ATOM 2596 CE  LYS B 135   -35.085  -5.352 -35.058 1.00 25.41   C
ATOM 2597 NZ  LYS B 135   -35.401  -5.416 -33.620 1.00 24.30   N
```

Fig. 5 cont.

```
ATOM  2598  C   LYS B 135     -30.632  -3.746 -33.076  1.00 14.63           C
ATOM  2599  O   LYS B 135     -30.980  -2.587 -32.784  1.00 14.18           O
ATOM  2600  N   ASP B 136     -30.508  -4.697 -32.152  1.00 13.71           N
ATOM  2601  CA  ASP B 136     -30.812  -4.348 -30.751  1.00 14.55           C
ATOM  2602  CB  ASP B 136     -31.601  -5.435 -30.016  1.00 15.14           C
ATOM  2603  CG  ASP B 136     -32.933  -5.799 -30.694  1.00 19.39           C
ATOM  2604  OD1 ASP B 136     -33.617  -4.933 -31.284  1.00 20.43           O
ATOM  2605  OD2 ASP B 136     -33.337  -6.983 -30.574  1.00 22.81           O
ATOM  2606  C   ASP B 136     -29.581  -4.002 -29.933  1.00 14.28           C
ATOM  2607  O   ASP B 136     -29.722  -3.655 -28.741  1.00 13.75           O
ATOM  2608  N   GLU B 137     -28.394  -4.058 -30.551  1.00 13.40           N
ATOM  2609  CA  GLU B 137     -27.127  -3.822 -29.838  1.00 13.09           C
ATOM  2610  CB  GLU B 137     -25.937  -4.550 -30.540  1.00 13.51           C
ATOM  2611  CG  GLU B 137     -26.124  -6.093 -30.517  1.00 14.36           C
ATOM  2612  CD  GLU B 137     -26.260  -6.654 -29.103  1.00 21.46           C
ATOM  2613  OE1 GLU B 137     -27.229  -7.384 -28.867  1.00 27.30           O
ATOM  2614  OE2 GLU B 137     -25.413  -6.383 -28.213  1.00 23.27           O
ATOM  2615  C   GLU B 137     -26.826  -2.339 -29.766  1.00 13.55           C
ATOM  2616  O   GLU B 137     -27.048  -1.604 -30.749  1.00 13.93           O
ATOM  2617  N   TYR B 138     -26.280  -1.907 -28.627  1.00 13.04           N
ATOM  2618  CA  TYR B 138     -25.825  -0.528 -28.472  1.00 14.76           C
ATOM  2619  CB  TYR B 138     -26.776   0.262 -27.569  1.00 16.35           C
ATOM  2620  CG  TYR B 138     -26.806  -0.223 -26.147  1.00 18.08           C
ATOM  2621  CD1 TYR B 138     -26.009   0.369 -25.175  1.00 19.20           C
ATOM  2622  CE1 TYR B 138     -26.023  -0.083 -23.886  1.00 17.57           C
ATOM  2623  CZ  TYR B 138     -26.861  -1.145 -23.560  1.00 20.68           C
ATOM  2624  OH  TYR B 138     -26.930  -1.607 -22.270  1.00 23.59           O
ATOM  2625  CE2 TYR B 138     -27.658  -1.737 -24.495  1.00 21.33           C
ATOM  2626  CD2 TYR B 138     -27.637  -1.277 -25.779  1.00 19.64           C
ATOM  2627  C   TYR B 138     -24.395  -0.398 -27.955  1.00 14.97           C
ATOM  2628  O   TYR B 138     -23.808   0.691 -28.032  1.00 14.23           O
ATOM  2629  N   LYS B 139     -23.838  -1.506 -27.438  1.00 14.30           N
ATOM  2630  CA  LYS B 139     -22.461  -1.487 -26.930  1.00 13.98           C
ATOM  2631  CB  LYS B 139     -22.417  -1.340 -25.411  1.00 13.76           C
ATOM  2632  CG  LYS B 139     -23.115  -2.435 -24.615  1.00 11.70           C
ATOM  2633  CD  LYS B 139     -22.983  -2.183 -23.099  1.00 14.05           C
ATOM  2634  CE  LYS B 139     -23.570  -3.398 -22.340  1.00 14.14           C
ATOM  2635  NZ  LYS B 139     -23.644  -3.241 -20.879  1.00 17.28           N
ATOM  2636  C   LYS B 139     -21.715  -2.747 -27.348  1.00 13.82           C
ATOM  2637  O   LYS B 139     -22.346  -3.773 -27.583  1.00 11.66           O
ATOM  2638  N   ILE B 140     -20.384  -2.636 -27.470  1.00 13.67           N
ATOM  2639  CA  ILE B 140     -19.512  -3.793 -27.768  1.00 15.50           C
ATOM  2640  CB  ILE B 140     -18.842  -3.758 -29.181  1.00 17.13           C
ATOM  2641  CG1 ILE B 140     -19.686  -3.055 -30.198  1.00 19.94           C
ATOM  2642  CD1 ILE B 140     -20.852  -3.870 -30.540  1.00 25.18           C
ATOM  2643  CG2 ILE B 140     -18.529  -5.203 -29.646  1.00 17.86           C
ATOM  2644  C   ILE B 140     -18.325  -3.660 -26.870  1.00 14.87           C
ATOM  2645  O   ILE B 140     -17.264  -3.202 -27.325  1.00 14.76           O
ATOM  2646  N   PRO B 141     -18.511  -3.976 -25.584  1.00 14.59           N
ATOM  2647  CA  PRO B 141     -17.501  -3.771 -24.560  1.00 13.49           C
ATOM  2648  CB  PRO B 141     -18.191  -4.252 -23.287  1.00 14.01           C
ATOM  2649  CG  PRO B 141     -19.632  -4.278 -23.564  1.00 14.95           C
ATOM  2650  CD  PRO B 141     -19.757  -4.557 -25.037  1.00 14.54           C
ATOM  2651  C   PRO B 141     -16.307  -4.685 -24.751  1.00 12.93           C
ATOM  2652  O   PRO B 141     -16.455  -5.842 -25.191  1.00 11.18           O
ATOM  2653  N   ARG B 142     -15.151  -4.225 -24.275  1.00 11.89           N
ATOM  2654  CA  ARG B 142     -13.991  -5.107 -24.210  1.00 11.27           C
ATOM  2655  CB  ARG B 142     -12.794  -4.321 -23.572  1.00 10.92           C
ATOM  2656  CG  ARG B 142     -11.586  -5.218 -23.219  1.00 11.19           C
ATOM  2657  CD  ARG B 142     -10.429  -4.399 -22.572  1.00 12.98           C
ATOM  2658  NE  ARG B 142      -9.391  -5.279 -21.958  1.00 13.78           N
ATOM  2659  CZ  ARG B 142      -8.258  -5.622 -22.571  1.00 17.33           C
ATOM  2660  NH1 ARG B 142      -8.001  -5.205 -23.798  1.00 17.24           N
ATOM  2661  NH2 ARG B 142      -7.369  -6.374 -21.953  1.00 20.41           N
ATOM  2662  C   ARG B 142     -14.351  -6.365 -23.418  1.00 10.86           C
ATOM  2663  O   ARG B 142     -15.140  -6.336 -22.433  1.00  9.65           O
ATOM  2664  N   ASN B 143     -13.779  -7.501 -23.831  1.00 11.40           N
ATOM  2665  CA  ASN B 143     -14.099  -8.828 -23.256  1.00 13.19           C
ATOM  2666  CB  ASN B 143     -13.872  -8.941 -21.731  1.00 15.19           C
ATOM  2667  CG  ASN B 143     -12.413  -8.800 -21.360  1.00 18.34           C
ATOM  2668  OD1 ASN B 143     -11.576  -9.679 -21.647  1.00 27.52           O
ATOM  2669  ND2 ASN B 143     -12.096  -7.711 -20.729  1.00 18.81           N
ATOM  2670  C   ASN B 143     -15.430  -9.446 -23.615  1.00 13.94           C
ATOM  2671  O   ASN B 143     -15.669 -10.628 -23.293  1.00 14.65           O
ATOM  2672  N   SER B 144     -16.311  -8.702 -24.263  1.00 12.65           N
ATOM  2673  CA  SER B 144     -17.521  -9.367 -24.759  1.00 13.58           C
ATOM  2674  CB  SER B 144     -18.626  -8.376 -25.203  1.00 14.41           C
ATOM  2675  OG  SER B 144     -18.203  -7.509 -26.181  1.00 14.12           O
ATOM  2676  C   SER B 144     -17.177 -10.385 -25.847  1.00 13.94           C
ATOM  2677  O   SER B 144     -16.160 -10.240 -26.563  1.00 11.75           O
ATOM  2678  N   THR B 145     -18.004 -11.427 -25.937  1.00 13.30           N
ATOM  2679  CA  THR B 145     -17.805 -12.530 -26.885  1.00 13.18           C
ATOM  2680  CB  THR B 145     -17.767 -13.871 -26.146  1.00 14.69           C
ATOM  2681  OG1 THR B 145     -16.724 -13.817 -25.164  1.00 17.86           O
ATOM  2682  CG2 THR B 145     -17.434 -15.027 -27.126  1.00 16.45           C
ATOM  2683  C   THR B 145     -18.939 -12.535 -27.924  1.00 12.83           C
ATOM  2684  O   THR B 145     -20.117 -12.344 -27.578  1.00 13.91           O
ATOM  2685  N   ILE B 146     -18.579 -12.656 -29.192  1.00 10.72           N
ATOM  2686  CA  ILE B 146     -19.552 -12.926 -30.273  1.00 11.49           C
ATOM  2687  CB  ILE B 146     -19.585 -11.778 -31.293  1.00 11.49           C
ATOM  2688  CG1 ILE B 146     -19.948 -10.470 -30.537  1.00 14.31           C
ATOM  2689  CD1 ILE B 146     -19.629  -9.178 -31.313  1.00 21.28           C
ATOM  2690  CG2 ILE B 146     -20.587 -12.097 -32.485  1.00 12.28           C
ATOM  2691  C   ILE B 146     -19.197 -14.232 -30.963  1.00 11.26           C
ATOM  2692  O   ILE B 146     -18.029 -14.434 -31.416  1.00 10.64           O
ATOM  2693  N   ASP B 147     -20.170 -15.137 -31.109  1.00 11.06           N
ATOM  2694  CA  ASP B 147     -19.875 -16.365 -31.863  1.00 10.85           C
ATOM  2695  CB  ASP B 147     -20.327 -17.624 -31.091  1.00 12.23           C
ATOM  2696  CG  ASP B 147     -19.339 -18.069 -29.993  1.00 16.93           C
ATOM  2697  OD1 ASP B 147     -18.205 -17.541 -29.904  1.00 16.35           O
ATOM  2698  OD2 ASP B 147     -19.715 -18.977 -29.202  1.00 18.24           O
ATOM  2699  C   ASP B 147     -20.608 -16.343 -33.203  1.00 10.34           C
ATOM  2700  O   ASP B 147     -21.831 -16.250 -33.206  1.00 10.49           O
ATOM  2701  N   LEU B 148     -19.883 -16.468 -34.326  1.00  8.58           N
ATOM  2702  CA  LEU B 148     -20.486 -16.525 -35.641  1.00  9.14           C
ATOM  2703  CB  LEU B 148     -19.650 -15.765 -36.687  1.00  8.26           C
ATOM  2704  CG  LEU B 148     -19.344 -14.298 -36.272  1.00  9.18           C
ATOM  2705  CD1 LEU B 148     -18.431 -13.733 -37.331  1.00 12.75           C
ATOM  2706  CD2 LEU B 148     -20.634 -13.466 -36.138  1.00 10.14           C
ATOM  2707  C   LEU B 148     -20.461 -17.993 -35.985  1.00 10.51           C
ATOM  2708  O   LEU B 148     -19.360 -18.565 -36.180  1.00 10.89           O
ATOM  2709  N   THR B 149     -21.627 -18.614 -36.026  1.00 11.34           N
ATOM  2710  CA  THR B 149     -21.687 -20.083 -36.182  1.00 12.21           C
ATOM  2711  CB  THR B 149     -22.637 -20.711 -35.106  1.00 12.24           C
ATOM  2712  OG1 THR B 149     -22.115 -20.397 -33.802  1.00 19.31           O
ATOM  2713  CG2 THR B 149     -22.638 -22.225 -35.179  1.00 14.47           C
ATOM  2714  C   THR B 149     -22.144 -20.461 -37.583  1.00 12.36           C
ATOM  2715  O   THR B 149     -23.201 -20.016 -38.015  1.00 13.97           O
ATOM  2716  N   LYS B 150     -21.351 -21.232 -38.329  1.00 11.42           N
ATOM  2717  CA  LYS B 150     -21.865 -21.834 -39.516  1.00 10.98           C
ATOM  2718  CB  LYS B 150     -20.820 -21.969 -40.625  1.00 10.92           C
ATOM  2719  CG  LYS B 150     -21.291 -22.789 -41.836  1.00 12.89           C
ATOM  2720  CD  LYS B 150     -20.177 -22.791 -42.927  1.00 11.91           C
ATOM  2721  CE  LYS B 150     -20.589 -23.642 -44.121  1.00 14.77           C
ATOM  2722  NZ  LYS B 150     -19.519 -23.583 -45.200  1.00 15.78           N
ATOM  2723  C   LYS B 150     -22.470 -23.199 -39.142  1.00 12.40           C
ATOM  2724  O   LYS B 150     -21.768 -24.160 -38.791  1.00 11.71           O
ATOM  2725  N   ASP B 151     -23.794 -23.241 -39.186  1.00 13.42           N
ATOM  2726  CA  ASP B 151     -24.522 -24.450 -38.861  1.00 14.72           C
ATOM  2727  CB  ASP B 151     -25.788 -24.043 -38.161  1.00 15.87           C
ATOM  2728  CG  ASP B 151     -25.608 -23.894 -36.663  1.00 23.74           C
ATOM  2729  OD1 ASP B 151     -26.351 -23.042 -36.107  1.00 28.39           O
ATOM  2730  OD2 ASP B 151     -24.750 -24.618 -36.048  1.00 24.74           O
ATOM  2731  C   ASP B 151     -24.832 -25.247 -40.133  1.00 13.74           C
ATOM  2732  O   ASP B 151     -24.574 -24.771 -41.257  1.00 13.26           O
ATOM  2733  N   PRO B 152     -25.354 -26.484 -39.969  1.00 13.07           N
ATOM  2734  CA  PRO B 152     -25.689 -27.282 -41.150  1.00 13.19           C
ATOM  2735  CB  PRO B 152     -26.383 -28.537 -40.559  1.00 12.90           C
ATOM  2736  CG  PRO B 152     -25.985 -28.617 -39.157  1.00 14.10           C
ATOM  2737  CD  PRO B 152     -25.660 -27.187 -38.696  1.00 13.34           C
ATOM  2738  C   PRO B 152     -26.643 -26.570 -42.115  1.00 11.93           C
ATOM  2739  O   PRO B 152     -27.508 -25.769 -41.697  1.00 11.81           O
ATOM  2740  N   GLY B 153     -26.502 -26.870 -43.408  1.00 12.46           N
ATOM  2741  CA  GLY B 153     -27.361 -26.267 -44.398  1.00 13.24           C
ATOM  2742  C   GLY B 153     -27.004 -24.796 -44.679  1.00 14.14           C
ATOM  2743  O   GLY B 153     -27.855 -24.029 -45.129  1.00 14.06           O
ATOM  2744  N   HIS B 154     -25.757 -24.415 -44.390  1.00 13.59           N
ATOM  2745  CA  HIS B 154     -25.254 -23.029 -44.665  1.00 13.98           C
ATOM  2746  CB  HIS B 154     -25.102 -22.806 -46.166  1.00 14.69           C
ATOM  2747  CG  HIS B 154     -24.279 -23.872 -46.821  1.00 15.61           C
ATOM  2748  ND1 HIS B 154     -22.907 -23.819 -46.874  1.00 20.14           N
ATOM  2749  CE1 HIS B 154     -22.447 -24.909 -47.465  1.00 23.77           C
ATOM  2750  NE2 HIS B 154     -23.476 -25.664 -47.804  1.00 19.07           N
ATOM  2751  CD2 HIS B 154     -24.633 -25.040 -47.410  1.00 21.50           C
ATOM  2752  C   HIS B 154     -26.094 -21.981 -44.004  1.00 12.92           C
ATOM  2753  O   HIS B 154     -26.467 -20.972 -44.601  1.00 14.37           O
ATOM  2754  N   VAL B 155     -26.404 -22.219 -42.733  1.00 11.26           N
ATOM  2755  CA  VAL B 155     -27.112 -21.256 -41.917  1.00  9.97           C
ATOM  2756  CB  VAL B 155     -28.161 -21.960 -41.062  1.00 10.85           C
ATOM  2757  CG1 VAL B 155     -28.803 -20.968 -40.070  1.00 11.34           C
ATOM  2758  CG2 VAL B 155     -29.228 -22.598 -42.010  1.00 10.77           C
ATOM  2759  C   VAL B 155     -26.086 -20.519 -41.019  1.00 11.36           C
ATOM  2760  O   VAL B 155     -25.433 -21.155 -40.202  1.00 10.77           O
ATOM  2761  N   LEU B 156     -25.990 -19.196 -41.141  1.00 10.79           N
ATOM  2762  CA  LEU B 156     -25.176 -18.411 -40.166  1.00 12.77           C
ATOM  2763  CB  LEU B 156     -24.740 -17.116 -40.800  1.00 12.40           C
ATOM  2764  CG  LEU B 156     -23.874 -16.290 -39.819  1.00 16.90           C
ATOM  2765  CD1 LEU B 156     -22.460 -16.787 -40.021  1.00 21.64           C
ATOM  2766  CD2 LEU B 156     -24.010 -14.862 -40.239  1.00 23.93           C
ATOM  2767  C   LEU B 156     -26.013 -18.062 -38.951  1.00 13.43           C
```

Fig. 5 cont.

```
ATOM  2768  O   LEU B 156    -27.067 -17.420 -39.116  1.00 13.80           O
ATOM  2769  N   SER B 157    -25.570 -18.460 -37.758  1.00 12.21           N
ATOM  2770  CA  SER B 157    -26.224 -18.076 -36.534  1.00 13.55           C
ATOM  2771  CB  SER B 157    -26.632 -19.293 -35.705  1.00 15.33           C
ATOM  2772  OG  SER B 157    -27.658 -19.955 -36.426  1.00 20.77           O
ATOM  2773  C   SER B 157    -25.245 -17.203 -35.791  1.00 13.81           C
ATOM  2774  O   SER B 157    -24.000 -17.380 -35.932  1.00 13.09           O
ATOM  2775  N   VAL B 158    -25.800 -16.220 -35.079  1.00 11.66           N
ATOM  2776  CA  VAL B 158    -24.981 -15.312 -34.275  1.00 11.18           C
ATOM  2777  CB  VAL B 158    -25.032 -13.854 -34.871  1.00 11.59           C
ATOM  2778  CG1 VAL B 158    -24.240 -12.864 -33.997  1.00 12.94           C
ATOM  2779  CG2 VAL B 158    -24.541 -13.855 -36.352  1.00 13.36           C
ATOM  2780  C   VAL B 158    -25.457 -15.346 -32.823  1.00 11.40           C
ATOM  2781  O   VAL B 158    -26.677 -15.284 -32.541  1.00 10.92           O
ATOM  2782  N   ALA B 159    -24.490 -15.440 -31.911  1.00 11.17           N
ATOM  2783  CA  ALA B 159    -24.746 -15.338 -30.460  1.00 11.35           C
ATOM  2784  CB  ALA B 159    -24.456 -16.668 -29.776  1.00 11.47           C
ATOM  2785  C   ALA B 159    -23.835 -14.252 -29.902  1.00 11.43           C
ATOM  2786  O   ALA B 159    -22.689 -14.150 -30.323  1.00 11.05           O
ATOM  2787  N   ILE B 160    -24.372 -13.421 -29.002  1.00 10.00           N
ATOM  2788  CA  ILE B 160    -23.636 -12.353 -28.371  1.00 11.33           C
ATOM  2789  CB  ILE B 160    -24.240 -11.005 -28.741  1.00 11.73           C
ATOM  2790  CG1 ILE B 160    -23.999 -10.750 -30.264  1.00 12.63           C
ATOM  2791  CD1 ILE B 160    -24.697  -9.493 -30.788  1.00 19.20           C
ATOM  2792  CG2 ILE B 160    -23.592  -9.905 -27.943  1.00 13.54           C
ATOM  2793  C   ILE B 160    -23.731 -12.556 -26.871  1.00 12.53           C
ATOM  2794  O   ILE B 160    -24.854 -12.651 -26.329  1.00 10.24           O
ATOM  2795  N   GLU B 161    -22.572 -12.648 -26.221  1.00 13.11           N
ATOM  2796  CA  GLU B 161    -22.512 -12.882 -24.785  1.00 14.00           C
ATOM  2797  CB  GLU B 161    -22.992 -11.625 -24.049  1.00 14.92           C
ATOM  2798  CG  GLU B 161    -21.966 -10.466 -24.149  1.00 18.39           C
ATOM  2799  CD  GLU B 161    -20.681 -10.742 -23.339  1.00 22.33           C
ATOM  2800  OE1 GLU B 161    -19.875 -11.645 -23.710  1.00 19.00           O
ATOM  2801  OE2 GLU B 161    -20.462 -10.025 -22.327  1.00 22.92           O
ATOM  2802  C   GLU B 161    -23.320 -14.112 -24.389  1.00 14.56           C
ATOM  2803  O   GLU B 161    -24.094 -14.081 -23.406  1.00 15.37           O
ATOM  2804  N   GLY B 162    -23.180 -15.164 -25.171  1.00 13.95           N
ATOM  2805  CA  GLY B 162    -23.839 -16.428 -24.907  1.00 16.38           C
ATOM  2806  C   GLY B 162    -25.298 -16.551 -25.283  1.00 16.75           C
ATOM  2807  O   GLY B 162    -25.899 -17.619 -25.072  1.00 19.01           O
ATOM  2808  N   ASN B 163    -25.901 -15.485 -25.802  1.00 17.07           N
ATOM  2809  CA  ASN B 163    -27.305 -15.573 -26.221  1.00 17.55           C
ATOM  2810  CB  ASN B 163    -28.148 -14.502 -25.548  1.00 17.76           C
ATOM  2811  CG  ASN B 163    -28.147 -14.640 -24.027  1.00 22.55           C
ATOM  2812  OD1 ASN B 163    -28.395 -15.731 -23.478  1.00 28.53           O
ATOM  2813  ND2 ASN B 163    -27.823 -13.558 -23.352  1.00 20.03           N
ATOM  2814  C   ASN B 163    -27.518 -15.466 -27.714  1.00 15.46           C
ATOM  2815  O   ASN B 163    -27.019 -14.547 -28.342  1.00 14.48           O
ATOM  2816  N   HIS B 164    -28.300 -16.390 -28.264  1.00 15.29           N
ATOM  2817  CA  HIS B 164    -28.601 -16.405 -29.710  1.00 15.59           C
ATOM  2818  CB  HIS B 164    -29.468 -17.625 -30.018  1.00 15.82           C
ATOM  2819  CG  HIS B 164    -29.822 -17.779 -31.461  1.00 16.20           C
ATOM  2820  ND1 HIS B 164    -31.125 -17.727 -31.921  1.00 17.28           N
ATOM  2821  CE1 HIS B 164    -31.135 -17.921 -33.229  1.00 13.27           C
ATOM  2822  NE2 HIS B 164    -29.897 -18.136 -33.630  1.00 18.24           N
ATOM  2823  CD2 HIS B 164    -29.052 -18.049 -32.542  1.00 15.96           C
ATOM  2824  C   HIS B 164    -29.321 -15.120 -30.094  1.00 16.27           C
ATOM  2825  O   HIS B 164    -30.242 -14.707 -29.371  1.00 16.63           O
ATOM  2826  N   VAL B 165    -28.881 -14.452 -31.167  1.00 15.69           N
ATOM  2827  CA  VAL B 165    -29.537 -13.221 -31.651  1.00 16.92           C
ATOM  2828  CB  VAL B 165    -28.571 -11.951 -31.705  1.00 18.24           C
ATOM  2829  CG1 VAL B 165    -27.862 -11.765 -30.373  1.00 19.70           C
ATOM  2830  CG2 VAL B 165    -27.515 -12.055 -32.754  1.00 17.76           C
ATOM  2831  C   VAL B 165    -30.334 -13.407 -32.981  1.00 17.03           C
ATOM  2832  O   VAL B 165    -31.149 -12.550 -33.348  1.00 18.67           O
ATOM  2833  N   GLY B 166    -30.060 -14.483 -33.704  1.00 14.05           N
ATOM  2834  CA  GLY B 166    -30.790 -14.832 -34.941  1.00 13.23           C
ATOM  2835  C   GLY B 166    -29.897 -15.484 -35.969  1.00 12.16           C
ATOM  2836  O   GLY B 166    -28.712 -15.717 -35.701  1.00 10.05           O
ATOM  2837  N   SER B 167    -30.456 -15.776 -37.155  1.00 12.00           N
ATOM  2838  CA  SER B 167    -29.756 -16.585 -38.147  1.00 12.98           C
ATOM  2839  CB  SER B 167    -30.277 -18.036 -38.035  1.00 14.46           C
ATOM  2840  OG  SER B 167    -29.979 -18.530 -36.737  1.00 18.54           O
ATOM  2841  C   SER B 167    -30.115 -16.091 -39.516  1.00 13.84           C
ATOM  2842  O   SER B 167    -31.166 -15.452 -39.680  1.00 13.04           O
ATOM  2843  N   VAL B 168    -29.274 -16.380 -40.505  1.00 13.18           N
ATOM  2844  CA  VAL B 168    -29.566 -16.053 -41.892  1.00 14.01           C
ATOM  2845  CB  VAL B 168    -28.729 -14.860 -42.442  1.00 13.54           C
ATOM  2846  CG1 VAL B 168    -29.000 -14.649 -43.959  1.00 12.75           C
ATOM  2847  CG2 VAL B 168    -29.039 -13.509 -41.646  1.00 13.92           C
ATOM  2848  C   VAL B 168    -29.111 -17.305 -42.643  1.00 17.68           C
ATOM  2849  O   VAL B 168    -28.048 -17.780 -42.497  1.00 14.13           O
ATOM  2850  N   LYS B 169    -30.081 -17.875 -43.431  1.00 14.20           N
ATOM  2851  CA  LYS B 169    -29.651 -18.972 -44.266  1.00 14.42           C
ATOM  2852  CB  LYS B 169    -30.823 -19.933 -44.553  1.00 15.92           C
ATOM  2853  CG  LYS B 169    -30.665 -20.859 -45.778  1.00 19.81           C
ATOM  2854  CD  LYS B 169    -29.975 -22.118 -45.442  1.00 24.77           C
ATOM  2855  CE  LYS B 169    -30.483 -23.340 -46.280  1.00 27.94           C
ATOM  2856  NZ  LYS B 169    -30.412 -24.582 -45.422  1.00 26.96           N
ATOM  2857  C   LYS B 169    -29.093 -18.382 -45.556  1.00 13.79           C
ATOM  2858  O   LYS B 169    -29.830 -17.677 -46.340  1.00 14.12           O
ATOM  2859  N   SER B 170    -27.820 -18.681 -45.834  1.00 11.75           N
ATOM  2860  CA  SER B 170    -27.208 -18.196 -47.069  1.00 11.67           C
ATOM  2861  CB  SER B 170    -27.036 -16.653 -47.024  1.00 11.30           C
ATOM  2862  OG  SER B 170    -26.192 -16.205 -48.114  1.00 12.10           O
ATOM  2863  C   SER B 170    -25.849 -18.838 -47.248  1.00 12.26           C
ATOM  2864  O   SER B 170    -24.983 -18.596 -46.428  1.00 11.97           O
ATOM  2865  N   HIS B 171    -25.662 -19.661 -48.291  1.00 12.68           N
ATOM  2866  CA  HIS B 171    -24.336 -20.223 -48.592  1.00 13.65           C
ATOM  2867  CB  HIS B 171    -24.382 -21.092 -49.832  1.00 15.60           C
ATOM  2868  CG  HIS B 171    -23.052 -21.696 -50.190  1.00 20.58           C
ATOM  2869  ND1 HIS B 171    -22.058 -20.996 -50.839  1.00 22.43           N
ATOM  2870  CE1 HIS B 171    -21.011 -21.785 -51.026  1.00 26.53           C
ATOM  2871  NE2 HIS B 171    -21.283 -22.973 -50.515  1.00 26.53           N
ATOM  2872  CD2 HIS B 171    -22.562 -22.949 -50.001  1.00 26.53           C
ATOM  2873  C   HIS B 171    -23.330 -19.092 -48.839  1.00 13.08           C
ATOM  2874  O   HIS B 171    -22.176 -19.125 -48.360  1.00 13.18           O
ATOM  2875  N   LEU B 172    -23.776 -18.118 -49.616  1.00 10.60           N
ATOM  2876  CA  LEU B 172    -22.909 -16.978 -49.960  1.00 11.44           C
ATOM  2877  CB  LEU B 172    -23.637 -16.036 -50.905  1.00 10.81           C
ATOM  2878  CG  LEU B 172    -22.869 -14.749 -51.288  1.00 13.68           C
ATOM  2879  CD1 LEU B 172    -21.585 -15.064 -51.970  1.00 12.51           C
ATOM  2880  CD2 LEU B 172    -23.717 -13.876 -52.156  1.00 14.79           C
ATOM  2881  C   LEU B 172    -22.416 -16.238 -48.717  1.00  9.95           C
ATOM  2882  O   LEU B 172    -21.217 -15.924 -48.607  1.00 10.48           O
ATOM  2883  N   LEU B 173    -23.324 -15.964 -47.780  1.00  9.45           N
ATOM  2884  CA  LEU B 173    -22.937 -15.210 -46.570  1.00  9.26           C
ATOM  2885  CB  LEU B 173    -24.182 -14.833 -45.725  1.00  8.34           C
ATOM  2886  CG  LEU B 173    -23.958 -14.022 -44.441  1.00 10.42           C
ATOM  2887  CD1 LEU B 173    -23.311 -12.666 -44.719  1.00 12.60           C
ATOM  2888  CD2 LEU B 173    -25.297 -13.864 -43.748  1.00  9.94           C
ATOM  2889  C   LEU B 173    -21.962 -15.956 -45.697  1.00  9.80           C
ATOM  2890  O   LEU B 173    -21.008 -15.385 -45.229  1.00  8.77           O
ATOM  2891  N   CYS B 174    -22.221 -17.247 -45.469  1.00  9.72           N
ATOM  2892  CA  CYS B 174    -21.364 -18.078 -44.629  1.00  9.22           C
ATOM  2893  CB  CYS B 174    -21.915 -19.525 -44.589  1.00 10.32           C
ATOM  2894  SG  CYS B 174    -23.327 -19.617 -43.505  1.00 14.04           S
ATOM  2895  C   CYS B 174    -19.969 -18.113 -45.206  1.00  9.97           C
ATOM  2896  O   CYS B 174    -18.984 -17.987 -44.461  1.00  8.06           O
ATOM  2897  N   ARG B 175    -19.887 -18.348 -46.508  1.00  9.38           N
ATOM  2898  CA  ARG B 175    -18.592 -18.506 -47.177  1.00 11.74           C
ATOM  2899  CB  ARG B 175    -18.779 -19.048 -48.617  1.00 13.05           C
ATOM  2900  CG  ARG B 175    -17.639 -18.602 -49.576  1.00 20.95           C
ATOM  2901  CD  ARG B 175    -17.360 -19.580 -50.629  1.00 26.54           C
ATOM  2902  NE  ARG B 175    -15.943 -19.732 -51.025  1.00 29.94           N
ATOM  2903  CZ  ARG B 175    -14.860 -19.225 -50.428  1.00 29.89           C
ATOM  2904  NH1 ARG B 175    -14.935 -18.449 -49.352  1.00 25.51           N
ATOM  2905  NH2 ARG B 175    -13.662 -19.490 -50.957  1.00 30.68           N
ATOM  2906  C   ARG B 175    -17.835 -17.175 -47.164  1.00 11.74           C
ATOM  2907  O   ARG B 175    -16.612 -17.140 -46.970  1.00 12.96           O
ATOM  2908  N   SER B 176    -18.560 -16.079 -47.335  1.00 10.95           N
ATOM  2909  CA  SER B 176    -17.933 -14.763 -47.432  1.00 11.55           C
ATOM  2910  CB  SER B 176    -18.930 -13.737 -47.902  1.00 10.33           C
ATOM  2911  OG  SER B 176    -19.311 -14.058 -49.262  1.00 12.33           O
ATOM  2912  C   SER B 176    -17.371 -14.381 -46.060  1.00 11.36           C
ATOM  2913  O   SER B 176    -16.310 -13.791 -45.983  1.00 11.65           O
ATOM  2914  N   ILE B 177    -18.116 -14.676 -44.996  1.00  9.57           N
ATOM  2915  CA  ILE B 177    -17.662 -14.360 -43.647  1.00 10.58           C
ATOM  2916  CB  ILE B 177    -18.772 -14.569 -42.596  1.00 10.02           C
ATOM  2917  CG1 ILE B 177    -19.783 -13.413 -42.684  1.00 12.52           C
ATOM  2918  CD1 ILE B 177    -21.104 -13.672 -41.918  1.00 14.13           C
ATOM  2919  CG2 ILE B 177    -18.154 -14.576 -41.142  1.00 11.54           C
ATOM  2920  C   ILE B 177    -16.456 -15.223 -43.288  1.00  9.78           C
ATOM  2921  O   ILE B 177    -15.475 -14.706 -42.751  1.00  9.48           O
ATOM  2922  N   LEU B 178    -16.531 -16.529 -43.553  1.00  7.83           N
ATOM  2923  CA  LEU B 178    -15.366 -17.373 -43.235  1.00  9.03           C
ATOM  2924  CB  LEU B 178    -15.654 -18.842 -43.570  1.00 10.29           C
ATOM  2925  CG  LEU B 178    -16.697 -19.553 -42.701  1.00 12.07           C
ATOM  2926  CD1 LEU B 178    -16.782 -20.972 -43.212  1.00 12.30           C
ATOM  2927  CD2 LEU B 178    -16.300 -19.561 -41.220  1.00 13.72           C
ATOM  2928  C   LEU B 178    -14.104 -16.933 -44.003  1.00  9.54           C
ATOM  2929  O   LEU B 178    -12.994 -17.003 -43.463  1.00  9.84           O
ATOM  2930  N   ASP B 179    -14.296 -16.495 -45.239  1.00  9.86           N
ATOM  2931  CA  ASP B 179    -13.193 -16.005 -46.107  1.00 11.60           C
ATOM  2932  CB  ASP B 179    -13.752 -15.449 -47.428  1.00 12.06           C
ATOM  2933  CG  ASP B 179    -12.703 -15.439 -48.532  1.00 17.68           C
ATOM  2934  OD1 ASP B 179    -12.325 -14.333 -48.990  1.00 18.79           O
ATOM  2935  OD2 ASP B 179    -12.232 -16.548 -48.881  1.00 20.44           O
ATOM  2936  C   ASP B 179    -12.335 -14.925 -45.411  1.00 11.88           C
ATOM  2937  O   ASP B 179    -11.111 -14.842 -45.633  1.00 11.73           O
```

Fig. 5 cont.

```
ATOM 2938 N   LEU B 180   -12.965 -14.106 -44.560 1.00 11.75   N
ATOM 2939 CA  LEU B 180   -12.228 -13.010 -43.892 1.00 12.00   C
ATOM 2940 CB  LEU B 180   -13.210 -12.111 -43.116 1.00 12.96   C
ATOM 2941 CG  LEU B 180   -14.238 -11.349 -43.955 1.00 11.41   C
ATOM 2942 CD1 LEU B 180   -15.310 -10.734 -43.006 1.00 14.62   C
ATOM 2943 CD2 LEU B 180   -13.571 -10.250 -44.829 1.00 15.25   C
ATOM 2944 C   LEU B 180   -11.183 -13.550 -42.920 1.00 12.11   C
ATOM 2945 O   LEU B 180   -10.176 -12.868 -42.610 1.00 11.61   O
ATOM 2946 N   TYR B 181   -11.417 -14.779 -42.441 1.00 10.51   N
ATOM 2947 CA  TYR B 181   -10.600 -15.375 -41.412 1.00 11.55   C
ATOM 2948 CB  TYR B 181   -11.492 -16.031 -40.317 1.00 12.19   C
ATOM 2949 CG  TYR B 181   -12.358 -14.974 -39.693 1.00 11.64   C
ATOM 2950 CD1 TYR B 181   -11.822 -14.093 -38.721 1.00 11.81   C
ATOM 2951 CE1 TYR B 181   -12.615 -13.055 -38.158 1.00 10.99   C
ATOM 2952 CZ  TYR B 181   -13.936 -12.926 -38.600 1.00 12.00   C
ATOM 2953 OH  TYR B 181   -14.745 -11.958 -38.076 1.00 10.32   O
ATOM 2954 CE2 TYR B 181   -14.473 -13.788 -39.544 1.00 10.08   C
ATOM 2955 CD2 TYR B 181   -13.673 -14.780 -40.130 1.00 10.76   C
ATOM 2956 C   TYR B 181   -9.696 -16.440 -41.980 1.00 13.08    C
ATOM 2957 O   TYR B 181   -8.588 -16.604 -41.497 1.00 13.12    O
ATOM 2958 N   ILE B 182   -10.172 -17.217 -42.957 1.00 13.63   N
ATOM 2959 CA  ILE B 182   -9.354 -18.370 -43.371 1.00 15.26    C
ATOM 2960 CB  ILE B 182   -9.923 -19.716 -42.831 1.00 15.22    C
ATOM 2961 CG1 ILE B 182   -11.403 -19.840 -43.218 1.00 14.90   C
ATOM 2962 CD1 ILE B 182   -12.092 -21.209 -42.759 1.00 16.62   C
ATOM 2963 CG2 ILE B 182   -9.712 -19.820 -41.310 1.00 16.82    C
ATOM 2964 C   ILE B 182   -9.184 -18.457 -44.866 1.00 15.29    C
ATOM 2965 O   ILE B 182   -8.779 -19.510 -45.393 1.00 16.65    O
ATOM 2966 N   GLY B 183   -9.447 -17.346 -45.547 1.00 15.50    N
ATOM 2967 CA  GLY B 183   -9.431 -17.321 -46.995 1.00 18.15    C
ATOM 2968 C   GLY B 183   -8.154 -16.688 -47.496 1.00 19.00    C
ATOM 2969 O   GLY B 183   -7.207 -16.544 -46.759 1.00 18.97    O
ATOM 2970 N   GLU B 184   -8.172 -16.251 -48.733 1.00 21.75    N
ATOM 2971 CA  GLU B 184   -6.942 -15.855 -49.444 1.00 24.82    C
ATOM 2972 CB  GLU B 184   -7.273 -15.658 -50.927 1.00 26.11    C
ATOM 2973 CG  GLU B 184   -6.118 -15.894 -51.865 1.00 31.78    C
ATOM 2974 CD  GLU B 184   -6.600 -16.055 -53.303 1.00 38.86    C
ATOM 2975 OE1 GLU B 184   -7.250 -15.114 -53.818 1.00 41.77    O
ATOM 2976 OE2 GLU B 184   -6.345 -17.126 -53.914 1.00 42.56    O
ATOM 2977 C   GLU B 184   -6.302 -14.584 -48.889 1.00 25.07    C
ATOM 2978 O   GLU B 184   -5.046 -14.459 -48.858 1.00 26.35    O
ATOM 2979 N   GLU B 185   -7.135 -13.628 -48.480 1.00 23.81    N
ATOM 2980 CA  GLU B 185   -6.606 -12.404 -47.840 1.00 23.44    C
ATOM 2981 CB  GLU B 185   -6.992 -11.169 -48.655 1.00 23.90    C
ATOM 2982 CG  GLU B 185   -6.756 -11.302 -50.162 1.00 30.90    C
ATOM 2983 CD  GLU B 185   -7.836 -10.592 -50.961 1.00 37.96    C
ATOM 2984 OE1 GLU B 185   -8.844 -11.255 -51.377 1.00 39.95    O
ATOM 2985 OE2 GLU B 185   -7.695 -9.358 -51.122 1.00 40.28     O
ATOM 2986 C   GLU B 185   -7.189 -12.274 -46.414 1.00 21.30    C
ATOM 2987 O   GLU B 185   -8.110 -11.492 -46.211 1.00 22.63    O
ATOM 2988 N   PRO B 186   -6.655 -13.026 -45.442 1.00 19.91    N
ATOM 2989 CA  PRO B 186   -7.305 -13.093 -44.138 1.00 18.20    C
ATOM 2990 CB  PRO B 186   -6.872 -14.446 -43.629 1.00 18.29    C
ATOM 2991 CG  PRO B 186   -5.502 -14.685 -44.304 1.00 19.33    C
ATOM 2992 CD  PRO B 186   -5.406 -13.810 -45.471 1.00 17.92    C
ATOM 2993 C   PRO B 186   -6.831 -11.975 -43.200 1.00 18.04    C
ATOM 2994 O   PRO B 186   -5.872 -11.205 -43.517 1.00 16.30    O
ATOM 2995 N   PHE B 187   -7.488 -11.881 -42.050 1.00 16.12    N
ATOM 2996 CA  PHE B 187   -7.147 -10.865 -41.061 1.00 16.50    C
ATOM 2997 CB  PHE B 187   -8.217 -10.811 -39.973 1.00 14.15    C
ATOM 2998 CG  PHE B 187   -9.490 -10.126 -40.394 1.00 14.71    C
ATOM 2999 CD1 PHE B 187   -10.707 -10.713 -40.131 1.00 13.52   C
ATOM 3000 CE1 PHE B 187   -11.897 -10.078 -40.474 1.00 14.09   C
ATOM 3001 CZ  PHE B 187   -11.884 -8.803 -41.093 1.00 15.34    C
ATOM 3002 CE2 PHE B 187   -10.656 -8.204 -41.365 1.00 13.43    C
ATOM 3003 CD2 PHE B 187   -9.472 -8.862 -40.978 1.00 13.45     C
ATOM 3004 C   PHE B 187   -5.805 -11.132 -40.406 1.00 16.29    C
ATOM 3005 O   PHE B 187   -5.112 -10.193 -40.029 1.00 17.52    O
ATOM 3006 N   ASP B 188   -5.447 -12.408 -40.267 1.00 16.98    N
ATOM 3007 CA  ASP B 188   -4.241 -12.813 -39.570 1.00 17.17    C
ATOM 3008 CB  ASP B 188   -4.578 -13.125 -38.113 1.00 16.41    C
ATOM 3009 CG  ASP B 188   -3.360 -13.444 -37.245 1.00 20.27    C
ATOM 3010 OD1 ASP B 188   -3.358 -13.057 -36.050 1.00 17.70    O
ATOM 3011 OD2 ASP B 188   -2.454 -14.189 -37.704 1.00 24.58    O
ATOM 3012 C   ASP B 188   -3.710 -14.031 -40.323 1.00 17.91    C
ATOM 3013 O   ASP B 188   -4.210 -15.146 -40.165 1.00 16.49    O
ATOM 3014 N   LYS B 189   -2.697 -13.823 -41.172 1.00 18.79    N
ATOM 3015 CA  LYS B 189   -2.158 -14.936 -41.970 1.00 20.57    C
ATOM 3016 CB  LYS B 189   -1.026 -14.443 -42.885 1.00 21.07    C
ATOM 3017 CG  LYS B 189   -1.485 -14.197 -44.291 1.00 25.08    C
ATOM 3018 CD  LYS B 189   -0.338 -14.377 -45.285 1.00 32.17    C
ATOM 3019 CE  LYS B 189   -0.840 -14.128 -46.699 1.00 34.12    C
ATOM 3020 NZ  LYS B 189   -1.602 -12.843 -46.783 1.00 37.08    N
ATOM 3021 C   LYS B 189   -1.665 -16.106 -41.145 1.00 20.76    C
ATOM 3022 O   LYS B 189   -1.818 -17.260 -41.528 1.00 21.96    O
ATOM 3023 N   ASN B 190   -1.043 -15.809 -40.007 1.00 21.90    N
ATOM 3024 CA  ASN B 190   -0.619 -16.824 -39.058 1.00 22.14    C
ATOM 3025 CB  ASN B 190   -0.042 -16.150 -37.822 1.00 23.77    C
ATOM 3026 CG  ASN B 190   0.701 -17.103 -36.942 1.00 27.06     C
ATOM 3027 OD1 ASN B 190   1.683 -17.703 -37.373 1.00 32.03     O
ATOM 3028 ND2 ASN B 190   0.249 -17.251 -35.692 1.00 29.01     N
ATOM 3029 C   ASN B 190   -1.749 -17.736 -38.601 1.00 21.61    C
ATOM 3030 O   ASN B 190   -1.610 -18.966 -38.609 1.00 19.61    O
ATOM 3031 N   ALA B 191   -2.878 -17.133 -38.182 1.00 19.66    N
ATOM 3032 CA  ALA B 191   -4.012 -17.929 -37.748 1.00 18.77    C
ATOM 3033 CB  ALA B 191   -5.123 -17.029 -37.200 1.00 18.13    C
ATOM 3034 C   ALA B 191   -4.536 -18.782 -38.907 1.00 17.46    C
ATOM 3035 O   ALA B 191   -4.960 -19.907 -38.696 1.00 17.08    O
ATOM 3036 N   ARG B 192   -4.533 -18.240 -40.122 1.00 17.70    N
ATOM 3037 CA  ARG B 192   -5.011 -19.025 -41.265 1.00 18.09    C
ATOM 3038 CB  ARG B 192   -5.034 -18.197 -42.538 1.00 18.21    C
ATOM 3039 CG  ARG B 192   -5.599 -18.999 -43.720 1.00 18.83    C
ATOM 3040 CD  ARG B 192   -5.401 -18.326 -45.019 1.00 21.76    C
ATOM 3041 NE  ARG B 192   -4.004 -18.284 -45.413 1.00 26.15    N
ATOM 3042 CZ  ARG B 192   -3.528 -17.585 -46.446 1.00 29.78    C
ATOM 3043 NH1 ARG B 192   -4.326 -16.849 -47.206 1.00 27.05    N
ATOM 3044 NH2 ARG B 192   -2.229 -17.610 -46.707 1.00 31.61    N
ATOM 3045 C   ARG B 192   -4.123 -20.270 -41.481 1.00 18.86    C
ATOM 3046 O   ARG B 192   -4.623 -21.364 -41.733 1.00 18.06    O
ATOM 3047 N   GLU B 193   -2.810 -20.094 -41.376 1.00 20.27    N
ATOM 3048 CA  GLU B 193   -1.858 -21.210 -41.609 1.00 21.53    C
ATOM 3049 CB  GLU B 193   -0.414 -20.691 -41.764 1.00 23.55    C
ATOM 3050 CG  GLU B 193   -0.223 -19.752 -42.991 1.00 26.49    C
ATOM 3051 CD  GLU B 193   -0.584 -20.398 -44.317 1.00 32.69    C
ATOM 3052 OE1 GLU B 193   0.221 -21.219 -44.819 1.00 34.91     O
ATOM 3053 OE2 GLU B 193   -1.658 -20.080 -44.874 1.00 33.44    O
ATOM 3054 C   GLU B 193   -1.964 -22.303 -40.562 1.00 20.97    C
ATOM 3055 O   GLU B 193   -1.981 -23.481 -40.913 1.00 22.28    O
ATOM 3056 N   ASP B 194   -2.091 -21.922 -39.283 1.00 19.22    N
ATOM 3057 CA  ASP B 194   -2.359 -22.860 -38.230 1.00 18.72    C
ATOM 3058 CB  ASP B 194   -2.400 -22.184 -36.858 1.00 19.30    C
ATOM 3059 CG  ASP B 194   -1.025 -21.810 -36.361 1.00 23.22    C
ATOM 3060 OD1 ASP B 194   -0.928 -20.924 -35.474 1.00 25.17    O
ATOM 3061 OD2 ASP B 194   -0.042 -22.419 -36.860 1.00 24.92    O
ATOM 3062 C   ASP B 194   -3.655 -23.580 -38.492 1.00 17.65    C
ATOM 3063 O   ASP B 194   -3.751 -24.803 -38.284 1.00 17.23    O
ATOM 3064 N   PHE B 195   -4.664 -22.824 -38.910 1.00 16.16    N
ATOM 3065 CA  PHE B 195   -5.952 -23.435 -39.170 1.00 16.27    C
ATOM 3066 CB  PHE B 195   -6.992 -22.388 -39.586 1.00 15.96    C
ATOM 3067 CG  PHE B 195   -8.287 -23.011 -40.032 1.00 17.17    C
ATOM 3068 CD1 PHE B 195   -8.535 -23.214 -41.381 1.00 18.23    C
ATOM 3069 CE1 PHE B 195   -9.713 -23.814 -41.816 1.00 17.22    C
ATOM 3070 CZ  PHE B 195   -10.649 -24.263 -40.881 1.00 17.20   C
ATOM 3071 CE2 PHE B 195   -10.412 -24.069 -39.529 1.00 20.10   C
ATOM 3072 CD2 PHE B 195   -9.221 -23.446 -39.104 1.00 18.55    C
ATOM 3073 C   PHE B 195   -5.851 -24.538 -40.241 1.00 15.23    C
ATOM 3074 O   PHE B 195   -6.329 -25.658 -40.033 1.00 17.39    O
ATOM 3075 N   LEU B 196   -5.235 -24.208 -41.351 1.00 16.43    N
ATOM 3076 CA  LEU B 196   -5.165 -25.117 -42.509 1.00 17.70    C
ATOM 3077 CB  LEU B 196   -4.754 -24.382 -43.755 1.00 18.21    C
ATOM 3078 CG  LEU B 196   -5.705 -23.298 -44.302 1.00 18.32    C
ATOM 3079 CD1 LEU B 196   -5.010 -22.464 -45.356 1.00 19.20    C
ATOM 3080 CD2 LEU B 196   -7.007 -23.946 -44.820 1.00 16.98    C
ATOM 3081 C   LEU B 196   -4.216 -26.276 -42.249 1.00 17.96    C
ATOM 3082 O   LEU B 196   -4.528 -27.412 -42.586 1.00 16.95    O
ATOM 3083 N   ASP B 197   -3.093 -25.990 -41.585 1.00 19.19    N
ATOM 3084 CA  ASP B 197   -2.215 -27.068 -41.069 1.00 19.19    C
ATOM 3085 CB  ASP B 197   -0.994 -26.470 -40.370 1.00 20.55    C
ATOM 3086 CG  ASP B 197   -0.068 -25.713 -41.309 1.00 22.91    C
ATOM 3087 OD1 ASP B 197   -0.196 -25.787 -42.553 1.00 30.01    O
ATOM 3088 OD2 ASP B 197   0.853 -25.015 -40.796 1.00 28.87     O
ATOM 3089 C   ASP B 197   -2.940 -28.042 -40.145 1.00 19.12    C
ATOM 3090 O   ASP B 197   -2.846 -29.283 -40.308 1.00 19.82    O
ATOM 3091 N   ASN B 198   -3.664 -27.525 -39.154 1.00 17.52    N
ATOM 3092 CA  ASN B 198   -4.337 -28.378 -38.200 1.00 18.02    C
ATOM 3093 CB  ASN B 198   -4.761 -27.631 -36.929 1.00 17.03    C
ATOM 3094 CG  ASN B 198   -3.555 -27.157 -36.109 1.00 21.66    C
ATOM 3095 OD1 ASN B 198   -2.572 -27.879 -35.992 1.00 21.11    O
ATOM 3096 ND2 ASN B 198   -3.619 -25.936 -35.572 1.00 17.84    N
ATOM 3097 C   ASN B 198   -5.540 -29.101 -38.806 1.00 17.96    C
ATOM 3098 O   ASN B 198   -5.830 -30.240 -38.426 1.00 19.89    O
ATOM 3099 N   ALA B 199   -6.217 -28.441 -39.748 1.00 19.17    N
ATOM 3100 CA  ALA B 199   -7.327 -29.072 -40.482 1.00 18.05    C
ATOM 3101 CB  ALA B 199   -7.940 -28.094 -41.471 1.00 16.53    C
ATOM 3102 C   ALA B 199   -6.818 -30.307 -41.236 1.00 18.99    C
ATOM 3103 O   ALA B 199   -7.404 -31.397 -41.116 1.00 19.32    O
ATOM 3104 N   ALA B 200   -5.756 -30.106 -42.010 1.00 19.64    N
ATOM 3105 CA  ALA B 200   -5.108 -31.151 -42.810 1.00 21.31    C
ATOM 3106 CB  ALA B 200   -4.001 -30.521 -43.661 1.00 20.46    C
ATOM 3107 C   ALA B 200   -4.559 -32.303 -41.967 1.00 22.11    C
```

Fig. 5 cont.

```
ATOM  3108  O   ALA B 200      -4.416 -33.450 -42.472  1.00 23.26           O
ATOM  3109  N   SER B 201      -4.250 -32.030 -40.695  1.00 22.75           N
ATOM  3110  CA  SER B 201      -3.750 -33.078 -39.775  1.00 23.18           C
ATOM  3111  CB  SER B 201      -2.891 -32.474 -38.659  1.00 23.84           C
ATOM  3112  OG  SER B 201      -1.845 -31.724 -39.238  1.00 28.21           O
ATOM  3113  C   SER B 201      -4.829 -33.970 -39.156  1.00 23.10           C
ATOM  3114  O   SER B 201      -4.557 -35.128 -38.849  1.00 21.78           O
ATOM  3115  N   LEU B 202      -6.064 -33.466 -39.025  1.00 23.07           N
ATOM  3116  CA  LEU B 202      -7.109 -34.166 -38.253  1.00 23.14           C
ATOM  3117  CB  LEU B 202      -8.444 -33.386 -38.234  1.00 24.13           C
ATOM  3118  CG  LEU B 202      -8.527 -32.054 -37.521  1.00 23.74           C
ATOM  3119  CD1 LEU B 202      -9.747 -31.271 -38.004  1.00 22.83           C
ATOM  3120  CD2 LEU B 202      -8.563 -32.250 -36.004  1.00 25.04           C
ATOM  3121  C   LEU B 202      -7.402 -35.565 -38.738  1.00 23.00           C
ATOM  3122  O   LEU B 202      -7.688 -36.442 -37.932  1.00 22.89           O
ATOM  3123  N   ALA B 203      -7.330 -35.763 -40.052  1.00 23.06           N
ATOM  3124  CA  ALA B 203      -7.580 -37.059 -40.665  1.00 23.71           C
ATOM  3125  CB  ALA B 203      -7.566 -36.931 -42.165  1.00 23.36           C
ATOM  3126  C   ALA B 203      -6.605 -38.144 -40.235  1.00 24.27           C
ATOM  3127  O   ALA B 203      -6.862 -39.323 -40.468  1.00 23.92           O
ATOM  3128  N   PHE B 204      -5.482 -37.757 -39.634  1.00 24.37           N
ATOM  3129  CA  PHE B 204      -4.448 -38.731 -39.251  1.00 25.25           C
ATOM  3130  CB  PHE B 204      -3.105 -38.322 -39.839  1.00 24.04           C
ATOM  3131  CG  PHE B 204      -3.152 -38.086 -41.299  1.00 22.12           C
ATOM  3132  CD1 PHE B 204      -3.272 -36.785 -41.797  1.00 21.35           C
ATOM  3133  CE1 PHE B 204      -3.342 -36.554 -43.161  1.00 21.01           C
ATOM  3134  CZ  PHE B 204      -3.299 -37.604 -44.040  1.00 21.48           C
ATOM  3135  CE2 PHE B 204      -3.186 -38.907 -43.578  1.00 19.34           C
ATOM  3136  CD2 PHE B 204      -3.129 -39.153 -42.198  1.00 21.96           C
ATOM  3137  C   PHE B 204      -4.333 -38.951 -37.733  1.00 26.66           C
ATOM  3138  O   PHE B 204      -5.103 -38.343 -36.979  1.00 28.63           O
ATOM  3139  C10 C10 C   1       4.802  -1.634  -1.363  1.00 38.18           C
ATOM  3140  C9  C10 C   1       4.013  -0.384  -1.734  1.00 37.18           C
ATOM  3141  C8  C10 C   1       2.972  -0.676  -2.814  1.00 36.28           C
ATOM  3142  C7  C10 C   1       1.975   0.469  -2.965  1.00 33.75           C
ATOM  3143  C6  C10 C   1       0.578  -0.029  -3.315  1.00 31.28           C
ATOM  3144  C5  C10 C   1      -0.418   1.073  -3.014  1.00 27.82           C
ATOM  3145  C4  C10 C   1      -1.767   0.846  -3.671  1.00 28.66           C
ATOM  3146  C3  C10 C   1      -2.633   2.100  -3.629  1.00 28.88           C
ATOM  3147  C2  C10 C   1      -3.401   2.197  -2.313  1.00 26.22           C
ATOM  3148  C1  C10 C   1      -4.381   3.350  -2.279  1.00 28.28           C
ATOM  3149  C10 C10 D   1     -17.055  -6.579 -33.395  1.00 16.71           C
ATOM  3150  C9  C10 D   1     -16.812  -6.475 -34.877  1.00 15.99           C
ATOM  3151  C8  C10 D   1     -15.746  -5.422 -35.204  1.00 17.14           C
ATOM  3152  C7  C10 D   1     -15.763  -5.180 -36.690  1.00 17.01           C
ATOM  3153  C6  C10 D   1     -14.499  -4.457 -37.130  1.00 20.15           C
ATOM  3154  C5  C10 D   1     -14.377  -3.138 -36.390  1.00 23.85           C
ATOM  3155  C4  C10 D   1     -13.251  -2.289 -36.913  1.00 26.16           C
ATOM  3156  C3  C10 D   1     -13.611  -0.822 -36.736  1.00 28.24           C
ATOM  3157  C2  C10 D   1     -12.996  -0.298 -35.450  1.00 30.33           C
ATOM  3158  C1  C10 D   1     -12.928   1.216 -35.420  1.00 31.33           C
ATOM  3159  O14 12C E   1     -13.884  -7.745 -38.414  1.00 12.97           O
ATOM  3160  C1  12C E   1     -14.641  -7.679 -39.425  1.00 16.44           C
ATOM  3161  O13 12C E   1     -14.717  -6.709 -40.234  1.00 14.68           O
ATOM  3162  C2  12C E   1     -15.490  -8.897 -39.710  1.00 16.90           C
ATOM  3163  C3  12C E   1     -16.544  -8.911 -38.637  1.00 20.17           C
ATOM  3164  C4  12C E   1     -17.725  -9.745 -39.131  1.00 25.57           C
ATOM  3165  C5  12C E   1     -18.383 -10.195 -37.859  1.00 25.15           C
ATOM  3166  C6  12C E   1     -19.595  -9.372 -37.597  1.00 28.56           C
ATOM  3167  C7  12C E   1     -19.270  -8.433 -36.492  1.00 26.72           C
ATOM  3168  C8  12C E   1     -20.363  -8.560 -35.465  1.00 27.25           C
ATOM  3169  C9  12C E   1     -20.600  -7.155 -34.988  1.00 25.93           C
ATOM  3170  C10 12C E   1     -21.352  -7.097 -33.676  1.00 26.54           C
ATOM  3171  C11 12C E   1     -21.733  -5.650 -33.428  1.00 27.19           C
ATOM  3172  C12 12C E   1     -22.697  -5.636 -32.253  1.00 31.18           C
ATOM  3173  O14 12C F   1      -5.842   0.565  -5.433  1.00 29.47           O
ATOM  3174  C1  12C F   1      -5.503   1.196  -6.456  1.00 27.71           C
ATOM  3175  O13 12C F   1      -4.422   0.952  -7.049  1.00 25.04           O
ATOM  3176  C2  12C F   1      -6.461   2.281  -6.886  1.00 28.12           C
ATOM  3177  C3  12C F   1      -6.852   3.042  -5.626  1.00 26.64           C
ATOM  3178  C4  12C F   1      -7.990   4.017  -5.887  1.00 23.42           C
ATOM  3179  C5  12C F   1      -8.218   4.794  -4.603  1.00 24.88           C
ATOM  3180  C6  12C F   1      -7.080   5.772  -4.340  1.00 23.66           C
ATOM  3181  C7  12C F   1      -7.227   6.386  -2.966  1.00 25.91           C
ATOM  3182  C8  12C F   1      -5.958   7.109  -2.564  1.00 28.87           C
ATOM  3183  C9  12C F   1      -6.007   7.503  -1.101  1.00 30.97           C
ATOM  3184  C10 12C F   1      -4.695   8.182  -0.728  1.00 35.88           C
ATOM  3185  C11 12C F   1      -4.904   9.149   0.425  1.00 36.65           C
ATOM  3186  C12 12C F   1      -3.720  10.080   0.418  1.00 38.62           C
ATOM  3187  O   HOH W   1       4.912 -12.366  -5.197  1.00  6.89           O
ATOM  3188  O   HOH W   2     -15.445  -1.686 -26.881  1.00 14.35           O
ATOM  3189  O   HOH W   4      -9.694 -10.362 -44.164  1.00 13.82           O
ATOM  3190  O   HOH W   5      -3.631  -9.733   8.994  1.00 13.56           O
ATOM  3191  O   HOH W   6      -6.987 -14.817 -40.046  1.00 16.41           O
ATOM  3192  O   HOH W   8     -25.564  -4.015 -26.844  1.00 13.20           O
ATOM  3193  O   HOH W   9     -21.548 -15.508 -27.505  1.00 13.30           O
ATOM  3194  O   HOH W  10     -24.881   3.187 -28.693  1.00 15.19           O
ATOM  3195  O   HOH W  11     -29.491  -7.490 -32.001  1.00 12.94           O
ATOM  3196  O   HOH W  12      -4.667  -7.297  10.656  1.00 19.67           O
ATOM  3197  O   HOH W  13       0.460   2.819   5.943  1.00 14.76           O
ATOM  3198  O   HOH W  15     -22.612 -12.717 -13.824  1.00 14.94           O
ATOM  3199  O   HOH W  16     -29.244 -25.435 -39.772  1.00 12.59           O
ATOM  3200  O   HOH W  17     -17.337 -24.388 -43.931  1.00 21.38           O
ATOM  3201  O   HOH W  18     -21.541 -11.363 -15.862  1.00 13.01           O
ATOM  3202  O   HOH W  19     -23.159 -25.571 -43.378  1.00 21.86           O
ATOM  3203  O   HOH W  20     -17.020 -11.312  -0.167  1.00 20.29           O
ATOM  3204  O   HOH W  21      -5.428  -0.281  -5.311  1.00 20.54           O
ATOM  3205  O   HOH W  22     -27.561  -3.519 -36.770  1.00 14.56           O
ATOM  3206  O   HOH W  23     -26.845  -1.191 -18.072  1.00 18.59           O
ATOM  3207  O   HOH W  24     -25.221 -12.345 -21.655  1.00 28.35           O
ATOM  3208  O   HOH W  25     -12.083  -7.440  -6.523  1.00 15.85           O
ATOM  3209  O   HOH W  26     -21.160 -15.948  -3.088  1.00 25.95           O
ATOM  3210  O   HOH W  27     -20.166  -8.545 -18.581  1.00 17.08           O
ATOM  3211  O   HOH W  28       1.284 -26.064 -53.052  1.00 26.02           O
ATOM  3212  O   HOH W  30     -19.709   6.660   2.355  1.00 21.11           O
ATOM  3213  O   HOH W  31      -5.049  -7.675  -5.211  1.00 19.73           O
ATOM  3214  O   HOH W  32     -25.755 -19.067 -12.436  1.00 20.44           O
ATOM  3215  O   HOH W  33     -32.672 -16.816 -43.438  1.00 20.30           O
ATOM  3216  O   HOH W  34      -3.011 -19.870 -34.270  1.00 20.30           O
ATOM  3217  O   HOH W  35     -27.736 -15.895 -50.187  1.00 18.25           O
ATOM  3218  O   HOH W  36     -10.351 -14.257 -22.586  1.00 22.04           O
ATOM  3219  O   HOH W  37     -19.330  -0.043 -27.262  1.00 16.24           O
ATOM  3220  O   HOH W  38     -26.488  -3.367 -44.347  1.00 18.76           O
ATOM  3221  O   HOH W  40     -26.943 -16.653 -20.812  1.00 24.91           O
ATOM  3222  O   HOH W  41     -14.974   2.680 -33.195  1.00 31.76           O
ATOM  3223  O   HOH W  42     -23.709 -18.443 -32.801  1.00 16.61           O
ATOM  3224  O   HOH W  43     -36.042  -7.405 -19.515  1.00 20.31           O
ATOM  3225  O   HOH W  44     -14.153  -5.567 -17.152  1.00 22.10           O
ATOM  3226  O   HOH W  45      -2.654  -6.293 -25.091  1.00 18.33           O
ATOM  3227  O   HOH W  46     -32.036 -10.823 -40.365  1.00 16.31           O
ATOM  3228  O   HOH W  48     -25.210  -0.782 -20.322  1.00 23.69           O
ATOM  3229  O   HOH W  49       1.957   8.209 -38.204  1.00 23.58           O
ATOM  3230  O   HOH W  50     -10.264 -17.102 -50.559  1.00 21.10           O
ATOM  3231  O   HOH W  51      -7.042  -2.508 -28.521  1.00 24.40           O
ATOM  3232  O   HOH W  52     -33.910 -18.080 -16.900  1.00 32.96           O
ATOM  3233  O   HOH W  53     -29.189 -23.520 -37.617  1.00 28.01           O
ATOM  3234  O   HOH W  54      -2.465  13.963  -4.636  1.00 30.33           O
ATOM  3235  O   HOH W  55     -23.696 -15.542  -1.962  1.00 23.55           O
ATOM  3236  O   HOH W  56     -32.847  -7.645 -46.005  1.00 21.22           O
ATOM  3237  O   HOH W  57     -27.321  -3.459 -47.396  1.00 24.30           O
ATOM  3238  O   HOH W  58       0.142  -5.673   5.285  1.00 19.65           O
ATOM  3239  O   HOH W  59      -5.094 -31.221 -35.796  1.00 21.03           O
ATOM  3240  O   HOH W  60     -20.798 -21.361 -29.864  1.00 24.68           O
ATOM  3241  O   HOH W  61     -31.015  -8.923  -8.266  1.00 29.87           O
ATOM  3242  O   HOH W  62     -27.141   0.891 -31.771  1.00 20.11           O
ATOM  3243  O   HOH W  63     -27.976 -10.185  -1.790  1.00 21.42           O
ATOM  3244  O   HOH W  64     -12.370  -2.434  10.763  1.00 21.75           O
ATOM  3245  O   HOH W  65      10.539  12.371  -4.931  1.00 34.75           O
ATOM  3246  O   HOH W  66      -5.354 -24.603 -49.843  1.00 34.48           O
ATOM  3247  O   HOH W  67       0.631   3.031   9.765  1.00 22.57           O
ATOM  3248  O   HOH W  68     -33.015 -18.020 -35.152  1.00 25.54           O
ATOM  3249  O   HOH W  69     -24.856  -6.934   3.446  1.00 19.21           O
ATOM  3250  O   HOH W  70       4.751 -35.564 -46.939  1.00 22.40           O
ATOM  3251  O   HOH W  71     -20.287  -2.958 -11.353  1.00 29.36           O
ATOM  3252  O   HOH W  72     -24.649  13.400  -7.711  1.00 25.80           O
ATOM  3253  O   HOH W  73     -13.309  -7.361 -46.959  1.00 23.79           O
ATOM  3254  O   HOH W  74     -21.531 -18.103 -27.352  1.00 27.82           O
ATOM  3255  O   HOH W  75     -12.946  -5.267 -19.583  1.00 23.76           O
ATOM  3256  O   HOH W  77     -15.519 -11.730   4.150  1.00 31.63           O
ATOM  3257  O   HOH W  78       2.413   6.425 -11.935  1.00 35.01           O
ATOM  3258  O   HOH W  79     -30.682   1.352 -12.011  1.00 22.54           O
ATOM  3259  O   HOH W  80     -21.679   5.376   1.086  1.00 29.19           O
ATOM  3260  O   HOH W  81     -20.822  -7.795 -27.275  1.00 26.74           O
ATOM  3261  O   HOH W  82     -10.630 -20.505 -22.445  1.00 29.11           O
ATOM  3262  O   HOH W  83     -10.982 -38.924 -43.498  1.00 25.35           O
ATOM  3263  O   HOH W  85     -22.604 -18.093  -9.008  1.00 23.02           O
ATOM  3264  O   HOH W  86      -9.597  -3.261 -41.671  1.00 37.41           O
ATOM  3265  O   HOH W  87     -28.446  -7.190 -21.202  1.00 27.99           O
ATOM  3266  O   HOH W  88     -17.481   9.540  -0.763  1.00 25.37           O
ATOM  3267  O   HOH W  89     -15.279  -1.552 -23.180  1.00 22.11           O
ATOM  3268  O   HOH W  90       0.847  -8.092   4.325  1.00 28.91           O
ATOM  3269  O   HOH W  91      -7.680  -4.735 -10.815  1.00 24.75           O
ATOM  3270  O   HOH W  92     -22.596  14.131  -5.384  1.00 29.86           O
ATOM  3271  O   HOH W  93     -19.257   0.761 -44.785  1.00 24.46           O
ATOM  3272  O   HOH W  94     -29.187 -18.978 -26.506  1.00 29.30           O
ATOM  3273  O   HOH W  95       4.075   2.404  -6.164  1.00 27.97           O
ATOM  3274  O   HOH W  96      -4.547  -0.370 -20.668  1.00 22.11           O
ATOM  3275  O   HOH W  97     -12.662  12.020 -11.202  1.00 25.33           O
ATOM  3276  O   HOH W  98      -6.809 -10.413  -3.208  1.00 27.17           O
ATOM  3277  O   HOH W  99     -28.328   6.573  -9.360  1.00 34.95           O
```

Fig. 5 cont.

```
ATOM 3278 O  HOH W 100   -5.560 -38.240 -47.174 1.00 26.07      O
ATOM 3279 O  HOH W 101  -29.855  -7.057 -53.037 1.00 28.29      O
ATOM 3280 O  HOH W 102   10.671 -16.058  -2.700 1.00 23.86      O
ATOM 3281 O  HOH W 103  -18.386  -2.655  10.892 1.00 29.45      O
ATOM 3282 O  HOH W 104  -16.181 -24.638 -24.376 1.00 31.48      O
ATOM 3283 O  HOH W 105    4.351  10.229  -6.700 1.00 32.12      O
ATOM 3284 O  HOH W 106  -28.130 -17.351 -17.897 1.00 28.85      O
ATOM 3285 O  HOH W 107  -23.021   0.976 -11.595 1.00 24.19      O
ATOM 3286 O  HOH W 108  -20.747 -22.667 -32.153 1.00 29.41      O
ATOM 3287 O  HOH W 110    1.449  15.452   0.139 1.00 31.21      O
ATOM 3288 O  HOH W 111    0.932 -24.480 -37.988 1.00 26.21      O
ATOM 3289 O  HOH W 112  -20.556 -29.763 -34.413 1.00 29.75      O
ATOM 3290 O  HOH W 113   -2.425  -3.222 -33.561 1.00 25.43      O
ATOM 3291 O  HOH W 114  -17.738 -32.645 -45.023 1.00 26.93      O
ATOM 3292 O  HOH W 115  -21.246  -6.155 -51.644 1.00 44.37      O
ATOM 3293 O  HOH W 116  -35.935 -11.034 -12.483 1.00 25.28      O
ATOM 3294 O  HOH W 117  -16.083 -17.521 -12.287 1.00 31.70      O
ATOM 3295 O  HOH W 118  -38.681  -8.889 -13.011 1.00 36.13      O
ATOM 3296 O  HOH W 119  -16.336 -28.395 -51.321 1.00 40.74      O
ATOM 3297 O  HOH W 121   -2.457  13.900   6.424 1.00 31.78      O
ATOM 3298 O  HOH W 122  -21.232 -21.849 -46.867 1.00 26.85      O
ATOM 3299 O  HOH W 123  -16.213 -38.084 -40.673 1.00 23.50      O
ATOM 3300 O  HOH W 124  -36.254  -0.281  -7.737 1.00 25.44      O
ATOM 3301 O  HOH W 125   -0.750   6.309 -15.463 1.00 29.45      O
ATOM 3302 O  HOH W 126  -13.658  -2.802 -42.131 1.00 29.19      O
ATOM 3303 O  HOH W 127  -26.178 -18.318 -51.287 1.00 17.88      O
ATOM 3304 O  HOH W 128   -7.857 -12.848  -6.828 1.00 24.65      O
ATOM 3305 O  HOH W 129  -21.128  -7.346 -22.124 1.00 32.66      O
ATOM 3306 O  HOH W 130  -16.833  10.391 -19.143 1.00 28.41      O
ATOM 3307 O  HOH W 131   -6.510  16.160  -0.118 1.00 27.78      O
ATOM 3308 O  HOH W 132  -32.037   1.124  -1.955 1.00 28.12      O
ATOM 3309 O  HOH W 133    7.008  10.667  -6.871 1.00 37.06      O
ATOM 3310 O  HOH W 134  -13.779 -17.957 -24.782 1.00 29.79      O
ATOM 3311 O  HOH W 135   -4.884  -1.446 -29.559 1.00 23.51      O
ATOM 3312 O  HOH W 136  -17.984 -17.947  -8.881 1.00 29.44      O
ATOM 3313 O  HOH W 137  -26.436   0.132 -40.286 1.00 29.63      O
ATOM 3314 O  HOH W 138   -0.203   1.851 -32.739 1.00 25.96      O
ATOM 3315 O  HOH W 139  -32.135 -24.489 -43.562 1.00 38.28      O
ATOM 3316 O  HOH W 140  -30.768  -0.603 -34.648 1.00 24.31      O
ATOM 3317 O  HOH W 141  -19.929  -5.788 -12.277 1.00 29.58      O
ATOM 3318 O  HOH W 142  -24.244   6.935 -10.800 1.00 35.04      O
ATOM 3319 O  HOH W 143   -6.068  -7.755 -39.103 1.00 23.71      O
ATOM 3320 O  HOH W 144  -32.348   4.968  -5.319 1.00 31.36      O
ATOM 3321 O  HOH W 145  -28.996  -9.681 -51.636 1.00 19.60      O
ATOM 3322 O  HOH W 146  -21.467 -15.822 -15.706 1.00 38.14      O
ATOM 3323 O  HOH W 147  -15.764  -3.897 -50.505 1.00 40.85      O
ATOM 3324 O  HOH W 148  -22.714  -6.330 -28.486 1.00 27.98      O
ATOM 3325 O  HOH W 149   -7.332 -25.487 -19.767 1.00 37.31      O
ATOM 3326 O  HOH W 150   -2.150  12.651 -12.142 1.00 28.45      O
ATOM 3327 O  HOH W 151   -1.479 -21.051 -24.965 1.00 35.82      O
ATOM 3328 O  HOH W 152  -11.282  -9.402 -51.585 1.00 41.73      O
ATOM 3329 O  HOH W 153    1.044  -6.374  -7.447 1.00 33.37      O
ATOM 3330 O  HOH W 154  -17.579 -12.675 -22.628 1.00 23.44      O
ATOM 3331 O  HOH W 155  -23.162 -28.456 -34.046 1.00 23.93      O
ATOM 3332 O  HOH W 156  -33.318 -15.278 -37.001 1.00 29.03      O
ATOM 3333 O  HOH W 157  -23.389  -6.426 -21.046 1.00 26.23      O
ATOM 3334 O  HOH W 158  -25.409   2.730 -35.905 1.00 31.87      O
ATOM 3335 O  HOH W 159   -0.140  -3.938  -7.879 1.00 32.12      O
ATOM 3336 O  HOH W 160    0.099 -12.907 -22.698 1.00 31.65      O
ATOM 3337 O  HOH W 161  -31.215 -12.918 -46.487 1.00 27.82      O
ATOM 3338 O  HOH W 162   -0.672   8.756 -35.897 1.00 35.37      O
ATOM 3339 O  HOH W 164  -14.823  -7.254 -53.559 1.00 26.95      O
ATOM 3340 O  HOH W 165  -30.896 -28.074 -38.872 1.00 29.13      O
ATOM 3341 O  HOH W 166   -2.602  -6.727   8.686 1.00 32.02      O
ATOM 3342 O  HOH W 167  -26.648 -10.785 -25.681 1.00 24.90      O
ATOM 3343 O  HOH W 168    0.043 -10.762  -4.170 1.00 34.36      O
ATOM 3344 O  HOH W 169  -11.724 -16.373 -21.346 1.00 30.02      O
ATOM 3345 O  HOH W 170  -19.379  12.034 -17.787 1.00 35.51      O
ATOM 3346 O  HOH W 171  -26.388 -19.012 -32.032 1.00 18.26      O
ATOM 3347 O  HOH W 172  -14.640 -36.861 -55.133 1.00 36.77      O
ATOM 3348 O  HOH W 173   -2.105 -18.322 -29.950 1.00 26.14      O
ATOM 3349 O  HOH W 174    4.339  13.011   3.501 1.00 25.69      O
ATOM 3350 O  HOH W 175  -22.714 -18.032 -21.143 1.00 33.67      O
ATOM 3351 O  HOH W 176    1.250   1.085 -39.561 1.00 35.27      O
ATOM 3352 O  HOH W 178   -7.055 -28.950 -56.526 1.00 42.49      O
ATOM 3353 O  HOH W 179   -5.685  15.518 -20.927 1.00 30.93      O
ATOM 3354 O  HOH W 180  -10.274   0.975  10.037 1.00 27.58      O
ATOM 3355 O  HOH W 181  -30.980 -15.357 -47.094 1.00 31.89      O
ATOM 3356 O  HOH W 183  -23.265   1.946   8.070 1.00 27.74      O
ATOM 3357 O  HOH W 185  -24.489   6.286   1.395 1.00 29.88      O
ATOM 3358 O  HOH W 186  -27.243 -15.204  -6.802 1.00 22.99      O
ATOM 3359 O  HOH W 188   -6.714  18.086 -14.237 1.00 31.53      O
ATOM 3360 O  HOH W 189  -22.198   7.710 -33.302 1.00 35.07      O
ATOM 3361 O  HOH W 190   -8.555  14.117 -19.578 1.00 35.28      O
ATOM 3362 O  HOH W 191  -25.080  -9.150   0.518 1.00 28.26      O
ATOM 3363 O  HOH W 192  -11.218 -23.659 -21.517 1.00 41.40      O
ATOM 3364 O  HOH W 193  -19.306  -0.231 -23.387 1.00 33.58      O
ATOM 3365 O  HOH W 194  -21.090 -18.841 -52.442 1.00 36.82      O
ATOM 3366 O  HOH W 195   -1.926 -16.362 -34.640 1.00 34.08      O
ATOM 3367 O  HOH W 196   -6.281  -3.529 -19.318 1.00 42.15      O
ATOM 3368 O  HOH W 197    2.600 -11.571   3.401 1.00 26.39      O
ATOM 3369 O  HOH W 198  -15.111   6.025 -34.389 1.00 35.33      O
ATOM 3370 O  HOH W 199  -14.422   8.218   4.850 1.00 23.87      O
ATOM 3371 O  HOH W 200  -22.709   5.168 -32.477 1.00 29.72      O
ATOM 3372 O  HOH W 201   -9.929  17.715  -8.593 1.00 32.94      O
ATOM 3373 O  HOH W 202   -0.018 -12.935 -38.059 1.00 34.29      O
ATOM 3374 O  HOH W 203  -17.636  -7.919 -18.797 1.00 31.93      O
ATOM 3375 O  HOH W 204  -25.589  -6.128 -22.610 1.00 29.53      O
ATOM 3376 O  HOH W 205  -32.937 -11.849 -35.586 1.00 41.25      O
ATOM 3377 O  HOH W 206  -17.533 -33.355 -47.870 1.00 28.01      O
ATOM 3378 O  HOH W 207    1.063   8.235  10.001 1.00 57.82      O
ATOM 3379 O  HOH W 208   -3.211  -9.691 -37.007 1.00 30.92      O
ATOM 3380 O  HOH W 209  -19.894   5.142 -15.265 1.00 38.26      O
ATOM 3381 O  HOH W 210   -0.958 -30.781 -41.517 1.00 33.61      O
ATOM 3382 O  HOH W 211  -10.465 -38.361 -52.739 1.00 31.00      O
ATOM 3383 O  HOH W 212  -16.021   0.206   8.190 1.00 26.59      O
ATOM 3384 O  HOH W 213  -19.522   3.171 -13.545 1.00 37.09      O
ATOM 3385 O  HOH W 215  -17.152  18.380  -4.002 1.00 38.40      O
ATOM 3386 O  HOH W 216  -32.958   3.734  -9.567 1.00 43.47      O
ATOM 3387 O  HOH W 217  -17.559   0.067 -25.389 1.00 30.90      O
ATOM 3388 O  HOH W 218    4.998   8.772   3.100 1.00 35.83      O
ATOM 3389 O  HOH W 219  -15.410   2.204 -39.432 1.00 36.29      O
ATOM 3390 O  HOH W 220  -10.498 -15.693 -53.286 1.00 47.22      O
ATOM 3391 O  HOH W 221  -10.994   4.728   9.789 1.00 40.59      O
ATOM 3392 O  HOH W 222   -8.248 -25.019 -56.908 1.00 48.13      O
ATOM 3393 O  HOH G   1   -1.450   2.095 -39.738 1.00 17.22      O
ATOM 3394 O  HOH G   2  -27.393  -4.260 -22.168 1.00 38.35      O
ATOM 3395 O  HOH G   3  -34.189  -4.118 -39.156 1.00 43.13      O
ATOM 3396 O  HOH G   5  -27.169   0.935   7.620 1.00 48.21      O
ATOM 3397 O  HOH G   6    1.857  12.502  -8.327 1.00 50.67      O
ATOM 3398 O  HOH G   7   -4.076   2.957  14.384 1.00 45.74      O
ATOM 3399 O  HOH G   8   -0.533 -10.802   0.929 1.00 24.24      O
ATOM 3400 O  HOH G   9  -28.202   4.262  -1.389 1.00 25.81      O
ATOM 3401 O  HOH G  10  -27.956 -20.757 -49.539 1.00 32.56      O
ATOM 3402 O  HOH G  11   -4.147 -25.770 -47.957 1.00 30.15      O
ATOM 3403 O  HOH G  12   -3.012 -24.928 -51.750 1.00 45.03      O
ATOM 3404 O  HOH G  14   -9.832 -25.592 -23.054 1.00 30.01      O
ATOM 3405 O  HOH G  15   -6.825  -3.112  13.281 1.00 40.15      O
ATOM 3406 O  HOH G  16   -1.503   0.671 -16.055 1.00 36.40      O
ATOM 3407 O  HOH G  17   -0.690  15.521  -5.702 1.00 39.58      O
ATOM 3408 O  HOH G  18   -1.888  -9.366   6.822 1.00 37.53      O
ATOM 3409 O  HOH G  19  -14.638  18.756  -5.688 1.00 39.12      O
ATOM 3410 O  HOH G  20   -9.635 -36.362 -34.155 1.00 36.29      O
ATOM 3411 O  HOH G  21   -6.238 -19.955 -20.284 1.00 35.96      O
ATOM 3412 O  HOH G  22  -13.158   6.332 -26.588 1.00 39.27      O
ATOM 3413 O  HOH G  23   -1.312 -11.340 -41.032 1.00 30.39      O
ATOM 3414 O  HOH G  24  -23.794   7.357  -3.883 1.00 24.32      O
ATOM 3415 O  HOH G  25  -38.643 -16.221 -16.891 1.00 34.90      O
ATOM 3416 O  HOH G  26   -2.688   7.305 -26.032 1.00 39.88      O
ATOM 3417 O  HOH G  27    6.317  -9.707  -8.567 1.00 44.38      O
ATOM 3418 O  HOH G  28  -10.861  -5.582 -14.744 1.00 39.90      O
ATOM 3419 O  HOH G  29  -28.733 -18.655 -23.872 1.00 46.46      O
ATOM 3420 O  HOH G  31  -32.795   0.254 -16.072 1.00 35.34      O
ATOM 3421 O  HOH G  32  -36.349   2.192 -14.489 1.00 37.13      O
ATOM 3422 O  HOH G  33  -28.975   2.845 -15.713 1.00 24.48      O
ATOM 3423 O  HOH G  34  -27.147 -26.816 -35.749 1.00 23.35      O
ATOM 3424 O  HOH G  35  -13.667 -12.144 -22.866 1.00 34.84      O
ATOM 3425 O  HOH G  36   -4.970  10.737   8.358 1.00 40.74      O
ATOM 3426 O  HOH G  37  -17.031   8.247   4.563 1.00 44.90      O
ATOM 3427 O  HOH G  38   -9.696  -7.073 -47.921 1.00 42.17      O
ATOM 3428 O  HOH G  39   -2.877 -33.692 -54.656 1.00 32.94      O
ATOM 3429 O  HOH G  40   -6.786  -2.263 -41.533 1.00 35.79      O
ATOM 3430 O  HOH G  41  -25.404  -2.071 -48.592 1.00 38.07      O
ATOM 3431 O  HOH G  42   -0.663 -31.288 -53.196 1.00 36.95      O
ATOM 3432 O  HOH G  43  -14.274   2.239   8.539 1.00 29.32      O
ATOM 3433 O  HOH G  44  -26.728 -14.381  -2.789 1.00 42.32      O
ATOM 3434 O  HOH G  45   -4.459 -46.782 -46.869 1.00 48.73      O
ATOM 3435 O  HOH G  47  -32.839 -12.313  -2.207 1.00 28.39      O
ATOM 3436 O  HOH G  48  -26.661   5.040   1.640 1.00 30.34      O
ATOM 3437 O  HOH G  49  -16.911  -0.254 -14.414 1.00 36.86      O
ATOM 3438 O  HOH G  50  -12.155  16.527 -14.695 1.00 40.66      O
ATOM 3439 O  HOH G  51    0.465  -7.359 -33.561 1.00 29.38      O
ATOM 3440 O  HOH G  54  -40.306 -12.357 -19.872 1.00 32.92      O
ATOM 3441 O  HOH G  55  -18.160 -14.082 -12.846 1.00 19.19      O
ATOM 3442 O  HOH G  57  -30.643 -17.283 -26.586 1.00 44.90      O
ATOM 3443 O  HOH G  58  -21.953 -26.947 -49.947 1.00 32.77      O
ATOM 3444 O  HOH G  59    0.441  17.232  -3.063 1.00 38.35      O
ATOM 3445 O  HOH G  62   -7.397 -14.822 -20.244 1.00 29.47      O
ATOM 3446 O  HOH G  63  -15.137  -4.244 -20.492 1.00 27.05      O
ATOM 3447 O  HOH G  64  -16.076  16.537   6.095 1.00 45.42      O
```

Fig. 5 cont.

```
ATOM 3448 O HOH G 65    -20.563   6.026   6.691 1.00 29.63      O
ATOM 3449 O HOH G 66    -32.641 -17.378 -18.903 1.00 32.96      O
ATOM 3450 O HOH G 69    -12.143  -7.827  14.094 1.00 38.56      O
ATOM 3451 O HOH G 70     -7.421 -41.745 -47.193 1.00 34.01      O
ATOM 3452 O HOH G 72    -15.793 -39.214 -38.467 1.00 34.01      O
ATOM 3453 O HOH G 73     -0.387 -41.120 -51.535 1.00 32.91      O
ATOM 3454 O HOH G 74    -24.307 -19.449 -18.447 1.00 43.34      O
ATOM 3455 O HOH G 75    -23.696   1.663 -41.522 1.00 33.92      O
ATOM 3456 O HOH G 76     -4.973  10.139   4.361 1.00 44.98      O
ATOM 3457 O HOH G 78     -0.812   0.013  -9.106 1.00 29.71      O
ATOM 3458 O HOH G 79    -18.546 -17.718 -56.031 1.00 33.21      O
ATOM 3459 O HOH G 80    -36.684 -11.153 -19.771 1.00 33.48      O
ATOM 3460 O HOH G 81    -14.776  12.296 -18.390 1.00 33.23      O
ATOM 3461 O HOH G 82    -32.219   4.229  -2.695 1.00 40.65      O
ATOM 3462 O HOH G 83     -7.056 -38.363 -53.578 1.00 40.55      O
ATOM 3463 O HOH G 85      3.433 -16.463  -1.691 1.00 36.30      O
ATOM 3464 O HOH G 86    -24.892 -31.256 -42.752 1.00 38.02      O
ATOM 3465 O HOH G 88     -2.828  -7.438  -7.028 1.00 38.27      O
ATOM 3466 O HOH G 90     -3.323   3.017 -31.440 1.00 34.62      O
ATOM 3467 O HOH G 91    -10.342 -32.553 -54.947 1.00 42.98      O
ATOM 3468 O HOH G 92      0.861 -22.159 -47.384 1.00 38.27      O
ATOM 3469 O HOH G 95     -5.432 -13.789   1.188 1.00 41.77      O
ATOM 3470 O HOH G 96     -7.559 -35.425 -54.415 1.00 40.31      O
ATOM 3471 O HOH G 98      0.272 -18.124 -47.654 1.00 39.61      O
ATOM 3472 O HOH G 99     10.178  -7.512  -3.015 1.00 45.74      O
ATOM 3473 O HOH G 100    -5.170 -44.037 -47.013 1.00 48.04      O
ATOM 3474 O HOH G 101   -12.802  18.077  -9.358 1.00 37.85      O
ATOM 3475 O HOH G 102   -41.523 -12.151 -12.254 1.00 35.90      O
ATOM 3476 O HOH G 103   -37.516  -0.668  -5.532 1.00 39.33      O
ATOM 3477 O HOH G 104   -37.953  -2.476 -12.932 1.00 51.33      O
ATOM 3478 O HOH G 105     4.892 -35.549 -50.100 1.00 41.72      O
ATOM 3479 O HOH G 106     6.226 -10.035   2.063 1.00 32.71      O
ATOM 3480 O HOH G 107    -3.706 -13.362 -51.796 1.00 49.85      O
ATOM 3481 O HOH G 108   -29.408  -8.467 -27.988 1.00 35.55      O
ATOM 3482 O HOH G 111   -29.140  10.124 -12.333 1.00 41.13      O
ATOM 3483 O HOH G 112   -30.290 -17.005 -49.326 1.00 41.85      O
ATOM 3484 O HOH G 114   -20.660 -30.700 -48.411 1.00 35.01      O
ATOM 3485 O HOH G 115   -32.663 -13.505 -40.407 1.00 33.54      O
ATOM 3486 O HOH G 117    -2.276  12.802 -14.878 1.00 40.27      O
ATOM 3487 O HOH G 119   -15.246 -15.877 -24.230 1.00 34.80      O
ATOM 3488 O HOH G 120   -25.137   3.936   7.627 1.00 40.66      O
ATOM 3489 O HOH G 123     2.620  -7.627 -36.363 1.00 37.20      O
ATOM 3490 O HOH G 125    -7.603 -10.857 -10.631 1.00 40.54      O
ATOM 3491 O HOH G 126   -21.261   1.646 -27.053 1.00 27.98      O
ATOM 3492 O HOH G 127   -21.915   0.710 -44.758 1.00 39.12      O
ATOM 3493 O HOH G 128    -0.710  -5.806  10.023 1.00 43.22      O
ATOM 3494 O HOH G 130   -20.285  -2.831 -48.338 1.00 34.10      O
ATOM 3495 O HOH G 131   -23.920 -28.396 -49.283 1.00 37.69      O
ATOM 3496 O HOH G 132   -19.590  -5.801  14.395 1.00 53.54      O
ATOM 3497 O HOH G 136    -3.878  -5.387 -27.108 1.00 34.66      O
ATOM 3498 O HOH G 137    -0.930  -1.543 -11.675 1.00 40.89      O
ATOM 3499 O HOH G 140   -20.599  16.426  -5.752 1.00 46.27      O
ATOM 3500 O HOH G 144     1.866 -13.204  -7.301 1.00 36.44      O
ATOM 3501 O HOH G 145   -30.885 -12.724 -27.542 1.00 35.13      O
ATOM 3502 O HOH G 146   -17.476   4.851 -39.961 1.00 38.97      O
ATOM 3503 O HOH G 152   -14.962  15.783 -15.537 1.00 43.80      O
ATOM 3504 O HOH G 155   -31.069 -15.537 -19.952 1.00 26.80      O
ATOM 3505 O HOH G 157     3.317 -14.976  -4.890 1.00 42.27      O
ATOM 3506 O HOH G 159   -14.689  -1.039 -27.611 1.00 35.79      O
ATOM 3507 O HOH G 169    -7.700 -46.748 -51.983 1.00 47.00      O
ATOM 3508 O HOH G 171   -18.833  12.356   8.228 1.00 42.82      O
ATOM 3509 O HOH G 175   -22.291 -27.279 -31.685 1.00 38.66      O
ATOM 3510 O HOH G 177   -12.526  -5.021  13.193 1.00 40.48      O
ATOM 3511 O HOH G 178     7.138  -5.888  -6.720 1.00 52.22      O
ATOM 3512 O HOH G 182   -37.665  -3.378 -19.885 1.00 39.88      O
ATOM 3513 O HOH G 188     5.783 -12.740  -7.641 1.00 51.77      O
ATOM 3514 O HOH G 193     3.059  10.735  -8.906 1.00 40.65      O
ATOM 3515 O HOH G 194   -25.944  -3.540 -57.344 1.00 31.11      O
ATOM 3516 O HOH G 195     2.537 -22.666 -41.981 1.00 41.41      O
ATOM 3517 O HOH G 196     1.616 -14.889   0.294 1.00 41.45      O
ATOM 3518 O HOH G 197   -26.261 -19.351 -22.924 1.00 39.31      O
ATOM 3519 O HOH G 198    -4.616  -4.158  14.539 1.00 44.12      O
ATOM 3520 O HOH G 199   -15.625   6.595 -25.982 1.00 47.36      O
ATOM 3521 O HOH G 201    -1.791 -24.372 -50.407 1.00 34.30      O
ATOM 3522 O HOH G 202    -3.526 -45.198 -48.679 1.00 63.57      O
ATOM 3523 O HOH G 206    -7.915  -8.249 -46.976 1.00 35.83      O
ATOM 3524 O HOH G 207    -1.886  17.108  -7.521 1.00 60.70      O
ATOM 3525 O HOH G 208     0.975  13.626 -10.443 1.00 75.98      O
ATOM 3526 O HOH G 209    -3.526 -45.198 -48.679 1.00 63.57      O
ATOM 3527 O HOH G 210    -1.886  17.108  -7.521 1.00 60.70      O
ATOM 3528 O HOH G 211     0.975  13.626 -10.443 1.00 75.98      O
END
```

Fig. 5 cont.

PDB AT287

REMARK TITLE [No title given]
REMARK LOG-LIKELIHOOD GAIN: 13.687
CRYST1 108.460 108.460 51.310 90.00 90.00 90.00 P 42 21 2  1
REMARK ENSEMBLE ensemble1 PDB
/usr/users1/florence/CHI/AtCHI287/ALSmay06_AtCHI287_Pt_16/molrep/atCHI287modelon279.pdb
REMARK EULER  72.441  32.351  18.190 ORTH  5.06813  41.79556  15.42681

```
ATOM    1  N   LEU A  1      18.776  25.634  21.841  1.00 41.04      1SG   2
ATOM    2  CA  LEU A  1      18.424  26.795  20.999  1.00 41.04      1SG   3
ATOM    3  CB  LEU A  1      19.025  28.077  21.595  1.00 41.04      1SG   4
ATOM    4  CG  LEU A  1      18.718  29.349  20.785  1.00 41.04      1SG   5
ATOM    5  CD1 LEU A  1      17.205  29.625  20.732  1.00 41.04      1SG   6
ATOM    6  CD2 LEU A  1      19.517  30.547  21.317  1.00 41.04      1SG   7
ATOM    7  C   LEU A  1      18.980  26.612  19.628  1.00 41.04      1SG   8
ATOM    8  O   LEU A  1      20.136  26.942  19.367  1.00 41.04      1SG   9
ATOM    9  N   LEU A  2      18.167  26.059  18.711  1.00117.88      1SG  10
ATOM   10  CA  LEU A  2      18.654  25.878  17.380  1.00117.88      1SG  11
ATOM   11  CB  LEU A  2      17.662  25.159  16.457  1.00117.88      1SG  12
ATOM   12  CG  LEU A  2      18.209  24.976  15.031  1.00117.88      1SG  13
ATOM   13  CD1 LEU A  2      19.496  24.131  15.027  1.00117.88      1SG  14
ATOM   14  CD2 LEU A  2      17.128  24.423  14.090  1.00117.88      1SG  15
ATOM   15  C   LEU A  2      18.902  27.236  16.815  1.00117.88      1SG  16
ATOM   16  O   LEU A  2      19.935  27.481  16.195  1.00117.88      1SG  17
ATOM   17  N   GLY A  3      17.963  28.175  17.039  1.00 21.07      1SG  18
ATOM   18  CA  GLY A  3      18.177  29.481  16.500  1.00 21.07      1SG  19
ATOM   19  C   GLY A  3      17.172  30.417  17.083  1.00 21.07      1SG  20
ATOM   20  O   GLY A  3      16.135  30.004  17.600  1.00 21.07      1SG  21
ATOM   21  N   THR A  4      17.476  31.727  17.003  1.00 95.56      1SG  22
ATOM   22  CA  THR A  4      16.587  32.733  17.496  1.00 95.56      1SG  23
ATOM   23  CB  THR A  4      17.152  33.517  18.643  1.00 95.56      1SG  24
ATOM   24  OG1 THR A  4      18.287  34.259  18.223  1.00 95.56      1SG  25
ATOM   25  CG2 THR A  4      17.545  32.531  19.757  1.00 95.56      1SG  26
ATOM   26  C   THR A  4      16.378  33.693  16.372  1.00 95.56      1SG  27
ATOM   27  O   THR A  4      17.226  33.816  15.488  1.00 95.56      1SG  28
ATOM   28  N   GLY A  5      15.232  34.400  16.362  1.00 16.12      1SG  29
ATOM   29  CA  GLY A  5      15.010  35.315  15.281  1.00 16.12      1SG  30
ATOM   30  C   GLY A  5      13.784  36.111  15.580  1.00 16.12      1SG  31
ATOM   31  O   GLY A  5      13.175  35.968  16.638  1.00 16.12      1SG  32
ATOM   32  N   PHE A  6      13.389  36.987  14.634  1.00 93.61      1SG  33
ATOM   33  CA  PHE A  6      12.226  37.790  14.862  1.00 93.61      1SG  34
ATOM   34  CB  PHE A  6      12.481  39.304  14.788  1.00 93.61      1SG  35
ATOM   35  CG  PHE A  6      13.539  39.644  15.776  1.00 93.61      1SG  36
ATOM   36  CD1 PHE A  6      13.225  39.963  17.076  1.00 93.61      1SG  37
ATOM   37  CD2 PHE A  6      14.859  39.631  15.392  1.00 93.61      1SG  38
ATOM   38  CE1 PHE A  6      14.218  40.273  17.975  1.00 93.61      1SG  39
ATOM   39  CE2 PHE A  6      15.854  39.941  16.288  1.00 93.61      1SG  40
ATOM   40  CZ  PHE A  6      15.534  40.263  17.584  1.00 93.61      1SG  41
ATOM   41  C   PHE A  6      11.264  37.493  13.762  1.00 93.61      1SG  42
ATOM   42  O   PHE A  6      11.660  37.135  12.653  1.00 93.61      1SG  43
ATOM   43  N   ARG A  7       9.956  37.621  14.056  1.00112.77      1SG  44
ATOM   44  CA  ARG A  7       8.980  37.406  13.033  1.00112.77      1SG  45
ATOM   45  CB  ARG A  7       7.536  37.263  13.553  1.00112.77      1SG  46
ATOM   46  CG  ARG A  7       6.553  36.730  12.505  1.00112.77      1SG  47
ATOM   47  CD  ARG A  7       5.820  37.811  11.705  1.00112.77      1SG  48
ATOM   48  NE  ARG A  7       4.998  37.118  10.671  1.00112.77      1SG  49
ATOM   49  CZ  ARG A  7       3.992  37.789  10.036  1.00112.77      1SG  50
ATOM   50  NH1 ARG A  7       3.731  39.091  10.350  1.00112.77      1SG  51
ATOM   51  NH2 ARG A  7       3.243  37.158   9.087  1.00112.77      1SG  52
ATOM   52  C   ARG A  7       9.058  38.616  12.168  1.00112.77      1SG  53
ATOM   53  O   ARG A  7       9.341  39.712  12.649  1.00112.77      1SG  54
ATOM   54  N   GLU A  8       8.810  38.446  10.859  1.00 65.51      1SG  55
ATOM   55  CA  GLU A  8       8.999  39.532   9.944  1.00 65.51      1SG  56
ATOM   56  CB  GLU A  8       9.409  39.057   8.543  1.00 65.51      1SG  57
ATOM   57  CG  GLU A  8      10.729  38.290   8.498  1.00 65.51      1SG  58
ATOM   58  CD  GLU A  8      10.731  37.489   7.202  1.00 65.51      1SG  59
ATOM   59  OE1 GLU A  8       9.661  36.911   6.869  1.00 65.51      1SG  60
ATOM   60  OE2 GLU A  8      11.795  37.446   6.530  1.00 65.51      1SG  61
ATOM   61  C   GLU A  8       7.706  40.247   9.745  1.00 65.51      1SG  62
ATOM   62  O   GLU A  8       6.652  39.627   9.621  1.00 65.51      1SG  63
ATOM   63  N   LYS A  9       7.762  41.594   9.734  1.00109.96      1SG  64
ATOM   64  CA  LYS A  9       6.590  42.352   9.417  1.00109.96      1SG  65
ATOM   65  CB  LYS A  9       6.088  43.263  10.553  1.00109.96      1SG  66
ATOM   66  CG  LYS A  9       4.635  43.708  10.353  1.00109.96      1SG  67
ATOM   67  CD  LYS A  9       3.632  42.558  10.506  1.00109.96      1SG  68
ATOM   68  CE  LYS A  9       2.170  42.946  10.270  1.00109.96      1SG  69
ATOM   69  NZ  LYS A  9       1.283  41.795  10.564  1.00109.96      1SG  70
ATOM   70  C   LYS A  9       6.996  43.220   8.272  1.00109.96      1SG  71
ATOM   71  O   LYS A  9       8.007  43.919   8.356  1.00109.96      1SG  72
ATOM   72  N   LYS A 10       6.215  43.190   7.174  1.00214.49      1SG  73
ATOM   73  CA  LYS A 10       6.539  43.916   5.978  1.00214.49      1SG  74
ATOM   74  CB  LYS A 10       6.403  45.453   6.052  1.00214.49      1SG  75
ATOM   75  CG  LYS A 10       7.522  46.155   6.831  1.00214.49      1SG  76
ATOM   76  CD  LYS A 10       7.671  47.639   6.473  1.00214.49      1SG  77
ATOM   77  CE  LYS A 10       8.389  47.867   5.139  1.00214.49      1SG  78
ATOM   78  NZ  LYS A 10       8.477  49.315   4.844  1.00214.49      1SG  79
ATOM   79  C   LYS A 10       7.960  43.610   5.642  1.00214.49      1SG  80
ATOM   80  O   LYS A 10       8.520  42.607   6.078  1.00214.49      1SG  81
ATOM   81  N   PHE A 11       8.577  44.472   4.819  1.00185.44      1SG  82
ATOM   82  CA  PHE A 11       9.957  44.256   4.531  1.00185.44      1SG  83
ATOM   83  CB  PHE A 11      10.559  45.298   3.575  1.00185.44      1SG  84
ATOM   84  CG  PHE A 11       9.866  45.104   2.270  1.00185.44      1SG  85
ATOM   85  CD1 PHE A 11       8.610  45.626   2.064  1.00185.44      1SG  86
ATOM   86  CD2 PHE A 11      10.473  44.401   1.256  1.00185.44      1SG  87
ATOM   87  CE1 PHE A 11       7.966  45.446   0.863  1.00185.44      1SG  88
ATOM   88  CE2 PHE A 11       9.837  44.217   0.051  1.00185.44      1SG  89
ATOM   89  CZ  PHE A 11       8.580  44.740  -0.144  1.00185.44      1SG  90
ATOM   90  C   PHE A 11      10.657  44.346   5.844  1.00185.44      1SG  91
ATOM   91  O   PHE A 11      10.249  45.091   6.734  1.00185.44      1SG  92
ATOM   92  N   ALA A 12      11.737  43.564   5.998  1.00 65.02      1SG  93
ATOM   93  CA  ALA A 12      12.417  43.512   7.253  1.00 65.02      1SG  94
ATOM   94  CB  ALA A 12      13.670  42.619   7.240  1.00 65.02      1SG  95
ATOM   95  C   ALA A 12      12.852  44.889   7.614  1.00 65.02      1SG  96
ATOM   96  O   ALA A 12      13.230  45.686   6.758  1.00 65.02      1SG  97
ATOM   97  N   ILE A 13      12.774  45.203   8.922  1.00 87.10      1SG  98
ATOM   98  CA  ILE A 13      13.177  46.487   9.407  1.00 87.10      1SG  99
ATOM   99  CB  ILE A 13      12.059  47.293  10.002  1.00 87.10      1SG 100
ATOM  100  CG2 ILE A 13      11.485  46.514  11.196  1.00 87.10      1SG 101
ATOM  101  CG1 ILE A 13      12.545  48.713  10.341  1.00 87.10      1SG 102
ATOM  102  CD1 ILE A 13      11.407  49.678  10.671  1.00 87.10      1SG 103
ATOM  103  C   ILE A 13      14.177  46.259  10.489  1.00 87.10      1SG 104
ATOM  104  O   ILE A 13      14.102  45.271  11.218  1.00 87.10      1SG 105
ATOM  105  N   ILE A 14      15.166  47.165  10.605  1.00142.40      1SG 106
ATOM  106  CA  ILE A 14      16.139  47.005  11.641  1.00142.40      1SG 107
ATOM  107  CB  ILE A 14      17.344  47.896  11.475  1.00142.40      1SG 108
ATOM  108  CG2 ILE A 14      16.879  49.356  11.611  1.00142.40      1SG 109
ATOM  109  CG1 ILE A 14      18.480  47.511  12.444  1.00142.40      1SG 110
ATOM  110  CD1 ILE A 14      18.176  47.769  13.919  1.00142.40      1SG 111
ATOM  111  C   ILE A 14      15.444  47.334  12.922  1.00142.40      1SG 112
ATOM  112  O   ILE A 14      14.748  48.342  13.028  1.00142.40      1SG 113
ATOM  113  N   GLY A 15      15.598  46.448  13.924  1.00 44.26      1SG 114
ATOM  114  CA  GLY A 15      14.963  46.645  15.192  1.00 44.26      1SG 115
ATOM  115  C   GLY A 15      14.136  45.431  15.434  1.00 44.26      1SG 116
ATOM  116  O   GLY A 15      14.288  44.425  14.740  1.00 44.26      1SG 117
ATOM  117  N   VAL A 16      13.234  45.481  16.431  1.00146.85      1SG 118
ATOM  118  CA  VAL A 16      12.418  44.325  16.639  1.00146.85      1SG 119
ATOM  119  CB  VAL A 16      11.892  44.185  18.036  1.00146.85      1SG 120
ATOM  120  CG1 VAL A 16      10.991  42.939  18.080  1.00146.85      1SG 121
ATOM  121  CG2 VAL A 16      13.072  44.137  19.022  1.00146.85      1SG 122
ATOM  122  C   VAL A 16      11.240  44.491  15.743  1.00146.85      1SG 123
ATOM  123  O   VAL A 16      10.420  45.389  15.932  1.00146.85      1SG 124
ATOM  124  N   LYS A 17      11.135  43.617  14.729  1.00149.13      1SG 125
ATOM  125  CA  LYS A 17      10.078  43.734  13.772  1.00149.13      1SG 126
ATOM  126  CB  LYS A 17      10.187  42.682  12.657  1.00149.13      1SG 127
ATOM  127  CG  LYS A 17      11.477  42.807  11.845  1.00149.13      1SG 128
ATOM  128  CD  LYS A 17      11.778  41.582  10.983  1.00149.13      1SG 129
ATOM  129  CE  LYS A 17      13.068  41.708  10.172  1.00149.13      1SG 130
ATOM  130  NZ  LYS A 17      14.234  41.449  11.045  1.00149.13      1SG 131
ATOM  131  C   LYS A 17       8.769  43.514  14.454  1.00149.13      1SG 132
ATOM  132  O   LYS A 17       7.843  44.308  14.302  1.00149.13      1SG 133
ATOM  133  N   VAL A 18       8.681  42.435  15.254  1.00247.87      1SG 134
ATOM  134  CA  VAL A 18       7.447  42.068  15.885  1.00247.87      1SG 135
ATOM  135  CB  VAL A 18       6.508  41.352  14.940  1.00247.87      1SG 136
ATOM  136  CG1 VAL A 18       7.195  40.111  14.336  1.00247.87      1SG 137
ATOM  137  CG2 VAL A 18       5.177  41.081  15.665  1.00247.87      1SG 138
ATOM  138  C   VAL A 18       7.797  41.232  17.081  1.00247.87      1SG 139
ATOM  139  O   VAL A 18       8.479  41.704  17.986  1.00247.87      1SG 140
ATOM  140  N   TYR A 19       7.296  39.982  17.147  1.00 84.14      1SG 141
ATOM  141  CA  TYR A 19       7.599  39.130  18.257  1.00 84.14      1SG 142
ATOM  142  CB  TYR A 19       6.459  38.162  18.620  1.00 84.14      1SG 143
ATOM  143  CG  TYR A 19       6.216  37.257  17.455  1.00 84.14      1SG 144
ATOM  144  CD1 TYR A 19       5.389  37.644  16.425  1.00 84.14      1SG 145
ATOM  145  CD2 TYR A 19       6.813  36.018  17.388  1.00 84.14      1SG 146
ATOM  146  CE1 TYR A 19       5.159  36.815  15.352  1.00 84.14      1SG 147
ATOM  147  CE2 TYR A 19       6.589  35.183  16.320  1.00 84.14      1SG 148
ATOM  148  CZ  TYR A 19       5.758  35.580  15.302  1.00 84.14      1SG 149
ATOM  149  OH  TYR A 19       5.524  34.727  14.204  1.00 84.14      1SG 150
ATOM  150  C   TYR A 19       8.785  38.292  17.903  1.00 84.14      1SG 151
ATOM  151  O   TYR A 19       8.874  37.744  16.804  1.00 84.14      1SG 152
ATOM  152  N   ALA A 20       9.751  38.210  18.840  1.00 32.79      1SG 153
ATOM  153  CA  ALA A 20      10.921  37.403  18.662  1.00 32.79      1SG 154
ATOM  154  CB  ALA A 20      12.082  37.792  19.594  1.00 32.79      1SG 155
ATOM  155  C   ALA A 20      10.542  35.992  18.978  1.00 32.79      1SG 156
ATOM  156  O   ALA A 20       9.609  35.749  19.742  1.00 32.79      1SG 157
ATOM  157  N   ALA A 21      11.258  35.017  18.384  1.00 29.56      1SG 158
ATOM  158  CA  ALA A 21      10.942  33.643  18.642  1.00 29.56      1SG 159
ATOM  159  CB  ALA A 21      10.117  32.986  17.521  1.00 29.56      1SG 160
ATOM  160  C   ALA A 21      12.221  32.879  18.748  1.00 29.56      1SG 161
```

Fig. 6

| ATOM | 161 | O   | ALA A 21 | 13.262 33.305 18.250 1.00 29.56 | 1SG 162 | ATOM | 246 | N   | LEU A 33 | 17.206 9.735 19.072 1.00184.21 | 1SG 247 |
|------|-----|-----|----------|--------------------------------|---------|------|-----|-----|----------|--------------------------------|---------|
| ATOM | 162 | N   | GLY A 22 | 12.172 31.720 19.433 1.00 27.75 | 1SG 163 | ATOM | 247 | CA  | LEU A 33 | 16.624 9.232 17.855 1.00184.21 | 1SG 248 |
| ATOM | 163 | CA  | GLY A 22 | 13.342 30.902 19.558 1.00 27.75 | 1SG 164 | ATOM | 248 | CB  | LEU A 33 | 16.491 10.303 16.757 1.00184.21 | 1SG 249 |
| ATOM | 164 | C   | GLY A 22 | 12.899 29.487 19.359 1.00 27.75 | 1SG 165 | ATOM | 249 | CG  | LEU A 33 | 15.455 11.396 17.084 1.00184.21 | 1SG 250 |
| ATOM | 165 | O   | GLY A 22 | 11.786 29.115 19.729 1.00 27.75 | 1SG 166 | ATOM | 250 | CD1 | LEU A 33 | 15.308 12.402 15.931 1.00184.21 | 1SG 251 |
| ATOM | 166 | N   | TYR A 23 | 13.781 28.653 18.774 1.00 97.91 | 1SG 167 | ATOM | 251 | CD2 | LEU A 33 | 14.115 10.773 17.501 1.00184.21 | 1SG 252 |
| ATOM | 167 | CA  | TYR A 23 | 13.438 27.283 18.515 1.00 97.91 | 1SG 168 | ATOM | 252 | C   | LEU A 33 | 17.480 8.124 17.321 1.00184.21 | 1SG 253 |
| ATOM | 168 | CB  | TYR A 23 | 13.691 26.886 17.049 1.00 97.91 | 1SG 169 | ATOM | 253 | O   | LEU A 33 | 16.951 7.091 16.917 1.00184.21 | 1SG 254 |
| ATOM | 169 | CG  | TYR A 23 | 12.818 27.752 16.202 1.00 97.91 | 1SG 170 | ATOM | 254 | N   | SER A 34 | 18.812 8.321 17.251 1.00200.02 | 1SG 255 |
| ATOM | 170 | CD1 | TYR A 23 | 13.128 29.079 16.013 1.00 97.91 | 1SG 171 | ATOM | 255 | CA  | SER A 34 | 19.730 7.266 16.909 1.00200.02 | 1SG 256 |
| ATOM | 171 | CD2 | TYR A 23 | 11.698 27.238 15.588 1.00 97.91 | 1SG 172 | ATOM | 256 | CB  | SER A 34 | 19.834 6.179 17.994 1.00200.02 | 1SG 257 |
| ATOM | 172 | CE1 | TYR A 23 | 12.332 29.886 15.232 1.00 97.91 | 1SG 173 | ATOM | 257 | OG  | SER A 34 | 18.586 5.521 18.151 1.00200.02 | 1SG 258 |
| ATOM | 173 | CE2 | TYR A 23 | 10.899 28.039 14.805 1.00 97.91 | 1SG 174 | ATOM | 258 | C   | SER A 34 | 19.320 6.626 15.622 1.00200.02 | 1SG 259 |
| ATOM | 174 | CZ  | TYR A 23 | 11.214 29.364 14.626 1.00 97.91 | 1SG 175 | ATOM | 259 | O   | SER A 34 | 19.738 5.508 15.318 1.00200.02 | 1SG 260 |
| ATOM | 175 | OH  | TYR A 23 | 10.395 30.186 13.823 1.00 97.91 | 1SG 176 | ATOM | 260 | N   | ALA A 35 | 18.498 7.318 14.818 1.00 70.42 | 1SG 261 |
| ATOM | 176 | C   | TYR A 23 | 14.341 26.452 19.372 1.00 97.91 | 1SG 177 | ATOM | 261 | CA  | ALA A 35 | 18.066 6.763 13.574 1.00 70.42 | 1SG 262 |
| ATOM | 177 | O   | TYR A 23 | 15.560 26.605 19.332 1.00 97.91 | 1SG 178 | ATOM | 262 | CB  | ALA A 35 | 17.069 7.666 12.831 1.00 70.42 | 1SG 263 |
| ATOM | 178 | N   | TYR A 24 | 13.753 25.550 20.188 1.00 51.45 | 1SG 179 | ATOM | 263 | C   | ALA A 35 | 19.285 6.644 12.736 1.00 70.42 | 1SG 264 |
| ATOM | 179 | CA  | TYR A 24 | 14.541 24.740 21.076 1.00 51.45 | 1SG 180 | ATOM | 264 | O   | ALA A 35 | 19.458 5.676 11.999 1.00 70.42 | 1SG 265 |
| ATOM | 180 | CB  | TYR A 24 | 14.271 25.012 22.569 1.00 51.45 | 1SG 181 | ATOM | 265 | N   | TRP A 36 | 20.154 7.665 12.805 1.00155.84 | 1SG 266 |
| ATOM | 181 | CG  | TYR A 24 | 14.765 26.379 22.899 1.00 51.45 | 1SG 182 | ATOM | 266 | CA  | TRP A 36 | 21.376 7.598 12.072 1.00155.84 | 1SG 267 |
| ATOM | 182 | CD1 | TYR A 24 | 13.971 27.482 22.687 1.00 51.45 | 1SG 183 | ATOM | 267 | CB  | TRP A 36 | 21.482 8.704 11.011 1.00155.84 | 1SG 268 |
| ATOM | 183 | CD2 | TYR A 24 | 16.027 26.558 23.420 1.00 51.45 | 1SG 184 | ATOM | 268 | CG  | TRP A 36 | 20.434 8.620 9.927 1.00155.84 | 1SG 269 |
| ATOM | 184 | CE1 | TYR A 24 | 14.429 28.744 22.989 1.00 51.45 | 1SG 185 | ATOM | 269 | CD2 | TRP A 36 | 20.581 7.833 8.736 1.00155.84 | 1SG 270 |
| ATOM | 185 | CE2 | TYR A 24 | 16.490 27.816 23.724 1.00 51.45 | 1SG 186 | ATOM | 270 | CD1 | TRP A 36 | 19.210 9.220 9.843 1.00155.84 | 1SG 271 |
| ATOM | 186 | CZ  | TYR A 24 | 15.688 28.912 23.510 1.00 51.45 | 1SG 187 | ATOM | 271 | NE1 | TRP A 36 | 18.581 8.849 8.678 1.00155.84 | 1SG 272 |
| ATOM | 187 | OH  | TYR A 24 | 16.157 30.206 23.820 1.00 51.45 | 1SG 188 | ATOM | 272 | CE2 | TRP A 36 | 19.415 7.996 7.987 1.00155.84 | 1SG 273 |
| ATOM | 188 | C   | TYR A 24 | 14.211 23.299 20.844 1.00 51.45 | 1SG 189 | ATOM | 273 | CE3 | TRP A 36 | 21.602 7.038 8.309 1.00155.84 | 1SG 274 |
| ATOM | 189 | O   | TYR A 24 | 13.077 22.949 20.518 1.00 51.45 | 1SG 190 | ATOM | 274 | CZ2 | TRP A 36 | 19.257 7.360 6.788 1.00155.84 | 1SG 275 |
| ATOM | 190 | N   | VAL A 25 | 15.227 22.425 20.990 1.00 41.95 | 1SG 191 | ATOM | 275 | CZ3 | TRP A 36 | 21.443 6.400 7.101 1.00155.84 | 1SG 276 |
| ATOM | 191 | CA  | VAL A 25 | 15.040 21.012 20.843 1.00 41.95 | 1SG 192 | ATOM | 276 | CH2 | TRP A 36 | 20.292 6.560 6.357 1.00155.84 | 1SG 277 |
| ATOM | 192 | CB  | VAL A 25 | 15.587 20.505 19.546 1.00 41.95 | 1SG 193 | ATOM | 277 | C   | TRP A 36 | 22.455 7.840 13.075 1.00155.84 | 1SG 278 |
| ATOM | 193 | CG1 | VAL A 25 | 15.465 18.982 19.554 1.00 41.95 | 1SG 194 | ATOM | 278 | O   | TRP A 36 | 22.907 8.970 13.250 1.00155.84 | 1SG 279 |
| ATOM | 194 | CG2 | VAL A 25 | 14.841 21.184 18.385 1.00 41.95 | 1SG 195 | ATOM | 279 | N   | THR A 37 | 22.918 6.778 13.760 1.00 56.04 | 1SG 280 |
| ATOM | 195 | C   | VAL A 25 | 15.816 20.366 21.952 1.00 41.95 | 1SG 196 | ATOM | 280 | CA  | THR A 37 | 23.927 7.018 14.744 1.00 56.04 | 1SG 281 |
| ATOM | 196 | O   | VAL A 25 | 16.886 20.842 22.330 1.00 41.95 | 1SG 197 | ATOM | 281 | CB  | THR A 37 | 23.904 6.061 15.897 1.00 56.04 | 1SG 282 |
| ATOM | 197 | N   | ASN A 26 | 15.292 19.262 22.520 1.00 53.33 | 1SG 198 | ATOM | 282 | OG1 | THR A 37 | 22.650 6.121 16.560 1.00 56.04 | 1SG 283 |
| ATOM | 198 | CA  | ASN A 26 | 16.009 18.617 23.583 1.00 53.33 | 1SG 199 | ATOM | 283 | CG2 | THR A 37 | 25.032 6.453 16.867 1.00 56.04 | 1SG 284 |
| ATOM | 199 | CB  | ASN A 26 | 15.167 17.596 24.373 1.00 53.33 | 1SG 200 | ATOM | 284 | C   | THR A 37 | 25.256 6.919 14.080 1.00 56.04 | 1SG 285 |
| ATOM | 200 | CG  | ASN A 26 | 16.005 17.070 25.531 1.00 53.33 | 1SG 201 | ATOM | 285 | O   | THR A 37 | 25.434 6.174 13.118 1.00 56.04 | 1SG 286 |
| ATOM | 201 | OD1 | ASN A 26 | 16.163 15.860 25.693 1.00 53.33 | 1SG 202 | ATOM | 286 | N   | GLY A 38 | 26.224 7.708 14.577 1.00 16.36 | 1SG 287 |
| ATOM | 202 | ND2 | ASN A 26 | 16.551 17.995 26.364 1.00 53.33 | 1SG 203 | ATOM | 287 | CA  | GLY A 38 | 27.544 7.668 14.031 1.00 16.36 | 1SG 288 |
| ATOM | 203 | C   | ASN A 26 | 17.162 17.893 22.966 1.00 53.33 | 1SG 204 | ATOM | 288 | C   | GLY A 38 | 27.507 8.351 12.706 1.00 16.36 | 1SG 289 |
| ATOM | 204 | O   | ASN A 26 | 17.003 17.177 21.979 1.00 53.33 | 1SG 205 | ATOM | 289 | O   | GLY A 38 | 28.427 8.212 11.901 1.00 16.36 | 1SG 290 |
| ATOM | 205 | N   | GLU A 27 | 18.366 18.076 23.540 1.00 65.43 | 1SG 206 | ATOM | 290 | N   | ARG A 39 | 26.438 9.123 12.440 1.00131.91 | 1SG 291 |
| ATOM | 206 | CA  | GLU A 27 | 19.554 17.473 23.005 1.00 65.43 | 1SG 207 | ATOM | 291 | CA  | ARG A 39 | 26.355 9.757 11.160 1.00131.91 | 1SG 292 |
| ATOM | 207 | CB  | GLU A 27 | 20.830 17.867 23.771 1.00 65.43 | 1SG 208 | ATOM | 292 | CB  | ARG A 39 | 24.936 9.768 10.567 1.00131.91 | 1SG 293 |
| ATOM | 208 | CG  | GLU A 27 | 21.079 19.373 23.857 1.00 65.43 | 1SG 209 | ATOM | 293 | CG  | ARG A 39 | 24.412 8.372 10.231 1.00131.91 | 1SG 294 |
| ATOM | 209 | CD  | GLU A 27 | 20.355 19.872 25.100 1.00 65.43 | 1SG 210 | ATOM | 294 | CD  | ARG A 39 | 25.384 7.560 9.375 1.00131.91 | 1SG 295 |
| ATOM | 210 | OE1 | GLU A 27 | 19.681 19.037 25.760 1.00 65.43 | 1SG 211 | ATOM | 295 | NE  | ARG A 39 | 25.655 8.347 8.141 1.00131.91 | 1SG 296 |
| ATOM | 211 | OE2 | GLU A 27 | 20.474 21.087 25.412 1.00 65.43 | 1SG 212 | ATOM | 296 | CZ  | ARG A 39 | 26.632 7.939 7.281 1.00131.91 | 1SG 297 |
| ATOM | 212 | C   | GLU A 27 | 19.450 15.992 23.154 1.00 65.43 | 1SG 213 | ATOM | 297 | NH1 | ARG A 39 | 27.366 6.825 7.569 1.00131.91 | 1SG 298 |
| ATOM | 213 | O   | GLU A 27 | 19.723 15.241 22.219 1.00 65.43 | 1SG 214 | ATOM | 298 | NH2 | ARG A 39 | 26.873 8.638 6.133 1.00131.91 | 1SG 299 |
| ATOM | 214 | N   | SER A 28 | 19.032 15.539 24.351 1.00 66.83 | 1SG 215 | ATOM | 299 | C   | ARG A 39 | 26.784 11.175 11.307 1.00131.91 | 1SG 300 |
| ATOM | 215 | CA  | SER A 28 | 19.004 14.139 24.652 1.00 66.83 | 1SG 216 | ATOM | 300 | O   | ARG A 39 | 26.538 11.815 12.329 1.00131.91 | 1SG 301 |
| ATOM | 216 | CB  | SER A 28 | 18.599 13.848 26.108 1.00 66.83 | 1SG 217 | ATOM | 301 | N   | SER A 40 | 27.472 11.691 10.273 1.00 22.35 | 1SG 302 |
| ATOM | 217 | OG  | SER A 28 | 18.585 12.446 26.341 1.00 66.83 | 1SG 218 | ATOM | 302 | CA  | SER A 40 | 27.911 13.050 10.292 1.00 22.35 | 1SG 303 |
| ATOM | 218 | C   | SER A 28 | 18.007 13.458 23.776 1.00 66.83 | 1SG 219 | ATOM | 303 | CB  | SER A 40 | 28.945 13.377 9.203 1.00 22.35 | 1SG 304 |
| ATOM | 219 | O   | SER A 28 | 18.267 12.375 23.252 1.00 66.83 | 1SG 220 | ATOM | 304 | OG  | SER A 40 | 30.156 12.677 9.454 1.00 22.35 | 1SG 305 |
| ATOM | 220 | N   | ILE A 29 | 16.835 14.085 23.570 1.00 83.55 | 1SG 221 | ATOM | 305 | C   | SER A 40 | 26.703 13.896 10.051 1.00 22.35 | 1SG 306 |
| ATOM | 221 | CA  | ILE A 29 | 15.815 13.415 22.820 1.00 83.55 | 1SG 222 | ATOM | 306 | O   | SER A 40 | 25.679 13.418 9.566 1.00 22.35 | 1SG 307 |
| ATOM | 222 | CB  | ILE A 29 | 14.541 14.188 22.698 1.00 83.55 | 1SG 223 | ATOM | 307 | N   | ALA A 41 | 26.806 15.193 10.391 1.00 21.97 | 1SG 308 |
| ATOM | 223 | CG2 | ILE A 29 | 13.637 13.378 21.757 1.00 83.55 | 1SG 224 | ATOM | 308 | CA  | ALA A 41 | 25.704 16.099 10.272 1.00 21.97 | 1SG 309 |
| ATOM | 224 | CG1 | ILE A 29 | 13.919 14.445 24.078 1.00 83.55 | 1SG 225 | ATOM | 309 | CB  | ALA A 41 | 26.051 17.525 10.732 1.00 21.97 | 1SG 310 |
| ATOM | 225 | CD1 | ILE A 29 | 13.570 13.163 24.833 1.00 83.55 | 1SG 226 | ATOM | 310 | C   | ALA A 41 | 25.302 16.183 8.835 1.00 21.97 | 1SG 311 |
| ATOM | 226 | C   | ILE A 29 | 16.297 13.177 21.430 1.00 83.55 | 1SG 227 | ATOM | 311 | O   | ALA A 41 | 24.115 16.251 8.519 1.00 21.97 | 1SG 312 |
| ATOM | 227 | O   | ILE A 29 | 16.127 12.084 20.893 1.00 83.55 | 1SG 228 | ATOM | 312 | N   | ASP A 42 | 26.288 16.167 7.923 1.00 97.59 | 1SG 313 |
| ATOM | 228 | N   | LEU A 30 | 16.896 14.200 20.799 1.00104.53 | 1SG 229 | ATOM | 313 | CA  | ASP A 42 | 25.986 16.318 6.533 1.00 97.59 | 1SG 314 |
| ATOM | 229 | CA  | LEU A 30 | 17.372 14.009 19.462 1.00104.53 | 1SG 230 | ATOM | 314 | CB  | ASP A 42 | 27.247 16.227 5.653 1.00 97.59 | 1SG 315 |
| ATOM | 230 | CB  | LEU A 30 | 17.755 15.309 18.743 1.00104.53 | 1SG 231 | ATOM | 315 | CG  | ASP A 42 | 26.887 16.641 4.233 1.00 97.59 | 1SG 316 |
| ATOM | 231 | CG  | LEU A 30 | 16.500 15.980 18.161 1.00104.53 | 1SG 232 | ATOM | 316 | OD1 | ASP A 42 | 25.793 17.241 4.047 1.00 97.59 | 1SG 317 |
| ATOM | 232 | CD1 | LEU A 30 | 15.391 16.068 19.219 1.00104.53 | 1SG 233 | ATOM | 317 | OD2 | ASP A 42 | 27.700 16.360 3.315 1.00 97.59 | 1SG 318 |
| ATOM | 233 | CD2 | LEU A 30 | 16.830 17.333 17.513 1.00104.53 | 1SG 234 | ATOM | 318 | C   | ASP A 42 | 25.075 15.207 6.124 1.00 97.59 | 1SG 319 |
| ATOM | 234 | C   | LEU A 30 | 18.500 13.037 19.447 1.00104.53 | 1SG 235 | ATOM | 319 | O   | ASP A 42 | 24.087 15.431 5.425 1.00 97.59 | 1SG 320 |
| ATOM | 235 | O   | LEU A 30 | 18.597 12.216 18.538 1.00104.53 | 1SG 236 | ATOM | 320 | N   | GLU A 43 | 25.379 13.974 6.557 1.00113.42 | 1SG 321 |
| ATOM | 236 | N   | SER A 31 | 19.381 13.082 20.460 1.00 30.29 | 1SG 237 | ATOM | 321 | CA  | GLU A 43 | 24.576 12.864 6.146 1.00113.42 | 1SG 322 |
| ATOM | 237 | CA  | SER A 31 | 20.471 12.152 20.478 1.00 30.29 | 1SG 238 | ATOM | 322 | CB  | GLU A 43 | 25.182 11.508 6.525 1.00113.42 | 1SG 323 |
| ATOM | 238 | CB  | SER A 31 | 21.387 12.335 21.701 1.00 30.29 | 1SG 239 | ATOM | 323 | CG  | GLU A 43 | 24.611 10.372 5.681 1.00113.42 | 1SG 324 |
| ATOM | 239 | OG  | SER A 31 | 21.983 13.624 21.674 1.00 30.29 | 1SG 240 | ATOM | 324 | CD  | GLU A 43 | 25.105 10.593 4.256 1.00113.42 | 1SG 325 |
| ATOM | 240 | C   | SER A 31 | 19.863 10.789 20.562 1.00 30.29 | 1SG 241 | ATOM | 325 | OE1 | GLU A 43 | 24.813 11.678 3.685 1.00113.42 | 1SG 326 |
| ATOM | 241 | O   | SER A 31 | 20.420 9.810 20.070 1.00 30.29 | 1SG 242 | ATOM | 326 | OE2 | GLU A 43 | 25.791 9.680 3.723 1.00113.42 | 1SG 327 |
| ATOM | 242 | N   | GLY A 32 | 18.677 10.717 21.186 1.00 38.70 | 1SG 243 | ATOM | 327 | C   | GLU A 43 | 23.214 12.959 6.759 1.00113.42 | 1SG 328 |
| ATOM | 243 | CA  | GLY A 32 | 17.934 9.510 21.400 1.00 38.70 | 1SG 244 | ATOM | 328 | O   | GLU A 43 | 22.215 12.684 6.099 1.00113.42 | 1SG 329 |
| ATOM | 244 | C   | GLY A 32 | 17.482 8.906 20.105 1.00 38.70 | 1SG 245 | ATOM | 329 | N   | ILE A 44 | 23.135 13.366 8.041 1.00 90.32 | 1SG 330 |
| ATOM | 245 | O   | GLY A 32 | 17.366 7.684 20.018 1.00 38.70 | 1SG 246 | ATOM | 330 | CA  | ILE A 44 | 21.870 13.426 8.714 1.00 90.32 | 1SG 331 |

Fig. 6 cont.

```
ATOM  331 CB  ILE A 44    22.012 13.907 10.130 1.00 90.32      1SG 332
ATOM  332 CG2 ILE A 44    20.603 14.097 10.713 1.00 90.32      1SG 333
ATOM  333 CG1 ILE A 44    22.872 12.929 10.942 1.00 90.32      1SG 334
ATOM  334 CD1 ILE A 44    22.248 11.544 11.053 1.00 90.32      1SG 335
ATOM  335 C   ILE A 44    20.993 14.410  8.005 1.00 90.32      1SG 336
ATOM  336 O   ILE A 44    19.836 14.121  7.700 1.00 90.32      1SG 337
ATOM  337 N   GLN A 45    21.537 15.599  7.697 1.00 75.11      1SG 338
ATOM  338 CA  GLN A 45    20.742 16.610  7.068 1.00 75.11      1SG 339
ATOM  339 CB  GLN A 45    21.456 17.964  6.909 1.00 75.11      1SG 340
ATOM  340 CG  GLN A 45    22.647 17.960  5.953 1.00 75.11      1SG 341
ATOM  341 CD  GLN A 45    23.145 19.394  5.860 1.00 75.11      1SG 342
ATOM  342 OE1 GLN A 45    22.676 20.272  6.583 1.00 75.11      1SG 343
ATOM  343 NE2 GLN A 45    24.115 19.644  4.940 1.00 75.11      1SG 344
ATOM  344 C   GLN A 45    20.340 16.137  5.710 1.00 75.11      1SG 345
ATOM  345 O   GLN A 45    19.237 16.426  5.250 1.00 75.11      1SG 346
ATOM  346 N   ARG A 46    21.222 15.382  5.031 1.00 50.93      1SG 347
ATOM  347 CA  ARG A 46    20.935 14.947  3.696 1.00 50.93      1SG 348
ATOM  348 CB  ARG A 46    22.042 14.092  3.062 1.00 50.93      1SG 349
ATOM  349 CG  ARG A 46    23.206 14.899  2.488 1.00 50.93      1SG 350
ATOM  350 CD  ARG A 46    24.075 14.075  1.534 1.00 50.93      1SG 351
ATOM  351 NE  ARG A 46    25.007 15.013  0.846 1.00 50.93      1SG 352
ATOM  352 CZ  ARG A 46    24.571 15.721 -0.236 1.00 50.93      1SG 353
ATOM  353 NH1 ARG A 46    23.269 15.624 -0.636 1.00 50.93      1SG 354
ATOM  354 NH2 ARG A 46    25.433 16.529 -0.920 1.00 50.93      1SG 355
ATOM  355 C   ARG A 46    19.699 14.110  3.669 1.00 50.93      1SG 356
ATOM  356 O   ARG A 46    18.899 14.240  2.747 1.00 50.93      1SG 357
ATOM  357 N   ASP A 47    19.503 13.234  4.673 1.00 48.63      1SG 358
ATOM  358 CA  ASP A 47    18.372 12.350  4.645 1.00 48.63      1SG 359
ATOM  359 CB  ASP A 47    18.267 11.445  5.884 1.00 48.63      1SG 360
ATOM  360 CG  ASP A 47    19.362 10.390  5.822 1.00 48.63      1SG 361
ATOM  361 OD1 ASP A 47    19.352  9.583  4.854 1.00 48.63      1SG 362
ATOM  362 OD2 ASP A 47    20.213 10.368  6.748 1.00 48.63      1SG 363
ATOM  363 C   ASP A 47    17.117 13.164  4.581 1.00 48.63      1SG 364
ATOM  364 O   ASP A 47    16.888 14.058  5.393 1.00 48.63      1SG 365
ATOM  365 N   SER A 48    16.266 12.863  3.583 1.00 32.50      1SG 366
ATOM  366 CA  SER A 48    15.031 13.572  3.421 1.00 32.50      1SG 367
ATOM  367 CB  SER A 48    14.301 13.223  2.110 1.00 32.50      1SG 368
ATOM  368 OG  SER A 48    13.900 11.861  2.118 1.00 32.50      1SG 369
ATOM  369 C   SER A 48    14.129 13.206  4.557 1.00 32.50      1SG 370
ATOM  370 O   SER A 48    13.255 13.982  4.939 1.00 32.50      1SG 371
ATOM  371 N   SER A 49    14.330 11.997  5.118 1.00 45.41      1SG 372
ATOM  372 CA  SER A 49    13.515 11.435  6.160 1.00 45.41      1SG 373
ATOM  373 CB  SER A 49    13.831  9.951  6.412 1.00 45.41      1SG 374
ATOM  374 OG  SER A 49    15.155  9.814  6.909 1.00 45.41      1SG 375
ATOM  375 C   SER A 49    13.707 12.148  7.469 1.00 45.41      1SG 376
ATOM  376 O   SER A 49    12.849 12.060  8.346 1.00 45.41      1SG 377
ATOM  377 N   LEU A 50    14.812 12.897  7.631 1.00 106.58     1SG 378
ATOM  378 CA  LEU A 50    15.144 13.473  8.905 1.00 106.58     1SG 379
ATOM  379 CB  LEU A 50    16.463 14.277  8.858 1.00 106.58     1SG 380
ATOM  380 CG  LEU A 50    16.912 14.929 10.189 1.00 106.58     1SG 381
ATOM  381 CD1 LEU A 50    16.066 16.156 10.572 1.00 106.58     1SG 382
ATOM  382 CD2 LEU A 50    16.992 13.890 11.320 1.00 106.58     1SG 383
ATOM  383 C   LEU A 50    14.049 14.376  9.387 1.00 106.58     1SG 384
ATOM  384 O   LEU A 50    13.684 14.339 10.561 1.00 106.58     1SG 385
ATOM  385 N   PHE A 51    13.477 15.204  8.500 1.00 49.19      1SG 386
ATOM  386 CA  PHE A 51    12.480 16.150  8.921 1.00 49.19      1SG 387
ATOM  387 CB  PHE A 51    11.946 16.957  7.725 1.00 49.19      1SG 388
ATOM  388 CG  PHE A 51    10.755 17.735  8.160 1.00 49.19      1SG 389
ATOM  389 CD1 PHE A 51    10.884 18.972  8.745 1.00 49.19      1SG 390
ATOM  390 CD2 PHE A 51     9.498 17.211  7.973 1.00 49.19      1SG 391
ATOM  391 CE1 PHE A 51     9.769 19.677  9.135 1.00 49.19      1SG 392
ATOM  392 CE2 PHE A 51     8.381 17.908  8.362 1.00 49.19      1SG 393
ATOM  393 CZ  PHE A 51     8.516 19.144  8.948 1.00 49.19      1SG 394
ATOM  394 C   PHE A 51    11.326 15.423  9.539 1.00 49.19      1SG 395
ATOM  395 O   PHE A 51    10.917 15.733 10.657 1.00 49.19      1SG 396
ATOM  396 N   VAL A 52    10.777 14.415  8.838 1.00 83.66      1SG 397
ATOM  397 CA  VAL A 52     9.629 13.721  9.349 1.00 83.66      1SG 398
ATOM  398 CB  VAL A 52     9.050 12.731  8.380 1.00 83.66      1SG 399
ATOM  399 CG1 VAL A 52    10.082 11.619  8.128 1.00 83.66      1SG 400
ATOM  400 CG2 VAL A 52     7.715 12.224  8.952 1.00 83.66      1SG 401
ATOM  401 C   VAL A 52     9.994 12.977 10.594 1.00 83.66      1SG 402
ATOM  402 O   VAL A 52     9.223 12.947 11.552 1.00 83.66      1SG 403
ATOM  403 N   SER A 53    11.191 12.358 10.618 1.00 74.30      1SG 404
ATOM  404 CA  SER A 53    11.566 11.539 11.733 1.00 74.30      1SG 405
ATOM  405 CB  SER A 53    12.964 10.908 11.573 1.00 74.30      1SG 406
ATOM  406 OG  SER A 53    13.952 11.923 11.470 1.00 74.30      1SG 407
ATOM  407 C   SER A 53    11.572 12.358 12.987 1.00 74.30      1SG 408
ATOM  408 O   SER A 53    11.058 11.924 14.017 1.00 74.30      1SG 409
ATOM  409 N   ILE A 54    12.142 13.576 12.935 1.00 94.96      1SG 410
ATOM  410 CA  ILE A 54    12.236 14.394 14.111 1.00 94.96      1SG 411
ATOM  411 CB  ILE A 54    13.028 15.650 13.886 1.00 94.96      1SG 412
ATOM  412 CG2 ILE A 54    14.455 15.233 13.493 1.00 94.96      1SG 413
ATOM  413 CG1 ILE A 54    12.345 16.555 12.850 1.00 94.96      1SG 414
ATOM  414 CD1 ILE A 54    12.932 17.963 12.795 1.00 94.96      1SG 415
ATOM  415 C   ILE A 54    10.870 14.774 14.599 1.00 94.96      1SG 416
ATOM  416 O   ILE A 54    10.593 14.689 15.794 1.00 94.96      1SG 417
ATOM  417 N   PHE A 55     9.966 15.192 13.694 1.00 57.05      1SG 418
ATOM  418 CA  PHE A 55     8.653 15.598 14.116 1.00 57.05      1SG 419
ATOM  419 CB  PHE A 55     7.808 16.223 12.994 1.00 57.05      1SG 420
ATOM  420 CG  PHE A 55     8.264 17.636 12.849 1.00 57.05      1SG 421
ATOM  421 CD1 PHE A 55     9.423 17.950 12.178 1.00 57.05      1SG 422
ATOM  422 CD2 PHE A 55     7.514 18.657 13.389 1.00 57.05      1SG 423
ATOM  423 CE1 PHE A 55     9.827 19.259 12.056 1.00 57.05      1SG 424
ATOM  424 CE2 PHE A 55     7.914 19.967 13.269 1.00 57.05      1SG 425
ATOM  425 CZ  PHE A 55     9.073 20.272 12.599 1.00 57.05      1SG 426
ATOM  426 C   PHE A 55     7.908 14.437 14.704 1.00 57.05      1SG 427
ATOM  427 O   PHE A 55     7.191 14.594 15.691 1.00 57.05      1SG 428
ATOM  428 N   GLN A 56     8.049 13.241 14.105 1.00 82.84      1SG 429
ATOM  429 CA  GLN A 56     7.336 12.072 14.544 1.00 82.84      1SG 430
ATOM  430 CB  GLN A 56     7.588 10.859 13.630 1.00 82.84      1SG 431
ATOM  431 CG  GLN A 56     7.110 11.052 12.189 1.00 82.84      1SG 432
ATOM  432 CD  GLN A 56     5.594 10.932 12.160 1.00 82.84      1SG 433
ATOM  433 OE1 GLN A 56     4.977 11.001 11.096 1.00 82.84      1SG 434
ATOM  434 NE2 GLN A 56     4.970 10.752 13.356 1.00 82.84      1SG 435
ATOM  435 C   GLN A 56     7.769 11.665 15.926 1.00 82.84      1SG 436
ATOM  436 O   GLN A 56     6.939 11.305 16.758 1.00 82.84      1SG 437
ATOM  437 N   ALA A 57     9.084 11.737 16.215 1.00 40.24      1SG 438
ATOM  438 CA  ALA A 57     9.623 11.234 17.451 1.00 40.24      1SG 439
ATOM  439 CB  ALA A 57    11.162 11.209 17.488 1.00 40.24      1SG 440
ATOM  440 C   ALA A 57     9.157 12.050 18.610 1.00 40.24      1SG 441
ATOM  441 O   ALA A 57     8.748 13.201 18.469 1.00 40.24      1SG 442
ATOM  442 N   GLN A 58     9.183 11.434 19.810 1.00 47.63      1SG 443
ATOM  443 CA  GLN A 58     8.795 12.164 20.976 1.00 47.63      1SG 444
ATOM  444 CB  GLN A 58     8.389 11.275 22.162 1.00 47.63      1SG 445
ATOM  445 CG  GLN A 58     7.106 10.477 21.934 1.00 47.63      1SG 446
ATOM  446 CD  GLN A 58     6.846  9.655 23.190 1.00 47.63      1SG 447
ATOM  447 OE1 GLN A 58     7.673  8.847 23.607 1.00 47.63      1SG 448
ATOM  448 NE2 GLN A 58     5.660  9.880 23.820 1.00 47.63      1SG 449
ATOM  449 C   GLN A 58    10.004 12.919 21.402 1.00 47.63      1SG 450
ATOM  450 O   GLN A 58    10.850 12.410 22.138 1.00 47.63      1SG 451
ATOM  451 N   ALA A 59    10.118 14.169 20.925 1.00 42.78      1SG 452
ATOM  452 CA  ALA A 59    11.219 14.991 21.311 1.00 42.78      1SG 453
ATOM  453 CB  ALA A 59    12.152 15.353 20.145 1.00 42.78      1SG 454
ATOM  454 C   ALA A 59    10.618 16.252 21.807 1.00 42.78      1SG 455
ATOM  455 O   ALA A 59     9.736 16.818 21.164 1.00 42.78      1SG 456
ATOM  456 N   GLU A 60    11.071 16.718 22.981 1.00 76.58      1SG 457
ATOM  457 CA  GLU A 60    10.516 17.930 23.491 1.00 76.58      1SG 458
ATOM  458 CB  GLU A 60    10.855 18.171 24.973 1.00 76.58      1SG 459
ATOM  459 CG  GLU A 60    10.111 19.346 25.608 1.00 76.58      1SG 460
ATOM  460 CD  GLU A 60    10.410 19.328 27.102 1.00 76.58      1SG 461
ATOM  461 OE1 GLU A 60    10.196 18.260 27.732 1.00 76.58      1SG 462
ATOM  462 OE2 GLU A 60    10.850 20.384 27.633 1.00 76.58      1SG 463
ATOM  463 C   GLU A 60    11.090 19.037 22.676 1.00 76.58      1SG 464
ATOM  464 O   GLU A 60    12.293 19.072 22.417 1.00 76.58      1SG 465
ATOM  465 N   LYS A 61    10.224 19.961 22.226 1.00 73.45      1SG 466
ATOM  466 CA  LYS A 61    10.680 21.083 21.468 1.00 73.45      1SG 467
ATOM  467 CB  LYS A 61    10.441 20.951 19.955 1.00 73.45      1SG 468
ATOM  468 CG  LYS A 61    11.265 19.821 19.335 1.00 73.45      1SG 469
ATOM  469 CD  LYS A 61    10.874 19.474 17.897 1.00 73.45      1SG 470
ATOM  470 CE  LYS A 61    11.662 18.297 17.320 1.00 73.45      1SG 471
ATOM  471 NZ  LYS A 61    13.106 18.614 17.313 1.00 73.45      1SG 472
ATOM  472 C   LYS A 61     9.891 22.239 21.965 1.00 73.45      1SG 473
ATOM  473 O   LYS A 61     8.711 22.101 22.284 1.00 73.45      1SG 474
ATOM  474 N   SER A 62    10.526 23.418 22.065 1.00 88.14      1SG 475
ATOM  475 CA  SER A 62     9.782 24.505 22.611 1.00 88.14      1SG 476
ATOM  476 CB  SER A 62    10.161 24.776 24.071 1.00 88.14      1SG 477
ATOM  477 OG  SER A 62     9.405 25.864 24.566 1.00 88.14      1SG 478
ATOM  478 C   SER A 62    10.110 25.728 21.837 1.00 88.14      1SG 479
ATOM  479 O   SER A 62    11.258 25.955 21.458 1.00 88.14      1SG 480
ATOM  480 N   LEU A 63     9.080 26.551 21.565 1.00 89.98      1SG 481
ATOM  481 CA  LEU A 63     9.349 27.783 20.905 1.00 89.98      1SG 482
ATOM  482 CB  LEU A 63     8.578 27.972 19.580 1.00 89.98      1SG 483
ATOM  483 CG  LEU A 63     9.042 29.159 18.700 1.00 89.98      1SG 484
ATOM  484 CD1 LEU A 63     8.200 29.243 17.417 1.00 89.98      1SG 485
ATOM  485 CD2 LEU A 63     9.084 30.498 19.457 1.00 89.98      1SG 486
ATOM  486 C   LEU A 63     8.908 28.834 21.867 1.00 89.98      1SG 487
ATOM  487 O   LEU A 63     7.802 28.775 22.406 1.00 89.98      1SG 488
ATOM  488 N   GLN A 64     9.790 29.814 22.125 1.00 83.93      1SG 489
ATOM  489 CA  GLN A 64     9.441 30.882 23.011 1.00 83.93      1SG 490
ATOM  490 CB  GLN A 64    10.583 31.338 23.938 1.00 83.93      1SG 491
ATOM  491 CG  GLN A 64    10.185 32.519 24.828 1.00 83.93      1SG 492
ATOM  492 CD  GLN A 64    10.874 33.091 25.473 1.00 83.93      1SG 493
ATOM  493 OE1 GLN A 64    12.518 32.498 25.410 1.00 83.93      1SG 494
ATOM  494 NE2 GLN A 64    11.306 34.286 26.108 1.00 83.93      1SG 495
ATOM  495 C   GLN A 64     9.144 32.058 22.150 1.00 83.93      1SG 496
ATOM  496 O   GLN A 64     9.925 32.400 21.264 1.00 83.93      1SG 497
ATOM  497 N   ILE A 65     7.982 32.699 22.370 1.00 40.49      1SG 498
ATOM  498 CA  ILE A 65     7.686 33.853 21.582 1.00 40.49      1SG 499
ATOM  499 CB  ILE A 65     6.539 33.653 20.637 1.00 40.49      1SG 500
ATOM  500 CG2 ILE A 65     6.128 35.020 20.075 1.00 40.49      1SG 501
```

Fig. 6 cont.

```
ATOM  501 CG1 ILE A 65    6.923 32.623 19.562 1.00 40.49    1SG 502
ATOM  502 CD1 ILE A 65    5.748 32.160 18.704 1.00 40.49    1SG 503
ATOM  503 C   ILE A 65    7.344 34.971 22.504 1.00 40.49    1SG 504
ATOM  504 O   ILE A 65    6.551 34.812 23.429 1.00 40.49    1SG 505
ATOM  505 N   VAL A 66    7.975 36.135 22.277 1.00 94.21    1SG 506
ATOM  506 CA  VAL A 66    7.685 37.306 23.045 1.00 94.21    1SG 507
ATOM  507 CB  VAL A 66    8.864 37.841 23.805 1.00 94.21    1SG 508
ATOM  508 CG1 VAL A 66    9.257 36.827 24.892 1.00 94.21    1SG 509
ATOM  509 CG2 VAL A 66    9.995 38.137 22.802 1.00 94.21    1SG 510
ATOM  510 C   VAL A 66    7.293 38.347 22.050 1.00 94.21    1SG 511
ATOM  511 O   VAL A 66    7.869 38.421 20.966 1.00 94.21    1SG 512
ATOM  512 N   LEU A 67    6.285 39.176 22.374 1.00179.01    1SG 513
ATOM  513 CA  LEU A 67    5.897 40.163 21.413 1.00179.01    1SG 514
ATOM  514 CB  LEU A 67    4.388 40.169 21.102 1.00179.01    1SG 515
ATOM  515 CG  LEU A 67    3.990 41.234 20.063 1.00179.01    1SG 516
ATOM  516 CD1 LEU A 67    4.638 40.958 18.698 1.00179.01    1SG 517
ATOM  517 CD2 LEU A 67    2.465 41.395 19.969 1.00179.01    1SG 518
ATOM  518 C   LEU A 67    6.241 41.507 21.956 1.00179.01    1SG 519
ATOM  519 O   LEU A 67    6.068 41.769 23.145 1.00179.01    1SG 520
ATOM  520 N   VAL A 68    6.776 42.393 21.093 1.00267.62    1SG 521
ATOM  521 CA  VAL A 68    7.093 43.713 21.551 1.00267.62    1SG 522
ATOM  522 CB  VAL A 68    8.566 43.971 21.657 1.00267.62    1SG 523
ATOM  523 CG1 VAL A 68    8.783 45.450 22.015 1.00267.62    1SG 524
ATOM  524 CG2 VAL A 68    9.160 42.986 22.678 1.00267.62    1SG 525
ATOM  525 C   VAL A 68    6.542 44.697 20.566 1.00267.62    1SG 526
ATOM  526 O   VAL A 68    6.618 44.469 19.360 1.00267.62    1SG 527
ATOM  527 N   ARG A 69    5.944 45.795 21.092 1.00474.48    1SG 528
ATOM  528 CA  ARG A 69    5.403 46.925 20.375 1.00474.48    1SG 529
ATOM  529 CB  ARG A 69    5.620 46.952 18.848 1.00474.48    1SG 530
ATOM  530 CG  ARG A 69    7.072 47.241 18.453 1.00474.48    1SG 531
ATOM  531 CD  ARG A 69    7.404 48.733 18.318 1.00474.48    1SG 532
ATOM  532 NE  ARG A 69    7.853 49.240 19.648 1.00474.48    1SG 533
ATOM  533 CZ  ARG A 69    6.982 49.887 20.477 1.00474.48    1SG 534
ATOM  534 NH1 ARG A 69    5.692 50.098 20.087 1.00474.48    1SG 535
ATOM  535 NH2 ARG A 69    7.406 50.329 21.698 1.00474.48    1SG 536
ATOM  536 C   ARG A 69    3.939 47.016 20.649 1.00474.48    1SG 537
ATOM  537 O   ARG A 69    3.360 46.147 21.300 1.00474.48    1SG 538
ATOM  538 N   ASP A 70    3.302 48.101 20.164 1.00238.54    1SG 539
ATOM  539 CA  ASP A 70    1.898 48.273 20.385 1.00238.54    1SG 540
ATOM  540 CB  ASP A 70    1.467 49.748 20.533 1.00238.54    1SG 541
ATOM  541 CG  ASP A 70    1.797 50.519 19.255 1.00238.54    1SG 542
ATOM  542 OD1 ASP A 70    2.848 50.195 18.635 1.00238.54    1SG 543
ATOM  543 OD2 ASP A 70    1.009 51.424 18.890 1.00238.54    1SG 544
ATOM  544 C   ASP A 70    1.157 47.666 19.238 1.00238.54    1SG 545
ATOM  545 O   ASP A 70    1.295 48.083 18.087 1.00238.54    1SG 546
ATOM  546 N   VAL A 71    0.342 46.636 19.522 1.00 52.06    1SG 547
ATOM  547 CA  VAL A 71   -0.387 46.040 18.447 1.00 52.06    1SG 548
ATOM  548 CB  VAL A 71    0.048 44.641 18.138 1.00 52.06    1SG 549
ATOM  549 CG1 VAL A 71   -0.873 44.072 17.048 1.00 52.06    1SG 550
ATOM  550 CG2 VAL A 71    1.537 44.675 17.753 1.00 52.06    1SG 551
ATOM  551 C   VAL A 71   -1.821 45.977 18.843 1.00 52.06    1SG 552
ATOM  552 O   VAL A 71   -2.145 45.887 20.027 1.00 52.06    1SG 553
ATOM  553 N   ASP A 72   -2.726 46.061 17.848 1.00 69.80    1SG 554
ATOM  554 CA  ASP A 72   -4.121 45.948 18.150 1.00 69.80    1SG 555
ATOM  555 CB  ASP A 72   -5.032 46.919 17.373 1.00 69.80    1SG 556
ATOM  556 CG  ASP A 72   -4.899 46.646 15.881 1.00 69.80    1SG 557
ATOM  557 OD1 ASP A 72   -3.775 46.818 15.337 1.00 69.80    1SG 558
ATOM  558 OD2 ASP A 72   -5.930 46.270 15.263 1.00 69.80    1SG 559
ATOM  559 C   ASP A 72   -4.530 44.536 17.868 1.00 69.80    1SG 560
ATOM  560 O   ASP A 72   -3.927 43.844 17.047 1.00 69.80    1SG 561
ATOM  561 N   GLY A 73   -5.578 44.077 18.576 1.00 34.29    1SG 562
ATOM  562 CA  GLY A 73   -6.031 42.716 18.521 1.00 34.29    1SG 563
ATOM  563 C   GLY A 73   -6.521 42.348 17.156 1.00 34.29    1SG 564
ATOM  564 O   GLY A 73   -6.282 41.232 16.698 1.00 34.29    1SG 565
ATOM  565 N   LYS A 74   -7.245 43.261 16.481 1.00100.50    1SG 566
ATOM  566 CA  LYS A 74   -7.816 42.935 15.204 1.00100.50    1SG 567
ATOM  567 CB  LYS A 74   -8.689 44.066 14.631 1.00100.50    1SG 568
ATOM  568 CG  LYS A 74  -10.021 44.241 15.367 1.00100.50    1SG 569
ATOM  569 CD  LYS A 74  -10.725 45.568 15.068 1.00100.50    1SG 570
ATOM  570 CE  LYS A 74  -10.884 45.854 13.575 1.00100.50    1SG 571
ATOM  571 NZ  LYS A 74   -9.591 46.297 13.004 1.00100.50    1SG 572
ATOM  572 C   LYS A 74   -6.731 42.653 14.214 1.00100.50    1SG 573
ATOM  573 O   LYS A 74   -6.795 41.666 13.482 1.00100.50    1SG 574
ATOM  574 N   THR A 75   -5.691 43.505 14.178 1.00 96.66    1SG 575
ATOM  575 CA  THR A 75   -4.639 43.312 13.221 1.00 96.66    1SG 576
ATOM  576 CB  THR A 75   -3.625 44.414 13.222 1.00 96.66    1SG 577
ATOM  577 OG1 THR A 75   -2.999 44.511 14.493 1.00 96.66    1SG 578
ATOM  578 CG2 THR A 75   -4.337 45.730 12.869 1.00 96.66    1SG 579
ATOM  579 C   THR A 75   -3.929 42.043 13.545 1.00 96.66    1SG 580
ATOM  580 O   THR A 75   -3.523 41.294 12.657 1.00 96.66    1SG 581
ATOM  581 N   PHE A 76   -3.772 41.775 14.849 1.00 56.09    1SG 582
ATOM  582 CA  PHE A 76   -3.045 40.639 15.323 1.00 56.09    1SG 583
ATOM  583 CB  PHE A 76   -3.029 40.613 16.860 1.00 56.09    1SG 584
ATOM  584 CG  PHE A 76   -1.873 39.795 17.312 1.00 56.09    1SG 585
ATOM  585 CD1 PHE A 76   -0.634 40.384 17.413 1.00 56.09    1SG 586
ATOM  586 CD2 PHE A 76   -2.016 38.469 17.643 1.00 56.09    1SG 587
ATOM  587 CE1 PHE A 76    0.457 39.660 17.830 1.00 56.09    1SG 588
ATOM  588 CE2 PHE A 76   -0.927 37.739 18.062 1.00 56.09    1SG 589
ATOM  589 CZ  PHE A 76    0.310 38.334 18.158 1.00 56.09    1SG 590
ATOM  590 C   PHE A 76   -3.730 39.396 14.832 1.00 56.09    1SG 591
ATOM  591 O   PHE A 76   -3.082 38.477 14.334 1.00 56.09    1SG 592
ATOM  592 N   TRP A 77   -5.073 39.347 14.937 1.00 64.30    1SG 593
ATOM  593 CA  TRP A 77   -5.809 38.179 14.541 1.00 64.30    1SG 594
ATOM  594 CB  TRP A 77   -7.331 38.302 14.732 1.00 64.30    1SG 595
ATOM  595 CG  TRP A 77   -7.825 38.316 16.156 1.00 64.30    1SG 596
ATOM  596 CD2 TRP A 77   -9.220 38.310 16.502 1.00 64.30    1SG 597
ATOM  597 CD1 TRP A 77   -7.135 38.336 17.334 1.00 64.30    1SG 598
ATOM  598 NE1 TRP A 77   -8.015 38.343 18.391 1.00 64.30    1SG 599
ATOM  599 CE2 TRP A 77   -9.300 38.329 17.890 1.00 64.30    1SG 600
ATOM  600 CE3 TRP A 77  -10.338 38.289 15.720 1.00 64.30    1SG 601
ATOM  601 CZ2 TRP A 77  -10.511 38.329 18.523 1.00 64.30    1SG 602
ATOM  602 CZ3 TRP A 77  -11.558 38.293 16.361 1.00 64.30    1SG 603
ATOM  603 CH2 TRP A 77  -11.642 38.312 17.737 1.00 64.30    1SG 604
ATOM  604 C   TRP A 77   -5.589 37.952 13.085 1.00 64.30    1SG 605
ATOM  605 O   TRP A 77   -5.400 36.817 12.653 1.00 64.30    1SG 606
ATOM  606 N   ASP A 78   -5.613 39.036 12.290 1.00 27.97    1SG 607
ATOM  607 CA  ASP A 78   -5.456 38.895 10.874 1.00 27.97    1SG 608
ATOM  608 CB  ASP A 78   -5.551 40.234 10.120 1.00 27.97    1SG 609
ATOM  609 CG  ASP A 78   -7.008 40.682 10.122 1.00 27.97    1SG 610
ATOM  610 OD1 ASP A 78   -7.870 39.904 10.613 1.00 27.97    1SG 611
ATOM  611 OD2 ASP A 78   -7.282 41.806  9.622 1.00 27.97    1SG 612
ATOM  612 C   ASP A 78   -4.110 38.308 10.584 1.00 27.97    1SG 613
ATOM  613 O   ASP A 78   -3.984 37.448  9.715 1.00 27.97    1SG 614
ATOM  614 N   ALA A 79   -3.065 38.755 11.305 1.00 39.19    1SG 615
ATOM  615 CA  ALA A 79   -1.736 38.286 11.027 1.00 39.19    1SG 616
ATOM  616 CB  ALA A 79   -0.670 38.969 11.901 1.00 39.19    1SG 617
ATOM  617 C   ALA A 79   -1.631 36.811 11.282 1.00 39.19    1SG 618
ATOM  618 O   ALA A 79   -1.084 36.079 10.459 1.00 39.19    1SG 619
ATOM  619 N   LEU A 80   -2.163 36.335 12.423 1.00104.62    1SG 620
ATOM  620 CA  LEU A 80   -2.048 34.952 12.799 1.00104.62    1SG 621
ATOM  621 CB  LEU A 80   -2.563 34.667 14.222 1.00104.62    1SG 622
ATOM  622 CG  LEU A 80   -1.733 35.344 15.333 1.00104.62    1SG 623
ATOM  623 CD1 LEU A 80   -2.226 34.928 16.728 1.00104.62    1SG 624
ATOM  624 CD2 LEU A 80   -0.229 35.101 15.136 1.00104.62    1SG 625
ATOM  625 C   LEU A 80   -2.813 34.089 11.852 1.00104.62    1SG 626
ATOM  626 O   LEU A 80   -2.365 32.999 11.502 1.00104.62    1SG 627
ATOM  627 N   ASP A 81   -3.999 34.546 11.414 1.00 33.44    1SG 628
ATOM  628 CA  ASP A 81   -4.785 33.727 10.540 1.00 33.44    1SG 629
ATOM  629 CB  ASP A 81   -6.125 34.375 10.150 1.00 33.44    1SG 630
ATOM  630 CG  ASP A 81   -7.032 34.371 11.374 1.00 33.44    1SG 631
ATOM  631 OD1 ASP A 81   -7.009 33.365 12.131 1.00 33.44    1SG 632
ATOM  632 OD2 ASP A 81   -7.757 35.382 11.570 1.00 33.44    1SG 633
ATOM  633 C   ASP A 81   -3.995 33.517  9.292 1.00 33.44    1SG 634
ATOM  634 O   ASP A 81   -3.989 32.422  8.730 1.00 33.44    1SG 635
ATOM  635 N   GLU A 82   -3.319 34.579  8.823 1.00 75.37    1SG 636
ATOM  636 CA  GLU A 82   -2.535 34.530  7.625 1.00 75.37    1SG 637
ATOM  637 CB  GLU A 82   -2.025 35.925  7.221 1.00 75.37    1SG 638
ATOM  638 CG  GLU A 82   -3.153 36.899  6.877 1.00 75.37    1SG 639
ATOM  639 CD  GLU A 82   -2.535 38.266  6.634 1.00 75.37    1SG 640
ATOM  640 OE1 GLU A 82   -1.286 38.338  6.494 1.00 75.37    1SG 641
ATOM  641 OE2 GLU A 82   -3.307 39.261  6.588 1.00 75.37    1SG 642
ATOM  642 C   GLU A 82   -1.337 33.647  7.808 1.00 75.37    1SG 643
ATOM  643 O   GLU A 82   -1.002 32.858  6.935 1.00 75.37    1SG 644
ATOM  644 N   ALA A 83   -0.616 33.754  8.933 1.00 45.30    1SG 645
ATOM  645 CA  ALA A 83    0.553 32.928  9.039 1.00 45.30    1SG 646
ATOM  646 CB  ALA A 83    1.375 33.233 10.302 1.00 45.30    1SG 647
ATOM  647 C   ALA A 83    0.144 31.495  9.107 1.00 45.30    1SG 648
ATOM  648 O   ALA A 83    0.676 30.645  8.394 1.00 45.30    1SG 649
ATOM  649 N   ILE A 84   -0.847 31.200  9.964 1.00 92.70    1SG 650
ATOM  650 CA  ILE A 84   -1.304 29.861 10.184 1.00 92.70    1SG 651
ATOM  651 CB  ILE A 84   -2.280 29.763 11.324 1.00 92.70    1SG 652
ATOM  652 CG2 ILE A 84   -3.534 30.571 10.965 1.00 92.70    1SG 653
ATOM  653 CG1 ILE A 84   -2.565 28.294 11.669 1.00 92.70    1SG 654
ATOM  654 CD1 ILE A 84   -3.332 28.114 12.978 1.00 92.70    1SG 655
ATOM  655 C   ILE A 84   -1.965 29.317  8.958 1.00 92.70    1SG 656
ATOM  656 O   ILE A 84   -1.731 28.168  8.592 1.00 92.70    1SG 657
ATOM  657 N   SER A 85   -2.788 30.139  8.277 1.00 93.60    1SG 658
ATOM  658 CA  SER A 85   -3.577 29.637  7.190 1.00 93.60    1SG 659
ATOM  659 CB  SER A 85   -4.473 30.710  6.531 1.00 93.60    1SG 660
ATOM  660 OG  SER A 85   -5.223 30.140  5.467 1.00 93.60    1SG 661
ATOM  661 C   SER A 85   -2.697 28.987  6.158 1.00 93.60    1SG 662
ATOM  662 O   SER A 85   -2.937 27.828  5.826 1.00 93.60    1SG 663
ATOM  663 N   PRO A 86   -1.684 29.608  5.615 1.00172.68    1SG 664
ATOM  664 CA  PRO A 86   -0.880 28.842  4.708 1.00172.68    1SG 665
ATOM  665 CD  PRO A 86   -1.842 30.953  5.091 1.00172.68    1SG 666
ATOM  666 CB  PRO A 86    0.007 29.840  3.980 1.00172.68    1SG 667
ATOM  667 CG  PRO A 86   -0.904 31.072  3.877 1.00172.68    1SG 668
ATOM  668 C   PRO A 86   -0.165 27.698  5.340 1.00172.68    1SG 669
ATOM  669 O   PRO A 86    0.151 26.741  4.635 1.00172.68    1SG 670
ATOM  670 N   ARG A 87    0.126 27.770  6.647 1.00137.68    1SG 671
```

Fig. 6 cont.

```
ATOM  671  CA  ARG A  87    0.789 26.665  7.263 1.00 137.68    1SG 672
ATOM  672  CB  ARG A  87    1.122 26.925  8.740 1.00 137.68    1SG 673
ATOM  673  CG  ARG A  87    2.146 25.942  9.308 1.00 137.68    1SG 674
ATOM  674  CD  ARG A  87    1.727 24.475  9.211 1.00 137.68    1SG 675
ATOM  675  NE  ARG A  87    0.592 24.257 10.150 1.00 137.68    1SG 676
ATOM  676  CZ  ARG A  87    0.851 23.984 11.462 1.00 137.68    1SG 677
ATOM  677  NH1 ARG A  87    2.143 23.962 11.901 1.00 137.68    1SG 678
ATOM  678  NH2 ARG A  87   -0.174 23.734 12.328 1.00 137.68    1SG 679
ATOM  679  C   ARG A  87   -0.167 25.516  7.200 1.00 137.68    1SG 680
ATOM  680  O   ARG A  87    0.210 24.386  6.899 1.00 137.68    1SG 681
ATOM  681  N   ILE A  88   -1.456 25.805  7.466 1.00  60.23    1SG 682
ATOM  682  CA  ILE A  88   -2.486 24.808  7.489 1.00  60.23    1SG 683
ATOM  683  CB  ILE A  88   -3.823 25.373  7.882 1.00  60.23    1SG 684
ATOM  684  CG2 ILE A  88   -4.895 24.295  7.650 1.00  60.23    1SG 685
ATOM  685  CG1 ILE A  88   -3.770 25.902  9.325 1.00  60.23    1SG 686
ATOM  686  CD1 ILE A  88   -4.946 26.803  9.703 1.00  60.23    1SG 687
ATOM  687  C   ILE A  88   -2.620 24.220  6.127 1.00  60.23    1SG 688
ATOM  688  O   ILE A  88   -2.656 22.998  5.992 1.00  60.23    1SG 689
ATOM  689  N   LYS A  89   -2.669 25.054  5.066 1.00 235.05    1SG 690
ATOM  690  CA  LYS A  89   -2.798 24.425  3.786 1.00 235.05    1SG 691
ATOM  691  CB  LYS A  89   -3.135 25.362  2.608 1.00 235.05    1SG 692
ATOM  692  CG  LYS A  89   -2.064 26.395  2.257 1.00 235.05    1SG 693
ATOM  693  CD  LYS A  89   -2.276 27.012  0.875 1.00 235.05    1SG 694
ATOM  694  CE  LYS A  89   -3.395 28.054  0.825 1.00 235.05    1SG 695
ATOM  695  NZ  LYS A  89   -3.548 28.564 -0.556 1.00 235.05    1SG 696
ATOM  696  C   LYS A  89   -1.494 23.759  3.536 1.00 235.05    1SG 697
ATOM  697  O   LYS A  89   -0.479 24.382  3.229 1.00 235.05    1SG 698
ATOM  698  N   SER A  90   -1.516 22.433  3.702 1.00 192.96    1SG 699
ATOM  699  CA  SER A  90   -0.368 21.594  3.621 1.00 192.96    1SG 700
ATOM  700  CB  SER A  90    0.521 21.774  4.869 1.00 192.96    1SG 701
ATOM  701  OG  SER A  90    1.089 23.075  4.858 1.00 192.96    1SG 702
ATOM  702  C   SER A  90   -0.967 20.218  3.528 1.00 192.96    1SG 703
ATOM  703  O   SER A  90   -1.998 20.091  2.868 1.00 192.96    1SG 704
ATOM  704  N   PRO A  91   -0.434 19.163  4.090 1.00 157.21    1SG 705
ATOM  705  CA  PRO A  91   -1.147 17.925  3.948 1.00 157.21    1SG 706
ATOM  706  CD  PRO A  91    1.006 18.921  4.085 1.00 157.21    1SG 707
ATOM  707  CB  PRO A  91   -0.181 16.821  4.372 1.00 157.21    1SG 708
ATOM  708  CG  PRO A  91    1.188 17.397  3.981 1.00 157.21    1SG 709
ATOM  709  C   PRO A  91   -2.460 17.895  4.661 1.00 157.21    1SG 710
ATOM  710  O   PRO A  91   -3.201 16.939  4.445 1.00 157.21    1SG 711
ATOM  711  N   SER A  92   -2.768 18.898  5.513 1.00 156.87    1SG 712
ATOM  712  CA  SER A  92   -3.984 18.847  6.280 1.00 156.87    1SG 713
ATOM  713  CB  SER A  92   -4.271 20.152  7.037 1.00 156.87    1SG 714
ATOM  714  OG  SER A  92   -3.257 20.403  7.998 1.00 156.87    1SG 715
ATOM  715  C   SER A  92   -5.147 18.616  5.368 1.00 156.87    1SG 716
ATOM  716  O   SER A  92   -5.598 17.483  5.219 1.00 156.87    1SG 717
ATOM  717  N   SER A  93   -5.621 19.689  4.710 1.00 207.86    1SG 718
ATOM  718  CA  SER A  93   -6.754 19.712  3.821 1.00 207.86    1SG 719
ATOM  719  CB  SER A  93   -8.024 19.003  4.340 1.00 207.86    1SG 720
ATOM  720  OG  SER A  93   -7.939 17.597  4.178 1.00 207.86    1SG 721
ATOM  721  C   SER A  93   -7.104 21.153  3.773 1.00 207.86    1SG 722
ATOM  722  O   SER A  93   -6.232 22.007  3.921 1.00 207.86    1SG 723
ATOM  723  N   GLU A  94   -8.385 21.477  3.520 1.00  92.95    1SG 724
ATOM  724  CA  GLU A  94   -8.743 22.855  3.671 1.00  92.95    1SG 725
ATOM  725  CB  GLU A  94   -9.723 23.392  2.614 1.00  92.95    1SG 726
ATOM  726  CG  GLU A  94   -9.087 23.573  1.231 1.00  92.95    1SG 727
ATOM  727  CD  GLU A  94  -10.089 24.293  0.340 1.00  92.95    1SG 728
ATOM  728  OE1 GLU A  94  -10.968 25.004  0.899 1.00  92.95    1SG 729
ATOM  729  OE2 GLU A  94   -9.989 24.149 -0.908 1.00  92.95    1SG 730
ATOM  730  C   GLU A  94   -9.395 22.919  5.013 1.00  92.95    1SG 731
ATOM  731  O   GLU A  94  -10.464 22.346  5.221 1.00  92.95    1SG 732
ATOM  732  N   ASP A  95   -8.755 23.617  5.971 1.00 144.37    1SG 733
ATOM  733  CA  ASP A  95   -9.270 23.585  7.307 1.00 144.37    1SG 734
ATOM  734  CB  ASP A  95   -8.237 23.057  8.313 1.00 144.37    1SG 735
ATOM  735  CG  ASP A  95   -7.936 21.604  7.962 1.00 144.37    1SG 736
ATOM  736  OD1 ASP A  95   -8.898 20.839  7.690 1.00 144.37    1SG 737
ATOM  737  OD2 ASP A  95   -6.730 21.243  7.938 1.00 144.37    1SG 738
ATOM  738  C   ASP A  95   -9.641 24.958  7.764 1.00 144.37    1SG 739
ATOM  739  O   ASP A  95   -8.999 25.512  8.655 1.00 144.37    1SG 740
ATOM  740  N   THR A  96  -10.706 25.542  7.184 1.00 112.31    1SG 741
ATOM  741  CA  THR A  96  -11.140 26.822  7.659 1.00 112.31    1SG 742
ATOM  742  CB  THR A  96  -12.238 27.428  6.835 1.00 112.31    1SG 743
ATOM  743  OG1 THR A  96  -13.400 26.616  6.886 1.00 112.31    1SG 744
ATOM  744  CG2 THR A  96  -11.749 27.572  5.384 1.00 112.31    1SG 745
ATOM  745  C   THR A  96  -11.666 26.607  9.041 1.00 112.31    1SG 746
ATOM  746  O   THR A  96  -11.478 27.431  9.935 1.00 112.31    1SG 747
ATOM  747  N   THR A  97  -12.341 25.459  9.241 1.00  93.69    1SG 748
ATOM  748  CA  THR A  97  -12.934 25.123 10.504 1.00  93.69    1SG 749
ATOM  749  CB  THR A  97  -13.610 23.784 10.465 1.00  93.69    1SG 750
ATOM  750  OG1 THR A  97  -12.651 22.757 10.255 1.00  93.69    1SG 751
ATOM  751  CG2 THR A  97  -14.630 23.779  9.313 1.00  93.69    1SG 752
ATOM  752  C   THR A  97  -11.838 25.029 11.517 1.00  93.69    1SG 753
ATOM  753  O   THR A  97  -11.959 25.528 12.634 1.00  93.69    1SG 754
ATOM  754  N   ALA A  98  -10.726 24.378 11.136 1.00  25.45    1SG 755
ATOM  755  CA  ALA A  98   -9.618 24.206 12.027 1.00  25.45    1SG 756
ATOM  756  CB  ALA A  98   -8.478 23.383 11.406 1.00  25.45    1SG 757
ATOM  757  C   ALA A  98   -9.072 25.554 12.370 1.00  25.45    1SG 758
ATOM  758  O   ALA A  98   -8.710 25.814 13.514 1.00  25.45    1SG 759
ATOM  759  N   LEU A  99   -9.013 26.461 11.379 1.00  39.28    1SG 760
ATOM  760  CA  LEU A  99   -8.470 27.767 11.611 1.00  39.28    1SG 761
ATOM  761  CB  LEU A  99   -8.498 28.657 10.354 1.00  39.28    1SG 762
ATOM  762  CG  LEU A  99   -7.921 30.069 10.585 1.00  39.28    1SG 763
ATOM  763  CD1 LEU A  99   -6.429 30.020 10.945 1.00  39.28    1SG 764
ATOM  764  CD2 LEU A  99   -8.223 31.001  9.399 1.00  39.28    1SG 765
ATOM  765  C   LEU A  99   -9.299 28.449 12.648 1.00  39.28    1SG 766
ATOM  766  O   LEU A  99   -8.765 29.124 13.527 1.00  39.28    1SG 767
ATOM  767  N   SER A 100  -10.634 28.295 12.571 1.00  30.12    1SG 768
ATOM  768  CA  SER A 100  -11.494 28.966 13.503 1.00  30.12    1SG 769
ATOM  769  CB  SER A 100  -12.996 28.828 13.177 1.00  30.12    1SG 770
ATOM  770  OG  SER A 100  -13.441 27.499 13.395 1.00  30.12    1SG 771
ATOM  771  C   SER A 100  -11.268 28.432 14.885 1.00  30.12    1SG 772
ATOM  772  O   SER A 100  -11.305 29.192 15.851 1.00  30.12    1SG 773
ATOM  773  N   THR A 101  -11.013 27.117 15.028 1.00  86.81    1SG 774
ATOM  774  CA  THR A 101  -10.850 26.601 16.358 1.00  86.81    1SG 775
ATOM  775  CB  THR A 101  -10.690 25.108 16.438 1.00  86.81    1SG 776
ATOM  776  OG1 THR A 101  -10.854 24.682 17.782 1.00  86.81    1SG 777
ATOM  777  CG2 THR A 101   -9.291 24.712 15.951 1.00  86.81    1SG 778
ATOM  778  C   THR A 101   -9.641 27.237 16.966 1.00  86.81    1SG 779
ATOM  779  O   THR A 101   -9.629 27.547 18.156 1.00  86.81    1SG 780
ATOM  780  N   PHE A 102   -8.583 27.439 16.157 1.00  47.52    1SG 781
ATOM  781  CA  PHE A 102   -7.364 28.041 16.619 1.00  47.52    1SG 782
ATOM  782  CB  PHE A 102   -6.287 28.092 15.523 1.00  47.52    1SG 783
ATOM  783  CG  PHE A 102   -5.112 28.810 16.087 1.00  47.52    1SG 784
ATOM  784  CD1 PHE A 102   -4.251 28.176 16.951 1.00  47.52    1SG 785
ATOM  785  CD2 PHE A 102   -4.865 30.119 15.744 1.00  47.52    1SG 786
ATOM  786  CE1 PHE A 102   -3.164 28.838 17.472 1.00  47.52    1SG 787
ATOM  787  CE2 PHE A 102   -3.780 30.785 16.261 1.00  47.52    1SG 788
ATOM  788  CZ  PHE A 102   -2.927 30.147 17.128 1.00  47.52    1SG 789
ATOM  789  C   PHE A 102   -7.641 29.450 17.050 1.00  47.52    1SG 790
ATOM  790  O   PHE A 102   -7.195 29.878 18.113 1.00  47.52    1SG 791
ATOM  791  N   ARG A 103   -8.413 30.195 16.238 1.00 125.33    1SG 792
ATOM  792  CA  ARG A 103   -8.714 31.574 16.515 1.00 125.33    1SG 793
ATOM  793  CB  ARG A 103   -9.627 32.214 15.458 1.00 125.33    1SG 794
ATOM  794  CG  ARG A 103   -8.951 32.543 14.128 1.00 125.33    1SG 795
ATOM  795  CD  ARG A 103   -9.957 33.058 13.098 1.00 125.33    1SG 796
ATOM  796  NE  ARG A 103  -11.166 33.474 13.867 1.00 125.33    1SG 797
ATOM  797  CZ  ARG A 103  -11.949 34.510 13.445 1.00 125.33    1SG 798
ATOM  798  NH1 ARG A 103  -11.620 35.192 12.310 1.00 125.33    1SG 799
ATOM  799  NH2 ARG A 103  -13.059 34.859 14.161 1.00 125.33    1SG 800
ATOM  800  C   ARG A 103   -9.453 31.665 17.813 1.00 125.33    1SG 801
ATOM  801  O   ARG A 103   -9.249 32.591 18.598 1.00 125.33    1SG 802
ATOM  802  N   GLY A 104  -10.322 30.678 18.071 1.00  33.40    1SG 803
ATOM  803  CA  GLY A 104  -11.175 30.662 19.222 1.00  33.40    1SG 804
ATOM  804  C   GLY A 104  -10.347 30.694 20.464 1.00  33.40    1SG 805
ATOM  805  O   GLY A 104  -10.797 31.209 21.486 1.00  33.40    1SG 806
ATOM  806  N   ILE A 105   -9.123 30.135 20.416 1.00  55.16    1SG 807
ATOM  807  CA  ILE A 105   -8.332 30.039 21.607 1.00  55.16    1SG 808
ATOM  808  CB  ILE A 105   -6.958 29.488 21.358 1.00  55.16    1SG 809
ATOM  809  CG2 ILE A 105   -6.186 29.532 22.689 1.00  55.16    1SG 810
ATOM  810  CG1 ILE A 105   -7.038 28.078 20.748 1.00  55.16    1SG 811
ATOM  811  CD1 ILE A 105   -5.709 27.569 20.192 1.00  55.16    1SG 812
ATOM  812  C   ILE A 105   -8.155 31.410 22.176 1.00  55.16    1SG 813
ATOM  813  O   ILE A 105   -8.320 31.599 23.381 1.00  55.16    1SG 814
ATOM  814  N   PHE A 106   -7.834 32.418 21.343 1.00 143.40    1SG 815
ATOM  815  CA  PHE A 106   -7.661 33.714 21.931 1.00 143.40    1SG 816
ATOM  816  CB  PHE A 106   -6.487 34.484 21.315 1.00 143.40    1SG 817
ATOM  817  CG  PHE A 106   -5.283 33.623 21.458 1.00 143.40    1SG 818
ATOM  818  CD1 PHE A 106   -5.000 32.684 20.493 1.00 143.40    1SG 819
ATOM  819  CD2 PHE A 106   -4.444 33.744 22.543 1.00 143.40    1SG 820
ATOM  820  CE1 PHE A 106   -3.896 31.873 20.597 1.00 143.40    1SG 821
ATOM  821  CE2 PHE A 106   -3.338 32.935 22.654 1.00 143.40    1SG 822
ATOM  822  CZ  PHE A 106   -3.063 32.000 21.683 1.00 143.40    1SG 823
ATOM  823  C   PHE A 106   -8.888 34.524 21.650 1.00 143.40    1SG 824
ATOM  824  O   PHE A 106   -8.804 35.596 21.052 1.00 143.40    1SG 825
ATOM  825  N   GLN A 107  -10.063 34.055 22.106 1.00 113.68    1SG 826
ATOM  826  CA  GLN A 107  -11.249 34.816 21.853 1.00 113.68    1SG 827
ATOM  827  CB  GLN A 107  -12.534 34.094 22.289 1.00 113.68    1SG 828
ATOM  828  CG  GLN A 107  -12.619 33.841 23.793 1.00 113.68    1SG 829
ATOM  829  CD  GLN A 107  -13.935 33.128 24.051 1.00 113.68    1SG 830
ATOM  830  OE1 GLN A 107  -14.679 33.496 24.957 1.00 113.68    1SG 831
ATOM  831  NE2 GLN A 107  -14.237 32.085 23.229 1.00 113.68    1SG 832
ATOM  832  C   GLN A 107  -11.130 36.089 22.618 1.00 113.68    1SG 833
ATOM  833  O   GLN A 107  -11.404 37.169 22.100 1.00 113.68    1SG 834
ATOM  834  N   ASN A 108  -10.709 35.995 23.891 1.00 175.18    1SG 835
ATOM  835  CA  ASN A 108  -10.522 37.198 24.638 1.00 175.18    1SG 836
ATOM  836  CB  ASN A 108  -11.316 37.245 25.953 1.00 175.18    1SG 837
ATOM  837  CG  ASN A 108  -11.123 38.635 26.546 1.00 175.18    1SG 838
ATOM  838  OD1 ASN A 108  -10.889 39.606 25.831 1.00 175.18    1SG 839
ATOM  839  ND2 ASN A 108  -11.215 38.734 27.899 1.00 175.18    1SG 840
ATOM  840  C   ASN A 108   -9.080 37.239 25.011 1.00 175.18    1SG 841
```

Fig. 6 cont.

```
ATOM 841 O   ASN A 108   -8.674 36.645 26.008 1.00 175.18  1SG 842
ATOM 842 N   ARG A 109   -8.256 37.941 24.210 1.00 180.82  1SG 843
ATOM 843 CA  ARG A 109   -6.876 37.995 24.574 1.00 180.82  1SG 844
ATOM 844 CB  ARG A 109   -6.013 36.969 23.819 1.00 180.82  1SG 845
ATOM 845 CG  ARG A 109   -4.535 36.997 24.211 1.00 180.82  1SG 846
ATOM 846 CD  ARG A 109   -4.292 36.518 25.641 1.00 180.82  1SG 847
ATOM 847 NE  ARG A 109   -4.790 35.117 25.737 1.00 180.82  1SG 848
ATOM 848 CZ  ARG A 109   -5.199 34.617 26.939 1.00 180.82  1SG 849
ATOM 849 NH1 ARG A 109   -5.154 35.403 28.055 1.00 180.82  1SG 850
ATOM 850 NH2 ARG A 109   -5.662 33.336 27.025 1.00 180.82  1SG 851
ATOM 851 C   ARG A 109   -6.344 39.351 24.237 1.00 180.82  1SG 852
ATOM 852 O   ARG A 109   -6.430 39.814 23.102 1.00 180.82  1SG 853
ATOM 853 N   PRO A 110   -5.831 40.006 25.238 1.00 157.52  1SG 854
ATOM 854 CA  PRO A 110   -5.179 41.267 25.008 1.00 157.52  1SG 855
ATOM 855 CD  PRO A 110   -6.547 39.991 26.504 1.00 157.52  1SG 856
ATOM 856 CB  PRO A 110   -5.268 42.038 26.322 1.00 157.52  1SG 857
ATOM 857 CG  PRO A 110   -6.497 41.435 27.023 1.00 157.52  1SG 858
ATOM 858 C   PRO A 110   -3.771 40.974 24.607 1.00 157.52  1SG 859
ATOM 859 O   PRO A 110   -3.316 39.855 24.843 1.00 157.52  1SG 860
ATOM 860 N   LEU A 111   -3.061 41.936 23.987 1.00 99.02   1SG 861
ATOM 861 CA  LEU A 111   -1.691 41.668 23.662 1.00 99.02   1SG 862
ATOM 862 CB  LEU A 111   -1.421 41.587 22.150 1.00 99.02   1SG 863
ATOM 863 CG  LEU A 111   -2.192 40.454 21.449 1.00 99.02   1SG 864
ATOM 864 CD1 LEU A 111   -1.758 39.072 21.962 1.00 99.02   1SG 865
ATOM 865 CD2 LEU A 111   -3.709 40.678 21.540 1.00 99.02   1SG 866
ATOM 866 C   LEU A 111   -0.887 42.808 24.184 1.00 99.02   1SG 867
ATOM 867 O   LEU A 111   -1.032 43.938 23.724 1.00 99.02   1SG 868
ATOM 868 N   ASN A 112   -0.001 42.545 25.161 1.00 86.78   1SG 869
ATOM 869 CA  ASN A 112    0.790 43.624 25.667 1.00 86.78   1SG 870
ATOM 870 CB  ASN A 112    0.501 44.010 27.132 1.00 86.78   1SG 871
ATOM 871 CG  ASN A 112    0.808 42.834 28.046 1.00 86.78   1SG 872
ATOM 872 OD1 ASN A 112    0.082 41.842 28.072 1.00 86.78   1SG 873
ATOM 873 ND2 ASN A 112    1.915 42.950 28.828 1.00 86.78   1SG 874
ATOM 874 C   ASN A 112    2.225 43.234 25.553 1.00 86.78   1SG 875
ATOM 875 O   ASN A 112    2.555 42.062 25.376 1.00 86.78   1SG 876
ATOM 876 N   LYS A 113    3.118 44.237 25.637 1.00 78.66   1SG 877
ATOM 877 CA  LYS A 113    4.522 44.008 25.495 1.00 78.66   1SG 878
ATOM 878 CB  LYS A 113    5.352 45.293 25.659 1.00 78.66   1SG 879
ATOM 879 CG  LYS A 113    5.120 45.975 27.010 1.00 78.66   1SG 880
ATOM 880 CD  LYS A 113    6.099 47.109 27.324 1.00 78.66   1SG 881
ATOM 881 CE  LYS A 113    5.811 47.800 28.661 1.00 78.66   1SG 882
ATOM 882 NZ  LYS A 113    6.700 48.970 28.834 1.00 78.66   1SG 883
ATOM 883 C   LYS A 113    4.952 43.063 26.564 1.00 78.66   1SG 884
ATOM 884 O   LYS A 113    4.476 43.120 27.696 1.00 78.66   1SG 885
ATOM 885 N   GLY A 114    5.867 42.143 26.202 1.00 24.99   1SG 886
ATOM 886 CA  GLY A 114    6.391 41.219 27.159 1.00 24.99   1SG 887
ATOM 887 C   GLY A 114    5.509 40.017 27.231 1.00 24.99   1SG 888
ATOM 888 O   GLY A 114    5.715 39.150 28.079 1.00 24.99   1SG 889
ATOM 889 N   SER A 115    4.493 39.918 26.353 1.00 35.09   1SG 890
ATOM 890 CA  SER A 115    3.673 38.746 26.428 1.00 35.09   1SG 891
ATOM 891 CB  SER A 115    2.392 38.815 25.580 1.00 35.09   1SG 892
ATOM 892 OG  SER A 115    1.517 39.809 26.093 1.00 35.09   1SG 893
ATOM 893 C   SER A 115    4.487 37.607 25.914 1.00 35.09   1SG 894
ATOM 894 O   SER A 115    5.310 37.773 25.015 1.00 35.09   1SG 895
ATOM 895 N   VAL A 116    4.286 36.407 26.493 1.00 31.33   1SG 896
ATOM 896 CA  VAL A 116    5.031 35.273 26.036 1.00 31.33   1SG 897
ATOM 897 CB  VAL A 116    5.883 34.635 27.094 1.00 31.33   1SG 898
ATOM 898 CG1 VAL A 116    6.545 33.382 26.493 1.00 31.33   1SG 899
ATOM 899 CG2 VAL A 116    6.883 35.678 27.617 1.00 31.33   1SG 900
ATOM 900 C   VAL A 116    4.055 34.236 25.599 1.00 31.33   1SG 901
ATOM 901 O   VAL A 116    3.005 34.051 26.212 1.00 31.33   1SG 902
ATOM 902 N   ILE A 117    4.383 33.547 24.492 1.00 47.17   1SG 903
ATOM 903 CA  ILE A 117    3.548 32.503 23.985 1.00 47.17   1SG 904
ATOM 904 CB  ILE A 117    2.985 32.835 22.640 1.00 47.17   1SG 905
ATOM 905 CG2 ILE A 117    2.231 31.605 22.104 1.00 47.17   1SG 906
ATOM 906 CG1 ILE A 117    2.123 34.104 22.758 1.00 47.17   1SG 907
ATOM 907 CD1 ILE A 117    1.816 34.784 21.427 1.00 47.17   1SG 908
ATOM 908 C   ILE A 117    4.426 31.310 23.837 1.00 47.17   1SG 909
ATOM 909 O   ILE A 117    5.548 31.412 23.342 1.00 47.17   1SG 910
ATOM 910 N   LEU A 118    3.944 30.137 24.285 1.00 121.79  1SG 911
ATOM 911 CA  LEU A 118    4.769 28.977 24.178 1.00 121.79  1SG 912
ATOM 912 CB  LEU A 118    4.802 28.135 25.465 1.00 121.79  1SG 913
ATOM 913 CG  LEU A 118    5.769 26.943 25.382 1.00 121.79  1SG 914
ATOM 914 CD1 LEU A 118    7.206 27.445 25.187 1.00 121.79  1SG 915
ATOM 915 CD2 LEU A 118    5.628 26.007 26.594 1.00 121.79  1SG 916
ATOM 916 C   LEU A 118    4.181 28.130 23.104 1.00 121.79  1SG 917
ATOM 917 O   LEU A 118    2.985 27.836 23.119 1.00 121.79  1SG 918
ATOM 918 N   LEU A 119    5.008 27.734 22.124 1.00 128.87  1SG 919
ATOM 919 CA  LEU A 119    4.497 26.903 21.079 1.00 128.87  1SG 920
ATOM 920 CB  LEU A 119    4.743 27.482 19.673 1.00 128.87  1SG 921
ATOM 921 CG  LEU A 119    4.070 26.716 18.517 1.00 128.87  1SG 922
ATOM 922 CD1 LEU A 119    4.669 25.315 18.316 1.00 128.87  1SG 923
ATOM 923 CD2 LEU A 119    2.542 26.705 18.679 1.00 128.87  1SG 924
ATOM 924 C   LEU A 119    5.223 25.606 21.193 1.00 128.87  1SG 925
ATOM 925 O   LEU A 119    6.451 25.566 21.278 1.00 128.87  1SG 926
ATOM 926 N   THR A 120    4.464 24.499 21.224 1.00 26.85   1SG 927
ATOM 927 CA  THR A 120    5.083 23.217 21.332 1.00 26.85   1SG 928
ATOM 928 CB  THR A 120    4.604 22.438 22.518 1.00 26.85   1SG 929
ATOM 929 OG1 THR A 120    4.854 23.168 23.710 1.00 26.85   1SG 930
ATOM 930 CG2 THR A 120    5.351 21.094 22.554 1.00 26.85   1SG 931
ATOM 931 C   THR A 120    4.686 22.437 20.086 1.00 26.85   1SG 932
ATOM 932 O   THR A 120    3.654 21.719 20.149 1.00 26.85   1SG 933
ATOM 933 OXT THR A 120    5.406 22.546 19.058 1.00 26.85   1SG 934
END
```

METABOLIC ENGINEERING OF LIPID METABOLISM BY IMPROVING FATTY ACID BINDING AND TRANSPORT

CROSS-REFERENCES TO RELATED APPLICATIONS

This application is a divisional of U.S. patent application Ser. No. 11/879,026, filed Jul. 13, 2007, now pending, which claims priority to and full benefit of U.S. Ser. No. 60/831,046, filed Jul. 13, 2006, METABOLIC ENGINEERING OF LIPID METABOLISM BY IMPROVING FATTY ACID BINDING AND TRANSPORT by Pojer et al., the full disclosure of each is incorporated herein by reference in its entirety.

STATEMENT AS TO RIGHTS TO INVENTIONS MADE UNDER FEDERALLY SPONSORED RESEARCH OR DEVELOPMENT

The application was supported in part by National Science Foundation MCB-0236027. The government may have certain rights in the invention.

FIELD OF THE INVENTION

This invention is in the field of metabolic pathway engineering of lipids in plants and in the field of protein crystallography and design.

BACKGROUND

Currently, the majority of vegetable oil production (estimated at 87 million metric tons with approximate market value of 40 billion U.S. dollars) goes into human consumption, with as much as 25% of human caloric intake in developed countries being derived from plant fatty acids. In addition to their importance in human nutrition, plant fatty acids are also major ingredients of nonfood products such as soaps, detergents, lubricants, biofuels, cosmetics, and paints. With the accelerating costs of petroleum, vegetable oils provide an increasingly cost-effective alternate source for raw materials.

Selecting plants for increased (and decreased) oil production by classical genetic selection methods has been ongoing for at least a century. Indeed, the complexity in determining trait-genotype associations for the seemingly simple trait of oil production has been demonstrated. For example, Laurie et al. (2004) "The Genetic Architecture of Response to Long-Term Artificial Selection for Oil Concentration in the Maize Kernel" Genetics 168:2141-2155 describe an association study that involved selection of the maize kernel for the simple phenotype of altered oil concentration, over a period of more than a century (one of the longest running selection experiments in biology). The association study detected about 50 "quantitative trait loci" (QTL) that contributed to changes in oil concentration over the 100+ year period, together accounting for only about 50% of the observed variance (suggesting that even more than the 50 identified QTL influence the oil concentration phenotype). The individual QTL effect estimates for the identified QTL were small and largely additive. In the oil phenotype experiment described by Laurie et al., the populations changed from a 4.7% oil content at the beginning of the experiment to a 19.3% oil content at the end, among the lines selected for high oil content, and a 1.1% oil content in the lines selected for low oil content.

The biochemical study of de novo fatty acid biosynthesis in plants is, thus, fundamentally important and practically essential for the metabolic engineering of fatty acid biosynthesis in agronomically important crops (see also, Thelen and Ohlrogge (2002) "Metabolic engineering of fatty acid biosynthesis in Plants," *Metabolic Engineering* 4: 12-21; Scowl et al. (1999) "Genetic engineering of plant lipids," *Annu. Rev. Nutr.* 19: 197-216). In plants, the majority of fatty acids are biosynthesized in the plastid. Over the last two decades nearly all aspects of fatty acid metabolism in plants have been uncovered. However, one of the remaining questions that has thus far resisted elucidation is how free fatty acids are transferred from an inner thylakoid membrane to an outer envelope of a plastid, where they are reactivated to acyl-CoAs for utilization in cytosolic glycerolipid synthesis. Without knowledge of how this mechanism works, efforts to increase, flux through fatty acid synthesis pathways by metabolic engineering have been hampered.

The present invention overcomes these previous difficulties, by providing a new family of chalcone-isomerase like genes that encode fatty acid binding proteins that, e.g., assist in transport of fatty acids from the thylakoid membrane to the outer plastid envelope. These and other features of the invention will be apparent upon review of the following.

SUMMARY OF THE INVENTION

The present invention provides the discovery that chalcone isomerase like fatty acid binding proteins are likely fatty acid transporters that facilitate transport of fatty acids from the thylakoid membrane to the outer plastid envelope. This discovery provides a target for engineering lipid metabolism, e.g., in plants. For example, lipid production is likely to be increased by overexpressing chalcone isomerase like fatty acid binding proteins in cells of the plants. In addition, the complete crystal structures of two of these proteins are provided. This crystal structure information makes it possible to engineer the proteins to modulate fatty acid binding and plastid transport, e.g., to increase transport activity.

Accordingly, in a first aspect, the invention provides a recombinant cell that expresses a heterologous chalcone isomerase like fatty acid binding protein gene, which encodes a chalcone isomerase like fatty acid binding protein that binds to a fatty acid in the cell.

A variety of examples of such genes and proteins are provided, including At287 (At1g53520), At279 (At3g63170), At396 (At2g26310) or homologs thereof, e.g., those identified in Example 2. Homologs include chalcone isomerase like fatty acid binding proteins that are at least 25% identical to At287, At279, or At396 and that encodes a conserved Arg amino acid residue in a position corresponding to Arg 103 of At279 or Arg 114 of At287, and that encodes a conserved Tyr residue in a position corresponding to Tyr 116 of At279 or Tyr 126 of At287, which conserved Arg and conserved Tyr residues participate in sequestering a carboxylic acid moiety on the fatty acid when the fatty acid is bound to the protein. Homologs with higher levels of identity are also a feature of the invention, including genes that are at least 60% identical to At287, At279, or At396.

Optionally, the gene is highly expressed, e.g., more highly expressed than a corresponding native chalcone isomerase like fatty acid binding protein gene of the cell. This high level of expression increases lipid content of the recombinant cell as compared to a corresponding cell that does not express the gene. That is, the protein may regulate transport of the fatty acid from an inner thylakoid membrane of the cell to an outer membrane of a plastid of the cell, and over expression of the protein may increase plastid transport.

The cell is optionally a plant cell and can be part of a recombinant plant. Examples of suitable plants that can be made recombinant include plants that are members of a family selected from: Graminae, Leguminosae, Compositae and Rosaciae, or wherein the plant is a member of a genus selected from *Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum. Hyoscyamus, Ipomoea, Lactuca, Lens, Lilium, Linum, Lolium, Lotus, Lycopersicon, Majorana, Mains, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea*, the Olyreae, and the Pharoideae. For example, the plant can be a *Zea mays*, soybean, cotton, *Brassica naupus, Brassica juncea*, tobacco, sunflower, safflower, rapeseed, canola, olive or *Arabidopsis thalina* plant.

The CHI like fatty acid binding protein can bind any of a variety of fatty acids, including oleic acid, Nude acid, myristic acid, palmitic acid and/or steric acid. The fatty acid can be saturated or unsaturated.

In a related aspect, the invention includes a recombinant cell that expresses a heterologous regulator of a chalcone isomerase like fatty acid binding protein gene. Such regulators include transcription factors that regulate expression of the gene, anti-sense nucleic acids that inhibit transcription or translation of an mRNA encoded by the gene, siRNAs that inhibits translation of an mRNA encoded by the gene, and miRNAs that inhibit translation of an mRNA encoded by the gene. The regulator can increase or decrease production of a chalcone isomerase like fatty acid binding protein in the cell, thereby increasing or decreasing lipid content of the cell. All of the above features apply to this embodiment as well, e.g., with respect to cells, plants, fatty acids, etc.

In another related aspect, an expression vector that encodes a chalcone isomerase like fatty acid binding protein is provided. All of the above features apply to this embodiment as well, e.g., the vector can encode the genes noted above, and can include an expression cassette expressible in a plant such as any of those noted above. A cassette of the vector is desirably configured for overexpression of the chalcone isomerase like fatty acid binding protein in a target cell (e.g., in a plant), e.g., to increase lipid production in the cell.

An isolated chalcone isomerase like fatty acid binding protein is also a feature of the invention. The isolated protein can be any of those noted above, e.g., At287, At279, At396 or a homolog thereof. A crystal comprising such protein is also a feature of the invention. The isolated protein or crystal optionally includes a ligand bound to the protein e.g., a fatty acid bound to the protein.

The invention also provides related methods. For example, the invention provides a method of making a recombinant cell. The method includes introducing a recombinant gene into a cell, which recombinant gene encodes a recombinant chalcone isomerase like fatty acid binding protein. Typically, the recombinant gene is expressed in the resulting recombinant cell. Any of the features noted above for the compositions apply to the methods as well, e.g., the genes, cells or plants can include any of those noted above, etc. The recombinant chalcone isomerase like fatty acid binding protein is optionally more highly expressed than a native chalcone isomerase like fatty acid binding protein homolog and expression of the recombinant chalcone isomerase like fatty acid binding protein optionally increases lipid content of the cell. A recombinant plant cell made by the method is also a feature of the invention.

In a related aspect, the invention provides a method of modulating lipid content of a cell. The method includes: expressing a recombinant chalcone isomerase like fatty acid protein gene in the cell, or expressing a heterologous modulator of a chalcone isomerase like fatty acid protein gene in the cell. Expression of the recombinant gene or heterologous modulator modulates lipid content of the cell. Any of the features noted above with respect to the methods or compositions apply equally here. For example, expression of the recombinant chalcone isomerase like fatty acid protein gene optionally increases lipid content of the cell. Expression of the modulator increases or decreases lipid content of the cell, depending on the intended application. A cell made by the method is also a feature of the invention.

The invention also provides for maker assisted selection to select plants for a lipid content phenotype. For example, a method of selecting a plant for lipid content is provided. The methods include identifying a polymorphism in a plant population that correlates with a phenotype encoded by a chalcone isomerase like fatty acid binding protein gene; and, performing marker assisted selection of the population to select a plant in the population for the polymorphism. Any of the various features noted above are applicable here as well. For example, the gene can be the same as or homologous to a gene that encodes At287, At279, or At396. A plant produced by the method is also a feature of the methods.

Similarly, transgenic plants in which the CHI like fatty acid binding protein genes are knocked down or knocked out, as well as upregulated and/or over-expressed are a feature of the invention. Such plants (e.g., *Arabidopsis*, tomato, tobacco, etc.) can be examined throughout their growth cycle for fatty acid and lipid/oil content in various tissues and seeds.

In another aspect, the invention provides a method of modifying a chalcone isomerase like fatty acid binding protein. The method includes accessing an information set derived from a crystal structure of the protein or homolog thereof, and, based on information in the information set, predicting whether making a change to the structure of the protein will increase or decrease binding to a fatty acid binding protein ligand. The protein is modified based upon on the prediction. The information set optionally includes crystal structure information as provided in the figures herein.

A system comprising an information storage module comprising an information set derived from a crystal structure of a chalcone isomerase like fatty acid binding protein is also a feature of the invention. For example, a computer comprising a database of such information is a feature of the invention.

BRIEF DESCRIPTION OF THE FIGURES

FIG. 1 is a clustalw alignment of CHI family members. At279 (At3g63170) and At287 (At1g53520) are shown on lines 5 and 4, respectively. At396 (at2g26310), the closest relative to At279 in the figure, is shown on line 6. The two conserved amino acids for sequestration of carboxylic acid moieties through hydrogen bonding with lauric acid are boxed. The catalytic authentic chalcone isomerase, AtCHI (at3g55120), as well as two close relatives, At233 (At5g6620) and At209 (At5g05270) are shown on lines 1, 2, and 3, respectively.

FIG. 4 is set of crystal structure coordinates for chalcone isomerase.

FIG. 5 is a set of crystal structure coordinates for AT279.

FIG. 6 is a set of crystal structure coordinates for AT287.

DETAILED DESCRIPTION

Figure 2A:
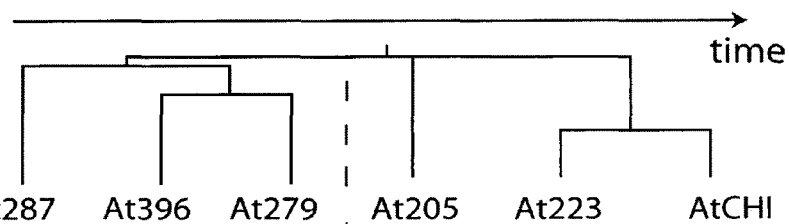
FIG. 2A is a table that includes a drawing of chalcone isomerase like proteins.

The current invention describes a sub-family of chalcone isomerase like genes, the protein products of which bind fatty acids (FA) with high affinity, Binding was established first by the elucidation of the high resolution crystal structure of one protein expressed and purified from *E. coli* (At3g63170) and confirmed by HPLC-MS-MS analyses of extractions of protein samples of At3g63170 and a close relative (At1g53520). The proteins that retain the same three dimensional fold of chalcone isomerase but lack key catalytic residues are widely distributed in plants, various bacteria, fungi and possibly other eukaryotic organisms. Bioinformatic analysis of the two genes in question strongly suggest that the nuclear encoded proteins are localized in the chloroplast, where the majority of plant fatty acid biosynthesis occurs. Moreover, it is likely that these two proteins are directly involved in the transport of free fatty acids from the inner thylakoid membrane to the outer envelope of the plastid where they are reactivated to acyl-CoAs for utilization in cytosolic glycerolipid synthesis.

Metabolic engineering of plant fatty acid biosynthesis (FAS) has progressed rapidly in the past 10 years and has led to the commercialization of several modified oilseed crops. However, it has been difficult to engineer plants with increased flux through the biosynthetic pathways (Thelen and Ohlrogge (2002) "Metabolic engineering of fatty acid biosynthesis in Plants," *Metabolic Engineering* 4: 12-21; Braun et al. (1999) "Genetic engineering of plant lipids," *Annu. Rev. Nutr.* 19: 197-216). Our discovery of a new FA binding protein family and their over-expression in FA bio-engineered plants can modulate/improve plant FA content by allowing natural FA to be transported more efficiently. The search for these transporters has been intense but was previously unresolved (Koo et al. (2004) "On the Export of Fatty Acids from the Chloroplast" *J. Biol. Chem.* 279(16): 16101-16110). Moreover, our knowledge of the detailed binding mode of natural FAs, as well as synthetic FAs, provide the necessary tools for structure-based engineering of modified FA transporters.

We discovered two naturally-occurring FA binding proteins using bioinformatic analysis of available genomic sequencing data from the plant *Arabidopsis thaliana*. These two homologs, referred to as AtCHi279 (At3g63170) and AtCHI1287 (At1g53520) based upon their amino acid length are small proteins located on different chromosomes. Sequence information can be found for At3g63170 and At1g53520, e.g., in the public UniProt database (on the world wide web at pir(dot)uniprot(dot)org), associated with accession numbers Q9M1X2 and Q9C8L2, respectively. Note that the At3g63170 and At1g53520 designations are accession numbers in the publicly available "The *Arabidopsis* Information Resource" (TAIR) database, found on the world wide web at *arabidopsis*(dot)org (which can also be linked to from the relevant accession numbers in UniProt and vice-versa). In plants, these proteins are ubiquitous and often abundantly expressed. The last 200 C-terminal amino acids share homology to our previously solved chalcone isomerase (CHI) crystal structure; however, they lack key residues previously identified in our laboratory that are critically involved in the near diffusion controlled ("Perfect Enzyme") and stereospecific conversion of chalcone into (2S)-naringenin (Jez and Noel (2001) "Reaction mechanism of Chalcone Isomerase" *J. Biol. Chem.* 277(2): 1361-1369.). Within the first 80-90 N-terminal amino acid residues, a plastid signal sequence is found. AtCHI279 was annotated as localized in the plastid stroma by the plastid proteome database, as we would expect.

We solved the x-ray crystal structure of AtCHI279, and have collected high quality x-ray data for AtCHI287. Crystal coordinates are provided in FIGS. 5-6; coordinates for chalcone isomerase are also provided for comparison in FIG. 4; crystal structure coordinates for various chalcone isomerases are available on-line, e.g., through portals to the protein data bank such as RCSB (on the world-wide web at rcsb(dot)org/pdb/home/home(dot)do), the interpro website (on the world wide web at ebi(dot)ac(dot)uk/interpro/) and the EMBL-EBI website (on the world wide web at ebi(dot)ac(dot)uk/). The structure of AtCHI279 recently completed confirms conservation of the unique open-faced β-sandwich fold of CHI but a highly divergent active site cavity as suggested by sequence alignments. As we elucidated the structure, a small molecule, the fatty acid Laurie acid likely derived from *E. coli*, was sequestered in a well-organized binding pocket in AtCHI279 that only partially overlaps with the previously characterized catalytic pocket of CHI. The carboxylic acid group is nicely sequestered by electrostatic interactions with absolutely conserved Arg and Tyr residues while the fatty acyl chain is bound in a new hydrophobic cavity formed in the CHI fold. Further, LC-MS-MS analysis of recombinantly prepared AtCHI1279 and AtCHI287 confirmed that they bind an entire set of linear fatty acids representative of *E. coli*'s fatty acid complement (C12 to C18 saturated, and monounsaturated), Identical analyses of the two most derived Cats clearly possessing authentic CHI activity showed no such fatty acid binding activity.

Together, these observations indicate that this CRT like fatty acid binding protein family can be used to improve the engineering of lipids in plants. Indeed, Homologs of these FA binding proteins are also found outside higher plants, for example in unicellular algae *Chlamydomonas*, as well as in eukaryotic slime mold *Dictyostelium*, suggesting an important role of this family of proteins in lipid metabolism beyond plants.

Definitions

Before describing the present invention in detail, it is to be understood that this invention is not limited to particular devices or biological systems, which can, of course, vary. It is also to be understood that the terminology used herein is for the purpose of describing particular embodiments only, and is not intended to be, limiting. As used in this specification and the appended claims, the singular forms "a", "an" and "the" include plural referents unless the content clearly dictates otherwise. Thus, for example, reference to "a plant" includes a combination of two or more plants; reference to a "cell" optionally includes mixtures/cultures of cells, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology wilt be used in accordance with the definitions set out below.

A Chalcone isomerase like fatty acid binding protein: is a protein that shares detectable homology with a chalcone isomerase or with At287, At279 or At396, wherein the protein binds one or more fatty acid. Typically, the chalcone isomerase like fatty acid binding protein does not comprise chalcone isomerase activity.

Expression vector: as used herein refers to a vector comprising operably linked polynucleotide sequences that facilitate expression of a coding sequence in a particular host organism (e.g., a bacterial expression vector or a plant expression vector). Polynucleotide sequences that facilitate expression in prokaryotes can include, e.g., a promoter, an enhancer, an operator, and a ribosome binding site, often along with other sequences. Eukaryotic cells can use promoters, enhancers, termination and polyadenylation signals and other sequences that are generally different from those used by prokaryotes.

A Genetic element or "gene" refers to a heritable sequence of nucleic acid (typically DNA), i.e., a genomic sequence, with functional significance. Genes typically include an expressible nucleic acid sequence.

A Genotype is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome, A "haplotype" is the genotype of an individual at a plurality of genetic loci. Typically, the genetic loci described by a haplotype are physically and genetically linked, i.e., on the same chromosome segment. The terms "phenotype," or "phenotypic trait" or "trait" refers to one or more trait of an organism. The phenotype can be observable to the naked eye, or by any other means of evaluation known in the art, e.g., microscopy, biochemical analysis, etc. In some cases, a phenotype is directly controlled by a single gene or genetic locus, i.e., a "single gene trait." The CHI like fatty acid binding protein genes herein can comprise single gene traits. In other cases, a phenotype (such as overall lipid production of a cell or plant) is the result of several interacting genes. A "quantitative trait loci" (QTL) is a genetic domain that is polymorphic and affects a phenotype that can be described in quantitative terms, e.g., lipid content, and, therefore, can be assigned a "phenotypic value" which corresponds to a quantitative value for the phenotypic trait. A QTL can act through a single gene mechanism or by a polygenic mechanism.

Germplasm: refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes, e.g. cells, seed or tissues from which new plants may be grown, or plant parts, such as leafs, stems, pollen, or cells, that can be cultured into a whole plant.

A Heterologous component of a cell is a component that is derived from a source other than the cell, or that appears in the cell in a non-natural (artificial) context.

Homologous: Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring CHI like fatty acid binding protein can be modified by any available mutagenesis method to produce a mutant CHI like fatty acid binding protein. Homology is generally inferred from sequence identity or similarity between two or more nucleic acids or proteins (or sequences thereof). The precise percentage of identity or similarity between sequences that is useful in establishing homology varies with the nucleic acid and protein at issue, but as little as 25% sequence similarity between proteins (and less between nucleic acids, due to the degeneracy of the genetic code) is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein and are generally available.

Plant: a plant can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, whether part of the plant, or taken from a plant, or derived through culture from a cell taken from a plant. Thus, the term "plant" includes whole plants, plant cells, plant protoplast, plant or tissue culture from which plants can be regenerated, plant calli, plant clumps and plant cells that are intact in plants or parts of plants, such as seeds, pods, flowers, cotyledons, leaves, stems, buds, roots, root tips and the like.

A Recombinant cell: is a cell that is made by artificial recombinant methods. The cell comprises one or more transgenes, e.g., heterologous CHI like fatty acid binding protein genes, introduced into the cell by artificial recombinant methods.

Transgenic plant: refers to a plant that comprises within its cells a heterologous polynucleotide. In many embodiments, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

A specified nucleic acid is derived from a given nucleic acid when it is constructed using the given nucleic acid's sequence, or when the specified nucleic acid is constructed using the given nucleic acid. For example, a cDNA or EST is derived from an expressed mRNA.

Chalcone Isomerase Like Fatty Acid Binding Proteins and Gene

CHI like fatty acid binding protein genes are expressed, e.g., to increase flux through fatty acid synthesis pathways. For example, elevated expression of CHI like fatty acid binding proteins may lead to increased transport of lipids such as C12 to C18 saturated, or monounsaturated lipids, including oleic acid, lauric acid, myristic acid, palmitic acid, steric acid, etc., from an inner thalakoid membrane to the outer surface of a plant plastid. This increases the rate at which such lipids are reactivated to acyl-CoAs for utilization in cytosolic glycerolipid synthesis.

CHI like fatty acid binding proteins are those fatty acid-binding proteins that share detectable homology to At287, At279, At396 and/or to a chalcone isomerase (including At287, At279 and At396). Nucleic acids are homologous when they derive from a common ancestral nucleic acid, e.g., through natural evolution, or through artificial methods (mutation, gene synthesis, recombination, etc.). Homology between two or more proteins is usually inferred by consideration of sequence similarity of the proteins. Typically, protein sequences with as little as 25% identity, when aligned for maximum correspondence, are easily identified as being homologous. In addition, many amino acid substitutions are "conservative" having little effect on protein function. Thus, sequence alignment algorithms typically account for whether differences in sequence are conservative or non-conservative.

Thus, homology can be inferred by performing a sequence alignment, e.g., using BLASTN (for coding nucleic acids) or BLASTP (for polypeptides), e.g., with the programs set to default parameters. For example, in one embodiment, the protein is at least about 25%, at least about 50%, at least about 75%, at least about 80%, at least about 90% or at least about 95% identical to At287, At279, and/or At396. Available examples of such homolgous proteins include those identified in Example 2.

Homologous CHI like fatty acid binding protein genes encode homologous CHI like fatty acid binding proteins. Because of the degeneracy of the genetic code, the percentage of identity or similarity at which homology can be detected can be substantially lower than for the encoded polypeptides.

Sequence Comparison, Identity, and Homology

"Identity" or "similarity" in the context of two or more nucleic acid or polypeptide sequences, refers to the degree of sequence relatedness of the sequences. Typically, the sequences are aligned for maximum correspondence, and the percent identity or similarity is measured using a commonly available sequence comparison algorithm, e.g., as described below (other algorithms are available to persons of skill and can readily be substituted). Similarity can also be determined simply by visual inspection. Preferably, "identity" or "similarity" exists over a region of the sequences that is at least about 50 residues in length, more preferably over a region of at least about 100 residues, and most preferably the sequences are related over at least about 150 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection see generally, Ausubel et al., infra).

One example of an algorithm that is suitable for determining percent sequence identity and sequence similarity is the BLAST algorithm, which is described, e.g., in Altschul et al., *J. Mol. Biol.* 215:403-410 (1990) and by Gish et al. (1993) "Identification of protein coding regions by database similarity search" *Nature Genetics* 3:266-72. Software for performing BLAST analyses is publicly available through the National Center for Biotechnology Information (www(dot)ncbi(dot)nlm(dot)nih(dot)gov/) and from Washington University (Saint Louis) at www(dot)blast(dot)wustl(dot)edu/. WU-blast 2.0 (latest release date Mar. 22, 2006) provides one convenient implementation of BLAST. A variety of database and search websites such as UniProt and TAIR provide BLAST search tools to search any of a variety of publicly available databases.

In general, this algorithm involves first identifying high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased, Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Details of a (TAIR) blast search of AT287. AT396 and AT287 against the UniProt Plant Proteins database is presented in Example 2

Generation of Expression Vectors, Transgene Cells and Transgenic Plants

The present invention also relates to host cells and organisms which comprise recombinant nucleic acids corresponding to CHI like fatty acid binding proteins. Additionally, the invention provides for the production of recombinant polypeptides that provide improved flux through one or more fatty acid biosynthesis pathways.

General texts which describe molecular biological techniques for the cloning and manipulation of nucleic acids and production of encoded polypeptides include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through the current date) ("Ausubel")). These texts describe mutagenesis, the use of expression vectors, promoters and many other relevant topics related to, e.g., the generation of clones that comprise nucleic acids of interest, e.g., CHI like fatty acid binding proteins and coding genes.

Host cells (plants, mammals, bacteria or others) are genetically engineered (e.g., transduced, transfected, transformed, etc.) with the vectors of this invention (e.g., vectors, such as expression vectors which comprise an ORF derived from or related to a CHI like fatty acid binding protein) which can be, for example, a cloning vector, a shuttle vector or an expression vector. Such vectors are, for example, in the form of a plasmid, a phagemid, an *agrobacterium*, a virus, a naked polynucleotide (linear or circular), or a conjugated polynucleotide. Vectors to be expressed in eukaryotes can first be introduced into bacteria, especially for the purpose of propagation, expansion and CHI like fatty acid binding protein production (e.g., for making crystals, etc.). The vectors are also optionally introduced into plant tissues, cultured plant cells or plant protoplasts by a variety of standard methods known in the art, including but not limited to electroporation (From et al. (1985) *Proc. Natl. Acad. Sci. USA* 82; 5824), infection by viral vectors such as cauliflower mosaic virus (CaMV) (Hohn et al. (1982) *Molecular Biology of Plant Tumors* (Academic Press, New York, pp. 549-560; Howell U.S. Pat. No. 4,407,956), high velocity ballistic penetration by small particles with the nucleic acid either within the matrix of small beads or particles, or on the surface (Klein et al., (1987) *Nature* 327:70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233:496; Fraley et al. (1983) *Proc. Natl. Acad. Sci. USA* 80:4803). Additional details regarding nucleic acid introduction methods are found in Sambrook, Berger and Ausubel, infra. The method of introducing a nucleic acid of the present invention into a host cell is not critical to the instant invention, and it is not intended that the invention be limited to any particular method for introducing exogenous genetic material into a host cell. Thus, any suitable method, e.g., including but not limited to the methods provided herein, which provides for effective introduction of a nucleic acid into a cell or protoplast can be employed and finds use with the invention.

The engineered host cells can be cultured in conventional nutrient media modified as appropriate for such activities as, for example, activating promoters or selecting transformants. These cells can optionally be cultured into transgenic plants. In addition to Sambrook, Berger and Ausubel, all infra. Plant regeneration from cultured protoplasts is described in Evans et al. (1983) "Protoplast Isolation and Culture," *Handbook of Plant Cell Cultures* 1, 124-176 (MacMillan Publishing Co., New York; Davey (1983) "Recent Developments in the Culture and Regeneration of Plant Protoplasts," *Protoplasts*, pp. 12-29, (Birkhauser, Basel); Dale (1983) "Protoplast Culture and Plant Regeneration of Cereals and Other Recalcitrant Crops," *Protoplasts* pp. 31-41, (Birkhauser, Basel); Binding (1985) "Regeneration of Plants," *Plant Protoplasts*, pp. 21-73, (CRC Press, Boca Raton, Fla.). Additional details regarding plant cell culture and regeneration include Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture Fundamental Methods* Springer Lab Manual, Springer-Verlag (Berlin Heidelberg New York) and *Plant Molecular Biology* (1993) R.R.D. Croy, Ed. Bios Scientific Publishers, Oxford, U.K. ISBN 0 12 198370 6. Cell culture media in general are also set forth in Atlas and Parks (eds) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc (St Louis, Mo.) ("Sigma-LSRCCC") and, e.g., *the Plant Culture Catalogue* and supplement (e.g., 1997 or later) also from Sigma-Aldrich, Inc (St Louis, Mo.) ("Sigma-PCCS").

The present invention also relates to the production of transgenic organisms, which may be bacteria, yeast, fungi, animals (e.g., mammals) or plants, transduced with the nucleic acids of the invention (e.g., nucleic acids comprising the CHI like fatty acid binding proteins or genes as noted herein). A thorough discussion of techniques relevant to bacteria, unicellular eukaryotes and cell culture is found in references enumerated herein and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith (1979) *Gene* 8:81; Roberts et al. (1987) *Nature* 328:731; Schneider et al. (1995) *Protein Expr. Purif.* 6435: 10; Ausubel, Sambrook, Berger (all infra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA*, Second Edition, Scientific American Books, N.Y. In addition, essentially any nucleic acid (and virtually any labeled nucleic acid, whether standard or nonstandard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.) Operon Technologies Inc. (Alameda, Calif.) and many others.

Additional Details for Introducing Nucleic Acids into Plants.

Embodiments of the present invention include the production of transgenic plants comprising cloned nucleic acids, e.g., CHI like fatty acid binding protein genes, Techniques for transforming plant cells with nucleic acids are widely available and can be readily adapted to the invention. Useful general references for plant cell cloning, culture and regeneration include Jones (ed) (1995) *Plant Gene Transfer and Expression Protocols—Methods in Molecular Biology, Volume* 49 Humana Press Towata N.J.; Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). Additional details regarding plant cell culture are found in Croy, (ed.) (1993) *Plant Molecular Biology*, Bios Scientific Publishers, Oxford, U.K.

The nucleic acid constructs of the invention, e.g., plasmids, cosmids, artificial chromosomes, which can include DNA or RNA, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acid acids of the present invention can be introduced into plants according to any of a variety of techniques known in the art. In addition to transformation of cells followed by regeneration, techniques for transforming a wide variety of higher plant species are also well known and described in widely available technical, scientific, and patent literature. See, for example, Weising et al. (1988) *Ann. Rev. Genet.* 22:421-477.

The constructs of the invention, e.g., CHI like fatty acid binding protein genes, which can be provided as components of, e.g., plasmids, phagemids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of a plant or plant cell using available techniques, such as electroporation and microinjection of plant cell protoplasts, or the DNA constructs can be introduced directly to plant cells using ballistic methods, such as DNA particle bombardment.

Microinjection techniques for injecting plant, e.g., cells, embryos, callus and protoplasts, are known in the art and well described in the scientific and patent literature. For example, a number of methods are described in Jones (ed) (1995) *Plant Gene Transfer and Expression Protocols—Methods in Molecular Biology, Volume* 49 Humana Press, Towata, N.J., as well as in the other references noted herein and available in the literature.

For example, the introduction of DNA constructs using polyethylene glycol precipitation is described in Paszkowski, et al., *EMBO J.* 3:2717 (1984). Electroporation techniques are described in Fromm, et al., *Proc. Natl. Acad. Sci. USA* 82:5824 (1985), Ballistic transformation techniques are described in Klein, et al. *Nature* 327:70-73 (1987). Additional details are found in Jones (1995) and Gamborg and Phillips (1995), supra, and in U.S. Pat. No. 5,990,387.

Alternatively, and in some cases preferably, *Agrobacterium* mediated transformation is employed to generate transgenic plants. *Agrobacterium*-mediated transformation techniques, including disarming and use of binary vectors, are also well described in the scientific literature. See, for example, Horsch, et al. (1984) *Science* 233:496; and Fraley et al. (1984) *Proc. Nat'l. Acad. Sci. USA* 80:4803 and recently reviewed in Hansen and Chilton (1998) *Current Topics in Microbiology* 240:22 and Das (1998) *Subcellular Biochemistry* 29: *Plant Microbe Interactions*, pp 343-363.

DNA constructs are optionally combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transform Illation include (1) *Agrobacterium rhizogenes*-mediated transformation (see, e.g., Lichtenstein and Fuller (1987) In: *Genetic Engineering*, vol. 6, PWJ Rigby, Ed., London, Academic Press; and Lichtenstein; C. P., and Draper (1985) In: *DNA Cloning*, Vol. II, a M. Glover, Ed., Oxford, Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) *Plant Cell Physiol.* 25:1353), (3) the vortexing method (see, e.g., Kindle (1990) *Proc. Natl. Acad. Sci.*, (*USA*) 87:1228.

DNA can also be introduced into plants by direct DNA transfer into pollen as described by Zhou et al. (1983) *Methods in Enzymology*, 101:433; D. Hess (1987) *Intern Rev. Cytol.* 107:367; Luo et al. (1988) *Plant Mol. Biol. Reporter* 6:165. Expression of polypeptide coding genes can be obtained by injection of the DNA into reproductive organs of a plant as described by Pena et al. (1987) *Nature* 325:274. DNA can also be injected directly into the cells of immature embryos and the desiccated embryos rehydrated as described by Neuhaus et al. (1987) *Theor. Appl. Genet.* 75:30; and Benbrook et al. (1986) in *Proceedings Bio Expo* Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Generation/Regeneration of Transgenic Plants

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Evans et al. (1983) *Protoplasts Isolation and Culture, Handbook of Plant Cell Culture* pp. 124-176, Macmillian Publishing Company, New York; and Binding (1985) *Regeneration of Plants, Plant Protoplasts* pp. 21-73, CRC Press, Boca Raton. Regeneration can also be obtained from plant callus, explants, somatic embryos (Dandekar et al. (1989) *J. Tissue Cult. Meth.* 12:145; McGranahan, et al. (1990) *Plant Cell Rep.* 8:512) organs, or parts thereof. Such regeneration techniques are described generally in Klee et al. (1987)., *Ann. Rev. of Plant Phys.* 38:467-486. Additional details are found in Payne (1992) and Jones (1995), both supra, and Weissbach and Weissbach, eds. (1988) *Methods for Plant Molecular Biology* Academic Press, Inc., San Diego, Calif. This regeneration and growth process includes the steps of selection of transformant cells and shoots, rooting the transformant shoots and growth of the plantlets in soil. These methods are adapted to the invention to produce transgenic plants bearing CHI like fatty acid binding protein genes.

In addition, the regeneration of plants containing the polynucleotide of the present invention and introduced by *Agrobacterium* into cells of leaf explants can be achieved as described by Horsch et al. (1985) *Science* 227:1229-1231. In this procedure, transformants are grown in the presence of a selection agent and in a medium that induces the regeneration of shoots in the plant species being transformed as described by Fraley et al. (1983) *Proc. Natl. Acad. Sci. (U.S.A.)* 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

It is not intended that plant transformation and expression of polypeptides that provide improved flux through a fatty acid pathway, as provided by the present invention, be limited to any particular plant species. Indeed, it is contemplated that CHI like fatty acid binding proteins can provide for lipid metabolism engineering when transformed and expressed in any agronomically and horticulturally important species. Such species include dicots, e.g., of the families: Leguminosae (including pea, beans, lentil, peanut, yam bean, cowpeas, velvet beans, soybean, clover, alfalfa, lupine, vetch, lotus, sweet clover, wisteria, and sweetpea); and, Compositae (the largest family of vascular plants, including at least 1,000 genera, including important commercial crops such as sunflower), as well as monocots, such as from the family Graminae. Plants of the Rosaciae are also preferred targets.

Additionally, preferred targets for modification with the nucleic acids of the invention, as well as those specified above, include plants from the genera: *Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datum, Daucus, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea*, the Olyreae, and the Pharoideae, and many others.

Common crop plants which are targets of the present invention include: *Arabidopsis thalina, Brassica naupus, Brassica juncea, Zea mays*, soybean, sunflower, safflower, rapeseed, tobacco, canola, peas, beans, lentils, peanuts, yam beans, cowpeas, velvet beans, clover, alfalfa, lupine, vetch, sweet clover, sweetpea, field pea, Cava bean, broccoli, Brussels sprouts, cabbage, cauliflower, kale, kohlrabi, celery, lettuce, carrot, onion, olive, pepper, potato, eggplant and tomato.

Additional Details Regarding Expression Cassettes

In construction of a recombinant expression cassette of the invention, a plant promoter fragment is optionally employed which directs expression of a nucleic acid in any or all tissues of a regenerated plant. Indeed, in one application, CM like fatty acid binding protein genes are desirably constitutively expressed, thereby increasing flux through one or more fatty acid synthesis pathways. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of the polynucleotide of the invention in a specific tissue (tissue-specific promoters), such as a fruit, seed or other site where oils are typically produced and/or sequestered, or may be otherwise under more precise environmental control (inducible promoters). Examples of tissue-specific promoters under developmental control include promoters that initiate transcription only in certain tissues, such as fruit, seeds or flowers.

Any of a number of promoters which direct transcription in plant cells can be suitable. The promoter can be either constitutive or inducible. In addition to the promoters noted above, promoters of bacterial origin that operate in plants include the octopine synthase promoter, the nopaline synthase promoter and other promoters derived from native Ti plasmids. See, Herrara-Estrella et al., (1983). *Nature*, 303: 209. Viral promoters include the 35S and 19S RNA promoters of cauliflower mosaic virus. See, Odell et al. (1985) *Nature* 313:810. Other plant promoters include Kunitz trypsin inhibitor promoter (KTI), SCP1, SUP, UCD3, the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J.* 7:3315. Many other promoters are in current use and can be coupled to an exogenous DNA sequence to direct expression of the nucleic acid.

If expression of a polypeptide from a CHI like fatty acid binding protein gene is desired, a polyadenylation region at the 3'-end of the coding region can be included in the recombinant construct. The polyadenylation region can be derived from the natural gene, from a variety of other plant genes, or from, e.g., T-DNA.

The expression vector comprising cassette sequences (e.g., promoters or coding regions) and genes encoding expression products and transgenes of the invention will typically also include a marker that confers an easily selectable, or alternatively, a screenable, phenotype on plant cells. For example, the marker can encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos or Basta). See, e.g., Padgette et al. (1996) In: *Herbicide-Resistant Crops* (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See, Vasil (1996) In: *Herbicide-Resistant Crops* (Duke, ed.), pp 85-91, CRC Lewis Publishers, Boca Raton) ("Vasil", 1996).

One of skill will recognize that after a recombinant expression cassette from such a vector is stably incorporated in a transgenic plant and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected CHI like fatty acid binding protein producing phenotype. Parts obtained from the regenerated plant, such as flowers, seeds, leaves, branches, fruit, and the like are included in the invention. Progeny and variants, and mutants of the regenerated plants are also included within the scope of the invention, provided that these parts comprise the introduced CHI like fatty acid binding protein genes.

Transgenic or introgressed plants expressing a polynucleotide of the present invention can be screened for transmission of the nucleic acid of the present invention by, for example, standard nucleic acid detection methods (marker assisted selection) or by immunoblot protocols. Expression at the RNA level can be monitored to identify and quantify expression-positive plants. Standard techniques for RNA analysis can be employed and include RT-PCR amplification assays using oligonucleotide primers designed to amplify only heterologous or introgressed RNA templates and solution hybridization assays using marker or linked QTL specific probes. Plants can also be analyzed for protein expression, e.g., by Western immunoblot analysis using antibodies that recognize the encoded CHI like fatty acid binding protein. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment of the invention is a transgenic plant that is homozygous for the added heterologous CHI like fatty acid binding protein nucleic acid; e.g., a transgenic plant that contains two added nucleic acid sequence copies of the CHI like fatty acid binding protein genes, e.g., such a gene at the same locus on each chromosome of a homologous chromosome pair. A homozygous transgenic plant can be obtained by sexually mating (self-fertilizing) a heterozygous transgenic plant that contains a single added heterologous nucleic acid, germinating some of the seed produced and analyzing the resulting plants produced for altered expression of a polynucleotide of the present invention relative to a control plant (e.g., a native, non-transgenic plant). Back-crossing to a parental plant and out-crossing with a non-transgenic plant can be used to introgress the heterologous nucleic acid into a selected background (e.g., an elite or exotic plant line).

Additional Details Regarding Transgenic Animals

In addition to making transgenic plants, transgenic livestock or domesticated animals can be made recombinant for a given polypeptide, or a modified form thereof, thereby changing the fat content or feeding behavior of the transgenic animal, e.g., to enhance yield of a domesticated or livestock animal. Xenopus and insect cells are also useful targets for modification, due to the ease with which such cells can be grown, studied and manipulated.

A transgenic animal is typically an animal that has had DNA introduced into one or more of its cells artificially. This is most commonly done in one of two ways. First, DNA can be integrated randomly by injecting it into the pronucleus of a fertilized ovum. In this case, the DNA can integrate anywhere in the genome. In this approach, there is no need for homology between the injected DNA and the host genome. Second, targeted insertion can be accomplished by introducing heterologous DNA into embryonic stem (ES) cells and selecting for cells in which the heterologous DNA has undergone homologous recombination with homologous sequences of the cellular genome. Typically, there are several kilobases of homology between the heterologous and genomic DNA, and positive selectable markers (e.g., antibiotic resistance genes) are included in the heterologous DNA to provide for selection of transformants. In addition, negative selectable markers (e.g., "toxic" genes such as barnase) can be used to select against cells that have incorporated DNA by non-homologous recombination (i.e., random insertion).

One common use of targeted insertion of DNA is to make knock-out or transgenic mice. Typically, homologous recombination is used to insert a selectable gene driven by a constitutive promoter into an essential exon of the gene that one wishes to disrupt (e.g., the first coding exon). To accomplish this, the selectable marker is flanked by large stretches of DNA that match the genomic sequences surrounding the desired insertion point. Once this construct is electroporated into ES cells, the cells' own machinery performs the homologous recombination. To make it possible to select against ES cells that incorporate DNA by non-homologous recombination, it is common for targeting constructs to include a negatively selectable gene outside the region intended to undergo recombination (typically the gene is cloned adjacent to the shorter of the two regions of genomic homology). Because DNA lying outside the regions of genomic homology is lost during homologous recombination, cells undergoing homologous recombination cannot be selected against, whereas cells undergoing random integration of DNA often can. A commonly used gene for negative selection is the herpes virus thymidine kinase gene, which confers sensitivity to the drug gancyclovir.

Following positive selection and negative selection if desired, ES cell clones are screened for incorporation of the construct into the correct genomic locus. Typically, one designs a targeting construct so that a band normally seen on a Southern blot or following PCR amplification becomes replaced by a band of a predicted size when homologous recombination occurs. Since ES cells are diploid, only one allele is usually altered by the recombination event so, when appropriate targeting has occurred, one usually sees bands representing both wild type and targeted alleles.

The embryonic stem (ES) cells that are used for targeted insertion are derived from the inner cell masses of blastocysts (early mouse embryos). These cells are pluripotent, meaning they can develop into any type of tissue.

Once positive ES clones have been grown up and frozen, the production of transgenic animals can begin. Donor females are mated, blastocysts are harvested, and several ES cells are injected into each blastocyst. Blastocysts are then implanted into a uterine horn of each recipient. By choosing an appropriate donor strain, the detection of chimeric offspring (i.e., those in which some fraction of tissue is derived from the transgenic ES cells) can be as simple as observing hair and/or eye color. If the transgenic ES cells do not contribute to the germline (sperm or eggs), the transgene cannot be passed on to offspring.

Isolating CHI Like Proteins from Natural or Recombinant Sources

Purification of CHI like fatty acid binding proteins can be accomplished using known techniques. Generally, cells expressing the proteins (naturally or by recombinant methods) are lysed, crude purification occurs to remove debris and some contaminating proteins, followed by chromatography to further purify the protein to the desired level of purity. Cells can be lysed by known techniques such as homogenization, sonication, detergent lysis and freeze-thaw techniques. Crude purification can occur using ammonium sulfate precipitation, centrifugation or other known techniques. Suitable chromatography includes anion exchange, cation exchange, high performance liquid chromatography (HPLC), gel filtration, affinity chromatography, hydrophobic interaction chromatography, etc. Well known techniques for refolding proteins can be used to obtain the active conformation of the protein when the protein is denatured during recombinant or natural synthesis, isolation or purification.

In general, CHI like fatty acid binding proteins can be purified, either partially (e.g., achieving a 5×, 10×, 100×, 500×, or 1000× or greater purification), or even substantially to homogeneity (e.g., where the protein is the main component of a solution, typically excluding the solvent (e.g., water, crystallization buffer, DMSO, or the like) and buffer components (e.g., salts and stabilizers) that the polypeptide is suspended in, e.g., if the polypeptide is in a liquid phase), according to standard procedures known to and used by those of skill in the art. Accordingly, polypeptides of the invention can be recovered and purified by any of a number of methods well known in the art, including, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against CM like fatty acid binding proteins are used as purification reagents, e.g., for affinity-based purification. Once purified, partially or to homogeneity, as desired, the polypeptides are optionally used e.g., as assay components, reagents, crystallization materials, or, e.g., as immunogens for antibody production.

In addition to other references noted herein, a variety of purification/protein purification methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods*, 2nd Edition Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein.

Those of skill in the art will recognize, that, after synthesis, expression and/or purification, proteins can possess a conformation different from the desired conformations of the relevant polypeptides. For example, polypeptides produced by prokaryotic systems often are optimized by exposure to chaotropic agents to achieve proper folding. During purification from, e.g., lysates derived from *E. coli*, the expressed protein is optionally denatured and then renatured. This is accomplished, e.g., by solubilizing the proteins in a chaotropic agent such as guanidine HCl. In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) J. Biol. Chem., 268: 14065-14070; Kreitman and Pastan (1993) Bioconjug. Chem., 4: 581-585; and Buchner, et al., (1992) Anal. Biochem., 205: 263-270). Debinski, et al., for example, describe the denaturation and reduction of inclusion body proteins in guanidine-DTE. The proteins can be refolded in a redox buffer containing, e.g., oxidized glutathione and L-arginine. Refolding reagents can be flowed or otherwise moved into contact with the one or more polypeptide or other expression product, or vice-versa.

CHI like fatty acid binding protein nucleic acids optionally comprise a coding sequence fused in-frame to a marker sequence which, e.g., facilitates purification of the encoded polypeptide. Such purification facilitating domains include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I., et al. (1984) *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide tinker sequence between the purification domain and the sequence of the invention is useful to facilitate purification.

Specific example methods of purifying CHI like fatty acid binding proteins are described in the Examples sections below.

Generating and Using Crystals and Crystal Structure Information for Modifying Chi Like Fatty Acid Binding Proteins The three-dimensional structures of proteins can be determined by x-ray crystallography. Typically, to determine the crystal structure of a protein, one or more crystals of the protein are obtained, diffraction data is collected from the crystals, and phases for the data are determined and used to calculate electronic density maps in which a model of the protein is built. Additional rounds of model building and refinement can then be carried out to produce a reasonable model of the protein's structure.

Making Chalcone Isomerase Like Protein Crystals

Proteins are typically purified prior to crystallization, e.g., as described above. Conditions for crystallizing proteins to obtain diffraction-quality crystals can be determined empirically using techniques known in the art. For example, crystallization conditions can be determined and optimized by screening a number of potential conditions, using vapor diffusion (e.g., hanging or sitting drop), microbatch, microdialysis, or similar techniques. Type and amount of precipitant (e.g., salt, polymer, and/or organic solvent), type and amount of additive, pH, temperature, etc. can be varied to identify conditions under which high quality crystals form.

See, e.g., McPherson (1999) *Crystallization of Biological Macromolecules* Cold Spring Harbor Laboratory, Bergfors (1999) *Protein Crystallization* International University Line, Mullin (1993) *Crystallization* Butterwoth-Heinemann, Baldock et al. (1996) "A comparison of microbatch and vapor diffusion for initial screening of crystallization conditions" J. Crystal Growth 168:170-174, Chayen (1998) "Comparative studies of protein crystallization by vapor diffusion and microbatch" Acta Cryst. D54:8-15, Chayen (1999) "Crystallization with oils: a new dimension in macromolecular crystal growth" J. Crystal Growth 196:434-44.1, Page et al. (2003) "Shotgun crystallization strategy for structural genomics: an optimized two-tiered crystallization screen against the *Thermotoga maritima proteome*" Acta Crystallogr. D Biol. Crystallogr. 59:1028, Kimber et al. (2003) "Data mining crystallization databases: knowledge-based approaches to optimize protein crystal screens" Proteins 51:562, and Newman et al. (2005) "Towards rationalization of crystallization screening for small- to medium-sized academic laboratories: the PACT/JCG+ strategy" Acta. Cryst. D61:1426.

Sparse matrix screening is described, e.g., in Jancarik and Kim (1991) "Sparse matrix sampling: a screening method for crystallization of proteins" J. Appl. Cryst. 24:409-411. Preformatted reagents for crystallization screening are commercially available, e.g., from Qiagen (www(dot)qiagen(dot) com) and Hampton Research www(dot)hamptonresearch (dot)com). Screening is optionally automated, for example, using a robotic reagent dispensing platform. Specific examples of crystallization conditions for two chalcone isomerase like proteins are described in the Examples sections below.

Crystal Structure Determination

Techniques for crystal structure determination are well known. See, for example, Stout and Jensen (1989) *X-ray structure determination: a practical Guide* 2nd Edition Wiley Publishers, New York; Ladd and Palmer (1993) *Structure determination by X-ray crystallography*, 3rd Edition Plenum Press, New York; Blundell and Johnson (1976) *Protein Crystallography* Academic Press, New York; Glusker and Trueblood (1985) *Crystal structure analysis: A primer*, 2nd Ed. Oxford University Press, New York; *International Tables for Crystallography, Vol. F. Crystallography of Biological Macromolecules*; McPherson (2002) *Introduction to Macromolecular Crystallography* Wiley-Liss; McRee and David (1999) *Practical Protein Crystallography, Second Edition* Academic Press; Drenth (1999) *Principles of Protein X-Ray Crystallography* (Springer Advanced Texts in Chemistry) Springer-Verlag; Fanchon and Hendrickson (1991) *Crystallographic Computing, Volume 5* IUCr/Oxford University Press; and Murthy (1996) *Crystallographic Methods and Protocols* Humana Press.

In brief, once diffraction-quality crystals of the protein have been obtained, diffraction data is collected at one or more wavelengths. The wavelength at which the diffraction data is collected can be essentially any convenient wavelength. For example, data can be conveniently collected using an in-house generator with a copper anode at the CuKα wavelength of 1.5418 Å. Alternatively or in addition, data can be collected at any of a variety of wavelengths at a synchrotron or other tunable source. For example, data is optionally collected at a wavelength selected to maximize anomalous signal from the particular heavy atom incorporated in the protein, minimize radiation damage to the protein crystal, and/or the like.

The diffraction data is then processed and used to model the protein's structure. When the structure of a related protein is already known, the structure can be solved by molecular replacement. As another example, the protein can be derivatized with one or more heavy atoms to permit phase determination and structure solution, for example, by multiple isomorphous replacement (MIR), single isomorphous replacement (SIR), multiple isomorphous replacement with anomalous signal (MIRAS), single isomorphous replacement with anomalous signal (SIRAS), multi wavelength anomalous dispersion (MAD), or single wavelength anomalous dispersion (SAD) methods.

For example, in SAD phasing the structure of the protein is determined by a process that comprises collecting diffraction data from the heavy atom-containing protein crystal at a single wavelength and measuring anomalous differences between Friedel mates, which result from the presence of the heavy atom in the crystal. In brief, collection of diffraction data involves measuring the intensities of a large number of reflections produced by exposure of one or more protein crystals to a beam of x-rays. Each reflection is identified by indices h, k, and l. Typically, the intensities of Friedel mates (pairs of reflections with indices h, k, l and −h, −k, −l) are the same. However, when a heavy atom is present in the protein crystal and the wavelength of the x-rays used is near an absorption edge for that heavy atom, anomalous scattering by the heavy atom results in differences between the intensities of certain Friedel mates. These anomalous differences can be used to calculate phases that, in combination with the measured intensities, permit calculation of an electron density map into which a model of the protein structure can be built.

As another example, MAD phasing can be used. Here the structure of the protein is determined by a process that comprises collecting diffraction data from the heavy atom-containing protein crystal at two or more wavelengths and measuring dispersive differences between data collected at different wavelengths. For example, data is optionally collected at two wavelengths, e.g., at the point of inflection of the absorption curve of the heavy atom and at a remote wavelength away from the absorption edge, e.g., utilizing a synchrotron as the radiation source.

Suitable heavy atom derivatives for SIR, MIR, SAD, MAD, or similar techniques can be obtained when necessary by methods well known in the art. For example, crystals of the native protein can be soaked in solutions containing the desired heavy atom(s). As another example, heavy atom containing amino acids such as selenomethionine, selenocysteine, or telluromethionine can be incorporated into the protein before the protein is purified and crystallized. See, e.g., Dauter et al. (2000) "Novel approach to phasing proteins: derivatization by short cryo-soaking with halides" Acta Crystallogr D 56(Pt 2):232-237, Nagem et al., (2001) "Protein crystal structure solution by fast incorporation of negatively and positively charged anomalous scatterers" Acta Crystallogr D 57:996-1002), Boles et al. (1994) "Bio-incorporation of telluromethionine into buried residues of dihydrofolate reductase" Nat Struct Biol 1:283-284, Budisa et al. (1997) "Bioincorporation of telluromethionine into proteins: a promising new approach for X-ray structure analysis of proteins" Mol Biol 270:616-623, and Strub et al. (2003) "Selenomethionine and selenocysteine double labeling strategy for crystallographic phasing" Structure 11:1359-67.

A variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" Methods in Enzymology 276:307-326), the CCP4 package (Collaborative Computational Project (1994) "The CCP4 suite: programs for protein crystallography" Acta Crystallogr D 50:760-763), SOLVE and RESOLVE (Terwilliger and Berendzen (1999) Acta Crystallogr D 55 (Pt 4):849-861), SHELXS and SHELXD (Schneider and Sheldrick (2002) "Substructure solution with SHELXD" Acta Crystallogr D Biol Crystallogr 58:1772-1779), Refmac5 (Murshudov et al. (1997) "Refinement of Macromolecular Structures by the Maximum-Likelihood Method" Acta Crystallogr D 53:240-255 and Vagin et al. (2004) Acta Crystallogr D Biol Crystallogr 60:2184-95), CNS (Brunger et al. (1998) Acta Crystallogr D Biol Crystallogr 54 (Pt 5):905-21), PRODRG (van Aalten et al. (1996) "PRODRG, a program for generating molecular topologies and unique molecular descriptors from coordinates of small molecules" J Comput Aided Mol Des 10:255-262), and O (Jones et (1991) "Improved methods for building protein models in electron density maps and the location of errors in these models" Acta Crystallogr A 47 (Pt 2):110-119).

Specific examples of determination of chalcone isomerase like protein structures are described in the Examples sections below.

Structure-Based Engineering of Chalcone Isomerase Like Proteins

Structural data for a chalcone isomerase like protein can be used to conveniently identify amino acid residues as candidates for mutagenesis to create variant chalcone isomerase like proteins having modified fatty acid binding or transport activity. For example, analysis of the three-dimensional structure of a chalcone isomerase like protein can identify residues that sterically hinder access to the binding pocket by a fatty acid; such residues can be mutated to increase access to the pocket. Similarly, residues can be identified that can be mutated to introduce a feature complementary to a desired fatty acid ligand, e.g., by adding or altering charge, hydrophobicity, size, and/or the like.

The structure of a given chalcone isomerase like protein, optionally complexed to a fatty acid ligand, can be directly determined as described herein by x-ray crystallography or by NMR spectroscopy. Alternatively, the structure of a chalcone isomerase like protein can be modeled based on homology with a chalcone isomerase like protein whose structure has already been determined, for example, either of the structures described herein in the Examples sections.

The binding pocket of the chalcone isomerase like protein can be identified, for example, by examination of a protein-ligand co-complex structure, homology with other chalcone isomerase like proteins, biochemical analysis of mutant proteins, and/or the like. The position of a fatty acid ligand in the binding pocket can be modeled, for example, by projecting the location of features of the ligand based on the previously determined location of another ligand in the binding pocket.

Such modeling of the ligand in the binding pocket can involve simple visual inspection of a model of the chalcone isomerase like protein, for example, using molecular graphics software such as the PyMOL viewer (open source, freely available on the World Wide Web at (www.)pymol.org) or Insight II (commercially available from Accelrys at (www (dot)accelrys(dot)com/products/insight). Alternatively, modeling of the ligand in the binding pocket of the chalcone isomerase like protein or a putative mutant chalcone isomerase like protein, for example, can involve computer-assisted docking, molecular dynamics, free energy minimization, and/or like calculations. Such modeling techniques have been well described in the literature; see, e.g., Babine and Abdel-Meguid (eds.) (2004) *Protein Crystallography in Drug Design*, Wiley-VCR, Weinheim; Lyne (2002) "Structure-based virtual screening: An overview" Drug Discov. Today 7:1047-1055; Molecular Modeling for Beginners, at (www(dot)usm(dot)maine(dot)edu/~rhodes/SPVTut/index (dot)html; and Methods for Protein Simulations and Drug Design at (www(dot)dddc(dot)ac(dot)cn/embo04; and references therein. Software to facilitate such modeling is widely available, for example, the CHARMm simulation package, available academically from Harvard University or commercially from Accelrys (at www(dot)accelrys(dot)com), the Discover simulation package (included in Insight II, supra), and Dynama (available at (www(dot)cs(dot)gsu(dot)edu/ ~cscrwh/progs/progs(dot)html). See also an extensive list of modeling software at (www(dot)netsci(dot)org/Resources/ Software/Modeling/MMMD/top(dot)html.

Visual inspection and/or computational analysis of a chalcone isomerase like protein model can identify relevant features of the binding region, including, for example, residues that can sterically inhibit entry of a ligand into the binding pocket (e.g., residues undesirably close to the projected location of one or more atoms within the ligand when the ligand is bound to the chalcone isomerase like protein). Such a residue can, for example, be deleted or replaced with a residue having a smaller side chain; for example, many residues can be conveniently replaced with a residue having similar characteristics but a shorter amino acid side chain, or, e.g., with alanine. Similarly, residues that can be altered to introduce desirable interactions with the ligand can be identified. Such a residue can be replaced with a residue that is complementary with a feature of the ligand, for example, with a charged residue (e.g., lysine, arginine, or histidine) that can electrostatically interact with an oppositely charged moiety on the ligand (e.g., a carboxylic acid group), a hydrophobic residue that can interact with a hydrophobic group on the ligand, or a residue that can hydrogen bond to the ligand (e.g., serine, threonine, histidine, asparagine, or glutamine).

Systems of the invention can include any of the various crystallographic or modeling software described above, e.g., implemented in a computer system. Systems also typically include one or more databases of crystallographic information, e.g., as set forth in the figures herein. Systems also optionally include a user input (e.g., keyboard or mouse) a user viewable display, an information storage module (e.g., disk drive or optical disk), etc. Optionally, the system can include one or more modules that assist in gathering crystallographic information, e.g., any of those noted above.

Modulating Lipid Production in Cells and Whole Organisms, Including Plants and Livestock Animals The CHI like fatty acid binding proteins of the invention can be expressed in a cell to modify lipid production in the cell, e.g., by increasing flux through one or more lipid biosynthesis pathways. For example, CHI like fatty acid binding proteins may act as transporters of fatty acids, e.g., such as C12 to C18 saturated, or monounsaturated fatty acids, including oleic acid, lauric acid, myristic acid, palmitic acid, steric acid, etc., from an inner thalakoid membrane to the outer surface of a plant plastid. This increases the rate at which such fatty acids are reactivated to acyl-CoAs for utilization in cytosolic glycerolipid synthesis.

Accordingly, in one embodiment, lipid production is increased by expressing one or more recombinant CHI like fatty acid binding protein genes in the cell. High levels of expression are expected to increase fatty acid transport, increasing cytosolic glycerolipid synthesis. Thus, such genes can be expressed in expression cassettes that utilize strong promoters, e.g., any of the various constitutive promoters noted herein, including poi UT promoters, strong Pol II promoters, etc. Strong tissue-specific promoters can also be used, e.g., where fatty acid content is desirably raised in a particular tissue (e.g., fruit, nut, seed, etc.).

A variety of plant promoters are known and available. One example database of plant promoters is PlantProm DB, an annotated collection of promoter sequences for RNA polymerase II from various plant species. See, e.g., Shahmuradov et al. (2003) "PlantProm: a database of plant promoter sequences" *Nucleic Acids Research* 31(1):114-117. The database was developed by Softberry in collaboration with Department of Computer Science at Royal Holloway, University of London (www(dot)softberry(dot)com/berry(dot)phtml?topic=plantprom&group=data&subgroup=plantprom). One relatively recent release of PlantProm DB contains 305 entries, including 71, 220 and 14 promoters from monocot, dicot and other plants, respectively. Another example database of suitable promoters is provided by the University of Georgia's plant genome mapping project. See, www(dot)plantgenome(dot)uga(dot)edu/links(dot)htm. Montgomery et al. (2006) "ORegAnno: an open access database and curation system for literature-derived promoters, transcription factor binding sites and regulatory variation" *Bioinformatics* 22(5): 637-640 describe an open access database for promoter identification from the literature. MOHANTY ET AL. (2005) "Detection and Preliminary Analysis of Motifs in Promoters of Anaerobically Induced Genes of Different Plant Species" *Ann. Bot.* 96(4): 669-681 describe a variety of promoters from different plant species. Xie et al. (2005) "Expression of *Arabidopsis* MIRNA Genes" *Plant Physiology* 138 (4): 2145-2154 describe promoters for *Arabidopsis* MIRNA Genes. Florquin et al. (2005) "Large-scale structural analysis of the core promoter in mammalian and plant genomes" Nucleic Acids Res. 33(13): 4255-4264 describe core promoters in mammalian and plant genomes. Shahmuradov et al. (2005) "Plant promoter prediction with confidence estimation" Nucleic Acids Res. 33(3): 1069-1076 provide plant promoter prediction methods for evaluating plant genomic data. Steffens et al (2004) "AthaMap: an online resource for in silico transcription factor binding sites in the *Arabidopsis thaliana* genome" *Nucleic Acids Res.* 32(90001): D368-372 describe predicted promoters in *Arabidopsis* thaliana. These and many other promoters and other genomic features (enhancers, etc.) are widely available to skilled practitioners. Further details regarding suitable promoters are found herein, e.g., in the section entitled "Expression Cassettes."

In addition to raising lipid content, the invention is also useful for decreasing lipid content. For example, it may be beneficial in some instances to decrease dietary lipids in plants or livestock animals, e.g., to combat obesity, metabolic syndrome, or the like in humans that consume the plants or livestock. In these cases, plants or livestock can be engineered that comprise one or more deletion or down regulating modification of a native CHI like fatty acid binding protein gene. Optionally, this native gene can be substituted with a recombinant expression cassette that includes a recombinant CHI like fatty acid binding protein gene under the control of a quantitatively inducible promoter, e.g., to modulate expression of the recombinant gene in response to selected environmental stimuli.

Modulators of native or recombinant CHI like fatty acid binding protein genes can also be engineered into a cell or plant of interest, Many modulators of protein expression are known, including transcription factors that trans-activate expression of genes, anti-sense expression that blocks transcription or translation, and various Si-RNA types of gene modulators.

For example, use of antisense nucleic acids is well known in the art. An antisense nucleic acid has a region of complementarity to a target nucleic acid, e.g., a target CHI like fatty acid binding protein mRNA or DNA. Typically, a nucleic acid comprising a nucleotide sequence in a complementary, antisense orientation with respect to a coding (sense) sequence of an endogenous gene is introduced into a cell. The antisense nucleic acid can be RNA, DNA, a PNA or any other appropriate molecule. A duplex can form between the antisense sequence and its complementary sense sequence, resulting in inactivation of the gene. The antisense nucleic acid can inhibit gene expression by forming a duplex with an RNA transcribed from the gene, by forming a triplex with duplex DNA, etc. An antisense nucleic acid can be produced, e.g., for any gene whose coding sequence is known or can be determined by a number of well-established techniques (e.g., chemical synthesis of an antisense RNA or oligonucleotide (optionally including modified nucleotides and/or linkages that increase resistance to degradation or improve cellular uptake) or in vitro transcription). Antisense nucleic acids and their use are described, e.g., in U.S. Pat. No. 6,242,258 to Haselton and Alexander (Jun. 5, 2001) entitled "Methods for the selective regulation of DNA and RNA transcription and translation by photoactivation"; U.S. Pat. No. 6,500,615; U.S. Pat. No. 6,498,035; U.S. Pat. No. 6,395,544; U.S. Pat. No. 5,563,050; E. Schuch et al (1991) *Symp Soc. Exp Biol* 45:117-127; de Lange et al., (1995) *Curr Top Microbiol Immunol* 197:57-75; Hamilton et al. (1995) *Curr Top Microbiol Immunol* 197:77-89; Finnegan et al., (1996) *Proc Natl Acad Sci USA* 93:8419-8454; Uhlmann and A. Pepan (1990), *Chem. Rev.* 90:543; P. D. Cook (1991), *Anti-Cancer Drug Design* 6:585; J. Goodchild, Bioconjugate Chem. 1 (1990) 165; and, S. L. Beaucage and R. P. Iyer (1993), *Tetrahedron* 49:6123; and F. Eckstein, Ed. (1991), *Oligonucleotides and Analogues—A Practical Approach*, IRL Press.

Gene expression can also be inhibited by RNA silencing or interference. "RNA silencing" refers to any mechanism through which the presence of a single-stranded or, typically, a double-stranded RNA in a cell results in inhibition of expression of a target gene comprising a sequence identical or nearly identical to that of the RNA, including, but not limited to, RNA interference, repression of translation of a target mRNA transcribed from the target gene without alteration of the mRNA's stability, and transcriptional silencing (e.g., histone acetylation and heterochromatin formation leading to inhibition of transcription of the target mRNA).

The term "RNA interference" ("RNAi," sometimes called RNA-mediated interference, post-transcriptional gene silencing, or quelling) refers to a phenomenon in which the presence of RNA, typically double-stranded RNA, in a cell results in inhibition of expression of a gene comprising a sequence identical, or nearly identical, to that of the double-stranded RNA. The double-stranded RNA responsible for inducing RNAi is called an "interfering RNA." Expression of the gene is inhibited by the mechanism of RNAi as described below, in which the presence of the interfering RNA results in degradation of mRNA transcribed from the gene and thus in decreased levels of the mRNA and any encoded protein.

The mechanism of RNAi has been and is being extensively investigated in a number of eukaryotic organisms and cell types. See, for example, the following reviews: McManus and Sharp (2002) "Gene silencing in mammals by small interfering RNAs" Nature Reviews Genetics 3:737-747; Hutvagner and Zamore (2002) "RNAi: Nature abhors a double strand" Curr Opin Genet & Dev 200:225-232; Harmon (2002) "RNA interference" Nature 418:244-251; Agami (2002) "RNAi and related mechanisms and their potential use for therapy" Curr Opin Chem Biol 6:829-834; Tuschl and Borkhardt (2002) "Small interfering RNAs: A revolutionary tool for the analysis of gene function and gene therapy" Molecular Interventions 2:158-167; Nishikura (2001) "A short primer on RNAi: RNA-directed RNA polymerase acts as a key catalyst" Cell 107:415-418; and Zamore (2001) "RNA interference: Listening to the sound of silence" Nature Structural Biology 8:746-750. RNAi is also described in the patent literature; see, e.g., CA 2359180 by Kreutzer and Limmer entitled "Method and medicament for inhibiting the expression of a given gene"; WO 01/68836 by Beach et al. entitled "Methods and compositions for RNA interference"; WO 01/70949 by Graham et al. entitled "Genetic silencing"; and WO 01/75164 by Tuschl et al. entitled "RNA sequence-specific mediators of RNA interference."

In brief, double-stranded RNA introduced into a cell (e.g., into the cytoplasm) is processed, for example by an RNAse III-like enzyme called Dicer, into shorter double-stranded fragments called small interfering RNAs (siRNAs, also called short interfering RNAs). The length and nature of the siRNAs produced is dependent on the species of the cell, although typically siRNAs are 21-25 nucleotides long (e.g., an siRNA may have a 19 base pair duplex portion with two nucleotide 3' overhangs at each end). Similar siRNAs can be produced in vitro (e.g., by chemical synthesis or in vitro transcription) and introduced into the cell to induce RNAi. The siRNA becomes associated with an RNA-induced silencing complex (RISC). Separation of the sense and antisense strands of the siRNA, and interaction of the siRNA antisense strand with its target mRNA through complementary base-pairing interactions, optionally occurs, Finally, the mRNA is cleaved and degraded.

Expression of a target gene in a cell can thus be specifically inhibited by introducing an appropriately chosen double-stranded RNA into the cell. Guidelines for design of suitable interfering RNAs are known to those of skill in the art. For example, interfering RNAs are typically designed against exon sequences, rather than introns or untranslated regions. Characteristics of high efficiency interfering RNAs may vary by cell type. For example, although siRNAs may require 3' overhangs and 5' phosphates for most efficient induction of RNAi in Drosophila cells, in mammalian cells blunt ended siRNAs and/or RNAs lacking 5' phosphates can induce RNAi as effectively as siRNAs with 3' overhangs and/or 5' phosphates (see, e.g., Czauderna et al. (2003) "Structural variations and stabilizing modifications of synthetic siRNAs in mammalian cells" Nucl Acids Res 31:2705-2716). As another example, since double-stranded RNAs greater than 30-80 base pairs long activate the antiviral interferon response in mammalian cells and result in non-specific silencing, interfering RNAs for use in mammalian cells are typically less than 30 base pairs (for example, Caplen et al. (2001) "Specific inhibition of gene expression by small double-stranded RNAs in invertebrate and vertebrate systems" Proc. Natl. Acad. Sci. USA 98:9742-9747, Elbashir et al. (2001) "Duplexes of 21-nucleotide RNAs mediate RNA interference in cultured mammalian cells" Nature 411:494-498 and Elbashir et al. (2002) "Analysis of gene function in somatic mammalian cells using small interfering RNAs" Methods 26:199-213 describe the use of 21 nucleotide siRNAs to specifically inhibit gene expression in mammalian cell lines, and Kim et al. (2005) "Synthetic dsRNA Dicer substrates enhance RNAi potency and efficacy" Nature Biotechnology 23:222-226 describes use of 25-30 nucleotide duplexes). The sense and antisense strands of a siRNA are typically, but not necessarily, completely complementary to each other over the double-stranded region of the siRNA (excluding any overhangs). The antisense strand is typically completely complementary to the target mRNA over the same region, although some nucleotide substitutions can be tolerated (e.g., a one or two nucleotide mismatch between the antisense strand and the mRNA can still result in RNAi, although at reduced efficiency). The ends of the double-stranded region are typically more tolerant to substitution than the middle; for example, as little as 15 bp (base pairs) of complementarity between the antisense strand and the target mRNA in the context of a 21 mer with a 19 bp double-stranded region has been shown to result in a functional siRNA (see, e.g., Czauderna et al. (2003) "Structural variations and stabilizing modifications of synthetic siRNAs in mammalian cells" Nucl Acids Res 31:2705-2716), Any overhangs can but need not be complementary to the target mRNA; for example, 11 (two 2'-deoxythymidines) overhangs are frequently used to reduce synthesis costs.

Although double-stranded RNAs (e.g., double-stranded siRNAs) were initially thought to be required to initiate RNAi, several recent reports indicate that the antisense strand of such siRNAs is sufficient to initiate RNAi. Single-stranded antisense siRNAs can initiate RNAi through the same pathway as double-stranded siRNAs (as evidenced, for example, by the appearance of specific mRNA endonucleolytic cleavage fragments). As for double-stranded interfering RNAs, characteristics of high-efficiency single-stranded siRNAs may vary by cell type (e.g., a 5' phosphate may be required on the antisense strand for efficient induction of RNAi in some cell types, while a free 5' hydroxyl is sufficient in other cell types capable of phosphorylating the hydroxyl). See, e.g., Martinez et al. (2002) "Single-stranded antisense siRNAs guide target RNA cleavage in RNAi" Cell 110:563-574; Amarzguioui et al. (2003) "Tolerance for mutations and chemical modifications in a siRNA" Nucl. Acids Res. 31:589-595; Holen et al. (2003) "Similar behavior of single-strand and double-strand siRNAs suggests that they act through a common RNAi pathway" Nucl. Acids Res. 31:2401-2407; and Schwarz et al. (2002) Mol. Cell 10:537-548.

Due to currently unexplained differences in efficiency between siRNAs corresponding to different regions of a given target mRNA, several siRNAs are typically designed and tested against the target mRNA to determine which siRNA is most effective. Interfering RNAs can also be produced as small hairpin RNAs (shRNAs, also called short hairpin RNAs), which are processed in the cell into siRNA-like molecules that initiate RNAi (see, e.g., Siolas et al. (2005) "Synthetic shRNAs as potent RNAi triggers" Nature Biotechnology 23:227-231).

The presence of RNA, particularly double-stranded RNA, in a cell can result in inhibition of expression of a gene comprising a sequence identical or nearly identical to that of the RNA through mechanisms other than RNAi. For example, double-stranded RNAs that are partially complementary to a target mRNA can repress translation of the mRNA without affecting its stability. As another example, double-stranded RNAs can induce histone methylation and heterochromatin formation, leading to transcriptional silencing of a gene comprising a sequence identical or nearly identical to that of the RNA (see, e.g., Schramke and Allshire (2003) "Hairpin RNAs and retrotransposon LTRs effect RNAi and chromatin-based gene silencing" Science 301:1069-1074; Kawasaki and Taira (2004) "Induction of DNA methylation and gene silencing by short interfering RNAs in human cells" Nature 431: 211-217; and Morris et al. (2004) "Small interfering RNA-induced transcriptional gene silencing in human cells" Science 305:1289-1292).

Short RNAs called microRNAs (miRNAs) have been identified in a variety of species. Typically, these endogenous RNAs are each transcribed as a long RNA and then processed to a pre-miRNA of approximately 60-75 nucleotides that forms an imperfect hairpin (stem-loop) structure. The pre-miRNA is typically then cleaved, e.g., by Dicer, to form the mature miRNA. Mature miRNAs are typically approximately 21-25 nucleotides in length, but can vary, e.g., from about 14 to about 25 or more nucleotides. Some, though not all, miRNAs have been shown to inhibit translation of mRNAs bearing partially complementary sequences. Such miRNAs contain one or more internal mismatches to the corresponding mRNA that are predicted to result in a bulge in the center of the duplex formed by the binding of the miRNA antisense strand to the mRNA. The mRNA typically fowls approximately 14-17 Watson-Crick base pairs with the mRNA; additional wobble base pairs can also be formed. In addition, short synthetic double-stranded RNAs (e.g., similar to siRNAs) containing central mismatches to the corresponding mRNA have been shown to repress translation (but not initiate degradation) of the mRNA. See, for example, Zeng et al. (2003) "MicroRNAs and small interfering RNAs can inhibit mRNA expression by similar mechanisms" Proc. Natl. Acad. Sci. USA 100:9779-9784; Doench et al. (2003) "siRNAs can function as miRNAs" Genes & Dev. 17:438-442; Bartel and Bartel (2003) "MicroRNAs: At the root of plant development?" Plant Physiology 132:709-717; Schwarz and Zamore (2002) "Why do miRNAs live in the miRNP?" Genes & Dev. 16:1025-1031; Tang et al. (2003) "A biochemical framework for RNA silencing in plants" Genes & Dev. 17:49-63; Meister et al. (2004) "Sequence-specific inhibition of microRNA- and siRNA-induced RNA silencing" RNA 10; 544-550; Nelson et al. (2003) "The microRNA world: Small is mighty" Trends Biochem. Sci. 28:534-540; Scacheri et al. (2004) "Short interfering RNAs can induce unexpected and divergent changes in the levels of untargeted proteins in mammalian cells" Proc. Natl. Acad. Sci. USA 101:1892-1897; Sempere et al. (2004) "Expression profiling of mammalian microRNAs uncovers a subset of brain-expressed microRNAs with possible roles in murine and human neuronal differentiation" Genome Biology 5:R13; Dykxhoorn et al. (2003) "Killing the messenger: Short RNAs that silence gene expression" Nature Reviews Molec. and Cell Biol. 4:457-467; McManus (2003) "MicroRNAs and cancer" Semin Cancer Biol. 13:253-288; and Stark et al. (2003) "Identification of *Drosophila* microRNA targets" PloS Biol, 1:E60.

The cellular machinery involved in translational repression of mRNAs by partially complementary RNAs (e.g., certain miRNAs) appears to partially overlap that involved in RNAi, although, as noted, translation of the mRNAs, not their stability, is affected and the mRNAs are typically not degraded. The location and/or size of the bulge(s) formed when the antisense strand of the RNA binds the mRNA can affect the ability of the RNA to repress translation of the mRNA. Similarly, location and/or size of any bulges within the RNA itself can also affect efficiency of translational repression. See, e.g., the references above. Typically, translational repression is most effective when the antisense strand of the RNA is complementary to the 3' untranslated region (3' UTR) of the mRNA. Multiple repeats, e.g., tandem repeats, of the sequence complementary to the antisense strand of the RNA can also provide more effective translational repression; for example, some mRNAs that are translationally repressed by endogenous miRNAs contain 7-8 repeats of the miRNA binding sequence at their 3' UTRs. It is worth noting that translational repression appears to be more dependent on concentration of the RNA than RNA interference does; translational repression is thought to involve binding of a single mRNA by each repressing RNA, while RNAi is thought to involve cleavage of multiple copies of the mRNA by a single siRNA-RISC complex.

Guidance for design of a suitable RNA to repress translation of a given target mRNA can be found in the literature (e.g., the references above and Doench and Sharp (2004) "Specificity of microRNA target selection in translational repression" Genes & Dev. 18:504-511; Rehmsmeier et al. (2004) "Fast and effective prediction of microRNA/target duplexes" RNA 10:1507-1517; Robins et al. (2005) "Incorporating structure to predict microRNA targets" Proc Natl Acad Sci 102:4006-4009; and Mattick and Makunin (2005) "Small regulatory RNAs in mammals" Hum. Mol. Genet. 14:R121-R132, among many others) and herein. However, due to differences in efficiency of translational repression between RNAs of different structure (e.g., bulge size, sequence, and/or location) and RNAs corresponding to different regions of the target mRNA, several RNAs are optionally designed and tested against the target mRNA to determine which is most effective at repressing translation of the target mRNA.

Measuring Lipid Content in Plants

Lipid content is measured in plants according to standard methods. Literally hundreds of lipid analysis methods for the analysis of plant lipids are known and available. These include basic methods of detecting lipid content, such as: liquid or gas chromatography, ion exchange chromatography, mass spectrometry, multi-dimensional chromatography and spectrometry, nmr analysis, combined extraction-esterification of fatty acids, gas chromatography of diacylglycerol derivatives (derived from phospholipids), and many others. Details regarding lipid analysis methods are found in the following references: Benning, (1998) "Biosynthesis and function of the sulfoquinovosyl diacylglycerol" *Ann. Rev, Plant Physiol. Plant Mol. Biol.,* 49:53-75; Benning and Ohta (2005) "Three enzyme systems for galactoglycerolipid biosynthesis are coordinately regulated in plants." *J. Biol. Chem.,* 280: 2397-2400; Dörmann and Benning (2002) "Galactolipids rule in seed plants." *Trends Plant Sci.* 7:12-118; Frentzen (2004) "Phosphatidylglycerol and sulfoquinovosyldiacylglycerol: anionic membrane lipids and phosphate regulation." *Current Opinion in Plant Biology,* 7: 270-276; Heinz (1996) "Plant glycolipids: structure, isolation and analysis." In: *Advances in Lipid Methodology—Three,* pp. 211-332 (ed, W. W. Christie, Oily Press, Dundee); Ishizuka (1997) "Chemistry and functional distribution of sulfoglycolipids." *Prog. Lipid Res.,* 36, 245-319; Joyard and Douce (1987) "Galactolipid synthesis. In: The Biochemistry of Plants. Vol. 9, Lipids: Structure and Function" pp. 215-274 (ed. P. K. Stumpf, Academic Press, Orlando); Kates, M. (ed.) (1990) *Handbook of Lipid Research 6. Glycolipids, Phospholycolipids and Sulfoglvcolipids,* (ed. M. Kates, Plenum Press, NY); and Schmid, and Ohlrogge (2002) "Lipid metabolism in plants," In: *Biochemistry of Lipids, Lipoproteins and Membranes,* 4th Edition, pp. 93-126 (ed. D. E. Vance and J. Vance, Elsevier, Amsterdam). Additional details regarding lipid analysis are also found at www(dot)lipidlibrary(dot)co(dot)uk/index(dot) html and the many lipid analysis references cited therein.

Selecting Plants for CHI Like Fatty Acid Bending Polypeptide Gene Polymorphisms

Marker assisted selection (MAS) is routinely performed to select crop varieties and livestock animals for traits of interest. The development of molecular markers has facilitated mapping and selection of agriculturally important traits in essentially every plant and livestock animal of commercial interest. Markers tightly linked to genes (in this case CHI like fatty acid binding protein genes) that influence lipid phenotype are a substantial asset in the rapid identification of plant and animal lines that comprise the phenotype of interest, with the markers being used as an easily screenable proxy for the actual phenotype. Introgressing CHI like fatty acid binding protein genes into a desired cultivar (e.g., an elite crop line) or livestock breed is also facilitated by using suitable markers.

Molecular Markers and Marker Assisted Selection

A genetic map is a graphical representation of a genome (or a portion of a genome such as a single chromosome) where the distances between landmarks on the chromosome are measured by the recombination frequencies between the landmarks. A genetic landmark can be any of a variety of known polymorphic markers, for example but not limited to, molecular markers such as SSR markers, RFLP markers, or SNP markers. Furthermore, SSR markers can be derived from genomic or expressed nucleic acids (e.g., ESTs). The nature of these physical landmarks and the methods used to detect them vary, but all of these markers are physically distinguishable from each other (as well as from the plurality of alleles of any one particular marker) on the basis of polynucleotide length and/or sequence.

Although specific DNA sequences that encode proteins are generally well-conserved across a species, other regions of DNA (typically non-coding) tend to accumulate polymorphisms, and therefore, are likely to be variable between individuals of the same species. Such regions provide the basis for numerous molecular genetic markers. In general, any differentially inherited polymorphic trait (including a nucleic acid polymorphism) that segregates among progeny is a potential marker. The genomic variability can be of any origin, for example, insertions, deletions, duplications, repetitive elements, point mutations, recombination events, or the presence and sequence of transposable elements. Similarly, numerous methods for detecting molecular markers are also well-established.

The primary motivation for developing molecular marker technologies from the point of view of plant breeders has been the possibility to increase breeding efficiency through MAS. A molecular marker allele that demonstrates linkage disequilibrium with a desired phenotypic trait (e.g., a quantitative trait locus, or QTL, such as resistance to a particular disease) provides a useful tool for the selection of a desired trait in a plant or animal population. The key components to the implementation of this approach are: (i) the creation of a dense genetic map of molecular markers, (ii) the detection of QTL based on statistical associations between marker and phenotypic variability, (iii) the definition of a set of desirable marker alleles based on the results of the QTL analysis, and (iv) the use and/or extrapolation of this information to the current set of breeding germplasm to enable marker-based selection decisions to be made.

Two types of markers are frequently used in marker assisted selection protocols, namely simple sequence repeat (SSR, also known as microsatellite) markers, and single nucleotide polymorphism (SNP) markers. The term SSR refers generally to any type of molecular heterogeneity that results in length variability, and most typically is a short (up to several hundred base pairs) segment of DNA that consists of multiple tandem repeats of a two or three base-pair sequence. These repeated sequences result in highly polymorphic DNA regions of variable length due to poor replication fidelity, e.g., caused by polymerase slippage. SSRs appear to be randomly dispersed through the genome and are generally flanked by conserved regions. SSR markers can also be derived from RNA sequences (in the form of a cDNA, a partial cDNA or an EST) as well as genomic material.

The characteristics of SSR heterogeneity make them well suited for use as molecular genetic markers; namely. SSR genomic variability is inherited, is multiallelic, codominant and is reproducibly detectable. The proliferation of increasingly sophisticated amplification-based detection techniques (e.g., PCR-based) provides a variety of sensitive methods for the detection of nucleotide sequence heterogeneity. Primers (or other types of probes) are designed to hybridize to conserved regions that flank the SSR domain, resulting in the amplification of the variable SSR region. The different sized amplicons generated from an SSR region have characteristic and reproducible sizes. The different sized SSR amplicons observed from two homologous chromosomes in an individual, or from different individuals in the plant population are generally termed "marker alleles." As long as there exists at least two SSR alleles that produce PCR products with at least two different sizes, the SSRs can be employed as a marker.

Various techniques have been developed for the detection of polymorphisms, including allele specific hybridization (ASH; see, e.g., Coryell et al., (1999) "Allele specific hybridization markers for soybean," *Theor. Appl. Genet.,* 98:690-696). Additional types of molecular markers are also widely used, including but not limited to expressed sequence tags (ESTs) and SSR markers derived from EST sequences, restriction fragment length polymorphism (RFLP), amplified fragment length polymorphism (AFLP), randomly amplified polymorphic DNA (RAPD) and isozyme markers. A wide range of protocols are known to one of skill in the art for detecting this variability, and these protocols are frequently specific for the type of polymorphism they are designed to detect. For example, PCR amplification, single-strand conformation polymorphisms (SSCP) and self-sustained sequence replication (3SR; see Chan and Fox, "NASBA and other transcription-based amplification methods for research and diagnostic microbiology," Reviews in Medical Microbiology 10:185-196 [1999]).

Linkage of one molecular marker to another molecular marker is measured as a recombination frequency. In general, the closer two loci (e.g., two SSR markers) are on the genetic map, the closer they lie to each other on the physical map. A relative genetic distance (determined by crossing over frequencies, measured in centimorgans; cM) is generally proportional to the physical distance (measured in base pairs, e.g., kilobase pairs [kb] or megabasepairs [Mbp]) that two linked loci are separated from each other on a chromosome. A lack of precise proportionality between cM and physical distance can result from variation in recombination frequencies for different chromosomal regions, e.g., some chromosomal regions are recombinational "hot spots," while others regions do not show any recombination, or only demonstrate rare recombination events. In general, the closer one marker is to another marker, whether measured in terms of recombination or physical distance, the more strongly they are linked. In some aspects, the closer a molecular marker is to a CHI like fatty acid binding protein gene that imparts a particular phenotype (e.g., increased or decreased oil production), whether measured in terms of recombination or physical distance, the better that marker serves to tag the desired phenotypic trait.

Techniques for Marker Detection

Markers corresponding to genetic polymorphisms between members of a population can be detected by methods well-established in the art (e.g., PCR-based sequence specific amplification, restriction fragment length polymorphisms (RFLPs), isozyme markers, allele specific hybridization (ASH), amplified variable sequences of the plant genome, self-sustained sequence replication, simple sequence repeat (SSR), single nucleotide polymorphism (SNP), random amplified polymorphic DNA ("RAPD") or amplified fragment length polymorphisms (AFLP). In one additional embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In general, the majority of genetic markers rely on one or more property of nucleic acids for their detection. For example, some techniques for detecting genetic markers utilize hybridization of a probe nucleic acid to nucleic acids corresponding to the genetic marker (e.g., amplified nucleic acids produced using genomic plant DNA as a template). Hybridization formats, including but not limited to solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, New York, as well as in Sambrook, Berger and Ausubel (herein).

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Determining one or more restriction enzyme that produces informative fragments for each cross is a simple procedure, well known in the art. After separation by length in an appropriate matrix (e.g., agarose or polyacrylamide) and transfer to a membrane (e.g., nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic heads, fluorescent dyes, radiolabels, enzymes, and colorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of fluorescent Probes and Research Chemicals Eighth Edition* by Molecular Probes, Inc. (Eugene Oreg.) (Available on CD ROM).

Amplification-Based Detection Methods

PCR, RT-PCR and LCR are in particularly broad use as amplification and amplification-detection methods for amplifying nucleic acids of interest (e.g., those comprising marker loci), facilitating detection of the markers. Details regarding the use of these and other amplification methods can be found in any of a variety of standard texts, including, e.g., Sambrook, Ausubel, Berger and Croy, herein. Many available biology texts also have extended discussions regarding PCR and related amplification methods. One of skill will appreciate that essentially any RNA can be converted into a double stranded DNA suitable for restriction digestion. PCR expansion and sequencing using reverse transcriptase and a polymerase ("Reverse Transcription-PCR, or "RT-PCR"). See also, Ausubel, Sambrook and Berger, above.

Real Time Amplification/Detection Methods

In one aspect, real time PCR or LCR is performed on the amplification mixtures described herein, e.g., using molecular beacons or TaqMan™ probes. A molecular beacon (MB) is an oligonucleotide or PNA which, wider appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources. See also, e.g., Leone et al, (1995) "Molecular beacon probes combined with amplification by NASBA enable homogenous real-time detection of RNA." *Nucleic Acids Res.* 26:2150-2155; Tyagi and Kramer (1996) "Molecular beacons: probes that fluoresce upon hybridization" *Nature Biotechnology* 14:303-308; Blok and Kramer (1997) "Amplifiable hybridization probes containing a molecular switch" Mol Cell Probes 11:187-194; Hsuih et al. (1997) "Novel, ligation-dependent PCR assay for detection of hepatitis C in serum" *J Clin Microbiol* 34:501-507; Kostrikis et al. (1998) "Molecular beacons: spectral genotyping of human alleles" *Science* 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Bonnet et al. (1999) "Thermodynamic basis of the chemical specificity of structured DNA probes" *Proc. Natl. Acad. Sci. U.S.A.* 96:6171-6176; Fang et al. (1999) "Designing a novel molecular beacon for surface-immobilized DNA hybridization studies" *J. Am. Chem. Soc.* 121:2921-2922; Manrras et al. (1999) "Multiplex detection of single-nucleotide variation using molecular beacons" *Genet. Anal, Biomol. Eng,* 14:151-156; and Vet et al. (1999) "Multiplex detection of four pathogenic retroviruses using molecular beacons" *Proc. Natl. Acad. Sci. U.S.A.* 96:6394-6399. Additional details regarding MB construction and use is found in the patent literature, e.g., U.S. Pat. No. 5,925,517 (Jul. 20, 1999) to Tyagi et al. entitled "Detectably labeled dual conformation oligonucleotide probes, assays and kits," U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits."

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes).

Additional Details Regarding Amplified Variable Sequences, SSR, AFLP ASH, SNPs and Isozyme Markers Amplified variable sequences refer to amplified sequences of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) Rnase H, and (3) a DNA-dependent RNA polymerase (Guatelli et al. (1990) *Proc Natl Acad Sci USA* 87:1874). By mimicking the retroviral strategy of RNA replication by means of cDNA intermediates, this reaction accumulates cDNA and RNA copies of the original target.

Amplified fragment length polymophisms (AFLP) can also be used as genetic markers (Vos et al. (1995) *Nucl Acids Res* 23:4407). The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping of plants (Becker et al (1995) *Mol Gen Genet* 249:65; and Meksem et al. (1995) *Mol Gen Genet* 249:74).

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. In one embodiment, this distinction is detected by differential migration patterns of an amplicon comprising the SNP on e.g., an acrylamide gel. However, alternative modes of detection, such as hybridization, e.g., ASH, or RFLP analysis are also appropriate.

Detection of Markers for Positional Cloning

In some embodiments, a nucleic acid probe is used to detect a nucleic acid that comprises a marker sequence. Such probes can be used, for example, in positional cloning to isolate nucleotide sequences (e.g., CHI like fatty acid binding protein genes) linked to the marker nucleotide sequence. It is not intended that the nucleic acid probes of the invention be limited to any particular size. In some embodiments, nucleic acid probe is at least 20 nucleotides in length, or alternatively, at least 50 nucleotides in length, or alternatively, at least 100 nucleotides in length, or alternatively, at least 200 nucleotides in length.

A hybridized probe is detected using, autoradiography, fluorography or other similar detection techniques depending on the label to be detected. Examples of specific hybridization protocols are widely available in the art, see, e.g., Berger, Sambrook, and Ausubel, all herein.

Additional Details Regarding Sequence Variations

A number of particular CHI like fatty acid binding polypeptides and coding nucleic acids are described herein by sequence (See, e.g., Examples 1 and 2 and the Figures herein). These polypeptides and coding nucleic acids can be modified, e.g., by mutation as described herein, or simply by artificial synthesis of a desired variant. Several types of example variants are described below.

Silent Variations

Due to the degeneracy of the genetic code, any of a variety of nucleic acids sequences encoding polypeptides of the invention are optionally produced, some which can bear various levels of sequence identity to the CHI like fatty acid binding protein nucleic acids in the Examples below. The following provides a typical codon table specifying the genetic code, found in many biology and biochemistry texts.

TABLE 1

Codon Table

| Amino acids | Codon |
|---|---|
| Alanine | Ala A GCA GCC GCG GCU |
| Cysteine | Cys C UGC UGU |
| Aspartic acid | Asp D GAC GAU |
| Glutamic acid | Glu E GAA GAG |
| Phenylalanine | Phe F UUC UUU |
| Glycine | Gly G GGA GGC GGG GGU |
| Histidine | His H CAC CAU |
| Isoleucine | Ile I AUA AUC AUU |
| Lysine | Lys K AAA AAG |
| Leucine | Leu L UUA UUG CUA CUC CUG CUU |
| Methionine | Met M AUG |
| Asparagine | Asn N AAC AAU |
| Proline | Pro P CCA CCC CCG CCU |
| Glutamine | Gln Q CAA CAG |
| Arginine | Arg R AGA AGG CGA CGC CGG CGU |
| Serine | Ser S AGC AGU UCA UCC UCG UCU |
| Threonine | Thr T ACA ACC ACG ACU |
| Valine | Val V GUA GUC GUG GUU |
| Tryptophan | Trp W UGG |
| Tyrosine | Tyr Y UAC UAU |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations", discussed below. One of skill will recognize that each codon in a nucleic acid (except ATG, which is ordinarily the only codon for methionine) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as net forth in Table 1, or as is commonly available in the art) as applied to the nucleic acid sequence encoding a polypeptide of the invention. All such variations of every nucleic acid herein are specifically provided and described by consideration of the sequence in combination with the genetic code. One of skill is fully able to make these silent substitutions using the methods herein.

Conservative Variations

"Conservatively modified variations" or, simply, "conservative variations" of a particular nucleic acid sequence or polypeptide are those which encode identical or essentially identical amino acid sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table 2 sets forth six groups which contain amino acids that are "conservative substitutions" for one another.

TABLE 2

Conservative Substitution Groups

| | | | |
|---|---|---|---|
| 1 Alanine (A) | Serine (S) | Threonine (T) | |
| 2 Aspartic acid (D) | Glutamic acid (E) | | |
| 3 Asparagine (N) | Glutamine (Q) | | |
| 4 Arginine (R) | Lysine (K) | | |
| 5 Isoleucine (I) | Leucine (L) | Methionine (M) | Valine (V) |
| 6 Phenylalanine (F) | Tyrosine (Y) | Tryptophan (W) | |

Thus, "conservatively substituted variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group.

Finally, the addition or deletion of sequences which do not alter the encoded activity of a nucleic acid molecule, such as the addition or deletion of a non-functional sequence, is a conservative variation of the basic nucleic acid or polypeptide.

One of skill will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

Antibodies

In another aspect, antibodies to CHI like fatty acid binding polypeptides can be generated using methods that are well known. The antibodies can be utilized for detecting and/or purifying polypeptides e.g., in situ to monitor localization of the polypeptide, or simply for polypeptide detection in a biological sample of interest, Antibodies can optionally discriminate CM like fatty acid binding polypeptide homologs. Antibodies can also, in some cases, be used to block function of CHI like fatty acid binding polypeptides, in vivo, in situ or in vitro (e.g., by binding to the fatty acid binding site on the protein). As used herein, the "antibody" includes, but is not limited to, polyclonal antibodies, monoclonal antibodies, humanized or chimeric antibodies and biologically functional antibody fragments, which are those fragments sufficient for binding of the antibody fragment to the protein.

For the production of antibodies to a polypeptide encoded by one of the disclosed sequences or conservative variant or fragment thereof, various host animals may be immunized by injection with the polypeptide, or a portion thereof. Such host animals may include, but are not limited to, rabbits, mice and rats, to name but a few. Various adjuvants may be used to enhance the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as target gene product, or an antigenic functional derivative thereof. For the production of polyclonal antibodies, host animals, such as those described above, may be immunized by injection with the encoded protein, or a portion thereof, supplemented with adjuvants as also described above.

Monoclonal antibodies (mAbs), which are homogeneous populations of antibodies to a particular antigen, may be obtained by any technique which provides for the production of antibody molecules by continuous cell lines in culture. These include, but are not limited to, the hybridoma technique of Kohler and Milstein (*Nature* 256:495-497, 1975; and U.S. Pat. No. 4,376,110), the human B-cell hybridoma technique (Kosbor et al., Immunology Today 4:72, 1983; Cole et al., *Proc. Nat'l. Acad. Sci. USA* 80:2026-2030, 1983), and the EBV-hybridoma technique (Cole et al., *Monoclonal Antibodies and Cancer Therapy,* Alan R. Liss, Inc., pp. 77-96, 1985). Such antibodies may be of any immunoglobulin class, including IgG, IgM, IgE, IgA, IgD, and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Nat'l. Acad. Sci. USA* 81:6851-6855, 1984; Neuberger et al., *Nature* 312:604-608, 1984; Takeda et al., *Nature* 314:452-454, 1985) by splicing the genes from a mouse antibody molecule of appropriate antigen specificity, together with genes from a human antibody molecule of appropriate biological activity, can be used. A chimeric antibody is a molecule in which different portions are derived from different animal species, such as those having a variable or hypervariable region derived from a murine mAb and a human immunoglobulin constant region.

Alternatively, techniques described for the production of single-chain antibodies (U.S. Pat. No. 4,946,778; Bird, *Science* 242:423-426, 1988; Huston et al., *Proc. Nat'l. Acad. Sci, USA* 85:5879-5883, 1988; and Ward et al., *Nature* 334:544-546, 1989) can be adapted to produce differentially expressed gene-single chain antibodies. Single chain antibodies are formed by linking the heavy and light chain fragments of the Fv region via an amino acid bridge, resulting in a single-chain polypeptide.

In one aspect, techniques useful for the production of "humanized antibodies" can be adapted to produce antibodies to the proteins, fragments or derivatives thereof. Such techniques are disclosed in U.S. Pat. Nos. 5,932,448; 5,693,762; 5,693,761; 5,585,089; 5,530,101; 5,569,825; 5,625,126; 5,633,425; 5,789,650; 5,661,016; and 5,770,429.

Antibody fragments which recognize specific epitopes may be generated by known techniques. For example, such fragments include, but are not limited to, the $F(ab')_2$ fragments, which can be produced by pepsin digestion of the antibody molecule, and the Fab fragments, which can be generated by reducing the disulfide bridges of the $F(ab')_2$ fragments. Alternatively, Fab expression libraries may be constructed (Huse et al., Science 246:1275-1281, 1989) to allow rapid and easy identification of monoclonal Fab fragments with the desired specificity.

The protocols for detecting and measuring the expression of the described polypeptides herein, using the above mentioned antibodies, are well known in the art. Such methods include, but are not limited to, dot blotting, western blotting, competitive and noncompetitive protein binding assays, enzyme-linked immunosorbant assays (ELISA), immunohistochemistry, fluorescence-activated cell sorting (FACS), and others commonly used and widely described in scientific and patent literature, and many employed commercially.

One method, for ease of detection, is the sandwich ELISA, of which a number of variations exist, all of which are intended to be encompassed by the present invention. For example, in a typical forward assay, unlabeled antibody is immobilized on a solid substrate and the sample to be tested is brought into contact with the bound molecule and incubated for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantified by comparing with a control sample containing known amounts of antigen. Variations on the forward assay include the simultaneous assay, in which both sample and antibody are added simultaneously to the bound antibody, or a reverse assay, in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody which is specific for the protein expressed by the gene of interest.

The most commonly used reporter molecules in this type of assay are either enzymes, fluorophore- or radionuclide-containing molecules. In the case of an enzyme immunoassay, an enzyme is conjugated to the second antibody, usually by means of glutaraldehyde or periodate. As will be readily recognized, however, a wide variety of different ligation techniques exist which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used, ft is also possible to employ fluorogenic substrates, which yield a fluorescent product, rather than the chromogenic substrates noted above. A solution containing the appropriate substrate is then added to the tertiary complex. The substrate reacts with the enzyme linked to the second antibody, giving a qualitative visual signal, which may be further quantified, usually spectrophotometrically.

Alternately, fluorescent compounds, such as fluorescein and rhodamine, can be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

EXAMPLES

The following examples are illustrative and not limiting. One of skill will recognize a variety of parameters that can be modified to achieve essentially similar results.

Example 1

A Sub-Family Chalcone Isomer Like Genes, Encoding Proteins that Bind Fatty Acids (FA) with High Affinity The current invention describes a novel sub-family of chalcone isomerase like genes, the protein products of which bind fatty acids (FA) with high affinity. Binding was established first by the elucidation of a high resolution crystal structure of one protein expressed and purified from *E. coli* (At3g63170, referred to as At279) and confirmed by HPLC-MS analyses of extractions of protein samples of At279 and a close homolog (At1g53520, referred to as At287). These proteins have a three-dimensional fold similar to chalcone isomerase (At3g55120, referred to as AtCHI) but, as compared to chalcone isomerase, lack key catalytic residues known to catalyze the formation of flavanones from chalcone substrates.

These members of the chalcone isomerase like gene family are widely distributed in plants, various bacteria, fungi and some eukaryotic organisms. Bioinformatic analyses of the two genes in question strongly suggests that the nuclear encoded proteins are localized in the chloroplast, where the majority of plant fatty acid biosynthesis occurs. Moreover, we hypothesize that these two proteins are directly involved in the transport of free fatty acids from the inner thylakoid membrane to the outer envelope of the plastid where they are reactivated to acyl-CoAs for utilization in cytosolic glycerolipid synthesis.

The metabolic engineering of plant fatty acid biosynthesis (FAS) has progressed rapidly in the past 10 years and has led to the commercialization of several modified oilseed crops. However, it has been difficult to engineer plants with increased flux through the biosynthetic pathways (1, 2). Our discovery of a new FA binding protein family and their future over-expression in FA bio-engineered plants may improve the plant FA content by allowing natural FA to be transported more efficiently. The search for these transporters has been intense but was previously unresolved (3). Moreover, our knowledge of the detailed binding mode of natural FAs, as well as synthetic FAs, provides the necessary tools for structure-based engineering of modified FA transporters.

Materials and Methods

Cloning, expression and purification of At3g63170 (At279) and At1g53520 (At287): *Arabidopsis thaliana* At3g63170 (At279) and At1g53520 (At287) genes were subcloned into the pHIS8 *Escherichia coli* expression vector derived from pET28a (+). For crystallization purpose, constructs of At279 and At287 lacking the transit peptide sequence found at the N-terminal region of the protein (~50 amino acids) were also created. Transformed *E. coli*. BL21 (DE3) cells were incubated with shaking at 37° C. in Terrific broth containing 50 μg/ml kanamycin until A(600 μm)=1.0. Protein expression was induced with 0.5 mM isopropyl 1-thio-β-galactopyranoside, and the cultures were incubated with shaking at 22° C. for an additional 6 h. Cells were harvested by centrifugation at 9,000×g and cell pellets re-suspended in lysis buffer (500 mM NaCl, 50 mM Tris-HCl (pH 8.0), 20 mM imidazole, 10% (v/v) glycerol 1% (v/v) Tween 20, 10 mM 3-mercaptoethanol) supplemented with 1 mg/ml lysozyme. Following sonication and centrifugation of the lysed cell debris at 100,000×g, the supernatant was passed over a Ni2+-NTA column (Qiagen, Valencia, Calif.) equilibrated in lysis buffer, washed with 10 bed volumes of wash buffer (500 mM NaCl, 50 mM Tris-HCl (pH 8.0), 20 mM imidazole, 10 mM β-mercaptoethanol), and the His-tagged protein eluted with 10 bed volumes of elution buffer (500 mM NaCl, 50 mM Tris-HCl (pH 8.0), 250 mM imidazole, 10 mM β-mercaptoethanol). The N-terminal His tag was cleaved by thrombin digestion during a 24-h dialysis against digestion buffer (500 mM NaCl, 50 mM Tris (pH 8.0), 10 mM β-mercaptoethanol) at 4° C. Cleaved protein was isolated by running the dialyzed sample over another Ni2+-NTA column equilibrated in digestion buffer to remove the His tag and uncleaved protein, followed by a benzamidine-Sepharose column to remove thrombin. A Superdex S75 gel filtration column (Amersham Biosciences) equilibrated in gel filtration buffer (500 mM NaCl, 25 mM HEPES (pH 7.5), 2 mM dithiothreitol (DTT) was utilized to isolate homogeneous At279 and A287. Peak fractions were collected and dialyzed against crystallization storage buffer (100 mM NaCl, 25 mM HEPES (pH 7.5), 2 mM DTT). The resulting samples were subjected to SDS-PAGE and judged to be >95% pure based upon Coomassie staining. At279 and At287 were subsequently concentrated to 10-15 mg/ml and stored at −80° C.

AT279 Crystal Structure

Crystallization and Data Collection of At3g63170 Protein Crystals (at279)

Crystals of the heterologously expressed At279 C-terminal construct (residues 77 to 279) were obtained by vapor diffusion in 2 μl hanging drops incubated at 4° C. and consisting of a 1:1 mixture of protein and crystallization buffer. The crystallization buffer contained 19% (w/v) PEG 3350, 0.3 M KCl, 2 mM DTT and 100 mM TAPS buffer at pH 8.5. Prior to freezing in liquid nitrogen, native crystals were passed through a cryogenic buffer identical to the crystallization buffer except for the use of 21% (w/v) PEG 3350 and the inclusion of 20% (v/v) ethylene glycol. For heavy atom derivatization, native At279 crystals were soaked overnight in crystallization buffer differing from the crystallization solution due to an increased PEG 3350 concentration (21% (w/v)) and the inclusion of 1 mM K2PtCl4 prior to cryogenic freezing as before. A multi-wavelength anomalous dispersion (MAD) data set was collected at the Pt edge on a K2PtCl4 derivative crystal at the Stanford Synchrotron Radiation Laboratory (SSRL) on beam line BL1-5. Data were processed with HKL2000 and reduced to a unique set of indexed intensities to a resolution of 2.6 Å. A single-wavelength native data set was collected at SSRL and processed with HXL2000 to a resolution of 1.9 Å. At279 crystals belong to the P2(1)2(1)2(1) space group, with average unit cell dimensions of a=56.44 Å, b=56.96 Å, c=140.37 Å, $\alpha=\beta=\gamma=90°$.

Structure Determination and Coordinate Refinement of At3g63170 Protein (At279)

The At279 structure was solved from the 2.6-Å platinum derivative data set. Experimental multiple wavelength anomalous dispersion phases were obtained using SOLVE (4). The experimental electron density maps were improved by bulk solvent density modification and automated building with RESOLVE (4). Additional rounds of building and refinement were carried out with O (5) and CNS (6), respectively, and then final rounds with REFMAC5 (7). Native At279 was solved by molecular replacement with MOLREP (8), part of the CCP4 Suite (9).

AT287 Crystal Structure

Crystallization and Data Collection of At1g53520 Protein Crystals (At287)

Crystals of the heterologously expressed At287 C-terminal construct (residues 90 to 287) were obtained by vapor diffusion in 2 μl hanging drops at 4° C. consisting of a 1:1 mixture of protein and crystallization buffer. The crystallization buffer contained 9% (w/v) PEG 8000, 0.2 M calcium acetate, 2 mM DTT and 100 mM PIPES buffer at pH 6.5. Prior to freezing in liquid nitrogen, crystals were passed through a cryogenic buffer identical to the crystallization buffer except for the use of 11% (w/v) PEG 8000 and the inclusion of 20% (v/v) ethylene glycol. A data set was collected at the Advanced Light Source at Berkeley (ALS) on beam line 8.2.2 and processed using XDS to a resolution of 2 Å (10). At287 crystals belong to the P4(2)2(1)2 space group, with average unit cell dimensions of a=b=108.46 Å, c=51.31 Å, $\alpha=\beta=\gamma=90°$.

Structure Determination and Coordinate Refinement of At287 Protein

The At287 structure was solved by molecular replacement using Phaser, part of the CCP4 suite. The previously described 1.9 Å At279 structure was used as a search model. The initial molecular replacement model was manually adjusted in COOT and refined with REFMAC5 (7). Structure figures were prepared with PyMol (11).

LC-MS Analysis of Fatty Acids (FA) Bound to Purified At279 and At287 Proteins

At279 and At287 proteins were purified to homogeneity as described above. Ice-cold HPLC grade ethanol (600 μl) was added to the proteins (150 μl protein sample at 10 mg/ml previously dialyzed against 20 mM ammonium bicarbonate). The samples were vortexed and incubated at −20° C. for 3 days. For LC-MS analysis, the samples were centrifuged, and the supernatant containing the FAs was removed and placed in a new glass vial. The solvent was evaporated at 25° C., and the remaining residue resuspended in 200 μl propanol. The extracts were analyzed by liquid chromatography (LC) using an Agilent 1100 HPLC employing a Gemini reversed-phase C18 column (4.6×150 mm, 5 μ) running at a flow rate of 1 ml/min, and coupled to an electrospray ionization (ESI) XCT ion trap mass spectrometer (Agilent) operated in the negative-ion mode employing a continual introduction of a 20 mM ammonium acetate solution flowing at 100 μl/min. A linear gradient of acetonitrile (30-100% v/v) in 25 mM ammonium bicarbonate, pH 8, was used. The negative ion-ESI mass spectra of FA standards were as follows: Laurie acid (C12:0) (m/z)=198.7 ([M-H]-), Myristic acid (C14:0) (m/z)=226.9 ([M-H]-), Palmitic acid (C16:0)/m/z)=254.9 ([M-H]-) and Stearic acid (C18:0) (m/z)=282.9 ([M-H]-). At279 and At287 extracts clearly showed the presence of saturated FA (C12:0, C14:0, C16:0 and C18:0) as well as unsaturated FA (C16:1 (m/z) 253.1 ([M-H]-) and C18:1 (m/z)=281.4 ([M-H]-) (see FIG. 3). Purified AtCHI protein was also analyzed for its FAS content; no trace of FAs was detected using the same method described above providing an appropriate negative control.

Results

Discovery and Bioinformatics Analyses of these New Fatty Acids Binding Proteins.

We discovered the genes and encoded proteins for these two naturally occurring FA binding proteins using bioinformatic analyses of available genomic sequencing data from the plant *Arabidopsis thaliana*, These two homologs, referred to as At279 (At3g63170) and At287 (At1g53520), named based upon their amino acid length, are small proteins located on different chromosomes. At279 and At287, as well as At396 (TAM accession number At2g26310; see also accession number Q58G09 in the UniProt database) form a novel sub-family of CHI like proteins in the *Arabidopsis* chalcone isomerase (CHI) family. The CHI family contains 6-members in *Arabidopsis* ranging from 209 to 396 amino acids in length, and exhibiting 25 to 60% amino acid sequence identity (FIG. 1). In plants, these proteins are ubiquitous and often abundantly expressed. The last 200 C-terminal amino acids of At279 and At287 (as well as At396) share homology to our previously solved *Medicago sativa* L. (Alfalfa) chalcone isomerase crystal structure; however, they lack key residues previously identified in our laboratory that are critically involved in the near diffusion controlled ("Perfect Enzyme") and stereospecific conversion of chalcone into (2S)-naringenin (12). Within the first 80-90 N-terminal amino acid residues, a plastid signal sequence is found. At279 was annotated as localized in the plastid stroma by the plastid proteome database (http://ppdb(dot)tc(dot)cornell(dot)edu/ and http://www(dot)plastid(dot)msu(dot)edu/), as expected based upon the sequence of their N-terminal extensions relative to authentic CHI. We are currently experimentally analyzing the locale of these two FA binding proteins and other sequence relatives using GFP fusion technology in transgenic *Arabidopsis thaliana* plants.

Three Dimensional Structure of At279 and At287

Figure 2B:
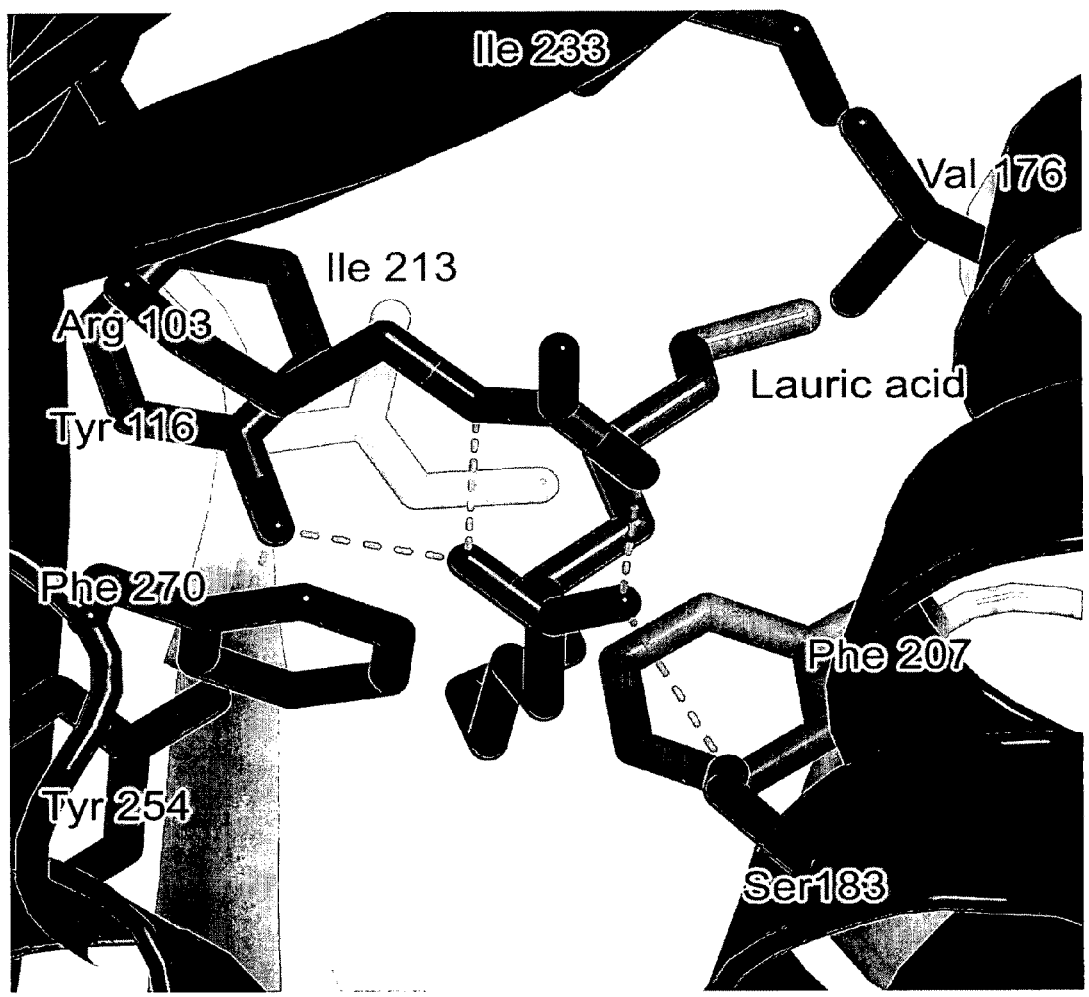
FIG. 2B shows an expansion of AT279 bound to Laurie acid.

*Arabidopsis thaliana* At279 and At287 were over-expressed in *E. coli*, purified to homogeneity and crystallized (see Materials and Methods). We solved the x-ray crystal structure of At279 and At287, as well as the crystal structure of *Arabidopsis thaliana* CHI (At3g55120, referred to as AtCHI) for comparative purposes. The structure of At279 recently completed confirms conservation of the unique open-faced β-sandwich fold of CHI (13). A large beta-sheet and a layer of alpha helices comprise the core structure with three short beta-strands on the opposite side of the large beta-sheet (FIG. 2A-B). However, a highly divergent (shape and amino acid distribution) active site cavity as suggested by sequence alignments between CHI and these FA binding proteins is clearly present (FIG. 1). Active site residues, which are conserved in all known CHIs, include Thr 59, Tyr 117, Asn 124, and Thr/Ser 201 (*Arabidopsis* CHI sequence annotation), and participate in the hydrogen bond network that mediates CHI substrate recognition and stereospecific flavanone formation. Moreover, a final invariant residue essential for catalysis, Arg 47, acts as an electrostatic component for substrate binding and orientation and also stabilizes the transition state of the cyclization reaction. Alteration of the Alfalfa CHI residue corresponding to this Arg (Arg 36) by site-directed mutation obliterates CHI activity (14). As is apparent from the alignment depicted in FIG. 1, At279 and At287 proteins contain Arg 47 but lack all of the hydrogen-bonding residues found in catalytically active CHIs. In fact, Thr 59 in AtCHI is replaced by Tyr 116 (in At279) or Tyr 126 (in At287), Tyr 117 in AtCHI is replaced by Val 176 (in At279) or Phe 183 (in At287), Asn 124 in AtCHI is replaced by Ser 183 (in At279) or Ala 190 (in At287), and Ser 201 in AtCHI is replaced by Leu 254 (in At279) or Val 263 (in At287).

During the very first stages of structure elucidation using x-ray crystallography, we observed a very well ordered and clearly defined small molecule bound in a cavity partially overlapping with the originally identified CHI active site. This small molecule was clearly the fatty acid lauric acid (C12:0), likely derived from *E. coli*. The carboxylic acid group is nicely sequestered by electrostatic interactions with the absolutely conserved Arg and Tyr residues (Arg 103 and Tyr 116 in At279, Arg 114 and Tyr 126 in At287). The fatty acyl chain is bound in a new hydrophobic cavity formed in the CHI fold and distinct from the active site cavity of AtCHI.

LC-MS Analysis of FAs Bound to Purified At279 and At287 Proteins

Figure 3:
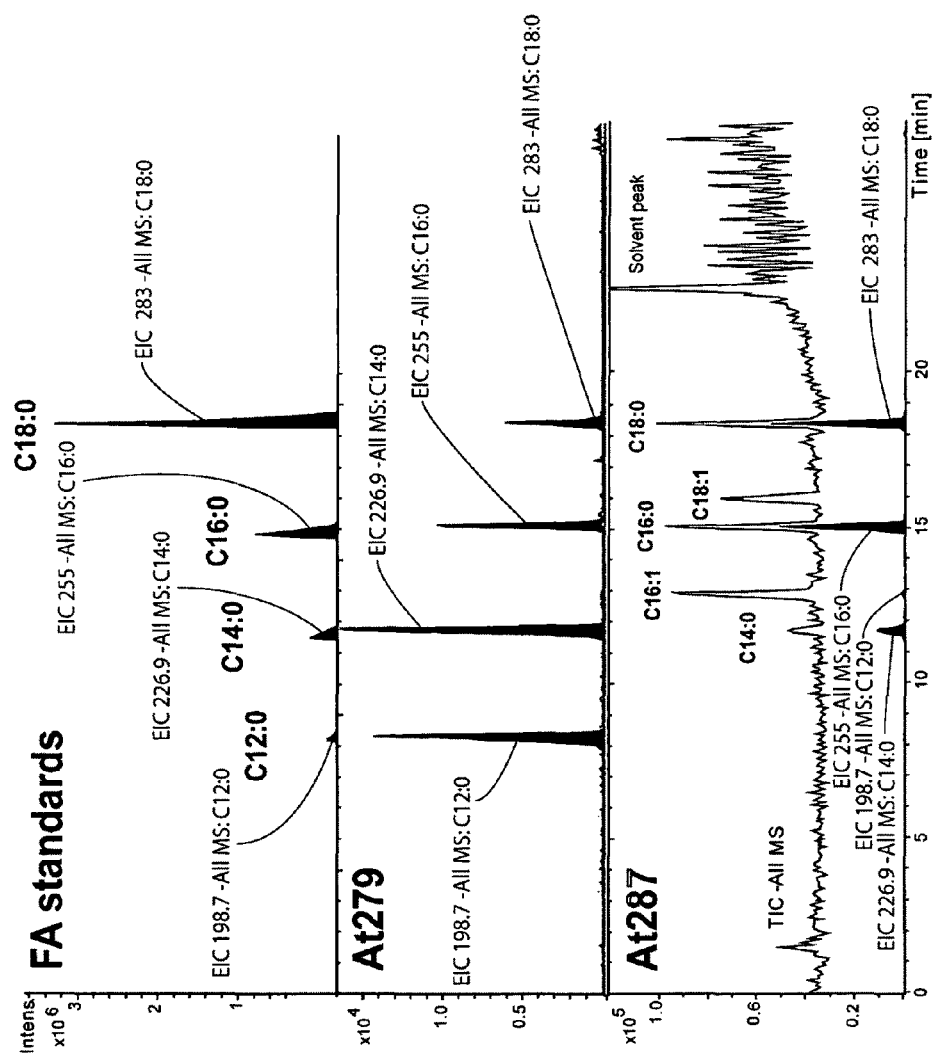
FIG. 3 is an LC-MS analysis of fatty acids bound to AT279 and At287. FAs were extracted from purified *E. coli* overexpressing At279 and At287. Extracted ion chromatograms (EEC) of negative mode mass spectrometer chromatograms (-All MS) of lauric acid (C:12:0) (ink). 198.7 ([M-H]-), myristic acid (C14:0) (m/z)=226.9 ([M-H]-), palmitic acid (C16:0) (m/z)=254.9 ([M-H]-) and steric acid (C18:0) (m/z) =282.9 ([M-H]-), presented compared to standards.

LC-MS analysis of recombinantly prepared At279 and At287 confirmed that they bind an entire set of linear fatty acids representative of *E. coli*'s saturated fatty acid (Laurie acid (C12:0) (m/z)=198.7 ([M-H]-), Myristic acid (C14:0) (m/z)=226.9 ([M-H]-), Palmitic acid (C16:0) (m/z)=254.9 ([M-H]-) and Stearic acid (C18:0) (m/z)=282.9 ([M-H]-)) as well as unsaturated FAs (C16:1 (m/z)=253.1 ([M-H]-) and C18:1 (m/z)=281.4 ([M-H]-) (FIG. 3). Identical analyses of AtCHI clearly possessing authentic CHI catalytic activity showed no such fatty acid binding activity (data not shown).

The discovery of this novel family of FA binding proteins in *Arabidopsis* using both protein x-ray crystallography and LC-MS analysis suggest that this *Arabidopsis* FA binding protein family may have considerable potential for improving the engineering of lipids in plants possibly using a structurally-guided approach to create novel variants using rational protein engineering. It is important to point out that homologs of these FA binding proteins are also found outside higher plants, for example in the unicellular algae Chlamydomonas, as well as in the eukaryotic slime mold Dictyostelium, suggesting an important role for these proteins in lipid metabolism and transport in other organisms.

References

1. Thelen, J. S. & Ohlrogge, J. B. (2002) *Metab Eng* 4, 12-21.
2. Broun, P., Gettner, S. & Somerville, C. (1999) *Annu Rev Nutr* 19, 197-216.
3. Koo, A. J., Ohlrogge, J. B. & Pollard, M. (2004) *J Biol Chem* 279, 16101-10.
4. Terwilliger, T. (2004) *J Synchrotron Radiat* 11, 49-52.
5. Jones, T. A., Zou, 3. Y., Cowan, S. W. & Kjeldgaard (1991) *Acta Crystallogr A* 47 (Pt 2), 110-9.
6. Brunger, A. T., Adams, P. D., Clore, G. M., DeLano, W. L., Gros, P., Grosse-Kunstieve, R. W., Jiang, J. S., Kuszewski, J., Nilges, M., Pannu, N. S., Read, R. J., Rice, L. M., Simonson, T. & Warren, C. L. (1998) *Acta Crystallogr D Biol Crystallogr* 54 (Pt 5), 905-21
7. Vagin, A. A., Steiner, R. A., Lebedev, A. A., Potterton, L., McNicholas, S., Long, F. & Murshudov, G. N. (2004) *Acta Crystallogr D Biol Crystallogr* 60, 2184-95.
8. Vagin, A. A. & Isupov, M. N. (2001) *Acta Crystallogr D Biol Crystallogr* 57, 1451-6.
9. C.C.P.4 (1999) *Acta cryst*. d50, 760-763.
10. Kabsch, W. (2001) XDS in International Tables for Crystallography (Kluwer Academic Publisher, Dordrecht).
11. DeLano, W. L. (2002) www(dot)pymol(dot)org.
12. Jez, S. M. & Noel, J. P. (2000) *J Biol Chem* 275, 39640-6.
13. Jez, J. M., Ferrer, S. L., Bowman, M. E., Austin, M. B., Schroder, J., Dixon, R. A. & Noel, J. P. (2001) *J Ind Microbiol Biotechnol* 27, 393-8.
14. Jez, J. M., Larsen, E., Pojer, F., Bowman, M. E. & Noel, J. P. (2006) in preparation.

Example 2

WU-BLAST 2.0 Queries

WU-BLAST 2.0 queries were performed by TAIR in the Uniprot Plant Proteins database. For full BLAST options and parameters, refer to the BLAST Documentation at NCBI. The release of BLASTP was 2.0 MP-WashU [10 Apr. 2004] [linux24-i686-ILP32F64 2004-04-11T01:00:13]. Well-known references for the relevant algorithms and BLAST programs include Altschul et al. (1990) "Basic local alignment search tool," *J. Mol. Biol.* 215:403-410; Gish et al. (1993) "Identification of protein coding regions by database similarity search," *Nature Genetics* 3:266-72 and Gish and Warren (1994) unpublished information in the BLAST2 Documentation.

At279 was searched using TAIR as described, using a query sequence length of 279 letters, in the database: /home/patlibs/Uniprot Plant Proteins, Table 3 provides results of the search. Sequence alignments between At279 and any of the sequences below can be produced by TAIR using WU-BLAST 2.0, e.g., set to default parameters, and viewed with publicly available sequence alignment tools such as those provided by TAIR (similar searches can be run directly in UniProt or other available databases). Sequences below are obtained by providing the indicated sequence accession number (in parentheses) to the UniProt database (e.g., on the world wide web at pir(dot)uniprot(dot)org).

TABLE 3

Blast Results for At279

| Sequences producing High-scoring Segment Pairs: | | | High score | Smallest Sum Probability P(N) | N |
|---|---|---|---|---|---|
| Q9M1X2_ARATH | (Q9M1X2) | Hypothetical protein F16M2_20 (Hypo . . . | 1231 | 1.6e−125 | 1 |
| Q6V7U9_LYCES | (Q6V7U9) | Putative chalcone isomerase - *Lycop* . . . | 391 | 1.6e−36 | 1 |
| Q69SP9_ORYSA | (Q69SP9) | Hypothetical protein OSJNBa0016O19 . . . | 364 | 1.2e−33 | 1 |

TABLE 3-continued

Blast Results for At279

| Sequences producing High-scoring Segment Pairs: | | | High score | Smallest Sum Probability P(N) | N |
|---|---|---|---|---|---|
| Q6K7H0_ORYSA | (Q6K7H0) | Hypothetical protein OJ1293_A01.5 - . . . | 360 | 3.1e−33 | 1 |
| Q58G09_ARATH | (Q58G09) | Hypothetical protein - *Arabidopsis* . . . | 300 | 7.1e−27 | 1 |
| Q84RK2_ARATH | (Q84RK2) | Hypothetical protein At2g26310/T1D1 . . . | 300 | 7.1e−27 | 1 |
| Q84RK3_ARATH | (Q84RK3) | Hypothetical protein At2g26310/T1D1 . . . | 300 | 7.1e−27 | 1 |
| Q8GXU6_ARATH | (Q8GXU6) | Hypothetical protein At2g26310 - *Ar* . . . | 300 | 7.1e−27 | 1 |
| Q6YTV0_ORYSA | (Q6YTV0) | Hypothetical protein OJ1121_A05.15 . . . | 258 | 2.0e−22 | 1 |
| O64841_ARATH | (O64841) | Hypothetical protein At2g26310 - *Ar* . . . | 112 | 6.9e−10 | 2 |
| Q9ZWR1_CITSI | (Q9ZWR1) | Chalcone isomerase - *Citrus sinensi* . . . | 128 | 1.2e−06 | 1 |
| Q53B73_SOYBN | (Q53B73) | Putative chalcone isomerase 3 - *Gly* . . . | 126 | 4.7e−06 | 1 |
| Q8LFP0_ARATH | (Q8LFP0) | Chalcone isomerase, putative - *Arab* . . . | 115 | 9.8e−05 | 1 |
| Q4AE12_FRAAN | (Q4AE12) | Chalcone isomerase - *Fragaria anana* . . . | 111 | 0.00018 | 1 |
| Q84T92_ORYSA | (Q84T92) | Chalcone isomerase - *Oryza sativa* (. . . | 108 | 0.00039 | 1 |
| Q8S911_IPOBA | (Q8S911) | Chalcone isomerase - *Ipomoea batata* . . . | 107 | 0.00057 | 1 |
| Q4AE11_FRAAN | (Q4AE11) | Chalcone isomerase - *Fragaria anana* . . . | 106 | 0.00071 | 1 |
| Q9LRF1_IPOBA | (Q9LRF1) | Chalcone isomerase (Fragment) - *Ipo* . . . | 105 | 0.00098 | 1 |
| CFI_ELAUM | (O65333) | Chalcone--flavonone isomerase (EC 5.5 . . . | 103 | 0.0019 | 1 |
| Q8S3X1_ORYSA | (Q8S3X1) | Chalcone isomerase (EC 5.5.1.6) - O . . . | 102 | 0.0020 | 1 |
| CFI_MAIZE | (Q08704) | Chalcone--flavonone isomerase (EC 5.5 . . . | 100 | 0.0034 | 1 |
| CFI_IPOPU | (O22604) | Chalcone--flavonone isomerase (EC 5.5 . . . | 99 | 0.0049 | 1 |
| Q6EQW2_ORYSA | (Q6EQW2) | Chalcone isomerase-like - *Oryza sat* . . . | 99 | 0.0067 | 1 |
| Q9FLC7_ARATH | (Q9FLC7) | Similarity to chalcone-flavonone is . . . | 94 | 0.013 | 1 |
| Q8S3X0_HORVD | (Q8S3X0) | Chalcone isomerase (EC 5.5.1.6) - H . . . | 95 | 0.013 | 1 |
| Q8VZW3_ARATH | (Q8VZW3) | Hypothetical protein At5g05270 (Con . . . | 94 | 0.013 | 1 |
| CFI_RAPSA | (O22651) | Chalcone--flavonone isomerase (EC 5.5 . . . | 94 | 0.020 | 1 |
| Q53B72_SOYBN | (Q53B72) | Putative chalcone isomerase 4 - *Gly* . . . | 88 | 0.066 | 1 |
| CFI_PUELO | (Q43056) | Chalcone--flavonone isomerase (EC 5.5 . . . | 87 | 0.10 | 1 |
| Q8LKP9_SAUME | (Q8LKP9) | Chalcone isomerase - *Saussurea medu* . . . | 87 | 0.11 | 1 |
| Q8H0G1_LOTJA | (Q8H0G1) | Putative chalcone isomerase - *Lotus* . . . | 86 | 0.12 | 1 |
| CFI_VITVI | (P51117) | Chalcone--flavonone isomerase (EC 5.5 . . . | 86 | 0.14 | 1 |
| CFI_ARATH | (P41088) | Chalcone--flavonone isomerase (EC 5.5 . . . | 85 | 0.19 | 1 |
| Q53B71_SOYBN | (Q53B71) | Chalcone isomerase 4B (Fragment) - . . . | 79 | 0.20 | 1 |
| CHI_ARALP | (Q9LKC3) | Chalcone--flavonone isomerase (EC 5.5 . . . | 84 | 0.24 | 1 |
| Q8LGS3_ROSHC | (Q8LGS3) | Chalcone isomerase (Fragment) - *Ros* . . . | 77 | 0.32 | 1 |
| Q6QHK0_ALLCE | (Q6QHK0) | Chalcone isomerase - *Allium cepa* (O . . . | 82 | 0.33 | 1 |
| Q66VY8_ALLCE | (Q66VY8) | Chalcone isomerase - *Allium cepa* (O . . . | 81 | 0.41 | 1 |
| Q66VY9_ALLCE | (Q66VY9) | Chalcone isomerase - *Allium cepa* (O . . . | 81 | 0.41 | 1 |
| Q45QI7_CAMSI | (Q45QI7) | Chalcone isomerase - *Camellia sinen* . . . | 78 | 0.70 | 1 |
| Q5VMY4_ORYSA | (Q5VMY4) | Putative DNA topoisomerase I - *Oryz* . . . | 84 | 0.81 | 1 |
| CFI_CALCH | (Q42663) | Chalcone--flavonone isomerase (EC 5.5 . . . | 76 | 0.88 | 1 |
| Q3Y4F4_9LILI | (Q3Y4F4) | Chalcone isomerase - *Canna generalis* | 73 | 0.99 | 1 |
| Q9SSD8_ARATH | (Q9SSD8) | F18B13.3 protein - *Arabidopsis thal* . . . | 80 | 0.991 | 1 |
| Q9CA97_ARATH | (Q9CA97) | Hypothetical protein F19K16.9 - *Ara* . . . | 80 | 0.993 | 1 |
| Q33B68_ORYSA | (Q33B68) | Hypothetical protein - *Oryza sativa* . . . | 53 | 0.996 | 1 |
| Q39946_HELAN | (Q39946) | HAHB-6 (Fragment) - *Helianthus annu* . . . | 51 | 0.9999 | 1 |
| Q9LMH8_ARATH | (Q9LMH8) | T2D23.13 protein - *Arabidopsis thal* . . . | 59 | 0.99993 | 1 |

Similarly, At287 was searched against UniProt using TAIR as described, using a query sequence length of 287 letters, in the database: /home/patlibs/Uniprot Plant Proteins. Table 4 provides results of the search. Sequence alignments between At287 and any of the sequences below are produced by WU-BLAST 2.0, e.g., set to default parameters and viewed with publicly available sequence alignment tools such as those provided by TAIR (similar searches can be run directly in UniProt or other available databases). Sequences below are obtained by providing the indicated sequence accession number (in parentheses) to the UniProt database (e.g., on the world wide web at pir(dot)uniprot(dot)org.

TABLE 4

Blast Results for At287

| Sequences producing High-scoring Segment Pairs: | | | High Score | Smallest Sum Probability P(N) | N |
|---|---|---|---|---|---|
| Q9C8L2_ARATH | (Q9C8L2) | Chalcone isomerase, putative; 94270 . . . | 1340 | 4.4e−137 | 1 |
| Q8LFP0_ARATH | (Q8LFP0) | Chalcone isomerase, putative - *Arab* . . . | 1331 | 4.0e−136 | 1 |
| Q9LPG8_ARATH | (Q9LPG8) | T3F20.16 protein - *Arabidopsis thal* . . . | 1217 | 4.8e−124 | 1 |
| Q53B73_SOYBN | (Q53B73) | Putative chalcone isomerase 3 - *Gly* . . . | 656 | 1.3e−64 | 1 |
| Q6EQW2_ORYSA | (Q6EQW2) | Chalcone isomerase-like - *Oryza sat* . . . | 390 | 2.1e−36 | 1 |
| Q565D8_GENTR | (Q565D8) | Chalcone flavonone isomerase - *Gent* . . . | 175 | 1.3e−13 | 1 |
| Q8H0G1_LOTJA | (Q8H0G1) | Putative chalcone isomerase - *Lotus* . . . | 167 | 1.2e−12 | 1 |

TABLE 4-continued

Blast Results for At287

| Sequences producing High-scoring Segment Pairs: | | | High Score | Smallest Sum Probability P(N) | N |
|---|---|---|---|---|---|
| Q6BEH3_EUSGR | (Q6BEH3) | Chalcone isomerase - *Eustoma grandi* . . . | 163 | 3.6e-12 | 1 |
| Q53B75_SOYBN | (Q53B75) | Chalcone isomerase 1B1 (EC 5.5.1.6) . . . | 162 | 2.8e-11 | 1 |
| Q3Y4F3_9LILI | (Q3Y4F3) | Chalcone isomerase - *Canna generalis* | 159 | 1.0e-10 | 1 |
| Q4AE12_FRAAN | (Q4AE12) | Chalcone isomerase - *Fragaria anana* . . . | 161 | 1.1e-10 | 1 |
| Q3Y4F4_9LILI | (Q3Y4F4) | Chalcone isomerase - *Canna generalis* | 158 | 1.5e-10 | 1 |
| Q53B72_SOYBN | (Q53B72) | Putative chalcone isomerase 4 - *Gly* . . . | 151 | 3.5e-10 | 1 |
| Q53B70_SOYBN | (Q53B70) | Chalcone isomerase 1B2 (EC 5.5.1.6) . . . | 155 | 4.5e-10 | 1 |
| Q8LKP9_SAUME | (Q8LKP9) | Chalcone isomerase - *Saussurea medu* . . . | 150 | 3.2e-09 | 1 |
| Q9ZWR1_CITSI | (Q9ZWR1) | Chalcone isomerase - *Citrus sinensi* . . . | 148 | 4.1e-09 | 1 |
| Q8S911_IPOBA | (Q8S911) | Chalcone isomerase - *Ipomoea batata* . . . | 149 | 6.2e-09 | 1 |
| Q33DL3_TOBAC | (Q33DL3) | Chalcone isomerase - *Nicotiana taba* . . . | 149 | 6.3e-09 | 1 |
| Q4AE11_FRAAN | (Q4AE11) | Chalcone isomerase - *Fragaria anana* . . . | 148 | 7.0e-09 | 1 |
| Q45QI7_CAMSI | (Q45QI7) | Chalcone isomerase - *Camellia sinen* . . . | 147 | 7.5e-09 | 1 |
| CFI_DIACA | (Q43754) | Chalcone--flavonone isomerase (EC 5.5 . . . | 144 | 1.4e-08 | 1 |
| CFI_IPOPU | (O22604) | Chalcone--flavonone isomerase (EC 5.5 . . . | 146 | 1.4e-08 | 1 |
| Q9LRF1_IPOBA | (Q9LRF1) | Chalcone isomerase (Fragment) - *Ipo* . . . | 145 | 1.9e-08 | 1 |
| Q53B74_SOYBN | (Q53B74) | Chalcone isomerase 2 (EC 5.5.1.6) - . . . | 142 | 3.1e-08 | 1 |
| Q8S3X0_HORVD | (Q8S3X0) | Chalcone isomerase (EC 5.5.1.6) - H . . . | 142 | 3.6e-08 | 1 |
| Q42925_MALSP | (Q42925) | Chalcone isomerase (EC 5.5.1.6) (Fr . . . | 124 | 9.9e-08 | 1 |
| CFI_MAIZE | (Q08704) | Chalcone--flavonone isomerase (EC 5.5 . . . | 138 | 1.1e-07 | 1 |
| Q84T92_ORYSA | (Q84T92) | Chalcone isomerase - *Oryza sativa* ( . . . | 138 | 1.2e-07 | 1 |
| CFI_VITVI | (P51117) | Chalcone--flavonone isomerase (EC 5.5 . . . | 137 | 1.7e-07 | 1 |
| Q42926_MALSP | (Q42926) | Chalcone isomerase (EC 5.5.1.6) (Fr . . . | 120 | 2.8e-07 | 1 |
| CFI_CALCH | (Q42663) | Chalcone--flavonone isomerase (EC 5.5 . . . | 135 | 3.1e-07 | 1 |
| Q9FLC7_ARATH | (Q9FLC7) | Similarity to chalcone-flavonone is . . . | 132 | 3.3e-07 | 1 |
| Q8VZW3_ARATH | (Q8VZW3) | Hypothetical protein At5g05270 (Con . . . | 132 | 3.8e-07 | 1 |
| Q66VY9_ALLCE | (Q66VY9) | Chalcone isomerase - *Allium cepa* (O . . . | 133 | 4.4e-07 | 1 |
| CFIA_PETHY | (P11650) | Chalcone--flavonone isomerase A (EC 5 . . . | 134 | 4.4e-07 | 1 |
| Q66VY8_ALLCE | (Q66VY8) | Chalcone isomerase - *Allium cepa* (O . . . | 132 | 5.9e-07 | 1 |
| Q8S3X1_ORYSA | (Q8S3X1) | Chalcone isomerase (EC 5.5.1.6) - O . . . | 132 | 6.8e-07 | 1 |
| CFIB_PETHY | (P11651) | Chalcone--flavonone isomerase B (EC 5 . . . | 131 | 6.8e-07 | 1 |
| CFI_ELAUM | (O65333) | Chalcone--flavonone isomerase (EC 5.5 . . . | 133 | 7.3e-07 | 1 |
| CFI_PUELO | (Q43056) | Chalcone--flavonone isomerase (EC 5.5 . . . | 130 | 9.9e-07 | 1 |
| Q38HM0_AQUFO | (Q38HM0) | Putative chalcone isomerase (Fragme . . . | 114 | 1.3e-06 | 1 |
| Q8H0G2_LOTJA | (Q8H0G2) | Putative chalcone isomerase - *Lotus* . . . | 128 | 1.8e-06 | 1 |
| Q53B71_SOYBN | (Q53B71) | Chalcone isomerase 4B (Fragment) - . . . | 112 | 2.1e-06 | 1 |
| Q9M5B3_PETHY | (Q9M5B3) | Chalcone isomerase A (EC 5.5.1.6) - . . . | 128 | 2.4e-06 | 1 |
| CHI_ARALP | (Q9LKC3) | Chalcone--flavonone isomerase (EC 5.5 . . . | 127 | 3.2e-06 | 1 |
| CFI_ARATH | (P41088) | Chalcone--flavonone isomerase (EC 5.5 . . . | 126 | 4.4e-06 | 1 |
| CFI2_MEDSA | (P28013) | Chalcone--flavonone isomerase 2 (EC 5 . . . | 122 | 5.1e-06 | 1 |
| Q6QHK0_ALLCE | (Q6QHK0) | Chalcone isomerase - *Allium cepa* (O . . . | 123 | 7.6e-06 | 1 |
| CFI1_MEDSA | (P28012) | Chalcone--flavonone isomerase 1 (EC 5 . . . | 122 | 9.3e-06 | 1 |
| Q8GXU6_ARATH | (Q8GXU6) | Hypothetical protein At2g26310 - *Ar* . . . | 119 | 2.0e-05 | 1 |
| Q9FKW3_ARATH | (Q9FKW3) | Chalcone isomerase-like protein - A . . . | 119 | 2.2e-05 | 1 |
| Q8H0F6_LOTJA | (Q8H0F6) | Chalcone isomerase - *Lotus japonicus* | 119 | 2.2e-05 | 1 |
| Q84RQ2_LOTJA | (Q84RQ2) | Chalcone isomerase (EC 5.5.1.6) - L . . . | 118 | 2.4e-05 | 1 |
| Q93XE6_SOYBN | (Q93XE6) | Chalcone isomerase 1A (EC 5.5.1.6) . . . | 117 | 3.5e-05 | 1 |
| Q84RK3_ARATH | (Q84RK3) | Hypothetical protein At2g26310/T1D1 . . . | 119 | 3.8e-05 | 1 |
| Q58G09_ARATH | (Q58G09) | Hypothetical protein - *Arabidopsis* . . . | 119 | 8.4e-05 | 1 |
| CFI_RAPSA | (O22651) | Chalcone--flavonone isomerase (EC 5.5 . . . | 114 | 0.00012 | 1 |
| CFI_SOYBN | (O81980) | Chalcone--flavonone isomerase (EC 5.5 . . . | 104 | 0.00051 | 1 |
| Q84RK2_ARATH | (Q84RK2) | Hypothetical protein At2g26310/T1D1 . . . | 111 | 0.00068 | 1 |
| CFI_PHAVU | (P14298) | Chalcone--flavonone isomerase (EC 5.5 . . . | 104 | 0.0013 | 1 |
| Q9SXS9_CICAR | (Q9SXS9) | Chalcone isomerase (Fragment) - *Cic* . . . | 93 | 0.0037 | 1 |
| Q84S97_RAPSA | (Q84S97) | Chalcone flavanone isomerase (Fragm . . . | 94 | 0.0089 | 1 |
| CFI_PEA | (P41089) | Chalcone--flavonone isomerase (EC 5.5.1 . . . | 96 | 0.011 | 1 |
| Q6K7H0_ORYSA | (Q6K7H0) | Hypothetical protein OJ1293_A01.5 - . . . | 100 | 0.013 | 1 |
| Q3HNP7_ASTME | (Q3HNP7) | Chalcone isomerase (Fragment) - *Ast* . . . | 89 | 0.013 | 1 |
| Q69SP9_ORYSA | (Q69SP9) | Hypothetical protein OSJNBa0016O19 . . . | 92 | 0.100 | 1 |
| Q94IU6_FRAVE | (Q94IU6) | Chalcone isomerase (Fragment) - *Fra* . . . | 69 | 0.11 | 1 |
| Q8LGS3_ROSHC | (Q8LGS3) | Chalcone isomerase (Fragment) - *Ros* . . . | 81 | 0.14 | 1 |
| Q8RVM9_MALDO | (Q8RVM9) | Chalcone isomerase (Fragment) - *Mal* . . . | 77 | 0.20 | 1 |
| Q4AEC1_WHEAT | (Q4AEC1) | Chalcone isomerase (Fragment) - *Tri* . . . | 72 | 0.80 | 1 |
| Q94KX0_BRANA | (Q94KX0) | Chalcone flavonone synthase (Fragme . . . | 58 | 0.84 | 1 |
| Q94KX4_BRANA | (Q94KX4) | Chalcone flavonone synthase (Fragme . . . | 57 | 0.90 | 1 |
| Q94KX1_BRAOL | (Q94KX1) | Chalcone flavonone synthase (Fragme . . . | 56 | 0.95 | 1 |
| Q76K33_PRUPE | (Q76K33) | Chalcone isomerase (Fragment) - *Pru* . . . | 55 | 0.98 | 1 |
| Q3E948_ARATH | (Q3E948) | Protein At5g25750 - *Arabidopsis tha* . . . | 55 | 0.98 | 1 |
| Q7G6C8_ORYSA | (Q7G6C8) | Hypothetical protein OSJNAb0022I16 . . . | 72 | 0.9998 | 1 |

Similarly, At396 was searched against UNIPROT as described, using a query sequence length of 396 letters, in the database: /home/patlibs/Uniprot Plant Proteins. Table 5 provides results of the search. Sequence alignments between At396 and any of the sequences below can be produced by WU-BLAST 2.0, e.g., set to default parameters and viewed with publicly available sequence alignment tools such as those provided by TAM (similar searches can be run directly in UniProt or other available databases). Sequences below are obtained by providing the indicated sequence accession number (in parentheses) to the UniProt database (e.g., on the world wide web at pir(dot)uniprot(dot)org.

TABLE 5

Blast Results for At396

| Sequences producing High-scoring Segment Pairs: | | | High Score | Smallest Sum Probability P(N) | N |
|---|---|---|---|---|---|
| Q58G09_ARATH | (Q58G09) | Hypothetical protein - Arabidopsis . . . | 1943 | 5.6e-201 | 1 |
| Q84RK2_ARATH | (Q84RK2) | Hypothetical protein At2g26310/T1D1 . . . | 1935 | 3.9e-200 | 1 |
| Q84RK3_ARATH | (Q84RK3) | Hypothetical protein At2g26310/T1D1 . . . | 1311 | 5.2e-134 | 1 |
| Q8GXU6_ARATH | (Q8GXU6) | Hypothetical protein At2g26310 - Ar . . . | 1002 | 2.9e-101 | 1 |
| Q6K7H0_ORYSA | (Q6K7H0) | Hypothetical protein OJ1293_A01.5 - . . . | 700 | 2.9e-69 | 1 |
| Q69SP9_ORYSA | (Q69SP9) | Hypothetical protein OSJNBa0016O19 . . . | 639 | 8.5e-63 | 1 |
| Q9M1X2_ARATH | (Q9M1X2) | Hypothetical protein F16M2_20 (Hypo . . . | 283 | 4.5e-25 | 1 |
| O64841_ARATH | (O64841) | Hypothetical protein At2g26310 - Ar . . . | 221 | 6.1e-23 | 2 |
| Q6V7U9_LYCES | (Q6V7U9) | Putative chalcone isomerase - Lycop . . . | 230 | 3.5e-19 | 1 |
| Q53B73_SOYBN | (Q53B73) | Putative chalcone isomerase 3 - Gly . . . | 133 | 2.1e-06 | 1 |
| Q8LFP0_ARATH | (Q8LFP0) | Chalcone isomerase, putative - Arab . . . | 119 | 8.6e-05 | 1 |
| Q6YTV0_ORYSA | (Q6YTV0) | Hypothetical protein OJ1121_A05.15 . . . | 99 | 0.00010 | 1 |
| Q9C8L2_ARATH | (Q9C8L2) | Chalcone isomerase, putative; 94270 . . . | 112 | 0.00054 | 1 |
| Q5M9R4_TOBAC | (Q5M9R4) | Hypothetical protein orf134b - Nico . . . | 71 | 0.98 | 1 |
| Q4G3B6_EMIHU | (Q4G3B6) | Hypothetical chloroplast RF40 - Emi . . . | 54 | 0.9995 | 1 |
| Q53B70_SOYBN | (Q53B70) | Chalcone isomerase 1B2 (EC 5.5.1.6) . . . | 73 | 0.9998 | 1 |
| Q84T92_ORYSA | (Q84T92) | Chalcone isomerase - Oryza sativa ( . . . | 73 | 0.9999 | 1 |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of increasing the lipid content of a cell and extracting lipid from the cell, the method comprising:
    expressing a recombinant chalcone isomerase like fatty acid binding protein gene in the cell, wherein said chalcone isomerase like fatty acid binding protein comprises a sequence at least 80% identical to SEQ ID NO:4 and has an arginine (Arg) residue in a position corresponding to Arg114 and a tyrosine (Tyr) residue in a position corresponding to Tyr126 of SEQ ID NO:4, and wherein expression of the recombinant gene increases the lipid content of the cell relative to the lipid content in a corresponding cell not expressing recombinant chalcone isomerase like fatty acid binding protein; and
    extracting lipid from the cell.

2. The method of claim 1, wherein the chalcone isomerase like fatty acid binding protein comprises a sequence at least 90% identical to SEQ ID NO:4.

3. The method of claim 1, wherein the cell is a plant cell.

4. The method of claim 3, wherein the plant cell is in a recombinant plant.

5. The method of claim 4, wherein the plant is a member of a family selected from Graminae, Leguminosae, Compositae and Rosaciae, or wherein the plant is a member of a genus selected from Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vida, Vigna, Vitis, Zea, the Olyreae, and the Pharoideae.

6. The method of claim 4, wherein the plant is a Zea mays, soybean, cotton, Brassica naupus, Brassica juncea, tobacco, sunflower, safflower, rapeseed, canola, olive or Arabidopsis thalina plant.

7. The method of claim 4, further comprising selecting a plant with increased lipid content.

8. The method of claim 1, wherein the chalcone isomerase like fatty acid binding protein comprises the sequence of SEQ ID NO:4.

9. The method of claim 1, further comprising determining the lipid content of the cell.

10. A method of increasing the lipid content of a cell, the method comprising:
    expressing a recombinant chalcone isomerase like fatty acid binding protein gene in the cell,
    wherein said chalcone isomerase like fatty acid binding protein comprises a sequence at least 80% identical to SEQ ID NO:4 and has an arginine (Arg) residue in a position corresponding to Arg114 and a tyrosine (Tyr) residue in a position corresponding to Tyr126 of SEQ ID NO:4; and
    determining the lipid content in the cell, wherein expression of the recombinant gene increases the lipid content of the cell relative to the lipid content in a corresponding cell not expressing recombinant chalcone isomerase like fatty acid binding protein.

11. The method of claim 10, wherein the chalcone isomerase like fatty acid binding protein comprises a sequence at least 90% identical to SEQ ID NO:4.

12. The method of claim 10, wherein the chalcone isomerase like fatty acid binding protein comprises the sequence of SEQ ID NO:4.

13. The method of claim 10, wherein the cell is a plant cell.

14. The method of claim 13, wherein the plant cell is in a recombinant plant.

15. The method of claim 14, wherein the plant is a member of a family selected from Graminae, Leguminosae, Compositae and Rosaciae, or wherein the plant is a member of a genus selected from Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vida, Vigna, Vitis, Zea, the Olyreae, and the Pharoideae.

16. The method of claim 14, wherein the plant is a Zea mays, soybean, cotton, Brassica naupus, Brassica juncea, tobacco, sunflower, safflower, rapeseed, canola, olive or Arabidopsis thalina plant.

17. The method of claim 14, further comprising selecting a plant with increased lipid content.

18. The method of claim 10, further comprising extracting lipid from the cell.

* * * * *

SEQUENCE LISTING

<160> NUMBER OF SEQ ID NOS: 6

<210> SEQ ID NO 1
<211> LENGTH: 246
<212> TYPE: PRT
<213> ORGANISM: Arabidopsis thaliana

<400> SEQUENCE: 1

Met Ser Ser Ser Asn Ala Cys Ala Ser Pro Ser Pro Phe Pro Ala Val
1               5                   10                  15

Thr Lys Leu His Val Asp Ser Val Thr Phe Val Pro Ser Val Lys Ser
            20                  25                  30

Pro Ala Ser Ser Asn Pro Leu Phe Leu Gly Gly Ala Gly Val Arg Gly
        35                  40                  45

Leu Asp Ile Gln Gly Lys Phe Val Ile Phe Thr Val Ile Gly Val Tyr
    50                  55                  60

Leu Glu Gly Asn Ala Val Pro Ser Leu Ser Val Lys Trp Lys Gly Lys

```
                65                  70                  75                  80
Thr Thr Glu Glu Leu Thr Glu Ser Ile Pro Phe Phe Arg Glu Ile Val
                        85                  90                  95
Thr Gly Ala Phe Glu Lys Phe Ile Lys Val Thr Met Lys Leu Pro Leu
                        100                 105                 110
Thr Gly Gln Gln Tyr Ser Glu Lys Val Thr Glu Asn Cys Val Ala Ile
                        115                 120                 125
Trp Lys Gln Leu Gly Leu Tyr Thr Asp Cys Glu Ala Lys Ala Val Glu
                        130                 135                 140
Lys Phe Leu Glu Ile Phe Lys Glu Gly Thr Phe Pro Pro Gly Ser Ser
145                     150                 155                 160
Ile Leu Phe Ala Leu Ser Pro Thr Gly Ser Leu Thr Val Ala Phe Ser
                        165                 170                 175
Lys Asp Asp Ser Ile Pro Glu Thr Gly Ile Ala Val Ile Glu Asn Lys
                        180                 185                 190
Leu Leu Ala Glu Ala Val Leu Glu Ser Ile Ile Gly Lys Asn Gly Val
                        195                 200                 205
Ser Pro Gly Thr Arg Leu Ser Val Ala Glu Arg Leu Ser Gln Leu Met
                        210                 215                 220
Met Lys Asn Lys Asp Glu Lys Glu Val Ser Asp His Ser Val Glu Glu
225                     230                 235                 240
Lys Leu Ala Lys Glu Asn
                        245

<210> SEQ ID NO 2
<211> LENGTH: 223
<212> TYPE: PRT
<213> ORGANISM: Arabidopsis thaliana

<400> SEQUENCE: 2

Met Pro Leu Pro Ser Val Thr Pro Leu His Val Asp Ala Phe Thr Phe
1               5                   10                  15
Pro Pro Ala Val Glu Ser Pro Ala Ser His Lys Arg Leu Phe Leu Gly
                        20                  25                  30
Gly Ala Gly Lys Phe Val Ile Val Thr Val Ile Gly Val Tyr Leu Glu
                        35                  40                  45
Ala Met Ala Leu Pro Ser Ile Ser Ala Lys Trp Lys Gly Lys Asn Ala
                        50                  55                  60
Lys Glu Leu Thr Glu Ser Val Pro Phe Phe Arg Gln Leu Val Thr Gly
65                      70                  75                  80
Glu Phe Glu Lys Leu Ala Arg Val Thr Met Lys Arg Leu Thr Gly
                        85                  90                  95
Ile Gln Tyr Ser Glu Lys Val Val Glu Asn Cys Glu Glu Ile Met Lys
                        100                 105                 110
Ala Ser Gly Lys Tyr Thr Arg Ser Glu Ala Lys Ala Ile Asp Gln Phe
                        115                 120                 125
Leu Met Val Phe Lys Asn Gln Asp Phe Pro Pro Gly Ser Ser Ile Ile
                        130                 135                 140
Phe Ala Ile Cys Pro Lys Gly Ser Leu Thr Ile Ala Phe Ser Lys Glu
145                     150                 155                 160
Glu Arg Val Pro Lys Thr Gly Lys Ala Val Ile Lys Asn Lys Leu Leu
                        165                 170                 175
Gly Glu Ala Val Leu Glu Ser Met Ile Gly Lys Asn Gly Val Ser Pro
                        180                 185                 190
Ala Thr Arg Lys Ser Leu Ala Glu Arg Leu Ser Lys Leu Met Asn Lys
```

```
                195                 200                 205

Lys Asp Pro Tyr Asn Glu Ala Asn Val Asn Val Ala Thr Lys Asn
    210                 215                 220

<210> SEQ ID NO 3
<211> LENGTH: 209
<212> TYPE: PRT
<213> ORGANISM: Arabidopsis thaliana

<400> SEQUENCE: 3

Met Gly Thr Glu Met Val Met Val His Glu Val Pro Phe Pro Gln
1               5                   10                  15

Ile Ile Thr Ser Lys Pro Leu Ser Leu Gly Gln Gly Ile Thr Asp
                20                  25                  30

Ile Glu Ile His Phe Leu Gln Val Lys Phe Thr Ala Ile Gly Val Tyr
                35                  40                  45

Leu Asp Pro Ser Asp Val Lys Thr His Leu Asp Asn Trp Lys Gly Lys
50                  55                  60

Thr Gly Lys Glu Leu Ala Gly Asp Asp Phe Phe Asp Ala Leu Ala
65                  70                  75                  80

Ser Ala Glu Met Glu Lys Val Ile Arg Val Val Ile Lys Glu Ile
                85                  90                  95

Lys Gly Ala Gln Tyr Gly Val Gln Leu Glu Asn Thr Val Arg Asp Arg
                100                 105                 110

Leu Ala Glu Glu Asp Lys Tyr Glu Glu Glu Glu Thr Glu Leu Glu
                115                 120                 125

Lys Val Val Gly Phe Phe Gln Ser Lys Tyr Phe Lys Ala Asn Ser Val
130                 135                 140

Ile Thr Tyr His Phe Ser Ala Lys Asp Gly Ile Cys Glu Ile Gly Phe
145                 150                 155                 160

Glu Thr Glu Gly Lys Glu Glu Glu Lys Leu Lys Val Glu Asn Ala Asn
                165                 170                 175

Val Val Gly Met Met Gln Arg Trp Tyr Leu Ser Gly Ser Arg Gly Val
                180                 185                 190

Ser Pro Ser Thr Ile Val Ser Ile Ala Asp Ser Ile Ser Ala Val Leu
                195                 200                 205

Thr

<210> SEQ ID NO 4
<211> LENGTH: 287
<212> TYPE: PRT
<213> ORGANISM: Arabidopsis thaliana

<400> SEQUENCE: 4

Met Asp Gly Ile Leu Ala Ala Val Pro Ser Ala Val Cys Val Ser Leu
1               5                   10                  15

Arg Ile Ser Cys Arg Asn Leu Asp Asn Ala Glu Ser Ile Tyr His Phe
                20                  25                  30

Pro Gly Lys Ser Leu Asn Arg Val Ser Val Leu Gln Thr Gly Asn Tyr
                35                  40                  45

Val Ser Arg Lys Gly Asn Ser Leu Leu Lys Asn Arg His Cys Gly Glu
50                  55                  60

Ile Ser Arg Val Ile Val Lys Ser Ala Ala Ser Ser Val Gly Asn Ala
65                  70                  75                  80

Glu Asp Tyr Ala Glu Glu Thr Ala Thr Ser Val Lys Phe Lys Arg Ser
                85                  90                  95
```

```
Val Thr Leu Pro Gly Cys Ser Ser Pro Leu Ser Leu Gly Thr Gly
            100                 105                 110

Phe Arg Glu Lys Lys Phe Ala Ile Ile Gly Val Lys Val Tyr Ala Ala
        115                 120                 125

Gly Tyr Tyr Val Asn Glu Ser Ile Leu Ser Gly Leu Ser Ala Trp Thr
    130                 135                 140

Gly Arg Ser Ala Asp Glu Ile Gln Arg Asp Ser Ser Leu Phe Val Ser
145                 150                 155                 160

Ile Phe Gln Ala Gln Ala Glu Lys Ser Leu Gln Ile Val Leu Val Arg
                165                 170                 175

Asp Val Asp Gly Lys Thr Phe Trp Asp Ala Leu Asp Glu Ala Ile Ser
            180                 185                 190

Pro Arg Ile Lys Ser Pro Ser Glu Asp Thr Thr Ala Leu Ser Thr
        195                 200                 205

Phe Arg Gly Ile Phe Gln Asn Arg Pro Leu Asn Lys Gly Ser Val Ile
    210                 215                 220

Leu Leu Thr Trp Ile Asn Thr Ser Asn Met Leu Val Ser Val Ser Ser
225                 230                 235                 240

Gly Gly Leu Pro Thr Asn Val Asp Ala Thr Ile Glu Ser Gly Asn Val
                245                 250                 255

Thr Ser Ala Leu Phe Asp Val Phe Phe Gly Asp Ser Pro Val Ser Pro
            260                 265                 270

Thr Leu Lys Ser Ser Val Ala Asn Gln Leu Ala Met Thr Leu Val
        275                 280                 285

<210> SEQ ID NO 5
<211> LENGTH: 279
<212> TYPE: PRT
<213> ORGANISM: Arabidopsis thaliana

<400> SEQUENCE: 5

Met Val Ser Phe Arg Phe Pro Phe Ser Phe Ser Gln Pro Pro Arg Ala
1               5                   10                  15

Thr Thr Ser Phe Ser Gly Phe Ser Ile Ser Ala Val Ala Val Ser Val
            20                  25                  30

Thr Val Gly Ala Ala Ala Ala Gly Ala Ala Ile Ala Ala Ser Arg Asn
        35                  40                  45

Pro Ser His Pro Ile Leu Glu Trp Ala Phe Ser Ser His Arg Ser Ser
    50                  55                  60

Leu Ser Pro Trp Gly Ser Ile Thr Leu Ala Asp Glu Ser Val Val Glu
65                  70                  75                  80

Pro Lys Thr Gly Phe Ser Phe Pro Ala Ser Ile Gly Asp Ser Arg Arg
                85                  90                  95

Leu Leu Gly Val Gly Leu Arg Lys Lys Ser Leu Leu Gly Leu Lys Asn
            100                 105                 110

Ile Asp Val Tyr Ala Phe Gly Val Tyr Ala Asp Cys Asp Asp Val Lys
        115                 120                 125

Lys Leu Val Gly Asp Lys Tyr Ala Asn Leu Pro Ala Ser Glu Ile Arg
    130                 135                 140

Gly Asn Lys Ser Phe Met Asp Asp Leu Met Glu Ala Asp Ile Lys Met
145                 150                 155                 160

Thr Ile Arg Leu Gln Ile Val Tyr Gly Lys Leu Asn Ile Arg Ser Val
                165                 170                 175

Arg Asn Ala Phe Gln Glu Ser Val Gly Asn Arg Leu Lys Lys Phe Gly
            180                 185                 190
```

```
Gly Ser Asp Asn Asp Glu Leu Leu Gln Ser Phe Thr Ser Leu Phe Lys
            195                 200                 205

Asp Glu Tyr Lys Ile Pro Arg Asn Ser Thr Ile Asp Leu Thr Lys Asp
    210                 215                 220

Pro Gly His Val Leu Ser Val Ala Ile Glu Gly Asn His Val Gly Ser
225                 230                 235                 240

Val Lys Ser His Leu Leu Cys Arg Ser Ile Leu Asp Leu Tyr Ile Gly
            245                 250                 255

Glu Glu Pro Phe Asp Lys Asn Ala Arg Glu Asp Phe Leu Asp Asn Ala
            260                 265                 270

Ala Ser Leu Ala Phe Asp Asn
            275

<210> SEQ ID NO 6
<211> LENGTH: 398
<212> TYPE: PRT
<213> ORGANISM: Arabidopsis thaliana

<400> SEQUENCE: 6

Met Ser Asn Met Asp Pro Asn Ser Val Leu Pro Lys Arg Ser Phe Leu
1               5                   10                  15

Gln His Glu Leu Phe Ser Gln Leu His Ile Pro Gly Ser Leu Ala Phe
            20                  25                  30

Glu Ala Phe Ser Cys Ile Ser Lys Phe Thr Gly Ala Leu Leu Cys Trp
        35                  40                  45

Phe Ser His Gly Asn Leu Gln Lys Glu Val Ser Lys His Gln Trp Gly
    50                  55                  60

Leu Thr Cys Lys Ser Arg Asp Ser Leu Lys His Val Phe Glu His Arg
65                  70                  75                  80

Asn Val Ser Val Phe Pro Phe His Tyr Val Ser Lys Asp Ile Ser Pro
                85                  90                  95

Gly Phe Pro Gly Asn Ile Ser Lys Ser Thr Ile Gln His Phe Val Asn
            100                 105                 110

Glu Ala Glu Arg Leu His Ser Cys Ser Leu Leu Ser Leu Ala Ala Ala
        115                 120                 125

Met Ile Pro Ser Leu Asn Val Met Ser Ala Asn Gly Leu Ala Leu Pro
    130                 135                 140

Leu Gly Ser Asn Asp Val Lys Leu Arg Glu Asn Ile Glu His Arg Thr
145                 150                 155                 160

Cys Pro Glu Asn Thr Glu His Arg Thr Cys Gln Val Gly Cys Glu Glu
                165                 170                 175

Tyr Ser Gly Leu Ser Phe Gln Lys Leu Asp Trp Thr Arg Gln Ser Val
            180                 185                 190

Glu Pro Arg Thr Gly Ile Glu Phe Pro Met Leu Leu Lys Glu Asn Ala
        195                 200                 205

Ser Arg Ser Asn Ser Glu Val Leu Val Ala Thr Gly Ser Arg Thr Met
    210                 215                 220

Lys Ile Ile Arg Ile Lys Ser Leu Lys Val Tyr Ala Phe Gly Phe Tyr
225                 230                 235                 240

Val His Pro Ser Ser Val Cys Gln Lys Leu Gly Arg Lys Tyr Ala Ser
                245                 250                 255

Val Pro Ala Ser Lys Leu Asp Lys Cys Asp Asp Leu Tyr Lys Asp Leu
            260                 265                 270

Leu Arg Glu Asp Ile Val Met Ser Val Arg Leu Val Asn Tyr Asn
        275                 280                 285
```

```
Gly Leu Lys Ile Asn Thr Val Arg Asp Val Phe Glu Lys Ser Leu Arg
    290                 295                 300

Ala Arg Leu Val Lys Ala Asn Pro Lys Thr Asp Phe Asn Cys Leu Asn
305             310                 315                     320

Asp Phe Gly Ser Phe Phe Arg Gln Asp Ile Pro Ile Pro Ala Gly Thr
                325                 330                 335

Ile Ile Asp Phe Arg Arg Thr Glu Asp Gly Gln Leu Ile Thr Glu Ile
            340                 345                 350

Gly Gly Asn Leu Ile Gly Ala Val Arg Ser Lys Asp Leu Cys Arg Ala
        355                 360                 365

Phe Phe Gly Met Tyr Ile Gly Asp Val Pro Val Ser Glu Gln Thr Lys
    370                 375                 380

Glu Glu Ile Gly Arg Lys Val Val Gly Ile Ile Lys Arg Cys
385                 390                 395
```